US011299487B2

(12) United States Patent
Natala et al.

(10) Patent No.: US 11,299,487 B2
(45) Date of Patent: Apr. 12, 2022

(54) COMPOUNDS AND COMPOSITIONS AS MODULATORS OF TLR SIGNALING

(71) Applicant: Neuropore Therapies, Inc., San Diego, CA (US)

(72) Inventors: Srinivasa Reddy Natala, San Diego, CA (US); Wolfgang J. Wrasidlo, La Jolla, CA (US); Emily M. Stocking, Encinitas, CA (US)

(73) Assignee: Neuropore Therapies, Inc., San Diego, CA (US)

( * ) Notice: Subject to any disclaimer, the term of this patent is extended or adjusted under 35 U.S.C. 154(b) by 0 days.

(21) Appl. No.: 16/830,110

(22) Filed: Mar. 25, 2020

(65) Prior Publication Data

US 2020/0308163 A1 Oct. 1, 2020

Related U.S. Application Data

(60) Provisional application No. 62/824,189, filed on Mar. 26, 2019, provisional application No. 62/824,170, filed on Mar. 26, 2019.

(51) Int. Cl.

| | | |
|---|---|---|
| *C07D 417/10* | (2006.01) |
| *C07C 235/56* | (2006.01) |
| *C07D 207/06* | (2006.01) |
| *C07D 211/10* | (2006.01) |
| *C07D 231/12* | (2006.01) |
| *C07D 265/30* | (2006.01) |
| *C07D 265/36* | (2006.01) |
| *C07D 401/06* | (2006.01) |
| *C07D 401/10* | (2006.01) |
| *C07D 403/10* | (2006.01) |
| *C07D 403/14* | (2006.01) |
| *C07D 405/04* | (2006.01) |
| *C07D 405/14* | (2006.01) |
| *C07D 409/10* | (2006.01) |
| *C07D 413/06* | (2006.01) |
| *C07D 413/10* | (2006.01) |
| *C07D 413/14* | (2006.01) |
| *C07D 471/08* | (2006.01) |
| *C07D 487/08* | (2006.01) |
| *C07D 498/02* | (2006.01) |

(52) U.S. Cl.
CPC .......... *C07D 417/10* (2013.01); *C07C 235/56* (2013.01); *C07D 207/06* (2013.01); *C07D 211/10* (2013.01); *C07D 231/12* (2013.01); *C07D 265/30* (2013.01); *C07D 265/36* (2013.01); *C07D 401/06* (2013.01); *C07D 401/10* (2013.01); *C07D 403/10* (2013.01); *C07D 403/14* (2013.01); *C07D 405/04* (2013.01); *C07D 405/14* (2013.01); *C07D 409/10* (2013.01); *C07D 413/06* (2013.01); *C07D 413/10* (2013.01); *C07D 413/14* (2013.01); *C07D 471/08* (2013.01); *C07D 487/08* (2013.01); *C07D 498/02* (2013.01)

(58) Field of Classification Search
CPC .. C07D 417/10; C07D 231/10; C07D 405/10; C07D 405/04; C07D 401/06; C07D 403/10; C07D 401/04; C07D 413/10; C07D 253/04; C07D 233/54; C07D 333/04; C07D 263/30; C07D 498/04; C07D 277/20; C07D 271/06; C07D 261/06; C07D 275/02; C07D 249/08; C07D 417/04; C07D 257/04; C07D 271/107

USPC ........ 544/111, 122, 130, 112, 183, 321, 162, 544/298, 328, 356, 359, 384, 398, 59, 544/114, 124, 131, 159, 180, 212, 235, 544/238, 242, 251, 253, 256, 284, 295, 544/296, 310, 311, 312, 319, 323, 331, 544/349, 360, 392, 58.2, 58.4

See application file for complete search history.

(56) References Cited

U.S. PATENT DOCUMENTS

| | | |
|---|---|---|
| 8,193,378 B2 | 6/2012 | Harada et al. |
| 2013/0096133 A1 | 4/2013 | Hergenrother |
| 2021/0024539 A1 | 1/2021 | Srinivasa |

FOREIGN PATENT DOCUMENTS

| | | | |
|---|---|---|---|
| CN | 101 805 338 | 8/2010 | |
| EP | 0 005 465 | 11/1979 | |
| EP | 1402887 | * 3/2004 | ............. A61K 31/17 |
| WO | WO 2008/154484 | 12/2008 | |
| WO | WO-2009/002790 | 12/2008 | |
| WO | WO-2013/013504 | 1/2013 | |
| WO | WO 2016/164414 | 10/2016 | |
| WO | WO-2018/026866 | 2/2018 | |
| WO | WO 2019/191189 | 10/2019 | |

OTHER PUBLICATIONS

Khadse, et al., Indian Journal of Chemistry, Section B: Organic Chemistry Including Medicinal Chemistry (1987), 26B(9), 856-60.*
Li, et al., European Journal of Medicinal Chemistry (2019), 166, 178-185.*

(Continued)

*Primary Examiner* — Jeffrey H Murray
(74) *Attorney, Agent, or Firm* — Morrison & Foerster LLP

(57) ABSTRACT

The present disclosure relates to substituted aryl and heteroaryl compounds, pharmaceutical compositions comprising such compounds, and use of such compounds in methods of treatment or in medicaments for treatment of inflammatory diseases and certain neurological disorders that are related to inflammatory signaling processes, including but not limited to misfolded proteins.

8 Claims, No Drawings

(56) References Cited

OTHER PUBLICATIONS

Bagshawe et al., "Antibody-directed enzyme prodrug therapy: A review," Drug Dev Res (1995) 34(2):220-230.

Balak et al., "IMO-8400, a Toll-Like Receptor 7, 8, and 9 Antagonist, Demonstrates Clinical Activity in a Phase 2a, Randomized, Placebo-Controlled Trial in Patients With Moderate-to-Severe Plaque Psoriasis," Clin Immunol (2017) 174:63-72.

Beraud et al., "Misfolded α-Synuclein and Toll-like Receptors: Therapeutic Targets for Parkinson's Disease," Parkinsonism Relat Disord (2012) 18 (Suppl 1) S17-S20.

Berge et al., "Pharmaceutical Salts," J Pharm Sci (1977) 66(1):1-19.

Bertolini et al., "A New Rational Hypothesis for the Pharmacophore of the Active Metabolite of Leflunomide, a Potent Immunosuppressive Drug," J Med Chem (1997) 40(13):2011-2016.

Bodor et al., "Novel approaches to the design of safer drugs : soft drugs and site-specific chemical delivery systems," Adv Drug Res (1984) 13:255-331.

Brooks, "Positron Emission Tomography and Single-Photon Emission Computed Tomography in Central Nervous System Drug Development," NeuroRx (2005) 2(2):226-236.

Brown et al., "Binding specificity of Toll-like receptor cytoplasmic domains," Eru J Immunol (2006) 36(3):742-753.

Cario, "Toll-like Receptors in Inflammatory Bowel Diseases: A Decade Later," Inflamm Bowel Dis (2010) 16(9):1583-1597.

Casula et al., "Toll-like Receptor Signaling in Amyotrophic Lateral Sclerosis Spinal Cord Tissue," Neuroscience (2011) 179:233-243.

Chen et al., "Engagement of Toll-like Receptor 2 on CD4(+) T Cells Facilitates Local Immune Responses in Patients With Tuberculous Pleurisy," J Infect Dis (2009) 200(3):399-408.

David et al., "A Toll-Like Receptor 9 Antagonist Reduces Pain Hypersensitivity and the Inflammatory Response in Spinal Cord Injury," Neurobiol Dis (2013) 54:194-205.

Di Marco Vieira et al., "Neuroinflammation in Multiple System Atrophy: Response to and Cause of α-Synuclein Aggregation," Front Cell Neurosci (2015) 9:437.

Dimauro et al., "Microwave-Assisted Preparation of Fused Bicyclic Heteroaryl Boronates: Application in One-Pot Suzuki Couplings," J Org Chem (2006) 71(10):3959-3962.

Gambuzza et al., "Toll-like Receptors in Alzheimer's Disease: A Therapeutic Perspective," CNS Neurol Disord Drug Targets (2014) 13(9):1542-1558.

Gangloff et al., "Toll-like receptors and immune response in allergic disease," Clin Rev Allergy Immunol (2004) 26(2):115-125.

Harding et al., "Regulation of antigen presentation by *Mycobacterium tuberculosis*: a role for Toll-like receptors," Nat Rev Microbiol (2010) 8(4):296-307.

Hong et al., "Preparation of fluoroionophores based on diamine-salicylaldehyde derivatives," Dyes and Pigments (2008) 94(3):371-379.

Howell et al., "Toll-like Receptors in Hepatitis C Infection: Implications for Pathogenesis and Treatment," J Gastroenterol Hepatol (2013) 28(5):766-776.

Hua et al., "Genomic Profile of Toll-like Receptor Pathways in Traumatically Brain-Injured Mice: Effect of Exogenous Progesterone," J Neuroinflammation (2011) 8:42.

Huang et al., "Roll of Toll like receptors in rheumatoid arthritis," Curr Rheumatol Rep (2009) 11(5):357-364.

Hussein et al., "Toll-like receptor agonists: a patent review (2011-2013)," Expert Opinion on Therapeutic Patents (2014) 24(4):453-470.

Ji et al., "Room-temperature borylation and one-pot two-step borylation/Suzuki-Miyaura cross-coupling reaction of aryl chlorides," RSC Adv (2018) 8:13543-13648.

Kajava et al., "A Network of Hydrogen Bonds on the Surface of TLR2 Controls Ligand Positioning and Cell Signaling," J boil Chem (2010) 285(9):6227-6234.

Kalathur et al., "Huntington's Disease and Its Therapeutic Target Genes: A Global Functional Profile Based on the HD Research Crossroads Database," BMC Neurol (2012) 12:47.

Kim et al., "Neuron-released Oligomeric α-Synuclein Is an Endogenous Agonist of TLR2 for Paracrine Activation of Microglia," Nat Commun (2013) 4:1562.

King et al., "Characterization of the Leukocyte Response in Acute Vocal Fold Injury," PLOS One (2015) 10(10):e0139260.

Koneni et al., "Antiplasmodial activity of novel keto-enamine chalcone-chloroquine based hybrid pharmacophores," Bioorganic & Medicinal Chemistry (2012) 20(9):2971-2981.

Koneni et al., "Synthesis of 3,6-epoxy[1,5 ]dioxocines from 2-hydroxyaromatic benzaldehydes",Tetrahedron Letters (2011) 52(43):5569-5663.

Li et al., "Astroglial TLR9 Antagonism Promotes Chemotaxis and Alternative Activation of Macrophages via Modulation of Astrocyte-Derived Signals: Implications for Spinal Cord Injury," J Neuroinflammation (2020) 17(1):73.

Li et al., "Toll-like Receptor 9 Antagonism Modulates Astrocyte Function and Preserves Proximal Axons Following Spinal Cord Injury," Brain Behav Immun (2019) 80:328-343.

Maatouk et al., "TLR9 Activation via Microglial Glucocorticoid Receptors Contributes to Degeneration of Midbrain Dopamine Neurons," Nat Commun (2018) 9(1):2450.

Maiti et al., "Palladium-catalyzed coupling of functionalized primary and secondary amines with aryl and heteroaryl halides: two ligands suffice in most cases," Chem Sci (2011) 2:57-68.

McAlpine et al., "Excessive endosomal TLR signaling causes inflammatory disease in mice with defective SMCR8-WDR41-C9ORF72 complex function," Proc Natl Acad Sci USA (2018) 115(49):E11523-E11531.

Miller et al., "Toll-like Receptors in Skin," Adv Dermatol (2008) 24:71-87.

Miranda-Hernandez et al., "Role of Toll-Like Receptors in Multiple Sclerosis," Am J Clin Exp Immunol (2013) 2(1):75-93.

Murgueitio et al., "Balancing Inflammation: Computational Design of Small-Molecule Toll-like Receptor Modulators," Trends in Pharmacological Sciences (2017) 38(2):155-168.

O'Rourke et al., "C9orf72 is required for proper macrophage and microglial function in mice," Science (2016) 351(6279):1324-1329.

Pallottie et al., "A Toll-Like Receptor 9 Antagonist Restores Below-Level Glial Glutamate Transporter Expression in the Dorsal Horn Following Spinal Cord Injury," Sci Rep (2018) 8(1):8723.

Prinz et al., "Innate immunity mediated by TLR9 modulates pathogenicity in an animal model of multiple sclerosis," J Clin Invest (2006) 116(2):456-464.

Santegoets et al., "Toll-like Receptors in Rheumatic Diseases: Are We Paying a High Price for Our Defense Against Bugs?" FEBS Lett (2011) 585(23):3660-3666.

Satyanarayana et al., "Highly Efficient Synthesis of Chalcones from Poly Carbonyl Aromatic Compounds Using BF 3 -Et 2 0 via a Regioselective Condensation Reaction," Cell Pharm Bull (2016) 64(6):570-576.

Schmausser et al., "Toll-like Receptors TLR4, TLR5 and TLR9 on Gastric Carcinoma Cells: An Implication for Interaction With Helicobacter Pylori," Int J Med Microbiol (2005) 295(3):179-185.

Shan et al., "Prodrug Strategies Based on Intramolecular Cyclization Reactions," J Pharm Sci (1997) 86(7):765-767.

Smith et al., "Role of Toll-like receptors in Helicobacter pylori infection and immunity," World J Gastrointest Pathophysiol (2014) 5(3):133-146.

Song et al., "Toll-like Receptor Polymorphisms and Vasculitis Susceptibility: Meta-Analysis and Systematic Review," Mol Biol Rep (2013) 40(2):1315-1323.

U.S. Appl. No. 16/322,440, filed Jan. 31, 2019, Wrasidlo et al. (Copy not provided).

Wang et al., "Inactivation of TLR9 by a Suppressive Oligodeoxynucleotides Can Ameliorate the Clinical Signs of EAN," Immunol Invest (2012) 41(2):171-182.

Wang et al., "Three New Resveratrol Derivatives from the Mangrove Endophytic Fungus *Alternaria* sp." Marine Drugs (2014) 12(5):2840-2850.

Zhang et al., "Differential expression of Toll-like receptor pathway genes in chronic rhinosinusitis with or without nasal polyps," Acta Otolaryngol (2013) 133(2):165-173.

(56) References Cited

OTHER PUBLICATIONS

Zhang et al., "Toll-like Receptor (TLR)-mediated Innate Immune Responses in the Control of Hepatitis B Virus (HBV) Infection," Med Microbiol Immunol (2015) 204(1):11-20.
Zuo et al., "Molecular Regulation of Toll-like Receptors in Asthma and COPD," Front Physiol (2015) 6:312.
International Search Report and Written Opinion for PCT/US2020/024728, dated Jun. 2, 2020, 15 pages.
Julakanti et al., "Highly Efficient Synthesis of Chalcones from Poly Carbonyl Aromatic Compounds Using BF 3 -Et 2 0 via a Regioselective Condensation Reaction," The Pharmaceutical Society of Japan Chem Pharm Bull (2016) 570-576.
Sashidhara et al., "Synthesis of 3,6-epoxy[1,5] dioxocines from 2-hydroxyaromatic benzaldehydes",Tetragedrib Letters (2011) 52(43):5659-5663.
Sashidhara et al., "Antiplasmodial activity of novel keto-enamine chalcone-chloroquine based hybrid pharmacophores," Bioorganic& Medicinal Chemistry (2012) 20(9):2971-2981.
Tanaka et a., "Studies on 1-110 5-aminosalicylaldehyde derivatives. II. Reduction of 5-(p-sulfophenylazo) Sal icylaldehyde through poly(5-nitrilosalicylidene) to 5-aminosal icylaldehyde derivatives," Bulletin of the Chemical Society of Japan (1967) 40(7):1724-1726.

\* cited by examiner

COMPOUNDS AND COMPOSITIONS AS MODULATORS OF TLR SIGNALING

CROSS-REFERENCE TO RELATED APPLICATIONS

This application claims priority to U.S. Provisional Application No. 62/824,170, filed Mar. 26, 2019, entitled "COMPOUNDS AS MODULATORS OF TLR2 SIGNALING" and U.S. Provisional Application No. 62/824,189, filed Mar. 26, 2019, entitled "COMPOUNDS AS MODULATORS OF TLR2 SIGNALING" the contents of which are hereby incorporated by reference in their entirety for all purposes.

TECHNICAL FIELD

The present disclosure relates to compounds, pharmaceutical compositions comprising such compounds, and use of such compounds in methods of treatment or in medicaments for treatment of inflammatory diseases and certain neurological disorders that are related to inflammatory signaling processes, including but not limited to misfolded proteins.

BACKGROUND

Toll-like receptors (TLRs) are sentinel receptors of the immune system. When these receptors are activated on cell surfaces, they initiate recruitment of a family of TIR-domain containing adapter proteins, which induce a signaling cascade that ultimately results in cell-type specific inflammatory responses, resulting in the elevation of pro-inflammatory mediators such as IL1, IL6, IL8 and TNFα. Of the different TLR receptors expressed on mammalian cells, TLR2 forms heterodimers with either TLR1 or TLR6 to initiate inflammatory responses with various microbial derived ligands. Among the various bacterial ligands are lipopolysaccharides (LPS), acylated lipopeptides, lipoglycans, peptidoglycans, porins, glycosylphosphatidyl-inosol anchors, and other bacterial cell wall components such as lipoteichoic acid (LTA) from streptococous pneumonia. In addition to the microbial activation of TLR2, it has also been found that abnormal aggregation of neuron released oligomeric proteins such as alpha-synuclein (aSyn) can induce similar inflammatory responses in animal models of neurodegenerative diseases, including Parkinson's disease (PD), dementia with Lewy bodies, multiple system atrophy (MSA) and Alzheimer's disease (AD). See, e.g., Kim et al., Nat. Commun. 2013, 4, 1562.

The ability of TLR2 to induce signaling via heterodimers allows discrimination between various recognition patterns, which allows for the design of ligands with specific inhibition patterns. Kajava et al., J. Biol. Chem. 2010, 285, 6227. Inhibitors that compete primarily with a specific pathological agonist, such as oligomeric pathogenic alpha-synuclein, but do not affect other ligands involved in pro-inflammatory signaling of bacterial or viral infections or non-competitive TIR-Myd88 inhibitors, such as compounds that function indirectly as non-competitive inhibitors of TLR2 though intracllualar TIR-Myd88 inhibition, would therefore be useful as potential therapeutic agents.

The function of Toll-like receptors has been linked to various protein folding, protein dimerization, and inflammatory processes and to related diseases such as Alzheimer's disease (Gambuzza, M. et al., "Toll-like receptors in Alzheimer's disease: a therapeutic perspective," CNS Neurol. Disord. Drug Targets 2014, 13(9), 1542-58), Parkinson's disease and Parkinson's disease with dementia (Beraud, D. et al., "Misfolded α-synuclein and Toll-like receptors: therapeutic targets for Parkinson's disease," Parkinsonism Relat. Disord. 2012, 18 (Suppl. 1), S17-20), fronto-temporal dementia, dementia with Lewy bodies (Lewy body disease), multiple system atrophy (Vieira, B. et al., "Neuroinflammation in multiple system atrophy: Response to and cause of a-synuclein aggregation," Front. Cell Neurosci. 2015, 9, 437), amyotrophic lateral sclerosis (Casula, M. et al., "Toll-like receptor signaling in amyotrophic lateral sclerosis spinal cord tissue," Neuroscience 2011, 179, 233-43), Huntington's disease (Kalathur, R. K. R. et al., "Huntington's disease and its therapeutic target genes: a global functional profile based on the HD Research Crossroads database," BMC Neurology 2012, 12, 47), inflammatory diseases, asthma and chronic obstructive pulmonary disease (COPD) (Zuo, L. et al., "Molecular regulation of Toll-like receptors in asthma and COPD," Front. Physiol. 2016, 6, 312), chronic peptic ulcers (Smith, S., "Roll of Toll-like receptors in Helicobacter pylori infection and immunity," World J. Gastrointest. Pathophysiol. 2014, 5(3), 133-146), tuberculosis (Harding, C. V. et al., "Regulation of antigen presentation by Mycobacterium tuberculosis: a role for Toll-like receptors," Nat. Rev. Microbiol. 2010, 8(4), 296-307), rheumatoid arthritis (Huang, Q.-Q. et al., "Roll of Toll like receptors in rheumatoid arthritis," Curr. Rheumatol. Rep. 2009, 11(5), 357-364), chronic sinusitis (Zhang, Q. et al., "Differential expression of Toll-like receptor pathway genes in chronic rhinosinusitis with or without nasal polyps," Acta Otolaryngol. 2013, 133(2), 165-173), hepatitis (including hepatitis B and C) (Zhang, E. et al., "Toll-like receptor (TLR)-mediated innate immune responses in control of hepatitis B virus (HBV) infection," Med. Microbiol. Immunol. 2015, 204(1), 11-20; Howell, J. et al., "Toll-like receptors in hepatitis C infection: implications for pathogenesis and treatment," J. Gastroenterol. Hepatol. 2013, 28(5), 766-776), gout, lupus, psoriasis, psoriatic arthritis (Santegoets, K. C. M. et al., "Toll-like receptors in rheumatic diseases: are we paying a high price for our defense against bugs?" FEBS Letters 2011, 585(23), 3660-3666), vasculitis, laryngitis, pleurisy (Chen, X. et al., "Engagement of Toll-like receptor 2 on CD4(+) T cells facilitates local immune responses in patients with tuberculous pleurisy," J. Infect. Dis. 2009, 200(3), 399-408), eczema (Miller, L. S., "Toll-like receptors in skin," Adv. Dermatol. 2008, 24, 71-87), gastritis (Schmausser, B. et al., "Toll-like receptors TLR4, TLR5 and TLR9 on gastric carcinoma cells: an implication for interaction with Helicobacter pylon," Int. J. Med. Microbiol. 2005, 295(3), 179-85), vasculitis (Song, G. G. et al., "Toll-like receptor polymorphisms and vasculitis susceptibility: meta-analysis and systematic review," Mol. Biol. Rep. 2013, 40(2), 1315-23), laryngitis (King, S. N. et al., "Characterization of the Leukocyte Response in Acute Vocal Fold Injury," PLoS One, 2015; 10(10): e0139260), allergic reactions (Gangloff, S. C. et al., "Toll-like receptors and immune response in allergic disease," Clin. Rev. Allergy Immunol. 2004, 26(2), 115-25), multiple sclerosis (Miranda-Hernandez, S. et al., "Role of toll-like receptors in multiple sclerosis," Am. J. Clin. Exp. Immunol. 2013, 2(1), 75-93), Crohn's disease (Cario, E., "Toll-like receptors in inflammatory bowel diseases: A decade later," Inflamm. Bowel Dis. 2010, 16(9), 1583-1597), and traumatic brain injury (Hua, F. et al., "Genomic profile of Toll-like receptor pathways in traumatically brain-injured mice: effect of exogenous progesterone," J. Neuroinflammation 2011, 8, 42).

The signal transduction path of TLR2 can be activated either through the external domain (agonist pocket) or by mechanisms involving the cytoplasmic TIR domain that mediates homotypic and heterotypic interactions during signaling. The proteins MyD88 and TIRAP (Mal) are involved in this type of signaling.

Importantly, a conserved proline P681 in TLR2 within the BB loop is (Brown V. et. al. (2006) European Journal of immunology 36, 742-753) is involved in the dimerization mechanism. A mutation in this loop from P681H abolishes recruitment of MyD88 and signaling. Thus compounds that bind in the vicinity of this loop and restrict its movement during the dimerization process would be useful as inhibitors of the activation of TLR2.

TLR9 is a pattern recognition receptor involved in host defense mechanisms. The persistent or inappropriate activation of TLR9 has been implicated in a number of different central nervous system (CNS) and peripheral disorders. Thus inhibition of TLR9, either alone or in combination with TLR2 blockade may provide therapeutic benefit. CNS disorders where TLR9 has been implicated include Parkinson's disease (Maatouk et al., *Nat Commun.* 2018, Jun. 22; 9(1): 2450); Amyotrophic lateral sclerosis (O'Rourke et al., *Science.* 2016, Mar. 18; 351(6279):1324-9); Guillain-Barre syndrome (Wang et al., *Immunol Invest.* 2011, 2012; 41(2): 171-82); spinal cord injury (Li et al., *Brain Behav Immun.* 2019 August; 80:328-343; Li et al., *J. Neuroinflammation.* 2020 Feb. 25; 17(1):73; David et al., *Neurobiol Dis.* 2013 June; 54:194-205; Pallottie et al., *Sci Rep.* 2018 Jun. 7; 8(1):8723) and; multiple sclerosis (Prinz et al., *J Clin Invest.* 2006 February; 116(2):456-64). Peripheral disorders where TLR9 has been implicated are wide ranging and include multiple forms of tissue injury (mcAlpine et al., *Proc Natl Acad Sci USA.* 2018 Dec. 4; 115(49):E11523-E11531), chronic pain (David et al., *Neurobiol Dis.* 2013 June; 54:194-205), and psoriasis (Balak et al., *Clin Immunol.* 2017 January; 174:63-72).

Described herein are compounds that serve as antagonists of TLR2 and/or inhibitors of TLR9 with high potency and selectivity.

SUMMARY

In one aspect, provided herein is a compound of Formula (A):

(A)

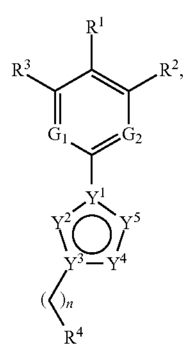

or a tautomer, or a pharmaceutically acceptable salt of any of the foregoing, wherein one of $R^1$ and $R^2$ is —OH and the other is selected from the group consisting of —CN, halogen, —C(O)$R^a$, —CH═N$R^j$, —S(O)$R^b$, —S(O)$_2R^c$, —NHC(O)$R^d$, —NHS(O)$_2R^e$, —$C_1$-$C_6$alkyl-$R^f$, —$C_2$-$C_6$alkenyl-$R^g$, unsubstituted or substituted $C_3$-$C_8$ cycloalkyl, unsubstituted or substituted $C_3$-$C_8$ cycloalkenyl, and unsubstituted or substituted heterocycloalkyl;

$R^a$, $R^b$, $R^c$, and $R^e$ are each independently H, $C_1$-$C_6$alkyl, $C_2$-$C_6$alkenyl, $C_2$-$C_6$alkynyl, $C_1$-$C_6$haloalkyl, unsubstituted or substituted heterocyclyl, unsubstituted or substituted heteroaryl, benzoyl, or styryl;

$R^d$ is H, $C_1$-$C_6$alkyl, $C_2$-$C_6$alkenyl, $C_2$-$C_6$alkynyl, $C_1$-$C_6$haloalkyl, unsubstituted or substituted heterocyclyl, unsubstituted or substituted heteroaryl, or benzoyl;

$R^f$ and $R^g$ are each independently —OH, unsubstituted heteroaryl, —N$R^m R^n$, benzoyl, or styryl;

$R^m$ and $R^n$ are each independently H, $C_1$-$C_6$alkyl, $C_2$-$C_6$alkenyl, $C_2$-$C_6$alkynyl, or unsubstituted or substituted cycloalkyl;

$R^j$ is unsubstituted or substituted heterocyclyl, unsubstituted or substituted heteroaryl, unsubstituted or substituted aryl, —O$R^k$, —NH$R^k$, —NHC(O)$R^k$, —NHS(O)$_2R^k$, or —NHC(NH)NH$R^{aa}$;

$R^{aa}$ is unsubstituted or substituted $C_1$-$C_6$alkyl, unsubstituted or substituted $C_3$-$C_8$cycloalkyl, unsubstituted or substituted aryl, unsubstituted or substituted heterocycloalkyl, or unsubstituted or substituted heteroaryl;

$R^k$ is $C_1$-$C_6$alkyl, $C_2$-$C_6$alkenyl, $C_2$-$C_6$alkynyl, $C_3$-$C_8$cycloalkyl, or aryl, wherein the $C_1$-$C_6$alkyl of $R^k$ is unsubstituted or substituted with heterocyclyl or heteroaryl;

$R^3$ is H, $C_1$-$C_6$alkyl, $C_1$-$C_6$alkoxy, or halogen, wherein the $C_1$-$C_6$alkyl and $C_1$-$C_6$alkoxy of $R^3$ are each independently unsubstituted or substituted with one or more halogen;

wherein when $R^2$ is Br, $R^3$ is H, $C_1$-$C_6$alkyl, $C_1$-$C_6$alkoxy, Cl, F, or I;

$G_1$ and $G_2$ are each independently CH or N, wherein when $G_1$ is N, $G_2$ is CH, and when $G_2$ is N, $G_1$ is CH;

indicates that the ring is aromatic;

$Y^1$ is C or N;

$Y^2$ is CH, N, NH, S, or O;

$Y^3$ is C or N;

$Y^4$ is CH, N, NH, S, or O;

$Y^5$ is $CR^7$, N, NH, S, or O;

wherein no more than one of $Y^1$, $Y^2$, $Y^3$, $Y^4$, and $Y^5$ is S or O and no more than four of $Y^1$, $Y^2$, $Y^3$, $Y^4$, and $Y^5$ are N or NH;

$R^7$ is H or $C_1$-$C_6$alkyl;

n is 0, 1, 2, or 3;

$R^4$ is alkoxy or

indicates that the ring is saturated, partially unsaturated, or fully unsaturated;

$G_3$ is $CH(X_1-R^{6a})$, $C(X_1-R^{6a})$, N, $N(X_1-R^{6a})$, S, or O;
$G_4$ is $CH(X_2-R^{6b})$, $C(X_2-R^{6b})$, N, $N(X_2-R^{6b})$, S, or O;
$G_5$ is $CH(X_3-R^{6c})$, $C(X_3-R^{6c})$, N, $N(X_3-R^{6c})$, S, or O;
$G_6$ is $CH(X_4-R^{6d})$, $C(X_4-R^{6d})$, N, $N(X_4-R^{6d})$, S, or O; and
$G_7$ is N, C, or CH;

$X_1$, $X_2$, $X_3$, and $X_4$ are each independently absent,

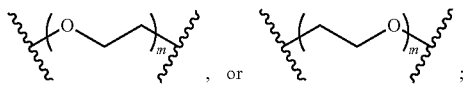, or ;

m is 1-6;

$R^{6a}$, $R^{6b}$, $R^{6c}$, and $R^{6d}$ are each independently hydrogen, $C_1$-$C_6$alkyl, $C_1$-$C_6$alkoxy, halo, —OH, —$NR^pR^q$, aryl, heterocyclyl, heteroaryl, —$C_1$-$C_6$alkyl-heterocyclyl, —OC(O)-heterocyclyl, —$C(O)R^h$, —$S(O)_2NR^{w1}R^{w2}$, —$S(O)_2R^y$, or —$NR^{z1}S(O)_2R^{z2}$, wherein the $C_1$-$C_6$alkyl and $C_1$-$C_6$alkoxy of $R^{6a}$, $R^{6b}$, $R^{6c}$, and $R^{6d}$ are each independently unsubstituted or substituted with one or more groups selected from the group consisting of cycloalkyl and halogen; the aryl and heteroaryl of $R^{6a}$, $R^{6b}$, $R^{6c}$, and $R^{6d}$ are each independently unsubstituted or substituted with one or more groups selected from the group consisting of $C_1$-$C_6$alkyl, $C_1$-$C_6$alkoxy, $C_3$-$C_8$cycloalkyl, —OH, and $C_1$-$C_6$alkyl-OH; and the heterocyclyl, —$C_1$-$C_6$alkyl-heterocyclyl, and —OC(O)-heterocyclyl of $R^{6a}$, $R^{6b}$, $R^{6c}$, and $R^{6d}$ are each independently unsubstituted or substituted with one or more groups selected from the group consisting of $C_1$-$C_6$alkyl, $C_1$-$C_6$alkoxy, halo, —OH, $C_1$-$C_6$alkyl-OH, =O, and =S;

each $R^h$ is independently selected from the group consisting of H, $C_1$-$C_6$alkyl, $C_1$-$C_6$alkoxy, and $C_3$-$C_8$cycloalkyl, and —$NR^rR^s$;

each $R^p$ is independently H or $C_1$-$C_6$alkyl;

each $R^q$ is independently $C_2$-$C_3$alkyl, —$C(O)R^t$, —$C(O)OR^u$, —$C(O)NR^v$;

each $R^r$, $R^s$, $R^{w1}$, and $R^{z1}$ is independently selected from H and $C_1$-$C_6$alkyl; and each $R^t$, $R^u$, $R^v$, $R^{w2}$, $R^y$, and $R^{z2}$ is independently selected from H, $C_1$-$C_6$alkyl, unsubstituted or substituted $C_3$-$C_8$cycloalkyl, and unsubstituted or substituted heterocyclyl;

or $G_5$ is $CH(X_3-R^{6c})$ or $C(X_3-R^{6c})$, $G_6$ is $CH(X_4-R^{6d})$ or $C(X_4-R^{6d})$, and $R^{6c}$ and $R^{6d}$ are taken together with the carbon atoms to which they are attached to form a 6-membered aryl, a 6-membered heterocyclyl, or a 6-membered heteroaryl ring; wherein the 6-membered aryl, 6-membered heterocyclyl, and 6-membered heteroaryl rings are each independently unsubstituted or substituted.

In some embodiments of Formula (A),
$Y^1$ is C or N;
$Y^2$ is CH, N, NH, S, or O;
$Y^3$ is C or N;
$Y^4$ is CH, N, NH, S, or O;
$Y^5$ is CH, N, NH, S, or O;

wherein no more than one of $Y^1$, $Y^2$, $Y^3$, $Y^4$, and $Y^5$ is S or O and no more than three of $Y^1$, $Y^2$, $Y^3$, $Y^4$, and $Y^5$ are N or NH.

In some embodiments of Formula (A), one of $R^1$ and $R^2$ is —OH and the other is selected from the group consisting of —CN, halogen, —$C(O)R^a$, —CH=$NR^j$, —$S(O)R^b$, —$S(O)_2R^c$, —$NHC(O)R^d$, —$NHS(O)_2R^e$, —$C_1$-$C_6$alkyl-$R^f$, —$C_2$-$C_6$alkenyl-$R^g$, unsubstituted or substituted $C_3$-$C_8$ cycloalkyl, unsubstituted or substituted $C_3$-$C_8$ cycloalkenyl, and unsubstituted or substituted heterocycloalkyl; $R^a$, $R^b$, $R^c$, and $R^e$ are each independently H, $C_1$-$C_6$alkyl, $C_2$-$C_6$alkenyl, $C_2$-$C_6$alkynyl, $C_1$-$C_6$haloalkyl, unsubstituted or substituted heterocyclyl, unsubstituted or substituted heteroaryl, benzoyl, or styryl; $R^d$ is H, $C_1$-$C_6$alkyl, $C_2$-$C_6$alkenyl, $C_2$-$C_6$alkynyl, $C_1$-$C_6$haloalkyl, unsubstituted or substituted heterocyclyl, unsubstituted or substituted heteroaryl, or benzoyl; $R^f$ and $R^g$ are each independently —OH, unsubstituted heteroaryl, —$NR^mR^n$, benzoyl, or styryl; $R^m$ and $R^n$ are each independently H, $C_1$-$C_6$alkyl, $C_2$-$C_6$alkenyl, $C_2$-$C_6$alkynyl, or unsubstituted or substituted cycloalkyl; $R^j$ is unsubstituted or substituted heterocyclyl, unsubstituted or substituted heteroaryl, unsubstituted or substituted aryl, —$OR^k$, —$NHR^k$, —$NHC(O)R^k$, —$NHS(O)_2R^k$, or —$NHC(NH)NH_2$; $R^k$ is $C_1$-$C_6$alkyl, $C_2$-$C_6$alkenyl, $C_2$-$C_6$alkynyl, $C_3$-$C_8$cycloalkyl, or aryl, wherein the $C_1$-$C_6$alkyl of $R^k$ is unsubstituted or substituted with heterocyclyl or heteroaryl.

In one aspect, provided herein is a compound of Formula (B):

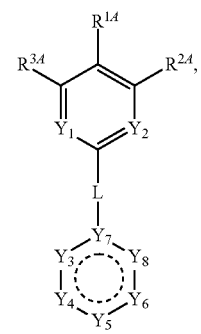

(B)

or a tautomer, or a pharmaceutically acceptable salt of any of the foregoing, wherein L is selected from the group consisting of —C≡C—, *—NHC(O)—, *—C(O)NH—, —NHC(O)NH—, *—NHS(O)$_2$—, *—NHS(O)(=NH)—, *—S(O)(=NH)NH—, *—S(O)$_2$NH—, *—S(O)NHNH—, *—NHNHS(O)—, *—C(O)NHNH—, *—NHNHC(O)—, *—NHC(O)O—, and *—OC(O)NH—, wherein * represents the point of attachment to $Y_7$;

$Y_1$ and $Y_2$ are each independently $CR^x$, or N;

$R^x$ is hydrogen or halogen;

when L is —C≡C—, one of $R^{1A}$ and $R^{2A}$ is —OH and the other is selected from the group consisting of —$C(O)R^{a1}$, —CH=$NR^{j1}$, —$S(O)R^{b1}$, —$S(O)_2R^{c1}$, —$NHC(O)R^{d1}$, —$NHS(O)_2R^{e1}$, —$C_1$-$C_6$alkyl-$R^{f1}$, —$C_2$-$C_6$alkenyl-$R^{g1}$, $C_3$-$C_8$ cycloalkyl, $C_3$-$C_8$ cycloalkenyl, and 5- or 6-membered heterocycloalkyl, wherein the $C_3$-$C_8$ cycloalkyl and $C_3$-$C_8$ cycloalkenyl are each independently unsubstituted or substituted with one or more =O, and the 5- or 6-membered heterocycloalkyl is unsubstituted or substituted with one or more substituents independently selected from the group consisting of $C_1$-$C_6$alkyl, $C_3$-$C_8$cycloalkyl, =O, and —C(O)O—$C_1$-$C_6$alkyl;

when L is *—NHC(O)—, *—C(O)NH—, —NHC(O)NH—, *—NHS(O)$_2$—, *—S(O)$_2$NH—, *—S(O)NHNH—, *—C(O)NHNH—, or *—NHC(O)O—, one of $R^{1A}$ and $R^{2A}$ is —OH and the other is selected from the group consisting of —C(O)H, —CH=$NR^{j1}$, and

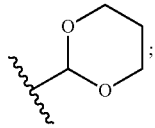 [SMILES: *C1OCCCO1]
;

$R^{a1}$ is H, $C_1$-$C_6$alkyl, $C_2$-$C_6$alkenyl, $C_2$-$C_6$alkynyl, $C_1$-$C_6$haloalkyl, 3- to 6-membered heterocyclyl, or 5- to 10-membered heteroaryl, or benzoyl, wherein the 3- to 10-membered heterocyclyl of $R^{a1}$ is unsubstituted or substituted with one or more groups independently selected from the group consisting of $C_1$-$C_6$alkyl, $C_3$-$C_8$ cycloalkyl, =O, and —C(O)O—$C_1$-$C_6$alkyl, and the 5- to 10-membered heteroaryl of $R^{a1}$ is unsubstituted or substituted with one or more groups independently selected from the group consisting of $C_1$-$C_6$alkyl, $C_3$-$C_8$cycloalkyl, and —C(O)O—$C_1$-$C_6$alkyl;

$R^{b1}$, $R^{c1}$, $R^{d1}$, and $R^{e1}$ are each independently H, $C_1$-$C_6$alkyl, $C_2$-$C_6$alkenyl, $C_2$-$C_6$alkynyl, $C_1$-$C_6$haloalkyl, 3- to 10-membered heterocyclyl, 5- to 10-membered heteroaryl, benzoyl, or styryl, wherein the 3- to 10-membered heterocyclyl and 5- to 10-membered heteroaryl of $R^{b1}$, $R^{c1}$, $R^{d1}$, and $R^{e1}$ are each independently selected from the group consisting of $C_1$-$C_6$alkyl, $C_3$-$C_8$cycloalkyl, and —C(O)O—$C_1$-$C_6$alkyl;

$R^{f1}$ and $R^{g1}$ are each independently —OH, unsubstituted 5- to 6-membered heteroaryl, —$NR^{m1}R^{n1}$, benzoyl, or styryl;

$R^{m1}$ is $C_3$-$C_8$ cycloalkyl, unsubstituted or substituted with one or more groups selected from $C_1$-$C_6$alkyl and halo;

$R^{n1}$ is H, $C_1$-$C_6$alkyl, $C_2$-$C_6$alkenyl, or $C_2$-$C_6$alkynyl;

$R^{j1}$ is $C_1$-$C_6$alkyl, 5- to 6-membered heterocyclyl, 5- to 6-membered heteroaryl, 6- to 12-membered aryl, —$OR^{k1}$, —$NHR^{k1}$, —$N(C_1$-$C_6$alkyl)$R^{k1}$, —NHC(O)$R^{k1}$, —NHS(O)$_2R^{k1}$, or —NHC(NH)$NHR^{bb}$, wherein the 5- to 6-membered heterocyclyl of $R^{j1}$ is unsubstituted or substituted with one or more substituents selected from the group consisting of $C_1$-$C_6$alkyl, $C_3$-$C_8$cycloalkyl, =O, —C(O)NH—$C_1$-$C_6$alkyl, and —C(O)O—$C_1$-$C_6$alkyl, and the 5- to 6-membered heteroaryl and 6- to 12-membered aryl of $R^{j1}$ are each independently unsubstituted or substituted with one or more substituents selected from the group consisting of $C_1$-$C_6$alkyl, $C_3$-$C_8$cycloalkyl, and —C(O)O—$C_1$-$C_6$alkyl;

$R^{bb}$ is unsubstituted or substituted $C_1$-$C_6$alkyl, unsubstituted or substituted $C_3$-$C_8$cycloalkyl, unsubstituted or substituted aryl, unsubstituted or substituted heterocycloalkyl, or unsubstituted or substituted heteroaryl;

each $R^{k1}$ is independently $C_1$-$C_6$alkyl, $C_2$-$C_6$alkenyl, $C_2$-$C_6$alkynyl, $C_3$-$C_8$cycloalkyl, or 6- to 12-membered aryl, wherein the $C_1$-$C_6$alkyl of $R^{k1}$ is unsubstituted or substituted with a 5- to 6-membered heterocyclyl or a 5- to 6-membered heteroaryl;

$R^{3A}$ is H, $C_1$-$C_6$alkyl, $C_1$-$C_6$alkoxy, or halogen, wherein the $C_1$-$C_6$alkyl and $C_1$-$C_6$alkoxy of $R^{3A}$ are each independently unsubstituted or substituted with one or more halogen;

indicates that the ring is saturated, partially unsaturated, or fully unsaturated;

$Y_3$ is CH($X_{1A}$—$R^{6a1}$), C($X_{1A}$—$R^{6a1}$), N, N($X_{1A}$—$R^{6a1}$), S, or O;

$Y_4$ is CH($X_{2A}$—$R^{6b1}$), C($X_{2A}$—$R^{6b1}$), N, N($X_{2A}$—$R^{6b1}$), S, or O;

$Y_5$ is CH($X_{3A}$—$R^{6c1}$), C($X_{3A}$—$R^{6c1}$), N, N($X_{3A}$—$R^{6c1}$), S, or O;

$Y_6$ is CH($X_{4A}$—$R^{6d1}$), C($X_{4A}$—$R^{6d1}$), N, N($X_{4A}$—$R^{6d1}$), S, or O;

$Y_7$ is N, C, or CH; and $Y_8$ is N, NH, C, or CH;

$X_{1A}$, $X_{2A}$, $X_{3A}$, and $X_{4A}$ are each independently absent,

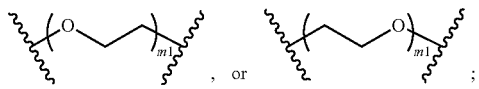
;

m1 is 1-6;

$R^{6a1}$, $R^{6b1}$, $R^{6c1}$, and $R^{6d1}$ are each independently hydrogen, $C_1$-$C_6$alkyl, $C_1$-$C_6$alkoxy, halo, —OH, —$NR^{p1}R^{q1}$, $C_6$-$C_{12}$ aryl, 3- to 10-membered heterocyclyl, 5- to 10-membered heteroaryl, —$C_1$-$C_6$alkyl-5- to 6-membered heterocyclyl, —OC(O)-5- to 6-membered heterocyclyl, —C(O)$R^{h1}$, —S(O)$_2NR^{w1a}R^{w2}$a, —S(O)$_2R^{y1}$, —$NR^{z1a}$S(O)$_2R^{z2a}$, or —N(CH$_3$)CH$_2$C(CH$_3$)$_3$, wherein the $C_1$-$C_6$alkyl and $C_1$-$C_6$alkoxy of $R^{6a1}$, $R^{6b1}$, $R^{6c1}$, and $R^{6d1}$ are each independently unsubstituted or substituted with one or more groups selected from the group consisting of $C_3$-$C_8$ cycloalkyl and halogen; the $C_6$-$C_{12}$ aryl and 5- to 10-membered heteroaryl of $R^{6a1}$, $R^{6b1}$, $R^{6c1}$, and $R^{6d1}$ are each independently unsubstituted or substituted with one or more groups selected from the group consisting of $C_1$-$C_6$alkyl, $C_1$-$C_6$alkoxy, —OH, and $C_1$-$C_6$alkyl-OH; and the 3- to 10-membered heterocyclyl, —$C_1$-$C_6$alkyl-5- to 6-membered heterocyclyl, and —OC(O)-5- to 6-membered heterocyclyl of $R^{6a1}$, $R^{6b1}$, $R^{6c1}$, and $R^{6d1}$ are each independently unsubstituted or substituted with one or more groups selected from the group consisting of $C_1$-$C_6$alkyl, $C_1$-$C_6$alkoxy, —OH, $C_1$-$C_6$alkyl-OH, =O, =S, halo, $C_3$-$C_8$cycloalkyl, —C(O)NH—$C_3$-$C_8$cycloalkyl, $C_6$-$C_{12}$ aryl, and 5- to 6-membered heterocyclyl;

each $R^{h1}$ is independently selected from the group consisting of H, $C_1$-$C_6$alkyl, $C_1$-$C_6$alkoxy, $C_3$-$C_8$cycloalkyl, and —$NR^{r1}R^{s1}$;

each $R^{p1}$ is independently H or $C_1$-$C_6$alkyl;

each $R^{q1}$ is independently $C_2$-$C_3$alkyl, —C(O)$R^{t1}$, —C(O)$OR^{u1}$, or —C(O)$NR^{v1}$;

each $R^{r1}$, $R^{s1}$, $R^{w1a}$ and $R^{z1a}$ is independently selected from H and $C_1$-$C_6$alkyl; and each $R^{t1}$, $R^{u1}$, $R^{v1}$, $R^{w2a}$, $R^{y1}$, and $R^{z2a}$ is independently selected from H, $C_1$-$C_6$alkyl, unsubstituted or substituted $C_3$-$C_8$cycloalkyl, and unsubstituted or substituted heterocyclyl;

or $Y_5$ is $CH(X_{3A}$—$R^{6c1})$ or $C(X_{3A}$—$R^{6c1})$, $Y_6$ is $CH(X_{4A}$—$R^{6d1})$ or $C(X_{4A}$—$R^{6d1})$, and $R^{6c1}$ and $R^{6d1}$ are taken together with the carbon atoms to which they are attached to form a 6-membered aryl, a 6-membered heterocyclyl, or a 6-membered heteroaryl ring; wherein the 6-membered aryl, 6-membered heterocyclyl, and 6-membered heteroaryl rings are each independently unsubstituted or substituted with one or more groups selected from the group consisting of $C_1$-$C_6$alkyl and —C(O)O—$C_1$-$C_6$alkyl;

wherein no more than one of $R^{6a1}$, $R^{6b1}$, $R^{6c1}$, and $R^{6d1}$ is $C_1$-$C_6$alkoxy or —OH; and (1) when L is —C≡C—, $Y_1$ and $Y_2$ are each CH, one of $R^{1A}$ and $R^{2A}$ is —C(O)H, —CH$_2$OH, —C(O)CH$_3$ or —NHC(O)CH$_3$, and $R^{3A}$ is H,

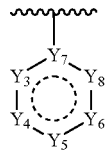

is other than cyclohexyl, phenyl, pyridyl, or naphthyl, and $R^{6c1}$ is hydrogen, $C_2$-$C_3$alkyl, $C_2$-$C_5$alkoxy, Br, Cl, I, —NR$^{p1}$R$^{q1}$, $C_6$-$C_{12}$ aryl, 3- to 10-membered heterocyclyl, 5- to 10-membered heteroaryl, —$C_1$-$C_6$alkyl-5- to 6-membered heterocyclyl, —OC(O)-5- to 6-membered heterocyclyl, —C(O)R$^{h1}$, —S(O)$_2$NR$^{w1a}$R$^{w2a}$, —S(O)$_2$R$^{y1}$, or —NR$^{z1a}$S(O)$_2$R$^{z2a}$, and each R$^{h1}$ is independently selected from the group consisting of $C_1$-$C_6$alkyl, $C_1$-$C_6$alkoxy, $C_3$-$C_8$cycloalkyl, and —NR$^{r1}$R$^{s1}$;

(2) when L is —C≡C—, $Y_1$ and $Y_2$ are each CH, one of $R^{1A}$ and $R^{2A}$ is —C(O)H, and $R^{3A}$ is —CH$_3$, t-Bu, or $C_2$-$C_3$alkoxy,

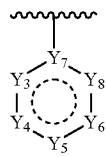

is other than phenyl and pyridyl, $R^{b1}$ and $R^{d1}$ are other than

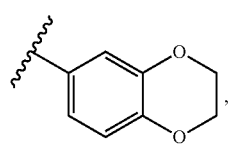 [SMILES: *c1ccc2c(c1)OCCO2]

and $R^{6c1}$ is other than —OH;

(3) when L is —C≡C—, $Y_1$ and $Y_2$ are each CH, one of $R^{1A}$ and $R^{2A}$ is piperidinyl, pyrrolidinyl, pyrrolidinone, piperazinyl, morpholinyl, or thiadiazolidinone 1,1-dioxide, and $R^{3A}$ is H,

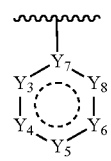

is other than naphthyl, and $R^{6c1}$ is other than fluoro;

(4) when L is *—NHS(O)$_2$— or *—S(O)$_2$NH—, $Y_1$ and $Y_2$ are each CH, one of $R^{1A}$ and $R^{2A}$ is —C(O)H, —CH=NR$^{j1}$, or

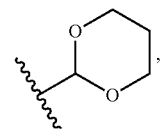

and $R^{3A}$ is H or Br,

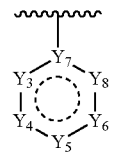

is other than phenyl, and $R^{6a1}$, $R^{6b1}$, $R^{6c1}$, and $R^{6d1}$ are each independently hydrogen, $C_2$-$C_6$alkyl, $C_1$-$C_6$alkoxy, —OH, —NR$^{p1}$R$^{q1}$, $C_6$-$C_{12}$ aryl, 3- to 10-membered heterocyclyl, 5- to 10-membered heteroaryl, —$C_1$-$C_6$alkyl-5- to 6-membered heterocyclyl, —OC(O)-5- to 6-membered heterocyclyl, —C(O)R$^{h1}$, —S(O)$_2$NR$^{w1a}$R$^{w2a}$, —S(O)$_2$R$^{y1}$, or —NR$^{z1a}$S(O)$_2$R$^{z2a}$;

(5) when L is *—C(O)NH— or *—NHC(O)—, $Y_1$ and $Y_2$ are each CH, one of $R^{1A}$ and $R^{2A}$ is —C(O)H, and $R^{3A}$ is H or Cl,

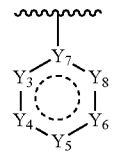

is other than phenyl, and $R^{6a1}$ is other than —CF$_3$; and (6) when L is —NHC(O)NH—, $Y_1$ and $Y_2$ are each CH, one of $R^{1A}$ and $R^{2A}$ is —C(O)H or

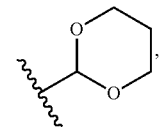 [SMILES: *C1OCCCO1]

and $R^{3A}$ is H or Cl,

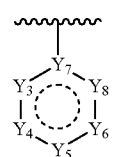

is other than cyclohexyl, and $R^{6c1}$ is other than chloro.

In some embodiments of Formula (B), $R^{j1}$ is $C_1$-$C_6$alkyl, 5- to 6-membered heterocyclyl, 5- to 6-membered heteroaryl, 6- to 12-membered aryl, —$OR^{k1}$, —$NHR^{k1}$, —$N(C_1$-$C_6$alkyl$)R^{k1}$, —$NHC(O)R^{k1}$, —$NHS(O)_2R^{k1}$, or —$NHC(NH)NH_2$, wherein the 5- to 6-membered heterocyclyl of $R^{j1}$ is unsubstituted or substituted with one or more substituents selected from the group consisting of $C_1$-$C_6$alkyl, $C_3$-$C_8$cycloalkyl, =O, —$C(O)NH$—$C_1$-$C_6$alkyl, and —$C(O)O$—$C_1$-$C_6$alkyl, and the 5- to 6-membered heteroaryl and 6- to 12-membered aryl of $R^{j1}$ are each independently unsubstituted or substituted with one or more substituents selected from the group consisting of $C_1$-$C_6$alkyl, $C_3$-$C_8$cycloalkyl, and —$C(O)O$—$C_1$-$C_6$alkyl; and $R^{6a1}$, $R^{6b1}$, $R^{6c1}$, and $R^{6d1}$ are each independently hydrogen, $C_1$-$C_6$alkyl, $C_1$-$C_6$alkoxy, halo, —OH, —$NR^{p1}R^{q1}$, $C_6$-$C_{12}$ aryl, 3- to 10-membered heterocyclyl, 5- to 10-membered heteroaryl, —$C_1$-$C_6$alkyl-5- to 6-membered heterocyclyl, —$OC(O)$-5- to 6-membered heterocyclyl, —$C(O)R^{h1}$, —$S(O)_2NR^{w1a}R^{w2a}$, —$S(O)_2R^{y1}$, or —$NR^{z1a}S(O)_2R^{z2a}$, wherein the $C_1$-$C_6$alkyl and $C_1$-$C_6$alkoxy of $R^{6a1}$, $R^{6b1}$, $R^{6c1}$, and $R^{6d1}$ are each independently unsubstituted or substituted with one or more groups selected from the group consisting of $C_3$-$C_8$ cycloalkyl and halogen; the $C_6$-$C_{12}$ aryl and 5- to 10-membered heteroaryl of $R^{6a1}$, $R^{6b1}$, $R^{6c1}$, and $R^{6d1}$ are each independently unsubstituted or substituted with one or more groups selected from the group consisting of $C_1$-$C_6$alkyl, $C_1$-$C_6$alkoxy, —OH, and $C_1$-$C_6$alkyl-OH; and the 3- to 10-membered heterocyclyl, —$C_1$-$C_6$alkyl-5- to 6-membered heterocyclyl, and —$OC(O)$-5- to 6-membered heterocyclyl of $R^{6a1}$, $R^{6b1}$, $R^{6c1}$, and $R^{6d1}$ are each independently unsubstituted or substituted with one or more groups selected from the group consisting of $C_1$-$C_6$alkyl, $C_1$-$C_6$alkoxy, —OH, $C_1$-$C_6$alkyl-OH, =O, and =S.

In a further aspect, provided herein are pharmaceutical compositions comprising at least one compound of Formula (A) or Formula (B), such as a compound of Table 1A or Table 1B, or a tautomer thereof, or a pharmaceutically acceptable salt of any of the foregoing, optionally further comprising a pharmaceutically acceptable excipient.

In another aspect, provided herein is a method of treating a disease or condition associated with TLR2 heterodimerization, comprising administering to a subject in need of such treatment an effective amount of at least one compound of Formula (A) or Formula (B), such as a compound of Table 1A or Table 1B, or a tautomer thereof, or a pharmaceutically acceptable salt of any of the foregoing, and/or a pharmaceutical composition comprising at least one compound of Formula (A) or Formula (B), such as a compound of Table 1A or Table 1B. In some embodiments of any of the methods described herein, the disease or condition is selected from the group consisting of: Alzheimer's disease, Parkinson's disease, fronto-temporal dementia, dementia with Lewy bodies (Lewy body disease), Parkinson's disease with dementia, multiple system atrophy, amyotrophic lateral sclerosis, Huntington's disease, Progressive Supranuclear Palsy (PSP), Niemann-Pick disease type C, inflammatory diseases, asthma, chronic obstructive pulmonary disease (COPD), chronic peptic ulcers, irritable bowel disease, tuberculosis, rheumatoid arthritis, osteoarthritis, chronic sinusitis, hepatitis, hepatitis B, hepatitis C, gout, lupus, pleurisy, eczema, gastritis, psoriasis, psoriatic arthritis, vasculitis, laryngitis, allergic reactions, multiple sclerosis, Crohn's disease, traumatic brain injury, CIDP (chronic inflammatory demyelinating polyneuropathy), stroke, ischemic heart disease, atopic dermatitis, acne vulgaris, rosacea, non-alcoholic fatty liver disease, non-alcoholic steatohepatisis, corneal wounds, corneal disorders, corneal HSV, Stargardt disease (Juvenile macular degeneration), age-related macular degeneration, sepsis, diabetic wounds, herpes simplex virus, and anti-fungal, anti-bacterial, anitviral and antitumor diseases or conditions.

In yet another aspect, provided herein is a method of interfering with the heterodimerization of TLR2 in a cell, or modulating, preventing, slowing, reversing, or inhibiting TLR2 heterodimerization in a cell, comprising contacting the cell with an effective amount of at least one compound of Formula (A) or Formula (B), such as a compound of Table 1A or Table 1B, or a tautomer thereof, or a pharmaceutically acceptable salt of any of the foregoing, and/or with at least one pharmaceutical composition comprising at least one compound of Formula (A) or Formula (B), such as a compound of Table 1A or Table 1B, wherein the contacting is in vitro, ex vivo, or in vivo.

In another aspect, provided herein is a method of treating a disease or condition associated with inhibition of TLR9, comprising administering to a subject in need of such treatment an effective amount of at least one compound of Formula (A) or Formula (B), such as a compound of Table 1A or Table 1B, or a tautomer thereof, or a pharmaceutically acceptable salt of any of the foregoing, and/or a pharmaceutical composition comprising at least one compound of Formula (A) or Formula (B), such as a compound of Table 1A or Table 1B. In some embodiments of any of the methods described herein, the disease or condition is a central nervous system (CNS) or peripheral disorder. In some embodiments, the CNS disorder is Parkinson's disease, Amyotrophic lateral sclerosis, Guillain-Barre syndrome, spinal cord injury, or multiple sclerosis. In some embodiments, the peripheral disorders include multiple forms of tissue injury, chronic pain, and psoriasis.

Additional embodiments, features, and advantages of the present disclosure will be apparent from the following detailed description and through practice of the present disclosure.

For the sake of brevity, the disclosures of publications cited in this specification, including patents, are herein incorporated by reference.

DETAILED DESCRIPTION

The present disclosure relates to compounds, pharmaceutical compositions comprising such compounds, and use of such compounds in methods of treatment or in medicaments for treatment of inflammatory diseases and certain neurological disorders that are related to inflammatory signaling processes, including but not limited to misfolded proteins.

It is to be understood that this disclosure is not limited to particular embodiments described, as such may, of course, vary. It is also to be understood that the terminology used herein is for the purpose of describing particular embodiments only, and is not intended to be limiting.

Unless defined otherwise, all technical and scientific terms used herein have the same meaning as is commonly understood by one of ordinary skill in the art to which this disclosure belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

As used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As used herein, the terms "including," "containing," and "comprising" are used in their open, non-limiting sense.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

The nomenclature used herein to name the subject compounds is illustrated in the Examples herein. This nomenclature has generally been derived using the commercially-available ChemBioDraw Ultra software, Version 14.0.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination. All combinations of the embodiments pertaining to the chemical groups represented by the variables are specifically embraced by the present disclosure and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present disclosure and are disclosed herein just as if each and every such sub-combination of chemical groups was individually and explicitly disclosed herein.

Compounds

Compounds and salts thereof (such as pharmaceutically acceptable salts) are detailed herein, including in the Summary and in the appended claims. Also provided are the use of all of the compounds described herein, including any and all stereoisomers, including geometric isomers (e.g., cis/trans isomers or E/Z isomers), enantiomers, diastereomers, and mixtures thereof in any ratio including racemic mixtures, salts and solvates of the compounds described herein, as well as methods of making such compounds. Any compound described herein may also be referred to as a drug.

In one aspect, provided are compounds of Formula (A):

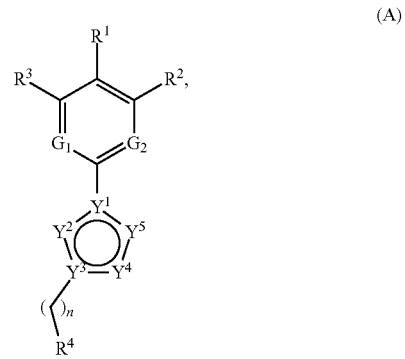

or a tautomer, or a pharmaceutically acceptable salt of any of the foregoing,
wherein
one of $R^1$ and $R^2$ is —OH and the other is selected from the group consisting of —CN, halogen, —C(O)$R^a$, —CH=N$R^j$, —S(O)$R^b$, —S(O)$_2R^c$, —NHC(O)$R^d$, —NHS(O)$_2R^e$, —$C_1$-$C_6$alkyl-$R^f$, —$C_2$-$C_6$alkenyl-$R^g$, unsubstituted or substituted $C_3$-$C_8$ cycloalkyl, unsubstituted or substituted $C_3$-$C_8$ cycloalkenyl, and unsubstituted or substituted heterocycloalkyl;

$R^a$, $R^b$, $R^c$, and $R^e$ are each independently H, $C_1$-$C_6$alkyl, $C_2$-$C_6$alkenyl, $C_2$-$C_6$alkynyl, $C_1$-$C_6$haloalkyl, unsubstituted or substituted heterocyclyl, unsubstituted or substituted heteroaryl, benzoyl, or styryl;

$R^d$ is H, $C_1$-$C_6$alkyl, $C_2$-$C_6$alkenyl, $C_2$-$C_6$alkynyl, $C_1$-$C_6$haloalkyl, unsubstituted or substituted heterocyclyl, unsubstituted or substituted heteroaryl, or benzoyl;

$R^f$ and $R^g$ are each independently —OH, unsubstituted heteroaryl, —N$R^mR^n$, benzoyl, or styryl;

$R^m$ and $R^n$ are each independently H, $C_1$-$C_6$alkyl, $C_2$-$C_6$alkenyl, $C_2$-$C_6$alkynyl, or unsubstituted or substituted cycloalkyl;

$R^j$ is unsubstituted or substituted heterocyclyl, unsubstituted or substituted heteroaryl, unsubstituted or substituted aryl, —O$R^k$, —NH$R^k$, —NHC(O)$R^k$, —NHS(O)$_2R^k$, or —NHC(NH)NH$R^{aa}$;

$R^{aa}$ is unsubstituted or substituted $C_1$-$C_6$alkyl, unsubstituted or substituted $C_3$-$C_8$cycloalkyl, unsubstituted or substituted aryl, unsubstituted or substituted heterocycloalkyl, or unsubstituted or substituted heteroaryl;

$R^k$ is $C_1$-$C_6$alkyl, $C_2$-$C_6$alkenyl, $C_2$-$C_6$alkynyl, $C_3$-$C_8$cycloalkyl, or aryl, wherein the $C_1$-$C_6$alkyl of $R^k$ is unsubstituted or substituted with heterocyclyl or heteroaryl;

$R^3$ is H, $C_1$-$C_6$alkyl, $C_1$-$C_6$alkoxy, or halogen, wherein the $C_1$-$C_6$alkyl and $C_1$-$C_6$alkoxy of $R^3$ are each independently unsubstituted or substituted with one or more halogen;

wherein when $R^2$ is Br, $R^3$ is H, $C_1$-$C_6$alkyl, $C_1$-$C_6$alkoxy, Cl, F, or I;

$G_1$ and $G_2$ are each independently CH or N, wherein when $G_1$ is N, $G_2$ is CH, and when $G_2$ is N, $G_1$ is CH;

indicates that the ring is aromatic;
$Y^1$ is C or N;
$Y^2$ is CH, N, NH, S, or O;
$Y^3$ is C or N;
$Y^4$ is CH, N, NH, S, or O;
$Y^5$ is $CR^7$, N, NH, S, or O;
wherein no more than one of $Y^1$, $Y^2$, $Y^3$, $Y^4$, and $Y^5$ is S or O and no more than four of $Y^1$, $Y^2$, $Y^3$, $Y^4$, and $Y^5$ are N or NH;
$R^7$ is H or $C_1$-$C_6$alkyl;
n is 0, 1, 2, or 3;
$R^4$ is alkoxy or

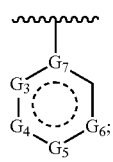

indicates that the ring is saturated, partially unsaturated, or fully unsaturated;
$G_3$ is $CH(X_1-R^{6a})$, $C(X_1-R^{6a})$, N, $N(X_1-R^{6a})$, S, or O;
$G_4$ is $CH(X_2-R^{6b})$, $C(X_2-R^{6b})$, N, $N(X_2-R^{6b})$, S, or O;
$G_5$ is $CH(X_3-R^{6c})$, $C(X_3-R^{6c})$, N, $N(X_3-R^{6c})$, S, or O;
$G_6$ is $CH(X_4-R^{6d})$, $C(X_4-R^{6d})$, N, $N(X_4-R^{6d})$, S, or O; and
$G_7$ is N, C, or CH;
$X_1$, $X_2$, $X_3$, and $X_4$ are each independently absent,

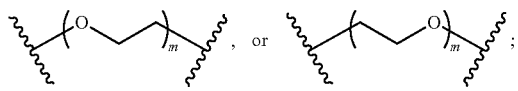

m is 1-6;
$R^{6a}$, $R^{6b}$, $R^{6c}$, and $R^{6d}$ are each independently hydrogen, $C_1$-$C_6$alkyl, $C_1$-$C_6$alkoxy, halo, —OH, —$NR^pR^q$, aryl, heterocyclyl, heteroaryl, —$C_1$-$C_6$alkyl-heterocyclyl, —OC(O)-heterocyclyl, —C(O)$R^h$, —S(O)$_2NR^{w1}R^{w2}$, —S(O)$_2R^y$, or —$NR^{z1}S(O)_2R^{z2}$, wherein the $C_1$-$C_6$alkyl and $C_1$-$C_6$alkoxy of $R^{6a}$, $R^{6b}$, $R^{6c}$, and $R^{6d}$ are each independently unsubstituted or substituted with one or more groups selected from the group consisting of cycloalkyl and halogen; the aryl and heteroaryl of $R^{6a}$, $R^{6b}$, $R^{6c}$, and $R^{6d}$ are each independently unsubstituted or substituted with one or more groups selected from the group consisting of $C_1$-$C_6$alkyl, $C_1$-$C_6$alkoxy, $C_3$-$C_8$cycloalkyl, —OH, and $C_1$-$C_6$alkyl-OH; and the heterocyclyl, —$C_1$-$C_6$alkyl-heterocyclyl, and —OC(O)-heterocyclyl of $R^{6a}$, $R^{6b}$, $R^{6c}$, and $R^{6d}$ are each independently unsubstituted or substituted with one or more groups selected from the group consisting of $C_1$-$C_6$alkyl, $C_1$-$C_6$alkoxy, halo, —OH, $C_1$-$C_6$alkyl-OH, =O, and =S;

each $R^h$ is independently selected from the group consisting of H, $C_1$-$C_6$alkyl, $C_1$-$C_6$alkoxy, and $C_3$-$C_8$cycloalkyl, and —$NR^rR^s$;
each $R^p$ is independently H or $C_1$-$C_6$alkyl;
each $R^q$ is independently $C_2$-$C_3$alkyl, —C(O)$R^t$, —C(O)O$R^u$, —C(O)$NR^v$;
each $R^r$, $R^s$, $R^{w1}$, and $R^{z1}$ is independently selected from H and $C_1$-$C_6$alkyl; and
each $R^t$, $R^u$, $R^v$, $R^{w2}$, $R^y$, and $R^{z2}$ is independently selected from H, $C_1$-$C_6$alkyl, unsubstituted or substituted $C_3$-$C_8$cycloalkyl, and unsubstituted or substituted heterocyclyl;

or $G_5$ is $CH(X_3-R^{6c})$ or $C(X_3-R^{6c})$, $G_6$ is $CH(X_4-R^{6d})$ or $C(X_4-R^{6d})$, and $R^{6c}$ and $R^{6d}$ are taken together with the carbon atoms to which they are attached to form a 6-membered aryl, a 6-membered heterocyclyl, or a 6-membered heteroaryl ring; wherein the 6-membered aryl, 6-membered heterocyclyl, and 6-membered heteroaryl rings are each independently unsubstituted or substituted.

In some embodiments of Formula (A),
$Y^1$ is C or N;
$Y^2$ is CH, N, NH, S, or O;
$Y^3$ is C or N;
$Y^4$ is CH, N, NH, S, or O;
$Y^5$ is CH, N, NH, S, or O;
wherein no more than one of $Y^1$, $Y^2$, $Y^3$, $Y^4$, and $Y^5$ is S or O and no more than three of $Y^1$, $Y^2$, $Y^3$, $Y^4$, and $Y^5$ are N or NH; and
one of $R^1$ and $R^2$ is —OH and the other is selected from the group consisting of —CN, halogen, —C(O)$R^a$, —CH=$NR^j$, —S(O)$R^b$, —S(O)$_2R^c$, —NHC(O)$R^d$, —NHS(O)$_2R^e$, —$C_1$-$C_6$alkyl-$R^f$, —$C_2$-$C_6$alkenyl-$R^g$, unsubstituted or substituted $C_3$-$C_8$ cycloalkyl, unsubstituted or substituted $C_3$-$C_8$ cycloalkenyl, and unsubstituted or substituted heterocycloalkyl; $R^a$, $R^b$, $R^c$, and $R^e$ are each independently H, $C_1$-$C_6$alkyl, $C_2$-$C_6$alkenyl, $C_2$-$C_6$alkynyl, $C_1$-$C_6$haloalkyl, unsubstituted or substituted heterocyclyl, unsubstituted or substituted heteroaryl, benzoyl, or styryl; $R^d$ is H, $C_1$-$C_6$alkyl, $C_2$-$C_6$alkenyl, $C_2$-$C_6$alkynyl, $C_1$-$C_6$haloalkyl, unsubstituted or substituted heterocyclyl, unsubstituted or substituted heteroaryl, or benzoyl; $R^f$ and $R^g$ are each independently —OH, unsubstituted heteroaryl, —$NR^mR^n$, benzoyl, or styryl; $R^m$ and $R^n$ are each independently H, $C_1$-$C_6$alkyl, $C_2$-$C_6$alkenyl, $C_2$-$C_6$alkynyl, or unsubstituted or substituted cycloalkyl; $R^j$ is unsubstituted or substituted heterocyclyl, unsubstituted or substituted heteroaryl, unsubstituted or substituted aryl, —$OR^k$, —$NHR^k$, —NHC(O)$R^k$, —NHS(O)$_2R^k$, or —NHC(NH)$NH_2$; $R^k$ is $C_1$-$C_6$alkyl, $C_2$-$C_6$alkenyl, $C_2$-$C_6$alkynyl, $C_3$-$C_8$cycloalkyl, or aryl, wherein the $C_1$-$C_6$alkyl of $R^k$ is unsubstituted or substituted with heterocyclyl or heteroaryl.

In some embodiments, when any particular group is substituted, the indicated group is substituted by one or more substituents selected from the group consisting of oxo, $C_1$-$C_6$ alkyl, $C_2$-$C_6$ alkenyl, $C_2$-$C_6$ alkynyl, halogen, —CN, —$OR^{41}$, —$SR^{41}$, —$NR^{42}R^{43}$, —$NO_2$, —C=NH(O$R^{41}$), —C(O)$R^{41}$, —OC(O)$R^{41}$, —C(O)O$R^{41}$, —C(O)$NR^{42}R^{43}$, —OC(O)NR$^{A2}$R$^{A3}$, —NR$^{A1}$C(O)R$^{A2}$, —NR$^{A1}$C(O)OR$^{A2}$, —NR$^{A1}$C(O)NR$^{A2}$R$^{A3}$, —S(O)R$^{A1}$, —S(O)$_2$R$^{A1}$, —NR$^{A1}$S(O)R$^{A2}$, —C(O)NR$^{A1}$S(O)R$^{A2}$, —NR$^{A1}$S(O)$_2$R$^{A2}$, —C(O)NR$^{A1}$S(O)$_2$R$^{A2}$, —S(O)NR$^{A2}$R$^{A3}$, —S(O)$_2$NR$^{A2}$R$^{A3}$, —P(O)(OR$^{A2}$)(OR$^{A3}$), C$_3$-C$_8$ cycloalkyl, 3-12-membered heterocyclyl, 5- to 10-membered heteroaryl, C$_6$-C$_{14}$ aryl, —(C$_1$-C$_3$ alkylene)CN, —(C$_1$-C$_3$ alkylene)OR$^{A1}$, —(C$_1$-C$_3$ alkylene)SR$^{A1}$, —(C$_1$-C$_3$ alkylene)NR$^{A2}$R$^{A3}$, —(C$_1$-C$_3$ alkylene)CF$_3$, —(C$_1$-C$_3$ alkylene)NO$_2$, —C=NH(OR$^{A1}$), —(C$_1$-C$_3$ alkylene)C(O)R$^{A1}$, —(C$_1$-C$_3$ alkylene)OC(O)R$^{A1}$, —(C$_1$-C$_3$ alkylene)C(O)OR$^{A1}$, —(C$_1$-C$_3$ alkylene)C(O)NR$^{A2}$R$^{A3}$, —(C$_1$-C$_3$ alkylene)OC(O)NR$^{A2}$R$^{A3}$, —(C$_1$-C$_3$ alkylene)NR$^{A1}$C(O)R$^{A2}$, —(C$_1$-C$_3$ alkylene)NR$^{A1}$C(O)OR$^{A2}$, —(C$_1$-C$_3$ alkylene)NR$^{A1}$C(O)NR$^{A2}$R$^{A3}$, —(C$_1$-C$_3$ alkylene)S(O)R$^{A1}$, —(C$_1$-C$_3$ alkylene)S(O)$_2$R$^{A1}$, —(C$_1$-C$_3$ alkylene)NR$^{A1}$S(O)R$^{A2}$, —C(O)(C$_1$-C$_3$ alkylene)NR$^{A1}$S(O)R$^{A2}$, —(C$_1$-C$_3$ alkylene)NR$^{A1}$S(O)$_2$R$^{A2}$, —(C$_1$-C$_3$ alkylene)C(O)NR$^{A1}$S(O)$_2$R$^{A2}$, —(C$_1$-C$_3$ alkylene)S(O)NR$^{A2}$R$^{A3}$, —(C$_1$-C$_3$ alkylene)S(O)$_2$NR$^{A2}$R$^{A3}$, —(C$_1$-C$_3$ alkylene)P(O)(OR$^{A2}$)(OR$^{A3}$), —(C$_1$-C$_3$ alkylene)(C$_3$-C$_8$ cycloalkyl), —(C$_1$-C$_3$ alkylene)(3-12-membered heterocyclyl), —(C$_1$-C$_3$ alkylene)(5-10-membered heteroaryl) and —(C$_1$-C$_3$ alkylene)(C$_6$-C$_{14}$ aryl), wherein the one or more substituents are each independently unsubstituted or substituted with one or more further substituents selected from the group consisting of halogen, oxo, —OR$^{A4}$, —NR$^{A4}$R$^{A5}$, —C(O)R$^{A4}$, —CN, —S(O)R$^{A4}$, —S(O)$_2$R$^{A4}$, —P(O)(OR$^{A4}$)(OR$^{A5}$), —(C$_1$-C$_3$ alkylene)OR$^{A4}$, —(C$_1$-C$_3$ alkylene)NR$^{A4}$R$^{A5}$, —(C$_1$-C$_3$ alkylene)C(O)R$^{A4}$, —(C$_1$-C$_3$ alkylene)S(O)R$^{A4}$, —(C$_1$-C$_3$ alkylene)S(O)$_2$R$^{A4}$, —(C$_1$-C$_3$ alkylene)P(O)(OR$^{A4}$)(OR$^{A5}$), C$_3$-C$_8$ cycloalkyl, C$_1$-C$_6$ alkyl, and C$_1$-C$_6$ alkyl substituted by oxo, —OH or halogen; wherein each R$^{A1}$ is independently hydrogen, C$_1$-C$_6$ alkyl, C$_2$-C$_6$ alkenyl, C$_2$-C$_6$ alkynyl, C$_3$-C$_8$ cycloalkyl, C$_6$-C$_{14}$ aryl, 5-6-membered heteroaryl or 3-6-membered heterocyclyl, wherein the C$_1$-C$_6$ alkyl, C$_2$-C$_6$ alkenyl, C$_2$-C$_6$ alkynyl, C$_3$-C$_8$ cycloalkyl, C$_6$-C$_{14}$ aryl, 5-6-membered heteroaryl and 3-6-membered heterocyclyl are independently unsubstituted or substituted by halogen, oxo, —CN, —OR$^{A6}$, —NR$^{A6}$R$^{A7}$, —P(O)(OR$^{A6}$)(OR$^{A6}$), phenyl, phenyl substituted by halogen, C$_1$-C$_6$ alkyl, or C$_1$-C$_6$ alkyl substituted by halogen, —OH or oxo; R$^{A2}$ and R$^{A3}$ are each independently hydrogen, C$_1$-C$_6$ alkyl, C$_2$-C$_6$ alkenyl, C$_2$-C$_6$ alkynyl, C$_3$-C$_8$ cycloalkyl, C$_6$-C$_{14}$ aryl, 5-6-membered heteroaryl or 3-6 membered heterocyclyl, wherein the C$_1$-C$_6$ alkyl, C$_2$-C$_6$ alkenyl, C$_2$-C$_6$ alkynyl, C$_3$-C$_8$ cycloalkyl, C$_6$-C$_{14}$ aryl, 5-6-membered heteroaryl and 3-6 membered heterocyclyl are each independently unsubstituted or substituted by halogen, oxo, —CN, —OR$^{A6}$, —NR$^{A6}$R$^{A7}$, C$_1$-C$_6$ alkyl, or C$_1$-C$_6$ alkyl substituted by halogen, —OH or oxo; and R$^{A4}$, R$^{A5}$, R$^{A6}$ and R$^{A7}$ are each independently hydrogen, C$_1$-C$_6$ alkyl, C$_2$-C$_6$ alkenyl, C$_2$-C$_6$ alkynyl, C$_1$-C$_6$ alkyl substituted by one or more halogen, C$_2$-C$_6$ alkenyl substituted by one or more halogen, or C$_2$-C$_6$ alkynyl substituted by one or more halogen.

In some embodiments, one of R$^1$ and R$^2$ is —OH and the other is selected from the group consisting of —CN, halogen, —C(O)R$^a$, —CH=NR$^j$, —S(O)R$^b$, —S(O)$_2$R$^c$, —NHC(O)R$^d$, —NHS(O)$_2$R$^e$, —C$_1$-C$_6$alkyl-R$^f$, —C$_2$-C$_6$alkenyl-R$^g$, C$_3$-C$_8$ cycloalkyl, C$_3$-C$_8$ cycloalkenyl, and 5- or 6-membered heterocycloalkyl, wherein the C$_3$-C$_8$ cycloalkyl and C$_3$-C$_8$ cycloalkenyl are each independently unsubstituted or substituted with one or more =O, and the 5- or 6-membered heterocycloalkyl is unsubstituted or substituted with one or more substituents selected from the group consisting of C$_1$-C$_6$alkyl, C$_3$-C$_8$cycloalkyl, =O, and —C(O)O—C$_1$-C$_6$alkyl;

R$^a$, R$^b$, R$^c$, and R$^e$ are each independently H, C$_1$-C$_6$alkyl, C$_2$-C$_6$alkenyl, C$_2$-C$_6$alkynyl, C$_1$-C$_6$haloalkyl, 3- to 10-membered heterocyclyl, 5- to 10-membered heteroaryl, benzoyl, or styryl, wherein the 3- to 10-membered heterocyclyl of R$^a$, R$^b$, R$^c$, and R$^e$ are each independently selected from the group consisting of C$_1$-C$_6$alkyl, C$_3$-C$_8$cycloalkyl, =O, and —C(O)O—C$_1$-C$_6$alkyl, and the 5- to 10-membered heteroaryl of R$^a$, R$^b$, R$^c$, and R$^e$ are each independently selected from the group consisting of C$_1$-C$_6$alkyl, C$_3$-C$_8$cycloalkyl, and —C(O)O—C$_1$-C$_6$alkyl;

R$^d$ is H, C$_1$-C$_6$alkyl, C$_2$-C$_6$alkenyl, C$_2$-C$_6$alkynyl, C$_1$-C$_6$haloalkyl, 3- to 10-membered heterocyclyl, 5- to 10-membered heteroaryl, or benzoyl, wherein the 3- to 10-membered heterocyclyl of R$^d$ is selected from the group consisting of C$_1$-C$_6$alkyl, C$_3$-C$_8$cycloalkyl, =O, and —C(O)O—C$_1$-C$_6$alkyl, and the 5- to 10-membered heteroaryl of R$^d$ is selected from the group consisting of C$_1$-C$_6$alkyl, C$_3$-C$_8$cycloalkyl, and —C(O)O—C$_1$-C$_6$alkyl;

R$^f$ and R$^g$ are each independently —OH, unsubstituted 5- to 6-membered heteroaryl, —NR$^m$R$^n$, benzoyl, or styryl;

R$^m$ and R$^n$ are each independently H, C$_1$-C$_6$alkyl, C$_2$-C$_6$alkenyl, C$_2$-C$_6$alkynyl, or C$_3$-C$_8$ cycloalkyl, wherein the C$_3$-C$_8$ cycloalkyl is unsubstituted or substituted with one or more groups selected from C$_1$-C$_6$alkyl and halo;

R$^j$ is 5- to 6-membered heterocyclyl, 5- to 6-membered heteroaryl, 6- to 12-membered aryl, —OR$^k$, —NHR$^k$, —NHC(O)R$^k$, —NHS(O)$_2$R$^k$, or —NHC(NH)NH$_2$, wherein the 5- to 6-membered heterocyclyl of R$^j$ is unsubstituted or substituted with one or more substituents selected from the group consisting of C$_1$-C$_6$alkyl, C$_3$-C$_8$cycloalkyl, =O, and —C(O)O—C$_1$-C$_6$alkyl, and the 5- to 6-membered heteroaryl and 6- to 12-membered aryl of R$^j$ are each independently unsubstituted or substituted with one or more substituents selected from the group consisting of C$_1$-C$_6$alkyl, C$_3$-C$_8$cycloalkyl, and —C(O)O—C$_1$-C$_6$alkyl; and R$^k$ is C$_1$-C$_6$alkyl, C$_2$-C$_6$alkenyl, C$_2$-C$_6$alkynyl, C$_3$-C$_8$cycloalkyl, or 6- to 12-membered aryl, wherein the C$_1$-C$_6$alkyl is unsubstituted or substituted with 5- to 6-membered heterocyclyl or 5- to 6-membered heteroaryl.

In some embodiments, R$^{6a}$, R$^{6b}$, R$^{6c}$, and R$^{6d}$ are each independently hydrogen, C$_1$-C$_6$alkyl, C$_1$-C$_6$alkoxy, halo, —OH, —NR$^p$R$^q$, C$_6$-C$_{12}$ aryl, 3- to 10-membered heterocyclyl, 5- to 10-membered heteroaryl, —C$_1$-C$_6$alkyl-5- to 6-membered heterocyclyl, —OC(O)-5- to 6-membered heterocyclyl, —C(O)R$^h$, —S(O)$_2$NR$^{w1}$R$^{w2}$, —S(O)$_2$R$^v$, or —NR$^{z1}$S(O)$_2$R$^{z2}$, wherein the C$_1$-C$_6$alkyl and C$_1$-C$_6$alkoxy of R$^{6a}$, R$^{6b}$, R$^{6c}$, and R$^{6d}$ are each independently unsubstituted or substituted with one or more groups selected from the group consisting of C$_3$-C$_8$ cycloalkyl and halogen; the C$_6$-C$_{12}$ aryl and 5- to 10-membered heteroaryl of R$^{6a}$, R$^{6b}$, R$^{6c}$, and R$^{6d}$ are each independently unsubstituted or substituted with one or more groups selected from the group consisting of C$_1$-C$_6$alkyl, C$_1$-C$_6$alkoxy, C$_3$-C$_8$cycloalkyl, —OH, and C$_1$-C$_6$alkyl-OH; and the 3- to 10-membered heterocyclyl, —C$_1$-C$_6$alkyl-5- to 6-membered heterocyclyl, and —OC(O)-5- to 6-membered heterocyclyl of R$^{6a}$, R$^{6b}$, R$^{6c}$, and R$^{6d}$ are each independently unsubstituted or substituted with one or more groups selected from the group consisting of C$_1$-C$_6$alkyl, C$_1$-C$_6$alkoxy, halo, —OH, C$_1$-C$_6$alkyl-OH, =O, and =S;

R$^h$ is selected from the group consisting of H, C$_1$-C$_6$alkyl, C$_1$-C$_6$alkoxy, C$_3$-C$_8$cycloalkyl, and —NR$^r$R$^s$;

R$^p$ is H or C$_1$-C$_6$alkyl;

R$^q$ is C$_2$-C$_3$alkyl, —C(O)R$^t$, —C(O)OR$^u$, —C(O)NR$^v$;

R$^r$, R$^s$, R$^{w1}$, and R$^{z1}$ each independently selected from H and C$_1$-C$_6$alkyl; and $R^t$, $R^u$, $R^v$, $R^{w2}$, $R^y$, and $R^{z2}$ are each independently selected from H, $C_1$-$C_6$alkyl, unsubstituted or substituted $C_3$-$C_8$cycloalkyl, and unsubstituted or substituted heterocyclyl;

or $G_5$ is CH($X_3$—$R^{6c}$) or C($X_3$—$R^{6c}$), $G_6$ is CH($X_4$—$R^{6d}$) or C($X_4$—$R^{6d}$), and $R^{6c}$ and $R^{6d}$ are taken together with the carbon atoms to which they are attached to form a 6-membered aryl, a 6-membered heterocyclyl, or a 6-membered heteroaryl ring; wherein the 6-membered aryl, 6-membered heterocyclyl, and 6-membered heteroaryl rings are each independently unsubstituted or substituted with one or more groups selected from the group consisting of $C_1$-$C_6$alkyl and —C(O)O—$C_1$-$C_6$alkyl; and wherein no more than one of $R^{6a}$, $R^{6b}$, $R^{6c}$, and $R^{6d}$ is $C_1$-$C_6$alkoxy or —OH.

In some embodiments, the compound of Formula (A) is a compound of Formula (A-1a) or (A-1b):

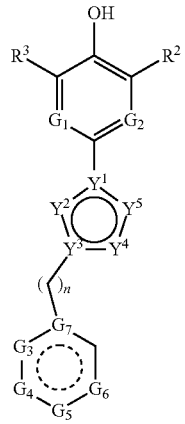

(A-1a)

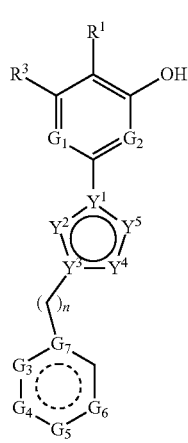

(A-1b)

wherein $R^1$, $R^2$, $R^3$, $G^1$, $G^2$, $G^3$, $G^4$, $G^5$, $G^6$, $G^7$, $Y^1$, $Y^2$, $Y^3$, $Y^4$, $Y^5$, and n are as defined for Formula (A).

In some embodiments, the compound of Formula (A) is a compound of Formula (A-2a) or (A-2b):

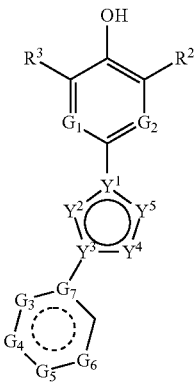

(A-2a)

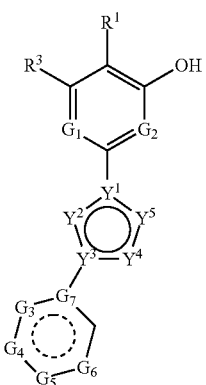

(A-2b)

wherein $R^1$, $R^2$, $R^3$, $G^1$, $G^2$, $G^3$, $G^4$, $G^5$, $G^6$, $G^7$, $Y^1$, $Y^2$, $Y^3$, $Y^4$, and $Y^5$ are as defined for Formula (A).

In some embodiments, the compound of Formula (A) is a compound of Formula (A-3a) or (A-3b),

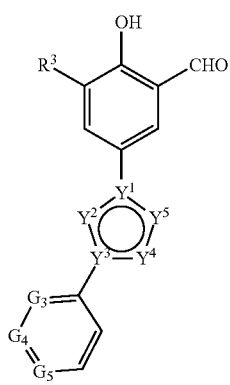

(A-3a)

(A-3b)
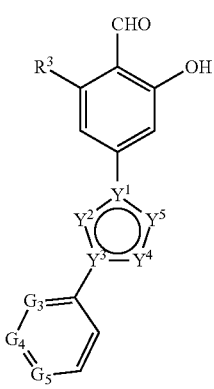
wherein $R^3$, $G^3$, $G^4$, $G^5$, $Y^1$, $Y^2$, $Y^3$, $Y^4$, and $Y^5$ are as defined for Formula (A).
In some embodiments, the compound of Formula (A) is a compound of Formula (A-4a), (A-4b), (A-4c), (A-4d), (A-4e), (A-4f), (A-4g), (A-4h), or (A-4i):
(A-4a)
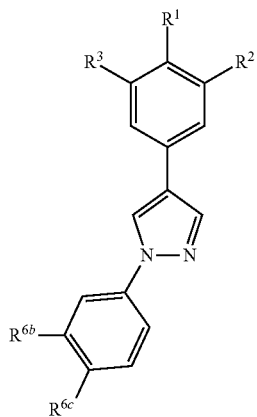
(A-4b)
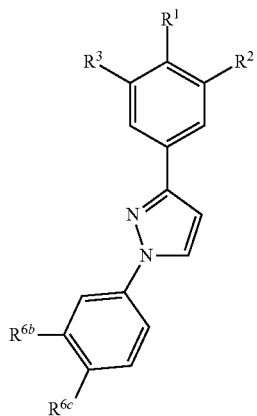
(A-4c)
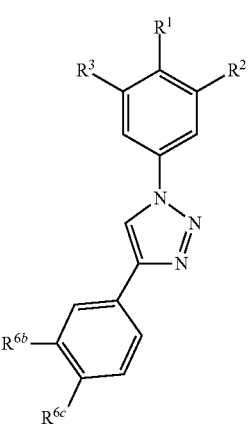
(A-4d)
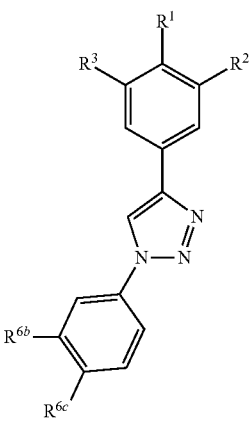
(A-4e)
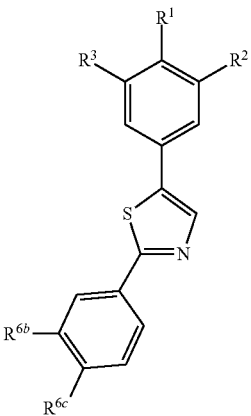

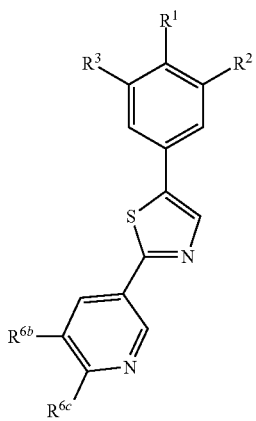
(A-4f)

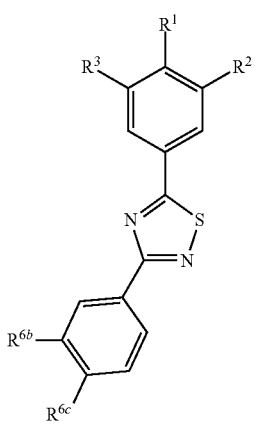
(A-4g)

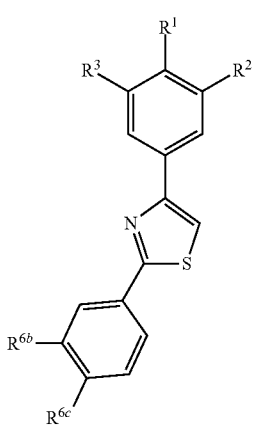
(A-4h)

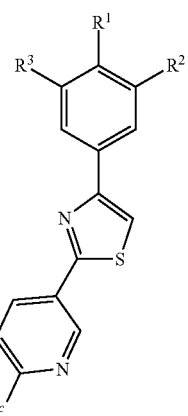
(A-4i)

wherein $R^1$, $R^2$, $R^3$, $R^{6b}$, and $R^{6c}$ are as defined for Formula (A).

In some embodiments of Formula (A), including Formula (A-1a), (A-1b), (A-2a), (A-2b), (A-3a), and (A-3b), $Y^1$ is C. In other embodiments, $Y^1$ is N. In some embodiments, $Y^2$ is CH. In some embodiments, $Y^2$ is N. In some embodiments $Y^2$ is NH. In some embodiments, $Y^2$ is S. In other embodiments, $Y^2$ is O. In some embodiments, $Y^3$ is C. In other embodiments, $Y^3$ is N. In some embodiments, $Y^4$ is CH. In some embodiments, $Y^4$ is N. In some embodiments, $Y^4$ is NH. In some embodiments, $Y^4$ is S. In other embodiments, $Y^4$ is O. In some embodiments, $Y^5$ is $CR^7$, wherein $R^1$ is H or $C_1$-$C_6$alkyl. In some embodiments, $Y^5$ is CH. In some embodiments, $Y^5$ is $CR^7$, wherein $R^7$ is $C_1$-$C_6$alkyl. In some embodiments, $Y^5$ is $C(CH_3)$. In some embodiments, $Y^5$ is N. In some embodiments, $Y^5$ is NH. In some embodiments, $Y^5$ is S. In other embodiments, $Y^5$ is O.

In some embodiments of Formula (A), including Formula (A-1a), (A-1b), (A-2a), (A-2b), (A-3a), and (A-3b), one of $Y^1$, $Y^2$, $Y^3$, $Y^4$, and $Y^5$ is N, and the rest are other than N. In some embodiments, two of $Y^1$, $Y^2$, $Y^3$, $Y^4$, and $Y^5$ are N, and the rest are other than N. In other embodiments, three of $Y^1$, $Y^2$, $Y^3$, $Y^4$, and $Y^5$ are N, and the rest are other than N. In other embodiments, four of $Y^1$, $Y^2$, $Y^3$, $Y^4$, and $Y^5$ are N. In some embodiments of Formula (A), one of $Y^1$, $Y^2$, $Y^3$, $Y^4$, and $Y^5$ is S, and the rest are other than S. In some embodiments of Formula (A), one of $Y^1$, $Y^2$, $Y^3$, $Y^4$, and $Y^5$ is O, and the rest are other than O. In some embodiments, no more than one of $Y^1$, $Y^2$, $Y^3$, $Y^4$, and $Y^5$ is S or O. In some embodiments, no more than three of $Y^1$, $Y^2$, $Y^3$, $Y^4$, and $Y^5$ are N or NH. In some embodiments, no more than four of $Y^1$, $Y^2$, $Y^3$, $Y^4$ and $Y^5$ are N or NH.

In some embodiments of Formula (A), including Formula (A-1a), (A-1b), (A-2a), (A-2b), (A-3a), and (A-3b),

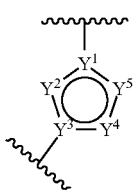

is selected from the group consisting of
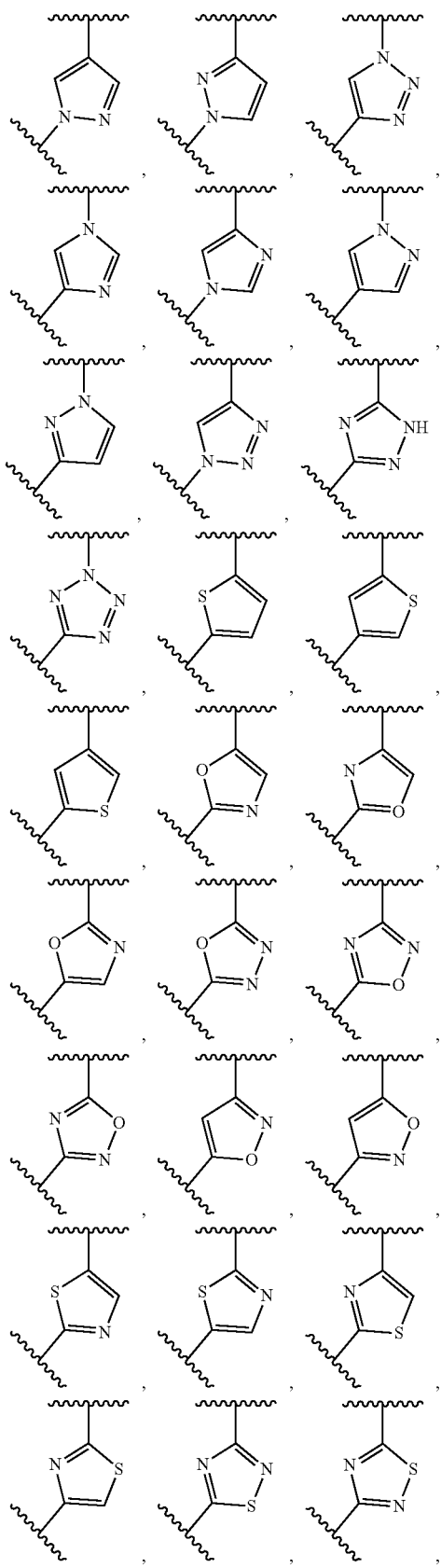
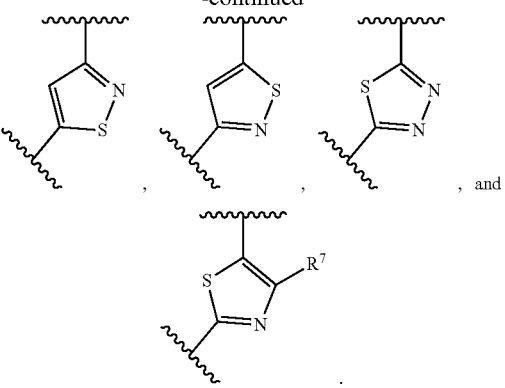
, and
In some embodiments of Formula (A), including Formula (A-1a), (A-1b), (A-2a), (A-2b), (A-3a), and (A-3b),
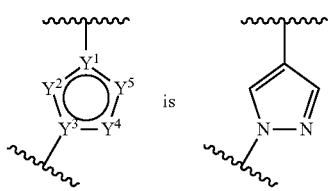
In some embodiments,
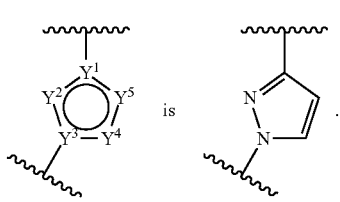
In some embodiments,
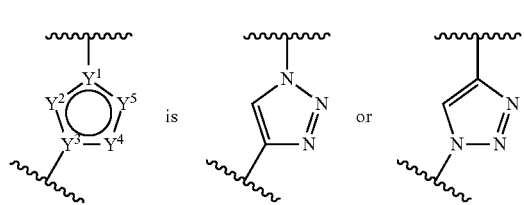
In some embodiments,
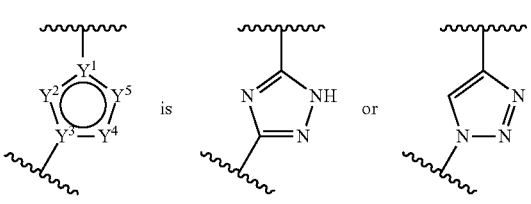

In some embodiments,
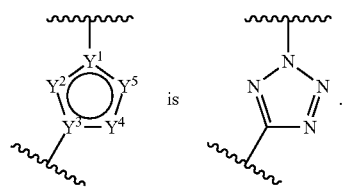 is 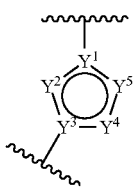.
In other embodiments,
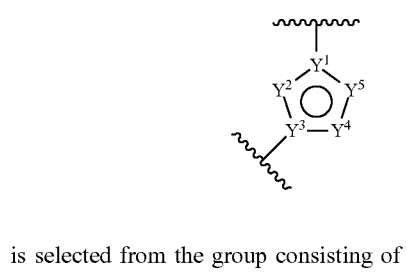
is selected from the group consisting of
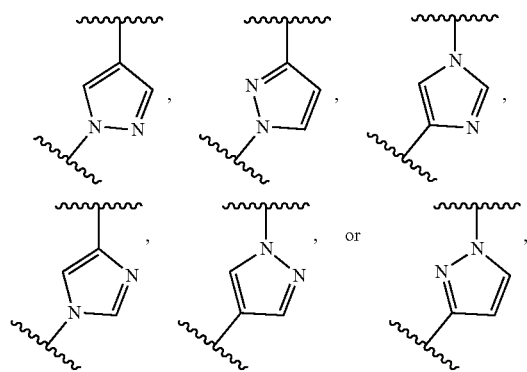
In some embodiments of Formula (A),
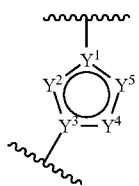
is selected from the group consisting of
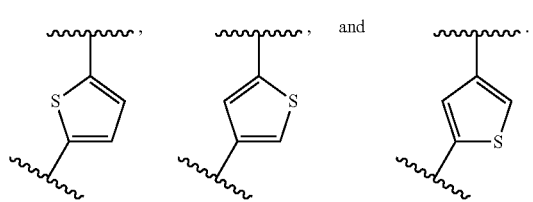 [SMILES: *c1ccc(*)s1 ; *c1csc(*)c1 ; *c1csc(*)c1]
In some embodiments,
is selected from the group consisting of
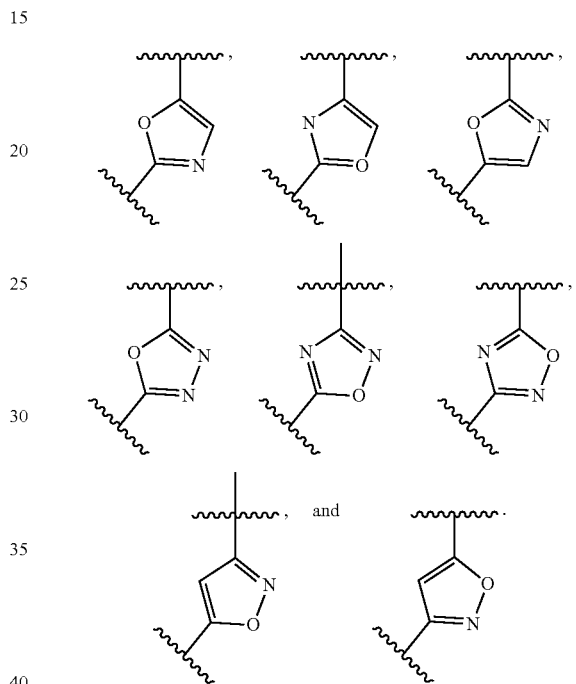
In some embodiments,
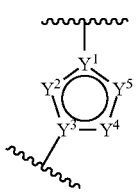
is selected from the group consisting of
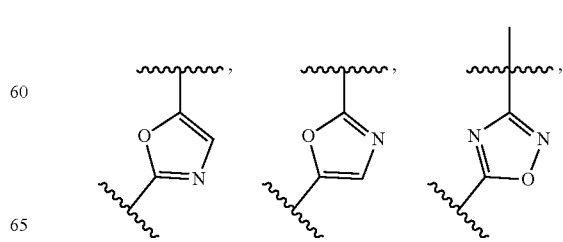

-continued

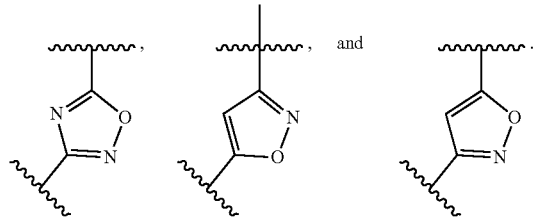

In other embodiments,

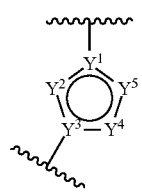

is selected from the group consisting of

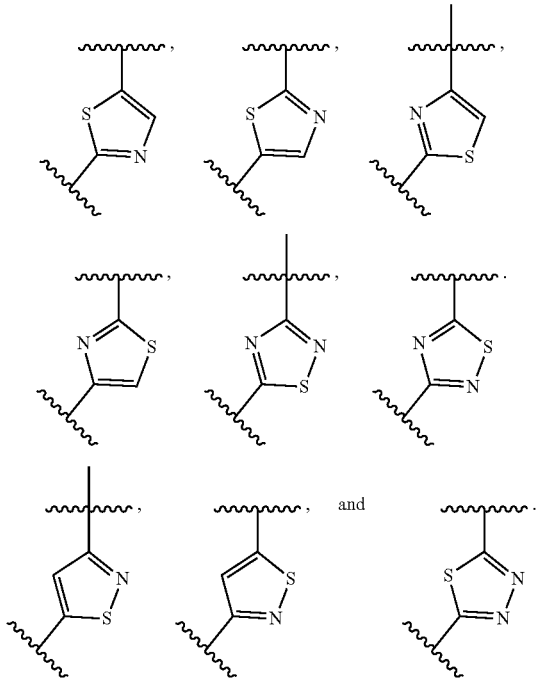

In some embodiments,

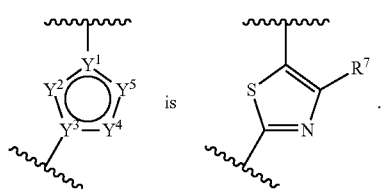

In some embodiments,

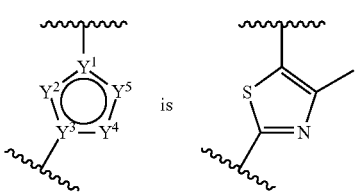

In some embodiments of Formula (A), including Formula (A-1a), (A-1b), (A-2a), (A-2b), (A-3a), and (A-3b),

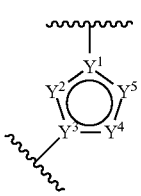

is selected from the group consisting of

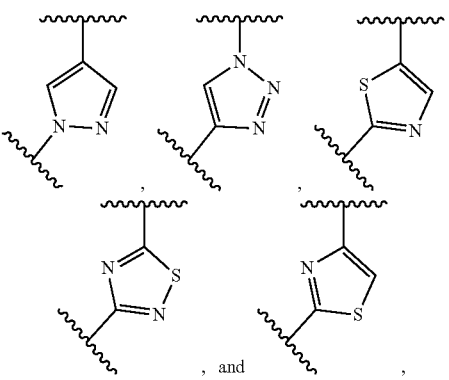

In some embodiments, $R^1$ is —OH and $R^2$ is —C(O)H. In other embodiments, $R^2$ is —OH and $R^1$ is —C(O)H. In some embodiments, $R^1$ is —OH, $R^2$ is —C(O)H, and $R^3$ is halo. In other embodiments, $R^2$ is —OH, $R^1$ is —C(O)H, and $R^3$ is halo. In some embodiments, $R^1$ is —OH, $R^2$ is —C(O)H, and $R^3$ is fluoro. In other embodiments, $R^2$ is —OH, $R^1$ is —C(O)H, and $R^3$ is fluoro.

In some embodiments of Formula (A), including Formula (A-1a), (A-2a), (A-3a), (A-4a), (A-4b), (A-4c), (A-4d), (A-4e), (A-4f), (A-4g), (A-4h), and (A-4i), $R^1$ is —OH and $R^2$ is selected from the group consisting of —CN, halogen, —C(O)$R^a$, —CH=N$R^j$, —S(O)$R^b$, —S(O)$_2R^c$, —NHC(O)$R^d$, —NHS(O)$_2R^e$, —C$_1$-C$_6$alkyl-$R^f$, —C$_2$-C$_6$alkenyl-$R^g$, unsubstituted or substituted C$_3$-C$_8$ cycloalkyl, unsubstituted or substituted C$_3$-C$_8$ cycloalkenyl, and unsubstituted or substituted heterocycloalkyl. In some embodiments, $R^1$ is —OH and $R^2$ is selected from the group consisting of —CN, halogen, —C(O)$R^a$, —CH=N$R^j$, —S(O)$R^b$, —S(O)$_2R^c$, —NHC(O)$R^d$, —NHS(O)$_2R^e$, —C$_1$-C$_6$alkyl-$R^f$, —C$_2$-C$_6$alkenyl-$R^g$, C$_3$-C$_8$ cycloalkyl, C$_3$-C$_8$ cycloalkenyl, and heterocycloalkyl, wherein the C$_3$-C$_8$ cycloalkyl, C$_3$-C$_8$ cycloalkenyl, and heterocycloalkyl are optionally substituted with one or more substituents selected from the group consisting of C$_1$-C$_6$ alkyl, C$_1$-C$_6$ haloalkyl, halo, —OH, —C(O)H, —C(O)OH, —C(O)OC$_1$-C$_6$ alkyl, —OC$_1$-C$_6$ alkyl, and C$_3$-C$_8$ cycloalkyl. In some embodiments, $R^a$, $R^b$, $R^c$, and $R^e$ are each independently H, C$_1$-C$_6$alkyl, $C_2$-$C_6$alkenyl, $C_2$-$C_6$alkynyl, $C_1$-$C_6$haloalkyl, unsubstituted or substituted heterocyclyl, unsubstituted or substituted heteroaryl, benzoyl, or styryl. In some embodiments $R^a$, $R^b$, $R^c$, and $R^e$ are each independently H, $C_1$-$C_6$alkyl, $C_2$-$C_6$alkenyl, $C_2$-$C_6$alkynyl, $C_1$-$C_6$haloalkyl, heterocyclyl, heteroaryl, benzoyl, or styryl, wherein the heterocyclyl and heteroaryl are optionally substituted with one or more substituents selected from the group consisting of $C_1$-$C_6$ alkyl, $C_1$-$C_6$ haloalkyl, halo, —OH, —C(O)H, —C(O)OH, —C(O)OC$_1$-$C_6$ alkyl, —OC$_1$-$C_6$ alkyl, and $C_3$-$C_8$ cycloalkyl. In some embodiments, $R^d$ is H, $C_1$-$C_6$alkyl, $C_2$-$C_6$alkenyl, $C_2$-$C_6$alkynyl, $C_1$-$C_6$haloalkyl, unsubstituted or substituted heterocyclyl, unsubstituted or substituted heteroaryl, or benzoyl. In some embodiments, $R^d$ is H, $C_1$-$C_6$alkyl, $C_2$-$C_6$alkenyl, $C_2$-$C_6$alkynyl, $C_1$-$C_6$haloalkyl, heterocyclyl, heteroaryl, or benzoyl, wherein the heterocyclyl and heteroaryl are optionally substituted with one or more substituents selected from the group consisting of $C_1$-$C_6$ alkyl, $C_1$-$C_6$ haloalkyl, halo, —OH, —C(O)H, —C(O)OH, —C(O)OC$_1$-$C_6$ alkyl, —OC$_1$-$C_6$ alkyl, and $C_3$-$C_8$ cycloalkyl. In some embodiments, R and $R^g$ are each independently —OH, unsubstituted heteroaryl, —NR$^m$R$^n$, benzoyl, or styryl, wherein R$^m$ and R$^n$ are each independently H, $C_1$-$C_6$alkyl, $C_2$-$C_6$alkenyl, $C_2$-$C_6$alkynyl, or $C_3$-$C_8$ cycloalkyl, wherein the $C_3$-$C_8$ cycloalkyl is optionally substituted with one or more substituents selected from the group consisting of $C_1$-$C_6$ alkyl, $C_1$-$C_6$ haloalkyl, halo, —OH, —C(O)H, —C(O)OH, —C(O)OC$_1$-$C_6$ alkyl, —OC$_1$-$C_6$ alkyl, and $C_3$-$C_8$ cycloalkyl. In some embodiments, $R^j$ is heterocyclyl, aryl, —OR$^k$, —NHR$^k$, —NHC(O)R$^k$, —NHS(O)$_2$R$^k$, or —NHC(NH)NH$_2$, wherein the heterocyclyl and aryl are optionally substituted with one or more substituents selected from the group consisting of $C_1$-$C_6$ alkyl, $C_1$-$C_6$ haloalkyl, halo, —OH, —C(O)H, —C(O)OH, —C(O)OC$_1$-$C_6$ alkyl, —OC$_1$-$C_6$ alkyl, and $C_3$-$C_8$ cycloalkyl. In some embodiments, $R^1$ is —OH and $R^2$ a is selected from the group consisting of —CN, halogen, —C(O)H, —CH=NR$^j$, unsubstituted or substituted $C_3$-$C_8$ cycloalkyl, unsubstituted or substituted $C_3$-$C_8$ cycloalkenyl, and unsubstituted or substituted heterocycloalkyl.

In some embodiments of Formula (A), including Formula (A-1b), (A-2b), (A-3b), (A-4a), (A-4b), (A-4c), (A-4d), (A-4e), (A-4f), (A-4g), (A-4h), and (A-4i), $R^2$ is —OH and $R^1$ a is selected from the group consisting of —CN, halogen, —C(O)R$^a$, —CH=NR$^j$, —S(O)R$^b$, —S(O)$_2$R$^c$, —NHC(O)R$^d$, —NHS(O)$_2$R$^e$, —C$_1$-C$_6$alkyl-R$^f$, —C$_2$-C$_6$alkenyl-R$^g$, unsubstituted or substituted $C_3$-$C_8$ cycloalkyl, unsubstituted or substituted $C_3$-$C_8$ cycloalkenyl, and unsubstituted or substituted heterocycloalkyl. In some embodiments, $R^2$ is —OH and $R^1$ is selected from the group consisting of —CN, halogen, —C(O)R$^a$, —CH=NR$^j$, —S(O)R$^b$, —S(O)$_2$R$^c$, —NHC(O)R$^d$, —NHS(O)$_2$R$^e$, —C$_1$-C$_6$alkyl-R$^f$, —C$_2$-C$_6$alkenyl-R$^g$, $C_3$-$C_8$ cycloalkyl, $C_3$-$C_8$ cycloalkenyl, and heterocycloalkyl, wherein the $C_3$-$C_8$ cycloalkyl, $C_3$-$C_8$ cycloalkenyl, and heterocycloalkyl are optionally substituted with one or more substituents selected from the group consisting of $C_1$-$C_6$ alkyl, $C_1$-$C_6$ haloalkyl, halo, —OH, —C(O)H, —C(O)OH, —C(O)OC$_1$-$C_6$ alkyl, —OC$_1$-$C_6$ alkyl, and $C_3$-$C_8$ cycloalkyl. In some embodiments, $R^a$, $R^b$, $R^c$, and $R^e$ are each independently H, $C_1$-$C_6$alkyl, $C_2$-$C_6$alkenyl, $C_2$-$C_6$alkynyl, $C_1$-$C_6$haloalkyl, unsubstituted or substituted heterocyclyl, unsubstituted or substituted heteroaryl, benzoyl, or styryl. In some embodiments $R^a$, $R^b$, $R^c$, and $R^e$ are each independently H, $C_1$-$C_6$alkyl, $C_2$-$C_6$alkenyl, $C_2$-$C_6$alkynyl, $C_1$-$C_6$haloalkyl, heterocyclyl, heteroaryl, benzoyl, or styryl, wherein the heterocyclyl and heteroaryl are optionally substituted with one or more substituents selected from the group consisting of $C_1$-$C_6$ alkyl, $C_1$-$C_6$ haloalkyl, halo, —OH, —C(O)H, —C(O)OH, —C(O)OC$_1$-$C_6$ alkyl, —OC$_1$-$C_6$ alkyl, and $C_3$-$C_8$ cycloalkyl. In some embodiments, $R^d$ is H, $C_1$-$C_6$alkyl, $C_2$-$C_6$alkenyl, $C_2$-$C_6$alkynyl, $C_1$-$C_6$haloalkyl, unsubstituted or substituted heterocyclyl, unsubstituted or substituted heteroaryl, or benzoyl. In some embodiments, $R^d$ is H, $C_1$-$C_6$alkyl, $C_2$-$C_6$alkenyl, $C_2$-$C_6$alkynyl, $C_1$-$C_6$haloalkyl, heterocyclyl, heteroaryl, or benzoyl, wherein the heterocyclyl and heteroaryl are optionally substituted with one or more substituents selected from the group consisting of $C_1$-$C_6$ alkyl, $C_1$-$C_6$ haloalkyl, halo, —OH, —C(O)H, —C(O)OH, —C(O)OC$_1$-$C_6$ alkyl, —OC$_1$-$C_6$ alkyl, and $C_3$-$C_8$ cycloalkyl. In some embodiments, $R^f$ and $R^g$ are each independently —OH, unsubstituted heteroaryl, —NR$^m$R$^n$, benzoyl, or styryl, wherein R$^m$ and R$^n$ are each independently H, $C_1$-$C_6$alkyl, $C_2$-$C_6$alkenyl, $C_2$-$C_6$alkynyl, or $C_3$-$C_8$ cycloalkyl, wherein the $C_3$-$C_8$ cycloalkyl is optionally substituted with one or more substituents selected from the group consisting of $C_1$-$C_6$ alkyl, $C_1$-$C_6$ haloalkyl, halo, —OH, —C(O)H, —C(O)OH, —C(O)OC$_1$-$C_6$ alkyl, —OC$_1$-$C_6$ alkyl, and $C_3$-$C_8$ cycloalkyl. In some embodiments, $R^j$ is heterocyclyl, aryl, —OR$^k$, —NHR$^k$, —NHC(O)R$^k$, —NHS(O)$_2$R$^k$, or —NHC(NH)NH$_2$, wherein the heterocyclyl and aryl are optionally substituted with one or more substituents selected from the group consisting of $C_1$-$C_6$ alkyl, $C_1$-$C_6$ haloalkyl, halo, —OH, —C(O)H, —C(O)OH, —C(O)OC$_1$-$C_6$ alkyl, —OC$_1$-$C_6$ alkyl, and $C_3$-$C_8$ cycloalkyl. In some embodiments, $R^2$ is —OH and $R^1$ a is selected from the group consisting of —CN, halogen, —C(O)H, —CH=NR$^j$, unsubstituted or substituted $C_3$-$C_8$ cycloalkyl, unsubstituted or substituted $C_3$-$C_8$ cycloalkenyl, and unsubstituted or substituted heterocycloalkyl.

In some embodiments of Formula (A), including Formula (A-1a), (A-1b), (A-2a), (A-2b), (A-3a), (A-3b), (A-4a), (A-4b), (A-4c), (A-4d), (A-4e), (A-4f), (A-4g), (A-4h), and (A-4i), one of $R^1$ and $R^2$ is —OH and the other is —CH=NR$^j$, wherein R$^j$ is unsubstituted or substituted heterocyclyl, unsubstituted or substituted aryl, —OR$^k$, —NHR$^k$, —NHC(O)R$^k$, —NHS(O)$_2$R$^k$, or —NHC(NH)NH$_2$. In some embodiments, one of $R^1$ and $R^2$ is —OH and the other is —CH=NR$^j$, wherein R$^j$ is unsubstituted or substituted heterocyclyl, unsubstituted or substituted aryl, —OR$^k$, —NHR$^k$, —NHC(O)R$^k$, —NHS(O)$_2$R$^k$, or —NHC(NH)NHR$^{aa}$, where R$^{aa}$ is unsubstituted or substituted $C_1$-$C_6$alkyl, unsubstituted or substituted $C_3$-$C_8$cycloalkyl, unsubstituted or substituted aryl, unsubstituted or substituted heterocycloalkyl, or unsubstituted or substituted heteroaryl. In some embodiments, R$^{aa}$ is unsubstituted or substituted $C_1$-$C_6$alkyl. In certain embodiments, R$^a$ is $C_1$-$C_6$alkyl substituted with —OH or —(OCH$_2$CH$_2$)$_v$OH, where v is 1, 2, or 3. In some embodiments, R$^{aa}$ is unsubstituted or substituted $C_3$-$C_8$cycloalkyl. In some embodiments, R$^{aa}$ is unsubstituted or substituted aryl. In some embodiments, R$^{aa}$ is unsubstituted or substituted $C_6$-$C_{14}$ aryl. In some embodiments, R$^{aa}$ is unsubstituted or substituted heterocycloalkyl. In some embodiments, R$^{aa}$ is unsubstituted or substituted 3- to 18-membered heterocycloalkyl. In some embodiments, R$^{aa}$ is unsubstituted or substituted 3- to 6-membered heterocycloalkyl. In some embodiments, R$^{aa}$ is unsubstituted or substituted heteroaryl. In some embodiments, R$^{aa}$ is unsubstituted or substituted 5- to 18-membered heteroaryl. In some embodiments, R$^{aa}$ is unsubstituted or substituted 5- to 10-membered heteroaryl. In some embodiments, R$^{aa}$ is $C_3$-$C_8$cycloalkyl, $C_6$-$C_{14}$ aryl, 3- to 18-membered heterocycloalkyl, or 5- to 18-membered heteroaryl, each optionally substituted with $C_1$-$C_6$alkyl. In some embodiments, one of $R^1$ and $R^2$ is —OH and the other is —CH=N$R^j$, wherein $R^j$ is unsubstituted or substituted 4- to 12-membered heterocyclyl. In some embodiments, one of $R^1$ and $R^2$ is —OH and the other is —CH=N$R^j$, wherein $R^j$ is unsubstituted or substituted 5- to 6-membered heterocyclyl. In certain embodiments, one of $R^1$ and $R^2$ is —OH and the other is —CH=N$R^j$, wherein $R^j$ is an unsubstituted heterocyclyl. In some embodiments, one of $R^1$ and $R^2$ is —OH and the other is —CH=N$R^j$, wherein $R^j$ is pyrrolidinyl, pyrazolidinyl, imidazolidinyl, tetrahydrofuranyl, 1,3-dioxolanyl, tetrahydrothiophenyl, oxathiolanyl, sulfolanyl, piperidinyl, piperazinyl, tetrahydropyranyl, dioxanyl, thianyl, dithianyl, trithianyl, morpholinyl, or thiomorpholinyl. In other embodiments, one of $R^1$ and $R^2$ is —OH and the other is —CH=N$R^j$, wherein $R^j$ is a heterocyclyl substituted with one or more substituents selected from the group consisting of $C_1$-$C_6$alkyl, $C_3$-$C_8$cycloalkyl, and oxo. In some embodiments, $R^j$ is a heterocyclyl, wherein the nitrogen and/or sulfur atom(s) of the heterocyclyl are optionally oxidized to provide for N-oxide, —S(O)—, or —SO$_2$— moieties.

In some embodiments of Formula (A), including Formula (A-1a), (A-1b), (A-2a), (A-2b), (A-3a), (A-3b), (A-4a), (A-4b), (A-4c), (A-4d), (A-4e), (A-4f), (A-4g), (A-4h), and (A-4i), one of $R^1$ and $R^2$ is —OH and the other is —CH=N$R^j$, wherein $R^j$ is unsubstituted or substituted aryl. In some embodiments, one of $R^1$ and $R^2$ is —OH and the other is —CH=N$R^j$, wherein $R^j$ is unsubstituted or substituted 6- to 14-membered aryl. In some embodiments, one of $R^1$ and $R^2$ is —OH and the other is —CH=N$R^j$, wherein $R^j$ is unsubstituted phenyl or naphthyl. In other embodiments, one of $R^1$ and $R^2$ is —OH and the other is —CH=N$R^j$, wherein $R^j$ is a phenyl or naphtyl substituted with one or more substituents selected from the group consisting of $C_1$-$C_6$alkyl, $C_3$-$C_8$cycloalkyl, and oxo.

In some embodiments of Formula (A), including Formula (A-1a), (A-1b), (A-2a), (A-2b), (A-3a), (A-3b), (A-4a), (A-4b), (A-4c), (A-4d), (A-4e), (A-4f), (A-4g), (A-4h), and (A-4i), one of $R^1$ and $R^2$ is —OH and the other is —CH=N$R^j$, wherein $R^j$ is —O$R^k$. In some embodiments, one of $R^1$ and $R^2$ is —OH and the other is —CH=N$R^j$, wherein $R^j$ is —O$C_1$-$C_6$alkyl. In some embodiments, one of $R^1$ and $R^2$ is —OH and the other is —CH=N$R^j$, wherein $R^j$ is —O$C_1$-$C_6$alkenyl or —O$C_1$-$C_6$alkynyl. In some embodiments, one of $R^1$ and $R^2$ is —OH and the other is —CH=N$R^j$, wherein $R^j$ is —O$C_3$-$C_8$cycloalkyl. In other embodiments, one of $R^1$ and $R^2$ is —OH and the other is —CH=N$R^j$, wherein $R^j$ is —O-aryl. In some embodiments, one of $R^1$ and $R^2$ is —OH and the other is —CH=N$R^j$, wherein $R^j$ is —NH$R^k$. In some embodiments, one of $R^1$ and $R^2$ is —OH and the other is —CH=N$R^j$, wherein $R^j$ is —NH$C_1$-$C_6$alkyl. In some embodiments, one of $R^1$ and $R^2$ is —OH and the other is —CH=N$R^j$, wherein $R^j$ is —NH$C_1$-$C_6$alkenyl or —NH$C_1$-$C_6$alkynyl. In some embodiments, one of $R^1$ and $R^2$ is —OH and the other is —CH=N$R^j$, wherein $R^j$ is —NH$C_3$-$C_8$cycloalkyl. In other embodiments, one of $R^1$ and $R^2$ is —OH and the other is —CH=N$R^j$, wherein $R^j$ is —NH-aryl. In some embodiments, one of $R^1$ and $R^2$ is —OH and the other is —CH=N$R^j$, wherein $R^j$ is —NHC(O)$R^k$. In some embodiments, one of $R^1$ and $R^2$ is —OH and the other is —CH=N$R^j$, wherein $R^j$ is —NHC(O)$C_1$-$C_6$alkyl. In some embodiments, one of $R^1$ and $R^2$ is —OH and the other is —CH=N$R^j$, wherein $R^j$ is —NHC(O)$C_1$-$C_6$alkenyl or —NHC(O)$C_1$-$C_6$alkynyl. In some embodiments, one of $R^1$ and $R^2$ is —OH and the other is —CH=N$R^j$, wherein $R^j$ is —NHC(O)$C_3$-$C_8$cycloalkyl. In other embodiments, one of $R^1$ and $R^2$ is —OH and the other is —CH=N$R^j$ is —NHC(O)-aryl. In some embodiments, one of $R^1$ and $R^2$ is —OH and the other is —CH=N$R^j$, wherein $R^j$ is —NHS(O)$_2$$R^k$. In some embodiments, one of $R^1$ and $R^2$ is —OH and the other is —CH=N$R^j$, wherein $R^j$ is —NHS(O)$_2$$C_1$-$C_6$alkyl. In some embodiments, one of $R^1$ and $R^2$ is —OH and the other is —CH=N$R^j$, wherein $R^j$ is —NHS(O)$_2$$C_1$-$C_6$alkenyl or —NHS(O)$_2$$C_1$-$C_6$alkynyl. In some embodiments, one of $R^1$ and $R^2$ is —OH and the other is —CH=N$R^j$, wherein $R^j$ is —NHS(O)$_2$$C_3$-$C_8$cycloalkyl. In other embodiments, one of $R^1$ and $R^2$ is —OH and the other is —CH=N$R^j$, wherein $R^j$ is —NHS(O)$_2$-aryl. In some embodiments, one of $R^1$ and $R^2$ is —OH and the other is —CH=N$R^j$, wherein $R^j$ is —NHC(NH)NH$R^{aa}$. In some embodiments, $R^{aa}$ is unsubstituted or substituted $C_1$-$C_6$alkyl. In certain embodiments, $R^{aa}$ is $C_1$-$C_6$alkyl substituted with —OH or —(OCH$_2$CH$_2$)$_v$OH, where v is 1, 2, or 3. In some embodiments, $R^{aa}$ is unsubstituted or substituted $C_3$-$C_8$cycloalkyl. In some embodiments, $R^{aa}$ is unsubstituted or substituted aryl. In some embodiments, $R^{aa}$ is unsubstituted or substituted $C_6$-$C_{14}$ aryl. In some embodiments, $R^{aa}$ is unsubstituted or substituted heterocycloalkyl. In some embodiments, $R^{aa}$ is unsubstituted or substituted 3- to 18-membered heterocycloalkyl. In some embodiments, $R^{aa}$ is unsubstituted or substituted 3- to 6-membered heterocycloalkyl. In some embodiments, $R^{aa}$ is unsubstituted or substituted heteroaryl. In some embodiments, $R^{aa}$ is unsubstituted or substituted 5- to 18-membered heteroaryl. In some embodiments, $R^{aa}$ is unsubstituted or substituted 5- to 10-membered heteroaryl. In some embodiments, $R^{aa}$ is $C_3$-$C_8$cycloalkyl, $C_6$-$C_{14}$ aryl, 3- to 18-membered heterocycloalkyl, or 5- to 18-membered heteroaryl, each optionally substituted with $C_1$-$C_6$alkyl.

In some embodiments of Formula (A), including Formula (A-1a), (A-1b), (A-2a), (A-2b), (A-3a), (A-3b), (A-4a), (A-4b), (A-4c), (A-4d), (A-4e), (A-4f), (A-4g), (A-4h), and (A-4i), one of $R^1$ and $R^2$ is —OH and the other is —CH=N$R^j$, wherein $R^j$ is —NHC(NH)NH$_2$. In some embodiments, one of $R^1$ and $R^2$ is —OH and the other is —CH=N$R^j$, wherein —CH=N$R^j$ is selected from the group consisting of

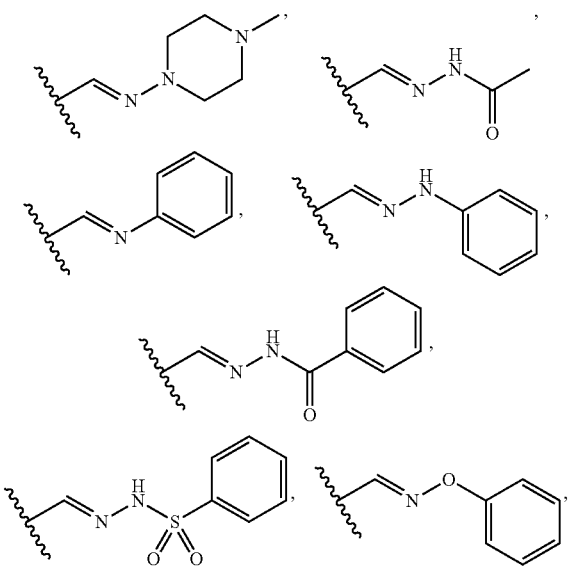

-continued

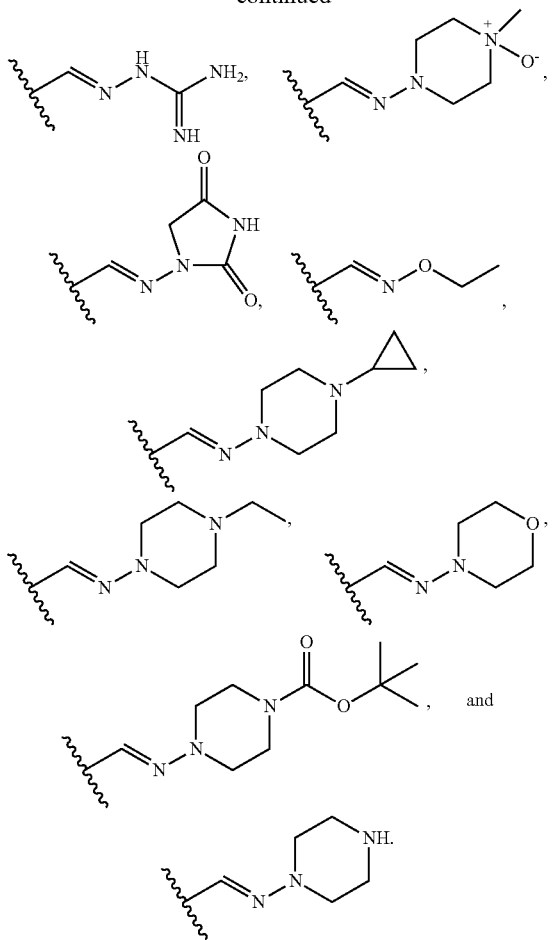

In some embodiments, —CH=NR$^j$ is selected from the group consisting of

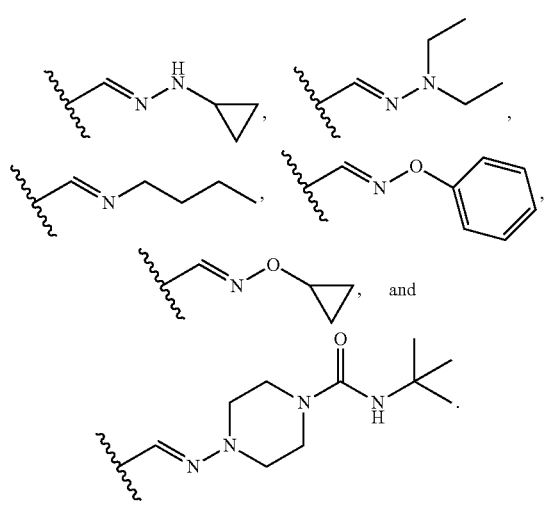

In some embodiments of Formula (A), including Formula (A-1a), (A-1b), (A-2a), (A-2b), (A-3a), (A-3b), (A-4a), (A-4b), (A-4c), (A-4d), (A-4e), (A-4f), (A-4g), (A-4h), and (A-4i), one of R$^1$ and R$^2$ is —OH and the other is —C$_1$-C$_6$alkyl-R$^f$, wherein R$^f$ is selected from the group consisting of —OH, unsubstituted heteroaryl, —NR'''R'', benzoyl, or styryl, and R''' and R'' are each independently H, C$_1$-C$_6$alkyl, C$_2$-C$_6$alkenyl, C$_2$-C$_6$alkynyl, or unsubstituted or substituted C$_3$-C$_8$ cycloalkyl. In some embodiments, one of R$^1$ and R$^2$ is —OH and the other is —C$_2$-C$_6$alkenyl-R$^g$, wherein R$^g$ is selected from the group consisting of —OH, unsubstituted heteroaryl, —NR'''R'', benzoyl, or styryl, and R''' and R'' are each independently H, C$_1$-C$_6$alkyl, C$_2$-C$_6$alkenyl, C$_2$-C$_6$alkynyl, or unsubstituted or substituted C$_3$-C$_8$ cycloalkyl. In some embodiments, R''' and R'' are each independently H, C$_1$-C$_6$alkyl, C$_2$-C$_6$alkenyl, C$_2$-C$_6$alkynyl, or unsubstituted C$_3$-C$_8$cycloalkyl, or C$_3$-C$_8$cycloalkyl substituted with one or more substituents selected from the group consisting of C$_1$-C$_6$alkyl, C$_2$-C$_6$alkenyl, C$_2$-C$_6$alkynyl, C$_1$-C$_6$alkoxy, C$_1$-C$_6$haloalkyl, —OH, and halo. In some embodiments, R''' is unsubstituted or substituted C$_3$-C$_8$ cycloalkyl, and R'' is H, C$_1$-C$_6$alkyl, C$_2$-C$_6$alkenyl, or C$_2$-C$_6$alkynyl. In some embodiments, R''' is C$_3$-C$_8$ cycloalkyl, and R'' is H.

In some embodiments of Formula (A), including Formula (A-1a), (A-1b), (A-2a), (A-2b), (A-3a), (A-3b), (A-4a), (A-4b), (A-4c), (A-4d), (A-4e), (A-4f), (A-4g), (A-4h), and (A-4i), one of R$^1$ and R$^2$ is —OH and the other is unsubstituted C$_3$-C$_8$ cycloalkyl. In other embodiments, one of R$^1$ and R$^2$ is —OH and the other is substituted C$_3$-C$_8$ cycloalkyl. In some embodiments, one of R$^1$ and R$^2$ is —OH and the other is unsubstituted C$_3$-C$_8$ cycloalkenyl. In other embodiments, one of R$^1$ and R$^2$ is —OH and the other is substituted C$_3$-C$_8$ cycloalkenyl.

In some embodiments of Formula (A), including Formula (A-1a), (A-1b), (A-2a), (A-2b), (A-3a), (A-3b), (A-4a), (A-4b), (A-4c), (A-4d), (A-4e), (A-4f), (A-4g), (A-4h), and (A-4i), R$^3$ is selected from the group consisting of C$_1$-C$_6$alkyl, C$_1$-C$_6$alkoxy, and halogen. In some embodiments, R$^3$ is methyl, ethyl, n-propyl, isopropyl, n-butyl, isobutyl, secbutyl, or tertbutyl. In some embodiments, R$^3$ is methyl, ethyl, isopropyl, or tertbutyl. In some embodiments, R$^3$ is methoxy, ethoxy, propoxy, isoproxy, butoxy, or tertbutoxy. In some embodiments, R$^3$ is F, Cl, Br, or I. In some embodiments, R$^3$ is —OCH$_3$. In some embodiments, R$^3$ is F. In other embodiments, R$^3$ is H.

In some embodiments of Formula (A), including Formula (A-1a), (A-1b), (A-2a), (A-2b), (A-3a), (A-3b), (A-4a), (A-4b), (A-4c), (A-4d), (A-4e), (A-4f), (A-4g), (A-4h), and (A-4i), one of R$^1$ and R$^2$ is —OH and the other is -C(O)H. In some embodiments, R$^1$ is —OH, R$^2$ is —C(O)H, and R$^3$ is H. In some embodiments, R$^1$ is —OH, R$^2$ is —C(O)H, and R$^3$ is unsubstituted C$_1$-C$_6$alkyl. In some embodiments, R$^1$ is —OH, R$^2$ is —C(O)H, and R$^3$ is C$_1$-C$_6$haloalkyl. In some embodiments, R$^1$ is —OH, R$^2$ is —C(O)H, and R$^3$ is unsubstituted C$_1$-C$_6$alkoxy. In some embodiments, R$^1$ is —OH, R$^2$ is —C(O)H, and R$^3$ is C$_1$-C$_6$alkoxy substituted with one or more halogen. In other embodiments, R$^1$ is —OH, R$^2$ is —C(O)H, and R$^3$ is halogen. In certain embodiments, R$^1$ is —OH, R$^2$ is —C(O)H, and R$^3$ is fluoro. In certain embodiments, R$^1$ is —OH, R$^2$ is —C(O)H, and R$^3$ is methyl. In some embodiments, R$^1$ is —OH, R$^2$ is —C(O)H, and R$^3$ is methoxy. In some embodiments, R$^2$ is —OH, R$^1$ is —C(O)H, and R$^3$ is H. In some embodiments, R$^2$ is —OH, R$^1$ is —C(O)H, and R$^3$ is unsubstituted C$_1$-C$_6$alkyl. In some embodiments, R$^2$ is —OH, R$^1$ is —C(O)H, and R$^3$ is C$_1$-C$_6$haloalkyl. In some embodiments, R$^2$ is —OH, R$^1$ is —C(O)H, and R$^3$ is unsubstituted C$_1$-C$_6$alkoxy. In some embodiments, R$^2$ is —OH, R$^1$ is —C(O)H, and R$^3$ is C$_1$-C$_6$alkoxy substituted with one or more halogen. In other embodiments, R$^2$ is —OH, R$^1$ is —C(O)H, and R$^3$ is halogen. In certain embodiments, R$^2$ is —OH, R$^1$ is —C(O)H, and $R^3$ is fluoro. In certain embodiments, $R^2$ is —OH, $R^1$ is —C(O)H, and $R^3$ is methyl. In some embodiments, $R^2$ is —OH, $R^1$ is —C(O)H, and $R^3$ is methoxy.

In some embodiments of Formula (A), including Formula (A-1a), (A-1b), (A-2a), and (A-2b), $G_1$ and $G_2$ are each CH. In some embodiments, $G_1$ is CH and $G_2$ is N. In other embodiments, $G_1$ is N and $G_2$ is CH.

In some embodiments of Formula (A), including Formula (A-1a) and (A-1b), n is 0. In some embodiments, n is 1. In some embodiments, n is 2. In other embodiments, n is 3. In some embodiments, $R^4$ is $C_1$-$C_6$ alkoxy. In some embodiments, $R^4$ is methoxy, ethoxy, propoxy, isopropoxy, butoxy, isobutoxy, secbutoxy, or tertbutoxy. In other embodiments, $R^4$ is

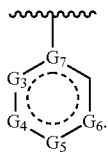

In some embodiments, n is 0 and $R^4$ is alkoxy. In some embodiments, n is 0 and $R^4$ is

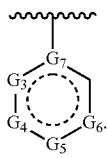

In some embodiments, n is 1 and $R^4$ is alkoxy. In some embodiments, n is 1 and $R^4$ is

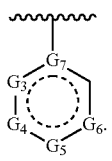

In some embodiments, n is 2 and $R^4$ is alkoxy. In some embodiments, n is 2 and $R^4$ is

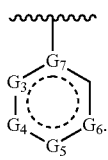

In some embodiments, n is 3 and $R^4$ is alkoxy. In some embodiments, n is 3 and $R^4$ is

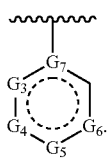

In some embodiments of Formula (A), including Formula (A-1a), (A-1b), (A-2a), and (A-2b), $G_3$ is CH($X_1$—$R^{6a}$), C($X_1$—$R^{6a}$), N, N($X_1$—$R^{6a}$), S, or O; $G_4$ is CH($X_2$—$R^{6b}$), C($X_2$—$R^{6b}$), N, N($X_2$—$R^{6b}$), S, or O; $G_5$ is CH($X_3$—$R^{6c}$), C($X_3$—$R^{6c}$), N, N($X_3$—$R^{6c}$), S, or O; $G_6$ is CH($X_4$—$R^{6d}$) C($X_4$—$R^{6d}$), N, N($X_4$—$R^{6d}$), S, O, or absent; and $G_7$ is N, C, or CH, wherein $G_1$, $G_2$, $G_3$, $G_4$, $G_5$, $G_6$, and $G_7$ each have a charge of zero (e.g., the nitrogen of $G_1$, $G_2$, $G_3$, $G_4$, $G_5$, $G_6$, and $G_7$ is not cationic).

In some embodiments of Formula (A), including Formula (A-1a), (A-1b), (A-2a), and (A-2b),

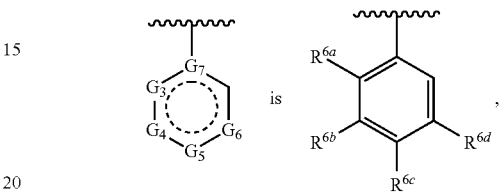

wherein one or more of $R^{6a}$, $R^{6b}$, $R^{6c}$, and $R^{6d}$ is selected from the group consisting of $C_1$-$C_6$alkyl, $C_1$-$C_6$alkoxy, halo, —OH, —$NR^pR^q$, $C_6$-$C_{12}$ aryl, 3- to 10-membered heterocyclyl, 5- to 10-membered heteroaryl, —$C_1$-$C_6$alkyl-5- to 6-membered heterocyclyl, —OC(O)-5- to 6-membered heterocyclyl, —C(O)$R^h$, —S(O)$_2$$NR^{w1}R^{w2}$, —S(O)$_2$$R^y$, and —$NR^{z1}$S(O)$_2$$R^{z2}$.

In some embodiments of Formula (A), including Formula (A-1a), (A-1b), (A-2a), and (A-2b),

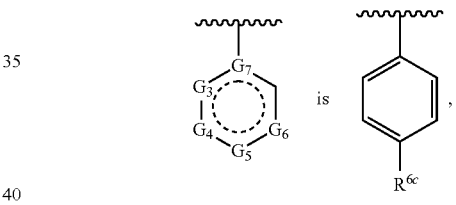

wherein $R^{6c}$ is selected from the group consisting of $C_1$-$C_6$alkyl, $C_1$-$C_6$alkoxy, halo, —OH, —$NR^pR^q$, $C_6$-$C_{12}$ aryl, 3- to 10-membered heterocyclyl, 5- to 10-membered heteroaryl, —$C_1$-$C_6$alkyl-5- to 6-membered heterocyclyl, —OC(O)-5- to 6-membered heterocyclyl, —C(O)$R^h$, —S(O)$_2$$NR^{w1}R^{w2}$, —S(O)$_2$$R^y$, or —$NR^{z1}$S(O)$_2$$R^{z2}$. In some embodiments, $R^{6c}$ is unsubstituted $C_1$-$C_6$alkyl. For instance, in some embodiments, $R^{6c}$ is methyl, ethyl, propyl, isopropyl, butyl, isobutyl, secbutyl, and tertbutyl. In some embodiments, $R^{6c}$ is $C_1$-$C_6$alkyl substituted with one or more groups selected from the group consisting of $C_3$-$C_8$ cycloalkyl and halogen. In some embodiments, $R^{6c}$ is $C_1$-$C_6$alkoxy. For instance, in some embodiments, $R^{6c}$ is methoxy, ethoxy, propoxy, isopropoxy, butoxy, isobutoxy, secbutoxy, and tertbutoxy. In some embodiments, $R^{6c}$ is $C_1$-$C_6$alkoxy substituted with one or more groups selected from the group consisting of $C_3$-$C_8$ cycloalkyl and halogen. In some embodiments, $R^{6c}$ is halo. For instance, in some embodiments, $R^{6c}$ is fluoro, chloro, or bromo. In other embodiments, $R^{6c}$ is $C_1$-$C_6$haloalkyl. For instance, in some embodiments, $R^{6c}$ is fluoroethyl, trifluoromethyl, difluoromethyl, trifluoromethyl, and trichloromethyl. In some embodiments, $R^{6c}$ is —C(O)$R^h$, wherein $R^h$ is H, $C_1$-$C_6$alkyl, $C_1$-$C_6$alkoxy, $C_3$-$C_8$cycloalkyl, or —NR'$R^s$. For instance, in some embodiments, $R^{6c}$ is —C(O)H, —C(O)CH$_3$, —C(O)OC(CH$_3$)$_3$, or —C(O)-cyclopropyl. In some embodiments, $R^{6c}$ is an unsubstituted 5- to 6-membered heterocycle. In some embodiments, $R^{6c}$ is a 5- to 6-membered heterocycle, substituted with one or more groups selected from the group consisting of $C_1$-$C_6$alkyl, $C_1$-$C_6$alkoxy, halo, —OH, $C_1$-$C_6$alkyl-OH, =O, and =S. In some embodiments, $R^{6c}$ is pyrrolidinyl, pyrazolidinyl, imidazolidinyl, tetrahydrofuranyl, 1,3-dioxolanyl, tetrahydrothiophenyl, oxathiolanyl, sulfolanyl, piperidinyl, piperazinyl, tetrahydropyranyl, dioxanyl, thianyl, dithianyl, trithianyl, morpholinyl, or thiomorpholinyl, each optionally substituted with one or more substituents selected from the group consisting of $C_1$-$C_6$alkyl, $C_1$-$C_6$alkoxy, halo, —OH, $C_1$-$C_6$alkyl-OH, =O, and =S. In some embodiments, $R^{6c}$ is pyrrolidinyl, pyrazolidinyl, imidazolidinyl, tetrahydrofuranyl, 1,3-dioxolanyl, tetrahydrothiophenyl, oxathiolanyl, sulfolanyl, piperidinyl, piperazinyl, tetrahydropyranyl, dioxanyl, thianyl, dithianyl, trithianyl, morpholinyl, or thiomorpholinyl. In some embodiments, $R^{6c}$ is pyrrolidinyl. In certain embodiments, $R^{6c}$ is 4-pyrrolidin-1-yl. In some embodiments, $R^{6c}$ is an unsubstituted 5- to 10-membered heteroaryl. In some embodiments, $R^{6c}$ is a 5- to 10-membered heteroaryl, substituted with one or more groups selected from the group consisting of $C_1$-$C_6$alkyl, $C_1$-$C_6$alkoxy, —OH, and $C_1$-$C_6$alkyl-OH. In some embodiments, $R^{6c}$ is pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridyl, pyridazinyl, pyrimidinyl, pyrazinyl, triazinyl, or tetrazinyl, each substituted with one or more substituents selected from the group consisting of $C_1$-$C_6$alkyl, $C_1$-$C_6$alkoxy, —OH, and $C_1$-$C_6$alkyl-OH. In some embodiments, $R^{6c}$ is pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridyl, pyridazinyl, pyrimidinyl, pyrazinyl, triazinyl, or tetrazinyl.

In some embodiments of Formula (A), including Formula (A-1a), (A-1b), (A-2a), and (A-2b),

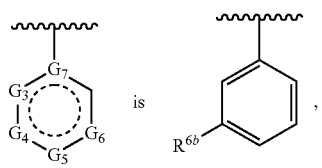 is 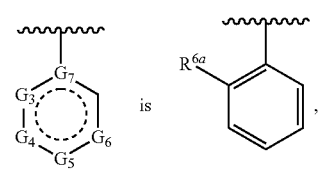, wherein $R^{6b}$ is selected from the group consisting of $C_1$-$C_6$alkyl, $C_1$-$C_6$alkoxy, halo, —OH, —$NR^pR^q$, $C_6$-$C_{12}$ aryl, 3- to 10-membered heterocyclyl, 5- to 10-membered heteroaryl, —$C_1$-$C_6$alkyl-5- to 6-membered heterocyclyl, —OC(O)-5- to 6-membered heterocyclyl, —C(O)$R^h$, —S(O)$_2$NR$^{w1}$R$^{w2}$, —S(O)$_2$R$^y$, or —NR$^{z1}$S(O)$_2$R$^{z2}$. In some embodiments, $R^{6b}$ is unsubstituted $C_1$-$C_6$alkyl. For instance, in some embodiments, $R^{6b}$ is methyl, ethyl, propyl, isopropyl, butyl, isobutyl, secbutyl, and tertbutyl. In some embodiments, $R^{6b}$ is $C_1$-$C_6$alkyl substituted with one or more groups selected from the group consisting of $C_3$-$C_8$ cycloalkyl and halogen. In some embodiments, $R^{6b}$ is $C_1$-$C_6$alkoxy. For instance, in some embodiments, $R^{6b}$ is methoxy, ethoxy, propoxy, isopropoxy, butoxy, isobutoxy, secbutoxy, and tertbutoxy. In some embodiments, $R^{6b}$ is $C_1$-$C_6$alkoxy substituted with one or more groups selected from the group consisting of $C_3$-$C_8$ cycloalkyl and halogen. In some embodiments, $R^{6b}$ is halo. For instance, in some embodiments, $R^{6b}$ is fluoro, chloro, or bromo. In other embodiments, $R^{6b}$ is $C_1$-$C_6$haloalkyl. For instance, in some embodiments, $R^{6b}$ is fluoroethyl, trifluoromethyl, difluoromethyl, trifluoroethyl, and trichloromethyl. In some embodiments, $R^{6b}$ is —C(O)$R^h$, wherein $R^h$ is H, $C_1$-$C_6$alkyl, $C_1$-$C_6$alkoxy, $C_3$-$C_8$cycloalkyl, or —NR$^r$R$^s$. For instance, in some embodiments, $R^{6b}$ is —C(O)H, —C(O)CH$_3$, —C(O)OC(CH$_3$)$_3$, or —C(O)-cyclopropyl. In some embodiments, $R^{6b}$ is an unsubstituted 5- to 6-membered heterocycle. In some embodiments, $R^{6b}$ is a 5- to 6-membered heterocycle, substituted with one or more groups selected from the group consisting of $C_1$-$C_6$alkyl, $C_1$-$C_6$alkoxy, halo, —OH, $C_1$-$C_6$alkyl-OH, =O, and =S. In some embodiments, $R^{6b}$ is pyrrolidinyl, pyrazolidinyl, imidazolidinyl, tetrahydrofuranyl, 1,3-dioxolanyl, tetrahydrothiophenyl, oxathiolanyl, sulfolanyl, piperidinyl, piperazinyl, tetrahydropyranyl, dioxanyl, thianyl, dithianyl, trithianyl, morpholinyl, or thiomorpholinyl, each substituted with one or more substituents selected from the group consisting of $C_1$-$C_6$alkyl, $C_1$-$C_6$alkoxy, halo, —OH, $C_1$-$C_6$alkyl-OH, =O, and =S. In some embodiments, $R^{6b}$ is pyrrolidinyl, pyrazolidinyl, imidazolidinyl, tetrahydrofuranyl, 1,3-dioxolanyl, tetrahydrothiophenyl, oxathiolanyl, sulfolanyl, piperidinyl, piperazinyl, tetrahydropyranyl, dioxanyl, thianyl, dithianyl, trithianyl, morpholinyl, or thiomorpholinyl. In some embodiments, $R^{6b}$ is an unsubstituted 5- to 10-membered heteroaryl. In some embodiments, $R^{6b}$ is a 5- to 10-membered heteroaryl, substituted with one or more groups selected from the group consisting of $C_1$-$C_6$alkyl, $C_1$-$C_6$alkoxy, —OH, and $C_1$-$C_6$alkyl-OH. In some embodiments, $R^{6b}$ is pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridyl, pyridazinyl, pyrimidinyl, pyrazinyl, triazinyl, or tetrazinyl, each substituted with one or more groups selected from the group consisting of $C_1$-$C_6$alkyl, $C_1$-$C_6$alkoxy, —OH, and $C_1$-$C_6$alkyl-OH. In some embodiments, $R^{6b}$ is pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridyl, pyridazinyl, pyrimidinyl, pyrazinyl, triazinyl, or tetrazinyl.

In some embodiments of Formula (A), including Formula (A-1a), (A-1b), (A-2a), and (A-2b), wherein $R^{6a}$ is selected from the group consisting of $C_1$-$C_6$alkyl, $C_1$-$C_6$alkoxy, halo, —OH, —$NR^pR^q$, $C_6$-$C_{12}$ aryl, 3- to 10-membered heterocyclyl, 5- to 10-membered heteroaryl, —$C_1$-$C_6$alkyl-5- to 6-membered heterocyclyl, —OC(O)-5- to 6-membered heterocyclyl, —C(O)$R^h$, —S(O)$_2$NR$^{w1}$R$^{w2}$, —S(O)$_2$R$^y$, or —NR$^{z1}$S(O)$_2$R$^{z2}$. In some embodiments, $R^{6a}$ is unsubstituted $C_1$-$C_6$alkyl. For instance, in some embodiments, $R^{6a}$ is methyl, ethyl, propyl, isopropyl, butyl, isobutyl, secbutyl, and tertbutyl. In some embodiments, $R^{6a}$ is $C_1$-$C_6$alkyl substituted with one or more groups selected from the group consisting of $C_3$-$C_8$ cycloalkyl and halogen. In some embodiments, $R^{6a}$ is $C_1$-$C_6$alkoxy. For instance, in some embodiments, $R^{6a}$ is methoxy, ethoxy, propoxy, isopropoxy, butoxy, isobutoxy, secbutoxy, and tertbutoxy. In some embodiments, $R^{6a}$ is $C_1$-$C_6$alkoxy substituted with one or more groups selected from the group consisting of $C_3$-$C_8$ cycloalkyl and halogen. In some embodiments, $R^{6a}$ is halo. For instance, in some embodiments, $R^{6a}$ is fluoro, chloro, or bromo. In other embodiments, $R^{6a}$ is $C_1$-$C_6$haloalkyl. For instance, in some embodiments, $R^{6a}$ is fluoroethyl, trifluoromethyl, difluoromethyl, trifluoroethyl, and trichloromethyl. In some embodiments, $R^{6a}$ is —C(O)$R^h$, wherein $R^h$ is H, $C_1$-$C_6$alkyl, $C_1$-$C_6$alkoxy, $C_3$-$C_8$cycloalkyl, or —NR'$R^s$. For instance, in some embodiments, $R^{6a}$ is —C(O)H, —C(O)CH$_3$, —C(O)OC(CH$_3$)$_3$, or —C(O)-cyclopropyl. In some embodiments, $R^{6a}$ is an unsubstituted 5- to 6-membered heterocycle. In some embodiments, $R^{6a}$ is a 5- to 6-membered heterocycle, substituted with one or more groups selected from the group consisting of $C_1$-$C_6$alkyl, $C_1$-$C_6$alkoxy, halo, —OH, $C_1$-$C_6$alkyl-OH, =O, and =S. In some embodiments, $R^{6a}$ is pyrrolidinyl, pyrazolidinyl, imidazolidinyl, tetrahydrofuranyl, 1,3-dioxolanyl, tetrahydrothiophenyl, oxathiolanyl, sulfolanyl, piperidinyl, piperazinyl, tetrahydropyranyl, dioxanyl, thianyl, dithianyl, trithianyl, morpholinyl, or thiomorpholinyl, each substituted with one or more substituents selected from the group consisting of $C_1$-$C_6$alkyl, $C_1$-$C_6$alkoxy, halo, —OH, $C_1$-$C_6$alkyl-OH, =O, and =S. In some embodiments, $R^{6a}$ is pyrrolidinyl, pyrazolidinyl, imidazolidinyl, tetrahydrofuranyl, 1,3-dioxolanyl, tetrahydrothiophenyl, oxathiolanyl, sulfolanyl, piperidinyl, piperazinyl, tetrahydropyranyl, dioxanyl, thianyl, dithianyl, trithianyl, morpholinyl, or thiomorpholinyl. In some embodiments, $R^{6a}$ is an unsubstituted 5- to 10-membered heteroaryl. In some embodiments, $R^{6a}$ is a 5- to 10-membered heteroaryl, substituted with one or more groups selected from the group consisting of $C_1$-$C_6$alkyl, $C_1$-$C_6$alkoxy, —OH, and $C_1$-$C_6$alkyl-OH. In some embodiments, $R^{6a}$ is pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridyl, pyridazinyl, pyrimidinyl, pyrazinyl, triazinyl, or tetrazinyl, each substituted with one or more substituents selected from the group consisting of $C_1$-$C_6$alkyl, $C_1$-$C_6$alkoxy, —OH, and $C_1$-$C_6$alkyl-OH. In some embodiments, $R^{6a}$ is pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridyl, pyridazinyl, pyrimidinyl, pyrazinyl, triazinyl, or tetrazinyl.

In some embodiments of Formula (A), including Formula (A-1a), (A-1b), (A-2a), and (A-2b),

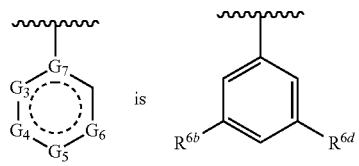

wherein $R^{6b}$ and $R^{6d}$ are each independently selected from the group consisting of $C_1$-$C_6$alkyl, $C_1$-$C_6$alkoxy, halo, —OH, —NR$^p$R$^q$, $C_6$-$C_{12}$ aryl, 3- to 10-membered heterocyclyl, 5- to 10-membered heteroaryl, —$C_1$-$C_6$alkyl-5- to 6-membered heterocyclyl, —OC(O)-5- to 6-membered heterocyclyl, —C(O)$R^h$, —S(O)$_2$NR$^{w1}$R$^{w2}$, —S(O)$_2$R$^y$, or —NR$^{z1}$S(O)$_2$R$^{z2}$. In some embodiments,

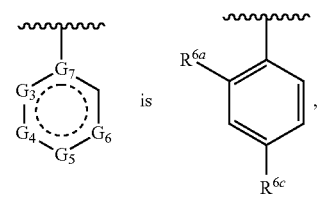

wherein $R^{6a}$ and $R^{6c}$ are each independently selected from the group consisting of $C_1$-$C_6$alkyl, $C_1$-$C_6$alkoxy, halo, —OH, —NR$^p$R$^q$, $C_6$-$C_{12}$ aryl, 3- to 10-membered heterocyclyl, 5- to 10-membered heteroaryl, —$C_1$-$C_6$alkyl-5- to 6-membered heterocyclyl, —OC(O)-5- to 6-membered heterocyclyl, —C(O)$R^h$, —S(O)$_2$NR$^{w1}$R$^{w2}$, —S(O)$_2$R$^y$, or —NR$^{z1}$S(O)$_2$R$^{z2}$. In some embodiments,

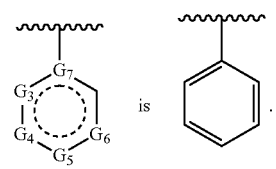

In some embodiments of Formula (A), including Formula (A-1a), (A-1b), (A-2a), and (A-2b),

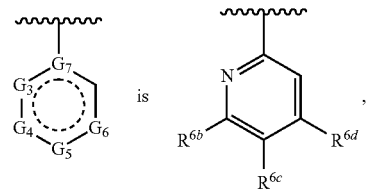

wherein one or more of $R^{6b}$, $R^{6c}$, and $R^{6d}$ is selected from the group consisting of $C_1$-$C_6$alkyl, $C_1$-$C_6$haloalkyl, halo, $C_6$-$C_{12}$ aryl, 3- to 10-membered heterocyclyl, and 5- to 10-membered heteroaryl. In some embodiments,

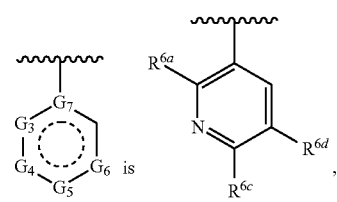

wherein one or more of $R^{6a}$, $R^{6c}$, and $R^{6d}$ is selected from the group consisting of $C_1$-$C_6$alkyl, $C_1$-$C_6$haloalkyl, halo, $C_6$-$C_{12}$ aryl, 3- to 10-membered heterocyclyl, and 5- to 10-membered heteroaryl. In some embodiments,

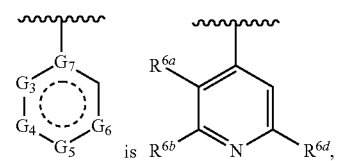

wherein one or more of $R^{6a}$, $R^{6b}$, and $R^{6d}$ is selected from the group consisting of $C_1$-$C_6$alkyl, $C_1$-$C_6$haloalkyl, halo, $C_6$-$C_{12}$ aryl, 3- to 10-membered heterocyclyl, and 5- to 10-membered heteroaryl. In some embodiments,

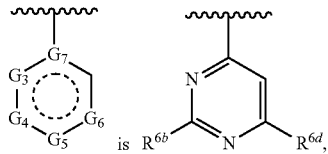

wherein one or both of $R^{6b}$ and $R^{6d}$ is selected from the group consisting of $C_1$-$C_6$alkyl, $C_1$-$C_6$haloalkyl, halo, $C_6$-$C_{12}$ aryl, 3- to 10-membered heterocyclyl, and 5- to 10-membered heteroaryl. In some embodiments,

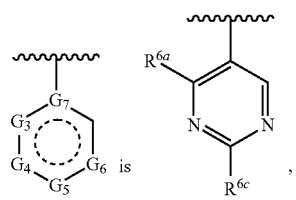

wherein one or both of $R^{6a}$ and $R^{6c}$ is selected from the group consisting of $C_1$-$C_6$alkyl, $C_1$-$C_6$haloalkyl, halo, $C_6$-$C_{12}$ aryl, 3- to 10-membered heterocyclyl, and 5- to 10-membered heteroaryl. In some embodiments,

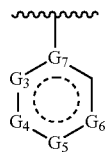

is selected from the group consisting of

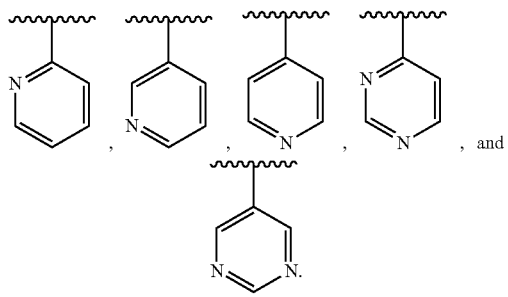

In some embodiments of Formula (A), including Formula (A-1a), (A-1b), (A-2a), and (A-2b),

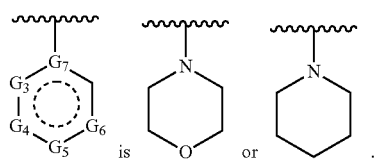

In some embodiments,

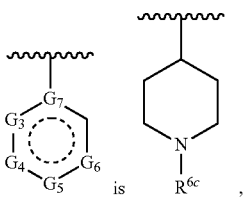

wherein $R^{6c}$ is selected from the group consisting of hydrogen, $C_1$-$C_6$alkyl, $C_1$-$C_6$alkoxy, halo, —OH, —$NR^pR^q$, $C_6$-$C_{12}$ aryl, 3- to 10-membered heterocyclyl, 5- to 10-membered heteroaryl, —$C_1$-$C_6$alkyl-5- to 6-membered heterocyclyl, —OC(O)-5- to 6-membered heterocyclyl, —C(O)$R^h$, —S(O)$_2$$NR^{w1}R^{w2}$, —S(O)$_2$$R^y$, and —$NR^{z1}$S(O)$_2$$R^{z2}$. In certain embodiments, $R^{6c}$ is —C(O)OC(CH$_3$)$_3$.

In some embodiments of Formula (A), including Formula (A-1a), (A-1b), (A-2a), and (A-2b),

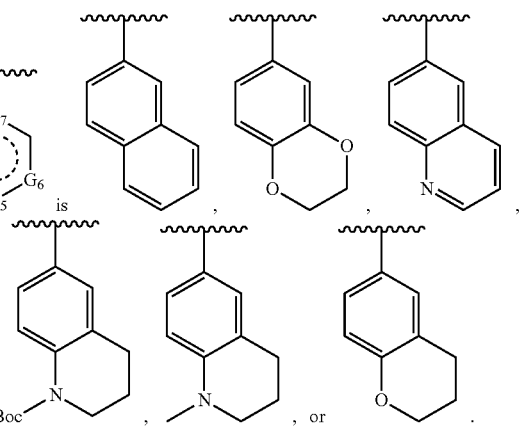

In some embodiments,

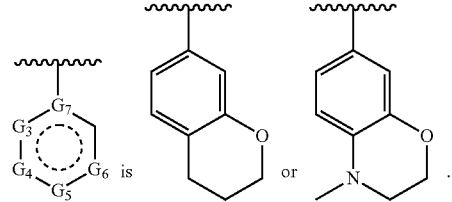

In any of the foregoing embodiments of Formula (A), including Formula (A-1a), (A-1b), (A-2a), and (A-2b), one or more of $R^{6a}$, $R^{6b}$, $R^{6c}$, and $R^{6d}$ is selected from the group consisting of $C_1$-$C_6$alkyl, $C_1$-$C_6$haloalkyl, halo, $C_6$-$C_{12}$ aryl, 3- to 10-membered heterocyclyl, and 5- to 10-membered heteroaryl. In some embodiments, one or more of $R^{6a}$, $R^{6b}$, $R^{6c}$, and $R^{6d}$ is $C_6$-$C_{12}$ aryl, unsubstituted or substituted with one or more groups selected from the group consisting of $C_1$-$C_6$alkyl, $C_1$-$C_6$alkoxy, —OH, and $C_1$-$C_6$alkyl-OH. For instance, in some embodiments, one of $R^{6a}$, $R^{6b}$, $R^{6c}$, and $R^{6d}$ is phenyl or naphthyl. In some embodiments, one or more of $R^{6a}$, $R^{6b}$, $R^{6c}$, and $R^{6d}$ is 3- to 10-membered heterocyclyl, unsubstituted or substituted with one or more groups selected from the group consisting of $C_1$-$C_6$alkyl, $C_1$-$C_6$alkoxy, halo, —OH, $C_1$-$C_6$alkyl-OH, =O, and =S.

For instance, in some embodiments, one of $R^{6a}$, $R^{6b}$, $R^{6c}$, and $R^{6d}$ is pyrrolidinyl, pyrazolidinyl, imidazolidinyl, tetrahydrofuranyl, 1,3-dioxolanyl, tetrahydrothiophenyl, oxathiolanyl, sulfolanyl, piperidinyl, piperazinyl, tetrahydropyranyl, dioxanyl, thianyl, dithianyl, trithianyl, morpholinyl, thiomorpholinyl, tetrahydroquinolinyl, tetrahydroisoquinolinyl, decahydroquinolinyl, decahydroisoquinolinyl, indolinyl, isoindolinyl, tetrahydronaphthyridinyl or hexahydrobenzoimidazolyl, each independently unsubstituted or substituted with one or more groups selected from the group consisting of $C_1$-$C_6$alkyl, $C_1$-$C_6$alkoxy, halo, —OH, $C_1$-$C_6$alkyl-OH, =O, and =S.

In some embodiments of Formula (A), including Formula (A-1a), (A-1b), (A-2a), and (A-2b), one of $R^{6a}$, $R^{6b}$, $R^{6c}$, and $R^{6d}$ is selected from the group consisting of $C_1$-$C_6$alkyl, $C_1$-$C_6$haloalkyl, halo, $C_6$-$C_{12}$ aryl, 3- to 10-membered heterocyclyl, and 5- to 10-membered heteroaryl. In certain embodiments, one of $R^{6a}$, $R^{6b}$, $R^{6c}$, and $R^{6d}$ is selected from the group consisting of methyl, ethyl, F, Cl, —$CF_3$, pyrrolidinyl, piperidinyl, morpholinyl, piperazinyl, pyrazolyl, and triazolyl. In certain embodiments, one of $R^{6a}$, $R^{6b}$, $R^{6c}$, and $R^{6d}$ is selected from the group consisting of pyrrolidinyl, piperidinyl, morpholinyl, piperazinyl, pyrazolyl, and triazolyl, each optionally substituted with one or more groups selected from the group consisting of $C_1$-$C_6$alkyl, $C_1$-$C_6$alkoxy, halo, —OH, $C_1$-$C_6$alkyl-OH, =O, and =S. In some embodiments, two or three of $R^{6a}$, $R^{6b}$, $R^{6c}$, and $R^{6d}$ is selected from the group consisting of methyl, ethyl, F, Cl, —$CF_3$, pyrrolidinyl, piperidinyl, morpholinyl, piperazinyl, pyrazolyl, and triazolyl. In some embodiments, one of $R^{6a}$, $R^{6b}$, $R^{6c}$, and $R^{6d}$ is selected from the group consisting of methyl, ethyl, methoxy, F, Cl, —$CF_3$,

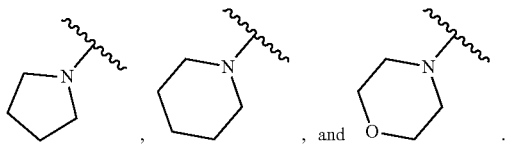 [SMILES: *N1CCCC1 ; *N1CCCCC1 ; *N1CCOCC1]

In some embodiments, one of $R^{6a}$, $R^{6b}$, $R^{6c}$, and $R^{6d}$ is selected from the group consisting of

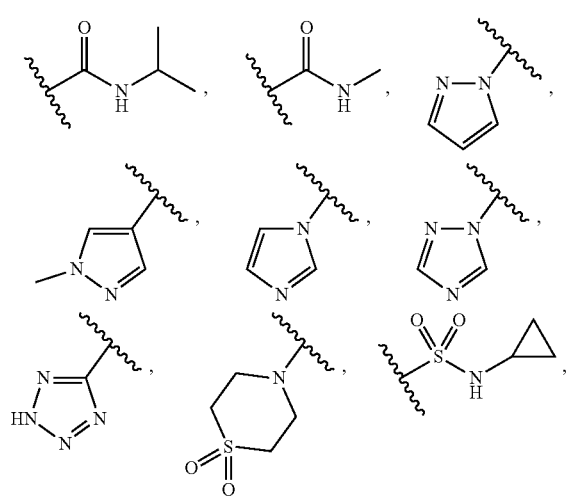

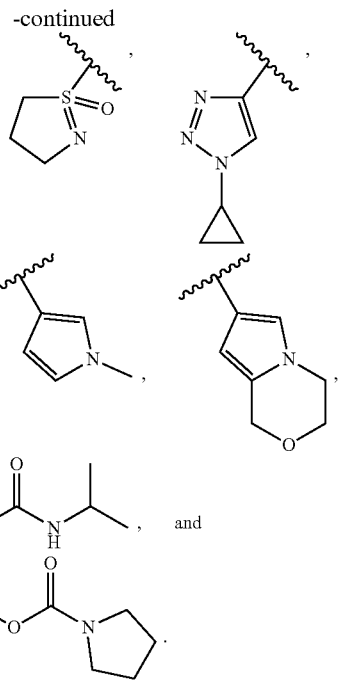

In other embodiments of Formula (A), including Formula (A-1a), (A-1b), (A-2a), and (A-2b), $R^{6a}$, $R^{6b}$, $R^{6c}$, and $R^{6d}$ are each H.

In some embodiments of Formula (A), including Formula (A-1a), (A-1b), (A-2a), (A-2b), (A-3a), and (A-3b), $G_3$ is $CH(X_1$—$R^{6a})$, $C(X_1$—$R^{6a})$, or $N(X_1$—$R^{6a})$, $X_1$ is absent,

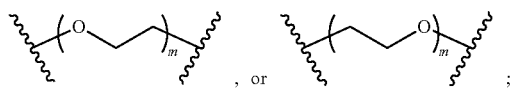

and $R^{6a}$ is hydrogen, $C_1$-$C_6$alkyl, $C_1$-$C_6$alkoxy, halo, —OH, —$NR^pR^q$, aryl, heterocyclyl, heteroaryl, —$C_1$-$C_6$alkyl-heterocyclyl, —OC(O)-heterocyclyl, —C(O)$R^h$, —S(O)$_2$NR$^{w1}$R$^{w2}$, —S(O)$_2$R$^y$, or —NR$^{z1}$S(O)$_2$R$^{z2}$, wherein the $C_1$-$C_6$alkyl and $C_1$-$C_6$alkoxy of $R^{6a}$ are each independently unsubstituted or substituted with one or more groups selected from the group consisting of cycloalkyl and halogen; the aryl and heteroaryl of $R^{6a}$ are each independently unsubstituted or substituted with one or more groups selected from the group consisting of $C_1$-$C_6$alkyl, $C_1$-$C_6$alkoxy, $C_3$-$C_8$cycloalkyl, —OH, and $C_1$-$C_6$alkyl-OH; and the heterocyclyl, —$C_1$-$C_6$alkyl-heterocyclyl, and —OC(O)-heterocyclyl of $R^{6a}$ are each independently unsubstituted or substituted with one or more groups selected from the group consisting of $C_1$-$C_6$alkyl, $C_1$-$C_6$alkoxy, halo, —OH, $C_1$-$C_6$alkyl-OH, =O, and =S; $R^h$ is selected from the group consisting of H, $C_1$-$C_6$alkyl, $C_1$-$C_6$alkoxy, and $C_3$-$C_8$cycloalkyl, and —NR'R$^s$; $R^p$ is H or $C_1$-$C_6$alkyl; $R^q$ is $C_2$-$C_3$alkyl, —C(O)$R^t$, —C(O)OR$^u$, —C(O)NR$^v$; R$^r$, R$^s$, R$^{w1}$, and R$^{z1}$ each independently selected from H and $C_1$-$C_6$alkyl; and R$^t$, R$^u$, R$^v$, R$^{w2}$, R$^y$, and R$^{z2}$ are each independently selected from H, $C_1$-$C_6$alkyl, unsubstituted or substituted $C_3$-$C_8$cycloalkyl, and unsubstituted or substituted heterocyclyl.

In some embodiments of Formula (A), including Formula (A-1a), (A-1b), (A-2a), (A-2b), (A-3a), and (A-3b), $G_3$ is $CH(X_1$—$R^{6a})$ or $C(X_1$—$R^{6a})$, wherein Xi is absent; $R^{6a}$ is hydrogen, $C_1$-$C_6$alkyl, $C_1$-$C_6$alkoxy, halo, —OH, —NR$^p$R$^q$, aryl, heterocyclyl, heteroaryl, or —C(O)R$^h$, wherein $C_1$-$C_6$alkyl and $C_1$-$C_6$alkoxy are unsubstituted or substituted with $C_3$-$C_8$ cycloalkyl or halogen; R$^p$ is H or $C_1$-$C_6$alkyl; R$^q$ is $C_2$-$C_3$alkyl; and R$^h$ is selected from the group consisting of H, $C_1$-$C_6$alkyl, $C_1$-$C_6$alkoxy, or $C_3$-$C_8$ cycloalkyl. In some embodiments, $G_3$ is CH($X_1$—R$^{6a}$) or C($X_1$—R$^{6a}$), wherein $X_1$ is

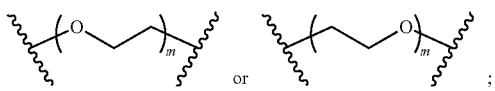

m is 1-6; R$^{6a}$ is hydrogen, $C_1$-$C_6$alkyl, $C_1$-$C_6$alkoxy, halo, —OH, —NR$^p$R$^q$, aryl, heterocyclyl, heteroaryl, or —C(O)R$^h$, wherein $C_1$-$C_6$alkyl and $C_1$-$C_6$alkoxy are unsubstituted or substituted with $C_3$-$C_8$ cycloalkyl or halogen; R$^p$ is H or $C_1$-$C_6$alkyl; R$^q$ is $C_2$-$C_3$alkyl; and R$^h$ is selected from the group consisting of H, $C_1$-$C_6$alkyl, $C_1$-$C_6$alkoxy, or $C_3$-$C_8$ cycloalkyl. In some embodiments, $G_3$ is N or N($X_1$—R$^{6a}$), wherein Xi is absent; R$^{6a}$ is hydrogen, $C_1$-$C_6$alkyl, $C_1$-$C_6$alkoxy, halo, —OH, —NR$^p$R$^q$, aryl, heterocyclyl, heteroaryl, or —C(O)R$^h$, wherein $C_1$-$C_6$alkyl and $C_1$-$C_6$alkoxy are unsubstituted or substituted with $C_3$-$C_8$ cycloalkyl or halogen; R$^p$ is H or $C_1$-$C_6$alkyl; R$^q$ is $C_2$-$C_3$alkyl; and R$^h$ is selected from the group consisting of H, $C_1$-$C_6$alkyl, $C_1$-$C_6$alkoxy, or $C_3$-$C_8$ cycloalkyl. In some embodiments, $G_3$ is N or N($X_1$—R$^{6a}$), wherein $X_1$ is

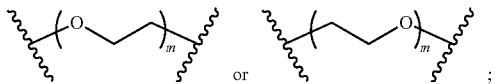

m is 1-6; R$^{6a}$ is hydrogen, $C_1$-$C_6$alkyl, $C_1$-$C_6$alkoxy, halo, —OH, —NR$^p$R$^q$, aryl, heterocyclyl, heteroaryl, or —C(O)R$^h$, wherein $C_1$-$C_6$alkyl and $C_1$-$C_6$alkoxy are unsubstituted or substituted with $C_3$-$C_8$ cycloalkyl or halogen; R$^p$ is H or $C_1$-$C_6$alkyl; R$^q$ is $C_2$-$C_3$alkyl; and R$^h$ is selected from the group consisting of H, $C_1$-$C_6$alkyl, $C_1$-$C_6$alkoxy, or $C_3$-$C_8$ cycloalkyl. In some of any of the preceding embodiments, R$^{6a}$ is methyl, ethyl, n-propyl, isopropyl, n-butyl, isobutyl, secbutyl, or tertbutyl. In some of any of the preceding embodiments, R$^{6a}$ is $C_1$-$C_6$ alkyl substituted with $C_3$-$C_8$ cycloalkyl or halogen. In some of any of the preceding embodiments, R$^{6a}$ is methoxy, ethoxy, n-propoxy, isopropoxy, n-butoxy, isobutoxy, secbutoxy, or tertbutoxy. In some of any of the preceding embodiments, R$^{6a}$ is $C_1$-$C_6$alkoxy substituted with $C_3$-$C_8$ cycloalkyl or halogen. In some of any of the preceding embodiments, R$^{6a}$ is fluoro, chloro, bromo, or iodo. In some of any of the preceding embodiments, R$^{6a}$ is —N(CH$_2$CH$_3$)$_2$, —N(CH$_2$CH$_2$CH$_3$)$_2$, or —N(CH$_2$CH$_3$)(CH$_2$CH$_2$CH$_3$). In some of any of the preceding embodiments, R$^{6a}$ is phenyl or naphthyl. In some of any of the preceding embodiments, R$^{6a}$ is a 5- to 14-membered heterocyclyl. In some embodiments, R$^{6a}$ is a 5- to 6-membered heterocyclyl. In some of any of the preceding embodiments, R$^{6a}$ is pyrrolidinyl, pyrazolidinyl, imidazolidinyl, tetrahydrofuranyl, 1,3-dioxolanyl, tetrahydrothiophenyl, oxathiolanyl, sulfolanyl, piperidinyl, piperazinyl, tetrahydropyranyl, dioxanyl, thianyl, dithianyl, trithianyl, morpholinyl, or thiomorpholinyl. In some of any of the preceding embodiments, R$^{6a}$ is a 5- to 14-membered heteroaryl. In some embodiments, R$^{6a}$ is a 5- to 6-membered heteroaryl. In some of any of the preceding embodiments, R$^{6a}$ is pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridyl, pyridazinyl, pyrimidinyl, pyrazinyl, triazinyl, or tetrazinyl. In some of any of the preceding embodiments, R$^{6a}$ is aryl, heterocyclyl, or heteroaryl, each substituted with $C_1$-$C_6$alkyl. In some of any of the preceding embodiments, R$^{6a}$ is —C(O)H, —C(O)$C_1$-$C_6$alkyl, —C(O)$C_1$-$C_6$alkoxy, or —C(O)$C_3$-$C_8$cycloalkyl. In some of any of the preceding embodiments, R$^{6a}$ is —OH, —NR$^p$R$^q$, aryl, heterocyclyl, heteroaryl, unsubstituted $C_1$-$C_6$alkoxy, or $C_1$-$C_6$alkoxy substituted with $C_3$-$C_8$ cycloalkyl or halogen. In some of any of the preceding embodiments, R$^{6a}$ is hydrogen, —CH$_3$, —OH, —OCH$_3$, —C(O)OC(CH$_3$)$_3$, —N(CH$_2$CH$_3$)$_2$, phenyl, morpholinyl, piperidinyl, piperazinyl, 4-ethylpiperazinyl, pyrrolidinyl, pyrazolyl, cyclopropylmethoxy, or cyclopropanecarbonyl. In some embodiments, $G_3$ is S. In other embodiments, $G_3$ is O.

In some embodiments of Formula (A), including Formula (A-1a), (A-1b), (A-2a), (A-2b), (A-3a), and (A-3b) $G_4$ is CH($X_2$—R$^{6b}$), C($X_2$—R$^{6b}$), or N($X_2$—R$^{6b}$), wherein $X_2$ is absent,

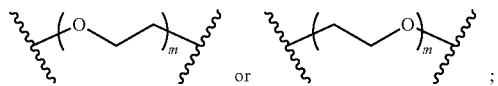

R$^{6b}$ is hydrogen, $C_1$-$C_6$alkyl, $C_1$-$C_6$alkoxy, halo, —OH, —NR$^p$R$^q$, aryl, heterocyclyl, heteroaryl, —$C_1$-$C_6$alkyl-heterocyclyl, —OC(O)-heterocyclyl, —C(O)R$^h$, —S(O)$_2$NR$^{w1}$R$^{w2}$, —S(O)$_2$R$^y$, or —NR$^{z1}$S(O)$_2$R$^{z2}$, wherein the $C_1$-$C_6$alkyl and $C_1$-$C_6$alkoxy of R$^{6b}$ are each independently unsubstituted or substituted with one or more groups selected from the group consisting of cycloalkyl and halogen; the aryl and heteroaryl of R$^{6b}$ are each independently unsubstituted or substituted with one or more groups selected from the group consisting of $C_1$-$C_6$alkyl, $C_1$-$C_6$alkoxy, $C_3$-$C_8$cycloalkyl, —OH, and $C_1$-$C_6$alkyl-OH; and the heterocyclyl, —$C_1$-$C_6$alkyl-heterocyclyl, and —OC(O)-heterocyclyl of R$^{6b}$ are each independently unsubstituted or substituted with one or more groups selected from the group consisting of $C_1$-$C_6$alkyl, $C_1$-$C_6$alkoxy, halo, —OH, $C_1$-$C_6$alkyl-OH, =O, and =S; R$^h$ is selected from the group consisting of H, $C_1$-$C_6$alkyl, $C_1$-$C_6$alkoxy, and $C_3$-$C_8$cycloalkyl, and —NR$^r$R$^s$; R$^p$ is H or $C_1$-$C_6$alkyl; R$^q$ is $C_2$-$C_3$alkyl, —C(O)R$^t$, —C(O)OR$^u$, —C(O)NR$^v$; R$^r$, R$^s$, R$^{w1}$, and R$^{z1}$ each independently selected from H and $C_1$-$C_6$alkyl; and R$^t$, R$^u$, R$^v$, R$^{w2}$, R$^y$, and R$^{z2}$ are each independently selected from H, $C_1$-$C_6$alkyl, unsubstituted or substituted $C_3$-$C_8$cycloalkyl, and unsubstituted or substituted heterocyclyl.

In some embodiments of Formula (A), including Formula (A-1a), (A-1b), (A-2a), (A-2b), (A-3a), and (A-3b), $G_4$ is CH($X_2$—R$^{6b}$) or C($X_2$—R$^{6b}$), wherein $X_2$ is absent; R$^{6b}$ is hydrogen, $C_1$-$C_6$alkyl, $C_1$-$C_6$alkoxy, halo, —OH, —NR$^p$R$^q$, aryl, heterocyclyl, heteroaryl, or —C(O)R$^h$, wherein $C_1$-$C_6$alkyl and $C_1$-$C_6$alkoxy are unsubstituted or substituted with $C_3$-$C_8$ cycloalkyl or halogen; R$^p$ is H or $C_1$-$C_6$alkyl; R$^q$ is $C_2$-$C_3$alkyl; and R$^h$ is selected from the group consisting of H, $C_1$-$C_6$alkyl, $C_1$-$C_6$alkoxy, or $C_3$-$C_8$ cycloalkyl. In some embodiments, $G_4$ is CH($X_2$—R$^{6b}$) or C($X_2$—R$^{6b}$), wherein $X_2$ is

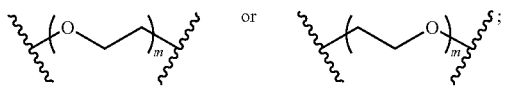

m is 1-6; $R^{6b}$ is hydrogen, $C_1$-$C_6$alkyl, $C_1$-$C_6$alkoxy, halo, —OH, —$NR^pR^q$, aryl, heterocyclyl, heteroaryl, or —C(O)$R^h$, wherein $C_1$-$C_6$alkyl and $C_1$-$C_6$alkoxy are unsubstituted or substituted with $C_3$-$C_8$ cycloalkyl or halogen; $R^p$ is H or $C_1$-$C_6$alkyl; $R^q$ is $C_2$-$C_3$alkyl; and $R^h$ is selected from the group consisting of H, $C_1$-$C_6$alkyl, $C_1$-$C_6$alkoxy, or $C_3$-$C_8$cycloalkyl. In some embodiments, $G_4$ is N or N($X_2$—$R^{6b}$), wherein $X_2$ is absent; $R^{6b}$ is hydrogen, $C_1$-$C_6$alkyl, $C_1$-$C_6$alkoxy, halo, —OH, —$NR^pR^q$, aryl, heterocyclyl, heteroaryl, or —C(O)$R^h$, wherein $C_1$-$C_6$alkyl and $C_1$-$C_6$alkoxy are unsubstituted or substituted with $C_3$-$C_8$ cycloalkyl or halogen; $R^p$ is H or $C_1$-$C_6$alkyl; $R^q$ is $C_2$-$C_3$alkyl; and $R^h$ is selected from the group consisting of H, $C_1$-$C_6$alkyl, $C_1$-$C_6$alkoxy, or $C_3$-$C_8$ cycloalkyl. In some embodiments, $G_4$ is N or N($X_2$—$R^{6b}$), wherein $X_2$

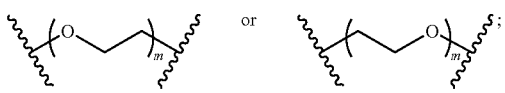

m is 1-6; $R^{6b}$ is hydrogen, $C_1$-$C_6$alkyl, $C_1$-$C_6$alkoxy, halo, —OH, —$NR^pR^q$, aryl, heterocyclyl, heteroaryl, or —C(O)$R^h$, wherein $C_1$-$C_6$alkyl and $C_1$-$C_6$alkoxy are unsubstituted or substituted with $C_3$-$C_8$ cycloalkyl or halogen; $R^p$ is H or $C_1$-$C_6$alkyl; $R^q$ is $C_2$-$C_3$alkyl; and $R^h$ is selected from the group consisting of H, $C_1$-$C_6$alkyl, $C_1$-$C_6$alkoxy, or $C_3$-$C_8$ cycloalkyl. In some of any of the preceding embodiments, $R^{6b}$ is methyl, ethyl, n-propyl, isopropyl, n-butyl, isobutyl, secbutyl, or tertbutyl. In some of any of the preceding embodiments, $R^{6b}$ is $C_1$-$C_6$alkyl substituted with $C_3$-$C_8$ cycloalkyl or halogen. In some of any of the preceding embodiments, $R^{6b}$ is methoxy, ethoxy, n-propoxy, isopropoxy, n-butoxy, isobutoxy, secbutoxy, or tertbutoxy. In some of any of the preceding embodiments, $R^{6b}$ is $C_1$-$C_6$alkoxy substituted with $C_3$-$C_8$ cycloalkyl or halogen. In some of any of the preceding embodiments, $R^{6b}$ is fluoro, chloro, bromo, or iodo. In some of any of the preceding embodiments, $R^{6b}$ is —$N(CH_2CH_3)_2$, —$N(CH_2CH_2CH_3)_2$, or —$N(CH_2CH_3)(CH_2CH_2CH_3)$. In some of any of the preceding embodiments, $R^{6b}$ is phenyl or naphthyl. In some of any of the preceding embodiments, $R^{6b}$ is a 5- to 14-membered heterocyclyl. In some embodiments, $R^{6b}$ is a 5- to 6-membered heterocyclyl. In some of any of the preceding embodiments, $R^{6b}$ is pyrrolidinyl, pyrazolidinyl, imidazolidinyl, tetrahydrofuranyl, 1,3-dioxolanyl, tetrahydrothiophenyl, oxathiolanyl, sulfolanyl, piperidinyl, piperazinyl, tetrahydropyranyl, dioxanyl, thianyl, dithianyl, trithianyl, morpholinyl, or thiomorpholinyl. In some of any of the preceding embodiments, $R^{6b}$ is a 5- to 14-membered heteroaryl. In some embodiments, $R^{6b}$ is a 5- to 6-membered heteroaryl. In some of any of the preceding embodiments, $R^{6b}$ is pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridyl, pyridazinyl, pyrimidinyl, pyrazinyl, triazinyl, or tetrazinyl. In some of any of the preceding embodiments, $R^{6b}$ is aryl, heterocyclyl, or heteroaryl, each substituted with $C_1$-$C_6$alkyl. In some of any of the preceding embodiments, $R^{6b}$ is —C(O)H, —C(O)$C_1$-$C_6$alkyl, —C(O)$C_1$-$C_6$alkoxy, or —C(O)$C_3$-$C_8$cycloalkyl. In some of any of the preceding embodiments, $R^{6b}$ is —OH, —$NR^pR^q$, aryl, heterocyclyl, heteroaryl, unsubstituted $C_1$-$C_6$alkoxy, or $C_1$-$C_6$alkoxy substituted with $C_3$-$C_8$ cycloalkyl or halogen. In some of any of the preceding embodiments, $R^{6b}$ is hydrogen, —$CH_3$, —OH, —$OCH_3$, —$C(O)OC(CH_3)_3$, —$N(CH_2CH_3)_2$, phenyl, morpholinyl, piperidinyl, piperazinyl, 4-ethylpiperazinyl, pyrrolidinyl, pyrazolyl, cyclopropylmethoxy, or cyclopropanecarbonyl. In some embodiments, $G_4$ is S. In other embodiments, $G_4$ is O.

In some embodiments of Formula (A), including Formula (A-1a), (A-1b), (A-2a), (A-2b) (A-3a), and (A-3b), $G_5$ is CH($X_3$—$R^{6c}$), C($X_3$—$R^{6c}$), or N($X_3$—$R^{6c}$), wherein $X_3$ is absent,

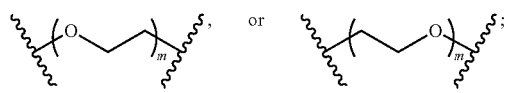

$R^{6c}$ is hydrogen, $C_1$-$C_6$alkyl, $C_1$-$C_6$alkoxy, halo, —OH, —$NR^pR^q$, aryl, heterocyclyl, heteroaryl, —$C_1$-$C_6$alkyl-heterocyclyl, —OC(O)-heterocyclyl, —C(O)$R^h$, —$S(O)_2NR^{w1}R^{w2}$, —$S(O)_2R^y$, or —$NR^{z1}S(O)_2R^{z2}$, wherein the $C_1$-$C_6$alkyl and $C_1$-$C_6$alkoxy of $R^{6c}$ are each independently unsubstituted or substituted with one or more groups selected from the group consisting of cycloalkyl and halogen; the aryl and heteroaryl of $R^{6c}$ are each independently unsubstituted or substituted with one or more groups selected from the group consisting of $C_1$-$C_6$alkyl, $C_1$-$C_6$alkoxy, $C_3$-$C_8$cycloalkyl, —OH, and $C_1$-$C_6$alkyl-OH; and the heterocyclyl, —$C_1$-$C_6$alkyl-heterocyclyl, and —OC(O)-heterocyclyl of $R^{6c}$ are each independently unsubstituted or substituted with one or more groups selected from the group consisting of $C_1$-$C_6$alkyl, $C_1$-$C_6$alkoxy, halo, —OH, $C_1$-$C_6$alkyl-OH, =O, and =S; $R^h$ is selected from the group consisting of H, $C_1$-$C_6$alkyl, $C_1$-$C_6$alkoxy, and $C_3$-$C_8$cycloalkyl, and —$NR'R^s$; $R^p$ is H or $C_1$-$C_6$alkyl; $R^q$ is $C_2$-$C_3$alkyl, —C(O)$R^t$, —C(O)$OR^u$, —C(O)$NR^v$; $R^r$, $R^s$, $R^{w1}$, and $R^{z1}$ each independently selected from H and $C_1$-$C_6$alkyl; and $R^t$, $R^u$, $R^v$, $R^{w2}$, $R^y$, and $R^{z2}$ are each independently selected from H, $C_1$-$C_6$alkyl, unsubstituted or substituted $C_3$-$C_8$cycloalkyl, and unsubstituted or substituted heterocyclyl.

In some embodiments of Formula (A), including Formula (A-1a), (A-1b), (A-2a), (A-2b), (A-3a), and (A-3b), $G_5$ is CH($X_3$—$R^{6c}$) or C($X_3$—$R^{6c}$), wherein $X_3$ is absent; $R^{6c}$ is hydrogen, $C_1$-$C_6$alkyl, $C_1$-$C_6$alkoxy, halo, —OH, —$NR^pR^q$, aryl, heterocyclyl, heteroaryl, or —C(O)$R^h$, wherein $C_1$-$C_6$alkyl and $C_1$-$C_6$alkoxy are unsubstituted or substituted with $C_3$-$C_8$ cycloalkyl or halogen; $R^p$ is H or $C_1$-$C_6$alkyl; $R^q$ is $C_2$-$C_3$alkyl; and $R^h$ is selected from the group consisting of H, $C_1$-$C_6$alkyl, $C_1$-$C_6$alkoxy or $C_3$-$C_8$ cycloalkyl. In some embodiments, $G_5$ is CH($X_3$—$R^{6c}$) or C($X_3$—$R^{6c}$), wherein $X_3$ is

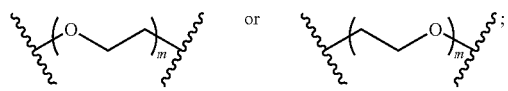

m is 1-6; $R^{6c}$ is hydrogen, $C_1$-$C_6$alkyl, $C_1$-$C_6$alkoxy, halo, —OH, —$NR^pR^q$, aryl, heterocyclyl, heteroaryl, or —C(O)$R^h$, wherein $C_1$-$C_6$alkyl and $C_1$-$C_6$alkoxy are unsubstituted or substituted with $C_3$-$C_8$ cycloalkyl or halogen; $R^p$ is H or $C_1$-$C_6$alkyl; $R^q$ is $C_2$-$C_3$alkyl; and $R^h$ is selected from the group consisting of H, $C_1$-$C_6$alkyl, $C_1$-$C_6$alkoxy, or $C_3$-$C_8$cycloalkyl. In some embodiments, $G_5$ is N or N($X_3$—$R^{6c}$), wherein $X_3$ is absent; $R^{6c}$ is hydrogen, $C_1$-$C_6$alkyl, $C_1$-$C_6$alkoxy, halo, —OH, —$NR^pR^q$, aryl, heterocyclyl, heteroaryl, or —C(O)$R^h$, wherein $C_1$-$C_6$alkyl and $C_1$-$C_6$alkoxy are unsubstituted or substituted with $C_3$-$C_8$ cycloalkyl or halogen; $R^p$ is H or $C_1$-$C_6$alkyl; $R^q$ is $C_2$-$C_3$alkyl; and $R^h$ is selected from the group consisting of H, $C_1$-$C_6$alkyl, $C_1$-$C_6$alkoxy, or $C_3$-$C_8$cycloalkyl. In some embodiments, $G_5$ is N or N($X_3$—$R^{6c}$), wherein $X_3$ is

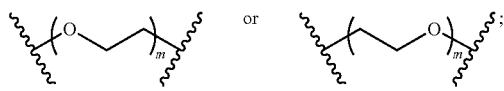

m is 1-6; $R^{6c}$ is hydrogen, $C_1$-$C_6$alkyl, $C_1$-$C_6$alkoxy, halo, —OH, —$NR^pR^q$, aryl, heterocyclyl, heteroaryl, or —C(O)$R^h$, wherein $C_1$-$C_6$alkyl and $C_1$-$C_6$alkoxy are unsubstituted or substituted with $C_3$-$C_8$ cycloalkyl or halogen; $R^p$ is H or $C_1$-$C_6$alkyl; $R^q$ is $C_2$-$C_3$alkyl; and $R^h$ is selected from the group consisting of H, $C_1$-$C_6$alkyl, $C_1$-$C_6$alkoxy, or $C_3$-$C_8$cycloalkyl. In some of any of the preceding embodiments, $R^{6c}$ is methyl, ethyl, n-propyl, isopropyl, n-butyl, isobutyl, secbutyl, or tertbutyl. In some of any of the preceding embodiments, $R^{6c}$ is $C_1$-$C_6$alkyl substituted with $C_3$-$C_8$ cycloalkyl or halogen. In some of any of the preceding embodiments, $R^{6c}$ is methoxy, ethoxy, n-propoxy, isopropoxy, n-butoxy, isobutoxy, secbutoxy, or tertbutoxy. In some of any of the preceding embodiments, $R^{6c}$ is $C_1$-$C_6$alkoxy substituted with $C_3$-$C_8$ cycloalkyl or halogen. In some of any of the preceding embodiments, $R^{6c}$ is fluoro, chloro, bromo, or iodo. In some of any of the preceding embodiments, $R^{6c}$ is —N($CH_2CH_3$)$_2$, —N($CH_2CH_2CH_3$)$_2$, or —N($CH_2CH_3$)($CH_2CH_2CH_3$). In some of any of the preceding embodiments, $R^{6c}$ is phenyl or naphthyl. In some of any of the preceding embodiments, $R^{6c}$ is a 5- to 14-membered heterocyclyl. In some embodiments, $R^{6c}$ is a 5- to 6-membered heterocyclyl. In some of any of the preceding embodiments, $R^{6c}$ is pyrrolidinyl, pyrazolidinyl, imidazolidinyl, tetrahydrofuranyl, 1,3-dioxolanyl, tetrahydrothiophenyl, oxathiolanyl, sulfolanyl, piperidinyl, piperazinyl, tetrahydropyranyl, dioxanyl, thianyl, dithianyl, trithianyl, morpholinyl, or thiomorpholinyl. In some of any of the preceding embodiments, $R^{6c}$ is a 5- to 14-membered heteroaryl. In some embodiments, $R^{6c}$ is a 5- to 6-membered heteroaryl. In some of any of the preceding embodiments, $R^{6c}$ is pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridyl, pyridazinyl, pyrimidinyl, pyrazinyl, triazinyl, or tetrazinyl. In some of any of the preceding embodiments, $R^{6c}$ is aryl, heterocyclyl, or heteroaryl, each substituted with $C_1$-$C_6$alkyl. In some of any of the preceding embodiments, $R^{6c}$ is —C(O)H, —C(O)$C_1$-$C_6$alkyl, —C(O)$C_1$-$C_6$alkoxy, or —C(O)$C_3$-$C_8$cycloalkyl. In some of any of the preceding embodiments, $R^{6c}$ is —OH, —$NR^pR^q$, aryl, heterocyclyl, heteroaryl, unsubstituted $C_1$-$C_6$alkoxy, or $C_1$-$C_6$alkoxy substituted with $C_3$-$C_8$ $C_3$-$C_8$ cycloalkyl or halogen. In some of any of the preceding embodiments, $R^{6c}$ is hydrogen, —$CH_3$, —OH, —$OCH_3$, —C(O)OC($CH_3$)$_3$, —N($CH_2CH_3$)$_2$, phenyl, morpholinyl, piperidinyl, piperazinyl, 4-ethylpiperazinyl, pyrrolidinyl, pyrazolyl, cyclopropylmethoxy, or cyclopropanecarbonyl. In some embodiments, $G_5$ is S. In other embodiments, $G_5$ is O.

In some embodiments of Formula (A), including Formula (A-1a), (A-1b), (A-2a), and (A-2b), $G_6$ is CH($X_4$—$R^{6d}$), C($X_4$—$R^{6d}$), or N($X_4$—$R^{6d}$), wherein $X_4$ is absent,

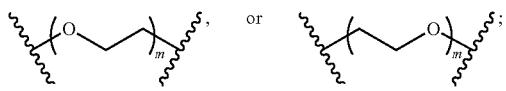

$R^{6d}$ is hydrogen, $C_1$-$C_6$alkyl, $C_1$-$C_6$alkoxy, halo, —OH, —$NR^pR^q$, aryl, heterocyclyl, heteroaryl, —$C_1$-$C_6$alkyl-heterocyclyl, —OC(O)-heterocyclyl, —C(O)$R^h$, —S(O)$_2$$NR^{w1}R^{w2}$, —S(O)$_2R^y$, or —$NR^{z1}S(O)_2R^{z2}$, wherein the $C_1$-$C_6$alkyl and $C_1$-$C_6$alkoxy of $R^{6d}$ are each independently unsubstituted or substituted with one or more groups selected from the group consisting of cycloalkyl and halogen; the aryl and heteroaryl of $R^{6d}$ are each independently unsubstituted or substituted with one or more groups selected from the group consisting of $C_1$-$C_6$alkyl, $C_1$-$C_6$alkoxy, $C_3$-$C_8$cycloalkyl, —OH, and $C_1$-$C_6$alkyl-OH; and the heterocyclyl, —$C_1$-$C_6$alkyl-heterocyclyl, and —OC(O)-heterocyclyl of $R^{6d}$ are each independently unsubstituted or substituted with one or more groups selected from the group consisting of $C_1$-$C_6$alkyl, $C_1$-$C_6$alkoxy, halo, —OH, $C_1$-$C_6$alkyl-OH, =O, and =S; $R^h$ is selected from the group consisting of H, $C_1$-$C_6$alkyl, $C_1$-$C_6$alkoxy, and $C_3$-$C_8$cycloalkyl, and —$NR^rR^s$; $R^p$ is H or $C_1$-$C_6$alkyl; $R^q$ is $C_2$-$C_3$alkyl, —C(O)$R^t$, —C(O)O$R^u$, —C(O)$NR^v$; $R^r$, $R^s$, $R^{w1}$, and $R^{z1}$ each independently selected from H and $C_1$-$C_6$alkyl; and $R^t$, $R^u$, $R^v$, $R^{w2}$, $R^y$, and $R^{z2}$ are each independently selected from H, $C_1$-$C_6$alkyl, unsubstituted or substituted $C_3$-$C_8$cycloalkyl, and unsubstituted or substituted heterocyclyl.

In some embodiments of Formula (A), including Formula (A-1a), (A-1b), (A-2a), and (A-2b), $G_6$ is CH($X_4$—$R^{6d}$) or C($X_4$—$R^{6d}$), wherein $X_4$ is absent; $R^{6d}$ is hydrogen, $C_1$-$C_6$alkyl, $C_1$-$C_6$alkoxy, halo, —OH, —$NR^pR^q$, aryl, heterocyclyl, heteroaryl, or —C(O)$R^h$, wherein $C_1$-$C_6$alkyl and $C_1$-$C_6$alkoxy are unsubstituted or substituted with $C_3$-$C_8$ cycloalkyl or halogen; $R^p$ is H or $C_1$-$C_6$alkyl; $R^q$ is $C_2$-$C_3$alkyl; and $R^h$ is selected from the group consisting of H, $C_1$-$C_6$alkyl, $C_1$-$C_6$alkoxy, or $C_3$-$C_8$cycloalkyl. In some embodiments, $G_6$ is CH($X_4$—$R^{6d}$) or C($X_4$—$R^{6d}$), wherein $X_4$ is

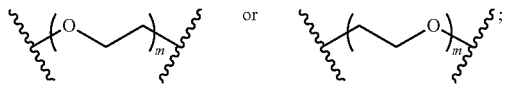

m is 1-6; $R^{6d}$ is hydrogen, $C_1$-$C_6$alkyl, $C_1$-$C_6$alkoxy, halo, —OH, —$NR^pR^q$, aryl, heterocyclyl, heteroaryl, or —C(O)$R^h$, wherein $C_1$-$C_6$alkyl and $C_1$-$C_6$alkoxy are unsubstituted or substituted with $C_3$-$C_8$ cycloalkyl or halogen; $R^p$ is H or $C_1$-$C_6$alkyl; $R^q$ is $C_2$-$C_3$alkyl; and $R^h$ is selected from the group consisting of H, $C_1$-$C_6$alkyl, $C_1$-$C_6$alkoxy, or $C_3$-$C_8$cycloalkyl. In some embodiments, $G_6$ is N or N($X_4$—$R^{6d}$), wherein $X_4$ is absent; $R^{6d}$ is hydrogen, $C_1$-$C_6$alkyl, $C_1$-$C_6$alkoxy, halo, —OH, —$NR^pR^q$, aryl, heterocyclyl, heteroaryl, or —C(O)$R^h$, wherein $C_1$-$C_6$alkyl and $C_1$-$C_6$alkoxy are unsubstituted or substituted with $C_3$-$C_8$ cycloalkyl or halogen; $R^p$ is H or $C_1$-$C_6$alkyl; $R^q$ is $C_2$-$C_3$alkyl; and $R^h$ is selected from the group consisting of H, $C_1$-$C_6$alkyl, $C_1$-$C_6$alkoxy, or $C_3$-$C_8$cycloalkyl. In some embodiments, $G_6$ is N or N($X_4$—$R^{6d}$), wherein $X_4$ is

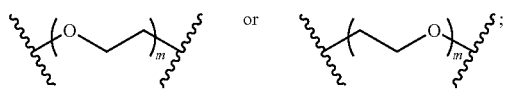

m is 1-6; $R^{6d}$ is hydrogen, $C_1$-$C_6$alkyl, $C_1$-$C_6$alkoxy, halo, —OH, —$NR^pR^q$, aryl, heterocyclyl, heteroaryl, or —C(O)$R^h$, wherein $C_1$-$C_6$alkyl and $C_1$-$C_6$alkoxy are unsubstituted or substituted with $C_3$-$C_8$ cycloalkyl or halogen; $R^p$ is H or $C_1$-$C_6$alkyl; $R^q$ is $C_2$-$C_3$alkyl; and $R^h$ is selected from the group consisting of H, $C_1$-$C_6$alkyl, $C_1$-$C_6$alkoxy, or $C_3$-$C_8$cycloalkyl. In some of any of the preceding embodiments, $R^{6d}$ is methyl, ethyl, n-propyl, isopropyl, n-butyl, isobutyl, secbutyl, or tertbutyl. In some of any of the preceding embodiments, $R^{6d}$ is $C_1$-$C_6$alkyl substituted with $C_3$-$C_8$ cycloalkyl or halogen. In some of any of the preceding embodiments, $R^{6d}$ is methoxy, ethoxy, n-propoxy, isopropoxy, n-butoxy, isobutoxy, secbutoxy, or tertbutoxy. In some of any of the preceding embodiments, $R^{6d}$ is $C_1$-$C_6$alkoxy substituted with $C_3$-$C_8$ cycloalkyl or halogen. In some of any of the preceding embodiments, $R^{6d}$ is fluoro, chloro, bromo, or iodo. In some of any of the preceding embodiments, $R^{6d}$ is —$N(CH_2CH_3)_2$, —$N(CH_2CH_2CH_3)_2$, or —$N(CH_2CH_3)(CH_2CH_2CH_3)$. In some of any of the preceding embodiments, $R^{6d}$ is phenyl or naphthyl. In some of any of the preceding embodiments, $R^{6d}$ is a 5- to 14-membered heterocyclyl. In some embodiments, $R^{6d}$ is a 5- to 6-membered heterocyclyl. In some of any of the preceding embodiments, $R^{6d}$ is pyrrolidinyl, pyrazolidinyl, imidazolidinyl, tetrahydrofuranyl, 1,3-dioxolanyl, tetrahydrothiophenyl, oxathiolanyl, sulfolanyl, piperidinyl, piperazinyl, tetrahydropyranyl, dioxanyl, thianyl, dithianyl, trithianyl, morpholinyl, or thiomorpholinyl. In some of any of the preceding embodiments, $R^{6d}$ is a 5- to 14-membered heteroaryl. In some embodiments, $R^{6d}$ is a 5- to 6-membered heteroaryl. In some of any of the preceding embodiments, $R^{6d}$ is pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridyl, pyridazinyl, pyrimidinyl, pyrazinyl, triazinyl, or tetrazinyl. In some of any of the preceding embodiments, $R^{6d}$ is aryl, heterocyclyl, or heteroaryl, each substituted with $C_1$-$C_6$alkyl. In some of any of the preceding embodiments, $R^{6d}$ is —C(O)H, —C(O)$C_1$-$C_6$alkyl, —C(O)$C_1$-$C_6$alkoxy, or —C(O)$C_3$-$C_8$cycloalkyl. In some of any of the preceding embodiments, $R^{6d}$ is —OH, —$NR^pR^q$, aryl, heterocyclyl, heteroaryl, unsubstituted $C_1$-$C_6$alkoxy, or $C_1$-$C_6$alkoxy substituted with $C_3$-$C_8$ cycloalkyl or halogen. In some of any of the preceding embodiments, $R^{6d}$ is hydrogen, —$CH_3$, —OH, —$OCH_3$, —$C(O)OC(CH_3)_3$, —$N(CH_2CH_3)_2$, phenyl, morpholinyl, piperidinyl, piperazinyl, 4-ethylpiperazinyl, pyrrolidinyl, pyrazolyl, cyclopropylmethoxy, or cyclopropanecarbonyl. In some embodiments, $G_6$ is S. In other embodiments, $G_6$ is O. In some embodiments, $G_6$ is absent.

In some embodiments of Formula (A), including Formula (A-1a), (A-1b), (A-2a), and (A-2b), $G_5$ is $CH(X_3$—$R^{6c})$, $G_6$ is $CH(X_4$—$R^{6d})$, ring

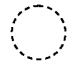

is saturated, and $R^{6c}$ and $R^{6d}$ are taken together with the carbon atoms to which they are attached to form a 6-membered heterocyclyl ring; wherein the heterocyclyl ring is unsubstituted or substituted. In some embodiments, $G_5$ is $C(X_3$—$R^{6c})$, $G_6$ is $C(X_4$—$R^{6d})$, is partially unsaturated or fully unsaturated, and $R^{6c}$ and $R^{6d}$ are taken together with the carbon atoms to which they are attached to form a 6-membered aryl, heterocyclyl, or heteroaryl ring; wherein each 6-membered aryl, heterocyclyl, and heteroaryl ring is unsubstituted or substituted. In some embodiments, $G_5$ is $C(X_3$—$R^{6c})$, $G_6$ is $C(X_4$—$R^{6d})$, is fully unsaturated, and $R^{6c}$ and $R^{6d}$ are taken together with the carbon atoms to which they are attached to form a 6-membered aryl, heterocyclyl, or heteroaryl ring; wherein each 6-membered aryl, heterocyclyl, and heteroaryl ring is unsubstituted or substituted. In some embodiments, $R^{6c}$ and $R^{6d}$ come together with the carbon atoms to which they are attached to form a phenyl ring. In some embodiments, $R^{6c}$ and $R^{6d}$ are taken together with the carbon atoms to which they are attached to form a 6-membered heterocyclyl or heteroaryl ring, wherein the 6-membered heterocyclyl or heteroaryl ring contains one, two, or three heteroatoms selected from the group consisting of N, S, and O. In some embodiments, $R^{6c}$ and $R^{6d}$ are taken together with the carbon atoms to which they are attached to form an unsubstituted 6-membered aryl, heterocyclyl, or heteroaryl ring. In some embodiments, $R^{6c}$ and $R^{6d}$ are taken together with the carbon atoms to which they are attached to form a 6-membered aryl, heterocyclyl, or heteroaryl ring, wherein the 6-membered aryl, heterocyclyl, or heteroaryl ring is substituted with one or more substituents selected from the group consisting of $C_1$-$C_6$ alkyl, $C_1$-$C_6$ haloalkyl, halo, —OH, —C(O)H, —C(O)OH, —C(O)O$C_1$-$C_6$ alkyl, —O$C_1$-$C_6$ alkyl, and $C_3$-$C_8$ cycloalkyl.

In some embodiments of Formula (A), including Formula (A-1a), (A-1b), (A-2a), and (A-2b), $G_7$ is N. In some embodiments, $G_7$ is C. In other embodiments, $G_7$ is CH.

In some embodiments of Formula (A), including Formula (A-1a), (A-1b), (A-2a), and (A-2b), one of $R^{6a}$, $R^{6b}$, $R^{6c}$, and $R^{6d}$ is selected from the group consisting of $C_1$-$C_6$alkyl, $C_1$-$C_6$alkoxy, halo, —OH, —$NR^pR^q$, aryl, heterocyclyl, heteroaryl, and —C(O)$R^h$, wherein the $C_1$-$C_6$alkyl and $C_1$-$C_6$alkoxy of $R^{6a}$, $R^{6b}$, $R^{6c}$, and $R^{6d}$ are each independently unsubstituted or substituted with $C_3$-$C_8$ cycloalkyl or halogen; and the rest of $R^{6a}$, $R^{6b}$, $R^{6c}$, and $R^{6d}$ are each H. In some embodiments, one of $R^{6a}$, $R^{6b}$, $R^{6c}$, and $R^{6d}$ is selected from the group consisting of $C_1$-$C_6$alkyl, $C_1$-$C_6$alkoxy, halo, —OH, —$NR^pR^q$, 6- to 12-membered aryl, 3- to 12-membered heterocyclyl, 5- to 12-membered heteroaryl, and —C(O)$R^h$, wherein the $C_1$-$C_6$alkyl and $C_1$-$C_6$alkoxy of $R^{6a}$, $R^{6b}$, $R^{6c}$, and $R^{6d}$ are each independently unsubstituted or substituted with $C_3$-$C_8$ cycloalkyl or halogen; and the rest of $R^{6a}$, $R^{6b}$, $R^{6c}$, and $R^{6d}$ are each H. In some embodiments, two of $R^{6a}$, $R^{6b}$, $R^{6c}$, and $R^{6d}$ are selected from the group consisting of $C_1$-$C_6$alkyl, $C_1$-$C_6$alkoxy, halo, —OH, —$NR^pR^q$, aryl, heterocyclyl, heteroaryl, and —C(O)$R^h$, wherein the $C_1$-$C_6$alkyl and $C_1$-$C_6$alkoxy of $R^{6a}$, $R^{6b}$, $R^{6c}$, and $R^{6d}$ are each independently unsubstituted or substituted with $C_3$-$C_8$ cycloalkyl or halogen; and the rest of $R^{6a}$, $R^{6b}$, $R^{6c}$, and $R^{6d}$ are each H. In some embodiments, two of $R^{6a}$, $R^{6b}$, $R^{6c}$, and $R^{6d}$ is selected from the group consisting of $C_1$-$C_6$alkyl, $C_1$-$C_6$alkoxy, halo, —OH, —$NR^pR^q$, 6- to 12-membered aryl, 3- to 12-membered heterocyclyl, 5- to 12-membered heteroaryl, and —$C(O)R^h$, wherein the $C_1$-$C_6$alkyl and $C_1$-$C_6$alkoxy of $R^{6a}$, $R^{6b}$, $R^{6c}$, and $R^{6d}$ are each independently unsubstituted or substituted with $C_3$-$C_8$ cycloalkyl or halogen; and the rest of $R^{6a}$, $R^{6b}$, $R^{6c}$, and $R^{6d}$ are each H.

In some embodiments of Formula (A), including Formula (A-1a), (A-1b), (A-2a), and (A-2b), one of $R^{6a}$, $R^{6b}$, $R^{6c}$, and $R^{6d}$ is selected from the group consisting of $C_1$-$C_6$alkyl, $C_1$-$C_6$alkoxy, halo, —OH, —$NR^pR^q$, aryl, heterocyclyl, heteroaryl, and —$C(O)R^h$, wherein the $C_1$-$C_6$alkyl and $C_1$-$C_6$alkoxy of $R^{6a}$, $R^{6b}$, $R^{6c}$, and $R^{6d}$ are each independently unsubstituted or substituted with $C_3$-$C_8$ cycloalkyl or halogen; and the rest of $R^{6a}$, $R^{6b}$, $R^{6c}$, and $R^{6d}$ are each H. In some embodiments, one of $R^{6a}$, $R^{6b}$, $R^{6c}$, and $R^{6d}$ is selected from the group consisting of —$C_1$-$C_6$alkyl-heterocyclyl, —OC(O)-heterocyclyl, —$S(O)_2NR^{w1}R^{w2}$, —$S(O)_2R^y$, and —$NR^{z1}S(O)_2R^{z2}$; wherein $R^{w1}$ and $R^{z1}$ each independently selected from H and $C_1$-$C_6$alkyl, and $R^{w2}$, $R^y$, and $R^{z2}$ are each independently selected from H, $C_1$-$C_6$alkyl, unsubstituted or substituted $C_3$-$C_8$cycloalkyl, and unsubstituted or substituted 3- to 12-membered heterocyclyl.

In some embodiments of Formula (A), including Formula (A-1a), (A-1b), (A-2a), and (A-2b), two of $R^{6a}$, $R^{6b}$, $R^{6c}$, and $R^{6d}$ is selected from the group consisting of $C_1$-$C_6$alkyl, $C_1$-$C_6$alkoxy, halo, —OH, —$NR^pR^q$, aryl, heterocyclyl, heteroaryl, and —$C(O)R^h$, wherein the $C_1$-$C_6$alkyl and $C_1$-$C_6$alkoxy of $R^{6a}$, $R^{6b}$, $R^{6c}$, and $R^{6d}$ are each independently unsubstituted or substituted with $C_3$-$C_8$ cycloalkyl or halogen; and the rest of $R^{6a}$, $R^{6b}$, $R^{6c}$, and $R^{6d}$ are each H.

In some embodiments of Formula (A), $R^3$ is H, $C_1$-$C_3$alkyl, $C_1$-$C_6$alkoxy, or halogen, wherein the $C_1$-$C_6$alkyl and $C_1$-$C_6$alkoxy of $R^3$ are each independently unsubstituted or substituted with one or more halogen. In some embodiments, when $R^2$ is —C(O)H, $R^3$ is methoxy, and

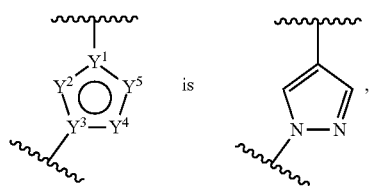

is at least one of $R^{6a}$, $R^{6b}$, $R^{6c}$, and $R^{6d}$ are selected from $C_1$-$C_6$alkyl, $C_1$-$C_6$alkoxy, halo, —OH, —$NR^pR^q$, aryl, heterocyclyl, heteroaryl, —$C_1$-$C_6$alkyl-heterocyclyl, —OC(O)-heterocyclyl, —$C(O)R^h$, —$S(O)_2NR^{w1}R^{w2}$, —$S(O)_2R^y$, and —$NR^{z1}S(O)_2R^{z2}$. In some embodiments, one of $R^1$ and $R^2$ is —OH and the other is —CH=$NR^j$, wherein $R^j$ is a phenyl or naphtyl substituted with one or more substituents selected from the group consisting of $C_1$-$C_6$alkyl, $C_3$-$C_8$cycloalkyl, and oxo. In some embodiments, n is 0 and $R^4$ is

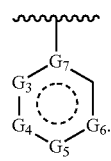

In some embodiments, one of $R^1$ and $R^2$ is —OH and the other is —CH=$NR^j$, wherein $NR^j$ is unsubstituted or substituted 4- to 12-membered heterocyclyl. In some embodiments,

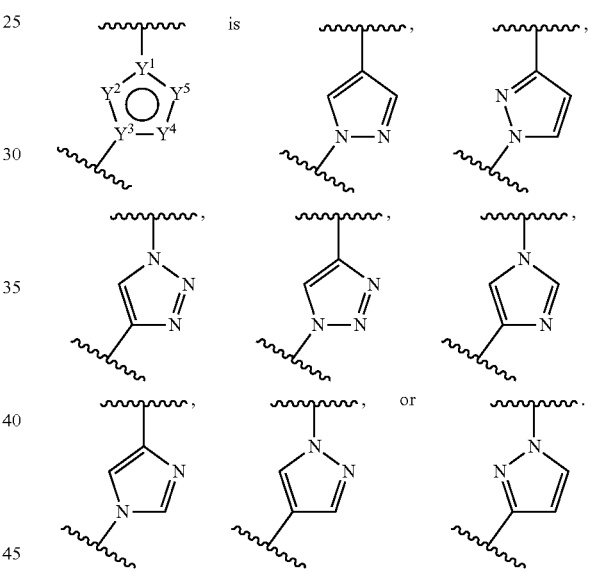

In some embodiments, provided herein are compounds and salts thereof described in Table 1A.

TABLE 1A

| Compound No. | Chemical Structure | Chemical Name |
|---|---|---|
| A1 | MeO, HO, OHC (structure) | 2-hydroxy-3-methoxy-5-(1-phenyl-1H-pyrazol-4-yl)benzaldehyde |

TABLE 1A-continued

| Compound No. | Chemical Structure | Chemical Name |
|---|---|---|
| A2 | 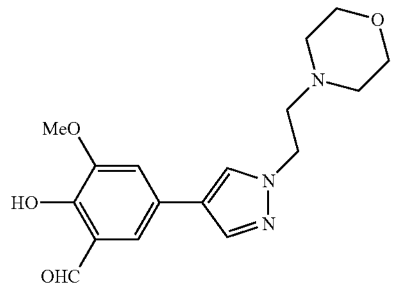 [SMILES: COc1cc(-c2cnn(CCN3CCOCC3)c2)cc(C=O)c1O] | 2-hydroxy-3-methoxy-5-(1-(2-morpholinoethyl)-1H-pyrazol-4-yl)benzaldehyde |
| A3 | 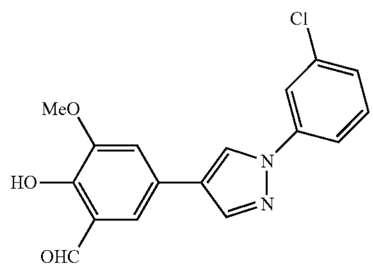 [SMILES: COc1cc(-c2cnn(-c3cccc(Cl)c3)c2)cc(C=O)c1O] | 5-(1-(3-chlorophenyl)-1H-pyrazol-4-yl)-2-hydroxy-3-methoxybenzaldehyde |
| A4 | 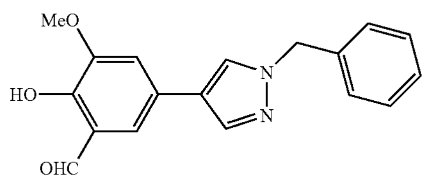 [SMILES: COc1cc(-c2cnn(Cc3ccccc3)c2)cc(C=O)c1O] | 5-(1-benzyl-1H-pyrazol-4-yl)-2-hydroxy-3-methoxybenzaldehyde |
| A5 | 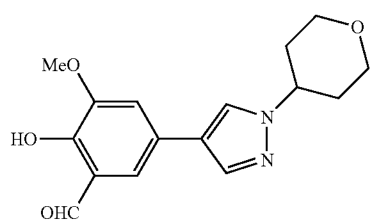 [SMILES: COc1cc(-c2cnn(C3CCOCC3)c2)cc(C=O)c1O] | 2-hydroxy-3-methoxy-5-(1-(tetrahydro-2H-pyran-4-yl)-1H-pyrazol-4-yl)benzaldehyde |
| A6 | 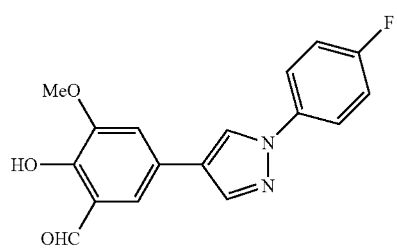 [SMILES: COc1cc(-c2cnn(-c3ccc(F)cc3)c2)cc(C=O)c1O] | 5-(1-(4-fluorophenyl)-1H-pyrazol-4-yl)-2-hydroxy-3-methoxybenzaldehyde |
| A7 | 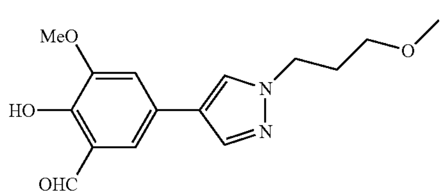 [SMILES: COCCCn1cc(-c2cc(C=O)c(O)c(OC)c2)cn1] | 2-hydroxy-3-methoxy-5-(1-(3-methoxypropyl)-1H-pyrazol-4-yl)benzaldehyde |
| A8 | 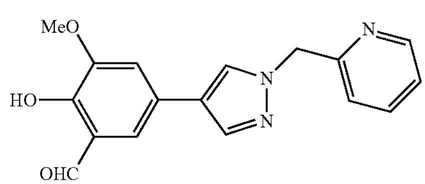 [SMILES: COc1cc(-c2cnn(Cc3ccccn3)c2)cc(C=O)c1O] | 2-hydroxy-3-methoxy-5-(1-(pyridin-2-ylmethyl)-1H-pyrazol-4-yl)benzaldehyde |

TABLE 1A-continued

| Compound No. | Chemical Structure | Chemical Name |
| --- | --- | --- |
| A9 | 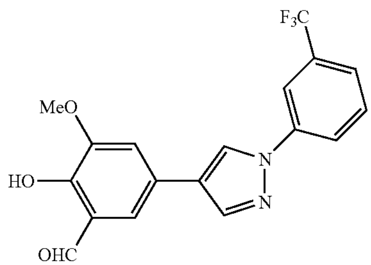 [SMILES: COc1cc(-c2cnn(-c3cccc(C(F)(F)F)c3)c2)cc(C=O)c1O] | 2-hydroxy-3-methoxy-5-(1-(3-(trifluoromethyl)phenyl)-1H-pyrazol-4-yl)benzaldehyde |
| A10 | 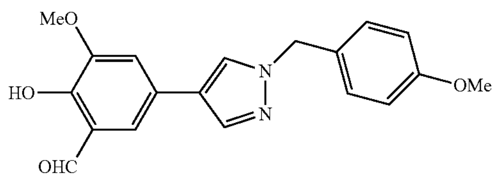 [SMILES: COc1ccc(Cn2cc(-c3cc(C=O)c(O)c(OC)c3)cn2)cc1] | 2-hydroxy-3-methoxy-5-(1-(4-methoxybenzyl)-1H-pyrazol-4-yl)benzaldehyde |
| A11 | 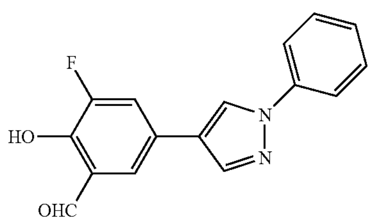 [SMILES: O=Cc1cc(-c2cnn(-c3ccccc3)c2)cc(F)c1O] | 3-fluoro-2-hydroxy-5-(1-phenyl-1H-pyrazol-4-yl)benzaldehyde |
| A12 | 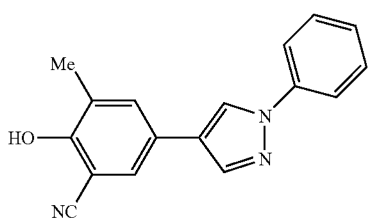 [SMILES: Cc1cc(-c2cnn(-c3ccccc3)c2)cc(C#N)c1O] | 2-hydroxy-3-methyl-5-(1-phenyl-1H-pyrazol-4-yl)benzonitrile |
| A13 | 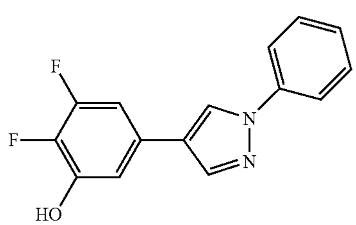 [SMILES: Oc1cc(-c2cnn(-c3ccccc3)c2)cc(F)c1F] | 2,3-difluoro-5-(1-phenyl-1H-pyrazol-4-yl)phenol |
| A14 | 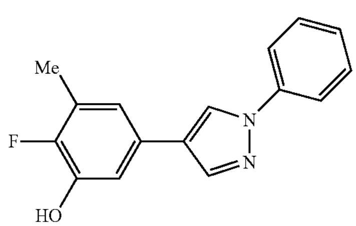 [SMILES: Cc1cc(-c2cnn(-c3ccccc3)c2)cc(O)c1F] | 2-fluoro-3-methyl-5-(1-phenyl-1H-pyrazol-4-yl)phenol |
| A15 | 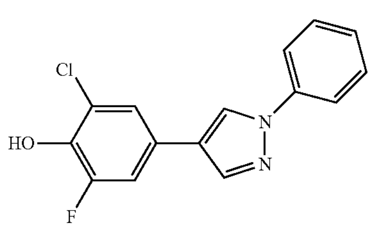 [SMILES: Oc1c(F)cc(-c2cnn(-c3ccccc3)c2)cc1Cl] | 2-chloro-6-fluoro-4-(1-phenyl-1H-pyrazol-4-yl)phenol |

TABLE 1A-continued

| Compound No. | Chemical Structure | Chemical Name |
| --- | --- | --- |
| A16 | 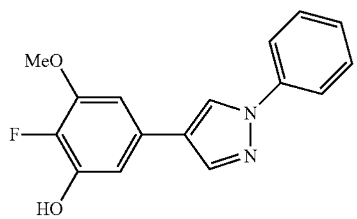 [SMILES: COc1cc(-c2cnn(-c3ccccc3)c2)cc(O)c1F] | 2-fluoro-3-methoxy-5-(1-phenyl-1H-pyrazol-4-yl)phenol |
| A17 | 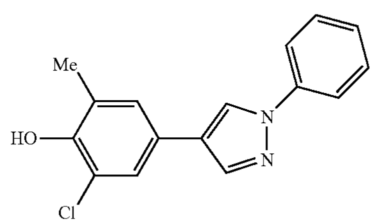 [SMILES: Cc1cc(-c2cnn(-c3ccccc3)c2)cc(Cl)c1O] | 2-chloro-6-methyl-4-(1-phenyl-1H-pyrazol-4-yl)phenol |
| A18 | 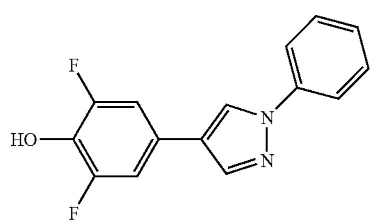 [SMILES: Oc1c(F)cc(-c2cnn(-c3ccccc3)c2)cc1F] | 2,6-difluoro-4-(1-phenyl-1H-pyrazol-4-yl)phenol |
| A19 | 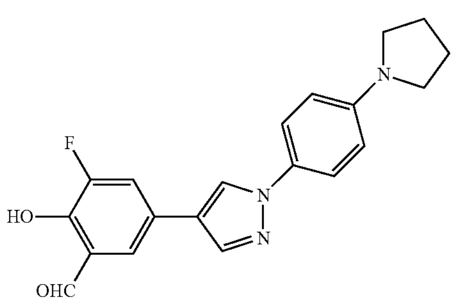 [SMILES: O=Cc1cc(-c2cnn(-c3ccc(N4CCCC4)cc3)c2)cc(F)c1O] | 3-fluoro-2-hydroxy-5-(1-(4-(pyrrolidin-1-yl)phenyl)-1H-pyrazol-4-yl)benzaldehyde |
| A20 | 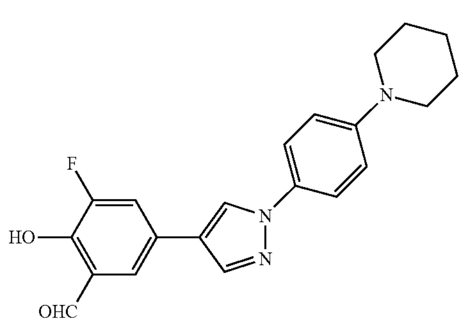 [SMILES: O=Cc1cc(-c2cnn(-c3ccc(N4CCCCC4)cc3)c2)cc(F)c1O] | 3-fluoro-2-hydroxy-5-(1-(4-(piperidin-1-yl)phenyl)-1H-pyrazol-4-yl)benzaldehyde |

TABLE 1A-continued

| Compound No. | Chemical Structure | Chemical Name |
| --- | --- | --- |
| A21 | 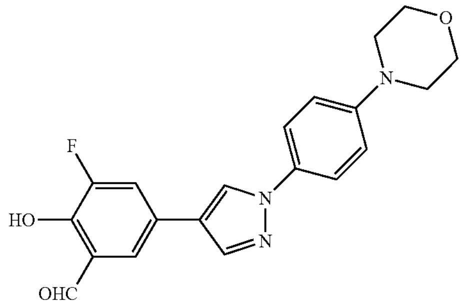 [SMILES: O=Cc1cc(-c2cnn(-c3ccc(N4CCOCC4)cc3)c2)cc(F)c1O] | 3-fluoro-2-hydroxy-5-(1-(4-morpholinophenyl)-1H-pyrazol-4-yl)benzaldehyde |
| A22 | 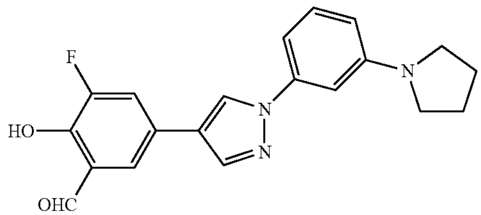 [SMILES: O=Cc1cc(-c2cnn(-c3cccc(N4CCCC4)c3)c2)cc(F)c1O] | 3-fluoro-2-hydroxy-5-(1-(3-(pyrrolidin-1-yl)phenyl)-1H-pyrazol-4-yl)benzaldehyde |
| A23 | 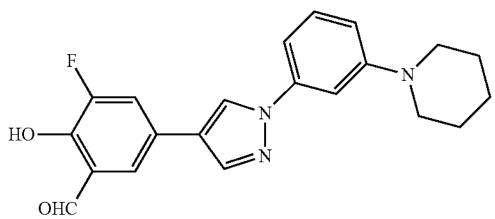 [SMILES: O=Cc1cc(-c2cnn(-c3cccc(N4CCCCC4)c3)c2)cc(F)c1O] | 3-fluoro-2-hydroxy-5-(1-(3-(pyiperidin-1-yl)phenyl)-1H-pyrazol-4-yl)benzaldehyde |
| A24 | 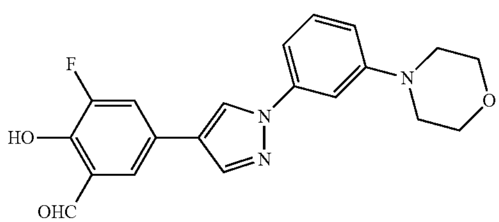 [SMILES: O=Cc1cc(-c2cnn(-c3cccc(N4CCOCC4)c3)c2)cc(F)c1O] | 3-fluoro-2-hydroxy-5-(1-(3-morpholinophenyl)-1H-pyrazol-4-yl)benzaldehyde |
| A25 | 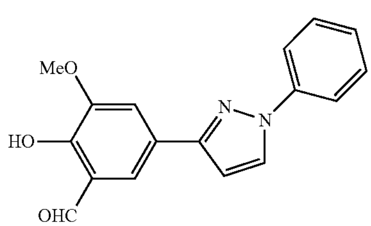 [SMILES: COc1cc(-c2ccn(-c3ccccc3)n2)cc(C=O)c1O] | 2-hydroxy-3-methoxy-5-(1-phenyl-1H-pyrazol-3-yl)benzaldehyde |
| A26 | 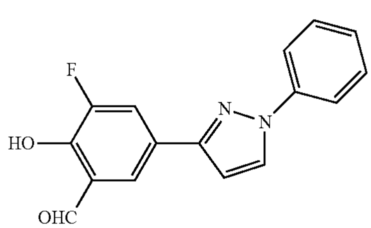 [SMILES: O=Cc1cc(-c2ccn(-c3ccccc3)n2)cc(F)c1O] | 3-fluoro-2-hydroxy-5-(1-phenyl-1H-pyrazol-3-yl)benzaldehyde |

TABLE 1A-continued

| Compound No. | Chemical Structure | Chemical Name |
|---|---|---|
| A27 | 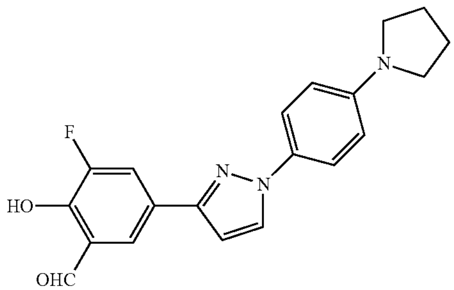 [SMILES: O=Cc1cc(-c2ccn(-c3ccc(N4CCCC4)cc3)n2)cc(F)c1O] | 3-fluoro-2-hydroxy-5-(1-(4-(pyrrolidin-1-yl)phenyl)-1H-pyrazol-3-yl)benzaldehyde/ |
| A28 | 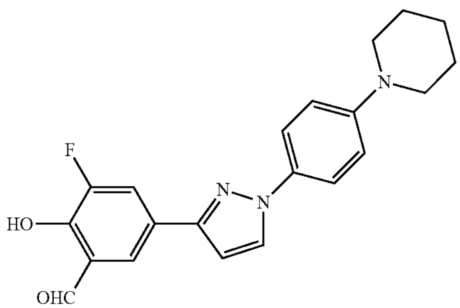 [SMILES: O=Cc1cc(-c2ccn(-c3ccc(N4CCCCC4)cc3)n2)cc(F)c1O] | 3-fluoro-2-hydroxy-5-(1-(4-(piperidin-1-yl)phenyl)-1H-pyrazol-3-yl)benzaldehyde |
| A29 | 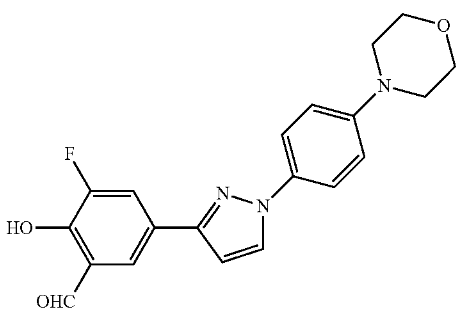 [SMILES: O=Cc1cc(-c2ccn(-c3ccc(N4CCOCC4)cc3)n2)cc(F)c1O] | 3-fluoro-2-hydroxy-5-(1-(4-morpholinophenyl)-1H-pyrazol-3-yl)benzaldehyde |
| A30 | 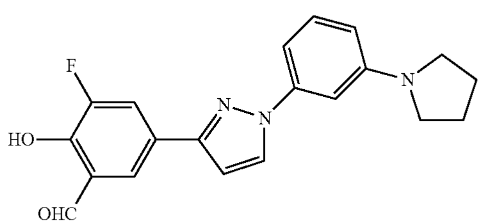 | 3-fluoro-2-hydroxy-5-(1-(3-(pyrrolidin-1-yl)phenyl)-1H-pyrazol-3-yl)benzaldehyde |
| A31 | 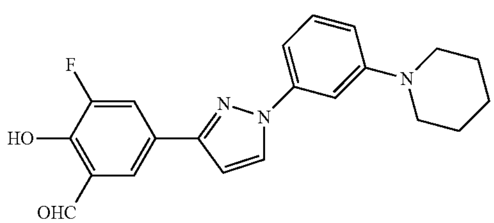 | 3-fluoro-2-hydroxy-5-(1-(3-(piperidin-1-yl)phenyl)-1H-pyrazol-3-yl)benzaldehyde |
| A32 | 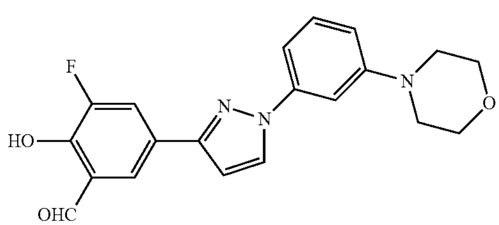 [SMILES: O=Cc1cc(-c2ccn(-c3cccc(N4CCOCC4)c3)n2)cc(F)c1O] | 3-fluoro-2-hydroxy-5-(1-(3-morpholinophenyl)-1H-pyrazol-3-yl)benzaldehyde |

TABLE 1A-continued

| Compound No. | Chemical Structure | Chemical Name |
| --- | --- | --- |
| A33 | 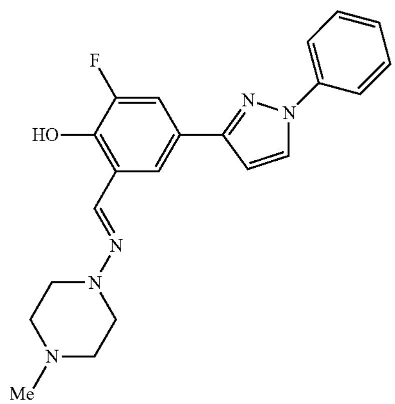 [SMILES: CN1CCN(/N=C/c2cc(-c3ccn(-c4ccccc4)n3)cc(F)c2O)CC1] | (E)-2-fluoro-6-(((4-methylpiperazin-1-yl)imino)methyl)-4-(1-phenyl-1H-pyrazol-3-yl)phenol |
| A34 | 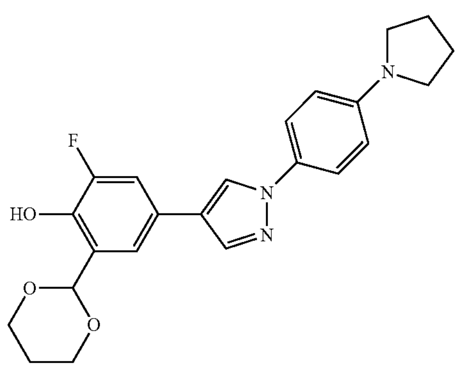 [SMILES: Oc1c(F)cc(-c2cnn(-c3ccc(N4CCCC4)cc3)c2)cc1C1OCCCO1] | 2-(1,3-dioxan-2-yl)-6-fluoro-4-(1-(4-(pyrrolidin-1-yl)phenyl)-1H-pyrazol-4-yl)phenol |
| A35 | 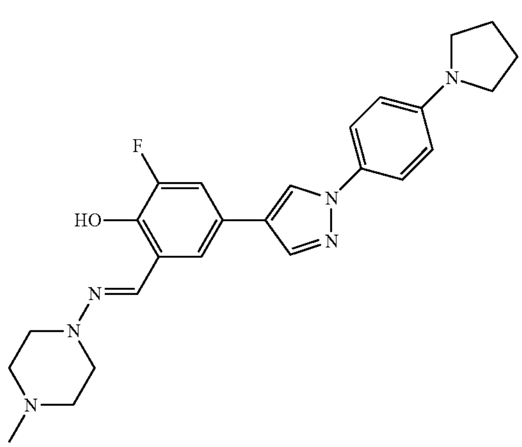 [SMILES: CN1CCN(/N=C/c2cc(-c3cnn(-c4ccc(N5CCCC5)cc4)c3)cc(F)c2O)CC1] | (E)-2-fluoro-6-(((4-methylpiperazin-1-yl)imino)methyl)-4-(1-(4-(pyrrolidin-1-yl)phenyl)-1H-pyrazol-4-yl)phenol |

TABLE 1A-continued

| Compound No. | Chemical Structure | Chemical Name |
|---|---|---|
| A36 | 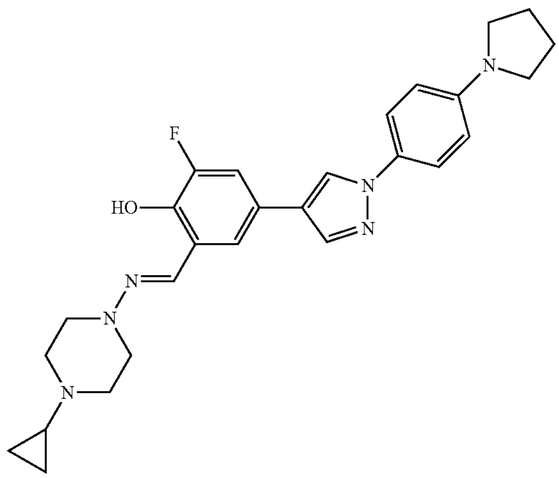 [SMILES: Oc1c(F)cc(-c2cnn(-c3ccc(N4CCCC4)cc3)c2)cc1/C=N/N1CCN(C2CC2)CC1] | (E)-2-(((4-cyclopropylpiperazin-1-yl)imino)methyl)-6-fluoro-4-(1-(4-(pyrrolidin-1-yl)phenyl)-1H-pyrazol-4-yl)phenol |
| A37 | 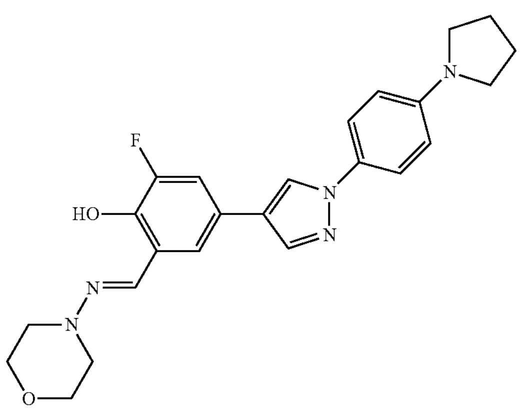 [SMILES: Oc1c(F)cc(-c2cnn(-c3ccc(N4CCCC4)cc3)c2)cc1/C=N/N1CCOCC1] | (E)-2-fluoro-6-((morpholinoimino)methyl)-4-(1-(4-(pyrrolidin-1-yl)phenyl)-1H-pyrazol-4-yl)phenol |
| A38 | 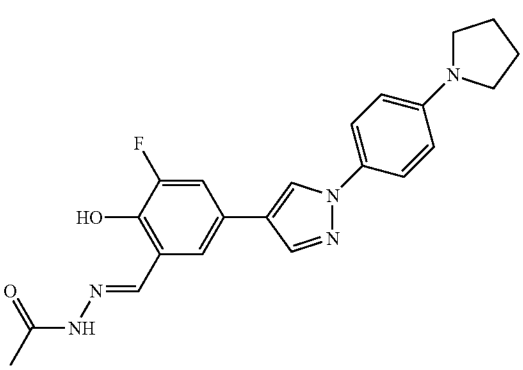 [SMILES: CC(=O)N/N=C/c1cc(-c2cnn(-c3ccc(N4CCCC4)cc3)c2)cc(F)c1O] | (E)-N'-(3-fluoro-2-hydroxy-5-(2-(4-(pyrrolidin-1-yl)phenyl)-1H-pyrazol-4-yl)benzylidene)acetohydrazide |

TABLE 1A-continued

| Compound No. | Chemical Structure | Chemical Name |
|---|---|---|
| A39 | 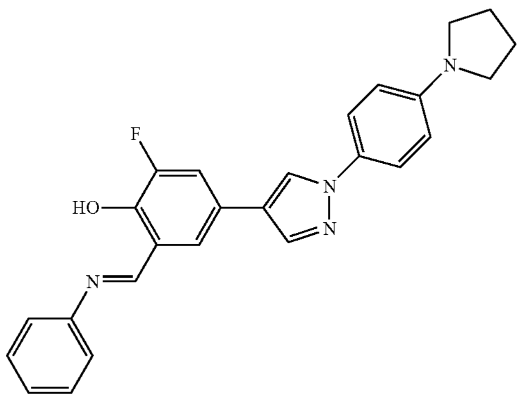 [SMILES: Oc1c(F)cc(-c2cnn(-c3ccc(N4CCCC4)cc3)c2)cc1/C=N/c1ccccc1] | (E)-2-fluoro-6-((phenylimino)methyl)-4-(1-(4-(pyrrolidin-1-yl)phenyl)-1H-pyrazol-4-yl)phenol |
| A40 | 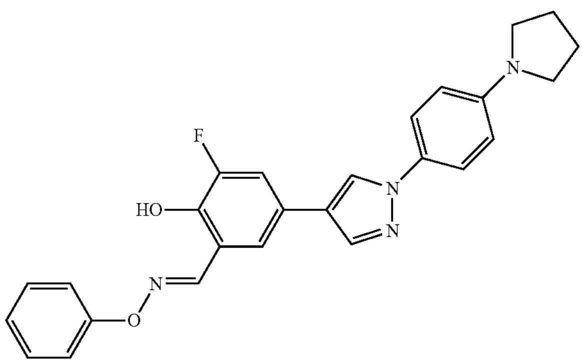 [SMILES: Oc1c(F)cc(-c2cnn(-c3ccc(N4CCCC4)cc3)c2)cc1/C=N/Oc1ccccc1] | (E)-3-fluoro-2-hydroxy-5-(1-(4-(pyrrolidin-1-yl)phenyl)-1H-pyrazol-4-yl)benzaldehyde O-phenyl oxime |
| A41 | 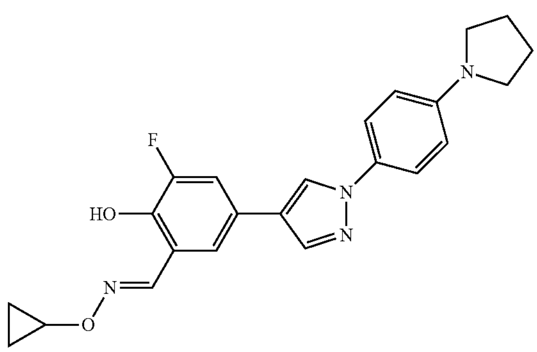 [SMILES: Oc1c(F)cc(-c2cnn(-c3ccc(N4CCCC4)cc3)c2)cc1/C=N/OC1CC1] | (E)-3-fluoro-2-hydroxy-5-(1-(4-(pyrrolidin-1-yl)phenyl)-1H-pyrazol-4-yl)benzaldehyde O-cyclopropyl oxime |
| A42 | 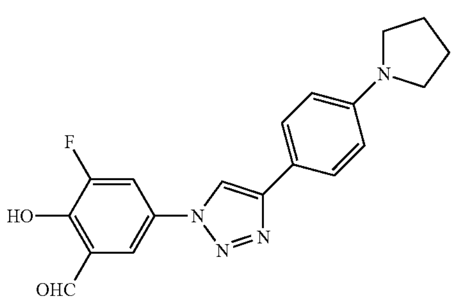 [SMILES: O=Cc1cc(-n2cc(-c3ccc(N4CCCC4)cc3)nn2)cc(F)c1O] | 3-fluoro-2-hydroxy-5-(4-(4-(pyrrolidin-1-yl)phenyl)-1H-1,2,3-triazol-1-yl)benzaldehyde |

TABLE 1A-continued

| Compound No. | Chemical Structure | Chemical Name |
|---|---|---|
| A43 | 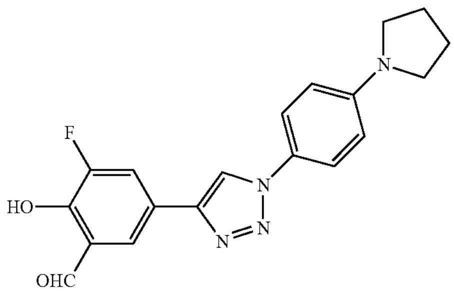 [SMILES: O=Cc1cc(-c2cn(-c3ccc(N4CCCC4)cc3)nn2)cc(F)c1O] | 3-fluoro-2-hydroxy-5-(1-(4-(pyrrolidin-1-yl)phenyl)-1H-1,2,3-triazol-4-yl)benzaldehyde |
| A44 | 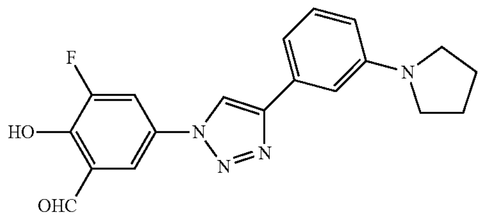 [SMILES: O=Cc1cc(-n2cc(-c3cccc(N4CCCC4)c3)nn2)cc(F)c1O] | 3-fluoro-2-hydroxy-5-(4-(3-(pyrrolidin-1-yl)phenyl)-1H-1,2,3-triazol-1-yl)benzaldehyde |
| A45 | 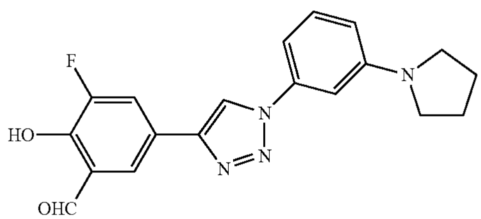 [SMILES: O=Cc1cc(-c2cn(-c3cccc(N4CCCC4)c3)nn2)cc(F)c1O] | 3-fluoro-2-hydroxy-5-(1-(3-(pyrrolidin-1-yl)phenyl)-1H-1,2,3-triazol-4-yl)benzaldehyde |
| A46 | 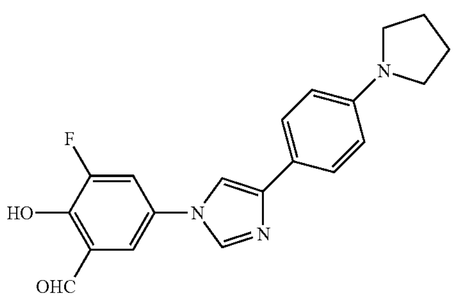 [SMILES: O=Cc1cc(-n2cnc(-c3ccc(N4CCCC4)cc3)c2)cc(F)c1O] | 3-fluoro-2-hydroxy-5-(4-(4-(pyrrolidin-1-yl)phenyl)-1H-imidazol-1-yl)benzaldehyde |
| A47 | 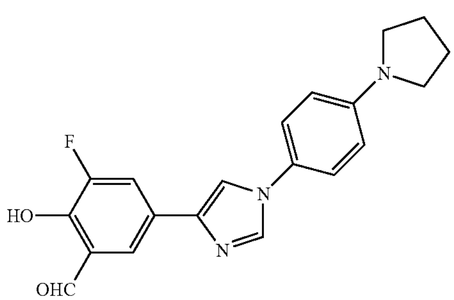 [SMILES: O=Cc1cc(-c2cn(-c3ccc(N4CCCC4)cc3)cn2)cc(F)c1O] | 3-fluoro-2-hydroxy-5-(1-(4-(pyrrolidin-1-yl)phenyl)-1H-imidazol-4-yl)benzaldehyde |

TABLE 1A-continued

| Compound No. | Chemical Structure | Chemical Name |
|---|---|---|
| A48 | 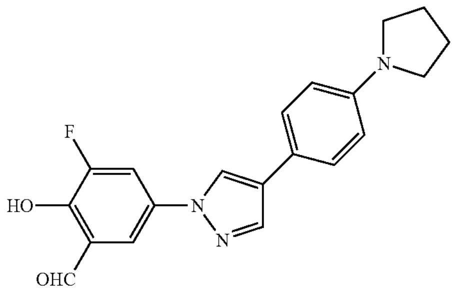 [SMILES: O=Cc1cc(-n2cc(-c3ccc(N4CCCC4)cc3)cn2)cc(F)c1O] | 3-fluoro-2-hydroxy-5-(4-(4-(pyrrolidin-1-yl)phenyl)-1H-pyrazol-1-yl)benzaldehyde |
| A49 | 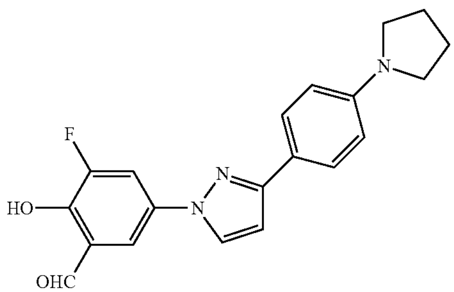 [SMILES: O=Cc1cc(-n2ccc(-c3ccc(N4CCCC4)cc3)n2)cc(F)c1O] | 3-fluoro-2-hydroxy-5-(3-(4-(pyrrolidin-1-yl)phenyl)-1H-pyrazol-1-yl)benzaldehyde |
| A50 | 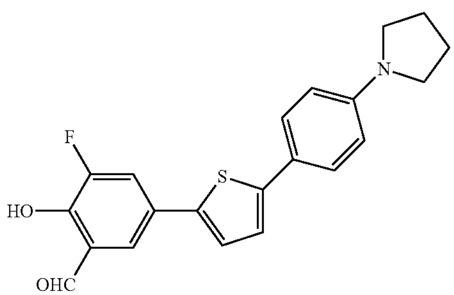 [SMILES: O=Cc1cc(-c2ccc(-c3ccc(N4CCCC4)cc3)s2)cc(F)c1O] | 3-fluoro-2-hydroxy-5-(5-(4-(pyrrolidin-1-yl)phenyl)thiophen-2-yl)benzaldehyde |
| A51 | 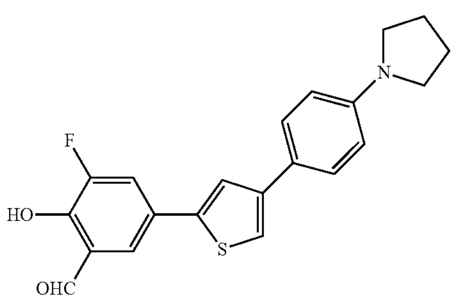 [SMILES: O=Cc1cc(-c2cc(-c3ccc(N4CCCC4)cc3)cs2)cc(F)c1O] | 3-fluoro-2-hydroxy-5-(4-(4-(pyrrolidin-1-yl)phenyl)thiophen-2-yl)benzaldehyde |
| A52 | 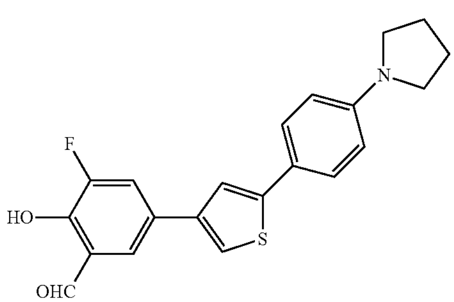 [SMILES: O=Cc1cc(-c2csc(-c3ccc(N4CCCC4)cc3)c2)cc(F)c1O] | 3-fluoro-2-hydroxy-5-(5-(4-(pyrrolidin-1-yl)phenyl)thiophen-3-yl)benzaldehyde |

TABLE 1A-continued

| Compound No. | Chemical Structure | Chemical Name |
|---|---|---|
| A53 | 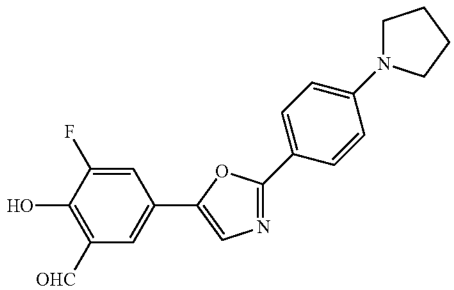 [SMILES: O=Cc1cc(-c2cnc(-c3ccc(N4CCCC4)cc3)o2)cc(F)c1O] | 3-fluoro-2-hydroxy-5-(2-(4-(pyrrolidin-1-yl)phenyl)oxazol-5-yl)benzaldehyde |
| A54 | 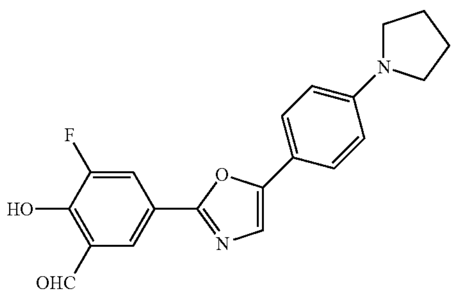 [SMILES: O=Cc1cc(-c2ncc(-c3ccc(N4CCCC4)cc3)o2)cc(F)c1O] | 3-fluoro-2-hydroxy-5-(5-(4-(pyrrolidin-1-yl)phenyl)oxazol-2-yl)benzaldehyde |
| A55 | 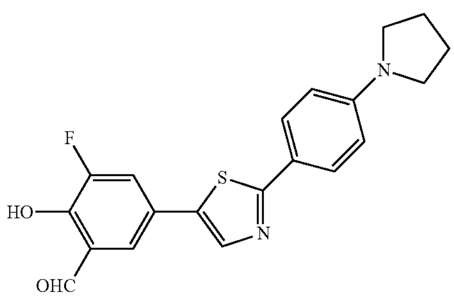 [SMILES: O=Cc1cc(-c2cnc(-c3ccc(N4CCCC4)cc3)s2)cc(F)c1O] | 3-fluoro-2-hydroxy-5-(2-(4-(pyrrolidin-1-yl)phenyl)thiazol-5-yl)benzaldehyde |
| A56 | 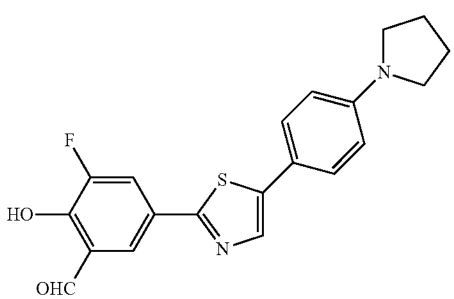 [SMILES: O=Cc1cc(-c2ncc(-c3ccc(N4CCCC4)cc3)s2)cc(F)c1O] | 3-fluoro-2-hydroxy-5-(5-(4-(pyrrolidin-1-yl)phenyl)thiazol-2-yl)benzaldehyde |
| A57 | 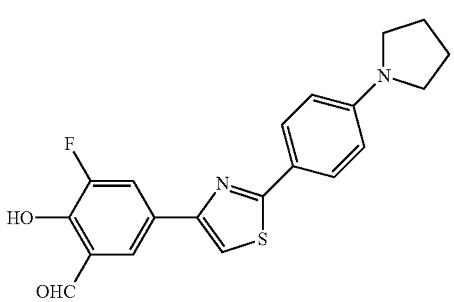 [SMILES: O=Cc1cc(-c2csc(-c3ccc(N4CCCC4)cc3)n2)cc(F)c1O] | 3-fluoro-2-hydroxy-5-(2-(4-(pyrrolidin-1-yl)phenyl)thiazol-4-yl)benzaldehyde |

TABLE 1A-continued

| Compound No. | Chemical Structure | Chemical Name |
|---|---|---|
| A58 | 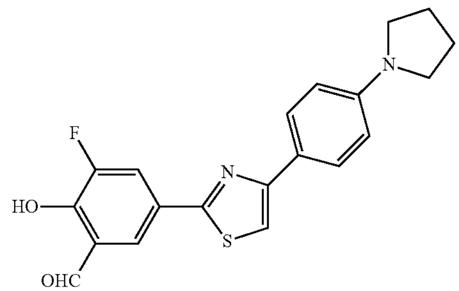 [SMILES: O=Cc1cc(-c2nc(-c3ccc(N4CCCC4)cc3)cs2)cc(F)c1O] | 3-fluoro-2-hydroxy-5-(4-(4-(pyrrolidin-1-yl)phenyl)thiazol-2-yl)benzaldehyde |
| A59 | 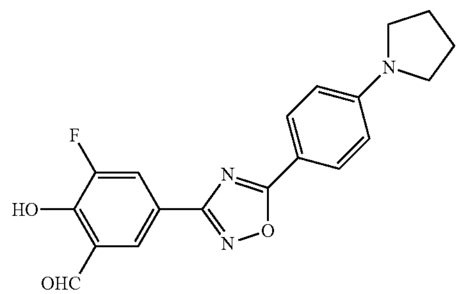 [SMILES: O=Cc1cc(-c2noc(-c3ccc(N4CCCC4)cc3)n2)cc(F)c1O] | 3-fluoro-2-hydroxy-5-(5-(4-(pyrrolidin-1-yl)phenyl)-1,2,4-oxadiazol-3-yl)benzaldehyde |
| A60 | 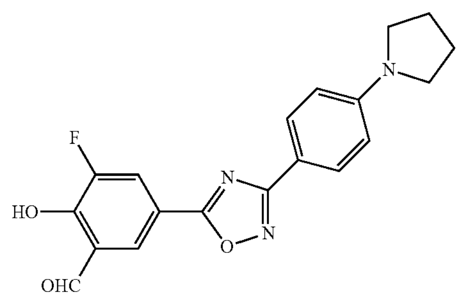 | 3-fluoro-2-hydroxy-5-(3-(4-(pyrrolidin-1-yl)phenyl)-1,2,4-oxadiazol-5-yl)benzaldehyde |
| A61 | 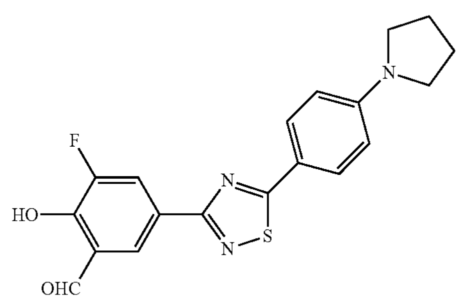 [SMILES: O=Cc1cc(-c2nsc(-c3ccc(N4CCCC4)cc3)n2)cc(F)c1O] | 3-fluoro-2-hydroxy-5-(5-(4-(pyrrolidin-1-yl)phenyl)-1,2,4-thiadiazol-3-yl)benzaldehyde |
| A62 | 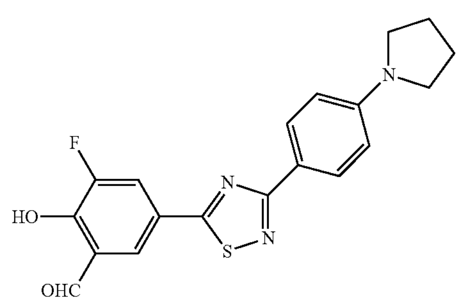 [SMILES: O=Cc1cc(-c2nc(-c3ccc(N4CCCC4)cc3)ns2)cc(F)c1O] | 3-fluoro-2-hydroxy-5-(3-(4-(pyrrolidin-1-yl)phenyl)-1,2,4-thiadiazol-5-yl)benzaldehyde |

TABLE 1A-continued

| Compound No. | Chemical Structure | Chemical Name |
|---|---|---|
| A63 | 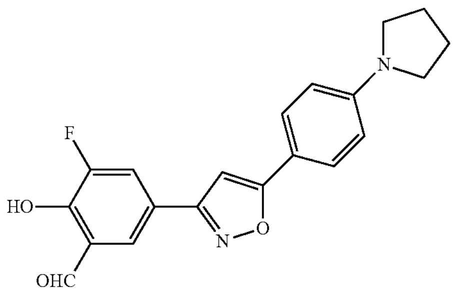 [SMILES: O=Cc1cc(-c2cc(-c3ccc(N4CCCC4)cc3)on2)cc(F)c1O] | 3-fluoro-2-hydroxy-5-(5-(4-(pyrrolidin-1-yl)phenyl)isoxazol-3-yl)benzaldehyde |
| A64 | 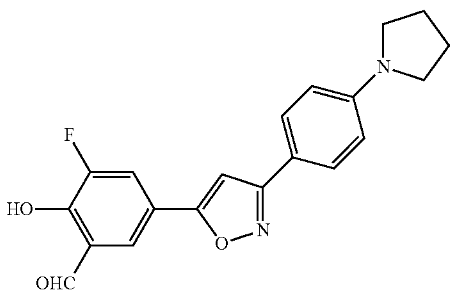 | 3-fluoro-2-hydroxy-5-(3-(4-(pyrrolidin-1-yl)phenyl)isoxazol-5-yl)benzaldehyde |
| A65 | 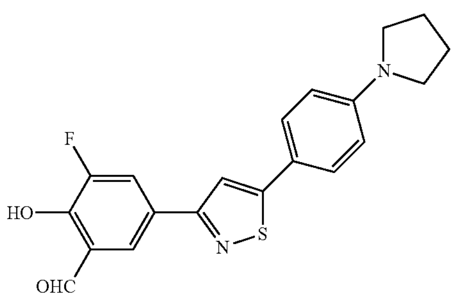 [SMILES: O=Cc1cc(-c2cc(-c3ccc(N4CCCC4)cc3)sn2)cc(F)c1O] | 3-fluoro-2-hydroxy-5-(5-(4-(pyrrolidin-1-yl)phenyl)isothiazol-3-yl)benzaldehyde |
| A66 | 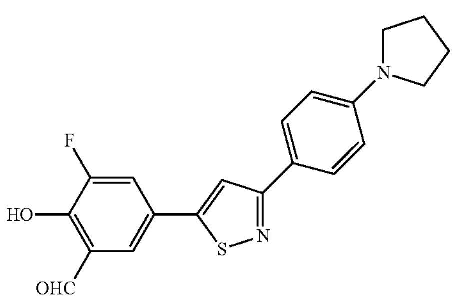 [SMILES: O=Cc1cc(-c2cc(-c3ccc(N4CCCC4)cc3)ns2)cc(F)c1O] | 3-fluoro-2-hydroxy-5-(3-(4-(pyrrolidin-1-yl)phenyl)isothiazol-5-yl)benzaldehyde |
| A67 | 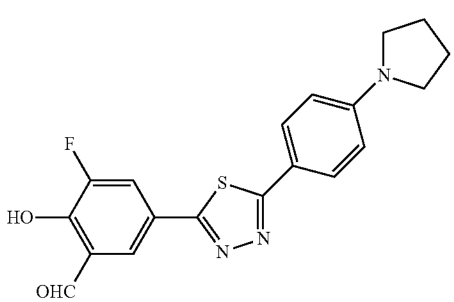 [SMILES: O=Cc1cc(-c2nnc(-c3ccc(N4CCCC4)cc3)s2)cc(F)c1O] | 3-fluoro-2-hydroxy-5-(5-(4-(pyrrolidin-1-yl)phenyl)-1,3,4-thiadiazol-2-yl)benzaldehyde |

TABLE 1A-continued

| Compound No. | Chemical Structure | Chemical Name |
|---|---|---|
| A68 | 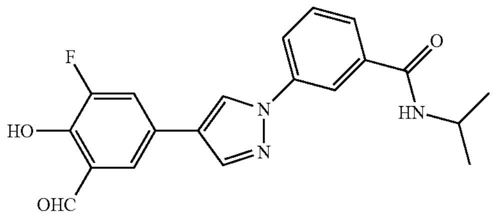 [SMILES: CC(C)NC(=O)c1cccc(-n2cc(-c3cc(F)c(O)c(C=O)c3)cn2)c1] | 3-(4-(3-fluoro-5-formyl-4-hydroxyphenyl)-1H-pyrazol-1-yl)-N-isopropylbenzamide |
| A69 | 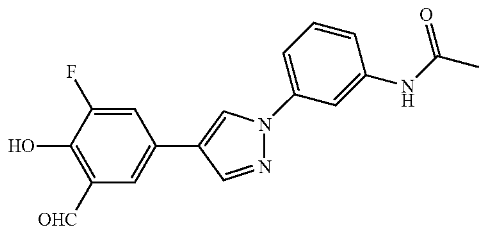 [SMILES: CC(=O)Nc1cccc(-n2cc(-c3cc(F)c(O)c(C=O)c3)cn2)c1] | N-(3-(4-(3-fluoro-5-formyl-4-hydroxyphenyl)-1H-pyrazol-1-yl)phenyl)acetamide |
| A70 | 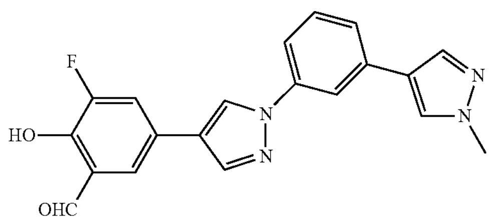 [SMILES: Cn1cc(-c2cccc(-n3cc(-c4cc(F)c(O)c(C=O)c4)cn3)c2)cn1] | 3-fluoro-2-hydroxy-5-(1-(3-(1-methyl-1H-pyrazol-4-yl)phenyl)-1H-pyrazol-4-yl)benzaldehyde |
| A71 | 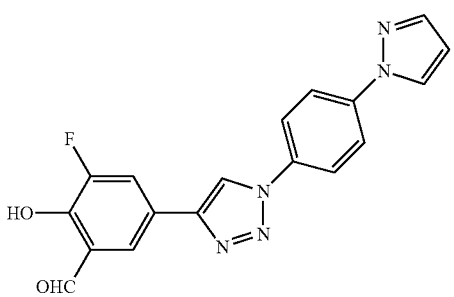 [SMILES: O=Cc1cc(-c2cn(-c3ccc(-n4cccn4)cc3)nn2)cc(F)c1O] | 5-(1-(4-(1H-pyrazol-1-yl)phenyl)-1H-1,2,3-triazol-4-yl)-3-fluoro-2-hydroxybenzaldehyde |
| A72 | 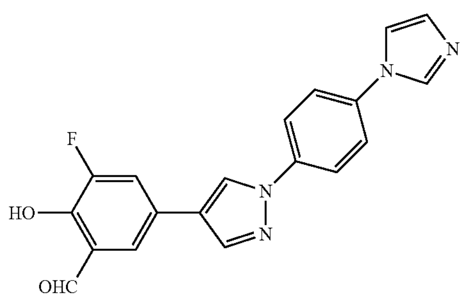 [SMILES: O=Cc1cc(-c2cnn(-c3ccc(-n4ccnc4)cc3)c2)cc(F)c1O] | 5-(1-(4-(1H-imidazol-1-yl)phenyl)-1H-pyrazol-4-yl)-3-fluoro-2-hydroxybenzaldehyde |
| A73 | 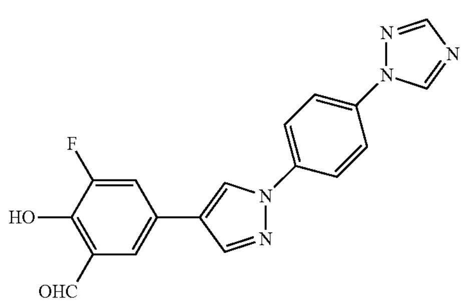 [SMILES: O=Cc1cc(-c2cnn(-c3ccc(-n4cncn4)cc3)c2)cc(F)c1O] | 5-(1-(4-(1H-1,2,4-triazol-1-yl)phenyl)-1H-pyrazol-4-yl)-3-fluoro-2-hydroxybenzaldehyde |

TABLE 1A-continued

| Compound No. | Chemical Structure | Chemical Name |
| --- | --- | --- |
| A74 | 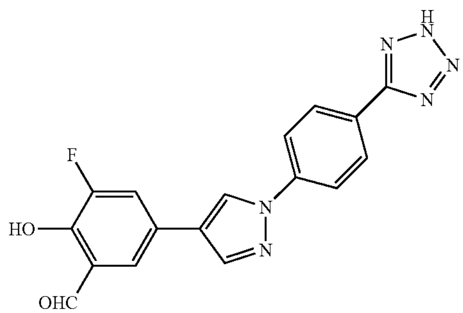 [SMILES: O=Cc1cc(-c2cnn(-c3ccc(-c4nn[nH]n4)cc3)c2)cc(F)c1O] | 5-(1-(4-(2H-tetrazol-5-yl)phenyl)-1H-pyrazol-4-yl)-3-fluoro-2-hydroxybenzaldehyde |
| A75 | 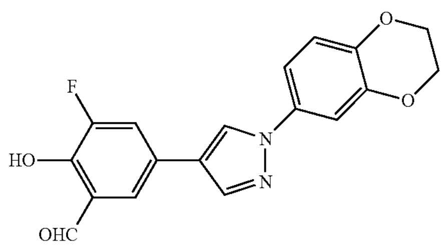 [SMILES: O=Cc1cc(-c2cnn(-c3ccc4c(c3)OCCO4)c2)cc(F)c1O] | 5-(1-(2,3-dihydrobenzo[b][1,4]dioxin-6-yl)-1H-pyrazol-4-yl)-3-fluoro-2-hydroxybenzaldehyde |
| A76 | 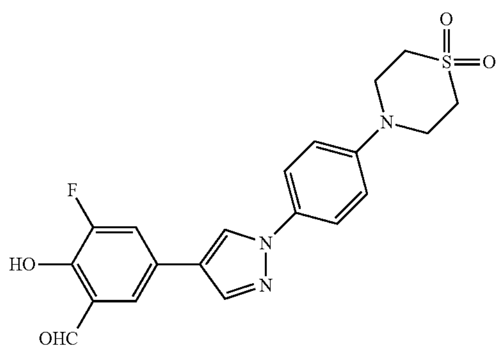 [SMILES: O=Cc1cc(-c2cnn(-c3ccc(N4CCS(=O)(=O)CC4)cc3)c2)cc(F)c1O] | 5-(1-(4-(1,1-dioxidothiomorpholino)phenyl)-1H-pyrazol-4-yl)-3-fluoro-2-hydroxybenzaldehyde |
| A77 | 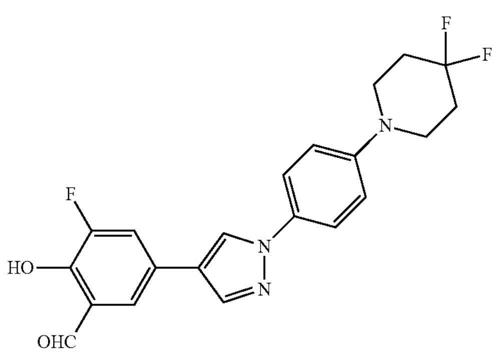 [SMILES: O=Cc1cc(-c2cnn(-c3ccc(N4CCC(F)(F)CC4)cc3)c2)cc(F)c1O] | 5-(1-(4-(4,4-difluoropiperidin-1-yl)phenyl)-1H-pyrazol-4-yl)-3-fluoro-2-hydroxybenzaldehyde |
| A78 | 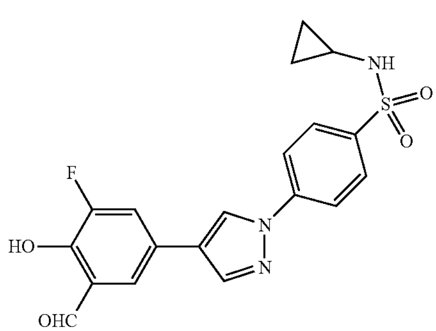 [SMILES: O=Cc1cc(-c2cnn(-c3ccc(S(=O)(=O)NC4CC4)cc3)c2)cc(F)c1O] | N-cyclopropyl-4-(4-(3-fluoro-5-formyl-4-hydroxyphenyl)-1H-pyrazol-1-yl)benzenesulfonamide |

TABLE 1A-continued

| Compound No. | Chemical Structure | Chemical Name |
|---|---|---|
| A79 | 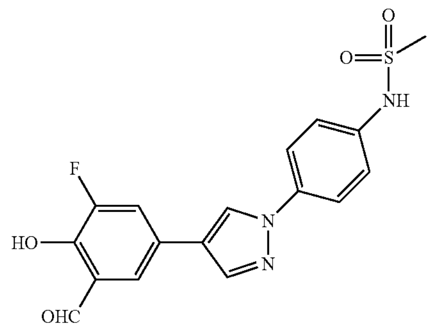 [SMILES: CS(=O)(=O)Nc1ccc(-n2cc(-c3cc(F)c(O)c(C=O)c3)cn2)cc1] | N-(4-(4-(3-fluoro-5-formyl-4-hydroxyphenyl)-1H-pyrazol-1-yl)phenyl)methanesulfonamide |
| A80 | 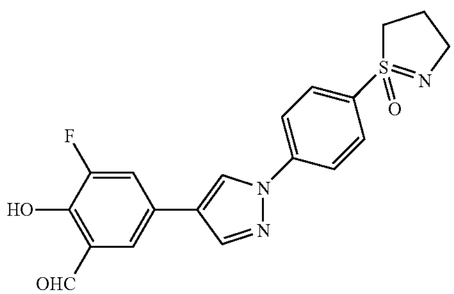 [SMILES: O=Cc1cc(-c2cnn(-c3ccc(S4(=O)=NCCC4)cc3)c2)cc(F)c1O] | 3-fluoro-2-hydroxy-5-(1-(4-(1-oxido-4,5-dihydro-3H-1λ6-isothiazol-1-yl)phenyl)-1H-pyrazol-4-yl)benzaldehyde |
| A81 | 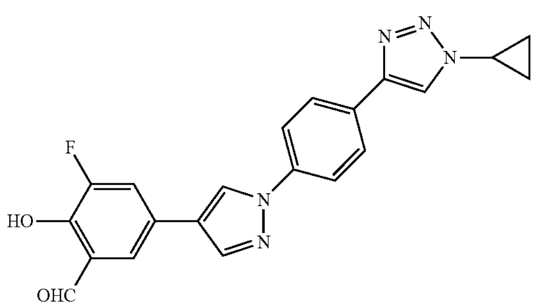 [SMILES: O=Cc1cc(-c2cnn(-c3ccc(-c4cn(C5CC5)nn4)cc3)c2)cc(F)c1O] | 5-(1-(4-(1-cyclopropyl-1H-1,2,3-triazol-4-yl)phenyl)-1H-pyrazol-4-yl)-3-fluoro-2-hydroxybenzaldehyde |
| A82 | 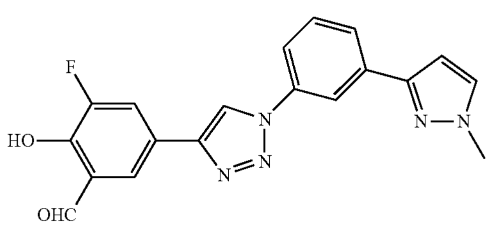 [SMILES: Cn1ccc(-c2cccc(-n3cc(-c4cc(F)c(O)c(C=O)c4)nn3)c2)n1] | 3-fluoro-2-hydroxy-5-(1-(3-(1-methyl-1H-pyrazol-3-yl)phenyl)-1H-1,2,3-triazol-4-yl)benzaldehyde |
| A83 | 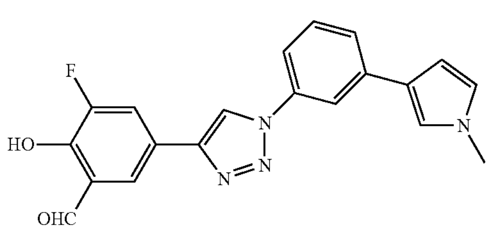 | 3-fluoro-2-hydroxy-5-(1-(3-(1-methyl-1H-pyrrol-3-yl)phenyl)-1H-1,2,3-triazol-4-yl)benzaldehyde |

TABLE 1A-continued

| Compound No. | Chemical Structure | Chemical Name |
|---|---|---|
| A84 | 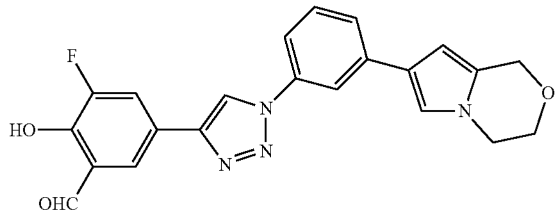 [SMILES: O=Cc1cc(-c2cn(-c3cccc(-c4cc5n(c4)CCOC5)c3)nn2)cc(F)c1O] | 5-(1-(3-(3,4-dihydro-1H-pyrrolo[2,1-c][1,4]oxazin-7-yl)phenyl)-1H-1,2,3-triazol-4-yl)-3-fluoro-2-hydroxybenzaldehyde |
| A85 | 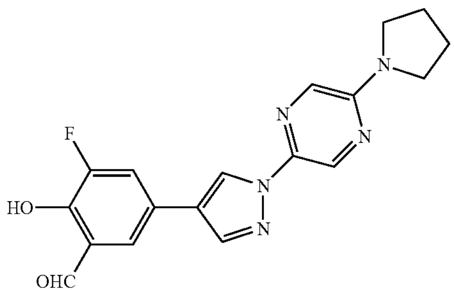 [SMILES: O=Cc1cc(-c2cnn(-c3cnc(N4CCCC4)cn3)c2)cc(F)c1O] | 3-fluoro-2-hydroxy-5-(1-(5-(pyrrolidin-1-yl)pyrazin-2-yl)-1H-pyrazol-4-yl)benzaldehyde |
| A86 | 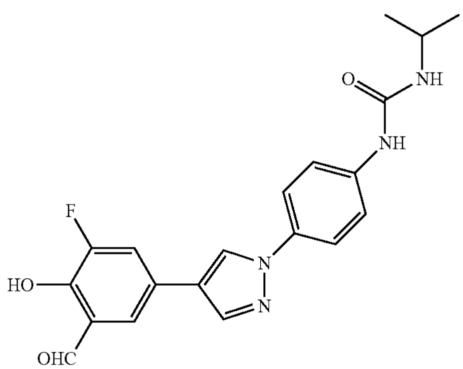 [SMILES: CC(C)NC(=O)Nc1ccc(-n2cc(-c3cc(F)c(O)c(C=O)c3)cn2)cc1] | 1-(4-(4-(3-fluoro-5-formyl-4-hydroxyphenyl)-1H-pyrazol-1-yl)phenyl)-3-isopropylurea |
| A87 | 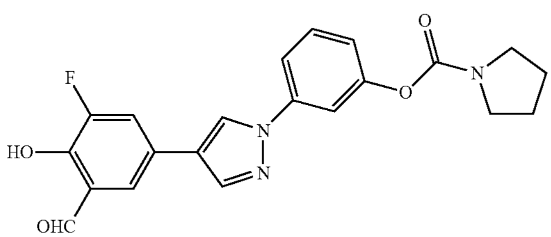 [SMILES: O=Cc1cc(-c2cnn(-c3cccc(OC(=O)N4CCCC4)c3)c2)cc(F)c1O] | 3-(4-(3-fluoro-5-formyl-4-hydroxyphenyl)-1H-pyrazol-1-yl)phenyl pyrrolidine-1-carboxylate |
| A88 | 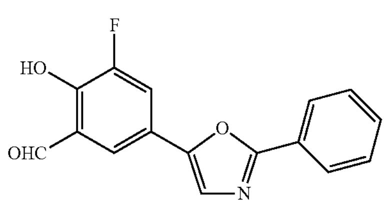 [SMILES: O=Cc1cc(-c2cnc(-c3ccccc3)o2)cc(F)c1O] | 3-fluoro-2-hydroxy-5-(2-phenyloxazol-5-yl)benzaldehyde |
| A89 | 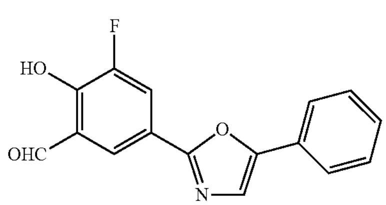 [SMILES: O=Cc1cc(-c2ncc(-c3ccccc3)o2)cc(F)c1O] | 3-fluoro-2-hydroxy-5-(5-phenyloxazol-2-yl)benzaldehyde |

TABLE 1A-continued

| Compound No. | Chemical Structure | Chemical Name |
| --- | --- | --- |
| A90 | 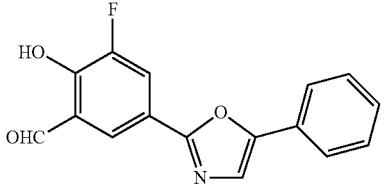 [SMILES: O=Cc1cc(-c2ncc(-c3ccccc3)o2)cc(F)c1O] | 3-fluoro-2-hydroxy-5-(4-phenyloxazol-2-yl)benzaldehyde |
| A91 | 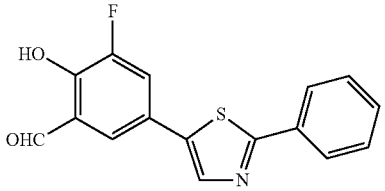 [SMILES: O=Cc1cc(-c2cnc(-c3ccccc3)s2)cc(F)c1O] | 3-fluoro-2-hydroxy-5-(2-phenylthiazol-5-yl)benzaldehyde |
| A92 | 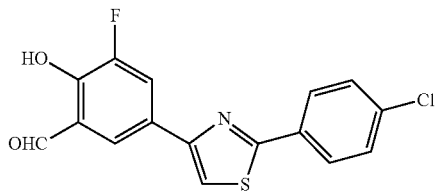 [SMILES: O=Cc1cc(-c2csc(-c3ccc(Cl)cc3)n2)cc(F)c1O] | 5-(2-(4-chlorophenyl)thiazol-4-yl)-3-fluoro-2-hydroxybenzaldehyde |
| A93 | 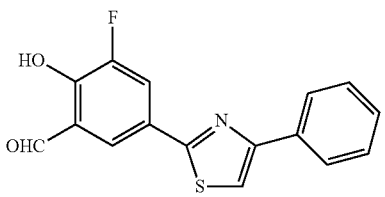 [SMILES: O=Cc1cc(-c2nc(-c3ccccc3)cs2)cc(F)c1O] | 3-fluoro-2-hydroxy-5-(4-phenylthiazol-2-yl)benzaldehyde |
| A94 | 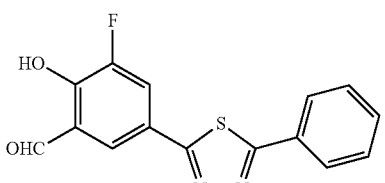 | 3-fluoro-2-hydroxy-5-(5-phenyl-1,3,4-thiadiazol-2-yl)benzaldehyde |
| A95 | 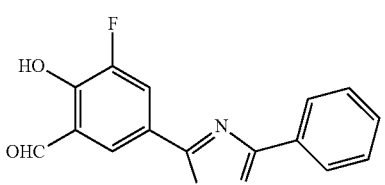 | 3-fluoro-2-hydroxy-5-(3-phenyl-1,2,4-thiadiazol-5-yl)benzaldehyde |
| A96 | 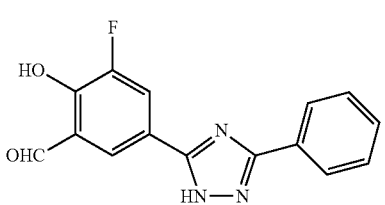 [SMILES: O=Cc1cc(-c2nc(-c3ccccc3)n[nH]2)cc(F)c1O] | 3-fluoro-2-hydroxy-5-(3-phenyl-1H-1,2,4-triazol-5-yl)benzaldehyde |

TABLE 1A-continued

| Compound No. | Chemical Structure | Chemical Name |
|---|---|---|
| A97 | 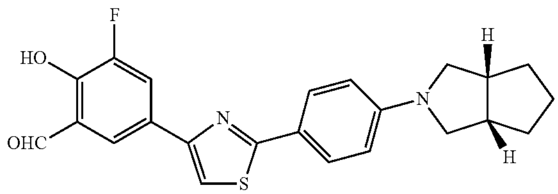 [SMILES: O=Cc1cc(-c2csc(-c3ccc(N4C[C@H]5CCC[C@H]5C4)cc3)n2)cc(F)c1O] | 3-fluoro-5-(2-(4-((3aR,6aS)-hexahydrocyclopenta[c]pyrrol-2(1H)-yl)phenyl)thiazol-4-yl)-2-hydroxybenzaldehyde |
| A98 | 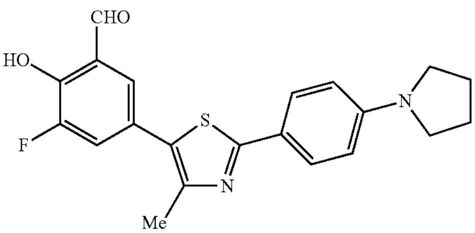 [SMILES: Cc1nc(-c2ccc(N3CCCC3)cc2)sc1-c1cc(F)c(O)c(C=O)c1] | 3-fluoro-2-hydroxy-5-(4-methyl-2-(4-(pyrrolidin-1-yl)phenyl)thiazol-5-yl)benzaldehyde |
| A99 | 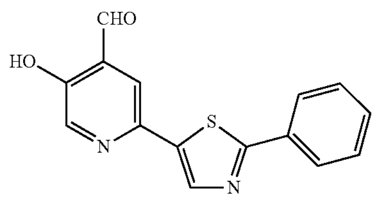 [SMILES: O=Cc1cc(-c2cnc(-c3ccccc3)s2)ncc1O] | 5-hydroxy-2-(2-phenylthiazol-5-yl)isonicotinaldehyde |
| A100 | 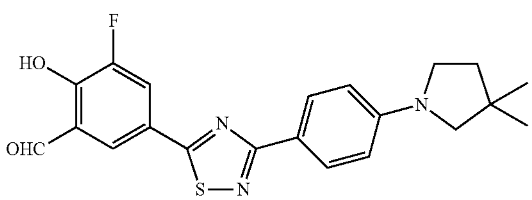 [SMILES: CC1(C)CCN(c2ccc(-c3nsc(-c4cc(F)c(O)c(C=O)c4)n3)cc2)C1] | 5-(3-(4-(3,3-dimethylpyrroldiin-1-yl)phenyl)-1,2,4-thiadiazol-5-yl)-3-fluoro-2-hydroxybenzaldehyde |
| A101 | 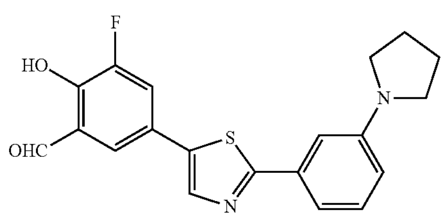 [SMILES: O=Cc1cc(-c2cnc(-c3cccc(N4CCCC4)c3)s2)cc(F)c1O] | 3-fluoro-2-hydroxy-5-(2-(3-(pyrrolidin-1-yl)phenyl)thiazol-5-yl)benzaldehyde |
| A102 | 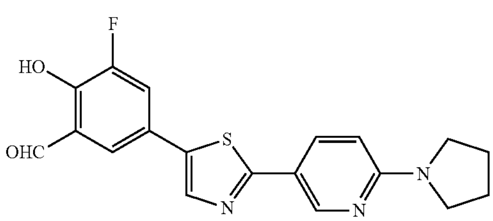 [SMILES: O=Cc1cc(-c2cnc(-c3ccc(N4CCCC4)nc3)s2)cc(F)c1O] | 3-fluoro-2-hydroxy-5-(2-(6-(pyrrolidin-1-yl)pyridin-3-yl)thiazol-5-yl)benzaldehyde |
| A103 | 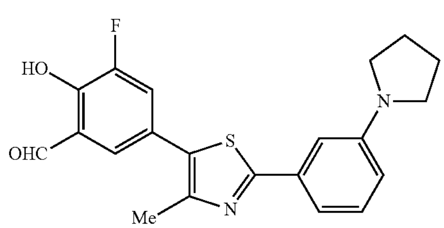 [SMILES: Cc1nc(-c2cccc(N3CCCC3)c2)sc1-c1cc(F)c(O)c(C=O)c1] | 3-fluoro-2-hydroxy-5-(4-methyl-2-(3-(pyrrolidin-1-yl)phenyl)thiazol-5-yl)benzaldehyde |

TABLE 1A-continued

| Compound No. | Chemical Structure | Chemical Name |
|---|---|---|
| A104 | 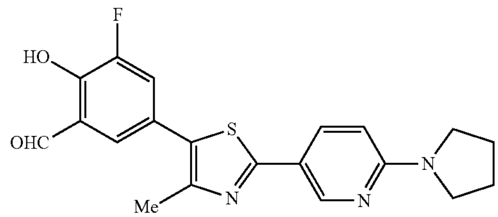 [SMILES: Cc1nc(-c2ccc(N3CCCC3)nc2)sc1-c1cc(F)c(O)c(C=O)c1] | 3-fluoro-2-hydroxy-5-(4-methyl-2-(6-(pyrrolidin-1-yl)pyridin-3-yl)thiazol-5-yl)benzaldehyde |
| A105 | 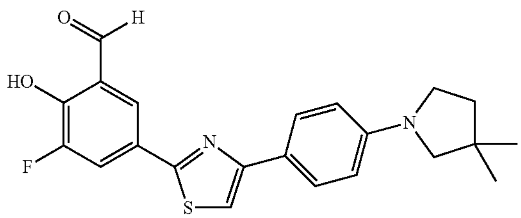 [SMILES: CC1(C)CCN(c2ccc(-c3csc(-c4cc(F)c(O)c(C=O)c4)n3)cc2)C1] | 5-(4-(4-(3,3-dimethylpyrrolidin-1-yl)phenyl)thiazol-2-yl)-3-fluoro-2-hydroxybenzaldehyde |
| A106 | 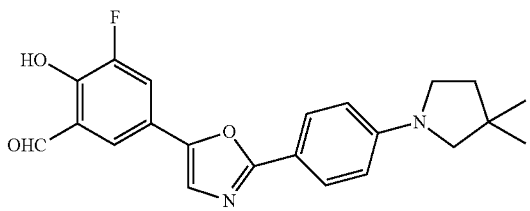 [SMILES: CC1(C)CCN(c2ccc(-c3ncc(-c4cc(F)c(O)c(C=O)c4)o3)cc2)C1] | 5-(2-(4-(3,3-dimethylpyrrolidin-1-yl)phenyl)oxazol-5-yl)-3-fluoro-2-hydroxybenzaldehyde |
| A107 | 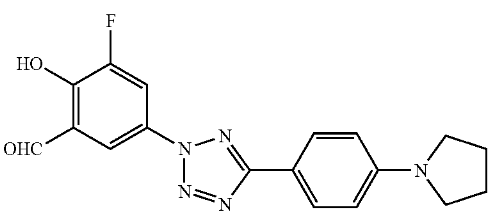 [SMILES: O=Cc1cc(-n2nnc(-c3ccc(N4CCCC4)cc3)n2)cc(F)c1O] | 3-fluoro-2-hydroxy-5-(5-(4-(pyrrolidin-1-yl)phenyl)-2H-tetrazol-2-yl)benzaldehyde |
| A108 | 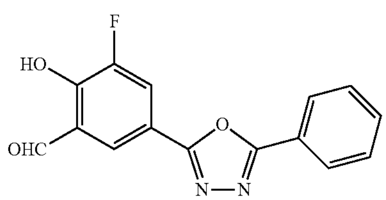 [SMILES: O=Cc1cc(-c2nnc(-c3ccccc3)o2)cc(F)c1O] | 3-fluoro-2-hydroxy-5-(5-phenyl-1,3,4-oxadiazol-2-yl)benzaldehyde |
| A109 | 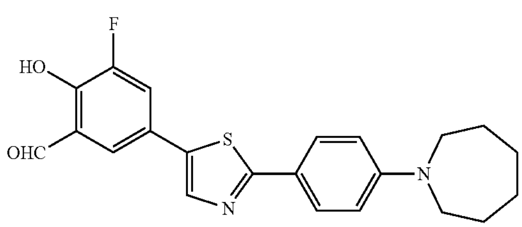 [SMILES: O=Cc1cc(-c2cnc(-c3ccc(N4CCCCCC4)cc3)s2)cc(F)c1O] | 5-(2-(4-(azepan-1-yl)phenyl)thiazol-5-yl)-3-fluoro-2-hydroxybenzaldehyde |
| A110 | 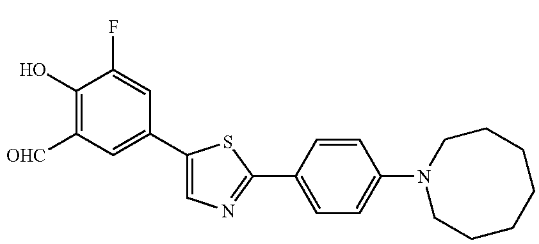 [SMILES: O=Cc1cc(-c2cnc(-c3ccc(N4CCCCCCC4)cc3)s2)cc(F)c1O] | 5-(2-(4-(azocan-1-yl)phenyl)thiazol-5-yl)-3-fluoro-2-hydroxybenzaldehyde |

TABLE 1A-continued

| Compound No. | Chemical Structure | Chemical Name |
|---|---|---|
| A111 | 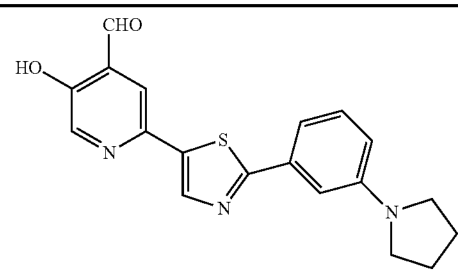 | 5-hydroxy-2-(2-(3-(pyrrolidin-1-yl)phenyl)thiazol-5-yl)isonicotinaldehyde |
| A112 | 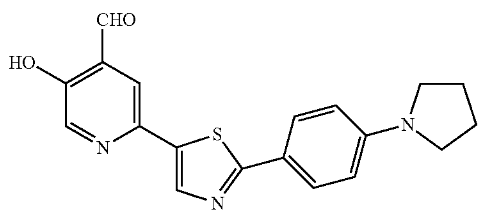 [SMILES: O=Cc1cc(-c2cnc(-c3ccc(N4CCCC4)cc3)s2)ncc1O] | 5-hydroxy-2-(2-(4-(pyrrolidin-1-yl)phenyl)thiazol-5-yl)isonicotinaldehyde |
| A113 | 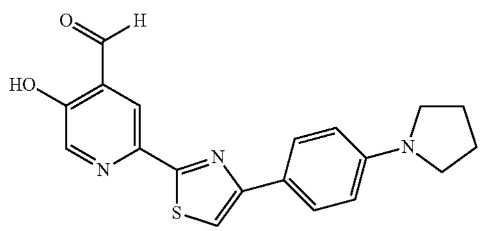 [SMILES: O=Cc1cc(-c2nc(-c3ccc(N4CCCC4)cc3)cs2)ncc1O] | 5-hydroxy-2-(4-(4-(pyrrolidin-1-yl)phenyl)thiazol-2-yl)isonicotinaldehyde |
| A114 | 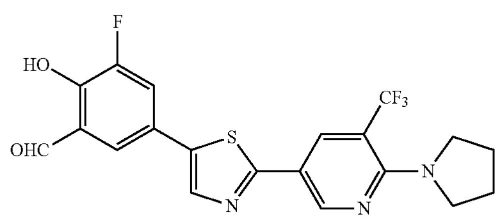 [SMILES: O=Cc1cc(-c2cnc(-c3cnc(N4CCCC4)c(C(F)(F)F)c3)s2)cc(F)c1O] | 3-fluoro-2-hydroxy-5-(2-(6-(pyrrolidin-1-yl)-5-(trifluoromethyl)pyridin-3-yl)thiazol-5-yl)benzaldehyde |
| A115 | 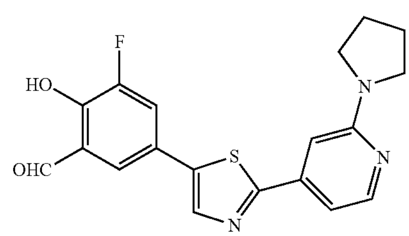 [SMILES: O=Cc1cc(-c2cnc(-c3ccnc(N4CCCC4)c3)s2)cc(F)c1O] | 3-fluoro-2-hydroxy-5-(2-(2-(pyrrolidin-1-yl)pyridin-4-yl)thiazol-5-yl)benzaldehyde |
| A116 | 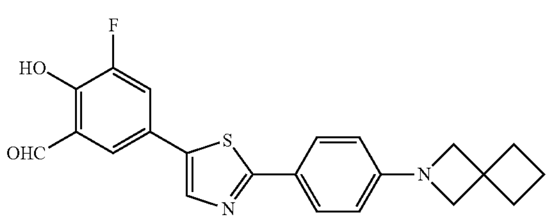 [SMILES: O=Cc1cc(-c2cnc(-c3ccc(N4CC5(CCC5)C4)cc3)s2)cc(F)c1O] | 5-(2-(4-(2-azaspiro[3.3]heptan-2-yl)phenyl)thiazol-5-yl)-3-fluoro-2-hydroxybenzaldehyde |
| A117 | 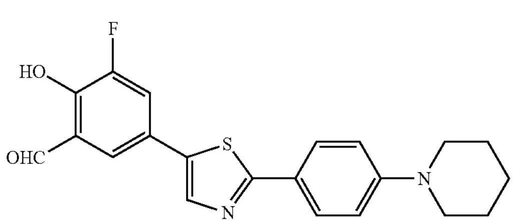 [SMILES: O=Cc1cc(-c2cnc(-c3ccc(N4CCCCC4)cc3)s2)cc(F)c1O] | 3-fluoro-2-hydroxy-5-(2-(4-(piperidin-1-yl)phenyl)thiazol-5-yl)benzaldehyde |

TABLE 1A-continued

| Compound No. | Chemical Structure | Chemical Name |
|---|---|---|
| A118 | 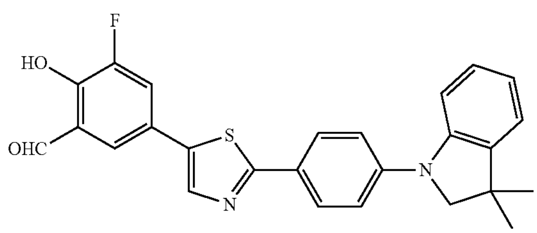 [SMILES: CC1(C)CN(c2ccc(-c3ncc(-c4cc(F)c(O)c(C=O)c4)s3)cc2)c2ccccc21] | 5-(2-(4-(3,3-dimethylindolin-1-yl)phenyl)thiazol-5-yl)-3-fluoro-2-hydroxybenzaldehyde |
| A119 | 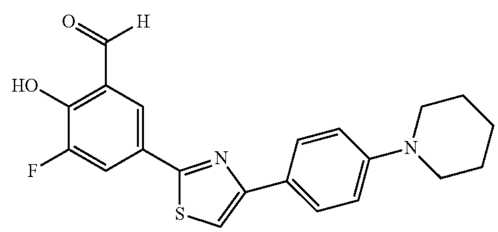 [SMILES: O=Cc1cc(-c2nc(-c3ccc(N4CCCCC4)cc3)cs2)cc(F)c1O] | 3-fluoro-2-hydroxy-5-(4-(4-(piperidin-1-yl)phenyl)thiazol-2-yl)benzaldehyde |
| A120 | 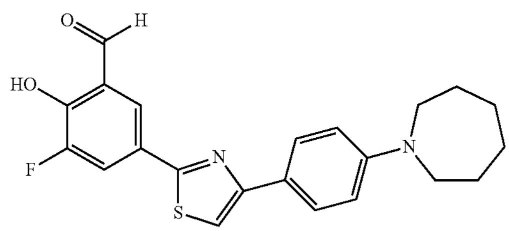 [SMILES: O=Cc1cc(-c2nc(-c3ccc(N4CCCCCC4)cc3)cs2)cc(F)c1O] | 5-(4-(4-(azepan-1-yl)phenyl)thiazol-2-yl)-3-fluoro-2-hydroxybenzaldehyde |
| A121 | 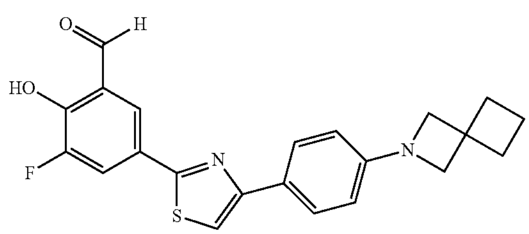 [SMILES: O=Cc1cc(-c2nc(-c3ccc(N4CC5(CCC5)C4)cc3)cs2)cc(F)c1O] | 5-(4-(4-(2-azaspiro[3.3]heptan-2-yl)phenyl)thiazol-2-yl)-3-fluoro-2-hydroxybenzaldehyde |
| A122 | 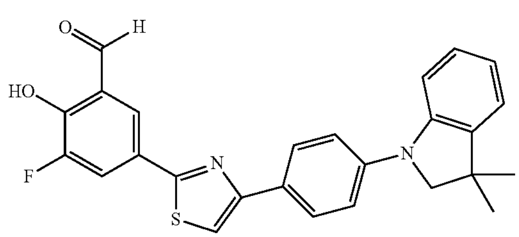 [SMILES: CC1(C)CN(c2ccc(-c3csc(-c4cc(F)c(O)c(C=O)c4)n3)cc2)c2ccccc21] | 5-(4-(4-(3,3-dimethylindolin-1-yl)phenyl)thiazol-2-yl)-3-fluoro-2-hydroxybenzaldehyde |
| A123 | 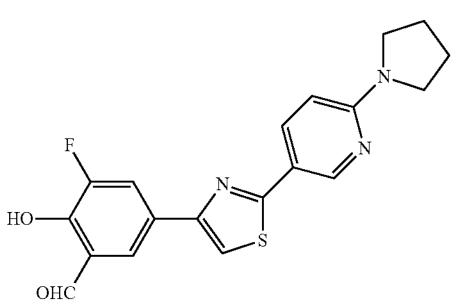 | 3-fluoro-2-hydroxy-5-(2-(6-(pyrrolidin-1-yl)pyridin-3-yl)thiazol-4-yl)benzaldehyde |

TABLE 1A-continued

| Compound No. | Chemical Structure | Chemical Name |
|---|---|---|
| A124 | 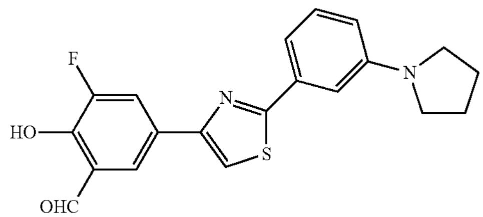 [SMILES: O=Cc1cc(-c2csc(-c3cccc(N4CCCC4)c3)n2)cc(F)c1O] | 3-fluoro-2-hydroxy-5-(2-(3-(pyrrolidin-1-yl)phenyl)thiazol-4-yl)benzaldehyde |
| A125 | 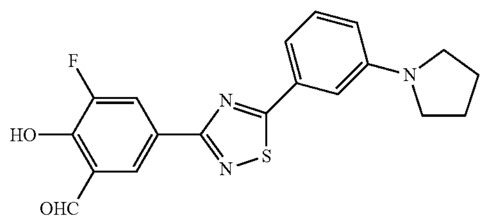 [SMILES: O=Cc1cc(-c2nsc(-c3cccc(N4CCCC4)c3)n2)cc(F)c1O] | 3-fluoro-2-hydroxy-5-(5-(3-(pyrrolidin-1-yl)phenyl)-1,2,4-thiadiazol-3-yl)benzaldehyde |
| A126 | 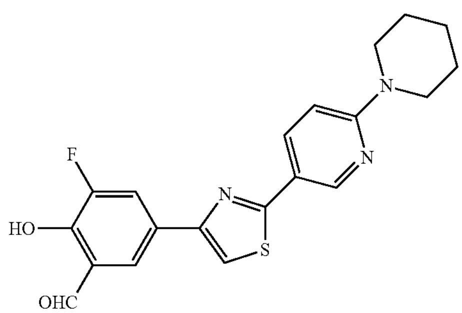 [SMILES: O=Cc1cc(-c2csc(-c3ccc(N4CCCCC4)nc3)n2)cc(F)c1O] | 3-fluoro-2-hydroxy-5-(2-(6-(piperidin-1-yl)pyridin-3-yl)thiazol-4-yl)benzaldehyde |
| A127 | 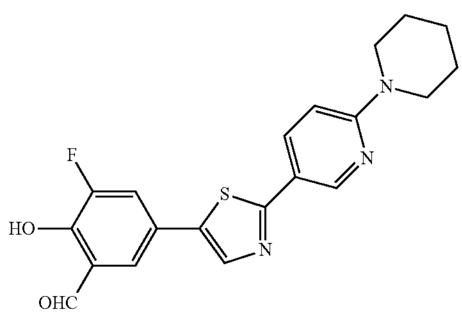 [SMILES: O=Cc1cc(-c2cnc(-c3ccc(N4CCCCC4)nc3)s2)cc(F)c1O] | 3-fluoro-2-hydroxy-5-(2-(6-(piperidin-1-yl)pyridin-3-yl)thiazol-5-yl)benzaldehyde |
| A128 | 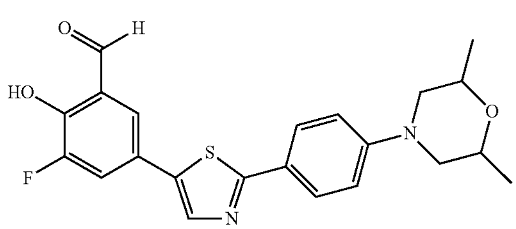 [SMILES: CC1CN(c2ccc(-c3ncc(-c4cc(F)c(O)c(C=O)c4)s3)cc2)CC(C)O1] | 5-(2-(4-(2,6-dimethylmorpholino)phenyl)thiazol-5-yl)-3-fluoro-2-hydroxybenzaldehyde |
| A129 | 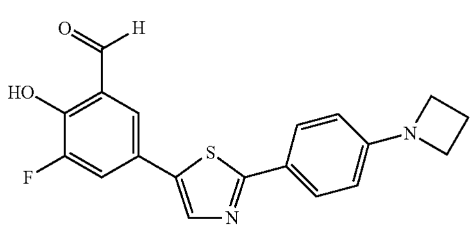 [SMILES: O=Cc1cc(-c2cnc(-c3ccc(N4CCC4)cc3)s2)cc(F)c1O] | 5-(2-(4-(azetidin-1-yl)phenyl)thiazol-5-yl)-3-fluoro-2-hydroxybenzaldehyde |

TABLE 1A-continued

| Compound No. | Chemical Structure | Chemical Name |
|---|---|---|
| A130 | 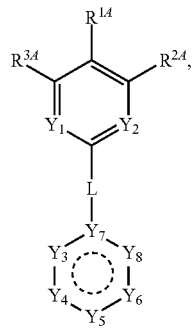 | 5-(2-(4-chlorophenyl)thiazol-5-yl)-3-fluoro-2-hydroxybenzaldehyde | and pharmaceutically acceptable salts thereof.

In one aspect, provided are compounds of Formula (B):

(B)

$$\text{structure}$$

or a tautomer, or a pharmaceutically acceptable salt of any of the foregoing, wherein L is selected from the group consisting of —C≡C—, *—NHC(O)—, *—C(O)NH—, —NHC(O)NH—, *—NHS(O)$_2$—, *—NHS(O)(=NH)—, *—S(O)(=NH)NH—, *—S(O)$_2$NH—, *—S(O)NHNH—, *—NHNHS(O)—, *—C(O)NHNH—, *—NHNHC(O)—, *—NHC(O)O—, and *—OC(O)NH—, wherein * represents the point of attachment to $Y_7$;

$Y_1$ and $Y_2$ are each independently $CR^x$ or N;

$R^x$ is hydrogen or halogen;

when L is —C≡C—, one of $R^{1A}$ and $R^{2A}$ is —OH and the other is selected from the group consisting of —C(O)$R^{a1}$, —CH=N$R^{j1}$, —S(O)$R^{b1}$, —S(O)$_2R^{c1}$, —NHC(O)$R^{d1}$, —NHS(O)$_2R^{e1}$, —C$_1$-C$_6$alkyl-$R^{f1}$, —C$_2$-C$_6$alkenyl-$R^{g1}$, C$_3$-C$_8$ cycloalkyl, C$_3$-C$_8$ cycloalkenyl, and 5- or 6-membered heterocycloalkyl, wherein the C$_3$-C$_8$ cycloalkyl and C$_3$-C$_8$ cycloalkenyl are each independently unsubstituted or substituted with one or more =O, and the 5- or 6-membered heterocycloalkyl is unsubstituted or substituted with one or more substituents independently selected from the group consisting of C$_1$-C$_6$alkyl, C$_3$-C$_8$cycloalkyl, =O, and —C(O)O—C$_1$-C$_6$alkyl;

when L is *—NHC(O)—, *—C(O)NH—, —NHC(O)NH—, *—NHS(O)$_2$—, *—S(O)$_2$NH—, *—S(O)NHNH—, *—C(O)NHNH—, or *—NHC(O)O—, one of $R^{1A}$ and $R^{2A}$ is —OH and the other is selected from the group consisting of —C(O)H, —CH=N$R^{j1}$, and

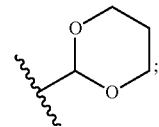

$R^{a1}$ is H, C$_1$-C$_6$alkyl, C$_2$-C$_6$alkenyl, C$_2$-C$_6$alkynyl, C$_1$-C$_6$haloalkyl, 3- to 6-membered heterocyclyl, or 5- to 10-membered heteroaryl, or benzoyl, wherein the 3- to 10-membered heterocyclyl of $R^{a1}$ is unsubstituted or substituted with one or more groups independently selected from the group consisting of C$_1$-C$_6$alkyl, C$_3$-C$_8$ cycloalkyl, =O, and —C(O)O—C$_1$-C$_6$alkyl, and the 5- to 10-membered heteroaryl of $R^{a1}$ is unsubstituted or substituted with one or more groups independently selected from the group consisting of C$_1$-C$_6$alkyl, C$_3$-C$_8$cycloalkyl, and —C(O)O—C$_1$-C$_6$alkyl;

$R^{b1}$, $R^{c1}$, $R^{d1}$, and $R^{e1}$ are each independently H, C$_1$-C$_6$alkyl, C$_2$-C$_6$alkenyl, C$_2$-C$_6$alkynyl, C$_1$-C$_6$haloalkyl, 3- to 10-membered heterocyclyl, 5- to 10-membered heteroaryl, benzoyl, or styryl, wherein the 3- to 10-membered heterocyclyl and 5- to 10-membered heteroaryl of $R^{b1}$, $R^{c1}$, $R^{d1}$, and $R^{e1}$ are each independently selected from the group consisting of C$_1$-C$_6$alkyl, C$_3$-C$_8$cycloalkyl, and —C(O)O—C$_1$-C$_6$alkyl;

$R^{f1}$ and $R^{g1}$ are each independently —OH, unsubstituted 5- to 6-membered heteroaryl, —N$R^{m1}R^{n1}$, benzoyl, or styryl;

$R^{m1}$ is C$_3$-C$_8$ cycloalkyl, unsubstituted or substituted with one or more groups selected from C$_1$-C$_6$alkyl and halo;

$R^{a1}$ is H, C$_1$-C$_6$alkyl, C$_2$-C$_6$alkenyl, or C$_2$-C$_6$alkynyl;

$R^{j1}$ is C$_1$-C$_6$alkyl, 5- to 6-membered heterocyclyl, 5- to 6-membered heteroaryl, 6- to 12-membered aryl, —O$R^{k1}$, —NH$R^{k1}$, —N(C$_1$-C$_6$alkyl)$R^{k1}$, —NHC(O)$R^{k1}$, —NHS(O)$_2R^{k1}$, or —NHC(NH)NH$R^{bb}$, wherein the 5- to 6-membered heterocyclyl of $R^{j1}$ is unsubstituted or substituted with one or more substituents selected from the group consisting of C$_1$-C$_6$alkyl, C$_3$-C$_8$cycloalkyl, =O, —C(O)NH—C$_1$-C$_6$alkyl, and —C(O)O—C$_1$-C$_6$alkyl, and the 5- to 6-membered heteroaryl and 6- to 12-membered aryl of $R^{j1}$ are each independently unsubstituted or substituted with one or more substituents selected from the group consisting of C$_1$-C$_6$alkyl, C$_3$-C$_8$cycloalkyl, and —C(O)O—C$_1$-C$_6$alkyl;

$R^{bb}$ is unsubstituted or substituted C$_1$-C$_6$alkyl, unsubstituted or substituted C$_3$-C$_8$cycloalkyl, unsubstituted or substituted aryl, unsubstituted or substituted heterocycloalkyl, or unsubstituted or substituted heteroaryl;

each $R^{k1}$ is independently $C_1$-$C_6$alkyl, $C_2$-$C_6$alkenyl, $C_2$-$C_6$alkynyl, $C_3$-$C_8$cycloalkyl, or 6- to 12-membered aryl, wherein the $C_1$-$C_6$alkyl of $R^{k1}$ is unsubstituted or substituted with a 5- to 6-membered heterocyclyl or a 5- to 6-membered heteroaryl;

$R^{3A}$ is H, $C_1$-$C_6$alkyl, $C_1$-$C_6$alkoxy, or halogen, wherein the $C_1$-$C_6$alkyl and $C_1$-$C_6$alkoxy of $R^{3A}$ are each independently unsubstituted or substituted with one or more halogen;

indicates that the ring is saturated, partially unsaturated, or fully unsaturated;

$Y_3$ is $CH(X_{1A}$—$R^{6a1})$, $C(X_{1A}$—$R^{6a1})$, N, $N(X_{1A}$—$R^{6a1})$, S, or O;

$Y_4$ is $CH(X_{2A}$—$R^{6b1})$, $C(X_{2A}$—$R^{6b1})$, N, $N(X_{2A}$—$R^{6b1})$, S, or O;

$Y_5$ is $CH(X_{3A}$—$R^{6c1})$, $C(X_{3A}$—$R^{6c1})$, N, $N(X_{3A}$—$R^{6c})$, S, or O;

$Y_6$ is $CH(X_{4A}$—$R^{6d1})$, $C(X_{4A}$—$R^{6d1})$, N, $N(X_{4A}$—$R^{6d1})$, S, or O;

$Y_7$ is N, C, or CH; and $Y_8$ is N, NH, C, or CH;

$X_{1A}$, $X_{2A}$, $X_{3A}$, and $X_{4A}$ are each independently absent,

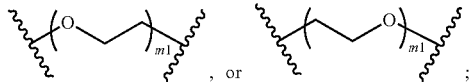

m1 is 1-6;

$R^{6a1}$, $R^{6b1}$, $R^{6c1}$, and $R^{6d1}$ are each independently hydrogen, $C_1$-$C_6$alkyl, $C_1$-$C_6$alkoxy, halo, —OH, —$NR^{p1}R^{q1}$, $C_6$-$C_{12}$ aryl, 3- to 10-membered heterocyclyl, 5- to 10-membered heteroaryl, —$C_1$-$C_6$alkyl-5- to 6-membered heterocyclyl, —OC(O)-5- to 6-membered heterocyclyl, —C(O)$R^{h1}$, —S(O)$_2$N$R^{w1a}R^{w2}$a, —S(O)$_2R^{y1}$, —N$R^{z1a}$S(O)$_2R^{z2}$a, or —N(CH$_3$)CH$_2$C(CH$_3$)$_3$, wherein the $C_1$-$C_6$alkyl and $C_1$-$C_6$alkoxy of $R^{6a1}$, $R^{6b1}$, $R^{6c1}$, and $R^{6d1}$ are each independently unsubstituted or substituted with one or more groups selected from the group consisting of $C_3$-$C_8$ cycloalkyl and halogen; the $C_6$-$C_{12}$ aryl and 5- to 10-membered heteroaryl of $R^{6a1}$, $R^{6b1}$, $R^{6c1}$, and $R^{6d1}$ are each independently unsubstituted or substituted with one or more groups selected from the group consisting of $C_1$-$C_6$alkyl, $C_1$-$C_6$alkoxy, —OH, and $C_1$-$C_6$alkyl-OH; and the 3- to 10-membered heterocyclyl, —$C_1$-$C_6$alkyl-5- to 6-membered heterocyclyl, and —OC(O)-5- to 6-membered heterocyclyl of $R^{6a1}$, $R^{6b1}$, $R^{6c1}$, and $R^{6d1}$ are each independently unsubstituted or substituted with one or more groups selected from the group consisting of $C_1$-$C_6$alkyl, $C_1$-$C_6$alkoxy, —OH, $C_1$-$C_6$alkyl-OH, =O, =S, halo, $C_3$-$C_8$cycloalkyl, —C(O)NH—$C_3$-$C_8$cycloalkyl, $C_6$-$C_{12}$ aryl, and 5- to 6-membered heterocyclyl;

each $R^{h1}$ is independently selected from the group consisting of H, $C_1$-$C_6$alkyl, $C_1$-$C_6$alkoxy, $C_3$-$C_8$cycloalkyl, and —N$R^{r1}R^{s1}$;

each $R^{p1}$ is independently H or $C_1$-$C_6$alkyl;

each $R^{q1}$ is independently $C_2$-$C_3$alkyl, —C(O)$R^{t1}$, —C(O)O$R^{u1}$, or —C(O)N$R^{v1}$;

each $R^{r1}$, $R^{s1}$, $R^{w1a}$, and $R^{z1a}$ is independently selected from H and $C_1$-$C_6$alkyl; and each $R^{t1}$, $R^{u1}$, $R^{v1}$, $R^{w2a}$, $R^{y1}$, and $R^{z2a}$ is independently selected from H, $C_1$-$C_6$alkyl, unsubstituted or substituted $C_3$-$C_8$cycloalkyl, and unsubstituted or substituted heterocyclyl;

or $Y_5$ is $CH(X_{3A}$—$R^{6c1})$ or $C(X_{3A}$—$R^{6c1})$, $Y_6$ is $CH(X_{4A}$—$R^{6d1})$ or $C(X_{4A}$—$R^{6d1})$, and $R^{6c1}$ and $R^{6d1}$ are taken together with the carbon atoms to which they are attached to form a 6-membered aryl, a 6-membered heterocyclyl, or a 6-membered heteroaryl ring; wherein the 6-membered aryl, 6-membered heterocyclyl, and 6-membered heteroaryl rings are each independently unsubstituted or substituted with one or more groups selected from the group consisting of $C_1$-$C_6$alkyl and —C(O)O—$C_1$-$C_6$alkyl; and wherein no more than one of $R^{6a1}$, $R^{6b1}$, $R^{6c1}$, and $R^{6d1}$ is $C_1$-$C_6$alkoxy or —OH.

In some embodiments, of Formula (B), one or more of the following applies:

(1) when L is —C≡C—, $Y_1$ and $Y_2$ are each CH, one of $R^{1A}$ and $R^{2A}$ is —C(O)H, —CH$_2$OH, —C(O)CH$_3$ or —NHC(O)CH$_3$, and $R^{3A}$ is H,

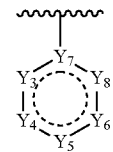

is other than cyclohexyl, phenyl, pyridyl, or naphthyl, and $R^{6c1}$ is hydrogen, $C_2$-$C_3$alkyl, $C_2$-$C_5$alkoxy, Br, Cl, I, —N$R^{p1}R^{q1}$, $C_6$-$C_{12}$ aryl, 3- to 10-membered heterocyclyl, 5- to 10-membered heteroaryl, —$C_1$-$C_6$alkyl-5- to 6-membered heterocyclyl, —OC(O)-5- to 6-membered heterocyclyl, —C(O)$R^{h1}$, —S(O)$_2$N$R^{w1a}R^{w2a}$, —S(O)$_2R^{y1}$, or —N$R^{z1a}$S(O)$_2R^{z2a}$, and each $R^{h1}$ is independently selected from the group consisting of $C_1$-$C_6$alkyl, $C_1$-$C_6$alkoxy, $C_3$-$C_8$cycloalkyl, and —N$R^{r1}R^{s1}$;

(2) when L is —C≡C—, $Y_1$ and $Y_2$ are each CH, one of $R^{1A}$ and $R^{2A}$ is —C(O)H, and $R^{3A}$ is —CH$_3$, t-Bu, or $C_2$-$C_3$alkoxy,

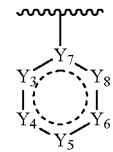

is other than phenyl and pyridyl, $R^{b1}$ and $R^{d1}$ are other than

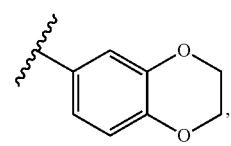 [SMILES: *c1ccc2c(c1)OCCO2]

and $R^{6c1}$ is other than —OH;

(3) when L is —C≡C—, $Y_1$ and $Y_2$ are each CH, one of $R^{1A}$ and $R^{2A}$ is piperidinyl, pyrrolidinyl, pyrrolidinone, piperazinyl, morpholinyl, or thiadiazolidinone 1,1-dioxide, and $R^{3A}$ is H,

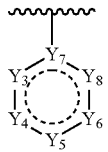

is other than naphthyl, and $R^{6c1}$ is other than fluoro;

(4) when L is *—NHS(O)$_2$— or *—S(O)$_2$NH—, $Y_1$ and $Y_2$ are each CH, one of $R^{1A}$ and $R^{2A}$ is —C(O)H, —CH=NR$^{j1}$, or

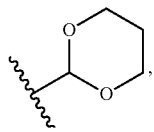

and $R^{3A}$ is H or Br,

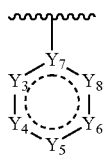

is other than phenyl, and $R^{6a1}$, $R^{6b1}$, $R^{6c1}$, and $R^{6d1}$ are each independently hydrogen, $C_2$-$C_6$alkyl, $C_1$-$C_6$alkoxy, —OH, —NR$^{p1}$R$^{q1}$, $C_6$-$C_{12}$ aryl, 3- to 10-membered heterocyclyl, 5- to 10-membered heteroaryl, —$C_1$-$C_6$alkyl-5- to 6-membered heterocyclyl, —OC(O)-5- to 6-membered heterocyclyl, —C(O)R$^{h1}$, —S(O)$_2$NR$^{w1a}$R$^{w2a}$, —S(O)$_2$R$^{y1}$, or —NR$^{z1a}$S(O)$_2$R$^{z2a}$;

(5) when L is *—C(O)NH— or *—NHC(O)—, $Y_1$ and $Y_2$ are each CH, one of $R^{1A}$ and $R^{2A}$ is —C(O)H, and $R^{3A}$ is H or Cl,

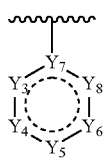

is other than phenyl, and $R^{6a1}$ is other than —CF$_3$; and (6) when L is —NHC(O)NH—, $Y_1$ and $Y_2$ are each CH, one of $R^{1A}$ and $R^{2A}$ is —C(O)H or

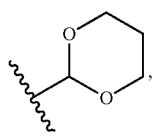

and $R^{3A}$ is H or Cl,

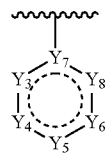

is other than cyclohexyl, and $R^{6c1}$ is other than chloro.

In some embodiments of Formula (B), $R^{j1}$ is $C_1$-$C_6$alkyl, 5- to 6-membered heterocyclyl, 5- to 6-membered heteroaryl, 6- to 12-membered aryl, —OR$^{k1}$, —NHR$^{k1}$, —N($C_1$-$C_6$alkyl)R$^{k1}$, —NHC(O)R$^{k1}$, —NHS(O)$_2$R$^{k1}$, or —NHC(NH)NH$_2$, wherein the 5- to 6-membered heterocyclyl of $R^{j1}$ is unsubstituted or substituted with one or more substituents selected from the group consisting of $C_1$-$C_6$alkyl, $C_3$-$C_8$cycloalkyl, =O, —C(O)NH—$C_1$-$C_6$alkyl, and —C(O)O—$C_1$-$C_6$alkyl, and the 5- to 6-membered heteroaryl and 6- to 12-membered aryl of $R^{j1}$ are each independently unsubstituted or substituted with one or more substituents selected from the group consisting of $C_1$-$C_6$alkyl, $C_3$-$C_8$cycloalkyl, and —C(O)O—$C_1$-$C_6$alkyl; and $R^{6a1}$, $R^{6b1}$, $R^{6c1}$, and $R^{6d1}$ are each independently hydrogen, $C_1$-$C_6$alkyl, $C_1$-$C_6$alkoxy, halo, —OH, —NR$^{p1}$R$^{q1}$, $C_6$-$C_{12}$ aryl, 3- to 10-membered heterocyclyl, 5- to 10-membered heteroaryl, —$C_1$-$C_6$alkyl-5- to 6-membered heterocyclyl, —OC(O)-5- to 6-membered heterocyclyl, —C(O)R$^{h1}$, —S(O)$_2$NR$^{w1a}$R$^{w2a}$, —S(O)$_2$R$^{y1}$, or —NR$^{z1a}$S(O)$_2$R$^{z2a}$, wherein the $C_1$-$C_6$alkyl and $C_1$-$C_6$alkoxy of $R^{6a1}$, $R^{6b1}$, $R^{6c1}$, and $R^{6d1}$ are each independently unsubstituted or substituted with one or more groups selected from the group consisting of $C_3$-$C_8$ cycloalkyl and halogen; the $C_6$-$C_{12}$ aryl and 5- to 10-membered heteroaryl of $R^{6a1}$, $R^{6b1}$, $R^{6c1}$, and $R^{6d1}$ are each independently unsubstituted or substituted with one or more groups selected from the group consisting of $C_1$-$C_6$alkyl, $C_1$-$C_6$alkoxy, —OH, and $C_1$-$C_6$alkyl-OH; and the 3- to 10-membered heterocyclyl, —$C_1$-$C_6$alkyl-5- to 6-membered heterocyclyl, and —OC(O)-5- to 6-membered heterocyclyl of $R^{6a1}$, $R^{6b1}$, $R^{6c1}$, and $R^{6d1}$ are each independently unsubstituted or substituted with one or more groups selected from the group consisting of $C_1$-$C_6$alkyl, $C_1$-$C_6$alkoxy, —OH, $C_1$-$C_6$alkyl-OH, =O, and =S.

In some embodiments, $R^{3A}$ is selected from the group consisting of $C_1$-$C_6$alkyl, $C_1$-$C_6$alkoxy, and halogen, wherein the $C_1$-$C_6$alkyl and $C_1$-$C_6$alkoxy of $R^{3A}$ are each independently unsubstituted or substituted with one or more halogen, and $R^{1A}$, $R^{2A}$, L, $Y_1$, $Y_2$, $Y_3$, $Y_4$, $Y_5$, $Y_6$, and $Y_7$ are as defined for Formula (B) or any variation or embodiment thereof. In some embodiments, $R^{3A}$ is selected from the group consisting of $C_1$-$C_6$alkyl, $C_1$-$C_6$alkoxy, and halogen, and $R^{1A}$, $R^{2A}$, L, $Y_1$, $Y_2$, $Y_3$, $Y_4$, $Y_5$, $Y_6$, and $Y_7$ are as defined for Formula (B) or any variation or embodiment thereof. In some embodiments, $R^{3A}$ is selected from the group consisting of $C_1$-$C_3$alkyl, methoxy, and F, wherein the $C_1$-$C_3$alkyl, methoxy are each independently unsubstituted or substituted with halogen, and $R^{1A}$, $R^{2A}$, L, $Y_1$, $Y_2$, $Y_3$, $Y_4$, $Y_5$, $Y_6$, and $Y_7$ are as defined for Formula (B) or any variation or embodiment thereof.

In some embodiments of Formula (B), $R^{6a1}$, $R^{6b1}$, $R^{6c1}$, and $R^{6d1}$ are each independently hydrogen, $C_1$-$C_6$alkyl, $C_1$-$C_6$alkoxy, halo, —OH, —NR$^{p1}$R$^{q1}$, $C_6$-$C_{12}$ aryl, 3- to 10-membered heterocyclyl, 5- to 10-membered heteroaryl, —$C_1$-$C_6$alkyl-5- to 6-membered heterocyclyl, —OC(O)-5- to 6-membered heterocyclyl, —C(O)R$^{h1}$, —S(O)$_2$NR$^{w1a}$R$^{w2a}$, —S(O)$_2$R$^{y1}$, or —NR$^{z1a}$S(O)$_2$R$^{z2a}$, wherein the $C_1$-$C_6$alkyl and $C_1$-$C_6$alkoxy of $R^{6a1}$, $R^{6b1}$, $R^{6c1}$, and $R^{6d1}$ are each independently unsubstituted or substituted with one or more groups selected from the group consisting of $C_3$-$C_8$ cycloalkyl and halogen; the $C_6$-$C_{12}$ aryl and 5- to 10-membered heteroaryl of $R^{6a1}$, $R^{6b1}$, $R^{6c1}$, and $R^{6d1}$ are each independently unsubstituted or substituted with one or more groups selected from the group consisting of $C_1$-$C_6$alkyl, $C_1$-$C_6$alkoxy, —OH, and $C_1$-$C_6$alkyl-OH; and the 3- to 10-membered heterocyclyl, —$C_1$-$C_6$alkyl-5- to 6-membered heterocyclyl, and —OC(O)-5- to 6-membered heterocyclyl of $R^{6a1}$, $R^{6b1}$, $R^{6c1}$, and $R^{6d1}$ are each independently unsubstituted or substituted with one or more groups selected from the group consisting of $C_1$-$C_6$alkyl, $C_1$-$C_6$alkoxy, —OH, $C_1$-$C_6$alkyl-OH, =O, and =S.

In some embodiments, the compound of Formula (B) is a compound of Formula (B-1a) or (B-1b):

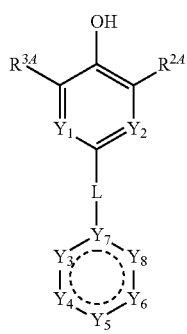
(B-1a)

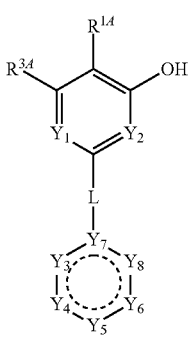
(B-1b)

wherein $R^{1A}$, $R^{2A}$, $R^{3A}$, $Y_1$, $Y_2$, $Y_3$, $Y_4$, $Y_5$, $Y_6$, $Y_7$, $Y_8$, and L are as defined for Formula (B).

In some embodiments, the compound of Formula (B) is a compound of Formula (B-2a), (B-2b), (B-2c), (B-2d), (B-2e), (B-2f), (B-2g), (B-2h), (B-2i), (B-2j), (B-2k), (B-2l), (B-2m), or (B-2n):

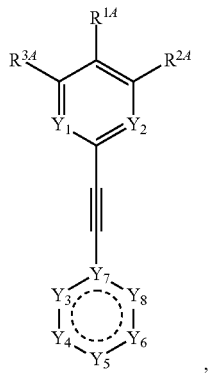
(B-2a)

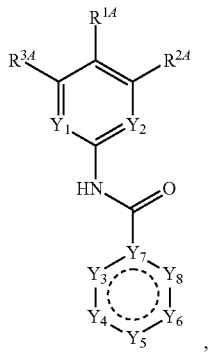
(B-2b)

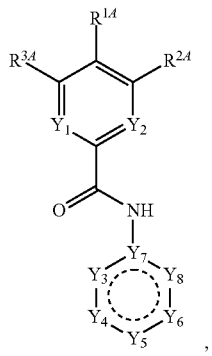
(B-2c)

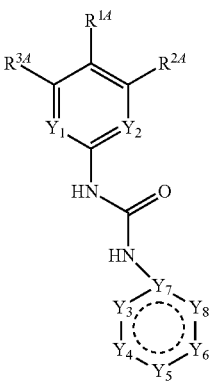
(B-2d)

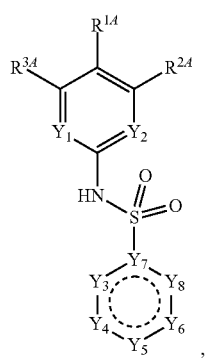 (B-2e)
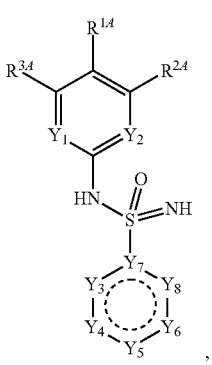 (B-2f)
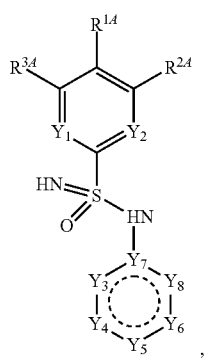 (B-2g)
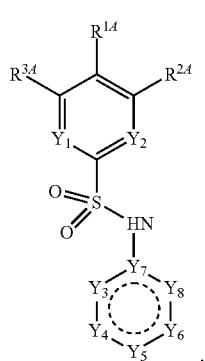 (B-2h)
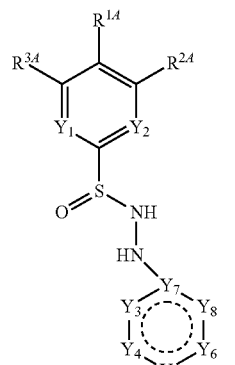 (B-2i)
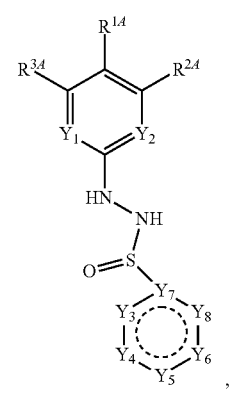 (B-2j)
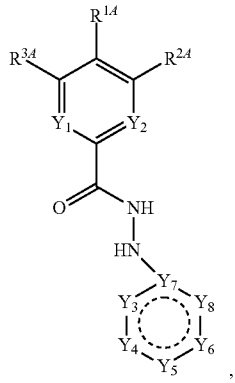 (B-2k)
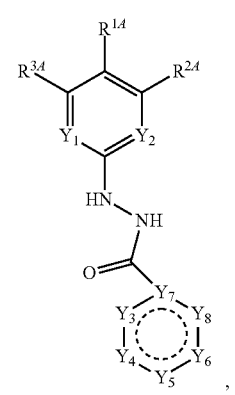 (B-2l)

-continued
(B-2m)
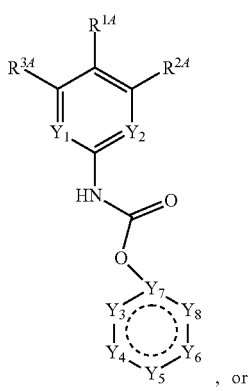, or
(B-2n)
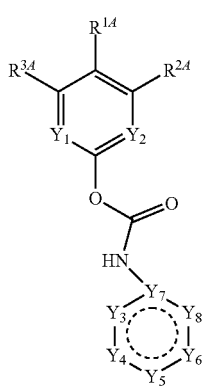,
wherein $R^{1A}$, $R^{2A}$, $R^{3A}$, $Y_1$, $Y_2$, $Y_3$, $Y_4$, $Y_5$, $Y_6$, $Y_7$, and $Y_8$ are as defined for Formula (B).
In some embodiments, the compound of Formula (B) is a compound of Formula (B-3a), (B-3b), (B-3c), (B-3d), (B-3e), (B-3f), (B-3g), (B-3h), (B-3i), (B-3j), (B-3k), (B-3l), (B-3m), or (B-3n):
(B-3a)
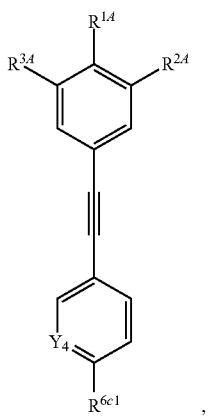,
(B-3b)
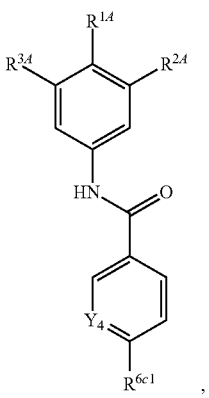,
(B-3c)
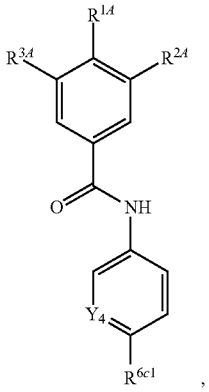,
(B-3d)
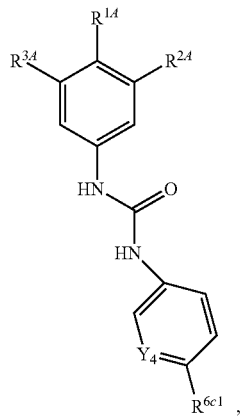,
(B-3e)
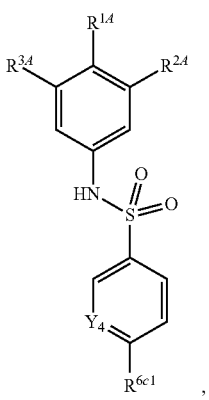,

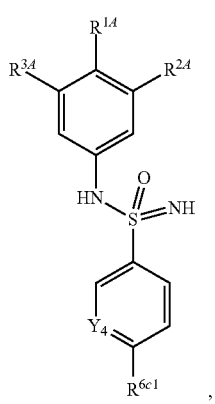 (B-3f)
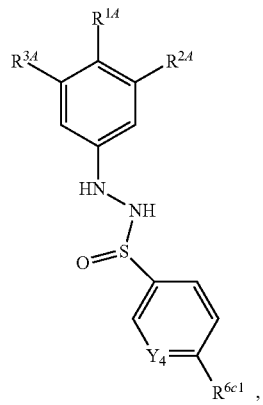 (B-3j)
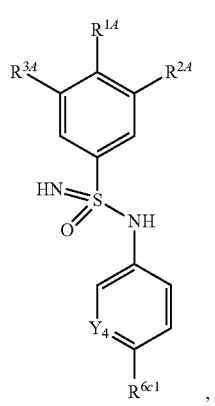 (B-3g)
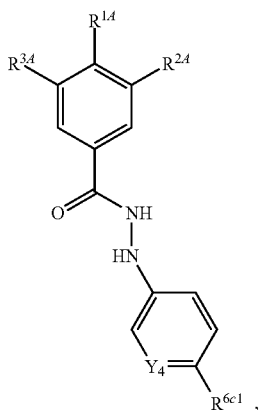 (B-3k)
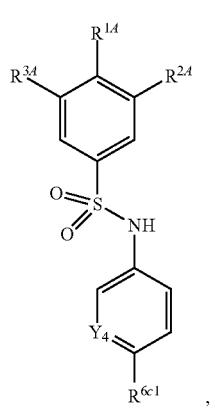 (B-3h)
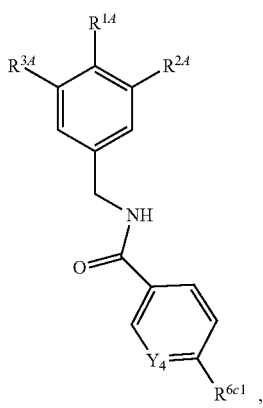 (B-3l)
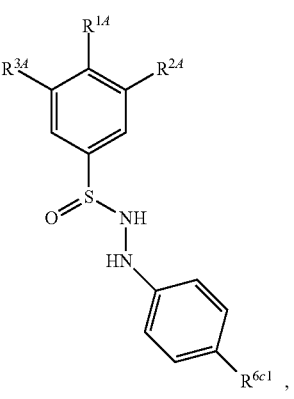 (B-3i)
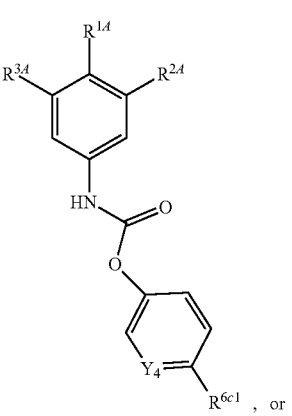 (B-3m)
, or -continued (B-3n)

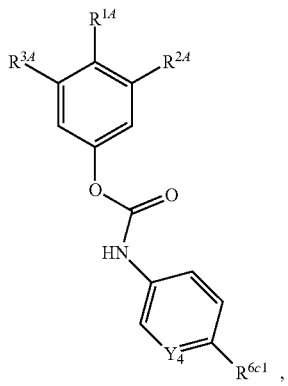

wherein $R^{1A}$, $R^{2A}$, $R^{3A}$, $Y_4$, and $R^{6c1}$ are as defined for Formula (B).

In some embodiments, when any particular group is substituted, the indicated group is substituted by one or more substituents selected from the group consisting of oxo, $C_1$-$C_6$ alkyl, $C_2$-$C_6$ alkenyl, $C_2$-$C_6$ alkynyl, halogen, —CN, —$OR^{A1}$, —$SR^{A1}$, —$NR^{A2}R^{A3}$, —$NO_2$, —C=NH($OR^{A1}$), —C(O)$R^{A1}$, —OC(O)$R^{A1}$, —C(O)$OR^{A1}$, —C(O)$NR^{A2}R^{A3}$, —OC(O)$NR^{A2}R^{A3}$, —$NR^{A1}$C(O)$R^{A2}$, —$NR^{A1}$C(O)$OR^{A2}$, —$NR^{A1}$C(O)$NR^{A2}R^{A3}$, —S(O)$R^{A1}$, —S(O)$_2R^{A1}$, —$NR^{A1}$S(O)$R^{A2}$, —C(O)$NR^{A1}$S(O)$R^{A2}$, —NRA'S(O)$_2R^{A2}$, —C(O)NRA'S(O)$_2R^{A2}$, —S(O)$NR^{A2}R^{A3}$, —S(O)$_2NR^{A2}R^{A3}$, —P(O)($OR^{A2}$)($OR^{A3}$), $C_3$-$C_8$ cycloalkyl, 3-12-membered heterocyclyl, 5- to 10-membered heteroaryl, $C_6$-$C_{14}$ aryl, —($C_1$-$C_3$ alkylene)CN, —($C_1$-$C_3$ alkylene)$OR^{A1}$, —($C_1$-$C_3$ alkylene)$SR^{A1}$, —($C_1$-$C_3$ alkylene)$NR^{A2}R^{A3}$, —($C_1$-$C_3$ alkylene)$CF_3$, —($C_1$-$C_3$ alkylene)$NO_2$, —C=NH($OR^{A1}$), —($C_1$-$C_3$ alkylene)C(O)$R^{A1}$, —($C_1$-$C_3$ alkylene)OC(O)$R^{A1}$, —($C_1$-$C_3$ alkylene)C(O)$OR^{A1}$, —($C_1$-$C_3$ alkylene)C(O)$NR^{A2}R^{A3}$, —($C_1$-$C_3$ alkylene)OC(O)$NR^{A2}R^{A3}$, —($C_1$-$C_3$ alkylene)$NR^{A1}$C(O)$R^{A2}$, —($C_1$-$C_3$ alkylene)$NR^{A1}$C(O)$OR^{A2}$, —($C_1$-$C_3$ alkylene)$NR^{A1}$C(O)$NR^{A2}R^{A3}$, —($C_1$-$C_3$ alkylene)S(O)$R^{A1}$, —($C_1$-$C_3$ alkylene)S(O)$_2R^{A1}$, —($C_1$-$C_3$ alkylene)$NR^{A1}$S(O)$R^{A2}$, —C(O)($C_1$-$C_3$ alkylene)$NR^{A1}$S(O)$R^{A2}$, —($C_1$-$C_3$ alkylene)$NR^{A1}$S(O)$_2R^{A2}$, —($C_1$-$C_3$ alkylene)C(O)$NR^{A1}$S(O)$_2R^{A2}$, —($C_1$-$C_3$ alkylene)S(O)$NR^{A2}R^{A3}$, —($C_1$-$C_3$ alkylene)S(O)$_2NR^{A2}R^{A3}$, —($C_1$-$C_3$ alkylene)P(O)($OR^{A2}$)($OR^{A3}$), —($C_1$-$C_3$ alkylene)($C_3$-$C_8$ cycloalkyl), —($C_1$-$C_3$ alkylene)(3-12-membered heterocyclyl), —($C_1$-$C_3$ alkylene)(5-10-membered heteroaryl) and —($C_1$-$C_3$ alkylene)($C_6$-$C_{14}$ aryl), wherein the one or more substituents are each independently unsubstituted or substituted with one or more further substituents selected from the group consisting of halogen, oxo, —$OR^{A4}$, —$NR^{A4}R^{A5}$, —C(O)$R^{A4}$, —CN, —S(O)$R^{A4}$, —S(O)$_2R^{A4}$, —P(O)($OR^{A4}$)($OR^{A5}$), —($C_1$-$C_3$ alkylene)$OR^{A4}$, —($C_1$-$C_3$ alkylene)$NR^{A4}R^{A5}$, —($C_1$-$C_3$ alkylene)C(O)$R^{A4}$, —($C_1$-$C_3$ alkylene)S(O)$R^{A4}$, —($C_1$-$C_3$ alkylene)S(O)$_2R^{A4}$, —($C_1$-$C_3$ alkylene)P(O)($OR^{A4}$)($OR^{A5}$), $C_3$-$C_8$ cycloalkyl, $C_1$-$C_6$ alkyl, and $C_1$-$C_6$ alkyl substituted by oxo, —OH or halogen; wherein each $R^{A1}$ is independently hydrogen, $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, 5-6-membered heteroaryl or 3-6-membered heterocyclyl, wherein the $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, 5-6-membered heteroaryl and 3-6-membered heterocyclyl are independently unsubstituted or substituted by halogen, oxo, —CN, —$OR^{A6}$, —$NR^{A6}R^{A7}$, —P(O)($OR^{A6}$)($OR^{A6}$), phenyl, phenyl substituted by halogen, $C_1$-$C_6$ alkyl, or $C_1$-$C_6$ alkyl substituted by halogen, —OH or oxo; $R^{A2}$ and $R^{A3}$ are each independently hydrogen, $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, 5-6-membered heteroaryl or 3-6 membered heterocyclyl, wherein the $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, 5-6-membered heteroaryl and 3-6 membered heterocyclyl are each independently unsubstituted or substituted by halogen, oxo, —CN, —$OR^{A6}$, —$NR^{A6}R^{A7}$, $C_1$-$C_6$ alkyl, or $C_1$-$C_6$ alkyl substituted by halogen, —OH or oxo; and $R^{A4}$, $R^{A5}$, $R^{A6}$ and $R^{A7}$ are each independently hydrogen, $C_1$-$C_6$ alkyl, $C_2$-$C_6$ alkenyl, $C_2$-$C_6$ alkynyl, $C_1$-$C_6$ alkyl substituted by one or more halogen, $C_2$-$C_6$ alkenyl substituted by one or more halogen, or $C_2$-$C_6$ alkynyl substituted by one or more halogen.

In some embodiments of Formula (B), including Formula (B-1a) and (B-1b), L is —C≡C—. In some embodiments, L is *—NHC(O)—, wherein * represents the point of attachment to $Y_7$. In some embodiments, L is *—C(O)NH—, wherein * represents the point of attachment to $Y_7$. In some embodiments, L is —NHC(O)NH—. In some embodiments, L is *—NHS(O)$_2$—, wherein * represents the point of attachment to $Y_7$. In some embodiments, L is *—NHS(O)(=NH)—, wherein * represents the point of attachment to $Y_7$. In some embodiments, L is *—S(O)(=NH)NH—, wherein * represents the point of attachment to $Y_7$. In some embodiments, L is *—S(O)$_2$NH—, wherein * represents the point of attachment to $Y_7$. In some embodiments, L is *—S(O)NHNH—, wherein * represents the point of attachment to $Y_7$. In some embodiments, L is *—NHNHS(O)—, wherein * represents the point of attachment to $Y_7$. In some embodiments, L is *—C(O)NHNH—, wherein * represents the point of attachment to $Y_7$. In some embodiments, L is *—NHNHC(O)—, wherein * represents the point of attachment to $Y_7$. In some embodiments, L is *—NHC(O)O—, wherein * represents the point of attachment to $Y_7$. In some embodiments, L is *—OC(O)NH—, wherein * represents the point of attachment to $Y_7$.

In some embodiments of Formula (B), including Formula (B-1a) and (B-1b), L is —C≡C—, and one of $R^{1A}$ and $R^{2A}$ is —OH and the other is —C(O)Rai. In some embodiments, L is —C≡C—, and one of $R^{1A}$ and $R^{2A}$ is —OH and the other is —C(O)H. In some embodiments, L is —C≡C—, and one of $R^{1A}$ and $R^{2A}$ is —OH and the other is —CHNR$^{j1}$. In some embodiments, L is —C≡C—, and one of $R^{1A}$ and $R^{2A}$ is —OH and the other is —S(O)$R^{b1}$ or —S(O)$_2R^{c1}$. In some embodiments, L is —C≡C—, and one of $R^{1A}$ and $R^{2A}$ is —OH and the other is —NHC(O)$R^{d1}$ or —NHS(O)$_2R^{e1}$. In some embodiments, L is —C≡C—, and one of $R^{1A}$ and $R^{2A}$ is —OH and the other is —$C_1$-$C_6$alkyl-$R^{f1}$ or —$C_2$-$C_6$alkenyl-$R^{g1}$. In some embodiments, L is —C≡C—, and one of $R^{1A}$ and $R^{2A}$ is —OH and the other is —C(O)H. In some embodiments, L is —C≡C—, and one of $R^{1A}$ and $R^{2A}$ is —OH and the other is —CHNR$^{j1}$. In some embodiments, L is —C≡C—, and one of $R^{1A}$ and $R^{2A}$ is —OH and the other is —CHNR$^{j1}$, wherein $R^{j1}$ is $C_1$-$C_6$alkyl. In some embodiments, L is —C≡C—, and one of $R^{1A}$ and $R^{2A}$ is —OH and the other is —CHNR$^{j1}$, wherein $R^{j1}$ is 5- to 6-membered heterocyclyl, unsubstituted or substituted with one or more substituents selected from the group consisting of $C_1$-$C_6$alkyl, $C_3$-$C_8$cycloalkyl, =O, —C(O)NH—$C_1$-$C_6$alkyl, and —C(O)O—$C_1$-$C_6$alkyl. In some embodiments, L is —C≡C—, and one of $R^{1A}$ and $R^{2A}$ is —OH and the other is —CHNR$^{j1}$, wherein $R^{j1}$ is 5- to 6-membered heteroaryl, unsubstituted or substituted with one or more substituents selected from the group consisting of $C_1$-$C_6$alkyl, $C_3$-$C_8$cycloalkyl, and —C(O)O—$C_1$-$C_6$alkyl. In other embodiments, L is —C≡C—, and one of $R^{1A}$ and $R^{2A}$ is —OH and the other is —CHNR$^{j1}$, wherein R$^{j1}$ is 6- to 12-membered aryl, unsubstituted or substituted with one or more substituents selected from the group consisting of C$_1$-C$_6$alkyl, C$_3$-C$_8$cycloalkyl, and —C(O)O—C$_1$-C$_6$alkyl. In some embodiments, L is —C≡C—, and one of R$^{1A}$ and R$^{2A}$ is —OH and the other is —CHNR$^{j1}$, wherein R$^{j1}$ is —OR$^{k1}$, wherein R$^{k1}$ is C$_1$-C$_6$alkyl, C$_2$-C$_6$alkenyl, C$_2$-C$_6$alkynyl, C$_3$-C$_8$cycloalkyl, or 6- to 12-membered aryl, wherein the C$_1$-C$_6$alkyl is unsubstituted or substituted with 5- to 6-membered heterocyclyl or 5- to 6-membered heteroaryl. In some embodiments, L is —C≡C—, and one of R$^{1A}$ and R$^{2A}$ is —OH and the other is —CHNR$^{j1}$, wherein R$^{j1}$ is —NHR$^{k1}$ or —N(C$_1$-C$_6$alkyl)R$^{k1}$, wherein R$^{k1}$ is C$_1$-C$_6$alkyl, C$_2$-C$_6$alkenyl, C$_2$-C$_6$alkynyl, C$_3$-C$_8$cycloalkyl, or 6- to 12-membered aryl, wherein the C$_1$-C$_6$alkyl is unsubstituted or substituted with 5- to 6-membered heterocyclyl or 5- to 6-membered heteroaryl. In some embodiments, L is —C≡C—, and one of R$^{1A}$ and R$^{2A}$ is —OH and the other is —CHNR$^{j1}$, wherein R$^{j1}$ is —NHC(O)R$^{k1}$, wherein R$^{k1}$ is C$_1$-C$_6$alkyl, C$_2$-C$_6$alkenyl, C$_2$-C$_6$alkynyl, C$_3$-C$_8$cycloalkyl, or 6- to 12-membered aryl, wherein the C$_1$-C$_6$alkyl is unsubstituted or substituted with 5- to 6-membered heterocyclyl or 5- to 6-membered heteroaryl. In other embodiments, L is —C≡C—, and one of R$^{1A}$ and R$^{2A}$ is —OH and the other is —CHNR$^{j1}$, wherein R$^{j1}$ is —NHS(O)$_2$R$^{k1}$, wherein R$^{k1}$ is C$_1$-C$_6$alkyl, C$_2$-C$_6$alkenyl, C$_2$-C$_6$alkynyl, C$_3$-C$_8$cycloalkyl, or 6- to 12-membered aryl, wherein the C$_1$-C$_6$alkyl is unsubstituted or substituted with 5- to 6-membered heterocyclyl or 5- to 6-membered heteroaryl. In yet other embodiments, L is —C≡C—, and one of R$^{1A}$ and R$^{2A}$ is —OH and the other is —CHNR$^{j1}$, wherein R$^{j1}$ is —NHC(NH)NH$_2$. In other embodiments, L is —C≡C—, and one of R$^{1A}$ and R$^{2A}$ is —OH and the other is In some embodiments of Formula (B), including Formula (B-1a) and (B-1b), L is *—NHC(O)—, and one of R$^{1A}$ and R$^{2A}$ is —OH and the other is —C(O)H. In some embodiments, L is *—NHC(O)—, and one of R$^{1A}$ and R$^{2A}$ is —OH and the other is —CHNR$^{j1}$. In some embodiments, L is *—NHC(O)—, and one of R$^{1A}$ and R$^{2A}$ is —OH and the other is —CHNR$^{j1}$, wherein R$^{j1}$ is C$_1$-C$_6$alkyl. In some embodiments, L is *—NHC(O)—, and one of R$^{1A}$ and R$^{2A}$ is —OH and the other is —CHNR$^{j1}$, wherein R$^{j1}$ is 5- to 6-membered heterocyclyl, unsubstituted or substituted with one or more substituents selected from the group consisting of C$_1$-C$_6$alkyl, C$_3$-C$_8$cycloalkyl, ═O, —C(O)NH—C$_1$-C$_6$alkyl, and —C(O)O—C$_1$-C$_6$alkyl. In some embodiments, L is *—NHC(O)—, and one of R$^{1A}$ and R$^{2A}$ is —OH and the other is —CHNR$^{j1}$, wherein R$^{j1}$ is 5- to 6-membered heteroaryl, unsubstituted or substituted with one or more substituents selected from the group consisting of C$_1$-C$_6$alkyl, C$_3$-C$_8$cycloalkyl, and —C(O)O—C$_1$-C$_6$alkyl. In other embodiments, L is *—NHC(O)—, and one of R$^{1A}$ and R$^{2A}$ is —OH and the other is —CHNR$^{j1}$, wherein R$^{j1}$ is 6- to 12-membered aryl, unsubstituted or substituted with one or more substituents selected from the group consisting of C$_1$-C$_6$alkyl, C$_3$-C$_8$cycloalkyl, and —C(O)O—C$_1$-C$_6$alkyl. In some embodiments, L is *—NHC(O)—, and one of R$^{1A}$ and R$^{2A}$ is —OH and the other is —CHNR$^{j1}$, wherein R$^{j1}$ is —OR$^{k1}$, wherein R$^{k1}$ is C$_1$-C$_6$alkyl, C$_2$-C$_6$alkenyl, C$_2$-C$_6$alkynyl, C$_3$-C$_8$cycloalkyl, or 6- to 12-membered aryl, wherein the C$_1$-C$_6$alkyl is unsubstituted or substituted with 5- to 6-membered heterocyclyl or 5- to 6-membered heteroaryl. In some embodiments, L is *—C(O)NH—, and one of $R^{1A}$ and $R^{2A}$ is —OH and the other is —CHNR$^{j1}$, wherein $R^{j1}$ is —NHR$^{k1}$ or —N(C$_1$-C$_6$alkyl)R$^{k1}$, wherein $R^{k1}$ is C$_1$-C$_6$alkyl, C$_2$-C$_6$alkenyl, C$_2$-C$_6$alkynyl, C$_3$-C$_8$cycloalkyl, or 6- to 12-membered aryl, wherein the C$_1$-C$_6$alkyl is unsubstituted or substituted with 5- to 6-membered heterocyclyl or 5- to 6-membered heteroaryl. In some embodiments, L is *—C(O)NH—, and one of $R^{1A}$ and $R^{2A}$ is —OH and the other is —CHNR$^{j1}$, wherein $R^{j1}$ is —NHC(O)R$^{k1}$, wherein $R^{k1}$ is C$_1$-C$_6$alkyl, C$_2$-C$_6$alkenyl, C$_2$-C$_6$alkynyl, C$_3$-C$_8$cycloalkyl, or 6- to 12-membered aryl, wherein the C$_1$-C$_6$alkyl is unsubstituted or substituted with 5- to 6-membered heterocyclyl or 5- to 6-membered heteroaryl. In other embodiments, L is *—C(O)NH—, and one of $R^{1A}$ and $R^{2A}$ is —OH and the other is —CHNR$^{j1}$, wherein $R^{j1}$ is —NHS(O)$_2$R$^{k1}$, wherein $R^{k1}$ is C$_1$-C$_6$alkyl, C$_2$-C$_6$alkenyl, C$_2$-C$_6$alkynyl, C$_3$-C$_8$cycloalkyl, or 6- to 12-membered aryl, wherein the C$_1$-C$_6$alkyl is unsubstituted or substituted with 5- to 6-membered heterocyclyl or 5- to 6-membered heteroaryl. In yet other embodiments, L is *—C(O)NH—, and one of $R^{1A}$ and $R^{2A}$ is —OH and the other is —CHNR$^{j1}$, wherein $R^{j1}$ is —NHC(NH)NH$_2$. In other embodiments, L is *—C(O)NH—, and one of $R^{1A}$ and $R^{2A}$ is —OH and the other is In some embodiments of Formula (B), including Formula (B-1a) and (B-1b), L is —NHC(O)NH—, and one of $R^{1A}$ and $R^{2A}$ is —OH and the other is —C(O)H. In some embodiments, L is —NHC(O)NH—, and one of $R^{1A}$ and $R^{2A}$ is —OH and the other is —CHNR$^{j1}$. In some embodiments, L is —NHC(O)NH—, and one of $R^{1A}$ and $R^{2A}$ is —OH and the other is —CHNR$^{j1}$, wherein $R^{j1}$ is C$_1$-C$_6$alkyl. In some embodiments, L is —NHC(O)NH—, and one of $R^{1A}$ and $R^{2A}$ is —OH and the other is —CHNR$^{j1}$, wherein $R^{j1}$ is 5- to 6-membered heterocyclyl, unsubstituted or substituted with one or more substituents selected from the group consisting of C$_1$-C$_6$alkyl, C$_3$-C$_8$cycloalkyl, =O, —C(O)NH—C$_1$-C$_6$alkyl, and —C(O)O—C$_1$-C$_6$alkyl. In some embodiments, L is —NHC(O)NH—, and one of $R^{1A}$ and $R^{2A}$ is —OH and the other is —CHNR$^{j1}$, wherein $R^{j1}$ is 5- to 6-membered heteroaryl, unsubstituted or substituted with one or more substituents selected from the group consisting of C$_1$-C$_6$alkyl, C$_3$-C$_8$cycloalkyl, and —C(O)O—C$_1$-C$_6$alkyl. In other embodiments, L is —NHC(O)NH—, and one of $R^{1A}$ and $R^{2A}$ is —OH and the other is —CHNR$^{j1}$, wherein $R^{j1}$ is 6- to 12-membered aryl, unsubstituted or substituted with one or more substituents selected from the group consisting of C$_1$-C$_6$alkyl, C$_3$-C$_8$cycloalkyl, and —C(O)O—C$_1$-C$_6$alkyl. In some embodiments, L is —NHC(O)NH—, and one of $R^{1A}$ and $R^{2A}$ is —OH and the other is —CHNR$^{j1}$, wherein $R^{j1}$ is —OR$^{k1}$, wherein $R^{k1}$ is C$_1$-C$_6$alkyl, C$_2$-C$_6$alkenyl, C$_2$-C$_6$alkynyl, C$_3$-C$_8$cycloalkyl, or 6- to 12-membered aryl, wherein the C$_1$-C$_6$alkyl is unsubstituted or substituted with 5- to 6-membered heterocyclyl or 5- to 6-membered heteroaryl. In some embodiments, L is —NHC(O)NH—, and one of $R^{1A}$ and $R^{2A}$ is —OH and the other is —CHNR$^{j1}$, wherein $R^{j1}$ is —NHR$^{k1}$, wherein $R^{k1}$ is C$_1$-C$_6$alkyl, C$_2$-C$_6$alkenyl, C$_2$-C$_6$alkynyl, C$_3$-C$_8$cycloalkyl, or 6- to 12-membered aryl, wherein the C$_1$-C$_6$alkyl is unsubstituted or substituted with 5- to 6-membered heterocyclyl or 5- to 6-membered heteroaryl. In some embodiments, L is —NHC(O)NH—, and one of $R^{1A}$ and $R^{2A}$ is —OH and the other is —CHNR$^{j1}$, wherein $R^{j1}$ is —NHC(O)R$^{k1}$ or —N(C$_1$-C$_6$alkyl)RY1, wherein $R^{k1}$ is C$_1$-C$_6$alkyl, C$_2$-C$_6$alkenyl, C$_2$-C$_6$alkynyl, C$_3$-C$_8$cycloalkyl, or 6- to 12-membered aryl, wherein the C$_1$-C$_6$alkyl is unsubstituted or substituted with 5- to 6-membered heterocyclyl or 5- to 6-membered heteroaryl. In other embodiments, L is —NHC(O)NH—, and one of $R^{1A}$ and $R^{2A}$ is —OH and the other is —CHNR$^{j1}$, wherein $R^{j1}$ is —NHS(O)$_2$R$^{k1}$, wherein $R^{k1}$ is C$_1$-C$_6$alkyl, C$_2$-C$_6$alkenyl, C$_2$-C$_6$alkynyl, C$_3$-C$_8$cycloalkyl, or 6- to 12-membered aryl, wherein the C$_1$-C$_6$alkyl is unsubstituted or substituted with 5- to 6-membered heterocyclyl or 5- to 6-membered heteroaryl. In yet other embodiments, L is —NHC(O)NH—, and one of $R^{1A}$ and $R^{2A}$ is —OH and the other is —CHNR$^{j1}$, wherein $R^{j1}$ is —NHC(NH)NH$_2$. In other embodiments, L is —NHC(O)NH—, and one of $R^{1A}$ and $R^{2A}$ is —OH and the other is In some embodiments of Formula (B), including Formula (B-1a) and (B-1b), L is *—NHS(O)$_2$—, and one of $R^{1A}$ and $R^{2A}$ is —OH and the other is —C(O)H. In some embodiments, L is *—NHS(O)$_2$—, and one of $R^{1A}$ and $R^{2A}$ is —OH and the other is —CHNR$^{j1}$. In some embodiments, L is *—NHS(O)$_2$—, and one of $R^{1A}$ and $R^{2A}$ is —OH and the other is —CHNR$^{j1}$, wherein $R^{j1}$ is C$_1$-C$_6$alkyl. In some embodiments, L is *—NHS(O)$_2$—, and one of $R^{1A}$ and $R^{2A}$ is —OH and the other is —CHNR$^{j1}$, wherein $R^{j1}$ is 5- to 6-membered heterocyclyl, unsubstituted or substituted with one or more substituents selected from the group consisting of C$_1$-C$_6$alkyl, C$_3$-C$_8$cycloalkyl, =O, —C(O)NH—C$_1$-C$_6$alkyl, and —C(O)O—C$_1$-C$_6$alkyl. In some embodiments, L is *—NHS(O)$_2$—, and one of $R^{1A}$ and $R^{2A}$ is —OH and the other is —CHNR$^{j1}$, wherein $R^{j1}$ is 5- to 6-membered heteroaryl, unsubstituted or substituted with one or more substituents selected from the group consisting of C$_1$-C$_6$alkyl, C$_3$-C$_8$cycloalkyl, and —C(O)O—C$_1$-C$_6$alkyl. In other embodiments, L is *—NHS(O)$_2$—, and one of $R^{1A}$ and $R^{2A}$ is —OH and the other is —CHNR$^{j1}$, wherein $R^{j1}$ is 6- to 12-membered aryl, unsubstituted or substituted with one or more substituents selected from the group consisting of C$_1$-C$_6$alkyl, C$_3$-C$_8$cycloalkyl, and —C(O)O—C$_1$-C$_6$alkyl. In some embodiments, L is *—NHS(O)$_2$—, and one of $R^{1A}$ and $R^{2A}$ is —OH and the other is —CHNR$^{j1}$, wherein $R^{j1}$ is —OR$^{k1}$, wherein $R^{k1}$ is C$_1$-C$_6$alkyl, C$_2$-C$_6$alkenyl, C$_2$-C$_6$alkynyl, C$_3$-C$_8$cycloalkyl, or 6- to 12-membered aryl, wherein the C$_1$-C$_6$alkyl is unsubstituted or substituted with 5- to 6-membered heterocyclyl or 5- to 6-membered heteroaryl. In some embodiments, L is *—NHS(O)$_2$—, and one of $R^{1A}$ and $R^{2A}$ is —OH and the other is —CHNR$^{j1}$, wherein $R^{j1}$ is —NHR$^{k1}$ or —N(C$_1$-C$_6$alkyl)R$^{k1}$, wherein $R^{k1}$ is C$_1$-C$_6$alkyl, C$_2$-C$_6$alkenyl, C$_2$-C$_6$alkynyl, C$_3$-C$_8$cycloalkyl, or 6- to 12-membered aryl, wherein the C$_1$-C$_6$alkyl is unsubstituted or substituted with 5- to 6-membered heterocyclyl or 5- to 6-membered heteroaryl. In some embodiments, L is *—NHS(O)$_2$—, and one of $R^{1A}$ and $R^{2A}$ is —OH and the other is —CHNR$^{j1}$, wherein $R^{j1}$ is —NHC(O)R$^{k1}$, wherein $R^{k1}$ is C$_1$-C$_6$alkyl, $C_2$-$C_6$alkenyl, $C_2$-$C_6$alkynyl, $C_3$-$C_8$cycloalkyl, or 6- to 12-membered aryl, wherein the $C_1$-$C_6$alkyl is unsubstituted or substituted with 5- to 6-membered heterocyclyl or 5- to 6-membered heteroaryl. In other embodiments, L is *—NHS(O)$_2$—, and one of $R^{1A}$ and $R^{2A}$ is —OH and the other is —CHN$R^{j1}$, wherein $R^{j1}$ is —NHS(O)$_2R^{k1}$, wherein $R^{k1}$ is $C_1$-$C_6$alkyl, $C_2$-$C_6$alkenyl, $C_2$-$C_6$alkynyl, $C_3$-$C_8$cycloalkyl, or 6- to 12-membered aryl, wherein the $C_1$-$C_6$alkyl is unsubstituted or substituted with 5- to 6-membered heterocyclyl or 5- to 6-membered heteroaryl. In yet other embodiments, L is *—NHS(O)$_2$—, and one of $R^{1A}$ and $R^{2A}$ is —OH and the other is —CHN$R^{j1}$, wherein $R^{j1}$ is —NHC(NH)NH$_2$. In other embodiments, L is *—NHS(O)$_2$—, and one of $R^{1A}$ and $R^{2A}$ is —OH and the other is

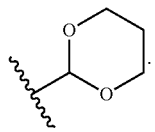 [SMILES: *C1OCCCO1]

In some embodiments of Formula (B), including Formula (B-1a) and (B-1b), L is *—NHS(O)(=NH)— or *—S(O)(=NH)NH—, and one of $R^{1A}$ and $R^{2A}$ is —OH and the other is —C(O)H. In some embodiments, L is *—NHS(O)(=NH)— or *—S(O)(=NH)NH—, and one of $R^{1A}$ and $R^{2A}$ is —OH and the other is —CHN$R^{j1}$. In some embodiments, L is *—NHS(O)(=NH)— or *—S(O)(=NH)NH—, and one of $R^{1A}$ and $R^{2A}$ is —OH and the other is —CHN$R^{j1}$, wherein $R^{j1}$ is $C_1$-$C_6$alkyl. In some embodiments, L is *—NHS(O)(=NH)— or *—S(O)(=NH)NH—, and one of $R^{1A}$ and $R^{2A}$ is —OH and the other is —CHN$R^{j1}$, wherein $R^{j1}$ is 5- to 6-membered heterocyclyl, unsubstituted or substituted with one or more substituents selected from the group consisting of $C_1$-$C_6$alkyl, $C_3$-$C_8$cycloalkyl, =O, —C(O)NH—$C_1$-$C_6$alkyl, and —C(O)O—$C_1$-$C_6$alkyl. In some embodiments, L is *—NHS(O)(=NH)— or *—S(O)(=NH)NH—, and one of $R^{1A}$ and $R^{2A}$ is —OH and the other is —CHN$R^{j1}$, wherein $R^{j1}$ is 5- to 6-membered heteroaryl, unsubstituted or substituted with one or more substituents selected from the group consisting of $C_1$-$C_6$alkyl, $C_3$-$C_8$cycloalkyl, and —C(O)O—$C_1$-$C_6$alkyl. In other embodiments, L is *—NHS(O)(=NH)— or *—S(O)(=NH)NH—, and one of $R^{1A}$ and $R^{2A}$ is —OH and the other is —CHN$R^{j1}$, wherein $R^{j1}$ is 6- to 12-membered aryl, unsubstituted or substituted with one or more substituents selected from the group consisting of $C_1$-$C_6$alkyl, $C_3$-$C_8$cycloalkyl, and —C(O)O—$C_1$-$C_6$alkyl. In some embodiments, L is *—NHS(O)(=NH)— or *—S(O)(=NH)NH—, and one of $R^{1A}$ and $R^{2A}$ is —OH and the other is —CHN$R^{j1}$, wherein $R^{j1}$ is —O$R^{k1}$, wherein $R^{k1}$ is $C_1$-$C_6$alkyl, $C_2$-$C_6$alkenyl, $C_2$-$C_6$alkynyl, $C_3$-$C_8$cycloalkyl, or 6- to 12-membered aryl, wherein the $C_1$-$C_6$alkyl is unsubstituted or substituted with 5- to 6-membered heterocyclyl or 5- to 6-membered heteroaryl. In some embodiments, L is *—NHS(O)(=NH)— or *—S(O)(=NH)NH—, and one of $R^{1A}$ and $R^{2A}$ is —OH and the other is —CHN$R^{j1}$, wherein $R^{j1}$ is —NH$R^{k1}$ or —N($C_1$-$C_6$alkyl)$R^{k1}$, wherein $R^{k1}$ is $C_1$-$C_6$alkyl, $C_2$-$C_6$alkenyl, $C_2$-$C_6$alkynyl, $C_3$-$C_8$cycloalkyl, or 6- to 12-membered aryl, wherein the $C_1$-$C_6$alkyl is unsubstituted or substituted with 5- to 6-membered heterocyclyl or 5- to 6-membered heteroaryl. In some embodiments, L is *—NHS(O)(=NH)— or *—S(O)(=NH)NH—, and one of $R^{1A}$ and $R^{2A}$ is —OH and the other is —CHN$R^{j1}$, wherein $R^{j1}$ is —NHC(O)$R^{k1}$, wherein $R^{k1}$ is $C_1$-$C_6$alkyl, $C_2$-$C_6$alkenyl, $C_2$-$C_6$alkynyl, $C_3$-$C_8$cycloalkyl, or 6- to 12-membered aryl, wherein the $C_1$-$C_6$alkyl is unsubstituted or substituted with 5- to 6-membered heterocyclyl or 5- to 6-membered heteroaryl. In other embodiments, L is *—NHS(O)(=NH)— or *—S(O)(=NH)NH—, and one of $R^{1A}$ and $R^{2A}$ is —OH and the other is —CHN$R^{j1}$, wherein $R^{j1}$ is —NHS(O)$_2R^{y1}$, wherein $R^{k1}$ is $C_1$-$C_6$alkyl, $C_2$-$C_6$alkenyl, $C_2$-$C_6$alkynyl, $C_3$-$C_8$cycloalkyl, or 6- to 12-membered aryl, wherein the $C_1$-$C_6$alkyl is unsubstituted or substituted with 5- to 6-membered heterocyclyl or 5- to 6-membered heteroaryl. In yet other embodiments, L is *—NHS(O)(=NH)— or *—S(O)(=NH)NH—, and one of $R^{1A}$ and $R^{2A}$ is —OH and the other is —CHN$R^{j1}$, wherein $R^{j1}$ is —NHC(NH)NH$_2$. In other embodiments, L is *—NHS(O)$_2$—, and one of $R^{1A}$ and $R^{2A}$ is —OH and the other is.

In some embodiments of Formula (B), including Formula (B-1a) and (B-1b), L is

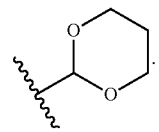 [SMILES: *C1OCCCO1]

S(O)$_2$NH—, and one of $R^{1A}$ and $R^{2A}$ is —OH and the other is —C(O)H. In some embodiments, L is *—S(O)$_2$NH—, and one of $R^{1A}$ and $R^{2A}$ is —OH and the other is —CHN$R^{j1}$. In some embodiments, L is *—S(O)$_2$NH—, and one of $R^{1A}$ and $R^{2A}$ is —OH and the other is —CHN$R^{j1}$, wherein $R^{j1}$ is $C_1$-$C_6$alkyl. In some embodiments, L is *—S(O)$_2$NH—, and one of $R^{1A}$ and $R^{2A}$ is —OH and the other is —CHN$R^{j1}$, wherein $R^{j1}$ is 5- to 6-membered heterocyclyl, unsubstituted or substituted with one or more substituents selected from the group consisting of $C_1$-$C_6$alkyl, $C_3$-$C_8$cycloalkyl, =O, —C(O)NH—$C_1$-$C_6$alkyl, and —C(O)O—$C_1$-$C_6$alkyl. In some embodiments, L is *—S(O)$_2$NH—, and one of $R^{1A}$ and $R^{2A}$ is —OH and the other is —CHN$R^{j1}$, wherein $R^{j1}$ is 5- to 6-membered heteroaryl, unsubstituted or substituted with one or more substituents selected from the group consisting of $C_1$-$C_6$alkyl, $C_3$-$C_8$cycloalkyl, and —C(O)O—$C_1$-$C_6$alkyl. In other embodiments, L is *—S(O)$_2$NH—, and one of $R^{1A}$ and $R^{2A}$ is —OH and the other is —CHN$R^{j1}$, wherein $R^{j1}$ is 6- to 12-membered aryl, unsubstituted or substituted with one or more substituents selected from the group consisting of $C_1$-$C_6$alkyl, $C_3$-$C_8$cycloalkyl, and —C(O)O—$C_1$-$C_6$alkyl. In some embodiments, L is *—S(O)$_2$NH—, and one of $R^{1A}$ and $R^{2A}$ is —OH and the other is —CHN$R^{j1}$, wherein $R^{j1}$ is —O$R^{k1}$, wherein $R^{k1}$ is $C_1$-$C_6$alkyl, $C_2$-$C_6$alkenyl, $C_2$-$C_6$alkynyl, $C_3$-$C_8$cycloalkyl, or 6- to 12-membered aryl, wherein the $C_1$-$C_6$alkyl is unsubstituted or substituted with 5- to 6-membered heterocyclyl or 5- to 6-membered heteroaryl. In some embodiments, L is *—S(O)$_2$NH—, and one of $R^{1A}$ and $R^{2A}$ is —OH and the other is —CHN$R^{j1}$, wherein $R^{j1}$ is —NH$R^{k1}$ or —N($C_1$-$C_6$alkyl)$R^{k1}$, wherein $R^{k1}$ is $C_1$-$C_6$alkyl, $C_2$-$C_6$alkenyl, $C_2$-$C_6$alkynyl, $C_3$-$C_8$cycloalkyl, or 6- to 12-membered aryl, wherein the $C_1$-$C_6$alkyl is unsubstituted or substituted with 5- to 6-membered heterocyclyl or 5- to 6-membered heteroaryl. In some embodiments, L is *—S(O)$_2$NH—, and one of $R^{1A}$ and $R^{2A}$ is —OH and the other is —CHN$R^{j1}$, wherein $R^{j1}$ is —NHC(O)$R^{k1}$, wherein $R^{k1}$ is $C_1$-$C_6$alkyl, $C_2$-$C_6$alkenyl, $C_2$-$C_6$alkynyl, $C_3$-$C_8$cycloalkyl, or 6- to 12-membered aryl, wherein the $C_1$-$C_6$alkyl is unsubstituted or substituted with 5- to 6-membered heterocyclyl or 5- to 6-membered heteroaryl. In other embodiments, L is *—S(O)₂NH—, and one of R^{1A} and R^{2A} is —OH and the other is —CHNR^{j1}, wherein R^{j1} is —NHS(O)₂R^{k1}, wherein R^{k1} is C₁-C₆alkyl, C₂-C₆alkenyl, C₂-C₆alkynyl, C₃-C₈cycloalkyl, or 6- to 12-membered aryl, wherein the C₁-C₆alkyl is unsubstituted or substituted with 5- to 6-membered heterocyclyl or 5- to 6-membered heteroaryl. In yet other embodiments, L is *—S(O)₂NH—, and one of R^{1A} and R^{2A} is —OH and the other is —CHNR^{j1}, wherein R^{j1} is —NHC(NH)NH₂. In other embodiments, L is *—S(O)₂NH—, and one of R^{1A} and R^{2A} is —OH and the other is

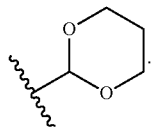 [SMILES: *C1OCCCO1]

In some embodiments of Formula (B), including Formula (B-1a) and (B-1b), L is *—S(O)NHNH— or *—NHNHS(O)—, and one of R^{1A} and R^{2A} is —OH and the other is —C(O)H. In some embodiments, L is *—S(O)NHNH— or *—NHNHS(O)—, and one of R^{1A} and R^{2A} is —OH and the other is —CHNR^{j1}. In some embodiments, L is *—S(O)NHNH— or *—NHNHS(O)—, and one of R^{1A} and R^{2A} is —OH and the other is —CHNR^{j1}, wherein R^{j1} is C₁-C₆alkyl. In some embodiments, L is *—S(O)NHNH— or *—NHNHS(O)—, and one of R^{1A} and R^{2A} is —OH and the other is —CHNR^{j1}, wherein R^{j1} is 5- to 6-membered heterocyclyl, unsubstituted or substituted with one or more substituents selected from the group consisting of C₁-C₆alkyl, C₃-C₈cycloalkyl, =O, —C(O)NH—C₁-C₆alkyl, and —C(O)O—C₁-C₆alkyl. In some embodiments, L is *—S(O)NHNH— or *—NHNHS(O)—, and one of R^{1A} and R^{2A} is —OH and the other is —CHNR^{j1}, wherein R^{j1} is 5- to 6-membered heteroaryl, unsubstituted or substituted with one or more substituents selected from the group consisting of C₁-C₆alkyl, C₃-C₈cycloalkyl, and —C(O)O—C₁-C₆alkyl. In other embodiments, L is *—S(O)NHNH— or *—NHNHS(O)—, and one of R^{1A} and R^{2A} is —OH and the other is —CHNR^{j1}, wherein R^{j1} is 6- to 12-membered aryl, unsubstituted or substituted with one or more substituents selected from the group consisting of C₁-C₆alkyl, C₃-C₈cycloalkyl, and —C(O)O—C₁-C₆alkyl. In some embodiments, L is *—S(O)NHNH— or *—NHNHS(O)—, and one of R^{1A} and R^{2A} is —OH and the other is —CHNR^{j1}, wherein R^{j1} is —OR^{k1}, wherein R^{k1} is C₁-C₆alkyl, C₂-C₆alkenyl, C₂-C₆alkynyl, C₃-C₈cycloalkyl, or 6- to 12-membered aryl, wherein the C₁-C₆alkyl is unsubstituted or substituted with 5- to 6-membered heterocyclyl or 5- to 6-membered heteroaryl. In some embodiments, L is *—S(O)NHNH— or *—NHNHS(O)—, and one of R^{1A} and R^{2A} is —OH and the other is —CHNR^{j1}, wherein R^{j1} is —NHR^{k1} or —N(C₁-C₆alkyl)R^{k1}, wherein R^{k1} is C₁-C₆alkyl, C₂-C₆alkenyl, C₂-C₆alkynyl, C₃-C₈cycloalkyl, or 6- to 12-membered aryl, wherein the C₁-C₆alkyl is unsubstituted or substituted with 5- to 6-membered heterocyclyl or 5- to 6-membered heteroaryl. In some embodiments, L is *—S(O)NHNH— or *—NHNHS(O)—, and one of R^{1A} and R^{2A} is —OH and the other is —CHNR^{j1}, wherein R^{j1} is —NHC(O)R^{k1}, wherein R^{k1} is C₁-C₆alkyl, C₂-C₆alkenyl, C₂-C₆alkynyl, C₃-C₈cycloalkyl, or 6- to 12-membered aryl, wherein the C₁-C₆alkyl is unsubstituted or substituted with 5- to 6-membered heterocyclyl or 5- to 6-membered heteroaryl. In other embodiments, L is *—S(O)NHNH— or *—NHNHS(O)—, and one of R^{1A} and R^{2A} is —OH and the other is —CHNR^{j1}, wherein R^{j1} is —NHS(O)₂R^{k1}, wherein R^{k1} is C₁-C₆alkyl, C₂-C₆alkenyl, C₂-C₆alkynyl, C₃-C₈cycloalkyl, or 6- to 12-membered aryl, wherein the C₁-C₆alkyl is unsubstituted or substituted with 5- to 6-membered heterocyclyl or 5- to 6-membered heteroaryl. In yet other embodiments, L is *—S(O)NHNH— or *—NHNHS(O)—, and one of R^{1A} and R^{2A} is —OH and the other is —CHNR^{j1}, wherein R^{j1} is —NHC(NH)NH₂. In other embodiments, L is *—S(O)NHNH— or *—NHNHS(O)—, and one of R^{1A} and R^{2A} is —OH and the other is

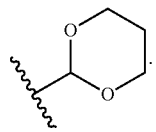 [SMILES: *C1OCCCO1]

In some embodiments of Formula (B), including Formula (B-1a) and (B-1b), L is *—C(O)NHNH— or *—NHNHC(O)—, and one of R^{1A} and R^{2A} is —OH and the other is —C(O)H. In some embodiments, L is *—C(O)NHNH— or *—NHNHC(O)—, and one of R^{1A} and R^{2A} is —OH and the other is —CHNR^{j1}. In some embodiments, L is *—C(O)NHNH— or *—NHNHC(O)—, and one of R^{1A} and R^{2A} is —OH and the other is —CHNR^{j1}, wherein R^{j1} is C₁-C₆alkyl. In some embodiments, L is *—C(O)NHNH— or *—NHNHC(O)—, and one of R^{1A} and R^{2A} is —OH and the other is —CHNR^{j1}, wherein R^{j1} is 5- to 6-membered heterocyclyl, unsubstituted or substituted with one or more substituents selected from the group consisting of C₁-C₆alkyl, C₃-C₈cycloalkyl, =O, —C(O)NH—C₁-C₆alkyl, and —C(O)O—C₁-C₆alkyl. In some embodiments, L is *—C(O)NHNH— or *—NHNHC(O)—, and one of R^{1A} and R^{2A} is —OH and the other is —CHNR^{j1}, wherein R^{j1} is 5- to 6-membered heteroaryl, unsubstituted or substituted with one or more substituents selected from the group consisting of C₁-C₆alkyl, C₃-C₈cycloalkyl, and —C(O)O—C₁-C₆alkyl. In other embodiments, L is *—C(O)NHNH— or *—NHNHC(O)—, and one of R^{1A} and R^{2A} is —OH and the other is —CHNR^{j1}, wherein R^{j1} is 6- to 12-membered aryl, unsubstituted or substituted with one or more substituents selected from the group consisting of C₁-C₆alkyl, C₃-C₈cycloalkyl, and —C(O)O—C₁-C₆alkyl. In some embodiments, L is *—C(O)NHNH— or *—NHNHC(O)—, and one of R^{1A} and R^{2A} is —OH and the other is —CHNR^{j1}, wherein R^{j1} is —OR^{k1}, wherein R^{k1} is C₁-C₆alkyl, C₂-C₆alkenyl, C₂-C₆alkynyl, C₃-C₈cycloalkyl, or 6- to 12-membered aryl, wherein the C₁-C₆alkyl is unsubstituted or substituted with 5- to 6-membered heterocyclyl or 5- to 6-membered heteroaryl. In some embodiments, L is *—C(O)NHNH— or *—NHNHC(O)—, and one of R^{1A} and R^{2A} is —OH and the other is —CHNR^{j1}, wherein R^{j1} is —NHR^{k1} or —N(C₁-C₆alkyl)R^{k1}, wherein R^{k1} is C₁-C₆alkyl, C₂-C₆alkenyl, C₂-C₆alkynyl, C₃-C₈cycloalkyl, or 6- to 12-membered aryl, wherein the C₁-C₆alkyl is unsubstituted or substituted with 5- to 6-membered heterocyclyl or 5- to 6-membered heteroaryl. In some embodiments, L is *—C(O)NHNH— or *—NHNHC(O)—, and one of R^{1A} and R^{2A} is —OH and the other is —CHNR^{j1}, wherein R^{j1} is —NHC(O)R^{k1}, wherein R^{k1} is C₁-C₆alkyl, C₂-C₆alkenyl, C₂-C₆alkynyl, C₃-C₈cycloalkyl, or 6- to 12-membered aryl, wherein the C₁-C₆alkyl is unsubstituted or substituted with 5- to 6-membered heterocyclyl or 5- to 6-membered heteroaryl. In other embodiments, L is *—C (O)NHNH— or *—NHNHC(O)—, and one of $R^{1A}$ and $R^{2A}$ is —OH and the other is —CHN$R^{j1}$, wherein $R^{j1}$ is —NHS(O)$_2R^{k1}$, wherein $R^{k1}$ is $C_1$-$C_6$alkyl, $C_2$-$C_6$alkenyl, $C_2$-$C_6$alkynyl, $C_3$-$C_8$cycloalkyl, or 6- to 12-membered aryl, wherein the $C_1$-$C_6$alkyl is unsubstituted or substituted with 5- to 6-membered heterocyclyl or 5- to 6-membered heteroaryl. In yet other embodiments, L is *—C(O)NHNH— or *—NHNHC(O)—, and one of $R^{1A}$ and $R^{2A}$ is —OH and the other is —CHN$R^{j1}$, wherein $R^{j1}$ is —NHC(NH)NH$_2$. In other embodiments, L is *—C(O)NHNH— or *—NHNHC(O)—, and one of $R^{1A}$ and $R^{2A}$ is —OH and the other is

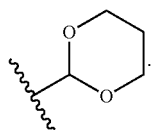 [SMILES: *C1OCCCO1]

In some embodiments of Formula (B), including Formula (B-1a) and (B-1b), L is *—NHC(O)O— or *—OC(O)NH—, and one of $R^{1A}$ and $R^{2A}$ is —OH and the other is —C(O)H. In some embodiments, L is *—NHC(O)O— or *—OC(O)NH—, and one of $R^{1A}$ and $R^{2A}$ is —OH and the other is —CHN$R^{j1}$. In some embodiments, L is *—NHC(O)O— or *—OC(O)NH—, and one of $R^{1A}$ and $R^{2A}$ is —OH and the other is —CHN$R^{j1}$, wherein $R^{j1}$ is $C_1$-$C_6$alkyl. In some embodiments, L is *—NHC(O)O— or *—OC(O)NH—, and one of $R^{1A}$ and $R^{2A}$ is —OH and the other is —CHN$R^{j1}$, wherein $R^{j1}$ is 5- to 6-membered heterocyclyl, unsubstituted or substituted with one or more substituents selected from the group consisting of $C_1$-$C_6$alkyl, $C_3$-$C_8$cycloalkyl, =O, —C(O)NH—$C_1$-$C_6$alkyl, and —C(O)O—$C_1$-$C_6$alkyl. In some embodiments, L is *—NHC(O)O— or *—OC(O)NH—, and one of $R^{1A}$ and $R^{2A}$ is —OH and the other is —CHN$R^{j1}$, wherein $R^{j1}$ is 5- to 6-membered heteroaryl, unsubstituted or substituted with one or more substituents selected from the group consisting of $C_1$-$C_6$alkyl, $C_3$-$C_8$cycloalkyl, and —C(O)O—$C_1$-$C_6$alkyl. In other embodiments, L is *—NHC(O)O— or *—OC(O)NH—, and one of $R^{1A}$ and $R^{2A}$ is —OH and the other is —CHN$R^{j1}$, wherein $R^{j1}$ is 6- to 12-membered aryl, unsubstituted or substituted with one or more substituents selected from the group consisting of $C_1$-$C_6$alkyl, $C_3$-$C_8$cycloalkyl, and —C(O)O—$C_1$-$C_6$alkyl. In some embodiments, L is *—NHC(O)O— or *—OC(O)NH—, and one of $R^{1A}$ and $R^{2A}$ is —OH and the other is —CHN$R^{j1}$, wherein $R^{j1}$ is —O$R^{k1}$, wherein $R^{k1}$ is $C_1$-$C_6$alkyl, $C_2$-$C_6$alkenyl, $C_2$-$C_6$alkynyl, $C_3$-$C_8$cycloalkyl, or 6- to 12-membered aryl, wherein the $C_1$-$C_6$alkyl is unsubstituted or substituted with 5- to 6-membered heterocyclyl or 5- to 6-membered heteroaryl. In some embodiments, L is *—NHC(O)O— or *—OC(O)NH—, and one of $R^{1A}$ and $R^{2A}$ is —OH and the other is —CHN$R^{j1}$, wherein $R^{j1}$ is —NH$R^{k1}$ or —N($C_1$-$C_6$alkyl)$R^{k1}$, wherein $R^{k1}$ is $C_1$-$C_6$alkyl, $C_2$-$C_6$alkenyl, $C_2$-$C_6$alkynyl, $C_3$-$C_8$cycloalkyl, or 6- to 12-membered aryl, wherein the $C_1$-$C_6$alkyl is unsubstituted or substituted with 5- to 6-membered heterocyclyl or 5- to 6-membered heteroaryl. In some embodiments, L is *—NHC(O)O— or *—OC(O)NH—, and one of $R^{1A}$ and $R^{2A}$ is —OH and the other is —CHN$R^{j1}$, wherein $R^{j1}$ is —NHC(O)$R^{k1}$, wherein $R^{k1}$ is $C_1$-$C_6$alkyl, $C_2$-$C_6$alkenyl, $C_2$-$C_6$alkynyl, $C_3$-$C_8$cycloalkyl, or 6- to 12-membered aryl, wherein the $C_1$-$C_6$alkyl is unsubstituted or substituted with 5- to 6-membered heterocyclyl or 5- to 6-membered heteroaryl. In other embodiments, L is *—NHC(O)O— or *—OC(O)NH—, and one of $R^{1A}$ and $R^{2A}$ is —OH and the other is —CHN$R^{j1}$, wherein $R^{j1}$ is —NHS(O)$_2R^{k1}$, wherein $R^{k1}$ is $C_1$-$C_6$alkyl, $C_2$-$C_6$alkenyl, $C_2$-$C_6$alkynyl, $C_3$-$C_8$cycloalkyl, or 6- to 12-membered aryl, wherein the $C_1$-$C_6$alkyl is unsubstituted or substituted with 5- to 6-membered heterocyclyl or 5- to 6-membered heteroaryl. In yet other embodiments, L is *—NHC(O)O— or *—OC(O)NH—, and one of $R^{1A}$ and $R^{2A}$ is —OH and the other is —CHN$R^{j1}$, wherein $R^{j1}$ is —NHC(NH)NH$_2$. In other embodiments L is *—NHC(O)O— or *—OC(O)NH—, and one of $R^{1A}$ and $R^{2A}$ is —OH and the other is

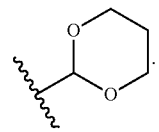 [SMILES: *C1OCCCO1]

In some of any of the foregoing embodiments, one of $R^{1A}$ and $R^{2A}$ is —OH and the other is —CHN$R^{j1}$, wherein $R^{j1}$ is a 5- to 6-membered heterocyclyl, wherein the 5- to 6-membered heterocyclyl of $R^{j1}$ is unsubstituted or substituted with one or more substituents selected from the group consisting of $C_1$-$C_6$alkyl, $C_3$-$C_8$cycloalkyl, =O, —C(O)NH—$C_1$-$C_6$alkyl, and —C(O)O—$C_1$-$C_6$alkyl. In some embodiments, $R^{j1}$ is selected from the group consisting of pyrrolidinyl, pyrazolidinyl, imidazolidinyl, tetrahydrofuranyl, 1,3-dioxolanyl, tetrahydrothiophenyl, oxathiolanyl, sulfolanyl, piperidinyl, piperazinyl, tetrahydropyranyl, dioxanyl, thianyl, dithianyl, trithianyl, morpholinyl, and thiomorpholinyl, each independently unsubstituted or substituted with one or more substituents selected from the group consisting of $C_1$-$C_6$alkyl, $C_3$-$C_8$cycloalkyl, =O, —C(O)NH—$C_1$-$C_6$alkyl, and —C(O)O—$C_1$-$C_6$alkyl. In some embodiments, $R^{j1}$ is a 5- to 6-membered heterocyclyl, wherein the nitrogen and/or sulfur atom(s) of the heterocyclyl are optionally oxidized to provide for N-oxide, —S(O)—, or —SO$_2$— moieties. In some of any of the foregoing embodiments, one of $R^{1A}$ and $R^{2A}$ is —OH and the other is —CHN$R^{j1}$, wherein $R^{j1}$ is a 5- to 6-membered heteroaryl, wherein the 5- to 6-membered heteroaryl of $R^{j1}$ is unsubstituted or substituted with one or more substituents selected from the group consisting of $C_1$-$C_6$alkyl, $C_3$-$C_8$cycloalkyl, and —C(O)O—$C_1$-$C_6$alkyl. In some embodiments, $R^{j1}$ is selected from the group consisting of pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridyl, pyridazinyl, pyrimidinyl, pyrazinyl, triazinyl, and tetrazinyl, each independently unsubstituted or substituted with one or more substituents selected from the group consisting of $C_1$-$C_6$alkyl, $C_3$-$C_8$cycloalkyl, and —C(O)O—$C_1$-$C_6$alkyl. In some of any of the foregoing embodiments, one of $R^{1A}$ and $R^{2A}$ is —OH and the other is —CHN$R^{j1}$, wherein $R^{j1}$ is a 6- to 12-membered aryl, wherein the 6- to 12-membered aryl of $R^{j1}$ is unsubstituted or substituted with one or more substituents selected from the group consisting of $C_1$-$C_6$alkyl, $C_3$-$C_8$cycloalkyl, and —C(O)O—$C_1$-$C_6$alkyl. In some embodiments, $R^{j1}$ is selected from the group consisting of phenyl and naphthyl, each independently unsubstituted or substituted with one or more substituents selected from the group consisting of $C_1$-$C_6$alkyl, $C_3$-$C_8$cycloalkyl, and —C(O)O—$C_1$-$C_6$alkyl. In some of any of the foregoing embodiments, one of $R^{1A}$ and $R^{2A}$ is —OH and the other is —CHN$R^{j1}$, wherein $R^{j1}$ is unsubstituted —O$C_1$-$C_6$alkyl, or —O$C_1$-$C_6$alkyl substituted with a 5- to 6-membered heterocyclyl or a 5- to 6-membered heteroaryl. In some of any of the foregoing embodiments, one of $R^{1A}$ and $R^{2A}$ is —OH and the other is —CHNR$^{j1}$, wherein R$^{j1}$ is —OC$_2$-C$_6$alkenyl or —OC$_2$-C$_6$alkynyl. In some embodiments, one of $R^{1A}$ and $R^{2A}$ is —OH and the other is —CHNR$^{j1}$, wherein R$^{j1}$ is —OC$_3$-C$_8$cycloalkyl or —O-6- to 12-membered aryl. In some of any of the foregoing embodiments, one of $R^{1A}$ and $R^{2A}$ is —OH and the other is —CHNR$^{j1}$, wherein R$^{j1}$ is —NHC$_1$-C$_6$alkyl, —NHC(O)C$_1$-C$_6$alkyl, or —NHS(O)$_2$C$_1$-C$_6$alkyl, each unsubstituted or substituted with a 5- to 6-membered heterocyclyl or a 5- to 6-membered heteroaryl. In some of any of the foregoing embodiments, one of $R^{1A}$ and $R^{2A}$ is —OH and the other is —CHNR$^{j1}$, wherein R$^{j1}$ is —NHC$_2$-C$_6$alkenyl, —NHC$_2$-C$_6$alkynyl, —NHC(O)C$_2$-C$_6$alkenyl, —NHC(O)C$_2$-C$_6$alkynyl, —NHS(O)$_2$C$_2$-C$_6$alkenyl, or —NHS(O)$_2$C$_2$-C$_6$alkynyl. In some embodiments, one of $R^{1A}$ and $R^{2A}$ is —OH and the other is —CHNR$^{j1}$, wherein R$^{j1}$ is —NHC$_3$-C$_8$cycloalkyl, —NH-6- to 12-membered aryl, —NHC(O)C$_3$-C$_8$cycloalkyl, —NHC(O)-6- to 12-membered aryl, —NHS(O)$_2$C$_3$-C$_8$cycloalkyl, or —NHS(O)$_2$-6- to 12-membered aryl. In some of any of the foregoing embodiments, one of $R^{1A}$ and $R^{2A}$ is —OH and the other is —CHNR$^{j1}$, wherein R$^{j1}$ is —NHC(NH)NH$_2$. In some embodiments, one of $R^{1A}$ and $R^{2A}$ is —OH and the other is —CH=NR$^{j1}$, wherein R$^{j1}$ is —NHC(NH)NHR$^{bb}$. In some embodiments, R$^{bb}$ is unsubstituted or substituted C$_1$-C$_6$alkyl. In certain embodiments, R$^{bb}$ is C$_1$-C$_6$alkyl substituted with —OH or —(OCH$_2$CH$_2$)$_v$OH, where v is 1, 2, or 3. In some embodiments, R$^{bb}$ is unsubstituted or substituted C$_3$-C$_8$cycloalkyl. In some embodiments, R$^{bb}$ is unsubstituted or substituted aryl. In some embodiments, R$^{bb}$ is unsubstituted or substituted C$_6$-C$_{14}$ aryl. In some embodiments, R$^{bb}$ is unsubstituted or substituted heterocycloalkyl. In some embodiments, R$^{bb}$ is unsubstituted or substituted 3- to 18-membered heterocycloalkyl. In some embodiments, R$^{bb}$ is unsubstituted or substituted 3- to 6-membered heterocycloalkyl. In some embodiments, R$^{bb}$ is unsubstituted or substituted heteroaryl. In some embodiments, R$^{bb}$ is unsubstituted or substituted 5- to 18-membered heteroaryl. In some embodiments, R$^{bb}$ is unsubstituted or substituted 5- to 10-membered heteroaryl. In some embodiments, R$^{bb}$ is C$_3$-C$_8$cycloalkyl, C$_6$-C$_{14}$ aryl, 3- to 18-membered heterocycloalkyl, or 5- to 18-membered heteroaryl, each optionally substituted with C$_1$-C$_6$alkyl.

In some of any of the foregoing embodiments, one of $R^{1A}$ and $R^{2A}$ is —OH and the other is —CHNR$^{j1}$, wherein —CHNR$^{j1}$ is selected from the group consisting of

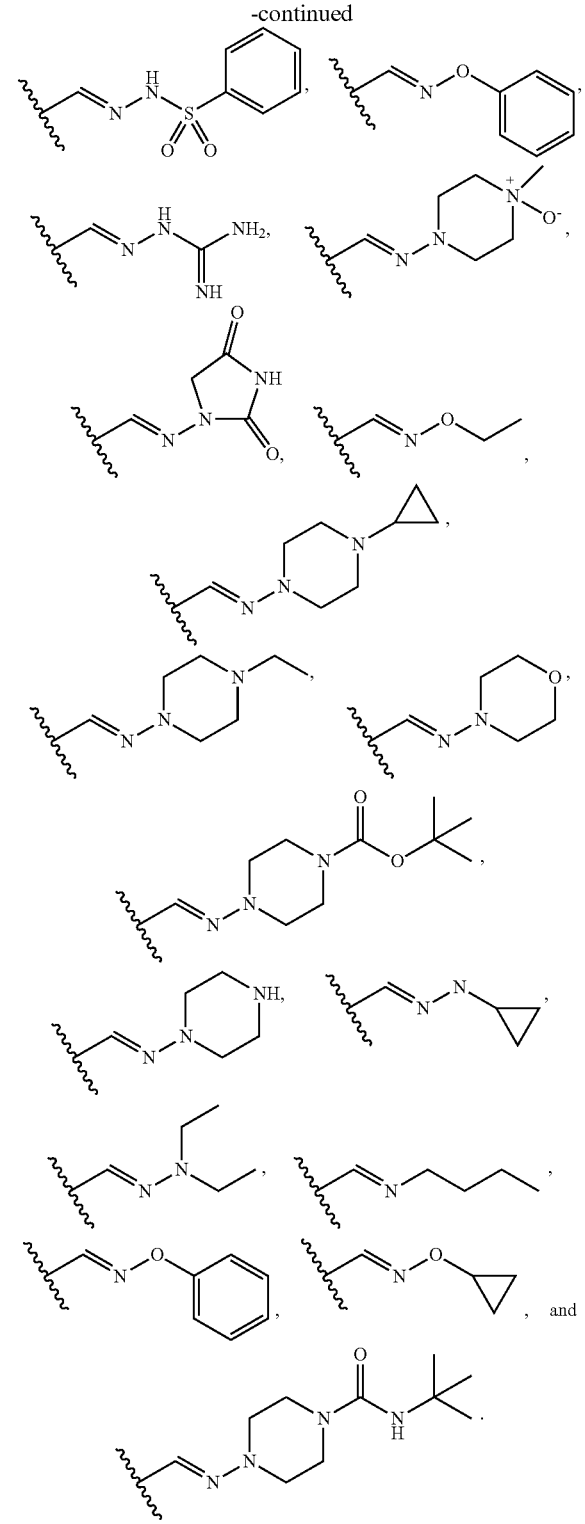

In some embodiments of Formula (B), including Formula (B-1a), (B-1b), (B-2a), (B-2b), (B-2c), (B-2d), (B-2e), (B-2f), (B-2g), (B-2h), (B-2i), (B-2j), (B-2k), (B-2l), (B-2m), (B-2n), (B-3a), (B-3b), (B-3c), (B-3d), (B-3e), (B-3f), (B-3g), (B-3h), (B-3i), (B-3j), (B-3k), (B-3l), (B-3m), and (B-3n), R$^{3A}$ is H. In some embodiments, R$^{3A}$ is unsubstituted C$_1$-C$_6$alkyl. In some embodiments, R$^{3A}$ is C$_1$-C$_6$alkyl substituted with one or more halogen. In some embodiments, $R^{3A}$ is unsubstituted $C_1$-$C_6$alkoxy. In some embodiments, $R^{3A}$ is $C_1$-$C_6$alkoxy substituted with one or more halogen. In other embodiments, $R^{3A}$ is halogen.

In some embodiments of Formula (B), including Formula (B-1a), (B-1b), (B-2a), (B-2b), (B-2c), (B-2d), (B-2e), (B-2f), (B-2g), (B-2h), (B-2i), (B-2j), (B-2k), (B-2l), (B-2m), (B-2n), (B-3a), (B-3b), (B-3c), (B-3d), (B-3e), (B-3f), (B-3g), (B-3h), (B-3i), (B-3j), (B-3k), (B-3l), (B-3m), and (B-3n), one of $R^{1A}$ and $R^{2A}$ is —OH and the other is —C(O)H. In some embodiments, $R^{1A}$ is —OH, $R^{2A}$ is —C(O)H, and $R^{3A}$ is H. In some embodiments, $R^{1A}$ is —OH, $R^{2A}$ is —C(O)H, and $R^{3A}$ is unsubstituted $C_1$-$C_6$alkyl. In some embodiments, $R^{1A}$ is —OH, $R^{2A}$ is —C(O)H, and $R^{3A}$ is $C_1$-$C_6$haloalkyl. In some embodiments, $R^{1A}$ is —OH, $R^{2A}$ is —C(O)H, and $R^{3A}$ is unsubstituted $C_1$-$C_6$alkoxy. In some embodiments, $R^{1A}$ is —OH, $R^{2A}$ is —C(O)H, and $R^{3A}$ is $C_1$-$C_6$alkoxy substituted with one or more halogen. In other embodiments, $R^{1A}$ is —OH, $R^{2A}$ is —C(O)H, and $R^{3A}$ is halogen. In certain embodiments, $R^{1A}$ is —OH, $R^{2A}$ is —C(O)H, and $R^{3A}$ is fluoro. In certain embodiments, $R^{1A}$ is —OH, $R^{2A}$ is —C(O)H, and $R^{3A}$ is methyl. In some embodiments, $R^{1A}$ is —OH, $R^{2A}$ is —C(O)H, and $R^{3A}$ is methoxy. In some embodiments, $R^{2A}$ is —OH, $R^{1A}$ is —C(O)H, and $R^{3A}$ is H. In some embodiments, $R^{2A}$ is —OH, $R^{1A}$ is —C(O)H, and $R^{3A}$ is unsubstituted $C_1$-$C_6$alkyl. In some embodiments, $R^{2A}$ is —OH, $R^{1A}$ is —C(O)H, and $R^{3A}$ is $C_1$-$C_6$haloalkyl. In some embodiments, $R^{2A}$ is —OH, $R^{1A}$ is —C(O)H, and $R^{3A}$ is unsubstituted $C_1$-$C_6$alkoxy. In some embodiments, $R^{2A}$ is —OH, $R^{1A}$ is —C(O)H, and $R^{3A}$ is $C_1$-$C_6$alkoxy substituted with one or more halogen. In other embodiments, $R^{2A}$ is —OH, $R^{1A}$ is —C(O)H, and $R^{3A}$ is halogen. In certain embodiments, $R^{2A}$ is —OH, $R^{1A}$ is —C(O)H, and $R^{3A}$ is fluoro. In certain embodiments, $R^{2A}$ is —OH, $R^{1A}$ is —C(O)H, and $R^{3A}$ is methyl. In some embodiments, $R^{2A}$ is —OH, $R^{1A}$ is —C(O)H, and $R^{3A}$ is methoxy.

In some embodiments of Formula (B), including Formula (B-1a), (B-1b), (B-2a), (B-2b), (B-2c), (B-2d), (B-2e), (B-2f), (B-2g), (B-2h), (B-2i), (B-2j), (B-2k), (B-2l), (B-2m), and (B-2n), $Y_1$ and $Y_2$ are each independently $CR^x$, wherein $R^x$ is H or halogen. In some embodiments, $Y_1$ and $Y_2$ are each independently CH, CF, CCl, or CBr. In some embodiments, $Y_1$ and $Y_2$ are each CH. In a particular embodiment, $Y_1$ is CF and $Y_2$ is CH. In another embodiment, $Y_1$ is CH and $Y_2$ is CF. In some embodiments, $Y_1$ is $CR^x$ and $Y_2$ is N. For instance, in some embodiments, $Y_1$ is CH, CF, CCl, or CBr, and $Y_2$ is N. In some embodiments, $Y_1$ is N and $Y_2$ is $CR^x$. For instance, in some embodiments, $Y_1$ is N and $Y_2$ is CH, CF, CCl, or CBr. In other embodiments, $Y_1$ and $Y_2$ are each N.

In some embodiments of Formula (B), including Formula (B-1a), (B-1b), (B-2a), (B-2b), (B-2c), (B-2d), (B-2e), (B-2f), (B-2g), (B-2h), (B-2i), (B-2j), (B-2k), (B-2l), (B-2m), and (B-2n), the ring bearing

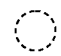

is saturated, such that the ring consists entirely of single bonds. Examples of saturated rings include, but are not limited to,

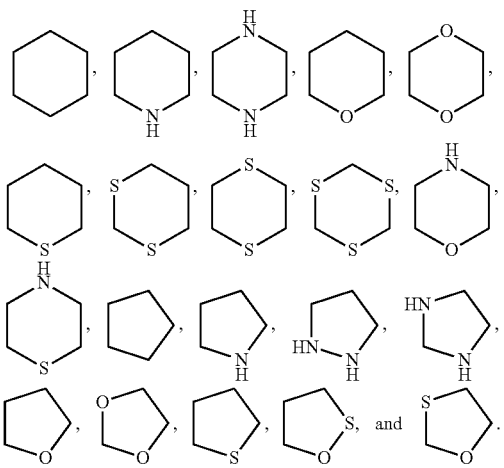

In some embodiments, the ring bearing

is partially unsaturated, such that the ring is nonaromatic and comprises at least one double bond, such as one or two double bonds. Examples of partially unsaturated rings include, but are not limited to,

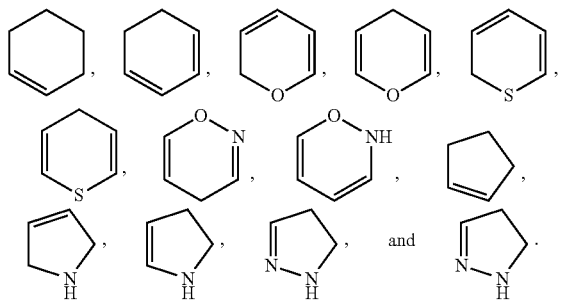

In other embodiments, the ring bearing

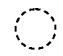

is fully unsaturated and comprises two or three double bonds. In certain embodiments, the ring bearing


is fully unsaturated. In certain embodiments, the ring bearing


is fully unsaturated and aromatic. Examples of fully unsaturated rings include, but are not limited to

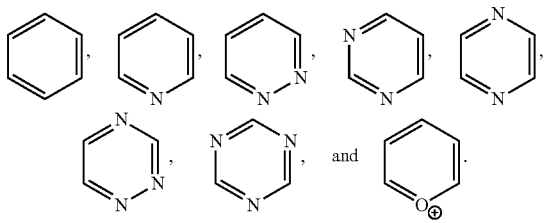

In some embodiments of Formula (B), including Formula (B-1a), (B-1b), (B-2a), (B-2b), (B-2c), (B-2d), (B-2e), (B-2f), (B-2g), (B-2h), (B-2i), (B-2j), (B-2k), (B-2l), (B-2m), and (B-2n), $Y_3$ is $CH(X_{1A}—R^{6a1})$ or $C(X_{1A}—R^{6a1})$, $Y_4$ is $CH(X_{2A}—R^{6b1})$ or $C(X_{2A}—R^{6b1})$, $Y_5$ is $CH(X_{3A}—R^{6c1})$ or $C(X_{3A}—R^{6c1})$, $Y_6$ is $CH(X_{4A}—R^{6d1})$ or $C(X_{4A}—R^{6d1})$, and the ring bearing $\bigcirc$ is partially unsaturated. In some embodiments, $Y_3$ is $C(X^{1A}—R^{6a1})$, $Y_4$ is $C(X_{2A}—R^{6b1})$, $Y_5$ is $C(X_{3A}—R^{6c1})$, $Y_6$ is $C(X_{4A}—R^{6d1})$, and the ring bearing $\bigcirc$ is fully unsaturated. In some embodiments, $Y_3$ is $CH(X^{1A}—R^{6a1})$, $Y_4$ is $CH(X_{2A}—R^{6b1})$, $Y_5$ is $CH(X_{3A}—R^{6c1})$, $Y_6$ is $CH(X_{4A}—R^{6d1})$, and the ring bearing $\bigcirc$ is saturated. In other embodiments, $Y_3$ is $CH(X_{1A}—R^{6a1})$ or $C(X_{1A}—R^{6a1})$, $Y_4$ is $CH(X_{2A}—R^{6b1})$ or $C(X_{2A}—R^{6b1})$, $Y_5$ is $CH(X_{3A}—R^{6c1})$ or $C(X_{3A}—R^{6c1})$, and $Y_6$ is absent.

In some embodiments of Formula (B), including Formula (B-1a), (B-1b), (B-2a), (B-2b), (B-2c), (B-2d), (B-2e), (B-2f), (B-2g), (B-2h), (B-2i), (B-2j), (B-2k), (B-2l), (B-2m), and (B-2n), $Y_3$ is $CH(X^{1A}—R^{6a1})$ or $C(X^{1A}—R^{6a1})$, $Y_4$ is N or $N(X_{2A}—R^{6b1})$, $Y_5$ is $CH(X_{3A}—R^{6c1})$ or $C(X_{3A}—R^{6c1})$, $Y_6$ is $CH(X_{4A}—R^{6d1})$ or $C(X_{4A}—R^{6d1})$, and the ring bearing $\bigcirc$ is partially unsaturated. In some embodiments, $Y_3$ is $C(X_{1A}—R^{6a1})$, $Y_4$ is N, $Y_5$ is $C(X_{3A}—R^{6c1})$, $Y_6$ is $C(X_{4A}—R^{6d1})$, and the ring bearing $\bigcirc$ is fully unsaturated. In some embodiments, $Y_3$ is $CH(X_{1A}—R^{6a1})$, $Y_4$ is $N(X_{2A}—R^{6b1})$, $Y_5$ is $CH(X_{3A}—R^{6c1})$, $Y_6$ is $CH(X_{4A}—R^{6d1})$, and the ring bearing $\bigcirc$ is saturated. In other embodiments, $Y_3$ is $CH(X_{1A}—R^{6a1})$ or $C(X_{1A}—R^{6a1})$, $Y_4$ is N or $N(X_{2A}—R^{6b1})$, $Y_5$ is $CH(X_{3A}—R^{6c1})$ or $C(X_{3A}—R^{6c1})$, and $Y_6$ is absent.

In some embodiments of Formula (B), including Formula (B-1a), (B-1b), (B-2a), (B-2b), (B-2c), (B-2d), (B-2e), (B-2f), (B-2g), (B-2h), (B-2i), (B-2j), (B-2k), (B-2l), (B-2m), and (B-2n), $Y_3$ is N or $N(X_{1A}—R^{6a1})$, $Y_4$ is $CH(X_{2A}—R^{6b1})$ or $C(X_{2A}—R^{6b1})$, $Y_5$ is $CH(X_{3A}—R^{6c1})$ or $C(X_{3A}—R^{6c1})$, $Y_6$ is $CH(X_{4A}—R^{6d1})$ or $C(X_{4A}—R^{6d1})$, and the ring bearing $\bigcirc$ is partially unsaturated. In some embodiments, $Y_3$ is N, $Y_4$ is $C(X_{2A}—R^{6b1})$, $Y_5$ is $C(X_{3A}—R^{6c})$, $Y_6$ is $C(X_{4A}—R^{6d1})$, and the ring bearing $\bigcirc$ is fully unsaturated. In some embodiments $Y_3$ is $N(X_{1A}—R^{6a1})$, $Y_4$ is $CH(X_{2A}—R^{6b1})$, $Y_5$ is $CH(X_{3A}—R^{6c1})$, $Y_6$ is $CH(X_{4A}—R^{6d1})$, and the ring bearing $\bigcirc$ is saturated. In other embodiments, $Y_3$ is N or $N(X_{1A}—R^{6a1})$, $Y_4$ is $CH(X_{2A}—R^{6b1})$ or $C(X_{2A}—R^{6b1})$, $Y_5$ is $CH(X_{3A}—R^{6c1})$ or $C(X_{3A}—R^{6c1})$, and $Y_6$ is absent.

In some embodiments of Formula (B), including Formula (B-1a), (B-1b), (B-2a), (B-2b), (B-2c), (B-2d), (B-2e), (B-2f), (B-2g), (B-2h), (B-2i), (B-2j), (B-2k), (B-2l), (B-2m), and (B-2n), $Y_3$ is $CH(X_{1A}—R^{6a1})$ or $C(X_{1A}—R^{6a1})$, $Y_4$ is $CH(X_{2A}—R^{6b1})$ or $C(X_{2A}—R^{6b1})$, $Y_5$ is N or $N(X_{3A}—R^{6c1})$, $Y_6$ is $CH(X_{4A}—R^{6d1})$ or $C(X_{4A}—R^{6d1})$, and the ring bearing $\bigcirc$ is partially unsaturated. In some embodiments, $Y_3$ is $C(X_{1A}—R^{6a1})$, $Y_4$ is $C(X_{2A}—R^{6b1})$, $Y_5$ is N, $Y_6$ is $C(X_{4A}—R^{6d1})$, and the ring bearing $\bigcirc$ is fully unsaturated. In some embodiments, $Y_3$ is $CH(X_{1A}—R^{6a1})$, $Y_4$ is $CH(X_{2A}—R^{6b1})$, $Y_5$ is $N(X_{3A}—R^{6c1})$, $Y_6$ is $CH(X_{4A}—R^{6d1})$, and the ring bearing $\bigcirc$ is saturated. In other embodiments, $Y_3$ is $CH(X_{1A}-R^{6a1})$ or $C(X_{1A}-R^{6a1})$, $Y_4$ is $CH(X_{2A}-R^{6b1})$ or $C(X_{2A}-R^{6b1})$ $Y_5$ is N or $N(X_{3A}-R^{6c1})$, and $Y_6$ is absent.

In other embodiments of Formula (B), including Formula (B-1a), (B-1b), (B-2a), (B-2b), (B-2c), (B-2d), (B-2e), (B-2f), (B-2g), (B-2h), (B-2i), (B-2j), (B-2k), (B-2l), (B-2m), and (B-2n), $Y_3$ is N or $N(X_{1A}-R^{6a1})$, $Y_4$ is $CH(X_{2A}-R^{6b1})$ or $C(X_{2A}-R^{6b1})$, $Y_5$ is N or $N(X_{1A}-R^{6c1})$, $Y_6$ is $CH(X_{4A}-R^{6d1})$ or $C(X_{4A}-R^{6d1})$, and the ring bearing

is partially unsaturated. In some embodiments, $Y_3$ is N, $Y_4$ is $C(X_{2A}-R^{6b1})$, $Y_5$ is N, $Y_6$ is $C(X_{4A}-R^{6d1})$, and the ring bearing

is fully unsaturated. In some embodiments, $Y_3$ is $N(X_{1A}-R^{6a1})$, $Y_4$ is $CH(X_{2A}-R^{6b1})$, $Y_5$ is $N(X_{1A}-R^{6c1})$, $Y_6$ is $CH(X_{4A}-R^{6d1})$, and the ring bearing

is saturated. In other embodiments, $Y_3$ is N or $N(X_{1A}-R^{6a1})$, $Y_4$ is $CH(X_{2A}-R^{6b1})$ or $C(X_{2A}-R^{6b1})$, $Y_5$ is N or $N(X_{1A}-R^{6c1})$, and $Y_6$ is absent.

In certain embodiments of Formula (B), including Formula (B-1a), (B-1b), (B-2a), (B-2b), (B-2c), (B-2d), (B-2e), (B-2f), (B-2g), (B-2h), (B-2i), (B-2j), (B-2k), (B-2l), (B-2m), and (B-2n), $R^4$ and $R^5$ come together to form —S—, $Y_3$ is $CH(X_{1A}-R^{6a1})$, $Y_4$ is $N(X_{2A}-R^{6b1})$, $Y_5$ is $CH(X_{1A}-R^{6a1})$, $Y_6$ is $CH(X_{1A}-R^{6a1})$, and the ring bearing

is a saturated ring. In certain embodiments, $R^4$ and $R^5$ come together to form —S—, $Y_3$, $Y_5$, and $Y_6$ are each $CH_2$, $Y_4$ is $N(X_{2A}-R^{6b1})$, and the ring bearing

is a saturated ring.

In some embodiments of Formula (B), including Formula (B-1a), (B-1b), (B-2a), (B-2b), (B-2c), (B-2d), (B-2e), (B-2f), (B-2g), (B-2h), (B-2i), (B-2j), (B-2k), (B-2l), (B-2m), and (B-2n), $Y_3$ is $CH(X_{1A}-R^{6a1})$ or $C(X_{1A}-R^{6a1})$, wherein $X_{1A}$ is absent. In some embodiments, $Y_3$ is $CH(X_{1A}-R^{6a1})$ or $C(X_{1A}-R^{6a1})$, wherein $X_{1A}$ is

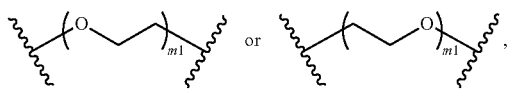

and m1 is 1-6. In some embodiments, $Y_3$ is N. In other embodiments, $Y_3$ is $N(X_{1A}-R^{6a1})$, wherein $X_{1A}$ is absent. In some embodiments, $Y_3$ is $N(X_{1A}-R^{6a1})$, wherein $X_{1A}$ is

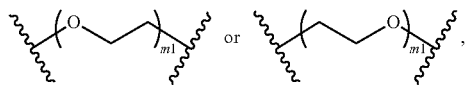

and m1 is is $CH(X_{1A}-R^{6a1})$ or $C(X_{1A}-R^{6a1})$; $X_{1A}$ is absent,

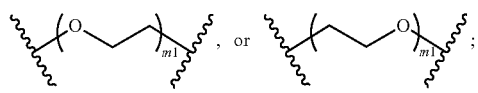

m1 is 1-6; $R^{6a1}$ is hydrogen, $C_1$-$C_6$alkyl, $C_1$-$C_6$haloalkyl, halo, $C_6$-$C_{12}$ aryl, 3- to 10-membered heterocyclyl, or 5- to 10-membered heteroaryl. In some embodiments, $Y_3$ is N or $N(X_{1A}-R^{6a1})$; $X_{1A}$ is absent,

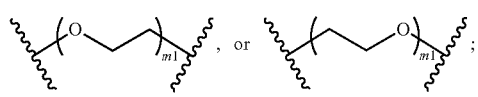

m1 is 1-6; and $R^{6a1}$ is hydrogen, $C_1$-$C_6$alkyl, $C_1$-$C_6$haloalkyl, halo, $C_6$-$C_{12}$ aryl, 3- to 10-membered heterocyclyl, or 5- to 10-membered heteroaryl.

In some embodiments of Formula (B), including Formula (B-1a), (B-1b), (B-2a), (B-2b), (B-2c), (B-2d), (B-2e), (B-2f), (B-2g), (B-2h), (B-2i), (B-2j), (B-2k), (B-2l), (B-2m), and (B-2n), $Y_4$ is $CH(X_{2A}-R^{6b1})$ or $C(X_{2A}-R^{6b1})$, wherein $X_{2A}$ is absent. In some embodiments, $Y_4$ is $CH(X_{2A}-R^{6b1})$ or $C(X_{2A}-R^{6b1})$, wherein $X_{2A}$ is

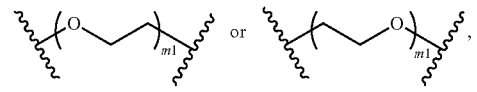

and m1 is 1-6. In some embodiments, $Y_4$ is N. In other embodiments, $Y_4$ is $N(X_{2A}-R^{6b1})$, wherein $X_{2A}$ is absent. In some embodiments, $Y_4$ is $N(X_{2A}-R^{6b1})$, wherein $X_{2A}$ is

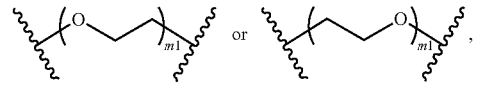

and m1 is 1-6. In some embodiments, $Y_4$ is S. In other embodiments, $Y_4$ is O. In some embodiments, $Y_4$ is $CH(X_{2A}-R^{6b1})$ or $C(X_{2A}-R^{6b1})$; $X_{2A}$ is absent,

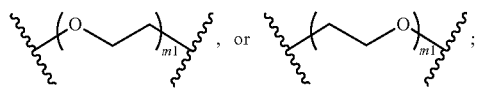

m1 is 1-6; and $R^{6b1}$ is hydrogen, $C_1$-$C_6$alkyl, $C_1$-$C_6$haloalkyl, halo, $C_6$-$C_{12}$ aryl, 3- to 10-membered heterocyclyl, or 5- to 10-membered heteroaryl. In some embodiments, $Y_4$ is N or $N(X_{2A}-R^{6b1})$; $X_{2A}$ is absent,

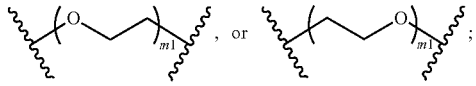

m1 is 1-6; and $R^{6b1}$ is hydrogen, $C_1$-$C_6$alkyl, $C_1$-$C_6$haloalkyl, halo, $C_6$-$C_{12}$ aryl, 3- to 10-membered heterocyclyl, or 5- to 10-membered heteroaryl.

In some embodiments, $Y_5$ is $CH(X_{3A}-R^{6c1})$ or $C(X_{3A}-R^{6c})$, wherein $X_3A$ is absent. In some embodiments, $Y_5$ is $CH(X_{3A}-R^{6c1})$ or $C(X_{3A}-R^{6c1})$, wherein $X_{3A}$ is

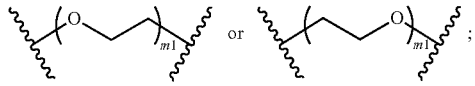

and m1 is 1-6. In some embodiments, $Y_5$ is N. In other embodiments, $Y_5$ is $N(X_{3A}-R^{6c1})$, wherein $X_{3A}$ is absent. In some embodiments, $Y_5$ is $N(X_{3A}-R^{6c1})$, wherein $X_{3A}$ is

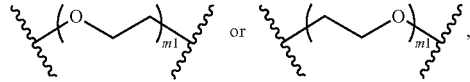

and m1 is 1-6. In some embodiments, $Y_5$ is S. In other embodiments, $Y_5$ is O. In some embodiments, $Y_5$ is $CH(X_{3A}-R^{6c1})$ or $C(X_{3A}-R^{6c1})$; $X_{3A}$ is absent,

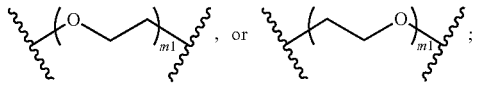

m1 is 1-6; and $R^{6c1}$ is hydrogen, $C_1$-$C_6$alkyl, $C_1$-$C_6$haloalkyl, halo, $C_6$-$C_{12}$ aryl, 3- to 10-membered heterocyclyl, or 5- to 10-membered heteroaryl. In some embodiments, $Y_5$ is N or $N(X_{3A}-R^{6c1})$; $X_{3A}$ is absent,

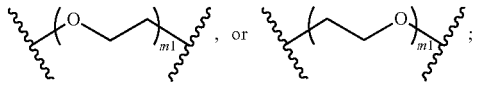

m1 is 1-6; and $R^{6c}$ is hydrogen, $C_1$-$C_6$alkyl, $C_1$-$C_6$haloalkyl, halo, $C_6$-$C_{12}$ aryl, 3- to 10-membered heterocyclyl, or 5- to 10-membered heteroaryl.

In some embodiments of Formula (B), including Formula (B-1a), (B-1b), (B-2a), (B-2b), (B-2c), (B-2d), (B-2e), (B-2f), (B-2g), (B-2h), (B-2i), (B-2j), (B-2k), (B-2l), (B-2m), and (B-2n), one of $Y_3$, $Y_4$, $Y_5$, and $Y_6$ is S or O. In some embodiments, one of $Y_3$, $Y_4$, and $Y_5$ is S or O. In some embodiments, $Y_3$ is S. In some embodiments, $Y_3$ is O. In some embodiments, $Y_4$ is S. In some embodiments, $Y_4$ is O. In some embodiments, $Y_5$ is S. In some embodiments, $Y_5$ is O. In some embodiments, $Y_6$ is S. In some embodiments, $Y_6$ is O.

In some embodiments of Formula (B), including Formula (B-1a), (B-1b), (B-2a), (B-2b), (B-2c), (B-2d), (B-2e), (B-2f), (B-2g), (B-2h), (B-2i), (B-2j), (B-2k), (B-2l), (B-2m), and (B-2n), one of $Y_3$, $Y_4$, $Y_5$, $Y_6$, $Y_7$, and $Y_8$ is N. In some embodiments, two of $Y_3$, $Y_4$, $Y_5$, $Y_6$, $Y_7$, and $Y_8$ are N. In other embodiments, three of $Y_3$, $Y_4$, $Y_5$, $Y_6$, $Y_7$, and $Y_8$ are N.

In some embodiments of Formula (B), including Formula (B-1a), (B-1b), (B-2a), (B-2b), (B-2c), (B-2d), (B-2e), (B-2f), (B-2g), (B-2h), (B-2i), (B-2j), (B-2k), (B-2l), (B-2m), and (B-2n), $Y_6$ is $CH(X_{4A}-R^{6d1})$ or $C(X_{4A}-R^{6d1})$, wherein $X_{4A}$ is absent. In some embodiments, $Y_6$ is $CH(X_{4A}-R^{6d1})$ or $C(X_{4A}-R^{6d1})$, wherein $X_{4A}$ is

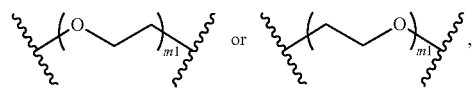

and m1 is 1-6. In some embodiments, $Y_6$ is N. In other embodiments, $Y_6$ is $N(X_{4A}-R^{6d1})$, wherein $X_{4A}$ is absent. In some embodiments, $Y_6$ is $N(X_{4A}-R^{6d1})$, wherein $X_{4A}$ is

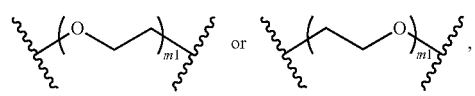

and m1 is 1-6. In some embodiments, $Y_6$ is S. In other embodiments, $Y_6$ is O. In some embodiments, $Y_6$ is $CH(X_{4A}-R^{6d1})$ or $C(X_{4A}-R^{6d1})$; $X_{4A}$ is absent,

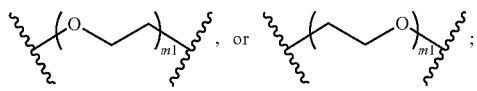

m1 is 1-6; and $R^{6d1}$ is hydrogen, $C_1$-$C_6$alkyl, $C_1$-$C_6$haloalkyl, halo, $C_6$-$C_{12}$ aryl, 3- to 10-membered heterocyclyl, or 5- to 10-membered heteroaryl. In some embodiments, $Y_6$ is N or $N(X_{4A}-R^{6d1})$; $X_{4A}$ is absent,

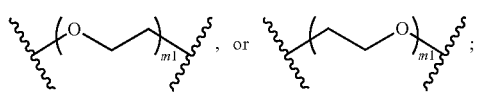

m1 is 1-6; and $R^{6d1}$ is hydrogen, $C_1$-$C_6$alkyl, $C_1$-$C_6$haloalkyl, halo, $C_6$-$C_{12}$ aryl, 3- to 10-membered heterocyclyl, or 5- to 10-membered heteroaryl.

In some embodiments of Formula (B), including Formula (B-1a), (B-1b), (B-2a), (B-2b), (B-2c), (B-2d), (B-2e), (B-2f), (B-2g), (B-2h), (B-2i), (B-2j), (B-2k), (B-2l), (B-2m), and (B-2n), $Y_5$ is $CH(X_{3A}-R^{6c1})$, $Y_6$ is $CH(X_{4A}-R^{6d1})$, ring

is saturated, and $R^{6c1}$ and $R^{6d1}$ are taken together with the carbon atoms to which they are attached to form a 6-membered heterocyclyl ring; wherein the heterocyclyl ring is unsubstituted or substituted with one or more groups selected from the group consisting of $C_1$-$C_6$alkyl and —C(O)O—$C_1$-$C_6$alkyl. In some embodiments, $Y_5$ is $C(X_{3A}$—$R^{6c1})$, $Y_6$ is $C(X_{4A}$—$R^{6d1})$,

is partially unsaturated or fully unsaturated, and $R^{6c1}$ and $R^{6d1}$ are taken together with the carbon atoms to which they are attached to form a 6-membered aryl, 6-membered heterocyclyl, or 6-membered heteroaryl ring; wherein the 6-membered aryl, 6-membered heterocyclyl, and 6-membered heteroaryl rings are each independently unsubstituted or substituted with one or more groups selected from the group consisting of $C_1$-$C_6$alkyl and —C(O)O—$C_1$-$C_6$alkyl. In some embodiments, $Y_5$ is $C(X_{3A}$—$R^{6c1})$, $Y_6$ is $C(X_{4A}$—$R^{6d1})$,

is fully unsaturated, and $R^{6c1}$ and $R^{6d1}$ are taken together with the carbon atoms to which they are attached to form a 6-membered aryl, a 6-membered heterocyclyl, or a 6-membered heteroaryl ring; wherein the 6-membered aryl, 6-membered heterocyclyl, and 6-membered heteroaryl rings are each independently unsubstituted or substituted with one or more groups selected from the group consisting of $C_1$-$C_6$alkyl and —C(O)O—$C_1$-$C_6$alkyl. In some embodiments, $R^{6c1}$ and $R^{6d1}$ come together with the carbon atoms to which they are attached to form a phenyl ring. In some embodiments, $R^{6c1}$ and $R^{6d1}$ are taken together with the carbon atoms to which they are attached to form a 6-membered heterocyclyl or 6-membered heteroaryl ring, wherein the 6-membered heterocyclyl or 6-membered heteroaryl ring each contains one, two, or three heteroatoms independently selected from the group consisting of N, S, and O. In some embodiments, $R^{6c1}$ and $R^{6d1}$ are taken together with the carbon atoms to which they are attached to form an unsubstituted 6-membered aryl, 6-membered heterocyclyl, or 6-membered heteroaryl ring. In some embodiments, $R^{6c1}$ and $R^{6d1}$ are taken together with the carbon atoms to which they are attached to form a 6-membered aryl, 6-membered heterocyclyl, or 6-membered heteroaryl ring, wherein the 6-membered aryl, 6-membered heterocyclyl, or 6-membered heteroaryl ring are each independently substituted with one or more substituents selected from the group consisting of $C_1$-$C_6$alkyl and —C(O)O—$C_1$-$C_6$alkyl.

In some embodiments of Formula (B), including Formula (B-1a), (B-1b), (B-2a), (B-2b), (B-2c), (B-2d), (B-2e), (B-2f), (B-2g), (B-2h), (B-2i), (B-2j), (B-2k), (B-2l), (B-2m), and (B-2n), $Y_7$ is N. In some embodiments, $Y_7$ is C. In other embodiments, $Y_7$ is CH. In some embodiments, $Y_8$ is N. In some embodiments, $Y_8$ is NH. In some embodiments, $Y_8$ is C. In other embodiments, $Y_8$ is CH.

In some embodiments, $Y_3$ is $CH(X_{1A}$—$R^{6a1})$, $C(X_{1A}$—$R^{6a1})$, N, $N(X_{1A}$—$R^{6a1})$, S, or O; $Y_4$ is $CH(X_{2A}$—$R^{6b1})$, $C(X_{2A}$—$R^{6b1})$, N, $N(X_{2A}$—$R^{6b1})$, S, or O; $Y_5$ is $CH(X_{3A}$—$R^{6c1})$, $C(X_{3A}$—$R^{6c1})$, N, $N(X_{3A}$—$R^{6c1})$, S, or O; $Y_6$ is $CH(X_{4A}$—$R^{6d1})$, $C(X_{4A}$—$R^{6d1})$, N, $N(X_{4A}$—$R^{6d1})$, S, O, or absent; and $G_7$ is N, C, or CH, wherein $Y_1$, $Y_2$, $Y_3$, $Y_4$, $Y_5$, $Y_6$, and $Y_7$ each have a charge of zero (e.g., the nitrogen of $Y_1$, $Y_2$, $Y_3$, $Y_4$, $Y_5$, $Y_6$, and $Y_7$ is not cationic).

In some embodiments of Formula (B), including Formula (B-1a), (B-1b), (B-2a), (B-2b), (B-2c), (B-2d), (B-2e), (B-2f), (B-2g), (B-2h), (B-2i), (B-2j), (B-2k), (B-2l), (B-2m), and (B-2n),

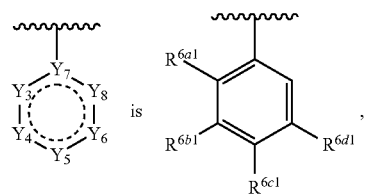

wherein one or more of $R^{6a1}$, $R^{6b1}$, $R^{6c1}$, and $R^{6d1}$ is selected from the group consisting of $C_1$-$C_6$alkyl, $C_1$-$C_6$alkoxy, halo, —OH, —$NR^{p1}R^{q1}$, $C_6$-$C_{12}$ aryl, 3- to 10-membered heterocyclyl, 5- to 10-membered heteroaryl, —$C_1$-$C_6$alkyl-5- to 6-membered heterocyclyl, —OC(O)-5- to 6-membered heterocyclyl, —C(O)$R^{h1}$, —S(O)$_2$$NR^{w1a}R^{w2a}$, —S(O)$_2$$R^{y1}$, and —$NR^{z1a}$S(O)$_2$$R^{z2a}$.

In some embodiments of Formula (B), including Formula (B-1a), (B-1b), (B-2a), (B-2b), (B-2c), (B-2d), (B-2e), (B-2f), (B-2g), (B-2h), (B-2i), (B-2j), (B-2k), (B-2l), (B-2m), and (B-2n),

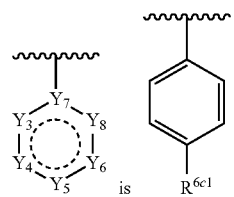

wherein $R^{6c1}$ is selected from the group consisting of $C_1$-$C_6$alkyl, $C_1$-$C_6$alkoxy, halo, —OH, —$NR^{p1}R^{q1}$, $C_6$-$C_{12}$ aryl, 3- to 10-membered heterocyclyl, 5- to 10-membered heteroaryl, —$C_1$-$C_6$alkyl-5- to 6-membered heterocyclyl, —OC(O)-5- to 6-membered heterocyclyl, —C(O)$R^{h1}$, —S(O)$_2$$NR^{w1a}R^{w2a}$, —S(O)$_2$$R^{y1}$, or —$NR^{z1a}$S(O)$_2$$R^{z2a}$. In some embodiments, $R^{6c1}$ is unsubstituted $C_1$-$C_6$alkyl. For instance, in some embodiments, $R^{6c1}$ is methyl, ethyl, propyl, isopropyl, butyl, isobutyl, secbutyl, and tertbutyl. In some embodiments, $R^{6c1}$ is $C_1$-$C_6$alkyl substituted with one or more groups selected from the group consisting of $C_3$-$C_8$ cycloalkyl and halogen. In some embodiments, $R^{6c1}$ is $C_1$-$C_6$alkoxy. For instance, in some embodiments, $R^{6c1}$ is methoxy, ethoxy, propoxy, isopropoxy, butoxy, isobutoxy, secbutoxy, and tertbutoxy. In some embodiments, $R^{6c1}$ is $C_1$-$C_6$alkoxy substituted with one or more groups selected from the group consisting of $C_3$-$C_8$ cycloalkyl and halogen. In some embodiments, $R^{6c1}$ is halo. For instance, in some embodiments, $R^{6c1}$ is fluoro, chloro, or bromo. In other embodiments, $R^{6c1}$ is $C_1$-$C_6$haloalkyl. For instance, in some embodiments, $R^{6c1}$ is fluoroethyl, trifluoromethyl, difluoromethyl, trifluoroethyl, and trichloromethyl. In some embodiments, $R^{6c1}$ is —C(O)$R^{h1}$, wherein $R^{h1}$ is H, $C_1$-$C_6$alkyl, $C_1$-$C_6$alkoxy, $C_3$-$C_8$cycloalkyl, or —$NR^{r1}R^{s1}$. For instance, in some embodiments, $R^{6c1}$ is —C(O)H, —C(O)$CH_3$, —C(O)OC($CH_3$)$_3$, or —C(O)— cyclopropyl. In some embodiments, $R^{6c1}$ is an unsubstituted 5- to 6-membered heterocycle. In some embodiments, $R^{6c1}$ is a 5- to 6-membered heterocycle, substituted with one or more groups selected from the group consisting of C₁-C₆alkyl, C₁-C₆alkoxy, —OH, C₁-C₆alkyl-OH, =O, =S, halo, C₃-C₈cycloalkyl, —C(O)NH—C₃-C₈cycloalkyl, C₆-C₁₂ aryl, and 5- to 6-membered heterocyclyl. In some embodiments, R^{6c1} is a 5- to 6-membered heterocycle, substituted with one or more groups selected from the group consisting of C₁-C₆alkyl, C₁-C₆alkoxy, —OH, C₁-C₆alkyl-OH, =O, and =S. In some embodiments, R^{6c1} is pyrrolidinyl, pyrazolidinyl, imidazolidinyl, tetrahydrofuranyl, 1,3-dioxolanyl, tetrahydrothiophenyl, oxathiolanyl, sulfolanyl, piperidinyl, piperazinyl, tetrahydropyranyl, dioxanyl, thianyl, dithianyl, trithianyl, morpholinyl, or thiomorpholinyl. In some embodiments, R^{6c1} is piperazinyl substituted with phenyl. In some embodiments, R^{6c1} is pyrrolidinyl. In certain embodiments, R^{6c1} is 4-pyrrolidin-1-yl. In some embodiments, R^{6c1} is a 5- to 10-membered heterocyclyl, substituted with one or more groups selected from the group consisting of C₁-C₆alkyl, C₁-C₆alkoxy, —OH, C₁-C₆alkyl-OH, =O, =S, halo, C₃-C₈cycloalkyl, —C(O)NH—C₃-C₈cycloalkyl, C₆-C₁₂ aryl, and 5- to 6-membered heterocyclyl. In some embodiments, R^{6c1} is azabicyclo[3.1.0]hexanyl, furo[3,4-c]pyrrolyl, azaspiro[3.3]heptane, 6-oxo-5-azaspiro[2.4]heptanyl, azaspiro[2.4]heptanyl, isoindolinyl, dihydroisoquinolinyl, pyrrolidin-1-yl)piperidinyl, indolinyl, benzo[b][1,4]oxazinyl, adamantan-1-yl)(methyl)amino, azabicyclo[2.2.1]heptanyl), azabicyclo[3.2.1]octanyl, or hexahydrocyclopenta[c]pyrrolyl, each optionally substituted with one or more substituents selected from the group consisting of C₁-C₆alkyl, C₁-C₆alkoxy, —OH, C₁-C₆alkyl-OH, =O, =S, halo, C₃-C₈cycloalkyl, —C(O)NH—C₃-C₈cycloalkyl, C₆-C₁₂ aryl, and 5- to 6-membered heterocyclyl. In some embodiments, R^{6c1} is an indolinyl, substituted with one or more groups selected from the group consisting of C₁-C₆alkyl, C₁-C₆alkoxy, —OH, C₁-C₆alkyl-OH, =O, =S, halo, C₃-C₈cycloalkyl, —C(O)NH—C₃-C₈cycloalkyl, C₆-C₁₂ aryl, and 5- to 6-membered heterocyclyl. In certain embodiments, R^{6c} is an indolinyl, substituted with one or more independently selected C₁-C₆alkyl and halo groups. In some embodiments, R^{6c1} is an unsubstituted 5- to 10-membered heteroaryl. In some embodiments, R^{6c1} is a 5- to 10-membered heteroaryl, substituted with one or more groups selected from the group consisting of C₁-C₆alkyl, C₁-C₆alkoxy, —OH, and C₁-C₆alkyl-OH. In some embodiments, R^{6c1} is pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridyl, pyridazinyl, pyrimidinyl, pyrazinyl, triazinyl, or tetrazinyl. In some embodiments, R^{6c1} is —N(CH₃)CH₂C(CH₃)₃. In some embodiments, R^{6c1} is

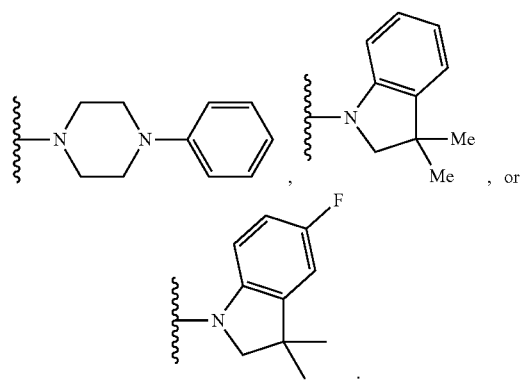

In some embodiments of Formula (B), including Formula (B-1a), (B-1b), (B-2a), (B-2b), (B-2c), (B-2d), (B-2e), (B-2f), (B-2g), (B-2h), (B-2i), (B-2j), (B-2k), (B-2l), (B-2m), and (B-2n),

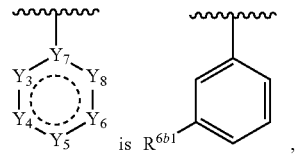 is R^{6b1}, wherein R^{6b1} is selected from the group consisting of C₁-C₆alkyl, C₁-C₆alkoxy, halo, —OH, —NR^{p1}R^{q1}, C₆-C₁₂ aryl, 3- to 10-membered heterocyclyl, 5- to 10-membered heteroaryl, —C₁-C₆alkyl-5- to 6-membered heterocyclyl, —OC(O)-5- to 6-membered heterocyclyl, —C(O)R^{h1}, —S(O)₂NR^{w1a}R^{w2}a, —S(O)₂R^{y1}, or —NR^{z1a}S(O)₂R^{z2a}. In some embodiments, R^{6b1} is unsubstituted C₁-C₆alkyl. For instance, in some embodiments, R^{6b1} is methyl, ethyl, propyl, isopropyl, butyl, isobutyl, secbutyl, and tertbutyl. In some embodiments, R^{6b1} is C₁-C₆alkyl substituted with one or more groups selected from the group consisting of C₃-C₈ cycloalkyl and halogen. In some embodiments, R^{6b1} is C₁-C₆alkoxy. For instance, in some embodiments, R^{6b1} is methoxy, ethoxy, propoxy, isopropoxy, butoxy, isobutoxy, secbutoxy, and tertbutoxy. In some embodiments, R^{6b1} is C₁-C₆alkoxy substituted with one or more groups selected from the group consisting of C₃-C₈ cycloalkyl and halogen. In some embodiments, R^{6b1} is halo. For instance, in some embodiments, R^{6b1} is fluoro, chloro, or bromo. In other embodiments, R^{6b1} is C₁-C₆haloalkyl. For instance, in some embodiments, R^{6b1} is fluoroethyl, trifluoromethyl, difluoromethyl, trifluoroethyl, and trichloromethyl. In some embodiments, R^{6b1} is —C(O)R^{h1}, wherein R^{h1} is H, C₁-C₆alkyl, C₁-C₆alkoxy, C₃-C₈cycloalkyl, or —NR^{r1}R^{s1}. For instance, in some embodiments, R^{6b1} is —C(O)H, —C(O)CH₃, —C(O)OC(CH₃)₃, or —C(O)— cyclopropyl. In some embodiments, R^{6b1} is a 5- to 10-membered heterocyclyl, substituted with one or more groups selected from the group consisting of C₁-C₆alkyl, C₁-C₆alkoxy, —OH, C₁-C₆alkyl-OH, =O, =S, halo, C₃-C₈cycloalkyl, —C(O)NH—C₃-C₈cycloalkyl, C₆-C₁₂ aryl, and 5- to 6-membered heterocyclyl. In some embodiments, R^{6b1} is azabicyclo[3.1.0]hexanyl, furo[3,4-c]pyrrolyl, azaspiro[3.3]heptane, 6-oxo-5-azaspiro[2.4]heptanyl, azaspiro[2.4]heptanyl, isoindolinyl, dihydroisoquinolinyl, pyrrolidin-1-yl)piperidinyl, indolinyl, benzo[b][1,4]oxazinyl, adamantan-1-yl)(methyl)amino, azabicyclo[2.2.1]heptanyl), azabicyclo[3.2.1]octanyl, or hexahydrocyclopenta[c]pyrrolyl, each optionally substituted with one or more substituents selected from the group consisting of C₁-C₆alkyl, C₁-C₆alkoxy, —OH, C₁-C₆alkyl-OH, =O, =S, halo, C₃-C₈cycloalkyl, —C(O)NH—C₃-C₈cycloalkyl, C₆-C₁₂ aryl, and 5- to 6-membered heterocyclyl. In some embodiments, R^{6b1} is an indolinyl, substituted with one or more groups selected from the group consisting of C₁-C₆alkyl, C₁-C₆alkoxy, —OH, C₁-C₆alkyl-OH, =O, =S, halo, C₃-C₈cycloalkyl, —C(O)NH—C₃-C₈cycloalkyl, C₆-C₁₂ aryl, and 5- to 6-membered heterocyclyl. In certain embodiments, R^{6b1} is an indolinyl, substituted with one or more independently selected C₁-C₆alkyl and halo groups. In some embodiments, R^{6b1} is an unsubstituted 5- to 6-membered heterocycle. In some embodiments, R^{6b1} is a 5- to 6-membered heterocycle, substituted with one or more groups selected from the group consisting of $C_1$-$C_6$alkyl, $C_1$-$C_6$alkoxy, —OH, $C_1$-$C_6$alkyl-OH, =O, =S, halo, $C_3$-$C_8$cycloalkyl, —C(O)NH—$C_3$-$C_8$cycloalkyl, $C_6$-$C_{12}$ aryl, and 5- to 6-membered heterocyclyl. In some embodiments, $R^{6b1}$ is a 5- to 6-membered heterocycle, substituted with one or more groups selected from the group consisting of $C_1$-$C_6$alkyl, $C_1$-$C_6$alkoxy, —OH, $C_1$-$C_6$alkyl-OH, =O, and =S. In some embodiments, $R^{6b1}$ is pyrrolidinyl, pyrazolidinyl, imidazolidinyl, tetrahydrofuranyl, 1,3-dioxolanyl, tetrahydrothiophenyl, oxathiolanyl, sulfolanyl, piperidinyl, piperazinyl, tetrahydropyranyl, dioxanyl, thianyl, dithianyl, trithianyl, morpholinyl, or thiomorpholinyl. In some embodiments, $R^{6b1}$ is piperazinyl substituted with phenyl. In some embodiments, $R^{6b1}$ is an unsubstituted 5- to 10-membered heteroaryl. In some embodiments, $R^{6b1}$ is a 5- to 10-membered heteroaryl, substituted with one or more groups selected from the group consisting of $C_1$-$C_6$alkyl, $C_1$-$C_6$alkoxy, —OH, and $C_1$-$C_6$alkyl-OH. In some embodiments, $R^{6b1}$ is pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridyl, pyridazinyl, pyrimidinyl, pyrazinyl, triazinyl, or tetrazinyl. In some embodiments, $R^{6b1}$ is —N(CH$_3$)CH$_2$C(CH$_3$)$_3$. In some embodiments, $R^{6b1}$ is

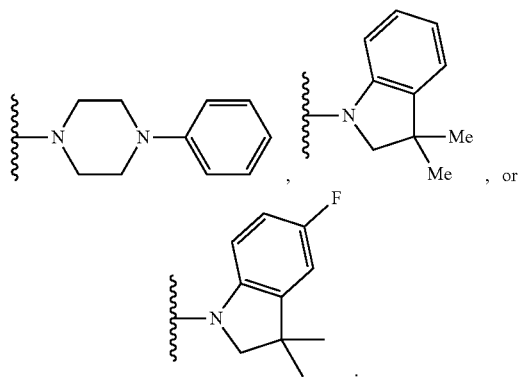

In some embodiments of Formula (B), including Formula (B-1a), (B-1b), (B-2a), (B-2b), (B-2c), (B-2d), (B-2e), (B-2f), (B-2g), (B-2h), (B-2i), (B-2j), (B-2k), (B-2l), (B-2m), and (B-2n),

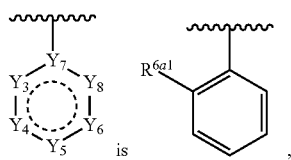

wherein $R^{6a1}$ is selected from the group consisting of $C_1$-$C_6$alkyl, $C_1$-$C_6$alkoxy, halo, —OH, —NR$^{p1}$R$^{q1}$, $C_6$-$C_{12}$ aryl, 3- to 10-membered heterocyclyl, 5- to 10-membered heteroaryl, —$C_1$-$C_6$alkyl-5- to 6-membered heterocyclyl, —OC(O)-5- to 6-membered heterocyclyl, —C(O)R$^{h1}$, —S(O)$_2$NR$^{w1a}$R$^{w2a}$, —S(O)$_2$R$^{y1}$, or —NR$^{z1a}$S(O)$_2$R$^{z2}$a. In some embodiments, $R^{6a1}$ is unsubstituted $C_1$-$C_6$alkyl. For instance, in some embodiments, $R^{6a1}$ is methyl, ethyl, propyl, isopropyl, butyl, isobutyl, secbutyl, and tertbutyl. In some embodiments, $R^{6a1}$ is $C_1$-$C_6$alkyl substituted with one or more groups selected from the group consisting of $C_3$-$C_8$ cycloalkyl and halogen. In some embodiments, $R^{6a1}$ is $C_1$-$C_6$alkoxy. For instance, in some embodiments, $R^{6a1}$ is methoxy, ethoxy, propoxy, isopropoxy, butoxy, isobutoxy, secbutoxy, and tertbutoxy. In some embodiments, $R^{6a1}$ is $C_1$-$C_6$alkoxy substituted with one or more groups selected from the group consisting of $C_3$-$C_8$ cycloalkyl and halogen. In some embodiments, $R^{6a1}$ is halo. For instance, in some embodiments, $R^{6a1}$ is fluoro, chloro, or bromo. In other embodiments, $R^{6a1}$ is $C_1$-$C_6$haloalkyl. For instance, in some embodiments, $R^{6a1}$ is fluoroethyl, trifluoromethyl, difluoromethyl, trifluoroethyl, and trichloromethyl. In some embodiments, $R^{6a1}$ is —C(O)R$^{h1}$, wherein R$^{h1}$ is H, $C_1$-$C_6$alkyl, $C_1$-$C_6$alkoxy, $C_3$-$C_8$cycloalkyl, or —NR$^{r1}$R$^{s1}$. For instance, in some embodiments, $R^{6a1}$ is —C(O)H, —C(O)CH$_3$, —C(O)OC(CH$_3$)$_3$, or —C(O)— cyclopropyl. In some embodiments, $R^{6a1}$ is an unsubstituted 5- to 6-membered heterocycle. In some embodiments, $R^{6a1}$ is a 5- to 6-membered heterocycle, substituted with one or more groups selected from the group consisting of $C_1$-$C_6$alkyl, $C_1$-$C_6$alkoxy, —OH, $C_1$-$C_6$alkyl-OH, =O, =S, halo, $C_3$-$C_8$cycloalkyl, —C(O)NH—$C_3$-$C_8$cycloalkyl, $C_6$-$C_{12}$ aryl, and 5- to 6-membered heterocyclyl. In some embodiments, $R^{6a1}$ is a 5- to 6-membered heterocycle, substituted with one or more groups selected from the group consisting of $C_1$-$C_6$alkyl, $C_1$-$C_6$alkoxy, —OH, $C_1$-$C_6$alkyl-OH, =O, and =S. In some embodiments, $R^{6a1}$ is pyrrolidinyl, pyrazolidinyl, imidazolidinyl, tetrahydrofuranyl, 1,3-dioxolanyl, tetrahydrothiophenyl, oxathiolanyl, sulfolanyl, piperidinyl, piperazinyl, tetrahydropyranyl, dioxanyl, thianyl, dithianyl, trithianyl, morpholinyl, or thiomorpholinyl. In some embodiments, $R^{6a1}$ is piperazinyl substituted with phenyl. In some embodiments, $R^{6a1}$ is a 5- to 10-membered heterocyclyl, substituted with one or more groups selected from the group consisting of $C_1$-$C_6$alkyl, $C_1$-$C_6$alkoxy, —OH, $C_1$-$C_6$alkyl-OH, =O, =S, halo, $C_3$-$C_8$cycloalkyl, —C(O)NH—$C_3$-$C_8$cycloalkyl, $C_6$-$C_{12}$ aryl, and 5- to 6-membered heterocyclyl. In some embodiments, $R^{6a1}$ is an indolinyl, substituted with one or more groups selected from the group consisting of $C_1$-$C_6$alkyl, $C_1$-$C_6$alkoxy, —OH, $C_1$-$C_6$alkyl-OH, =O, =S, halo, $C_3$-$C_8$cycloalkyl, —C(O)NH—$C_3$-$C_8$cycloalkyl, $C_6$-$C_{12}$ aryl, and 5- to 6-membered heterocyclyl. In some embodiments, $R^{6a1}$ is azabicyclo[3.1.0]hexanyl, furo[3,4-c]pyrrolyl, azaspiro[3.3]heptane, 6-oxo-5-azaspiro[2.4]heptanyl, azaspiro[2.4]heptanyl, isoindolinyl, dihydroisoquinolinyl, pyrrolidin-1-yl)piperidinyl, indolinyl, benzo[b][1,4]oxazinyl, adamantan-1-yl)(methyl)amino, azabicyclo[2.2.1]heptanyl), azabicyclo[3.2.1]octanyl, or hexahydrocyclopenta[c]pyrrolyl, each optionally substituted with one or more substituents selected from the group consisting of $C_1$-$C_6$alkyl, $C_1$-$C_6$alkoxy, —OH, $C_1$-$C_6$alkyl-OH, =O, =S, halo, $C_3$-$C_8$cycloalkyl, —C(O)NH—$C_3$-$C_8$cycloalkyl, $C_6$-$C_{12}$ aryl, and 5- to 6-membered heterocyclyl. In certain embodiments, $R^{6a1}$ is an indolinyl, substituted with one or more independently selected $C_1$-$C_6$alkyl and halo groups. In some embodiments, $R^{6a1}$ is an unsubstituted 5- to 10-membered heteroaryl. In some embodiments, $R^{6a1}$ is a 5- to 10-membered heteroaryl, substituted with one or more groups selected from the group consisting of $C_1$-$C_6$alkyl, $C_1$-$C_6$alkoxy, —OH, and $C_1$-$C_6$alkyl-OH. In some embodiments, $R^{6a1}$ is pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridyl, pyridazinyl, pyrimidinyl, pyrazinyl, triazinyl, or tetrazinyl. In some embodiments, $R^{6a1}$ is —N(CH$_3$)CH$_2$C(CH$_3$)$_3$. In some embodiments, $R^{6a1}$ is

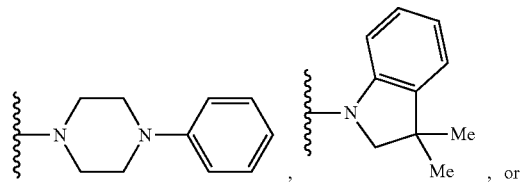

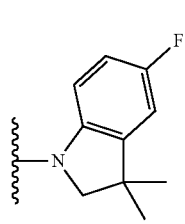

In some embodiments of Formula (B), including Formula (B-1a), (B-1b), (B-2a), (B-2b), (B-2c), (B-2d), (B-2e), (B-2f), (B-2g), (B-2h), (B-2i), (B-2j), (B-2k), (B-2l), (B-2m), and (B-2n),

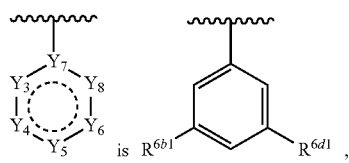

wherein $R^{6b1}$ and $R^{6d1}$ are each independently selected from the group consisting of C$_1$-C$_6$alkyl, C$_1$-C$_6$alkoxy, halo, —OH, —NR$^{p1}$R$^{q1}$, C$_6$-C$_{12}$ aryl, 3- to 10-membered heterocyclyl, 5- to 10-membered heteroaryl, —C$_1$-C$_6$alkyl-5- to 6-membered heterocyclyl, —OC(O)-5- to 6-membered heterocyclyl, —C(O)R$^{h1}$, —S(O)$_2$NR$^{w1a}$R$^{w2a}$, —S(O)$_2$R$^{y1}$, or —NR$^{z1a}$S(O)$_2$R$^{z2a}$. In some embodiments,

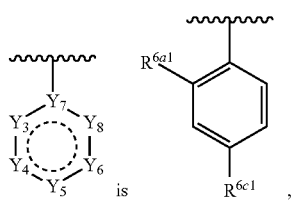

wherein $R^{6a1}$ and $R^{6c1}$ are each independently selected from the group consisting of C$_1$-C$_6$alkyl, C$_1$-C$_6$alkoxy, halo, —OH, —NR$^{p1}$R$^{q1}$, C$_6$-C$_{12}$ aryl, 3- to 10-membered heterocyclyl, 5- to 10-membered heteroaryl, —C$_1$-C$_6$alkyl-5- to 6-membered heterocyclyl, —OC(O)-5- to 6-membered heterocyclyl, —C(O)R$^{h1}$, —S(O)$_2$NR$^{w1a}$R$^{w2a}$, —S(O)$_2$R$^{y1}$, or —NR$^{z1a}$S(O)$_2$R$^{z2a}$. In some embodiments,

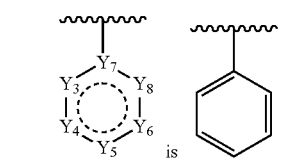

In some embodiments of Formula (B), including Formula (B-1a), (B-1b), (B-2a), (B-2b), (B-2c), (B-2d), (B-2e), (B-2f), (B-2g), (B-2h), (B-2i), (B-2j), (B-2k), (B-2l), (B-2m), and (B-2n),

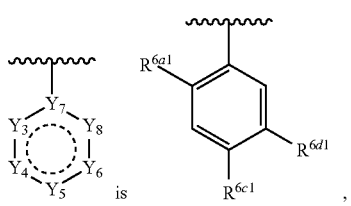

wherein one or more of $R^{6b1}$, $R^{6c1}$, and $R^{6d1}$ is selected from the group consisting of C$_1$-C$_6$alkyl, C$_1$-C$_6$haloalkyl, halo, C$_6$-C$_{12}$ aryl 3- to 10-membered heterocyclyl, and 5- to 10-membered heteroaryl. In some embodiments,

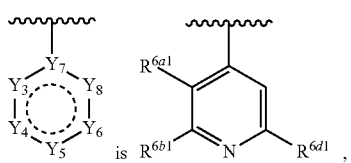

wherein one or more of $R^{6a1}$, $R^{6c1}$, and $R^{6d1}$ is selected from the group consisting of C$_1$-C$_6$alkyl, C$_1$-C$_6$haloalkyl, halo, C$_6$-C$_{12}$ aryl, 3- to 10-membered heterocyclyl, and 5- to 10-membered heteroaryl. In some embodiments,

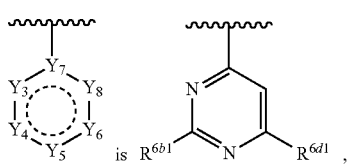

wherein one or more of $R^{6a1}$, $R^{6b1}$, and $R^{6d1}$ is selected from the group consisting of C$_1$-C$_6$alkyl, C$_1$-C$_6$haloalkyl, halo, C$_6$-C$_{12}$ aryl, 3- to 10-membered heterocyclyl, and 5- to 10-membered heteroaryl. In some embodiments, wherein one or both of $R^{6b1}$ and $R^{6d1}$ is selected from the group consisting of C$_1$-C$_6$alkyl, C$_1$-C$_6$haloalkyl, halo, C$_6$-C$_{12}$ aryl, 3- to 10-membered heterocyclyl, and 5- to 10-membered heteroaryl. In some embodiments,

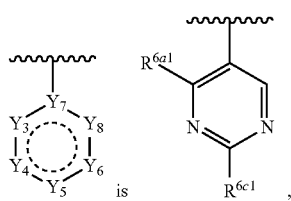

wherein one or both of $R^{6a1}$ and $R^{6c1}$ is selected from the group consisting of $C_1$-$C_6$alkyl, $C_1$-$C_6$haloalkyl, halo, $C_6$-$C_{12}$ aryl, 3- to 10-membered heterocyclyl, and 5- to 10-membered heteroaryl. In some embodiments,

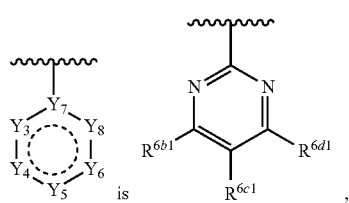

wherein one or more of $R^{6b1}$, $R^{6c1}$, and $R^{6d1}$ is selected from the group consisting of $C_1$-$C_6$alkyl, $C_1$-$C_6$haloalkyl, halo, $C_6$-$C_{12}$ aryl, 3- to 10-membered heterocyclyl, and 5- to 10-membered heteroaryl. In some embodiments

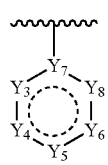

is selected from the group consisting of

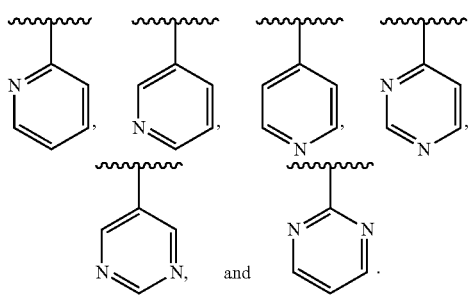

and

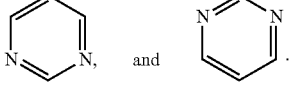

In some embodiments of Formula (B), including Formula (B-1a), (B-1b), (B-2a), (B-2b), (B-2c), (B-2d), (B-2e), (B-2f), (B-2g), (B-2h), (B-2i), (B-2j) (B-2k) (B-2l) (B-2m), and (B-2n),

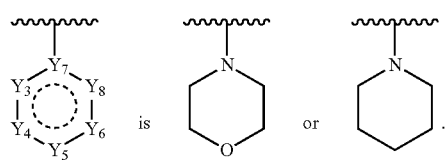

In some embodiments,

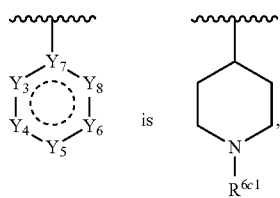

wherein $R^{6c1}$ is selected from the group consisting of hydrogen, $C_1$-$C_6$alkyl, $C_1$-$C_6$alkoxy, halo, —OH, —$NR^{p1}R^{q1}$, $C_6$-$C_{12}$ aryl, 3- to 10-membered heterocyclyl, 5- to 10-membered heteroaryl, —$C_1$-$C_6$alkyl-5- to 6-membered heterocyclyl, —OC(O)-5- to 6-membered heterocyclyl, —$C(O)R^{h1}$, —$S(O)_2NR^{w1a}R^{w2a}$, —$S(O)_2R^{y1}$, and —$NR^{z1a}S(O)_2R^{z2a}$. In certain embodiments, $R^{6c1}$ is —$C(O)OC(CH_3)_3$.

In some embodiments of Formula (B), including Formula (B-1a), (B-1b), (B-2a), (B-2b), (B-2c), (B-2d), (B-2e), (B-2f), (B-2g), (B-2h), (B-2i), (B-2j), (B-2k), (B-2l), (B-2m), and (B-2n),

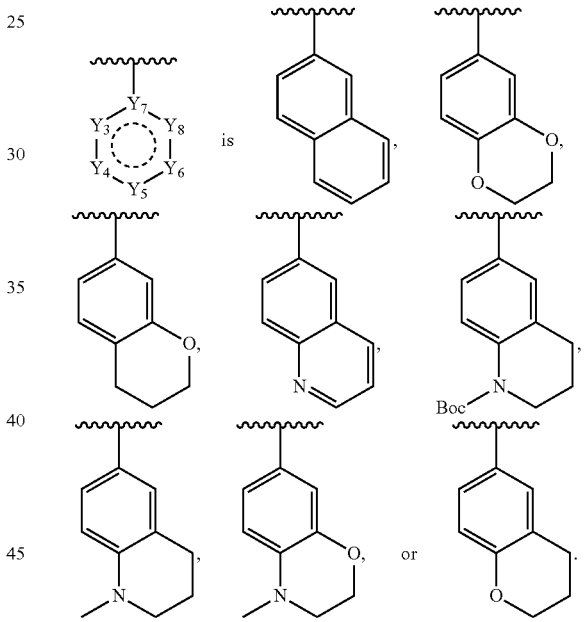

In any of the foregoing embodiments, one or more of $R^{6a1}$, $R^{6b1}$, $R^{6c1}$, and $R^{6d1}$ is selected from the group consisting of $C_1$-$C_6$alkyl, $C_1$-$C_6$haloalkyl, halo, $C_6$-$C_{12}$ aryl, 3- to 10-membered heterocyclyl, and 5- to 10-membered heteroaryl. In some embodiments, one or more of $R^{6a1}$, $R^{6b1}$, $R^{6c1}$, and $R^{6d1}$ is $C_6$-$C_{12}$ aryl, unsubstituted or substituted with one or more groups selected from the group consisting of $C_1$-$C_6$alkyl, $C_1$-$C_6$alkoxy, —OH, and $C_1$-$C_6$alkyl-OH. For instance, in some embodiments, one of $R^{6a1}$, $R^{6b1}$, $R^{6c1}$, and $R^{6d1}$ is phenyl or naphthyl. In some embodiments, one or more of $R^{6a1}$, $R^{6b1}$, $R^{6c1}$, and $R^{6d1}$ is 3- to 10-membered heterocyclyl, unsubstituted or substituted with one or more groups selected from the group consisting of $C_1$-$C_6$alkyl, $C_1$-$C_6$alkoxy, —OH, $C_1$-$C_6$alkyl-OH, =O, =S, halo, $C_3$-$C_8$cycloalkyl, —C(O)NH—$C_3$-$C_8$cycloalkyl, $C_6$-$C_{12}$ aryl, and 5- to 6-membered heterocyclyl. In some embodiments, one or more of $R^{6a1}$, $R^{6b1}$, $R^{6c1}$, and $R^{6d1}$ is 3- to 10-membered heterocyclyl, unsubstituted or substituted with one or more groups selected from the group consisting of $C_1$-$C_6$alkyl, $C_1$-$C_6$alkoxy, —OH, $C_1$-$C_6$alkyl-OH, =O, and =S. For instance, in some embodiments, one of $R^{6a1}$, $R^{6b1}$, $R^{6c1}$, and $R^{6d1}$ is pyrrolidinyl, pyrazolidinyl, imidazolidinyl, tetrahydrofuranyl, 1,3-dioxolanyl, tetrahydrothiophenyl, oxathiolanyl, sulfolanyl, piperidinyl, piperazinyl, tetrahydropyranyl, dioxanyl, thianyl, dithianyl, trithianyl, morpholinyl, thiomorpholinyl, tetrahydroquinolinyl, tetrahydroisoquinolinyl, decahydroquinolinyl, decahydroisoquinolinyl, indolinyl, isoindolinyl, tetrahydronaphthyridinyl or hexahydrobenzoimidazolyl, each independently unsubstituted or substituted with one or more groups selected from the group consisting of $C_1$-$C_6$alkyl, $C_1$-$C_6$alkoxy, —OH, $C_1$-$C_6$alkyl-OH, =O, =S, halo, $C_3$-$C_8$cycloalkyl, —C(O)NH—$C_3$-$C_8$cycloalkyl, $C_6$-$C_{12}$ aryl, and 5- to 6-membered heterocyclyl. For instance, in some embodiments, one of $R^{6a1}$, $R^{6b1}$, $R^{6c1}$, and $R^{6d1}$ is pyrrolidinyl, pyrazolidinyl, imidazolidinyl, tetrahydrofuranyl, 1,3-dioxolanyl, tetrahydrothiophenyl, oxathiolanyl, sulfolanyl, piperidinyl, piperazinyl, tetrahydropyranyl, dioxanyl, thianyl, dithianyl, trithianyl, morpholinyl, thiomorpholinyl, tetrahydroquinolinyl, tetrahydroisoquinolinyl, decahydroquinolinyl, decahydroisoquinolinyl, indolinyl, isoindolinyl, tetrahydronaphthyridinyl or hexahydrobenzoimidazolyl, each independently unsubstituted or substituted with one or more groups selected from the group consisting of $C_1$-$C_6$alkyl, $C_1$-$C_6$alkoxy, —OH, $C_1$-$C_6$alkyl-OH, =O, and =S.

In some embodiments of Formula (B), including Formula (B-1a), (B-1b), (B-2a), (B-2b), (B-2c), (B-2d), (B-2e), (B-2f), (B-2g), (B-2h), (B-2i), (B-2j), (B-2k), (B-2l), (B-2m), and (B-2n), one of $R^{6a1}$, $R^{6b1}$, $R^{6c1}$, and $R^{6d1}$ is selected from the group consisting of $C_1$-$C_6$alkyl, $C_1$-$C_6$haloalkyl, halo, $C_6$-$C_{12}$ aryl, 3- to 10-membered heterocyclyl, and 5- to 10-membered heteroaryl. In certain embodiments, one of $R^{6a1}$, $R^{6b1}$, $R^{6c1}$, and $R^{6d1}$ is selected from the group consisting of methyl, ethyl, F, Cl, —$CF_3$, pyrrolidinyl, piperidinyl, morpholinyl, piperazinyl, pyrazolyl, and triazolyl. In certain embodiments, one of $R^{6a1}$, $R^{6b1}$, $R^{6c1}$, and $R^{6d1}$ is selected from the group consisting of pyrrolidinyl, piperidinyl, morpholinyl, piperazinyl, pyrazolyl, and triazolyl, each optionally substituted with one or more groups selected from the group consisting of $C_1$-$C_6$alkyl, $C_1$-$C_6$alkoxy, —OH, $C_1$-$C_6$alkyl-OH, =O, =S, halo, $C_3$-$C_8$cycloalkyl, —C(O)NH—$C_3$-$C_8$cycloalkyl, $C_6$-$C_{12}$ aryl, and 5- to 6-membered heterocyclyl. In certain embodiments, one of $R^{6a1}$, $R^{6b1}$, $R^{6c1}$, and $R^{6d1}$ is selected from the group consisting of pyrrolidinyl, piperidinyl, morpholinyl, piperazinyl, pyrazolyl, and triazolyl, each optionally substituted with one or more groups selected from the group consisting of $C_1$-$C_6$alkyl, $C_1$-$C_6$alkoxy, —OH, $C_1$-$C_6$alkyl-OH, =O, and =S. In some embodiments, two or three of $R^{6a1}$, $R^{6b1}$, $R^{6c1}$, and $R^{6d1}$ is selected from the group consisting of methyl, ethyl, F, Cl, —$CF_3$, pyrrolidinyl, piperidinyl, morpholinyl, piperazinyl, pyrazolyl, and triazolyl. In other embodiments, $R^{6a1}$, $R^{6b1}$, $R^{6c1}$, and $R^{6d1}$ are each H.

In some embodiments of Formula (B), including Formula (B-1a), (B-1b), (B-2a), (B-2b), (B-2c), (B-2d), (B-2e), (B-2f), (B-2g), (B-2h), (B-2i), (B-2j), (B-2k), (B-2l), (B-2m), and (B-2n), one of $R^{6a1}$, $R^{6b1}$, $R^{6c1}$, and $R^{6d1}$ is indolinyl optionally substituted with one or more groups selected from the group consisting of $C_1$-$C_6$alkyl, $C_1$-$C_6$alkoxy, —OH, $C_1$-$C_6$alkyl-OH, =O, =S, halo, $C_3$-$C_8$cycloalkyl, —C(O)NH—$C_3$-$C_8$cycloalkyl, $C_6$-$C_{12}$ aryl, and 5- to 6-membered heterocyclyl. In some embodiments, one of $R^{6a1}$, $R^{6b1}$, $R^{6c1}$, and $R^{6d1}$ is indolinyl optionally substituted with one or more independently selected $C_1$-$C_6$alkyl and halo groups. In some embodiments, one of $R^{6a1}$, $R^{6b1}$, $R^{6c1}$, and $R^{6d1}$ is 3,3-dimethylindolin-1-yl or 5-fluoro-3,3-dimethylindolin-1-yl. In some embodiments, $R^{6c1}$ is 3,3-dimethylindolin-1-yl or 5-fluoro-3,3-dimethylindolin-1-yl. In some embodiments, one of $R^{6a1}$, $R^{6b1}$, $R^{6c1}$, and $R^{6d1}$ is piperazinyl optionally substituted with phenyl. In some embodiments, one of $R^{6a}$, $R^{6b1}$, $R^{6c1}$, and $R^{6d1}$ is 4-phenylpiperazinyl. In some embodiments, $R^{6c1}$ is 4-phenylpiperazinyl.

In some embodiments, provided herein are compounds and salts thereof described in Table 1B.

TABLE 1B

| Compound No. | Chemical Structure | Chemical Name |
| --- | --- | --- |
| B1 | 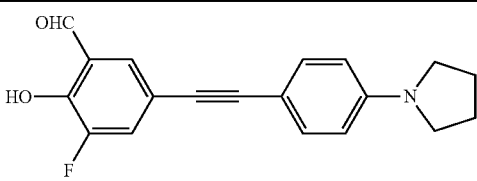 | 3-fluoro-2-hydroxy-5-((4-(pyrrolidin-1-yl)phenyl)ethynyl)benzaldehyde |
| B2 | 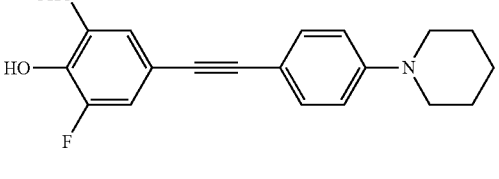 | 3-fluoro-2-hydroxy-5-((4-(piperidin-1-yl)phenyl)ethynyl)benzaldehyde |
| B3 | 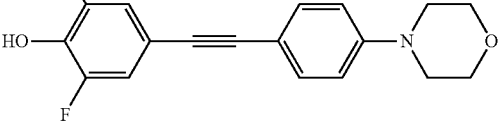 | 3-fluoro-2-hydroxy-5-((4-morpholinophenyl)ethynyl)benzaldehyde |

TABLE 1B-continued

| Compound No. | Chemical Structure | Chemical Name |
|---|---|---|
| B4 | 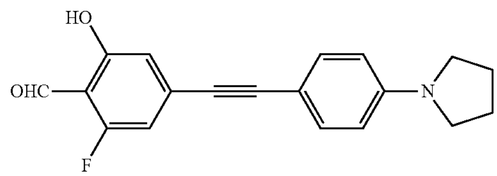 [SMILES: O=Cc1c(O)cc(C#Cc2ccc(N3CCCC3)cc2)cc1F] | 2-fluoro-6-hydroxy-4-((4-(pyrrolidin-1-yl)phenyl)ethynyl)benzaldehyde |
| B5 | 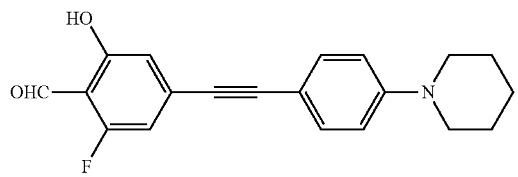 [SMILES: O=Cc1c(O)cc(C#Cc2ccc(N3CCCCC3)cc2)cc1F] | 2-fluoro-6-hydroxy-4-((4-(piperidin-1-yl)phenyl)ethynyl)benzaldehyde |
| B6 | 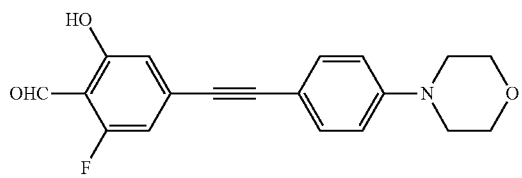 [SMILES: O=Cc1c(O)cc(C#Cc2ccc(N3CCOCC3)cc2)cc1F] | 2-fluoro-6-hydroxy-4-((4-morpholinophenyl)ethynyl)benzaldehyde |
| B7 | 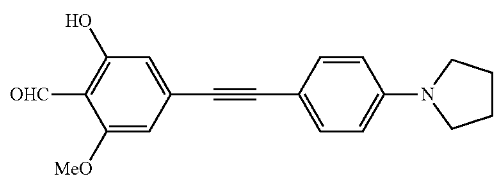 [SMILES: COc1cc(C#Cc2ccc(N3CCCC3)cc2)cc(O)c1C=O] | 2-hydroxy-6-methoxy-4-((4-(pyrrolidin-1-yl)phenyl)ethynyl)benzaldehyde |
| B8 | 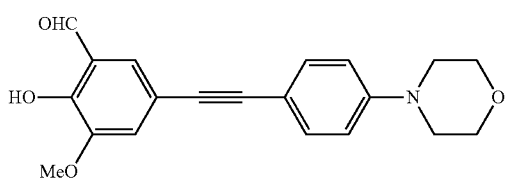 [SMILES: COc1cc(C#Cc2ccc(N3CCOCC3)cc2)cc(C=O)c1O] | 2-hydroxy-3-methoxy-5-((4-morpholinophenyl)ethynyl)benzaldehyde |
| B9 | 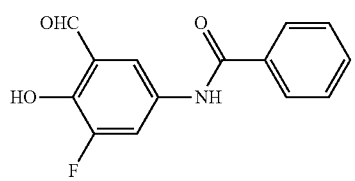 [SMILES: O=Cc1cc(NC(=O)c2ccccc2)cc(F)c1O] | N-(3-fluoro-5-formyl-4-hydroxyphenyl)benzamide |
| B10 | 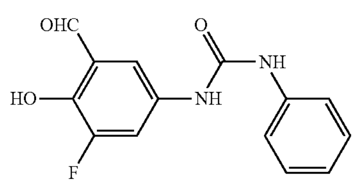 [SMILES: O=Cc1cc(NC(=O)Nc2ccccc2)cc(F)c1O] | 1-(3-fluoro-5-formyl-4-hydroxyphenyl)-3-phenylurea |
| B11 | 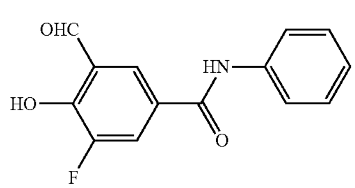 [SMILES: O=Cc1cc(C(=O)Nc2ccccc2)cc(F)c1O] | 3-fluoro-5-formyl-4-hydroxy-N-phenylbenzamide |

TABLE 1B-continued

| Compound No. | Chemical Structure | Chemical Name |
|---|---|---|
| B12 | 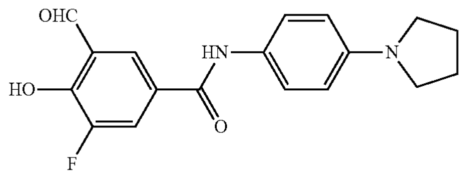 [SMILES: O=Cc1cc(C(=O)Nc2ccc(N3CCCC3)cc2)cc(F)c1O] | 3-fluoro-5-formyl-4-hydroxy-N-(4-(pyrrolidin-1-yl)phenyl)benzamide |
| B13 | 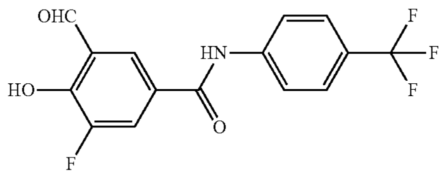 [SMILES: O=Cc1cc(C(=O)Nc2ccc(C(F)(F)F)cc2)cc(F)c1O] | 3-fluoro-5-formyl-4-hydroxy-N-(4-(trifluoromethyl)phenyl)benzamide |
| B14 | 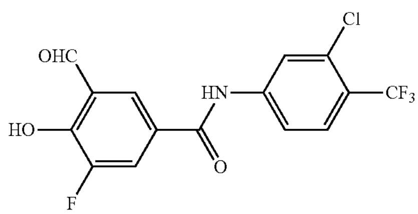 [SMILES: O=Cc1cc(C(=O)Nc2ccc(C(F)(F)F)c(Cl)c2)cc(F)c1O] | N-(3-chloro-4-(trifluoromethyl)phenyl)-3-fluoro-5-formyl-4-hydroxybenzamide |
| B15 | 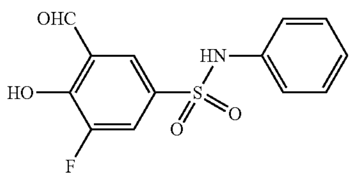 [SMILES: O=Cc1cc(S(=O)(=O)Nc2ccccc2)cc(F)c1O] | 3-fluoro-5-formyl-4-hydroxy-N-phenylbenzenesulfonamide |
| B16 | 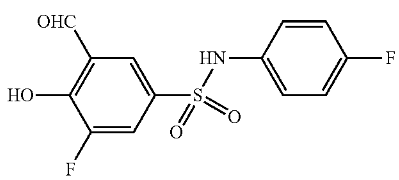 [SMILES: O=Cc1cc(S(=O)(=O)Nc2ccc(F)cc2)cc(F)c1O] | 3-fluoro-N-(4-fluorophenyl)-5-formyl-4-hydroxybenzenesulfonamide |
| B17 | 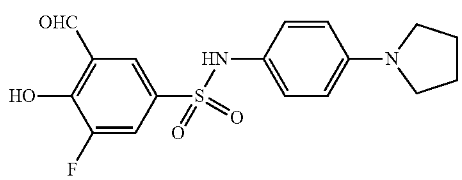 [SMILES: O=Cc1cc(S(=O)(=O)Nc2ccc(N3CCCC3)cc2)cc(F)c1O] | 3-fluoro-5-formyl-4-hydroxy-N-(4-(pyrrolidin-1-yl)phenyl)benzenesulfonamide |
| B18 | 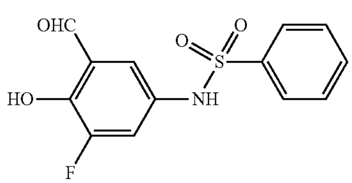 [SMILES: O=Cc1cc(NS(=O)(=O)c2ccccc2)cc(F)c1O] | N-(3-fluoro-5-formyl-4-hydroxyphenyl)benzenesulfonamide |
| B19 | 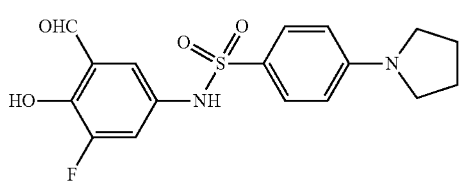 [SMILES: O=Cc1cc(NS(=O)(=O)c2ccc(N3CCCC3)cc2)cc(F)c1O] | N-(3-fluoro-5-formyl-4-hydroxyphenyl)-4-(pyrrolidin-1-yl)benzenesulfonamide |

TABLE 1B-continued

| Compound No. | Chemical Structure | Chemical Name |
|---|---|---|
| B20 | 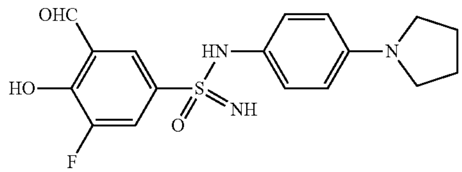 [SMILES: N=S(=O)(Nc1ccc(N2CCCC2)cc1)c1cc(F)c(O)c(C=O)c1] | 3-fluoro-5-formyl-4-hydroxy-N-(4-(pyrrolidin-1-yl)phenyl)benzenesulfonimidamide |
| B21 | 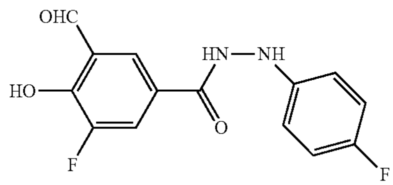 [SMILES: O=Cc1cc(C(=O)NNc2ccc(F)cc2)cc(F)c1O] | 3-fluoro-N'-(4-fluorophenyl)-5-formyl-4-hydroxybenzohydrazide |
| B22 | 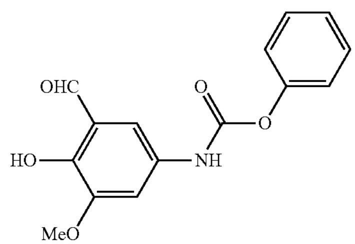 [SMILES: COc1cc(NC(=O)Oc2ccccc2)cc(C=O)c1O] | phenyl(3-formyl-4-hydroxy-5-methoxyphenyl)carbamate |
| B23 | 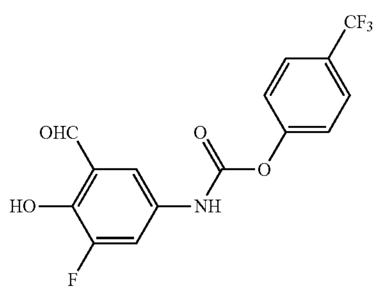 [SMILES: O=Cc1cc(NC(=O)Oc2ccc(C(F)(F)F)cc2)cc(F)c1O] | 4-(trifluoromethyl)phenyl(3-fluoro-5-formyl-4-hydroxyphenyl)carbamate |
| B24 | 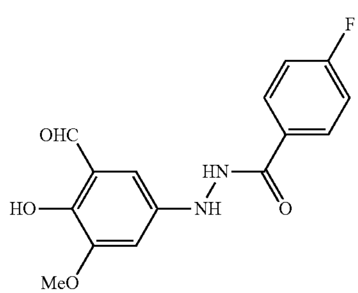 [SMILES: COc1cc(NNC(=O)c2ccc(F)cc2)cc(C=O)c1O] | 4-fluoro-N'-(3-formyl-4-hydroxy-5-methoxyphenyl)benzohydrazide |
| B25 | 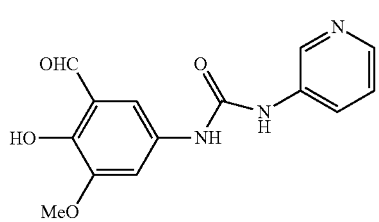 [SMILES: COc1cc(NC(=O)Nc2cccnc2)cc(C=O)c1O] | 1-(3-formyl-4-hydroxy-5-methoxyphenyl)-3-(pyridin-3-yl)urea |

TABLE 1B-continued

| Compound No. | Chemical Structure | Chemical Name |
|---|---|---|
| B26 | 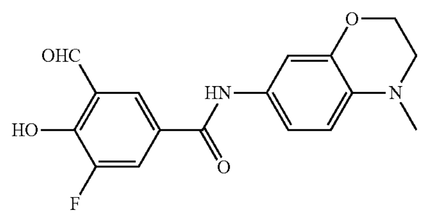 [SMILES: CN1CCOc2cc(NC(=O)c3cc(F)c(O)c(C=O)c3)ccc21] | 3-fluoro-5-formyl-4-hydroxy-N-(4-methyl-3,4-dihydro-2H-benzo[b][1,4]oxazin-7-yl)benzamide |
| B27 | 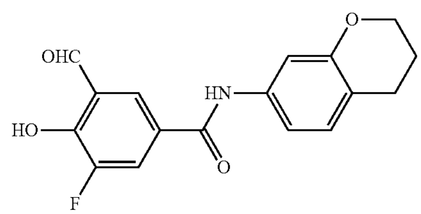 [SMILES: O=Cc1cc(C(=O)Nc2ccc3c(c2)OCCC3)cc(F)c1O] | N-(chroman-7-yl)-3-fluoro-5-formyl-4-hydroxybenzamide |
| B28 | 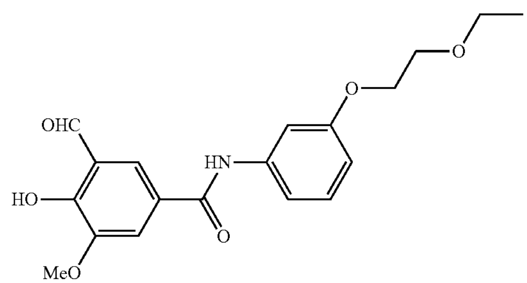 [SMILES: CCOCCOc1cccc(NC(=O)c2cc(C=O)c(O)c(OC)c2)c1] | N-(3-(2-ethoxyethoxy)phenyl)-3-formyl-4-hydroxy-5-methoxybenzamide |
| B29 | 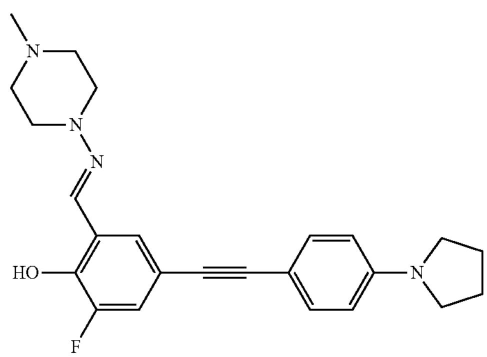 [SMILES: CN1CCN(/N=C/c2cc(C#Cc3ccc(N4CCCC4)cc3)cc(F)c2O)CC1] | 2-fluoro-6-(((4-methylpiperazin-1-yl)imino)methyl)-4-((4-(pyrrolidin-1-yl)phenyl)ethynyl)phenol |
| B30 | 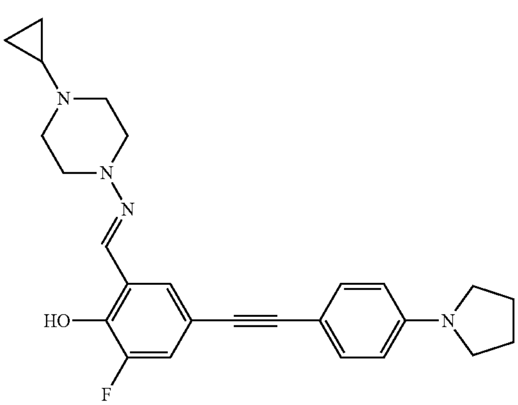 [SMILES: Oc1c(F)cc(C#Cc2ccc(N3CCCC3)cc2)cc1/C=N/N1CCN(C2CC2)CC1] | 2-(((4-cyclopropylpiperazin-1-yl)imino)methyl)-6-fluoro-4-((4-(pyrrolidin-1-yl)phenyl)ethynyl)phenol |

TABLE 1B-continued

| Compound No. | Chemical Structure | Chemical Name |
|---|---|---|
| B31 | 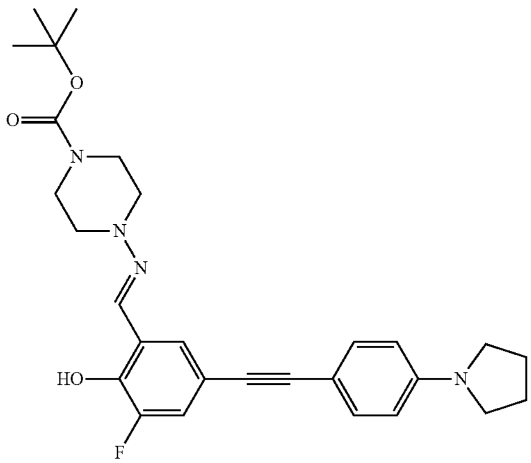 [SMILES: CC(C)(C)OC(=O)N1CCN(/N=C/c2cc(C#Cc3ccc(N4CCCC4)cc3)cc(F)c2O)CC1] | tert-butyl 4-((3-fluoro-2-hydroxy-5-((4-(pyrrolidin-1-yl)phenyl)ethynyl)benzylidene)amino)piperazine-1-carboxylate |
| B32 | 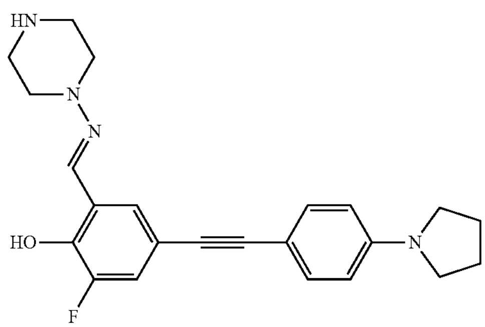 [SMILES: Oc1c(F)cc(C#Cc2ccc(N3CCCC3)cc2)cc1/C=N/N1CCNCC1] | 2-fluoro-6-((piperazin-1-ylimino)methyl)-4-((4-(pyrrolidin-1-yl)phenyl)ethynyl)phenol |
| B33 | 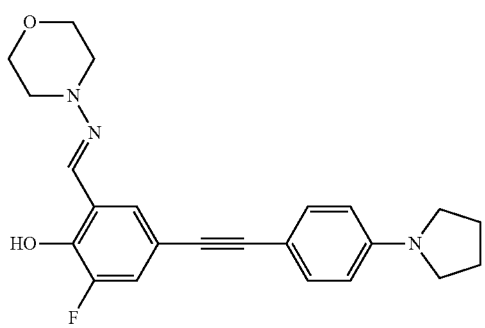 [SMILES: Oc1c(F)cc(C#Cc2ccc(N3CCCC3)cc2)cc1/C=N/N1CCOCC1] | 2-fluoro-6-((morpholinoimino)methyl)-4-((4-(pyrrolidin-1-yl)phenyl)ethynyl)phenol |
| B34 | 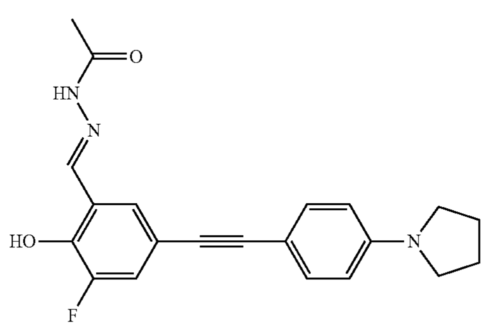 [SMILES: CC(=O)N/N=C/c1cc(C#Cc2ccc(N3CCCC3)cc2)cc(F)c1O] | N'-(3-fluoro-2-hydroxy-5-((4-(pyrrolidin-1-yl)phenyl)ethynyl)benzylidene)acetohydrazide |

TABLE 1B-continued

| Compound No. | Chemical Structure | Chemical Name |
|---|---|---|
| B35 | 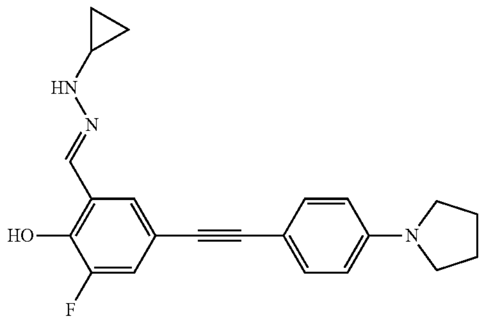 [SMILES: Oc1c(F)cc(C#Cc2ccc(N3CCCC3)cc2)cc1/C=N/NC1CC1] | 2-((2-cyclopropylhydrazono)methyl)-6-fluoro-4-((4-(pyrrolidin-1-yl)phenyl)ethynyl)phenol |
| B36 | 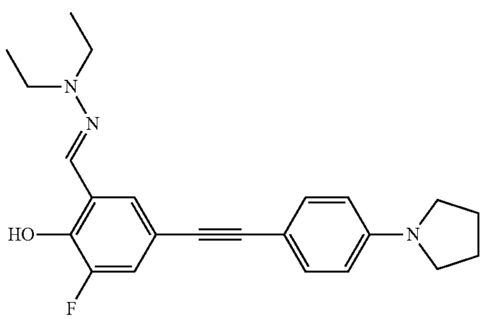 [SMILES: CCN(CC)/N=C/c1cc(C#Cc2ccc(N3CCCC3)cc2)cc(F)c1O] | (2-((2,2-diethylhydrazono)methyl)-6-fluoro-4-((4-(pyrrolidin-1-yl)phenyl)ethynyl)phenol |
| B37 | 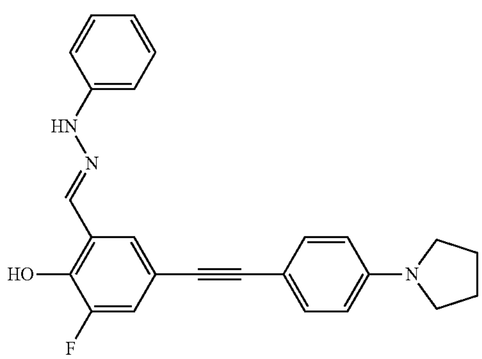 [SMILES: Oc1c(F)cc(C#Cc2ccc(N3CCCC3)cc2)cc1/C=N/Nc1ccccc1] | 2-fluoro-6-((2-phenylhydrazono)methyl)-4-((4-(pyrrolidin-1-yl)phenyl)ethynyl)phenol |
| B38 | 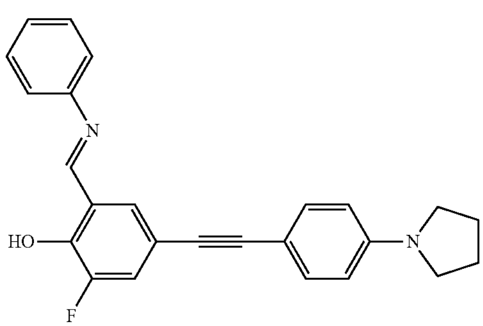 [SMILES: Oc1c(F)cc(C#Cc2ccc(N3CCCC3)cc2)cc1/C=N/c1ccccc1] | 2-fluoro-6-((phenylimino)methyl)-4-((4-(pyrrolidin-1-yl)phenyl)ethynyl)phenol |

TABLE 1B-continued

| Compound No. | Chemical Structure | Chemical Name |
|---|---|---|
| B39 | 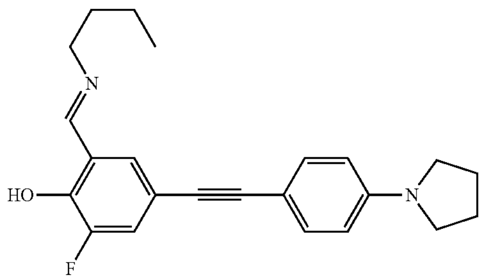 [SMILES: CCCC/N=C/c1cc(C#Cc2ccc(N3CCCC3)cc2)cc(F)c1O] | 2-((butylimino)methyl)-6-fluoro-4-((4-(pyrrolidin-1-yl)phenyl)ethynyl)phenol |
| B40 | 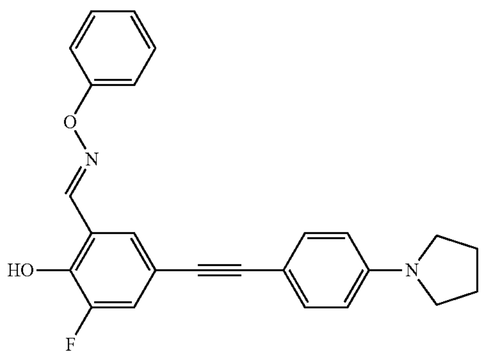 [SMILES: Oc1c(F)cc(C#Cc2ccc(N3CCCC3)cc2)cc1/C=N/Oc1ccccc1] | 3-fluoro-2-hydroxy-5-((4-(pyrrolidin-1-yl)phenyl)ethynyl)benzaldehyde O-phenyl oxime |
| B41 | 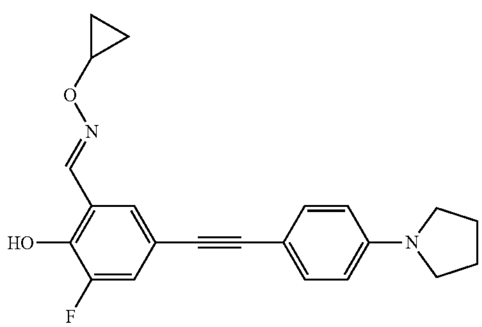 [SMILES: Oc1c(F)cc(C#Cc2ccc(N3CCCC3)cc2)cc1/C=N/OC1CC1] | 3-fluoro-2-hydroxy-5-((4-(pyrrolidin-1-yl)phenyl)ethynyl)benzaldehyde O-cyclopropyl oxime |
| B42 | 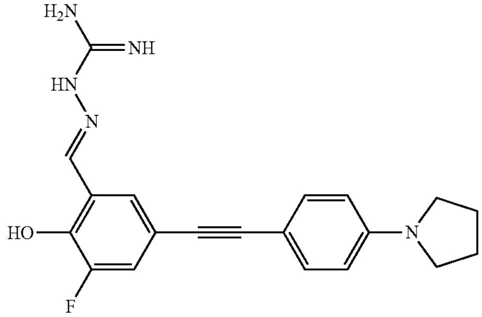 [SMILES: N=C(N)N/N=C/c1cc(C#Cc2ccc(N3CCCC3)cc2)cc(F)c1O] | 2-(3-fluoro-2-hydroxy-5-((4-(pyrrolidin-1-yl)phenyl)ethynyl)benzylidene)hydrazine-1-carboximidamide |

TABLE 1B-continued

| Compound No. | Chemical Structure | Chemical Name |
|---|---|---|
| B43 | 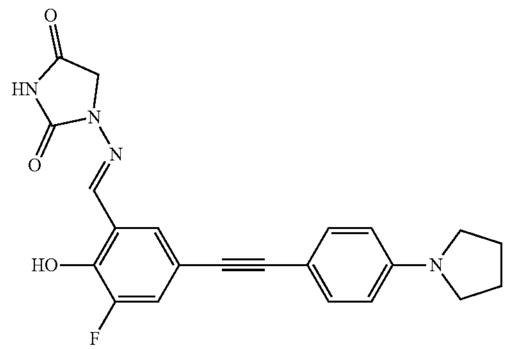 [SMILES: O=C1CN(/N=C/c2cc(C#Cc3ccc(N4CCCC4)cc3)cc(F)c2O)C(=O)N1] | 1-((3-fluoro-2-hydroxy-5-((4-(pyrrolidin-1-yl)phenyl)ethynyl)benzylidene)amino)imidazolidine-2,4-dione |
| B44 | 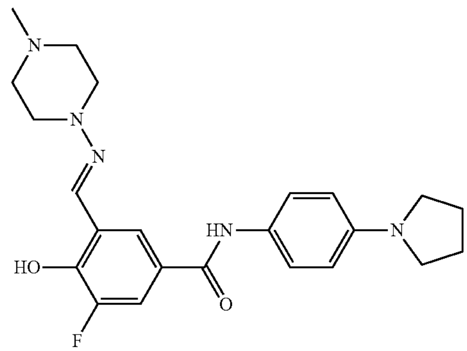 [SMILES: CN1CCN(/N=C/c2cc(C(=O)Nc3ccc(N4CCCC4)cc3)cc(F)c2O)CC1] | 3-fluoro-4-hydroxy-5-(((4-methylpiperazin-1-yl)imino)methyl)-N-(4-(pyrrolidin-1-yl)phenyl)benzamide |
| B45 | 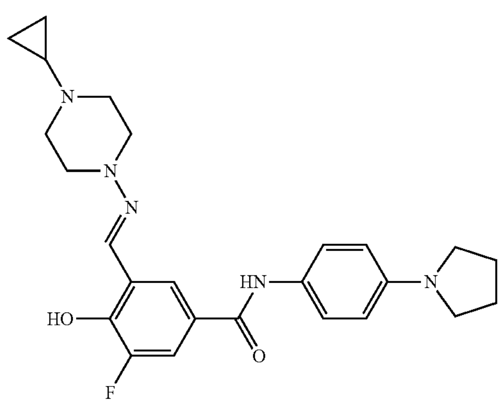 [SMILES: O=C(Nc1ccc(N2CCCC2)cc1)c1cc(F)c(O)c(/C=N/N2CCN(C3CC3)CC2)c1] | 3-(((4-cyclopropylpiperazin-1-yl)imino)methyl)-5-fluoro-4-hydroxy-N-(4-(pyrrolidin-1-yl)phenyl)benzamide |
| B46 | 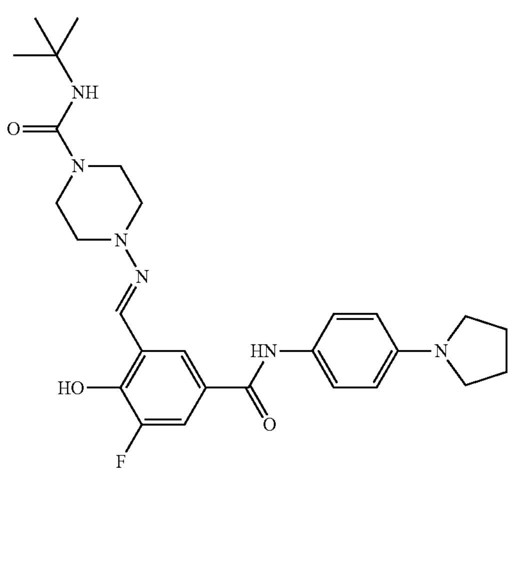 [SMILES: CC(C)(C)NC(=O)N1CCN(/N=C/c2cc(C(=O)Nc3ccc(N4CCCC4)cc3)cc(F)c2O)CC1] | N-(tert-butyl)-4-((3-fluoro-2-hydroxy-5-((4-(pyrrolidin-1-yl)phenyl)carbamoyl)benzylidene)amino)piperazine-1-carboxamide |

TABLE 1B-continued

| Compound No. | Chemical Structure | Chemical Name |
|---|---|---|
| B47 | 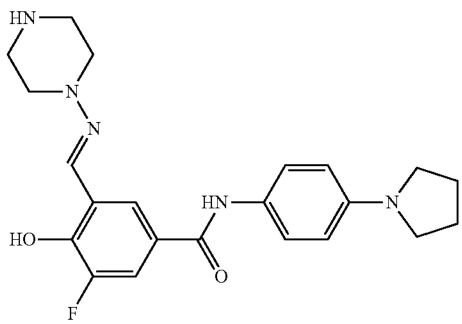 [SMILES: O=C(Nc1ccc(N2CCCC2)cc1)c1cc(F)c(O)c(/C=N/N2CCNCC2)c1] | 3-fluoro-4-hydroxy-5-((piperazin-1-ylimino)methyl)-N-(4-(pyrrolidin-1-yl)phenyl)benzamide |
| B48 | 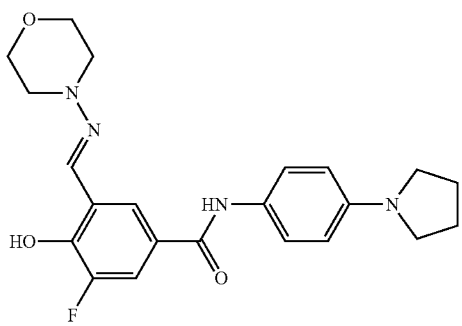 [SMILES: O=C(Nc1ccc(N2CCCC2)cc1)c1cc(F)c(O)c(/C=N/N2CCOCC2)c1] | 3-fluoro-4-hydroxy-5-((morpholinoimino)methyl)-N-(4-(pyrrolidin-1-yl)phenyl)benzamide |
| B49 | 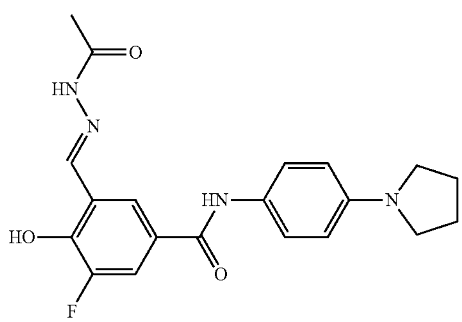 [SMILES: CC(=O)N/N=C/c1cc(C(=O)Nc2ccc(N3CCCC3)cc2)cc(F)c1O] | 3-((2-acetylhydrazono)methyl)-5-fluoro-4-hydroxy-N-(4-(pyrrolidin-1-yl)phenyl)benzamide |
| B50 | 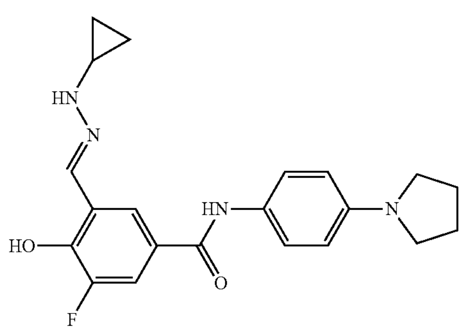 [SMILES: O=C(Nc1ccc(N2CCCC2)cc1)c1cc(F)c(O)c(/C=N/NC2CC2)c1] | 3-((2-cyclopropylhydrazono)methyl)-5-fluoro-4-hydroxy-N-(4-(pyrrolidin-1-yl)phenyl)benzamide |

TABLE 1B-continued

| Compound No. | Chemical Structure | Chemical Name |
|---|---|---|
| B51 | 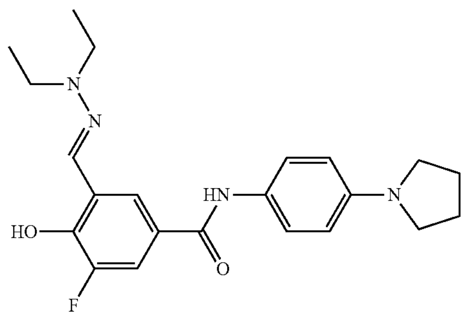 [SMILES: CCN(CC)/N=C/c1cc(C(=O)Nc2ccc(N3CCCC3)cc2)cc(F)c1O] | 3-((2,2-diethylhydrazono)methyl)-5-fluoro-4-hydroxy-N-(4-(pyrrolidin-1-yl)phenyl)benzamide |
| B52 | 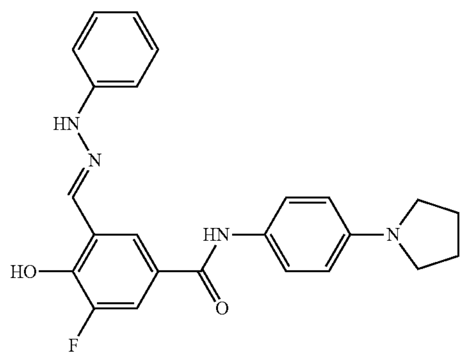 [SMILES: O=C(Nc1ccc(N2CCCC2)cc1)c1cc(F)c(O)c(/C=N/Nc2ccccc2)c1] | 3-fluoro-4-hydroxy-5-((2-phenylhydrazono)methyl)-N-(4-(pyrrolidin-1-yl)phenyl)benzamide |
| B53 | 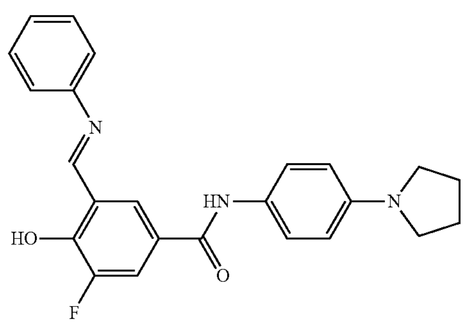 [SMILES: O=C(Nc1ccc(N2CCCC2)cc1)c1cc(F)c(O)c(/C=N/c2ccccc2)c1] | 3-fluoro-4-hydroxy-5-((phenylimino)methyl)-N-(4-(pyrrolidin-1-yl)phenyl)benzamide |
| B54 | 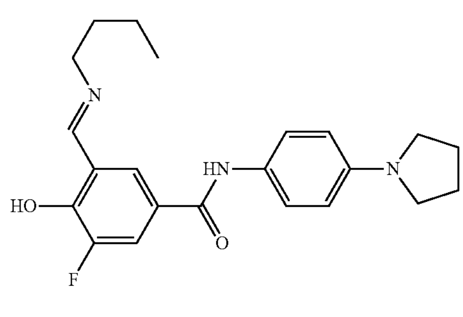 [SMILES: CCCC/N=C/c1cc(C(=O)Nc2ccc(N3CCCC3)cc2)cc(F)c1O] | 3-((butylimino)methyl)-5-fluoro-4-hydroxy-N-(4-(pyrrolidin-1-yl)phenyl)benzamide |

TABLE 1B-continued

| Compound No. | Chemical Structure | Chemical Name |
|---|---|---|
| B55 | 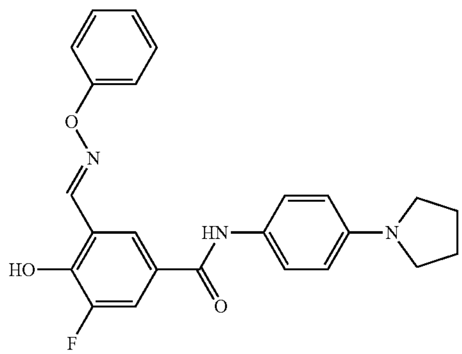 [SMILES: O=C(Nc1ccc(N2CCCC2)cc1)c1cc(F)c(O)c(/C=N/Oc2ccccc2)c1] | 3-fluoro-4-hydroxy-5-((phenoxyimino)methyl)-N-(4-(pyrrolidin-1-yl)phenyl)benzamide |
| B56 | 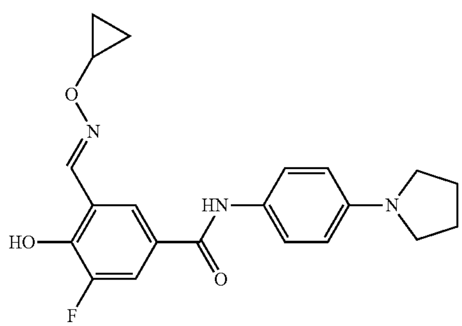 [SMILES: O=C(Nc1ccc(N2CCCC2)cc1)c1cc(F)c(O)c(/C=N/OC2CC2)c1] | 3-((cyclopropoxyimino)methyl)-5-fluoro-4-hydroxy-N-(4-(pyrrolidin-1-yl)phenyl)benzamide |
| B57 | 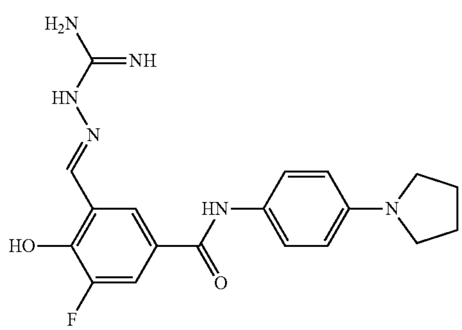 [SMILES: N=C(N)N/N=C/c1cc(C(=O)Nc2ccc(N3CCCC3)cc2)cc(F)c1O] | 3-((2-carbamimidoylhydrazono)methyl)-5-fluoro-4-hydroxy-N-(4-(pyrrolidin-1-yl)phenyl)benzamide |
| B58 | 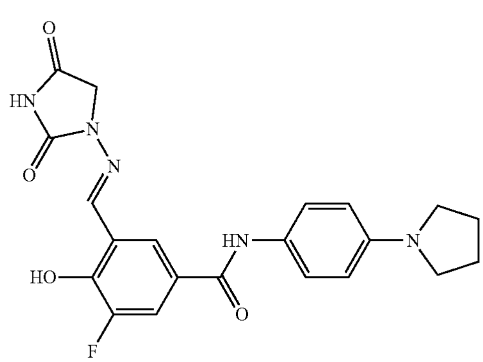 [SMILES: O=C1CN(/N=C/c2cc(C(=O)Nc3ccc(N4CCCC4)cc3)cc(F)c2O)C(=O)N1] | 3-(((2,4-dioxoimidazolidin-1-yl)imino)methyl)-5-fluoro-4-hydroxy-N-(4-(pyrrolidin-1-yl)phenyl)benzamide |
| B59 | 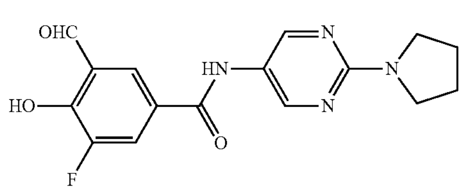 | 3-fluoro-5-formyl-4-hydroxy-N-(2-(pyrrolidin-1-yl)pyrimidin-5-yl)benzamide |

TABLE 1B-continued

| Compound No. | Chemical Structure | Chemical Name |
|---|---|---|
| B60 | 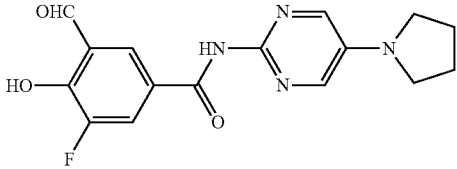 | 3-fluoro-5-formyl-4-hydroxy-N-(5-(pyrrolidin-1-yl)pyrimidin-2-yl)benzamide |
| B61 | 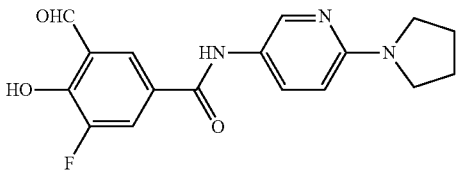 [SMILES: O=Cc1cc(C(=O)Nc2ccc(N3CCCC3)nc2)cc(F)c1O] | 3-fluoro-5-formyl-4-hydroxy-N-(6-(pyrrolidin-1-yl)pyridin-3-yl)benzamide |
| B62 | 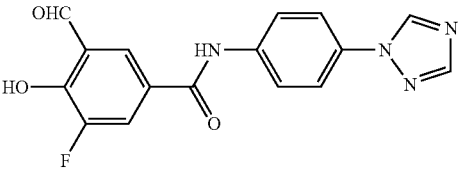 [SMILES: O=Cc1cc(C(=O)Nc2ccc(-n3cncn3)cc2)cc(F)c1O] | N-(4-(1H-1,2,4-triazol-1-yl)phenyl)-3-fluoro-5-formyl-4-hydroxybenzamide |
| B63 | 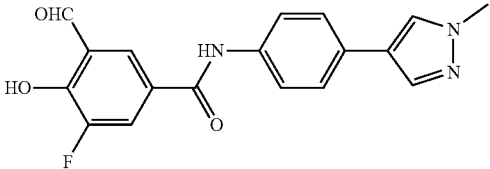 [SMILES: Cn1cc(-c2ccc(NC(=O)c3cc(F)c(O)c(C=O)c3)cc2)cn1] | 3-fluoro-5-formyl-4-hydroxy-N-(4-(1-methyl-1H-pyrazol-4-yl)phenyl)benzamide |
| B64 | 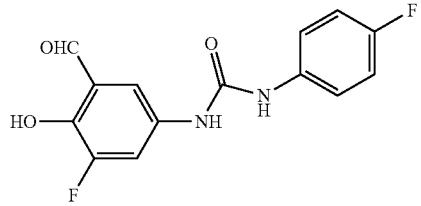 [SMILES: O=Cc1cc(NC(=O)Nc2ccc(F)cc2)cc(F)c1O] | 1-(3-fluoro-5-formyl-4-hydroxyphenyl)-3-(4-fluorophenyl)urea |
| B65 | 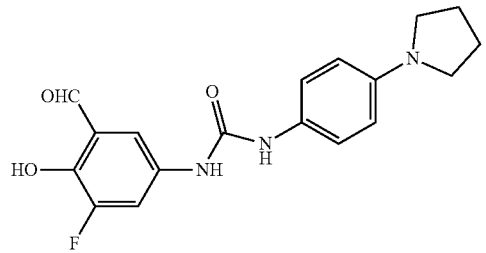 [SMILES: O=Cc1cc(NC(=O)Nc2ccc(N3CCCC3)cc2)cc(F)c1O] | 1-(3-fluoro-5-formyl-4-hydroxyphenyl)-3-(4-(pyrrolidin-1-yl)phenyl)urea |
| B66 | 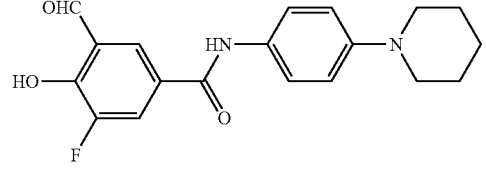 [SMILES: O=Cc1cc(C(=O)Nc2ccc(N3CCCCC3)cc2)cc(F)c1O] | 3-fluoro-5-formyl-4-hydroxy-N-(4-(piperidin-1-yl)phenyl)benzamide |
| B67 | 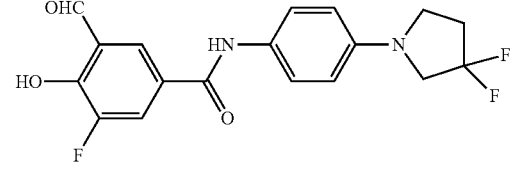 [SMILES: O=Cc1cc(C(=O)Nc2ccc(N3CCC(F)(F)C3)cc2)cc(F)c1O] | N-(4-(3,3-difluoropyrrolidin-1-yl)phenyl)-3-fluoro-5-formyl-4-hydroxybenzamide |

TABLE 1B-continued

| Compound No. | Chemical Structure | Chemical Name |
|---|---|---|
| B68 | 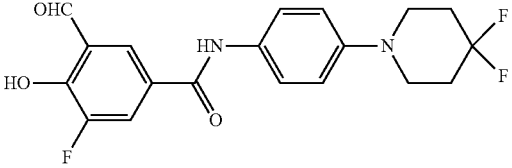 [SMILES: O=Cc1cc(C(=O)Nc2ccc(N3CCC(F)(F)CC3)cc2)cc(F)c1O] | N-(4-(4,4-difluoropiperidin-1-yl)phenyl)-3-fluoro-5-formyl-4-hydroxybenzamide |
| B69 | 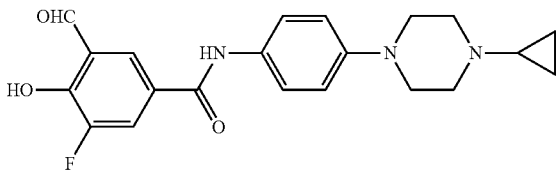 [SMILES: O=Cc1cc(C(=O)Nc2ccc(N3CCN(C4CC4)CC3)cc2)cc(F)c1O] | N-(4-(4-cyclopropylpiperazin-1-yl)phenyl)-3-fluoro-5-formyl-4-hydroxybenzamide |
| B70 | 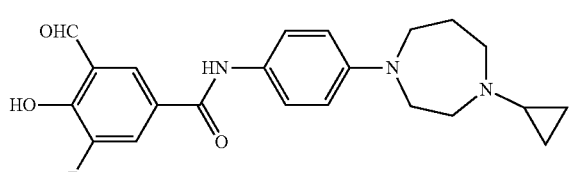 | N-(4-(4-cyclopropyl-1,4-diazepan-1-yl)phenyl)-3-fluoro-5-formyl-4-hydroxybenzamide |
| B71 | 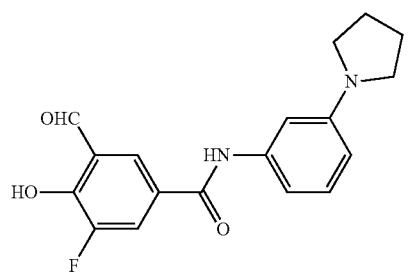 [SMILES: O=Cc1cc(C(=O)Nc2cccc(N3CCCC3)c2)cc(F)c1O] | 3-fluoro-5-formyl-4-hydroxy-N-(3-(pyrrolidin-1-yl)phenyl)benzamide |
| B72 | 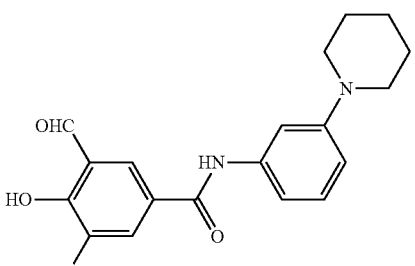 | 3-fluoro-5-formyl-4-hydroxy-N-(3-(piperidin-1-yl)phenyl)benzamide |
| B73 | 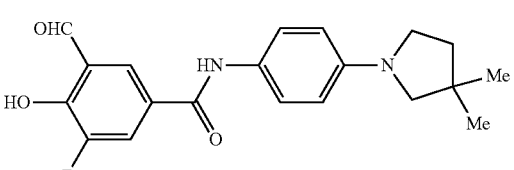 | N-(4-(3,3-dimethylpyrrolidin-1-yl)phenyl)-3-fluoro-5-formyl-4-hydroxybenzamide |
| B74 | 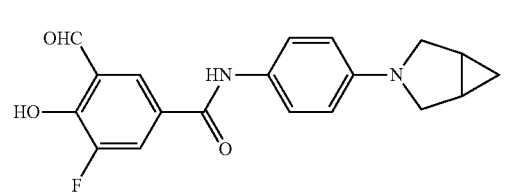 [SMILES: O=Cc1cc(C(=O)Nc2ccc(N3CC4CC4C3)cc2)cc(F)c1O] | N-(4-(3-azabicyclo[3.1.0]hexan-3-yl)phenyl)-3-fluoro-5-formyl-4-hydroxybenzamide |

TABLE 1B-continued

| Compound No. | Chemical Structure | Chemical Name |
|---|---|---|
| B75 | 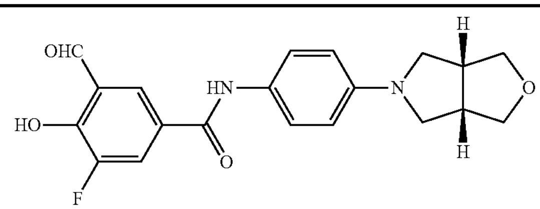 | 3-fluoro-5-formyl-4-hydroxy-N-(4-((3aR,6aS)-tetrahydro-1H-furo[3,4-c]pyrrol-5(3H)-yl)phenyl)benzamide |
| B76 | 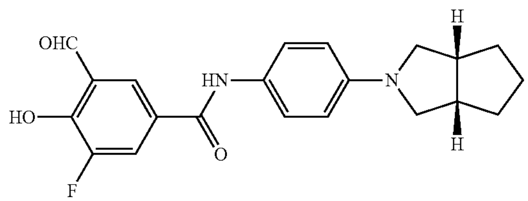 [SMILES: O=Cc1cc(C(=O)Nc2ccc(N3C[C@H]4CCC[C@H]4C3)cc2)cc(F)c1O] | 3-fluoro-5-formyl-N-(4-((3aR,6aS)-hexahydrocyclopenta[c]pyrrol-2(1H)-yl)phenyl)-4-hydroxybenzamide |
| B77 | 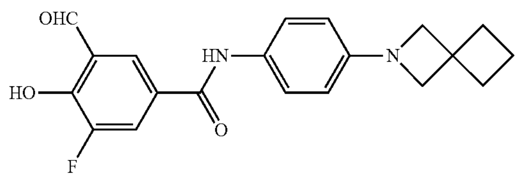 [SMILES: O=Cc1cc(C(=O)Nc2ccc(N3CC4(CCC4)C3)cc2)cc(F)c1O] | N-(4-(2-azaspiro[3.3]heptan-2-yl)phenyl)-3-fluoro-5-formyl-4-hydroxybenzamide |
| B78 | 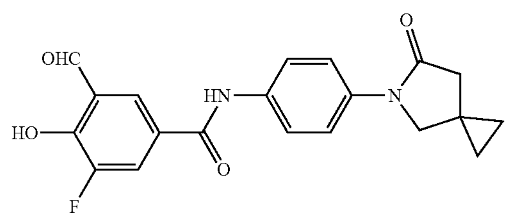 [SMILES: O=Cc1cc(C(=O)Nc2ccc(N3CC4(CC4)CC3=O)cc2)cc(F)c1O] | 3-fluoro-5-formyl-4-hydroxy-N-(4-(6-oxo-5-azaspiro[2.4]heptan-5-yl)phenyl)benzamide |
| B79 | 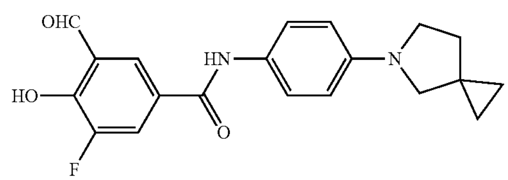 [SMILES: O=Cc1cc(C(=O)Nc2ccc(N3CCC4(CC4)C3)cc2)cc(F)c1O] | N-(4-(5-azaspiro[2.4]heptan-5-yl)phenyl)-3-fluoro-5-formyl-4-hydroxybenzamide |
| B80 | 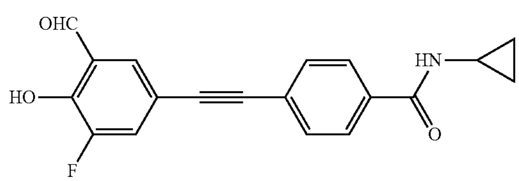 [SMILES: O=Cc1cc(C#Cc2ccc(C(=O)NC3CC3)cc2)cc(F)c1O] | N-cyclopropyl-4-((3-fluoro-5-formyl-4-hydroxyphenyl)ethynyl)benzamide |
| B81 | 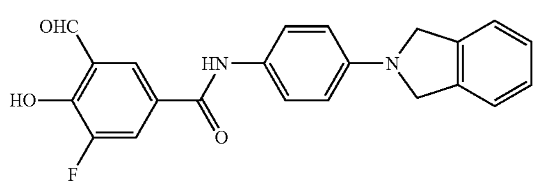 [SMILES: O=Cc1cc(C(=O)Nc2ccc(N3Cc4ccccc4C3)cc2)cc(F)c1O] | 3-fluoro-5-formyl-4-hydroxy-N-(4-(isoindolin-2-yl)phenyl)benzamide |
| B82 | 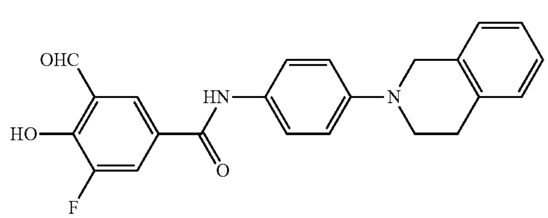 [SMILES: O=Cc1cc(C(=O)Nc2ccc(N3CCc4ccccc4C3)cc2)cc(F)c1O] | N-(4-(3,4-dihydroisoquinolin-2(1H)-yl)phenyl)-3-fluoro-5-formyl-4-hydroxybenzamide |

TABLE 1B-continued

| Compound No. | Chemical Structure | Chemical Name |
|---|---|---|
| B83 | 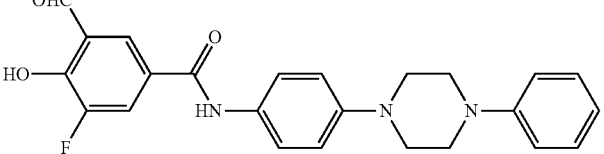 | 3-fluoro-5-formyl-4-hydroxy-N-(4-(4-phenylpiperazin-1-yl)phenyl)benzamide |
| B84 | 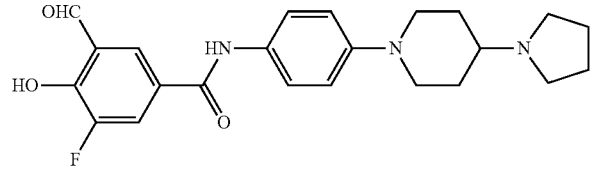 [SMILES: O=Cc1cc(C(=O)Nc2ccc(N3CCC(N4CCCC4)CC3)cc2)cc(F)c1O] | 3-fluoro-5-formyl-4-hydroxy-N-(4-(4-(pyrrolidin-1-yl)piperidin-1-yl)phenyl)benzamide |
| B85 | 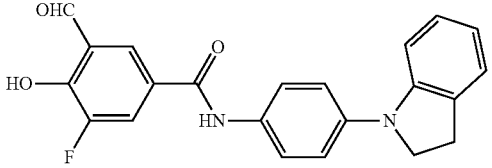 [SMILES: O=Cc1cc(C(=O)Nc2ccc(N3CCc4ccccc43)cc2)cc(F)c1O] | 3-fluoro-5-formyl-4-hydroxy-N-(4-(4-(pyrrolidin-1-yl)piperidin-1-yl)phenyl)benzamide |
| B86 | 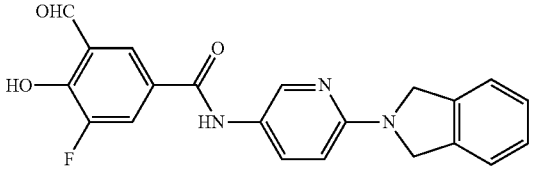 [SMILES: O=Cc1cc(C(=O)Nc2ccc(N3Cc4ccccc4C3)nc2)cc(F)c1O] | 3-fluoro-5-formyl-4-hydroxy-N-(6-(isoindolin-2-yl)pyridin-3-yl)benzamide |
| B87 | 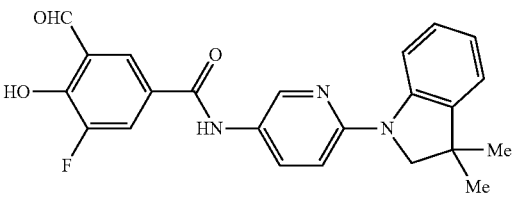 [SMILES: CC1(C)CN(c2ccc(NC(=O)c3cc(F)c(O)c(C=O)c3)cn2)c2ccccc21] | N-(6-(3,3-dimethylindolin-1-yl)pyridin-3-yl)-3-fluoro-5-formyl-4-hydroxybenzamide |
| B88 | 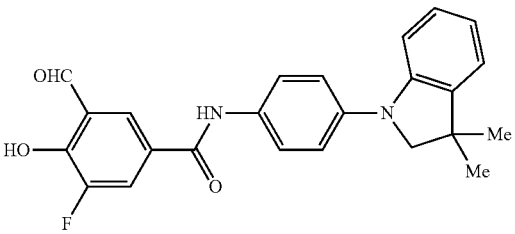 [SMILES: CC1(C)CN(c2ccc(NC(=O)c3cc(F)c(O)c(C=O)c3)cc2)c2ccccc21] | N-(4-(3,3-dimethylindolin-1-yl)phenyl)-3-fluoro-5-formyl-4-hydroxybenzamide |
| B89 | 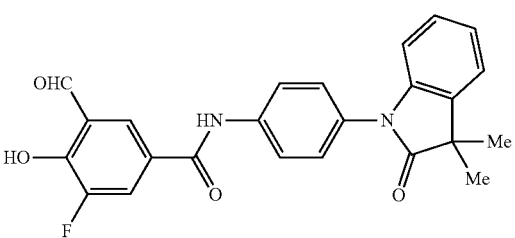 [SMILES: CC1(C)C(=O)N(c2ccc(NC(=O)c3cc(F)c(O)c(C=O)c3)cc2)c2ccccc21] | N-(4-(3,3-dimethyl-2-oxoindolin-1-yl)phenyl)-3-fluoro-5-formyl-4-hydroxybenzamide |

TABLE 1B-continued

| Compound No. | Chemical Structure | Chemical Name |
|---|---|---|
| B90 | 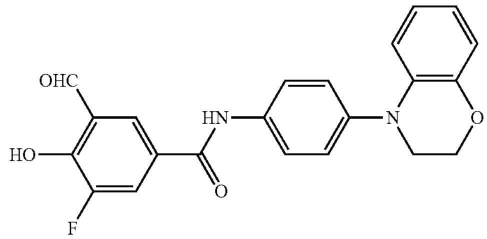 [SMILES: O=Cc1cc(C(=O)Nc2ccc(N3CCOc4ccccc43)cc2)cc(F)c1O] | N-(4-(2,3-dihydro-4H-benzo[b][1,4]oxazin-4-yl)phenyl)-3-fluoro-5-formyl-4-hydroxybenzamide |
| B91 | 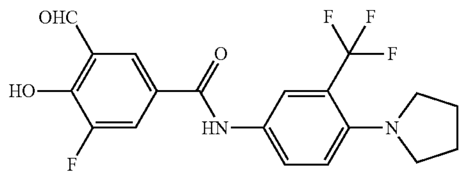 [SMILES: O=Cc1cc(C(=O)Nc2ccc(N3CCCC3)c(C(F)(F)F)c2)cc(F)c1O] | 3-fluoro-5-formyl-4-hydroxy-N-(4-(pyrrolidin-1-yl)-3-(trifluoromethyl)phenyl)benzamide |
| B92 | 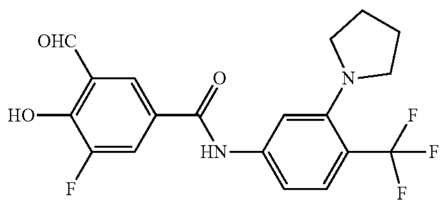 [SMILES: O=Cc1cc(C(=O)Nc2ccc(C(F)(F)F)c(N3CCCC3)c2)cc(F)c1O] | 3-fluoro-5-formyl-4-hydroxy-N-(3-(pyrrolidin-1-yl)-4-(trifluoromethyl)phenyl)benzamide |
| B93 | 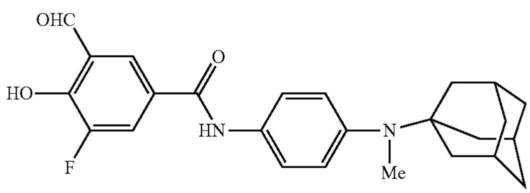 [SMILES: CN(c1ccc(NC(=O)c2cc(F)c(O)c(C=O)c2)cc1)C12CC3CC(CC(C3)C1)C2] | N-(4-(((3s,5s,7s)-adamantan-1-yl)(methyl)amino)phenyl)-3-fluoro-5-formyl-4-hydroxybenzamide |
| B94 | 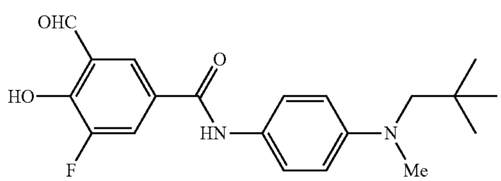 [SMILES: CN(CC(C)(C)C)c1ccc(NC(=O)c2cc(F)c(O)c(C=O)c2)cc1] | 3-fluoro-5-formyl-4-hydroxy-N-(4-(methyl(neopentyl)amino)phenyl)benzamide |
| B95 | 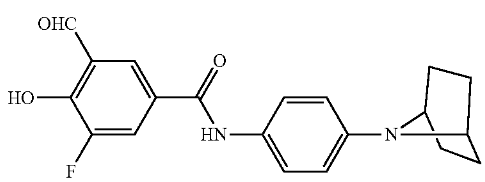 [SMILES: O=Cc1cc(C(=O)Nc2ccc(N3C4CCC3CC4)cc2)cc(F)c1O] | N-(4-((1s,4s)-7-azabicyclo[2.2.1]heptan-7-yl)phenyl)-3-fluoro-5-formyl-4-hydroxybenzamide |
| B96 | 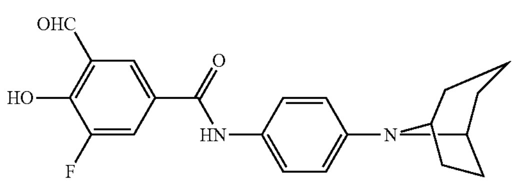 [SMILES: O=Cc1cc(C(=O)Nc2ccc(N3C4CCCC3CC4)cc2)cc(F)c1O] | N-(4-((1R,5S)-8-azabicyclo[3.2.1]octan-8-yl)phenyl)-3-fluoro-5-formyl-4-hydroxybenzamide |
| B97 | 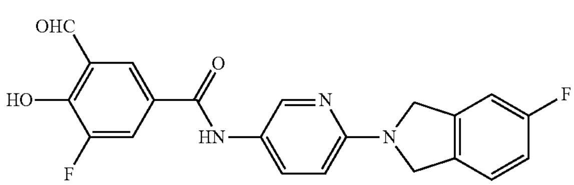 [SMILES: O=Cc1cc(C(=O)Nc2ccc(N3Cc4ccc(F)cc4C3)nc2)cc(F)c1O] | 3-fluoro-N-(6-(5-fluoroisoindolin-2-yl)pyridin-3-yl)-5-formyl-4-hydroxybenzamide |

TABLE 1B-continued

| Compound No. | Chemical Structure | Chemical Name |
|---|---|---|
| B98 | 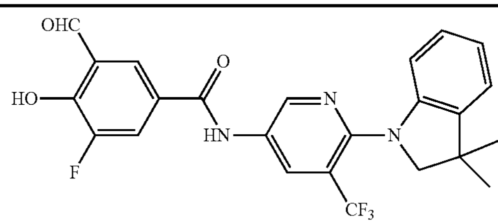 | N-(6-(3,3-dimethylindolin-1-yl)-5-(trifluoromethyl)pyridin-3-yl)-3-fluoro-5-formyl-4-hydroxybenzamide |
| B99 | 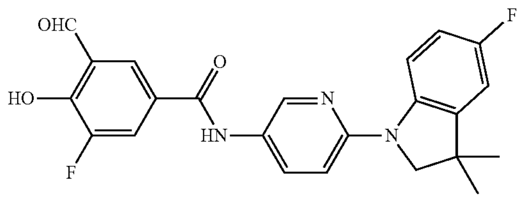 [SMILES: CC1(C)CN(c2ccc(NC(=O)c3cc(F)c(O)c(C=O)c3)cn2)c2ccc(F)cc21] | 3-fluoro-N-(6-(5-fluoro-3,3-dimethylindolin-1-yl)pyridin-3-yl)-5-formyl-4-hydroxybenzamide |
| B100 | 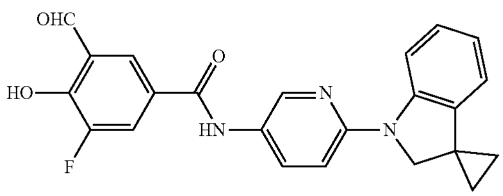 [SMILES: O=Cc1cc(C(=O)Nc2ccc(N3CC4(CC4)c4ccccc43)nc2)cc(F)c1O] | 3-fluoro-5-formyl-4-hydroxy-N-(6-(spiro[cyclopropane-1,3'-indolin]-1'-yl)pyridin-3-yl)benzamide |
| B101 | 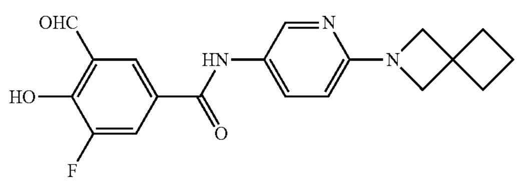 [SMILES: O=Cc1cc(C(=O)Nc2ccc(N3CC4(CCC4)C3)nc2)cc(F)c1O] | N-(6-(2-azaspiro[3.3]heptan-2-yl)pyridin-3-yl)-3-fluoro-5-formyl-4-hydroxybenzamide |
| B102 | 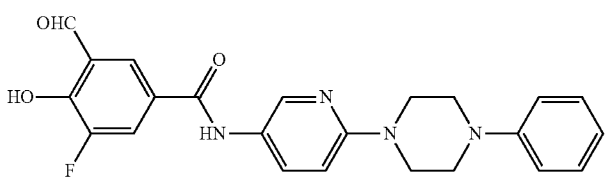 | 3-fluoro-5-formyl-4-hydroxy-N-(6-(4-phenylpiperazin-1-yl)pyridin-3-yl)benzamide |
| B103 | 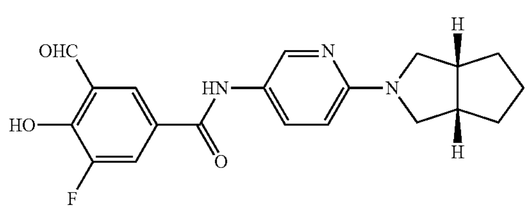 | 3-fluoro-5-formyl-N-(6-((3aR,6aS)-hexahydrocyclopenta[c]pyrrol-2(1H)-yl)pyridin-3-yl)-4-hydroxybenzamide |
| B104 | | 3-fluoro-5-formyl-4-hydroxy-N-(4-((4-methylpiperazin-1-yl)methyl)-3-(trifluoromethyl)phenyl)benzamide | and pharmaceutically acceptable salts thereof.

Any formula or compound given herein, such as Formula (I), Formula (A), or Formula (B), or compounds of Table 1A and Table 1B, is intended to represent compounds having structures depicted by the structural formula as well as certain variations or forms. In particular, compounds of any formula given herein may contain bonds with restricted rotation and therefore exist in different geometric configurations. Additionally, compounds of any formula provided herein may have asymmetric centers and therefore exist in different enantiomeric or diastereomeric forms. All optical isomers and stereoisomers of the compounds of the general formula, and mixtures thereof in any ratio, are considered within the scope of the formula. Thus, any formula given herein is intended to represent a racemate, one or more enantiomeric forms, one or more diastereomeric forms, one or more atropisomeric forms (e.g., geoisomeric forms), and mixtures thereof in any ratio. Where a compound of Table 1A or Table 1B is depicted with a particular stereochemical configuration, also provided herein is any alternative stereochemical configuration of the compound, as well as a mixture of stereoisomers of the compound in any ratio. Any compound of Table 1A or Table 1B is intended to represent a racemate, one or more enantiomeric forms, one or more diastereomeric forms, one or more atropisomeric forms (e.g., geoisomeric forms), and mixtures thereof in any ratio. Furthermore, certain structures may exist as tautomers or as atropisomers. Additionally, any formula given herein is intended to refer to hydrates, solvates, and amorphous forms of such compounds, and mixtures thereof, even if such forms are not listed explicitly. In some embodiments, the solvent is water and the solvates are hydrates.

The compounds of Formula (A) and Formula (B), or Table 1A and Table 1B may be prepared and/or formulated as pharmaceutically acceptable salts. In some embodiments, pharmaceutically acceptable salts include acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like. These salts may be derived from inorganic or organic acids. Non-limiting examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. In some embodiments, pharmaceutically acceptable salts are formed when an acidic proton present in the parent compound either is replaced by a metal ion, e.g., an alkali metal ion, an alkaline earth ion, or an aluminum ion; or coordinates with an organic base. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, trimetharnine, dicyclohexylamine, caffeine, procaine, hydrabamine, choline, betaine, ethylenediamine, glucosamine, N-ethylglucamine, N-methylglucamine, theobromine, purines, piperazine, piperidine, N-ethylpiperidine, polyamine resins, amino acids such as lysine, arginine, histidine, and the like. Examples of pharmaceutically acceptable base addition salts include those derived from inorganic bases such as sodium, potassium, lithium, ammonium, calcium, magnesium, iron, zinc, copper, manganese, aluminum salts and the like. In some embodiments, the organic non-toxic bases are L-amino acids, such as L-lysine and L-arginine, tromethamine, N-ethylglucamine and N-methylglucamine. Acceptable inorganic bases include aluminum hydroxide, calcium hydroxide, potassium hydroxide, sodium carbonate, sodium hydroxide, and the like. Lists of other suitable pharmaceutically acceptable salts are found in Remington's Pharmaceutical Sciences, 17th Edition, Mack Publishing Company, Easton, Pa., 1985.

For a compound described herein that contains a basic nitrogen, a pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, benzenesulfonic acid, or ethanesulfonic acid, or any compatible mixture of acids such as those given as examples herein, and any other acid and mixture thereof that are regarded as equivalents or acceptable substitutes in light of the ordinary level of skill in this technology.

The compounds depicted herein may be present as salts even if salts are not depicted, and it is understood that the compositions and methods provided herein embrace all salts and solvates of the compounds depicted here, as well as the non-salt and non-solvate form of the compound, as is well understood by the skilled artisan. In some embodiments, the salts of the compounds provided herein are pharmaceutically acceptable salts.

Representative examples of compounds detailed herein, including intermediates and final compounds, are depicted in the tables and elsewhere herein. It is understood that in one aspect, any of the compounds may be used in the methods detailed herein, including, where applicable, intermediate compounds that may be isolated and administered to an individual.

In one variation, the compounds herein are synthetic compounds prepared for administration to an individual. In another variation, compositions are provided containing a compound in substantially pure form. In another variation, provided are pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

Any variation or embodiment of $R^1$, $R^2$, $R^3$, $R^4$, $Y^1$, $Y^2$, $Y^3$, $Y^4$, $Y^5$, $G_1$, $G_2$, $G_3$, $G_4$, $G_5$, $G_6$, $G_7$, $R^a$, $R^b$, $R^c$, $R^d$, $R^e$, $R^f$, $R^g$, $R^h$, $R^j$, $R^k$, $R^m$, $R^n$, $R^p$, $R^q$, $R^r$, $R^s$, $R^t$, $R^u$, $R^v$, $R^{w1}$, $R^{w2}$, $R^x$, $R^y$, $R^{z1}$, $R^{z2}$, $X_1$, $X_2$, $X_3$, $X_4$, m, n, $R^{6a}$, $R^{6b}$, $R^{6c}$, and $R^{6d}$ provided herein can be combined with every other variation or embodiment of $R^1$, $R^2$, $R^3$, $R^4$, $Y^1$, $Y^2$, $Y^3$, $Y^4$, $Y^5$, $G_1$, $G_2$, $G_3$, $G_4$, $G_5$, $G_6$, $G_7$, $R^a$, $R^b$, $R^c$, $R^d$, $R^e$, $R^f$, $R^g$, $R^h$, $R^j$, $R^k$, $R^m$, $R^n$, $R^p$, $R^q$, $R^r$, $R^s$, $R^t$, $R^u$, $R^v$, $R^{w1}$, $R^{w2}$, $R^x$, $R^y$, $R^{z1}$, $R^{z2}$, $X_1$, $X_2$, $X_3$, $X_4$, m, n, $R^{6a}$, $R^{6b}$, $R^{6c}$, and $R^{6d}$ as if each combination had been individually and specifically described.

Any variation or embodiment of $R^{1A}$, $R^{2A}$, $R^{3A}$, L, $Y_1$, $Y_2$, $Y_3$, $Y_4$, $Y_5$, $Y_6$, $Y_7$, $Y_8$, $R^{a1}$, $R^{b1}$, $R^{c1}$, $R^{d1}$, $R^{e1}$, $R^{f1}$, $R^{g1}$, $R^{h1}$, $R^{j1}$, $R^{k1}$, $R^{m1}$, $R^{n1}$, $R^{p1}$, $R^{q1}$, $R^{r1}$, $R^{s1}$, $R^{t1}$, $R^{u1}$, $R^{v1}$, $R^{w1a}$, $R^{w2a}$, $R^x$, $R^{y1}$, $R^{z1a}$, $R^{z2a}$, $X_{1A}$, $X_{2A}$, $X_{3A}$, $X_{4A}$, m1, $R^{6a1}$, $R^{6b1}$, $R^{6c1}$, and $R^{6d1}$ provided herein can be combined with every other variation or embodiment of $R^{1A}$, $R^{2A}$, $R^{3A}$, L, $Y_1$, $Y_2$, $Y_3$, $Y_4$, $Y_5$, $Y_6$, $Y_7$, $Y_8$, $R^{a1}$, $R^{b1}$, $R^{c1}$, $R^{d1}$, $R^{e1}$, $R^{f1}$, $R^{g1}$, $R^{h1}$, $R^{j1}$, $R^{k1}$, $R^{m1}$, $R^{n1}$, $R^{p1}$, $R^{q1}$, $R^{r1}$, $R^{s1}$, $R^{t1}$, $R^{u1}$, $R^{v1}$, $R^{w1a}$, $R^{w2a}$, $R^x$, $R^{y1}$, $R^{z1a}$, $R^{z2}$a, $X_{1A}$, $X_{2A}$, $X_{3A}$, $X_4$A, m1, $R^{6a1}$, $R^{6b1}$, $R^{6c1}$, and $R^{6d1}$, as if each combination had been individually and specifically described.

Any variation or embodiment of $R^1$, $R^2$, $R^3$, $R^4$, $Y^1$, $Y^2$, $Y^3$, $Y^4$, $Y^5$, $G_1$, $G_2$, $G_3$, $G_4$, $G_5$, $G_6$, $G_7$, $R^a$, $R^b$, $R^c$, $R^d$, $R^e$, $R^f$, $R^g$, $R^h$, $R^j$, $R^k$, $R^m$, $R^n$, $R^p$, $R^q$, $R^r$, $R^s$, $R^t$, $R^u$, $R^v$, $R^{w1}$, $R^{w2}$, $R^x$, $R^y$, $R^{z1}$, $R^{z2}$, $X_1$, $X_2$, $X_3$, $X_4$, m, n, $R^{6a}$, $R^{6b}$, $R^{6c}$, $R^{6d}$, $R^{1A}$, $R^{2A}$, $R^{3A}$, L, $Y_1$, $Y_2$, $Y_3$, $Y_4$, $Y_5$, $Y_6$, $Y_7$, $Y_8$, $R^{a1}$, $R^{b1}$, $R^{c1}$, $R^{d1}$, $R^{e1}$, $R^{f1}$, $R^{g1}$, $R^{h1}$, $R^{j1}$, $R^{k1}$, $R^{m1}$, $R^{n1}$, $R^{p1}$, $R^{q1}$, $R^{r1}$, $R^{s1}$, $R^{t1}$, $R^{u1}$, $R^{v1}$, $R^{w1a}$, $R^{w2a}$, $R^x$, $R^{y1}$, $R^{z1a}$, $R^{z2a}$, $X_{1A}$, $X_{2A}$, $X_{3A}$, $X_{4A}$, m1, $R^{6a}$, $R^{6b1}$, $R^{6c1}$, and $R^{6d1}$ provided herein can be combined with every other variation or embodiment of $R^1$, $R^2$, $R^3$, $R^4$, $Y^1$, $Y^2$, $Y^3$, $Y^4$, $Y^5$, $G_1$, $G_2$, $G_3$, $G_4$, $G_5$, $G_6$, $G_7$, $R^a$, $R^b$, $R^c$, $R^d$, $R^e$, $R^f$, $R^g$, $R^h$, $R^j$, $R^k$, $R^m$, $R^n$, $R^p$, $R^q$, $R_r$, $R^s$, $R^t$, $R^u$, $R^v$, $R^{w1}$, $R^{w2}$, $R^x$, $R^y$, $R^{z1}$, $R^{z2}$, $X_1$, $X_2$, $X_3$, $X_4$, m, n, $R^{6a}$, $R^{6b}$, $R^{6c}$, $R^{6d}$, $R^{1A}$, $R^{2A}$, $R^{3A}$, L, $Y_1$, $Y_2$, $Y_3$, $Y_4$, $Y_5$, $Y_6$, $Y_7$, $Y_8$, $R^{a1}$, $R^{b1}$, $R^{c1}$, $R^{d1}$, $R^{w1}$, $R^{f1}$, $R^{g1}$, $R^{h1}$, $R^{j1}$, $R^{k1}$, $R^{m1}$, $R^{n1}$, $R^{p1}$, $R^{q1}$, $R_{r1}$, $R^{s1}$, $R^{t1}$, $R^{u1}$, $R^{v1}$, $R^{w1a}$, $R^{w2a}$, $R^x$, $R^{y1}$, $R^{z2a}$, $X_{1A}$, $X_{2A}$, $X_{3A}$, $X_{4A}$, m1, $R^{6a1}$, $R^{6b1}$, $R^{6c1}$, and $R^{6d1}$ as if each combination had been individually and specifically described.

The embodiments also relate to pharmaceutically acceptable prodrugs of the compounds described herein, and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (A) of Formula (B)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

The embodiments also relate to pharmaceutically active metabolites of compounds described herein, and uses of such metabolites in the methods provided herein. A "pharmaceutically active metabolite" means a pharmacologically active product of metabolism in the body of a compound described herein or salt thereof. Prodrugs and active metabolites of a compound may be determined using routine techniques known or available in the art. See, e.g., Bertolini et al., *J. Med. Chem.* 1997, 40, 2011-2016; Shan et al., *J. Pharm. Sci.* 1997, 86 (7), 765-767; Bagshawe, *Drug Dev. Res.* 1995, 34, 220-230; Bodor, *Adv. Drug Res.* 1984, 13, 255-331; Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

Chemical Definitions

The following terms have the following meanings unless otherwise indicated. Any undefined terms have their art recognized meanings.

The term "alkyl" refers to a straight- or branched-chain univalent saturated hydrocarbon group, or combination thereof, having the number of carbon atoms designated (i.e., $C_1$-$C_{10}$ means one to ten carbon atoms). Examples of alkyl groups include, but are not limited to, methyl (Me), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "alkoxy" refers to an —O-alkyl. Examples of alkoxy include, but are not limited to, methoxy, ethoxy, n-propoxy, isopropoxy, n-butoxy, iso-butoxy, sec-butoxy, and tert-butoxy.

The term "alkenyl" refers to an unsaturated straight- or branched-chain hydrocarbon group, or combination thereof, having the indicated number of carbon atoms, and having one or more double bonds. Examples of alkenyl groups include, but are not limited to, ethenyl (or vinyl), allyl, and but-3-en-1-yl. Included within this term are cis and trans isomers and mixtures thereof.

The term "alkynyl" refers to an unsaturated straight- or branched-chain hydrocarbon group having the indicated number of carbon atoms (e.g., 2 to 8 or 2 to 6 carbon atoms) and at least one carbon-carbon triple bond. Examples of alkynyl groups include, but are not limited to, acetylenyl (—C≡CH) and propargyl (—CH$_2$C≡CH).

The term "alkylene" refers to a divalent group that is a radical of an alkane. The alkylene can be a straight- or branched-chain divalent alkyl radical. "$C_{1-4}$ alkylene" refers to alkylene groups with 1 to 4 carbon atoms.

The term "aryl" refers to a monovalent aromatic carbocyclic group of from 6 to 18 annular carbon atoms having a single ring (a phenyl group) or a multiple condensed ring (such as napthyl, anthracenyl, or indanyl), in which condensed rings are optionally aromatic, provided that the point of attachment of the aryl group to the parent structure is through an atom of an aromatic ring. "Aryl" as defined herein encompasses groups such as phenyl and fluorenyl.

The term "cycloalkyl" refers to cyclic hydrocarbon groups of from 3 to 10 annular carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like. In some instances, the cycloalkyl is a monocyclic ring. In some instances, cycloalkyl is a 3- to 6-membered ring.

The term "cycloalkenyl" refers to a cyclic alkenyl group of from 4 to 10 annular carbon atoms having a single cyclic ring and at least one point of internal unsaturation which can be optionally substituted with from 1 to 3 alkyl groups. Examples of suitable cycloalkenyl groups include, for instance, cyclopent-3-enyl, cyclohex-2-enyl, cyclooct-3-enyl and the like.

The term "haloalkyl" refers to an alkyl group as described above, wherein one or more hydrogen atoms on the alkyl group have been replaced with a halo group. Examples of such groups include, without limitation, fluoroalkyl groups, such as fluoroethyl, trifluoromethyl, difluoromethyl, trifluoroethyl, and the like.

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

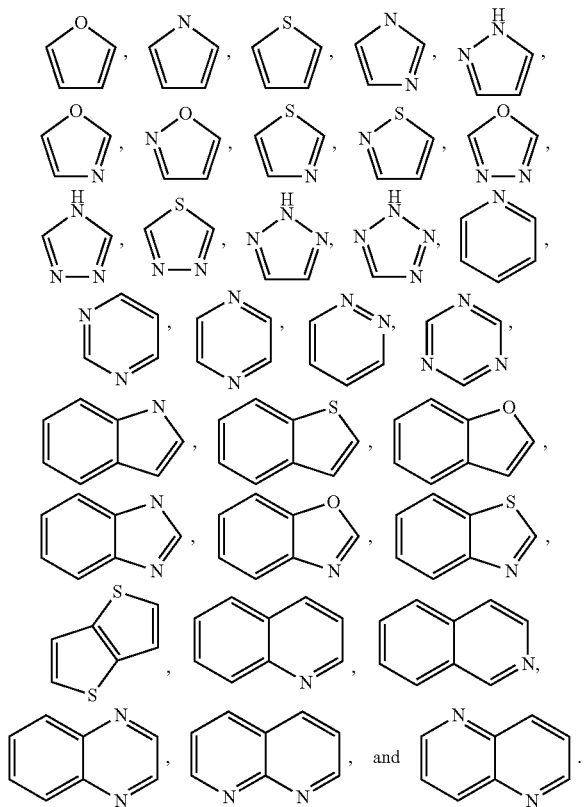

The terms "heterocyclyl" or "heterocycloalkyl" refer to a saturated or partially unsaturated group having a single ring or multiple condensed rings, including fused, bridged, or spiro ring systems, and having from 3 to 20 ring atoms, including 1 to 10 heteroatoms. These ring atoms are selected from the group consisting of carbon, nitrogen, sulfur, or oxygen. In certain embodiments, the nitrogen and/or sulfur atom(s) of the heterocyclic group are optionally oxidized to provide for N-oxide, —S(O)—, or —SO$_2$— moieties. Illustrative examples of heterocyclic groups include the following entities, in the form of properly bonded moieties:

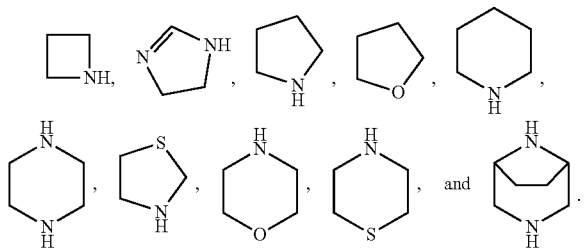

The term "halogen" represents chlorine, fluorine, bromine, or iodine. The term "halo" represents chloro, fluoro, bromo, or iodo.

The term "oxo" represents a carbonyl oxygen. For example, a cyclopentyl substituted with oxo is cyclopentanone.

Those skilled in the art will recognize that the species listed or illustrated above are not exhaustive, and that additional species within the scope of these defined terms may also be selected.

The term "substituted" means that the specified group or moiety bears one or more substituents including, but not limited to, substituents such as alkoxy, acyl, acyloxy, carbonylalkoxy, acylamino, amino, aminoacyl, aminocarbonylamino, aminocarbonyloxy, cycloalkyl, cycloalkenyl, aryl, heteroaryl, aryloxy, cyano, azido, halo, hydroxyl, nitro, carboxyl, thiol, thioalkyl, cycloalkyl, cycloalkenyl, alkyl, alkenyl, alkynyl, heterocyclyl, aralkyl, aminosulfonyl, sulfonylamino, sulfonyl, oxo, carbonylalkylenealkoxy and the like. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. When a group or moiety bears more than one substituent, it is understood that the substituents may be the same or different from one another. In some embodiments, a substituted group or moiety bears from one to five substituents. In some embodiments, a substituted group or moiety bears one substituent. In some embodiments, a substituted group or moiety bears two substituents. In some embodiments, a substituted group or moiety bears three substituents. In some embodiments, a substituted group or moiety bears four substituents. In some embodiments, a substituted group or moiety bears five substituents.

Any formula depicted herein is intended to represent a compound of that structural formula as well as certain variations or forms. For example, a formula given herein is intended to include a racemic form, or one or more enantiomeric, diastereomeric, or geometric isomers, or a mixture thereof. Additionally, any formula given herein is intended to refer also to a hydrate, solvate, or polymorph of such a compound, or a mixture thereof.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the present disclosure include isotopes of hydrogen, carbon, nitrogen, oxygen, phosphorous, fluorine, chlorine, and iodine, such as $^{2}$H, $^{3}$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl, and $^{125}$I, respectively. Such isotopically labelled compounds are useful in metabolic studies (preferably with $^{14}$C), reaction kinetic studies (with, for example $^{2}$H or $^{3}$H), detection or imaging techniques [such as positron emission tomography (PET) or single-photon emission computed tomography (SPECT)] including drug or substrate tissue distribution assays, or in radioactive treatment of patients. In particular, an $^{18}$F or $^{11}$C labeled compound may be particularly preferred for PET or SPECT studies. PET and SPECT studies may be performed as described, for example, by Brooks, D. J., "Positron Emission Tomography and Single-Photon Emission Computed Tomography in Central Nervous System Drug Development," *NeuroRx* 2005, 2(2), 226-236, and references cited therein. Further, substitution with heavier isotopes such as deuterium (i.e., $^{2}$H) may afford certain therapeutic advantages resulting from greater metabolic stability, for example increased in vivo half-life or reduced dosage requirements. Isotopically labeled compounds of the present disclosure and prodrugs thereof can generally be prepared by carrying out the procedures disclosed in the schemes or in the examples and preparations described below by substituting a readily available isotopically labeled reagent for a non-isotopically labeled reagent.

The nomenclature "$C_{i-j}$" with j>i, when applied herein to a class of substituents, is meant to refer to embodiments of the present disclosure for which each and every one of the number of carbon members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

Any disubstituent referred to herein is meant to encompass the various attachment possibilities when more than one of such possibilities are allowed. For example, reference to disubstituent -A-B-, where A≠B, refers herein to such disubstituent with A attached to a first substituted member and B attached to a second substituted member, and it also refers to such disubstituent with A attached to the second substituted member and B attached to the first substituted member.

The present disclosure also includes pharmaceutically acceptable salts of the compounds represented by Formula (A) and Formula (B), or the compounds of Table 1A and Table 1B, and pharmaceutical compositions comprising such salts, and methods of using such salts.

A "pharmaceutically acceptable salt" is intended to mean a salt of a free acid or base of a compound represented herein that is non-toxic, biologically tolerable, or otherwise biologically suitable for administration to the subject. See, generally, S. M. Berge, et al., "Pharmaceutical Salts," J. Pharm. Sci., 1977, 66, 1-19. Particular pharmaceutically acceptable salts are those that are pharmacologically effective and suitable for contact with the tissues of subjects without undue toxicity, irritation, or allergic response. A compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington's Pharmaceutical Sciences, 17th Edition, Mack Publishing Company, Easton, Pa., 1985.

For a compound of Formula (A) or Formula (B), or a compound of Table 1A or Table 1B that contains a basic nitrogen, a pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, or ethanesulfonic acid, or any compatible mixture of acids such as those given as examples herein, and any other acid and mixture thereof that are regarded as equivalents or acceptable substitutes in light of the ordinary level of skill in this technology.

The present disclosure also relates to pharmaceutically acceptable prodrugs of the compounds of Formula (A) or Formula (B), or the compounds of Table 1A and Table 1B, and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the formula compound). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

The present disclosure also relates to pharmaceutically active metabolites of compounds of Formula (A) or Formula (B), or the compounds of Table 1A and Table 1B, and uses of such metabolites in the methods provided herein. A "pharmaceutically active metabolite" means a pharmacologically active product of metabolism in the body of a compound of Formula (A) or Formula (B), or the compounds of Table 1A and Table 1B, or a salt of any of the foregoing. Prodrugs and active metabolites of a compound may be determined using routine techniques known or available in the art. See, e.g., Bertolini et al., *J. Med. Chem.* 1997, 40, 2011-2016; Shan et al., *J. Pharm. Sci.* 1997, 86 (7), 765-767; Bagshawe, *Drug Dev. Res.* 1995, 34, 220-230; Bodor, *Adv. Drug Res.* 1984, 13, 255-331; Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

Pharmaceutical Compositions

For treatment purposes, pharmaceutical compositions comprising the compounds described herein may further comprise one or more pharmaceutically-acceptable excipients. A pharmaceutically-acceptable excipient is a substance that is non-toxic and otherwise biologically suitable for administration to a subject. Such excipients facilitate administration of the compounds described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In particular embodiments, pharmaceutical compositions according to the present disclosure are sterile compositions.

Pharmaceutical compositions may be prepared using compounding techniques known or that become available to those skilled in the art.

Sterile compositions are also contemplated by the present disclosure, including compositions that are in accord with national and local regulations governing such compositions.

The pharmaceutical compositions and compounds described herein may be formulated as solutions, emulsions, suspensions, or dispersions in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. Pharmaceutical compositions of the present disclosure may be administered by a suitable route of delivery, such as oral, parenteral, rectal, nasal, topical, or ocular routes, or by inhalation. In some embodiments, the compositions are formulated for intravenous or oral administration.

For oral administration, the compounds of the present disclosure may be provided in a solid form, such as a tablet or capsule, or as a solution, emulsion, or suspension. To prepare the oral compositions, the compounds of the present disclosure may be formulated to yield a dosage of, e.g., from about 0.01 to about 50 mg/kg daily, or from about 0.05 to about 20 mg/kg daily, or from about 0.1 to about 10 mg/kg daily. Additional dosages include from about 0.1 mg to 1 g daily, from about 1 mg to about 10 mg daily, from about 10 mg to about 50 mg daily, from about 50 mg to about 250 mg daily, or from about 250 mg to 1 g daily. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The inventive compositions may be formulated for rectal administration as a suppository. For parenteral use, including intravenous, intramuscular, intraperitoneal, intranasal, or subcutaneous routes, the agents of the present disclosure may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days.

For nasal, inhaled, or oral administration, the inventive pharmaceutical compositions may be administered using, for example, a spray formulation also containing a suitable carrier.

For topical applications, the compounds of the present disclosure may be formulated as creams or ointments or a similar vehicle suitable for topical administration. For topical administration, the inventive compounds may be mixed with a pharmaceutical carrier at a concentration of about 0.10% to about 10% of drug to vehicle. Another mode of administering the agents of the present disclosure may utilize a patch formulation to effect transdermal delivery.

As used herein, "treatment" or "treating" is an approach for obtaining a beneficial or desired result, including clinical results. For purposes of this disclosure, beneficial or desired results include, but are not limited to: reducing the severity of or suppressing the worsening of a disease, symptom, or condition, alleviating a symptom and/or diminishing the extent of a symptom and/or preventing a worsening of a symptom associated with a condition, arresting the development of a disease, symptom, or condition, relieving the disease, symptom, or condition, causing regression of the disease, disorder, or symptom (in terms of severity or frequency of negative symptoms), or stopping the symptoms of the disease or condition. Beneficial or desired results can also be slowing, halting, or reversing the progressive course of a disease or condition. For example, beneficial effects may include slowing the progression of Parkinson's disease from an earlier stage (e.g., prodromal stage or stage 1, 2 or 3) to a later stage (e.g., stage 4 or 5), or halting Parkinson's disease at a prodromal or early stage.

As used herein, "delaying" development of a disease or condition means to defer, hinder, slow, retard, stabilize and/or postpone development of the disease or condition. This delay can be of varying lengths of time, depending on the history of the disease and/or individual being treated. As is evident to one skilled in the art, a sufficient or significant delay can, in effect, encompass prevention, in that the individual does not develop the disease or condition. For example, a method that "delays" development of Parkinson's disease (e.g., in a prodromal individual) is a method that reduces probability of disease development in a given time frame and/or reduces extent of the disease in a given time frame, when compared to not using the method.

The term "subject" refers to a mammalian patient in need of such treatment, such as a human. A "subject" may be a human, or may be a cat, dog, cow, rat, mouse, horse, rabbit, or other domesticated mammal.

Exemplary diseases that are characterized by protein aggregation include Alzheimer's disease, Parkinson's disease, fronto-temporal dementia, dementia with Lewy bodies (Lewy body disease), Parkinson's disease with dementia, multiple system atrophy, amyotrophic lateral sclerosis, Huntington's disease, Progressive Supranuclear Palsy (PSP), and Niemann-Pick disease type C, as well inflammatory diseases, such as asthma, chronic obstructive pulmonary disease (COPD), chronic peptic ulcers, irritable bowel disease, tuberculosis, rheumatoid arthritis, osteoarthritis, chronic sinusitis, hepatitis (such as hepatitis B or C), gout, lupus, pleurisy, eczema, gastritis, psoriasis, psoriatic arthritis, vasculitis, laryngitis, allergic reactions, multiple sclerosis, Crohn's disease, traumatic brain injury, CIDP (chronic inflammatory demyelinating polyneuropathy), stroke, ischemic heart disease, atopic dermatitis, acne vulgaris, rosacea, non-alcoholic fatty liver disease, non-alcoholic steatohepatisis, corneal wounds, corneal disorders, corneal HSV, Stargardt disease (Juvenile macular degeneration), age-related macular degeneration, sepsis, diabetic wounds, herpes simplex virus, and anti-fungal, anti-bacterial, anitviral and anti-tumor diseases or conditions.

In one aspect, the compounds and pharmaceutical compositions of the present disclosure specifically target TLR2 protein dimers. Thus, these compounds and pharmaceutical compositions can be used to prevent, reverse, slow, or inhibit dimerization of TLR2 proteins with other natural protein ligands, and are used in methods of the present disclosure to treat neurological and inflammatory diseases related to or caused by such dimerization. In some embodiments, methods of treatment target Parkinson's disease, Alzheimer's disease, Lewy body disease, multiple system atrophy, atopic dermatitis, traumatic brain injury, or multiple sclerosis. The compounds, compositions, and method of the present disclosure are also used to mitigate deleterious effects that are secondary to protein dimerization and/or misfolding, such as neuronal cell death. In another aspect, the compounds and pharmaceutical compositions of the present disclosure are inhibitors of TLR9. In some embodiments, the compounds and pharmaceutical compositions of the present disclosure are used in methods of the present disclosure to treat central nervous system (CNS) and peripheral disorders. In some embodiments, methods of treatment target Parkinson's disease, Amyotrophic lateral sclerosis, Guillain-Barre syndrome, spinal cord injury, multiple sclerosis, multiple forms of tissue injury, chronic pain, or psoriasis.

In some aspects, the compounds, compositions, and methods of the present disclosure are used to inhibit TLR2 dimerization. In alternative aspects, the compounds, compositions, and methods of the present disclosure are used to inhibit TLR2 dimerization with TLR1, or with TLR6, or both.

In the inhibitory methods of the present disclosure, an "effective amount" means an amount sufficient to reduce, slow the progression of, or reverse TLR2 dimerization. Measuring the amount of dimerization may be performed by routine analytical methods such as those described below. Such modulation is useful in a variety of settings, including in vitro assays. In some embodiments of such methods, the cell is a nerve cell or an HEK or THP cell.

In treatment methods according to the present disclosure, an "effective amount" means an amount or dose sufficient to generally bring about the desired therapeutic benefit in subjects needing such treatment. Effective amounts or doses of the compounds of the present disclosure may be ascertained by routine methods, such as modeling, dose escalation, or clinical trials, taking into account routine factors, e.g., the mode or route of administration or drug delivery, the pharmacokinetics of the agent, the severity and course of the infection, the subject's health status, condition, and weight, and the judgment of the treating physician. An exemplary dose is in the range of about 1 µg to 2 mg of active agent per kilogram of subject's body weight per day, such as about 0.05 to 100 mg/kg/day, or about 1 to 35 mg/kg/day, or about 0.1 to 10 mg/kg/day. In alternative embodiments an exemplary dose is in the range of about 1 mg to about 1 g per day, or about 1-500, 1-250, 1-100, 1-50, 50-500, or 250-500 mg per day. The total dosage may be given in single or divided dosage units (e.g., BID, TID, QID).

Once improvement of the patient's disease has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms. Patients may also require chronic treatment on a long-term basis.

Drug Combinations

The inventive compounds described herein may be used in pharmaceutical compositions or methods in combination with one or more additional active ingredients in the treatment of neurodegenerative disorders. Further additional active ingredients for cancer applications include other cancer therapeutics or agents that mitigate adverse effects of cancer chemotherapeutic agents. Such combinations may serve to increase efficacy, ameliorate other disease symptoms, decrease one or more side effects, or decrease the required dose of an inventive compound. The additional active ingredients may be administered in a separate pharmaceutical composition from a compound of the present disclosure or may be included with a compound of the present disclosure in a single pharmaceutical composition. The additional active ingredients may be administered simultaneously with, prior to, or after administration of a compound of the present disclosure.

Combination agents include additional active ingredients are those that are known or discovered to be effective in treating the diseases, disorders, conditions, and symptoms discussed herein, including those active against another target associated with the disease, disorder, or symptom such as but not limited to, a) compounds that address protein misfolding (such as drugs which reduce the production of these proteins, which increase their clearance or which alter their aggregation and/or propagation); b) compounds that treat symptoms of such disorders (e.g., dopamine replacement therapies); and c) drugs that act as neuroprotectants by complementary mechanisms (e.g., those targeting autophagy, those that are anti-oxidants, and those acting by other mechanisms such as adenosine A2A antagonists).

For example, compositions and formulations of the present disclosure, as well as methods of treatment, can further comprise other drugs or pharmaceuticals, e.g., other active agents useful for treating or palliative for a neurological or inflammatory diseases related to or caused by TLR2 dimerization, e.g., Parkinson's disease, Alzheimer's Disease (AD), Lewy body disease (LBD) and multiple system atrophy (MSA), or related symptoms or conditions. For example, the pharmaceutical compositions of the present disclosure may additional comprise one or more of such active agents, and methods of treatment may additionally comprise administering an effective amount of one or more of such active agents. In certain embodiments, additional active agents may be antibiotics (e.g., antibacterial or bacteriostatic peptides or proteins), e.g., those effective against gram positive or negative bacteria, fluids, cytokines, immunoregulatory agents, anti-inflammatory agents, complement activating agents, such as peptides or proteins comprising collagen-like domains or fibrinogen-like domains (e.g., a ficolin), carbohydrate-binding domains, and the like and combinations thereof. Additional active agents include those useful in such compositions and methods include dopamine therapy drugs, catechol-O-methyl transferase (COMT) inhibitors, monamine oxidase inhibitors, cognition enhancers (such as acetylcholinesterase inhibitors or memantine), adenosine 2A receptor antagonists, beta-secretase inhibitors, or gamma-secretase inhibitors. In particular embodiments, at least one compound of the present disclosure may be combined in a pharmaceutical composition or a method of treatment with one or more drugs selected from the group consisting of: tacrine (Cognex), donepezil (Aricept), rivastigmine (Exelon) galantamine (Reminyl), physostigmine, neostigmine, Icopezil (CP-118954, 5,7-dihydro-3-[2-[1-(phenylmethyl)-4-piperidinyl]ethyl]-6H-pyrrolo-[4,5-f-]-1, 2-benzisoxazol-6-one maleate), ER-127528 (4-[(5,6-dimethoxy-2-fluoro-1-indanon)-2-yl]methyl-1-(3-fluorobenzyl) piperidine hydrochloride), zanapezil (TAK-147; 3-[l-(phenylmethyl)piperidin-4-yl]-1-(2,3,4,5-tetrahydro-1H-1-benzazepin-8-yl)-1-propane fumarate), Metrifonate (T-588; (−)-R-.alpha.-[[2-(dimethylamino)ethoxy]methyl] benzo[b] thiophene-5-methanol hydrochloride), FK-960 (N-(4-acetyl-1-piperazinyl)-p-fluorobenzamide-hydrate), TCH-346 (N-methyl-N-2-pyropinyldibenz[b,f]oxepine-10-methanamine), SDZ-220-581 ((S)-alpha-amino-5-(phosphonomethyl)-[1,1'-biphenyl]-3-propionic acid), memantine (Namenda/Exiba) and 1,3,3,5,5-pentamethylcyclohexan-1-amine (Neramexane), tarenflurbil (Flurizan), tramiprosate (Alzhemed), clioquinol, PBT-2 (an 8-hydroxyquinilone derivative), 1-(2-(2-Naphthyl)ethyl)-4-(3-trifluoromethylphenyl)-1, 2,3,6-tetrahydropyridine, Huperzine A, posatirelin, leuprolide or derivatives thereof, ispronicline, (3-aminopropyl)(n-butyl)phosphinic acid (SGS-742), N-methyl-5-(3-(5-isopropoxypyridinyl))-4-penten-2-amine (ispronicline), 1-decanaminium, N-(2-hydroxy-3-sulfopropyl)-N-methyl-N-octyl-, inner salt (zt-1), salicylates, aspirin, amoxiprin, benorilate, choline magnesium salicylate, diflunisal, faislamine, methyl salicylate, magnesium salicylate, salicyl salicylate, diclofenac, aceclofenac, acemetacin, bromfenac, etodolac, indometacin, nabumetone, sulindac, tolmetin, ibuprofen, carprofen, fenbufen, fenoprofen, flurbiprofen, ketoprofen, ketorolac, loxoprofen, naproxen, tiaprofenic acid, suprofen, mefenamic acid, meclofenamic acid, phenylbutazone, azapropazone, metamizole, oxyphenbutazone, sulfinprazone, piroxicam, lornoxicam, meloxicam, tenoxicam, celecoxib, etoricoxib, lumiracoxib, parecoxib, rofecoxib, valdecoxib, nimesulide, arylalkanoic acids, 2-arylpropionic acids (profens), N-arylanthranilic acids (fenamic acids), pyrazolidine derivatives, oxicams, COX-2 inhibitors, sulphonanilides, essential fatty acids, and Minozac (2-(4-(4-methyl-6-phenylpyridazin-3-yl)piperazin-1-yl)pyrimidine dihydrochloride hydrate), or a combination thereof.

Methods of Use

The compounds and pharmaceutical compositions herein may be used to treat or prevent a disease or condition in an individual. In some embodiments, provided are methods of treating a disease or condition associated with TLR2 heterodimerization, comprising administering to the individual in need thereof a compound of Formula (A) or Formula (B), or a compound of Table 1A or Table 1B, or a tautomer thereof, or a pharmaceutically acceptable salt of any of the foregoing. In some embodiments, provided are methods of treating a disease or condition associated with TLR2 heterodimerization comprising administering to the subject a therapeutically effective amount of at least one chemical entity as described herein.

In some embodiments, provided are compositions containing one or more compounds of Formula (A) or Formula (B), or a compound of Table 1A or Table 1B, or a tautomer thereof, or a pharmaceutically acceptable salt of any of the foregoing, for use in the treatment of a disease or condition associated with TLR2 heterodimerization. In some embodiments, provided are compositions containing at least one chemical entity as described herein for use in the treatment of a disease or condition associated with TLR2 heterodimerization.

Also provided herein is the use of a compound of Formula (A) or Formula (B), or a compound of Table 1A or Table 1B, or a tautomer thereof, or a pharmaceutically acceptable salt of any of the foregoing, in the manufacture of a medicament for treatment of a disease or condition associated with TLR2 heterodimerization. In some embodiments, provided is the use of at least one chemical entity as described herein in the manufacture of a medicament for treatment of a disease or condition associated with TLR2 heterodimerization.

In some embodiments, the disease or condition is selected from Alzheimer's disease, Parkinson's disease, fronto-temporal dementia, dementia with Lewy bodies (Lewy body disease), Parkinson's disease with dementia, multiple system atrophy, amyotrophic lateral sclerosis, Huntington's disease, Progressive Supranuclear Palsy (PSP), Niemann-Pick disease type C, inflammatory diseases, asthma, chronic obstructive pulmonary disease (COPD), chronic peptic ulcers, irritable bowel disease, tuberculosis, rheumatoid arthritis, osteoarthritis, chronic sinusitis, hepatitis, hepatitis B, hepatitis C, gout, lupus, pleurisy, eczema, gastritis, psoriasis, psoriatic arthritis, vasculitis, laryngitis, allergic reactions, multiple sclerosis, Crohn's disease, traumatic brain injury, CIDP (chronic inflammatory demyelinating polyneuropathy), stroke, ischemic heart disease, atopic dermatitis, acne vulgaris, rosacea, non-alcoholic fatty liver disease, non-alcoholic steatohepatisis, corneal wounds, corneal disorders, corneal HSV, Stargardt disease (Juvenile macular degeneration), age-related macular degeneration, sepsis, diabetic wounds, herpes simplex virus, and anti-fungal, anti-bacterial, anitviral and antitumor diseases or conditions. In some embodiments, the disease or condition is selected from Alzheimer's disease, Parkinson's disease, fronto-temporal dementia, dementia with Lewy bodies (Lewy body disease), Parkinson's disease with dementia, multiple system atrophy, amyotrophic lateral sclerosis, Huntington's disease, inflammatory diseases, asthma, chronic obstructive pulmonary disease (COPD), chronic peptic ulcers, tuberculosis, rheumatoid arthritis, chronic sinusitis, hepatitis, hepatitis B, hepatitis C, gout, lupus, pleurisy, eczema, gastritis, psoriasis, psoriatic arthritis, vasculitis, laryngitis, allergic reactions, multiple sclerosis, Crohn's disease, and traumatic brain injury.

Also provided are methods for interfering with the heterodimerization of TLR2 in a cell, or modulating, preventing, slowing, reversing, or inhibiting TLR2 heterodimerization in a cell which involves contacting the cell with an effective amount of at least one compound of Formula (A) or Formula (B), or a compound of Table 1A or Table 1B, or a tautomer thereof, or a pharmaceutically acceptable salt of any of the foregoing. In some embodiments, provided are methods for interfering with the heterodimerization of TLR2 in a cell, or modulating, preventing, slowing, reversing, or inhibiting TLR2 heterodimerization in a cell which involves contacting the cell with an effective amount of at least one chemical entity as described herein. In some embodiments, provided are methods of inhibiting TLR2 activation in a cell, comprising contacting the cell with an effective amount of at least one compound of Formula (A) or Formula (B), or a compound of Table 1A or Table 1B, or a tautomer thereof, or a pharmaceutically acceptable salt of any of the foregoing, or a pharmaceutical composition comprising any of the foregoing, wherein the contacting is in vitro, ex vivo, or in vivo.

Also provided herein are compositions containing one or more compounds of Formula (A) or Formula (B), or a compound of Table 1A or Table 1B, or a tautomer thereof, or a pharmaceutically acceptable salt of any of the foregoing, for use in interfering with the heterodimerization of TLR2 in a cell, or modulating, preventing, slowing, reversing, or inhibiting TLR2 heterodimerization in a cell. In some embodiments, provided are compositions containing at least one chemical entity as described herein for use in interfering with the heterodimerization of TLR2 in a cell, or modulating, preventing, slowing, reversing, or inhibiting TLR2 heterodimerization in a cell.

Additionally provided herein is the use of at least one chemical entity as described herein, such as a compound of Formula (A) or Formula (B), or a compound of Table 1A or Table 1B, or a tautomer thereof, or a pharmaceutically acceptable salt of any of the foregoing, in the manufacture of a medicament for interfering with the heterodimerization of TLR2, or modulating, preventing, slowing, reversing, or inhibiting TLR2 heterodimerization.

In some embodiments, provided are methods of treating a disease or condition associated with inhibition of TLR9, comprising administering to the individual in need thereof a compound of Formula (A) or Formula (B), or a compound of Table 1A or Table 1B, or a tautomer thereof, or a pharmaceutically acceptable salt of any of the foregoing.

In some embodiments, provided are compositions containing one or more compounds of Formula (A) or Formula (B), or a compound of Table 1A or Table 1B, or a tautomer thereof, or a pharmaceutically acceptable salt of any of the foregoing, for use in the treatment of a disease or condition associated with inhibition of TLR9. In some embodiments, provided are compositions containing at least one chemical entity as described herein for use in the treatment of a disease or condition associated with inhibition of TLR9.

Also provided herein is the use of a compound of Formula (A) or Formula (B), or a compound of Table 1A or Table 1B, or a tautomer thereof, or a pharmaceutically acceptable salt of any of the foregoing, in the manufacture of a medicament for treatment of a disease or condition associated with inhibition of TLR9. In some embodiments, provided is the use of at least one chemical entity as described herein in the manufacture of a medicament for treatment of a disease or condition associated with inhibition of TLR9.

In some embodiments, the disease or condition is central nervous system (CNS) or peripheral disorder. In some embodiments, the disease or condition is Parkinson's disease, Amyotrophic lateral sclerosis, Guillain-Barre syndrome, spinal cord injury, multiple sclerosis, multiple forms of tissue injury, chronic pain, or psoriasis.

Also provided are methods of inhibiting TLR9 in a cell, which involves contacting the cell with an effective amount of at least one compound of Formula (A) or Formula (B), or a compound of Table 1A or Table 1B, or a tautomer thereof, or a pharmaceutically acceptable salt of any of the foregoing. In some embodiments, provided are methods for inhibiting TLR9 in a cell, which involves contacting the cell with an effective amount of at least one chemical entity as described herein. In some embodiments, provided are methods of inhibiting TLR9 activation in a cell, comprising contacting the cell with an effective amount of at least one compound of Formula (A) or Formula (B), or a compound of Table 1A or Table 1B, or a tautomer thereof, or a pharmaceutically acceptable salt of any of the foregoing, or a pharmaceutical composition comprising any of the foregoing, wherein the contacting is in vitro, ex vivo, or in vivo.

Also provided herein are compositions containing one or more compounds of Formula (A) or Formula (B), or a compound of Table 1A or Table 1B, or a tautomer thereof, or a pharmaceutically acceptable salt of any of the foregoing, for use in inhibiting TLR9 in a cell. In some embodiments, provided are compositions containing at least one chemical entity as described herein for use in inhibiting TLR9 in a cell.

Additionally provided herein is the use of at least one chemical entity as described herein, such as a compound of Formula (A) or Formula (B), or a compound of Table 1A or Table 1B, or a tautomer thereof, or a pharmaceutically acceptable salt of any of the foregoing, in the manufacture of a medicament for inhibiting TLR9.

In some embodiments, compounds described herein, such as a compound of Formula (A) or Formula (B), or a compound of Table 1A or Table 1B, or a tautomer thereof, or a pharmaceutically acceptable salt of any of the foregoing, inhibit both TLR2 and TLR9. In some embodiments, provided are methods of treating a disease or condition associated with TLR2 heterodimerization and/or inhibition of TLR9, comprising administering to the individual in need thereof a compound of Formula (A) or Formula (B), or a compound of Table 1A or Table 1B, or a tautomer thereof, or a pharmaceutically acceptable salt of any of the foregoing. In some embodiments, provided are methods of treating a disease or condition associated with TLR2 heterodimerization and/or inhibition of TLR9 comprising administering to the subject a therapeutically effective amount of at least one chemical entity as described herein.

In some embodiments, provided are compositions containing one or more compounds of Formula (A) or Formula (B), or a compound of Table 1A or Table 1B, or a tautomer thereof, or a pharmaceutically acceptable salt of any of the foregoing, for use in the treatment of a disease or condition associated with TLR2 heterodimerization and/or inhibition of TLR9. In some embodiments, provided are compositions containing at least one chemical entity as described herein for use in the treatment of a disease or condition associated with TLR2 heterodimerization and/or inhibition of TLR9.

Also provided herein is the use of a compound of Formula (A) or Formula (B), or a compound of Table 1A or Table 1B, or a tautomer thereof, or a pharmaceutically acceptable salt of any of the foregoing, in the manufacture of a medicament for treatment of a disease or condition associated with TLR2 heterodimerization and/or inhibition of TLR9. In some embodiments, provided is the use of at least one chemical entity as described herein in the manufacture of a medicament for treatment of a disease or condition associated with TLR2 heterodimerization and/or inhibition of TLR9.

Kits

Also provided are articles of manufacture and kits containing any of the compounds or pharmaceutical compositions provided herein. The article of manufacture may comprise a container with a label. Suitable containers include, for example, bottles, vials, and test tubes. The containers may be formed from a variety of materials such as glass or plastic. The container may hold a pharmaceutical composition provided herein. The label on the container may indicate that the pharmaceutical composition is used for preventing, treating or suppressing a condition described herein, and may also indicate directions for either in vivo or in vitro use.

In one aspect, provided herein are kits containing a compound or composition described herein and instructions for use. The kits may contain instructions for use in the treatment of a disease or condition associated with TLR2 heterodimerization in an individual in need thereof and/or instructions for use in the treatment of a disease or condition associated with inhibition of TLR9 in an individual in need thereof. A kit may additionally contain any materials or equipment that may be used in the administration of the compound or composition, such as vials, syringes, or IV bags. A kit may also contain sterile packaging.

General Synthetic Methods

The compounds of the present disclosure may be prepared by a number of processes as generally described below and more specifically in the Examples hereinafter (such as the schemes provided in the Examples below). In the following process descriptions, the symbols when used in the formulae depicted are to be understood to represent those groups described above in relation to the formulae herein.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g., a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

Solvates of a compound provided herein or a pharmaceutically acceptable salt thereof are also contemplated. Solvates contain either stoichiometric or non-stoichiometric amounts of a solvent, and are often formed during the process of crystallization. Hydrates are formed when the solvent is water, or alcoholates are formed when the solvent is alcohol.

In some embodiments, compounds of the Formula (A) may be synthesized according to Scheme A-1.

Scheme A-1.

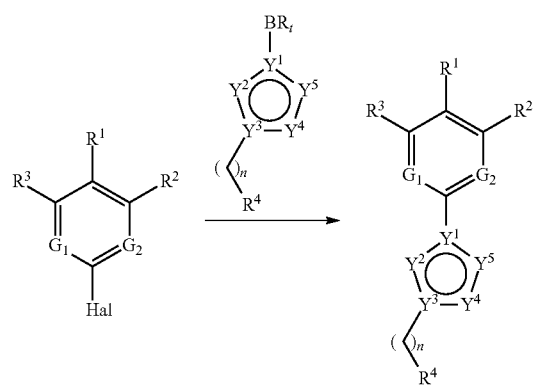

wherein $R^1$, $R^2$, $R^3$, $R^4$, $G_1$, $G_2$, $Y^1$, $Y^2$, $Y^3$, $Y^4$, $Y^5$, and n are as defined for Formula (A), or any variation thereof detailed herein; Hal is a halogen; t is 2 or 3; and R is —OH, —Oalkyl, or halogen, or —BR$_t$ is

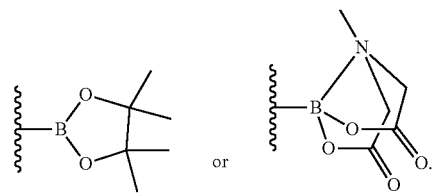

In some variations of the foregoing Scheme A-1, compounds of the Formula (A) may be synthesized according to Scheme A-1a.

Scheme A-1a.

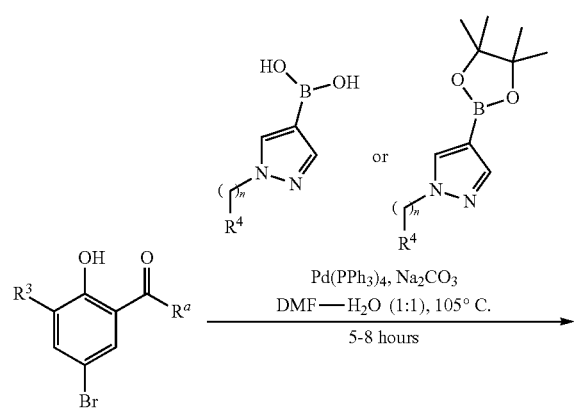

-continued

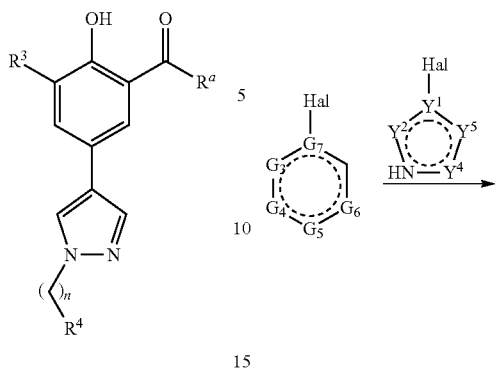

wherein $R^3$, $R^4$, $R^a$, and n are as defined for Formula (A), or any variation thereof detailed herein.

In some variations of the foregoing Scheme A-1, compounds of the Formula (A) may be synthesized according to Scheme A-1b.

Scheme A-1b.

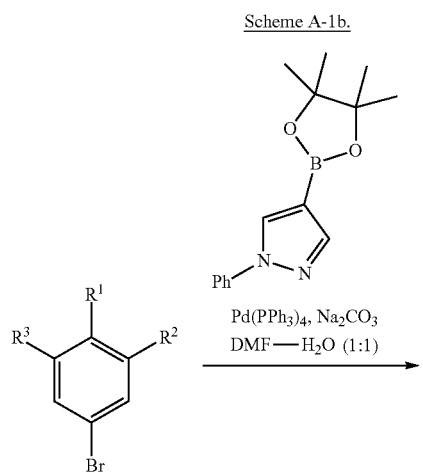

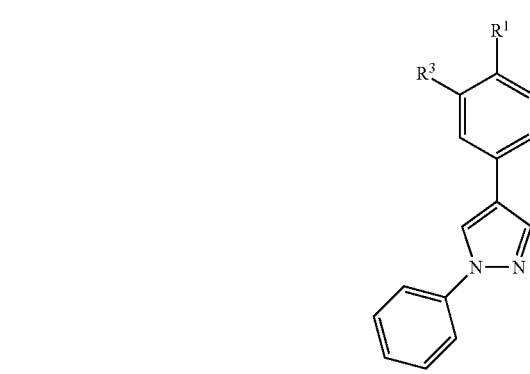

wherein $R^1$, $R^2$, and $R^3$ are as defined for Formula (A), or any variation thereof detailed herein.

In some embodiments, compounds of the Formula (A) may be synthesized according to Scheme A-2.

Scheme A-2.

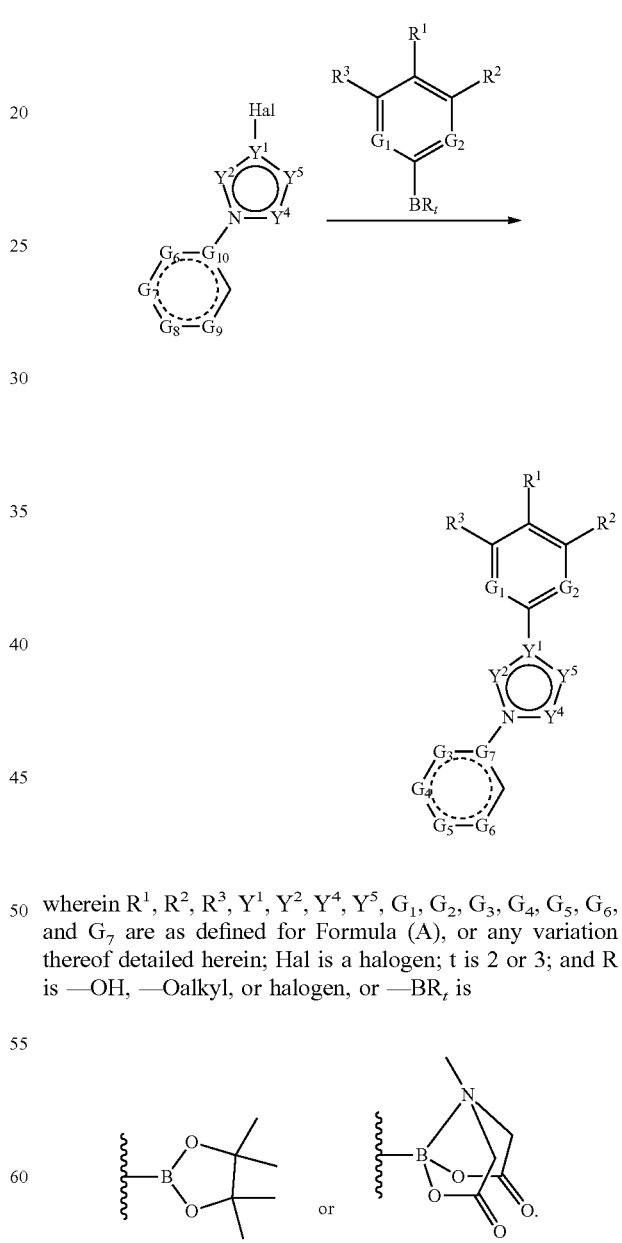

wherein $R^1$, $R^2$, $R^3$, $Y^1$, $Y^2$, $Y^4$, $Y^5$, $G_1$, $G_2$, $G_3$, $G_4$, $G_5$, $G_6$, and $G_7$ are as defined for Formula (A), or any variation thereof detailed herein; Hal is a halogen; t is 2 or 3; and R is —OH, —Oalkyl, or halogen, or —$BR_t$ is In some variations of the foregoing Scheme A-2, compounds of the Formula (A) may be synthesized according to Scheme A-2a.

Scheme A-2a.

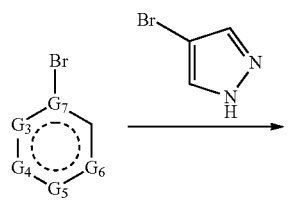

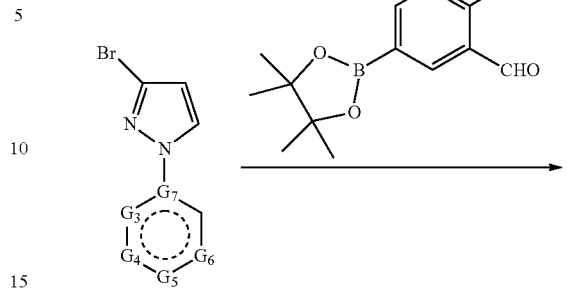

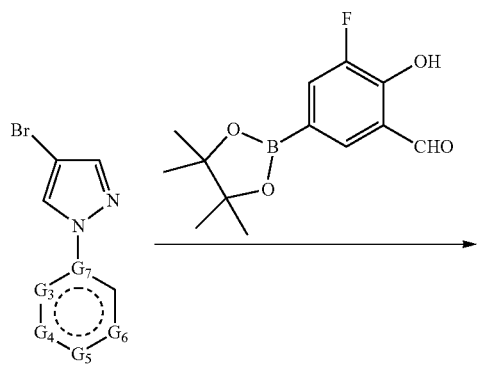

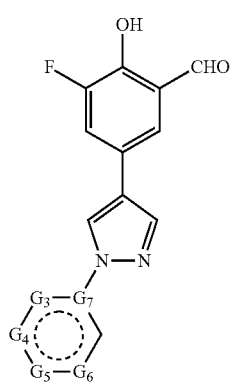

wherein $G_3$, $G_4$, $G_5$, $G_6$, and $G_7$ are as defined for Formula (A), or any variation thereof detailed herein.

In some variations of the foregoing Scheme A-2, compounds of the Formula (A) may be synthesized according to Scheme A-2b.

Scheme A-2b.

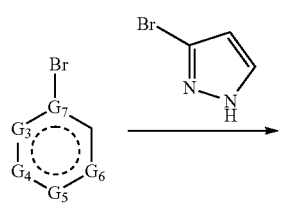

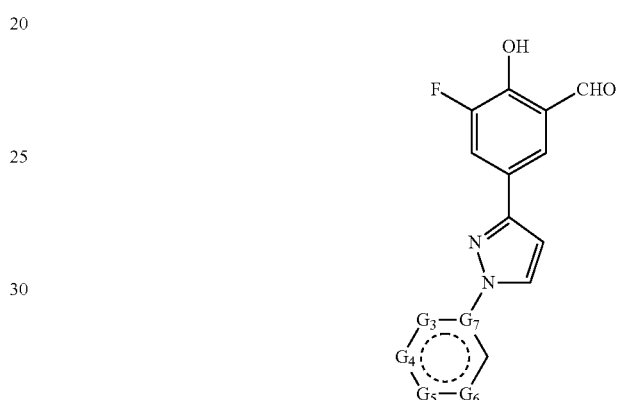

wherein $G_3$, $G_4$, $G_5$, $G_6$, and $G_7$ are as defined for Formula (A), or any variation thereof detailed herein.

In some embodiments, compounds of the Formula (A) may be synthesized according to Scheme A-3.

Scheme A-3.

207
-continued

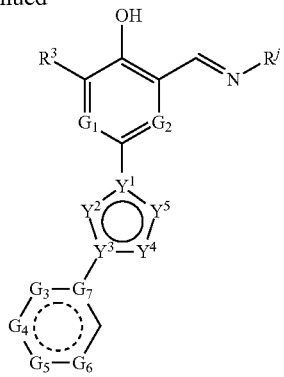

wherein $R^3$, $R^j$, $Y^1$, $Y^2$, $Y^3$, $Y^4$, $Y^5$, $G_1$, $G_2$, $G_3$, $G_4$, $G_5$, $G_6$, and $G_7$ are as defined for Formula (A), or any variation thereof detailed herein.

In some variations of the foregoing Scheme A-3, compounds of the Formula (A) may be synthesized according to Scheme A-3-A.

Scheme A-3-A.

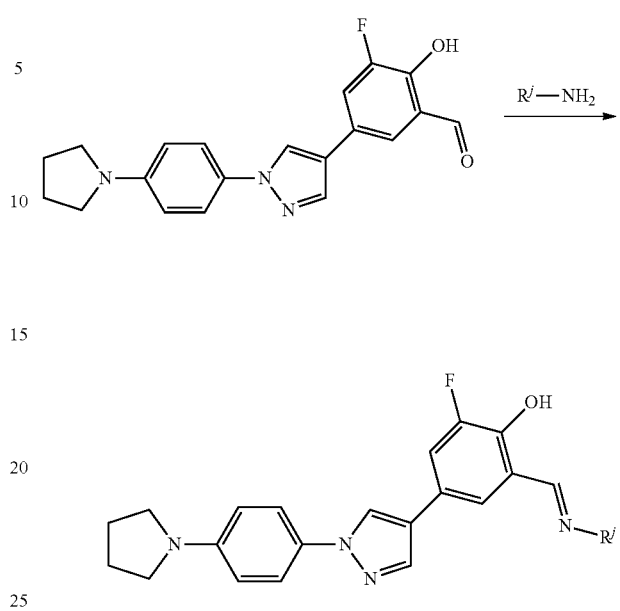

wherein $R^j$ is as defined for Formula (A), or any variation thereof detailed herein.

In some embodiments, compounds of the Formula (A) may be synthesized according to Scheme A-4.

Scheme A-4.

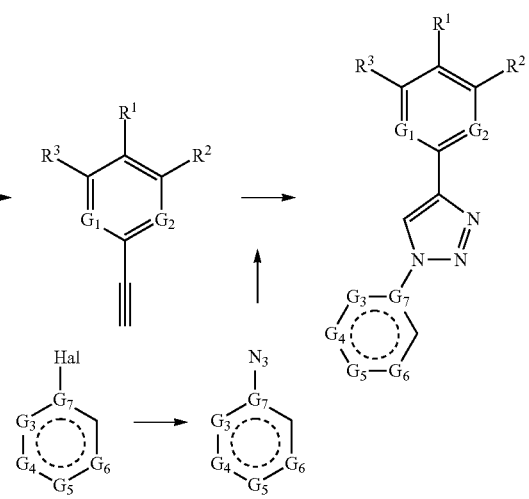

wherein $R^1$, $R^2$, $R^3$, $G_1$, $G_2$, $G_3$, $G_4$, $G_5$, $G_6$, and $G_7$ are as defined for Formula (A), or any variation thereof detailed herein, and Hal is a halogen.

In some variations of the foregoing Scheme A-4, compounds of the Formula (A) may be synthesized according to Scheme A-4-A.

Scheme A-4-A.

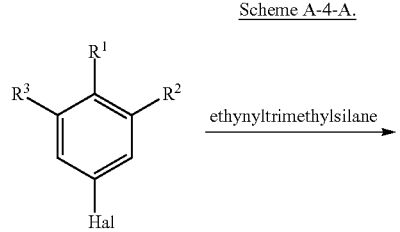

-continued

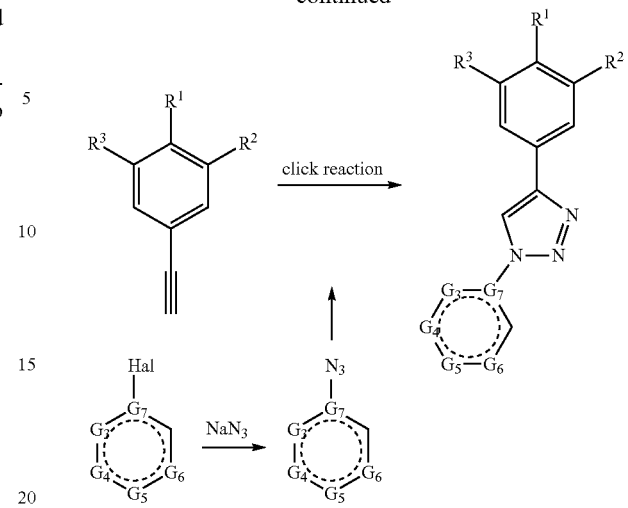

wherein $R^1$, $R^2$, $R^3$, $G_3$, $G_4$, $G_5$, $G_6$, and $G_7$ are as defined for Formula (A), or any variation thereof detailed herein, and Hal is a halogen.

In some embodiments, compounds of the Formula (A) may be synthesized according to Scheme A-5.

Scheme A-5.

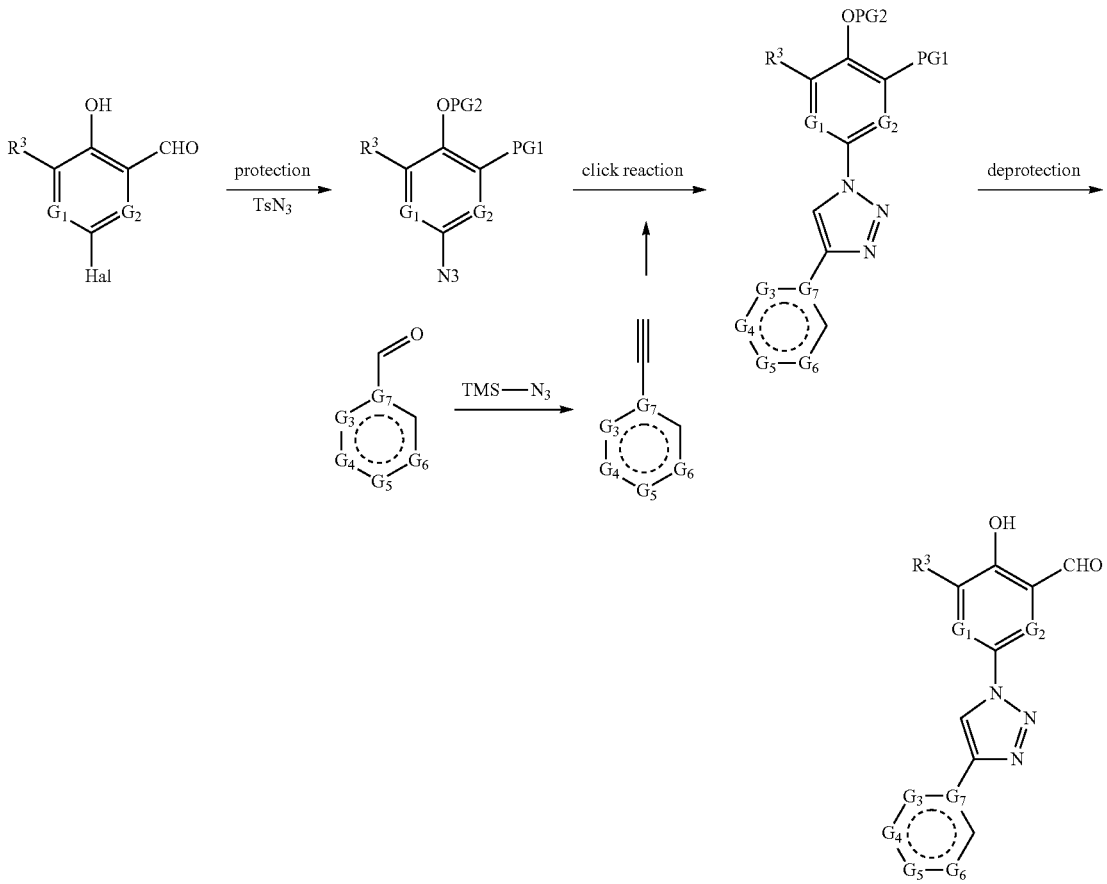

wherein $R^3$, $G_1$, $G_2$, $G_3$, $G_4$, $G_5$, $G_6$, and $G_7$ are as defined for Formula (A), or any variation thereof detailed herein, Hal is a halogen, and PG1 and PG2 are suitable protecting groups.

In some variations of the foregoing Scheme A-5, compounds of the Formula (A) may be synthesized according to Scheme A-5-A.

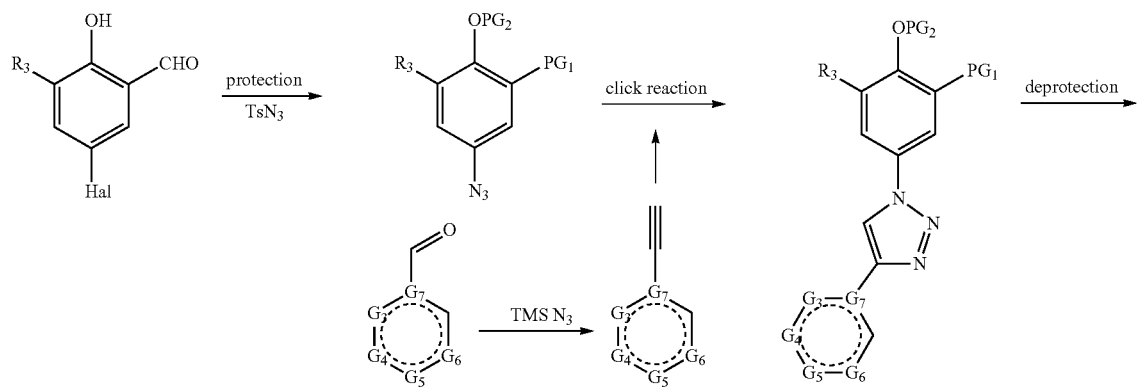

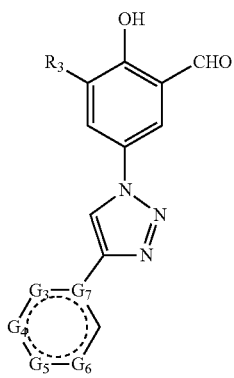

wherein $R^3$, $G_3$, $G_4$, $G_5$, $G_6$, and $G_7$ are as defined for Formula (A), or any variation thereof detailed herein, Hal is a halogen, and PG1 and PG2 are suitable protecting groups.

In some embodiments, compounds of the Formula (B) may be synthesized according to Scheme B-1.

Scheme B-1.

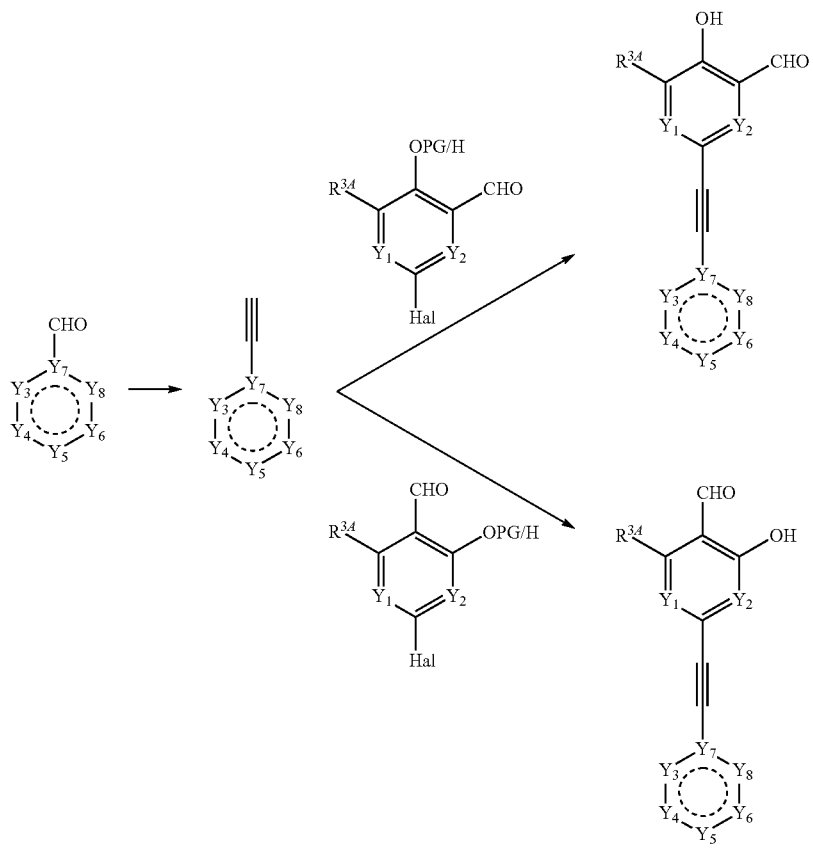

wherein $R^{34}$, $Y_1$, $Y_2$, $Y_3$, $Y_4$, $Y_5$, $Y_6$, $Y_7$, and $Y_8$ are as defined for Formula (B), or any variation thereof detailed herein; Hal is a halogen; and PG is any suitable protecting group. In some variations, a suitable protecting group is not necessary, and no protecting group is present on the phenolic group. In other variations, the suitable protecting group is a PMB (4-methoxybenzyl) group.

In some variations of the foregoing Scheme B-1, compounds of the Formula (B) may be synthesized according to Scheme B-1a.

Scheme B-1a.

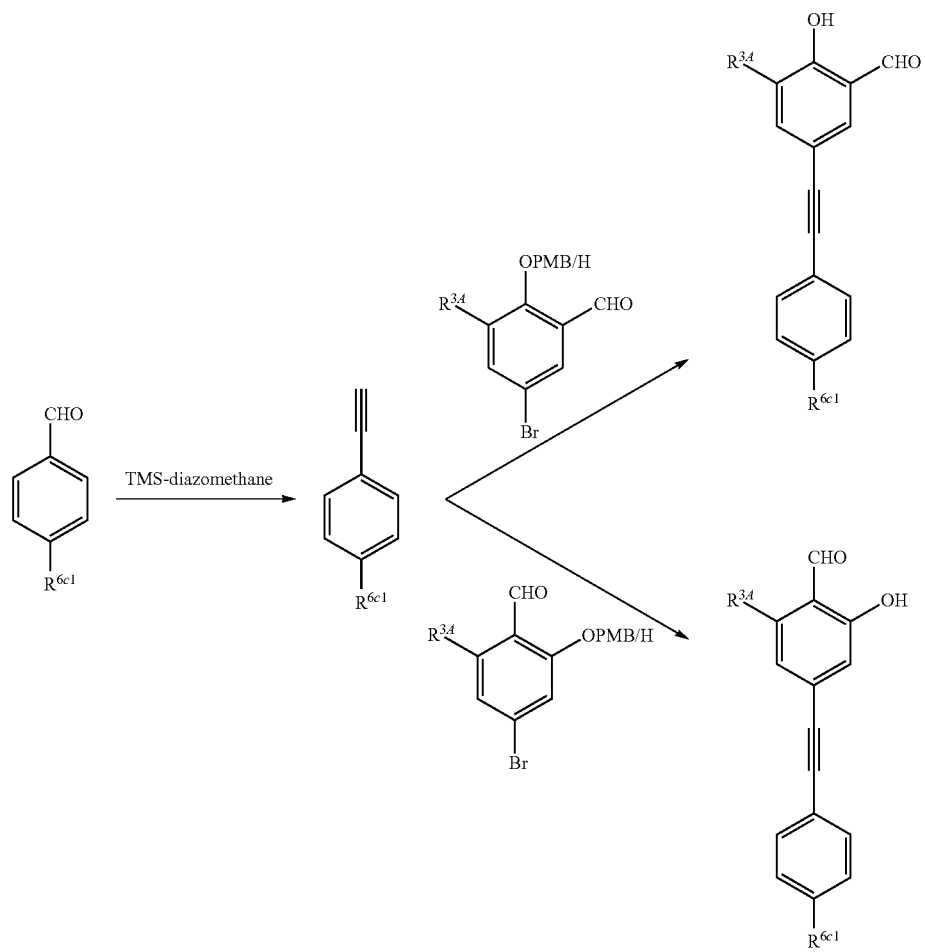

wherein $R^{3A}$ and $R^{6c1}$ are as defined for Formula (B), or any variation thereof detailed herein. In some variations, PMP is a suitable protecting group for an aromatic alcohol. In some variations, a suitable protecting group is not necessary, and no protecting group is present on the phenolic group.

In some embodiments, compounds of the Formula (B) may be synthesized according to Scheme B-2A or Scheme B-2B.

Scheme B-2A.

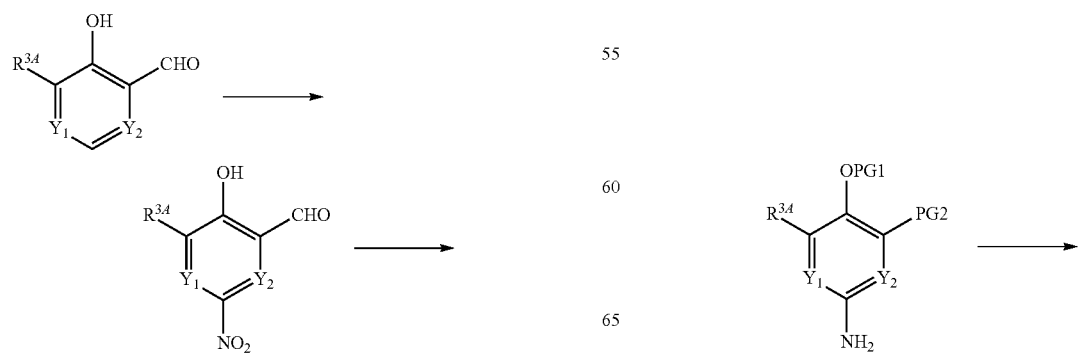

-continued

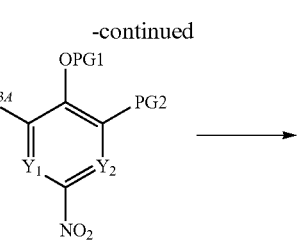

217

-continued

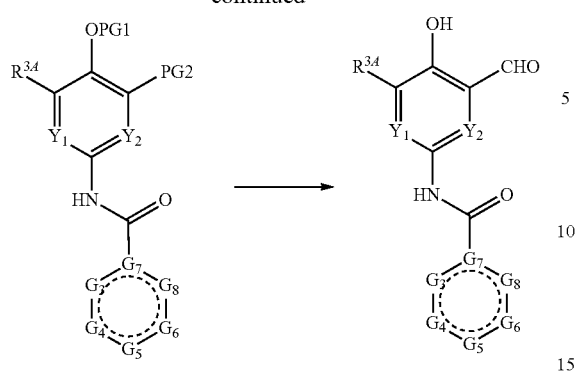

Scheme B-2B.

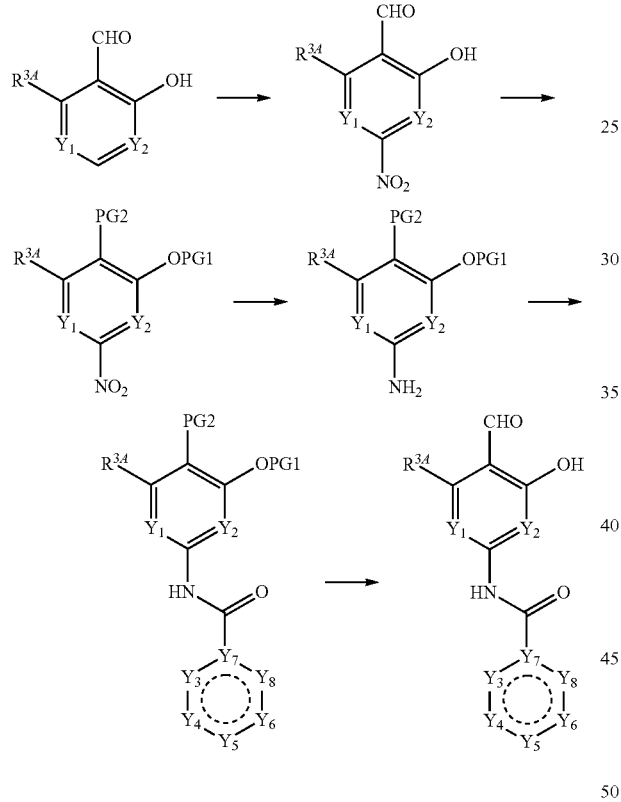

wherein $R^{3A}$, $Y_1$, $Y_2$, $Y_3$, $Y_4$, $Y_5$, $Y_6$, $Y_7$, and $Y_8$ are as defined for Formula (B), or any variation thereof detailed herein; and PG1 and PG2 are suitable protecting groups.

In some variations of the foregoing Scheme B-2A, compounds of the Formula (B) may be synthesized according to Scheme B-2Aa.

Scheme B-2Aa.

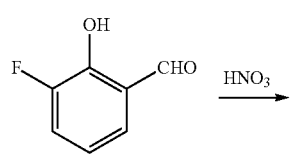

218

-continued

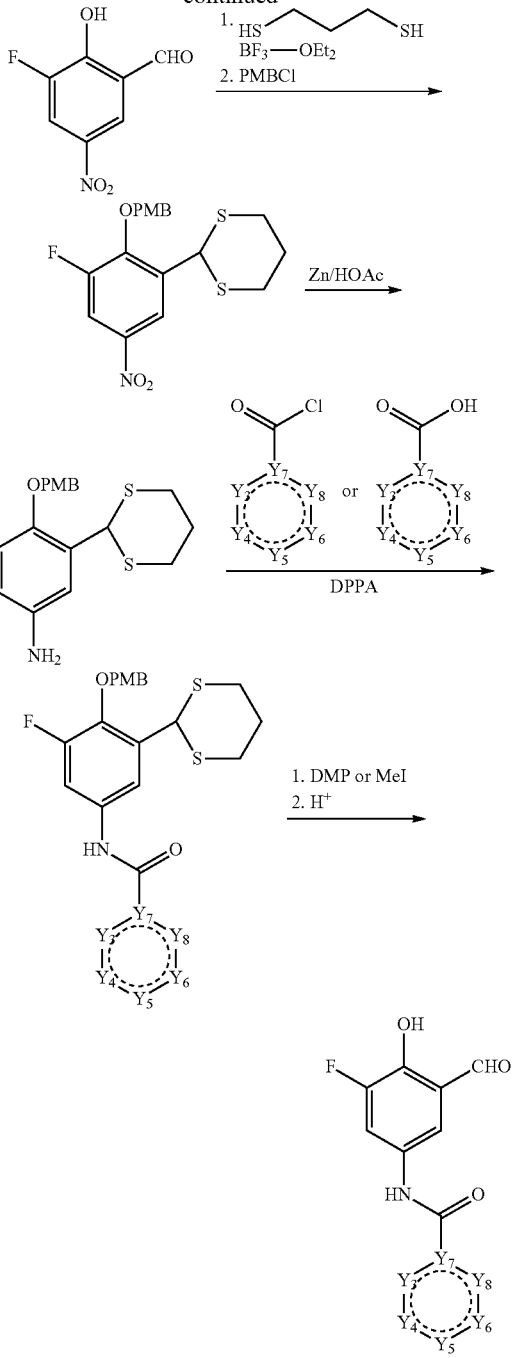

wherein $Y_3$, $Y_4$, $Y_5$, $Y_6$, $Y_7$, and $Y_8$ are as defined for Formula (B), or any variation thereof detailed herein.

In some embodiments, compounds of the Formula (B) may be synthesized according to Scheme B-3A or Scheme B-3B.

Scheme B-3A.

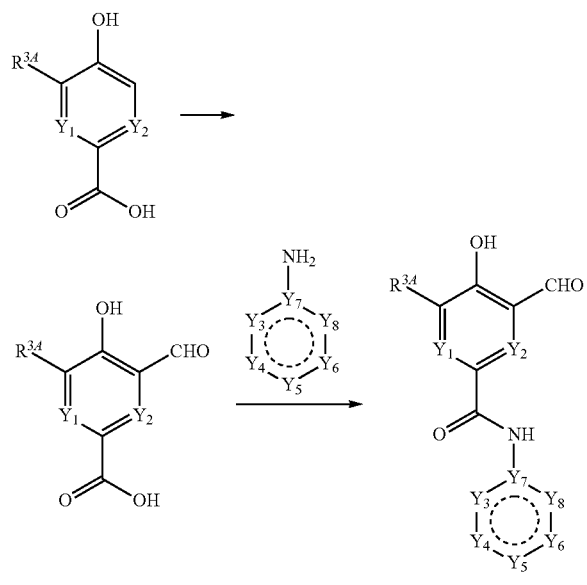

Scheme B-3Aa.

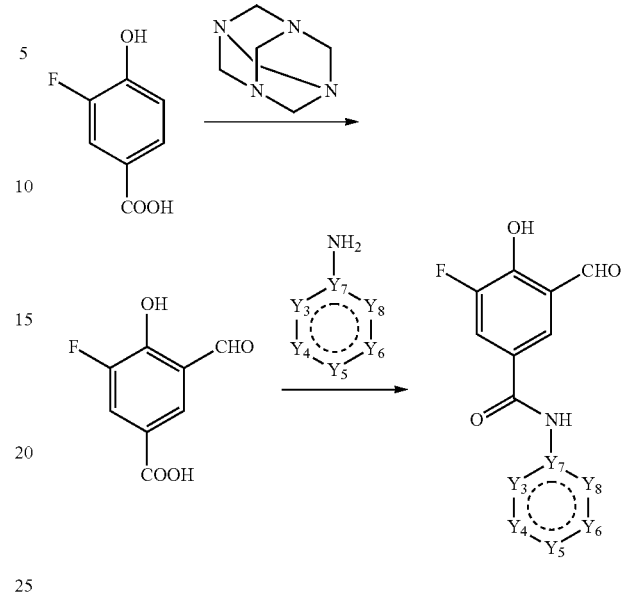

wherein $Y_3$, $Y_4$, $Y_5$, $Y_6$, $Y_7$, and $Y_8$ are as defined for Formula (B), or any variation thereof detailed herein.

In some embodiments, compounds of the Formula (B) may be synthesized according to Scheme B-4A or Scheme B-4B.

Scheme B-3B.

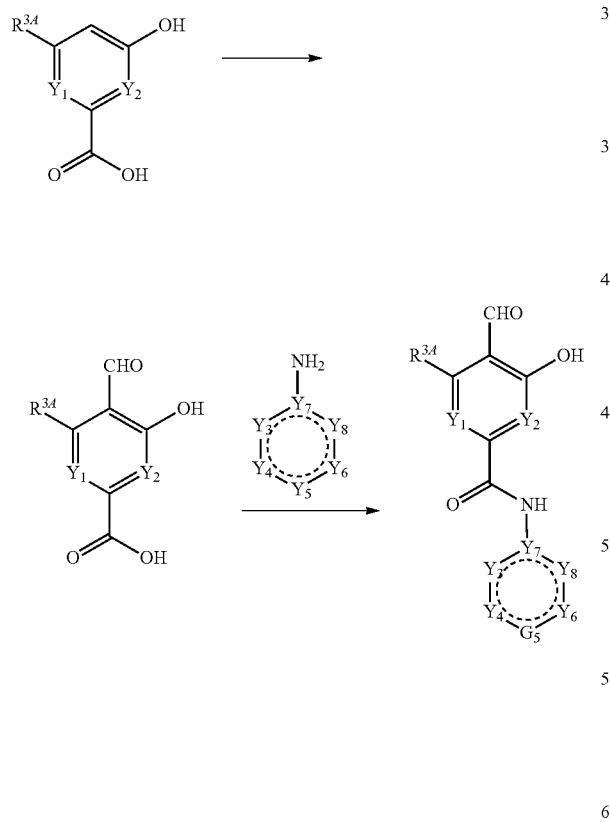

wherein $R^{3A}$, $Y_1$, $Y_2$, $Y_3$, $Y_4$, $Y_5$, $Y_6$, $Y_7$, and $Y_8$ are as defined for Formula (B), or any variation thereof detailed herein.

In some variations of the foregoing Scheme B-3A, compounds of the Formula (B) may be synthesized according to Scheme B-3Aa.

Scheme B-4A.

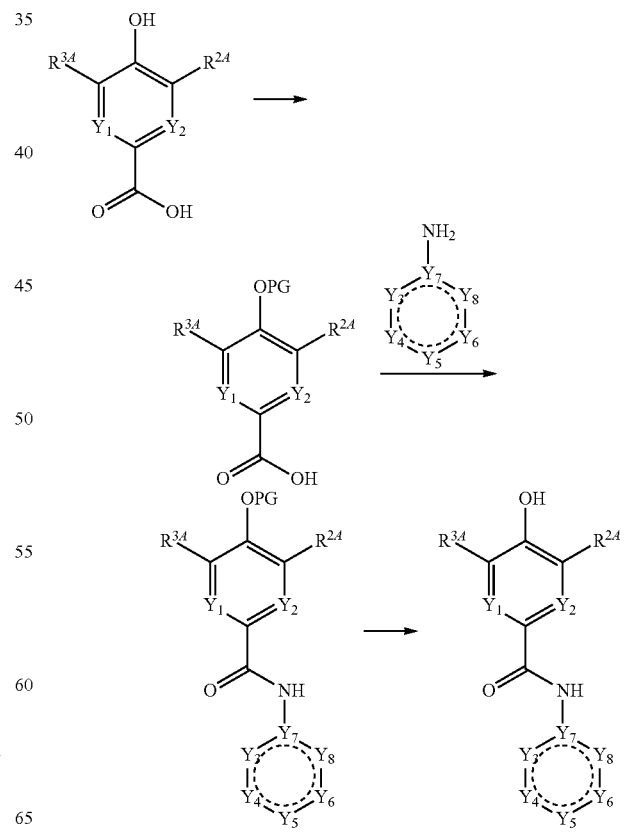

Scheme B-4B.

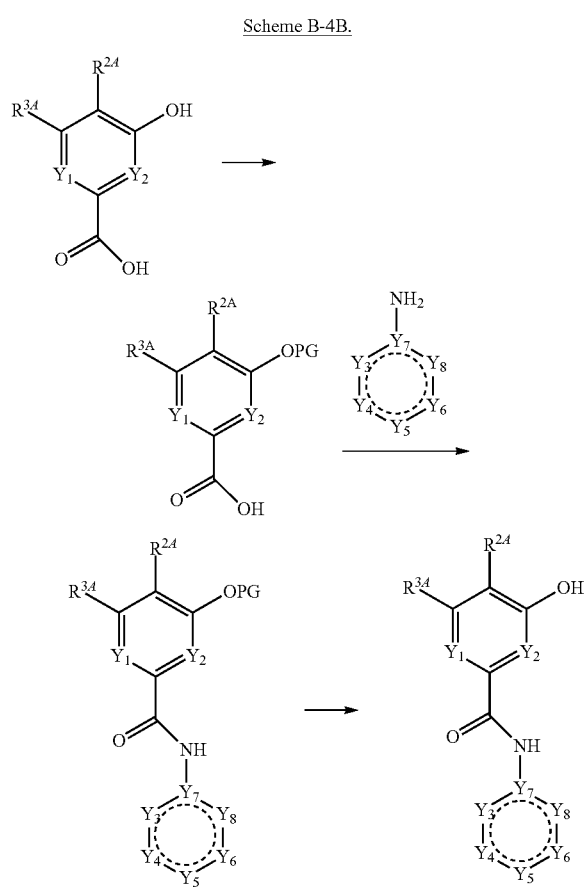

wherein $R^{2A}$, $R^{3A}$, $Y_1$, $Y_2$, $Y_3$, $Y_4$, $Y_5$, $Y_6$, $Y_7$, and $Y_8$ are as defined for Formula (B), or any variation thereof detailed herein, and PG is a suitable protecting group.

In some variations of the foregoing Scheme B-4A, compounds of the Formula (B) may be synthesized according to Scheme B-4Aa.

Scheme B-4Aa.

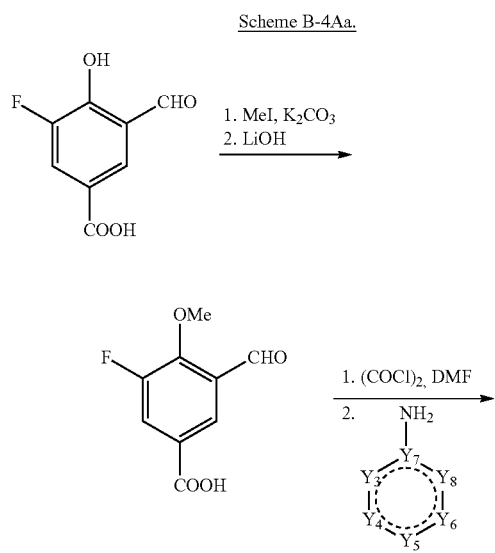

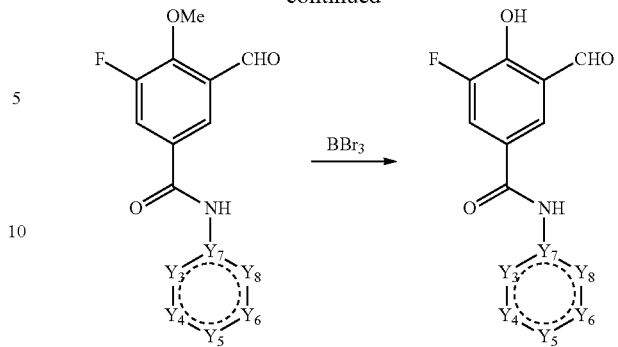

wherein $Y_3$, $Y_4$, $Y_5$, $Y_6$, $Y_7$, and $Y_8$ are as defined for Formula (B), or any variation thereof detailed herein.

Chemical Synthesis

Exemplary chemical entities useful in methods of the present disclosure will now be described by reference to the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups. Each of the reactions depicted in the general schemes may be run at a temperature from about 0° C. to the reflux temperature of the organic solvent used. Isotopically labeled compounds as described herein are prepared according to the methods described below, using suitably labeled starting materials. Such materials are generally available from commercial suppliers of radiolabeled chemical reagents.

EXAMPLES

The following examples are offered to illustrate but not to limit the present disclosure. One of skill in the art will recognize that the following synthetic reactions and schemes may be modified by choice of suitable starting materials and reagents in order to access other compounds of Formula (A) and Formula (B). The compounds are prepared using the general methods described above.

The following abbreviations are used throughout the Examples: BuLi (butyl lithium), DCM (dichloromethane), DMF (N,N-dimethylformamide), DMSO (dimethyl sulfoxide), EA or EtOAc (Ethyl acetate), MeOH (methanol), PdCl$_2$(dppf) ((1,1'-bis(diphenylphosphino)ferrocene))palladium(II) dichloride), dppf (1,1'-bis(diphenylphosphino)ferrocene), Pd(PPh$_3$)$_2$Cl$_2$ (bis(triphenylphosphine)palladium(II) dichloride), Pd(PPh$_3$)$_4$ (tetrakis(triphenylphosphine)palladium(0)), PMB (4-methoxybenzyl), PPh$_3$ (triphenylphosphane), Ruphos (2-Dicyclohexylphosphino-2',6'-diisopropoxybiphenyl), RuPhos Pd G3 ((2-Dicyclohexylphosphino-2',6'-diisopropoxy-1,1'-biphenyl)[2-(2'-amino-1,1'-biphenyl)]palladium(II) methanesulfonate ), TBAF (tetrabutylammonium fluoride), TFA (trifluoroacetic acid), THF (tetrahydrofuran), TMS-diazomethane (tetramethylsilyldiazomethane), TLC (thin layer chromatography), Xant- Phos (4,5-Bis(diphenylphosphino)-9,9-dimethylxanthene), XantPhos Pd G3 ([(4,5-Bis(diphenylphosphino)-9,9-dimethylxanthene)-2-(2'-amino-1,1'-biphenyl)]palladium(II) methanesulfonate), Xphos (2-Dicyclohexylphosphino-2',4',6'-triisopropylbiphenyl), and XPhos Pd G3 ((2-Dicyclohexylphosphino-2',4',6'-triisopropyl-1,1'-biphenyl)[2-(2'-amino-1,1'-biphenyl)]palladium(II) methanesulfonate).

Example A1: 2-hydroxy-3-methoxy-5-(1-phenyl-1H-pyrazol-4-yl)benzaldehyde (Compound No. A1)

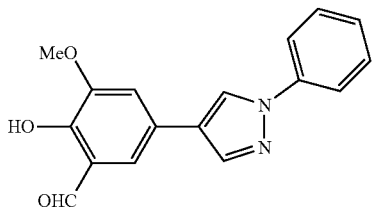 [SMILES: COc1cc(-c2cnn(-c3ccccc3)c2)cc(C=O)c1O]

In a 30 mL sealed cap glass vial, 5-bromo-2-hydroxy-3-methoxybenzaldehyde (231 mg, 1.0 mmol), 1-phenyl-4-(4,4,5,5-tetramethyl-1,3,2-dioxaborolan-2-yl)-1H-pyrazole (324 mg, 1.2 mmol) and $Na_2CO_3$ (666 mg, 6.0 mmol) were suspended in DMF-water (10 mL). Then bubbled Argon gas for one minute and added $Pd(PPh_3)_4$ (63 mg, 0.05 mmol) to the reaction vial and closed with sealed cap and continued at 105° C. for 16 hours on a stirrer plate with metallic beads contained dish. Then cooled to room temperature and diluted with water (10 mL) and transferred into a separating funnel using dichloromethane. Acidified the aqueous layer with 1.0 N HCl to pH~3.0-4.0 and extracted with additional dichloromethane (2×50 mL). The combined organic layer washed with brine, dried over sodium sulfate and evaporated. The resulted crude product purified using silica gel column chromatography (hexane through hexane-EtOAc (0-100%)) to give the title compound as a light yellow solid (63 mg, 21% yield). $^1$H NMR (500 MHz, Chloroform-d) δ 11.01 (s, 1H), 9.99 (s, 1H), 8.14 (s, 1H), 7.96 (s, 1H), 7.78-7.70 (m, 2H), 7.49 (t, J=7.9 Hz, 2H), 7.39-7.30 (m, 2H), 7.27 (m, 1H) 4.01 (s, 3H); LC-MS m/z [M+H]$^+$ calc'd for $C_{17}H_{14}N_2O_3$, 295; found, 295.

Example A2: 2-hydroxy-3-methoxy-5-(1-(2-morpholinoethyl)-1H-pyrazol-4-yl)benzaldehyde (Compound No. A2)

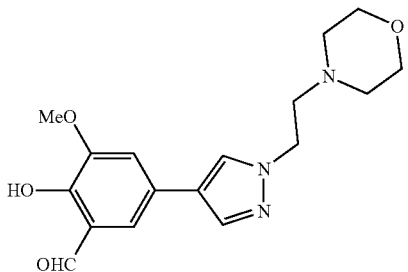 [SMILES: COc1cc(-c2cnn(CCN3CCOCC3)c2)cc(C=O)c1O]

The title compound was prepared from 5-bromo-2-hydroxy-3-methoxybenzaldehyde (231 mg, 1.0 mmol) and 4-(2-(4-(4,4,5,5-tetramethyl-1,3,2-dioxaborolan-2-yl)-1H-pyrazol-1-yl)ethyl)morpholine (369 mg, 1.2 mmol) as described in Example A1 to give the title compound as a yellow gummy solid (108 mg, 33% yield). $^1$H NMR (500 MHz, Chloroform-d) δ 10.95 (s, 1H), 9.95 (s, 1H), 7.68 (s, 1H), 7.50 (s, 1H), 7.46 (d, J=2.3 Hz, 1H), 7.18 (d, J=2.0 Hz, 1H), 4.27 (m, 2H), 3.97 (s, 3H), 3.69 (m, 6H), 2.81 (m, 2H), 2.48-2.41 (m, 4H); LC-MS m/z [M+H]$^+$ calc'd for $C_{17}H_{21}N_3O_4$, 332; found, 332.

Example A3: 5-(1-(3-chlorophenyl)-1H-pyrazol-4-yl)-2-hydroxy-3-methoxybenzaldehyde (Compound No. A3)

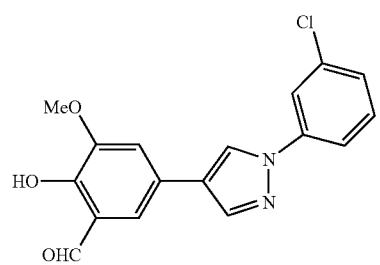 [SMILES: COc1cc(-c2cnn(-c3cccc(Cl)c3)c2)cc(C=O)c1O]

The title compound was prepared from 5-bromo-2-hydroxy-3-methoxybenzaldehyde (231 mg, 1.0 mmol) and 1-(3-chlorophenyl)-4-(4,4,5,5-tetramethyl-1,3,2-dioxaborolan-2-yl)-1H-pyrazole (267 mg, 1.2 mmol) as described in Example A1 to give the title compound cis/trans mixture as a yellow solid (53 mg, 16% yield). $^1$H NMR (500 MHz, Chloroform-d) δ 11.01 (s, 1H), 9.99 (s, 1H), 8.13 (s, 1H), 7.96 (s, 1H), 7.79 (t, J=2.1 Hz, 1H), 7.64 (dd, J=8.3, 2.1 Hz, 1H), 7.42 (t, J=8.1 Hz, 1H), 7.35 (d, J=1.9 Hz, 1H), 7.33-7.28 (m, 1H), 7.25 (d, J=1.9 Hz, 1H), 4.01 (s, 3H); LC-MS m/z [M+H]$^+$ calc'd for $C_{17}H_{13}ClN_2O_3$, 330; found, 330.

Example A4: 5-(1-benzyl-1H-pyrazol-4-yl)-2-hydroxy-3-methoxybenzaldehyde (Compound No. A4)

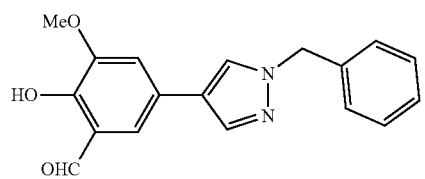 [SMILES: COc1cc(-c2cnn(Cc3ccccc3)c2)cc(C=O)c1O]

The title compound was prepared from 5-bromo-2-hydroxy-3-methoxybenzaldehyde (231 mg, 1.0 mmol) and 1-benzyl-4-(4,4,5,5-tetramethyl-1,3,2-dioxaborolan-2-yl)-1H-pyrazole (341 mg, 1.2 mmol) as described in Example A1 to give the title compound as a brown solid (115 mg, 37% yield). $^1$H NMR (500 MHz, Chloroform-d) δ 10.94 (s, 1H), 9.93 (s, 1H), 7.78 (s, 1H), 7.59 (d, J=3.9 Hz, 1H), 7.43-7.31 (m, 3H), 7.30-7.26 (m, 2H), 7.24 (d, J=2.0 Hz, 1H), 7.16 (d, J=1.9 Hz, 1H), 5.32 (s, 2H), 3.95 (s, 3H); LC-MS m/z [M+H]$^+$ calc'd for $C_{18}H_{16}N_2O_3$, 309; found, 309.

Example A5: 2-hydroxy-3-methoxy-5-(1-(tetrahydro-2H-pyran-4-yl)-1H-pyrazol-4-yl)benzaldehyde (Compound No. A5)

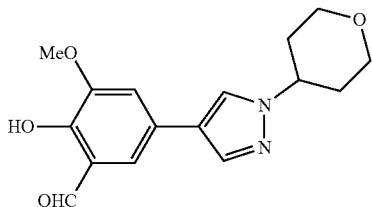 [SMILES: COc1cc(-c2cnn(C3CCOCC3)c2)cc(C=O)c1O]

The title compound was prepared from 5-bromo-2-hydroxy-3-methoxybenzaldehyde (231 mg, 1.0 mmol) and 1-(tetrahydro-2H-pyran-4-yl)-4-(4,4,5,5-tetramethyl-1,3,2-dioxaborolan-2-yl)-1H-pyrazole (334 mg, 1.2 mmol) as described in Example A1 to give the title compound as a brown solid (68 mg, 23% yield). $^1$H NMR (500 MHz, Chloroform-d) δ 10.95 (s, 1H), 9.95 (s, 1H), 7.75 (s, 1H), 7.69 (m, 1H), 7.27 (d, J=2.0 Hz, 1H), 7.19 (d, J=2.0 Hz, 1H), 4.39 (tt, J=10.4, 4.9 Hz, 1H), 4.21-4.08 (m, 2H), 3.97 (s, 3H), 3.57 (td, J=11.6, 2.9 Hz, 2H), 2.22-2.01 (m, 4H); LC-MS m/z [M+H]$^+$ calc'd for $C_{16}H_{18}N_2O_4$, 303; found, 303.

Example A6: 5-(1-(4-fluorophenyl)-1H-pyrazol-4-yl)-2-hydroxy-3-methoxybenzaldehyde (Compound No. A6)

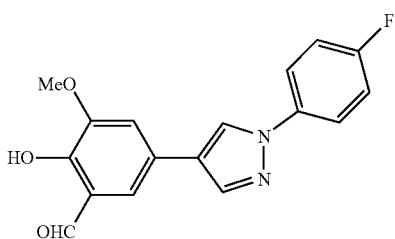 [SMILES: COc1cc(-c2cnn(-c3ccc(F)cc3)c2)cc(C=O)c1O]

The title compound was prepared from 5-bromo-2-hydroxy-3-methoxybenzaldehyde (231 mg, 1.0 mmol) and (1-(4-fluorophenyl)-1H-pyrazol-4-yl)boronic acid (247 mg, 1.2 mmol) as described in Example A1 to give the title compound as a yellow solid (52 mg, 17% yield). $^1$H NMR (500 MHz, Chloroform-d) δ 11.00 (s, 1H), 9.99 (s, 1H), 8.07 (d, J=0.7 Hz, 1H), 7.95 (d, J=0.7 Hz, 1H), 7.73-7.68 (m, 2H), 7.35 (d, J=2.1 Hz, 1H), 7.25 (d, J=2.0 Hz, 1H), 7.21-7.16 (m, 2H), 4.00 (s, 3H); LC-MS m/z [M+H]$^+$ calc'd for $C_{17}H_{13}FN_2O_3$, 313; found, 313.

Example A7: 2-hydroxy-3-methoxy-5-(1-(3-methoxypropyl)-1H-pyrazol-4-yl)benzaldehyde (Compound No. A7)

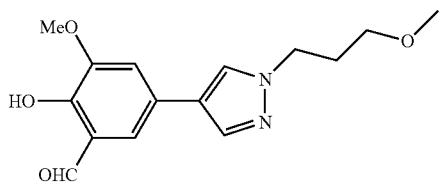 [SMILES: COCCCn1cc(-c2cc(C=O)c(O)c(OC)c2)cn1]

The title compound was prepared from 5-bromo-2-hydroxy-3-methoxybenzaldehyde (231 mg, 1.0 mmol) and 1-(3-methoxypropyl)-4-(4,4,5,5-tetramethyl-1,3,2-dioxaborolan-2-yl)-1H-pyrazole (319 mg, 1.2 mmol) as described in Example A1 to give the title compound as a black gummy solid (132 mg, 45% yield). $^1$H NMR (500 MHz, Chloroform-d) δ 10.95 (s, 1H), 9.95 (s, 1H), 7.74 (d, J=0.9 Hz, 1H), 7.62 (d, J=0.9 Hz, 1H), 7.26 (d, J=1.9 Hz, 1H), 7.19 (d, J=2.1 Hz, 1H), 4.26 (t, J=6.9 Hz, 2H), 3.97 (s, 3H), 3.37 (t, J=5.9 Hz, 2H), 3.35 (s, 3H), 2.16 (ddd, J=12.8, 7.0, 5.9 Hz, 2H); LC-MS m/z [M+H]$^+$ calc'd for $C_{15}H_{18}N_2O_4$, 291; found, 291.

Example A8: 2-hydroxy-3-methoxy-5-(1-(pyridin-2-ylmethyl)-1H-pyrazol-4-yl)benzaldehyde (Compound No. A8)

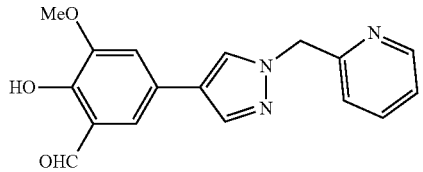

The title compound was prepared from 5-bromo-2-hydroxy-3-methoxybenzaldehyde (231 mg, 1.0 mmol) and 2-((4-(4,4,5,5-tetramethyl-1,3,2-dioxaborolan-2-yl)-1H-pyrazol-1-yl)methyl)pyridine (342 mg, 1.2 mmol) as described in Example A1 to give the title compound as an off-white solid (76 mg, 25% yield). $^1$H NMR (500 MHz, Chloroform-d) δ 10.96 (s, 1H), 9.94 (s, 1H), 8.60 (dt, J=4.8, 1.4 Hz, 1H), 7.79 (d, J=8.2 Hz, 2H), 7.67 (qd, J=7.5, 1.7 Hz, 1H), 7.27 (d, J=2.0 Hz, 1H), 7.25-7.22 (m, 1H), 7.19 (d, J=1.9 Hz, 1H), 7.15 (dt, J=7.9, 1.1 Hz, 1H), 5.47 (s, 2H), 3.96 (s, 3H); LC-MS m/z [M+H]$^+$ calc'd for $C_{17}H_{15}N_3O_3$, 310; found, 310.

Example A9: 2-hydroxy-3-methoxy-5-(1-(3-(trifluoromethyl)phenyl)-1H-pyrazol-4-yl)benzaldehyde (Compound No. A9)

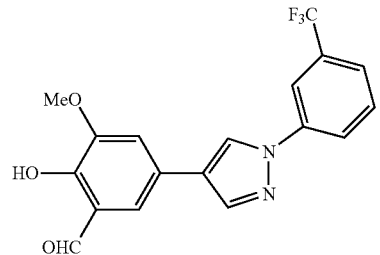 [SMILES: COc1cc(-c2cnn(-c3cccc(C(F)(F)F)c3)c2)cc(C=O)c1O]

The title compound was prepared from 5-bromo-2-hydroxy-3-methoxybenzaldehyde (231 mg, 1.0 mmol) and (1-(3-(trifluoromethyl)phenyl)-1H-pyrazol-4-yl)boronic acid (307 mg, 1.2 mmol) as described in Example A1 to give the title compound as a yellow solid (97 mg, 27% yield). $^1$H NMR (500 MHz, Chloroform-d) δ 11.01 (s, 1H), 9.99 (s, 1H), 8.19 (s, 1H), 8.02 (d, J=1.9 Hz, 1H), 7.99 (s, 1H), 7.96 (dt, J=7.9, 1.6 Hz, 1H), 7.62 (t, J=7.9 Hz, 1H), 7.58 (d, J=7.8 Hz, 1H), 7.37 (d, J=2.0 Hz, 1H), 7.26 (s, 1H), 4.01 (s, 3H); LC-MS m/z [M+H]$^+$ calc'd for $C_{18}H_{13}F_3N_2O_3$, 363; found, 363.

Example A10: 2-hydroxy-3-methoxy-5-(1-(4-methoxybenzyl)-1H-pyrazol-4-yl)benzaldehyde (Compound No. A10)

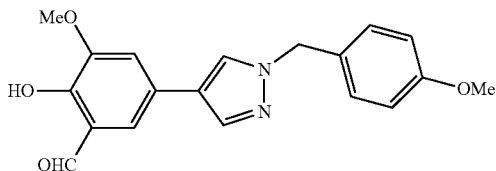 [SMILES: COc1ccc(Cn2cc(-c3cc(C=O)c(O)c(OC)c3)cn2)cc1]

The title compound was prepared from 5-bromo-2-hydroxy-3-methoxybenzaldehyde (231 mg, 1.0 mmol) and 1-(4-methoxybenzyl)-4-(4,4,5,5-tetramethyl-1,3,2-dioxaborolan-2-yl)-1H-pyrazole (377 mg, 1.2 mmol) as described in Example A1 to give the title compound as a yellow solid (90 mg, 27% yield). $^1$H NMR (500 MHz, Chloroform-d) δ 10.94 (s, 1H), 9.93 (s, 1H), 7.76 (s, 1H), 7.54 (s, 1H), 7.26-7.22 (m, 3H), 7.15 (d, J=1.9 Hz, 1H), 6.94-6.89 (m, 2H), 5.28 (s, 2H), 3.95 (s, 3H), 3.80 (s, 3H); LC-MS m/z [M+H]$^+$ calc'd for $C_{19}H_{18}N_2O_4$, 339; found, 339.

Example A11: 3-fluoro-2-hydroxy-5-(1-phenyl-1H-pyrazol-4-yl)benzaldehyde (Compound No. A11)

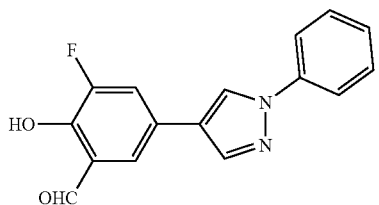 [SMILES: O=Cc1cc(-c2cnn(-c3ccccc3)c2)cc(F)c1O]

The title compound was prepared from 5-bromo-3-fluoro-2-hydroxybenzaldehyde (219 mg, 1.0 mmol) and 1-phenyl-4-(4,4,5,5-tetramethyl-1,3,2-dioxaborolan-2-yl)-1H-pyrazole (324 mg, 1.2 mmol) as described in Example A1 to give the title compound as a yellow solid (86 mg, 30% yield). $^1$H NMR (500 MHz, Chloroform-d) δ 10.89 (s, 1H), 10.00 (d, J=1.9 Hz, 1H), 8.13 (s, 1H), 7.95 (s, 1H), 7.76-7.70 (m, 2H), 7.58-7.52 (m, 2H), 7.49 (dt, J=8.4, 7.0 Hz, 2H), 7.38-7.29 (m, 1H); LC-MS m/z [M+H]$^+$ calc'd for $C_{16}H_{11}FN_2O_2$, 283; found, 283.

Example A12: 2-hydroxy-3-methyl-5-(1-phenyl-1H-pyrazol-4-yl)benzonitrile (Compound No. A12)

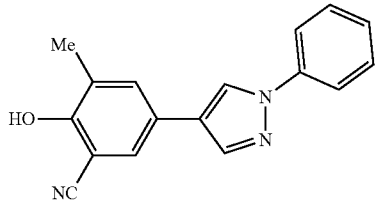 [SMILES: Cc1cc(-c2cnn(-c3ccccc3)c2)cc(C#N)c1O]

The title compound was prepared from 5-bromo-2-hydroxy-3-methylbenzonitrile (216 mg, 1.0 mmol) and 1-phenyl-4-(4,4,5,5-tetramethyl-1,3,2-dioxaborolan-2-yl)-1H-pyrazole (324 mg, 1.2 mmol) as described in Example A1 to give the title compound as an off-white solid (98 mg, 36% yield). $^1$H NMR (500 MHz, Chloroform-d) δ 8.10 (s, 1H), 7.92 (s, 1H), 7.74-7.69 (m, 2H), 7.55-7.52 (m, 1H), 7.52-7.49 (m, 1H), 7.49-7.45 (m, 2H), 7.33 (td, J=7.3, 1.0 Hz, 1H), 5.87 (s, 1H), 2.34 (s, 3H); LC-MS m/z [M+H]$^+$ calc'd for $C_{17}H_{13}N_3O$, 276; found, 276.

Example A13: 2,3-difluoro-5-(1-phenyl-1H-pyrazol-4-yl)phenol (Compound No. A13)

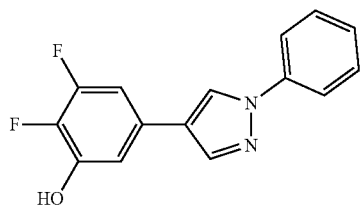 [SMILES: Oc1cc(-c2cnn(-c3ccccc3)c2)cc(F)c1F]

The title compound was prepared from 5-bromo-2,3-difluorophenol (209 mg, 1.0 mmol) and 1-phenyl-4-(4,4,5,5-tetramethyl-1,3,2-dioxaborolan-2-yl)-1H-pyrazole (324 mg, 1.2 mmol) as described in Example A1 to give the title compound as an off-white solid (172 mg, 63% yield). $^1$H NMR (500 MHz, Chloroform-d) δ 8.08 (s, 1H), 7.90 (s, 1H), 7.76-7.66 (m, 2H), 7.53-7.43 (m, 2H), 7.39-7.28 (m, 1H), 6.97 (dt, J=7.1, 2.0 Hz, 1H), 6.91 (ddd, J=10.7, 6.6, 2.2 Hz, 1H), 5.55 (s, 1H); LC-MS m/z [M+H]$^+$ calc'd for $C_{15}H_{10}F_2N_2O$, 273; found, 273.

Example A14: 2-fluoro-3-methyl-5-(1-phenyl-1H-pyrazol-4-yl)phenol (Compound No. A14)

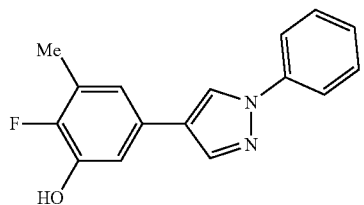 [SMILES: Cc1cc(-c2cnn(-c3ccccc3)c2)cc(O)c1F]

The title compound was prepared from 5-bromo-2-fluoro-3-methylphenol (205 mg, 1.0 mmol) and 1-phenyl-4-(4,4,5,5-tetramethyl-1,3,2-dioxaborolan-2-yl)-1H-pyrazole (324 mg, 1.2 mmol) as described in Example A1 to give the title compound as a white solid (102 mg, 38% yield). $^1$H NMR (500 MHz, Chloroform-d) δ 8.07 (s, 1H), 7.91 (s, 1H), 7.77-7.64 (m, 2H), 7.51-7.40 (m, 2H), 7.36-7.29 (m, 1H), 7.02 (dd, J=7.9, 2.3 Hz, 1H), 6.90 (dd, J=6.5, 2.2 Hz, 1H), 5.40 (s, 1H), 2.32 (d, J=2.1 Hz, 3H); LC-MS m/z [M+H]$^+$ calc'd for $C_{16}H_{13}FN_2O$, 269; found, 269.

Example A15: 2-chloro-6-fluoro-4-(1-phenyl-1H-pyrazol-4-yl)phenol (Compound No. A15)

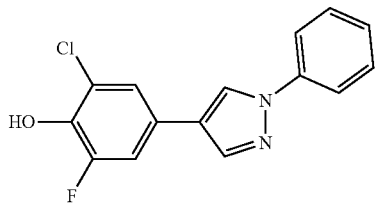 [SMILES: Oc1c(F)cc(-c2cnn(-c3ccccc3)c2)cc1Cl]

The title compound was prepared from 4-bromo-2-chloro-6-fluorophenol (225 mg, 1.0 mmol) and 1-phenyl-4-(4,4,5,5-tetramethyl-1,3,2-dioxaborolan-2-yl)-1H-pyrazole (324 mg, 1.2 mmol) as described in Example A1 to give the title compound as an off-white solid (196 mg, 68% yield). $^1$H NMR (500 MHz, Chloroform-d) δ 8.08 (s, 1H), 7.89 (d, J=4.1 Hz, 1H), 7.79-7.65 (m, 2H), 7.51-7.44 (m, 2H), 7.36-7.30 (m, 2H), 7.20 (dd, J=11.0, 2.1 Hz, 1H), 5.90 (s, 1H); LC-MS m/z [M+H]$^+$ calc'd for $C_{15}H_{10}ClFN_2O$, 290; found, 290.

Example A16: 2-fluoro-3-methoxy-5-(1-phenyl-1H-pyrazol-4-yl)phenol (Compound No. A16)

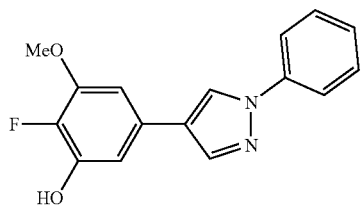 [SMILES: COc1cc(-c2cnn(-c3ccccc3)c2)cc(O)c1F]

The title compound was prepared from 5-bromo-2-fluoro-3-methoxyphenol (221 mg, 1.0 mmol) and 1-phenyl-4-(4,4,5,5-tetramethyl-1,3,2-dioxaborolan-2-yl)-1H-pyrazole (324 mg, 1.2 mmol) as described in Example A1 to give the title compound as a brown solid (205 mg, 72% yield). $^1$H NMR (500 MHz, Chloroform-d) δ 8.09 (s, 1H), 7.92 (s, 1H), 7.82-7.67 (m, 2H), 7.56-7.42 (m, 2H), 7.36-7.28 (m, 1H), 6.82 (dd, J=7.2, 2.1 Hz, 1H), 6.69 (dd, J=7.2, 2.1 Hz, 1H), 5.41 (d, J=3.9 Hz, 1H), 3.95 (s, 3H); LC-MS m/z [M+H]$^+$ calc'd for $C_{16}H_{13}FN_2O_2$, 285; found, 285.

Example A17: 2-chloro-6-methyl-4-(1-phenyl-1H-pyrazol-4-yl)phenol (Compound No. A17)

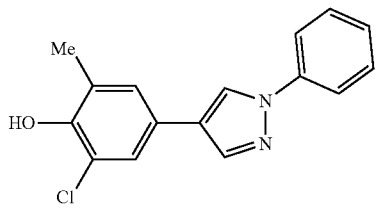 [SMILES: Cc1cc(-c2cnn(-c3ccccc3)c2)cc(Cl)c1O]

The title compound was prepared from 4-bromo-2-chloro-6-methylphenol (222 mg, 1.0 mmol) and 1-phenyl-4-(4,4,5,5-tetramethyl-1,3,2-dioxaborolan-2-yl)-1H-pyrazole (324 mg, 1.2 mmol) as described in Example A1 to give the title compound as a brown solid (179 mg, 63% yield). $^1$H NMR (500 MHz, Chloroform-d) δ 8.07 (s, 1H), 7.90 (s, 1H), 7.75-7.69 (m, 2H), 7.51-7.44 (m, 2H), 7.36 (d, J=2.1 Hz, 1H), 7.31 (td, J=7.4, 1.3 Hz, 1H), 7.23 (d, J=2.0 Hz, 1H), 5.60 (s, 1H), 2.33 (s, 3H); LC-MS m/z [M+H]$^+$ calc'd for $C_{16}H_{13}ClN_2O$, 286; found, 286.

Example A18: 2,6-difluoro-4-(1-phenyl-1H-pyrazol-4-yl)phenol (Compound No. A18)

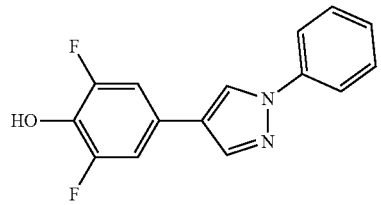 [SMILES: Oc1c(F)cc(-c2cnn(-c3ccccc3)c2)cc1F]

The title compound was prepared from 4-bromo-2,6-difluorophenol (209 mg, 1.0 mmol) and 1-phenyl-4-(4,4,5,5-tetramethyl-1,3,2-dioxaborolan-2-yl)-1H-pyrazole (324 mg, 1.2 mmol) as described in Example A1 to give the title compound as a white solid (195 mg, 72% yield). $^1$H NMR (500 MHz, Chloroform-d) δ 8.08 (s, 1H), 7.89 (s, 1H), 7.76-7.66 (m, 2H), 7.55-7.41 (m, 2H), 7.39-7.29 (m, 1H), 7.17-7.03 (m, 2H), 5.34 (s, 1H); LC-MS m/z [M+H]$^+$ calc'd for $C_{15}H_{10}F_2N_2O$, 273; found, 273.

Example A19: 3-fluoro-2-hydroxy-5-(1-(4-(pyrrolidin-1-yl)phenyl)-1H-pyrazol-4-yl)benzaldehyde (Compound No. A19)

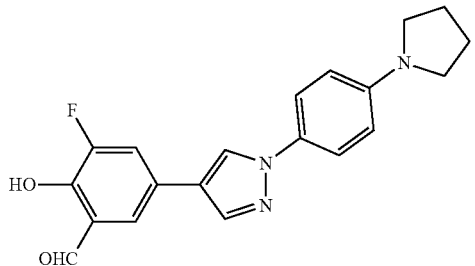 [SMILES: O=Cc1cc(-c2cnn(-c3ccc(N4CCCC4)cc3)c2)cc(F)c1O]

Step 1: 4-Bromo-1-(4-(pyrrolidin-1-yl)phenyl)-1H-pyrazole

A mixture of 4-bromo-1H-pyrazole (1.75 g, 12 mmol), 1-(4-bromophenyl)pyrrolidine (2.25 g, 10 mmol) potassium carbonate (4.14 g, 30 mmol), CuI (190 mg, 1.0 mmol), and (1S,2S)—N,N'-dimethyl-1,2-cyclohexanediamine (284 mg, 2 mmol) in toluene (100 mL) was refluxed overnight under nitrogen protection. The mixture was cooled to room temperature and filtered. The cake was washed with ethyl acetate. The filtrate and wash were combined and concentrated. The residue was purified by silica gel column to give the desired title product (910 mg, 31% yield). LC-MS m/z [M+H]$^+$ calc'd for $C_{13}H_{14}BrN_3$, 292; found, 292.

Step 2

A mixture of 4-Bromo-1-(4-(pyrrolidin-1-yl)phenyl)-1H-pyrazole (292 mg, 1.0 mmol), 3-fluoro-2-hydroxy-5-(4,4,5, 5-tetramethyl-1,3,2-dioxaborolan-2-yl)benzaldehyde (532 mg, 2.0 mmol), potassium carbonate (414 mg, 3.0 mmol), PdCl$_2$(dppf) (74 mg, 0.1 mmol) in dioxane/water (3:1) (12 mL) was heated at 95° C. for 2 hours under nitrogen atmosphere. The mixture was cooled to room temperature and filtered. The cake was washed with ethyl acetate. The filtrate and wash were combined, washed with water, dried over anhydrous sodium sulfate, and concentrated. The residue was purified by silica gel column chromatography to give the title product as a yellow solid (49 mg, 14% yield). $^1$H NMR (DMSO-d6, 400 MHz) δ: 10.87 (br, 1H), 10.32 (s, 1H), 8.83 (s, 1H), 8.12 (s, 1H), 7.92 (d, J=12.0 Hz, 1H), 7.79 (s, 1H), 7.64 (d, J=8.4 Hz, 2H), 6.64 (d, J=8.4 Hz, 2H), 3.27 (m, 4H), 1.97 (m, 4H); LC-MS m/z [M+H]$^+$ calc'd for C$_{20}$H$_{18}$FN$_3$O$_2$, 352; found, 352.

Example A20: 3-fluoro-2-hydroxy-5-(1-(4-(piperidin-1-yl)phenyl)-1H-pyrazol-4-yl)benzaldehyde (Compound No. A20)

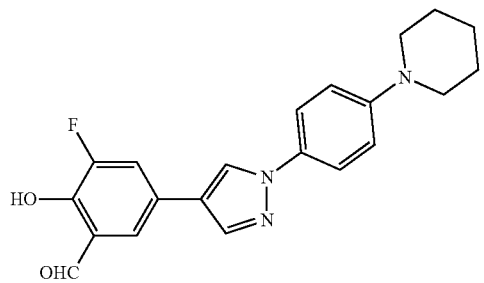

Step 1: 1-(4-(4-bromo-1H-pyrazol-1-yl)phenyl)piperidine

The title compound was prepared from 4-bromo-1H-pyrazole (1.75 g, 12 mmol), 1-(4-bromophenyl)piperidine (2.40 g, 10 mmol) as described in Step 1 of Example A19 to give the title compound (1.16 g, 38% yield). LC-MS m/z [M+H]$^+$ calc'd for C$_{14}$H$_{16}$BrN$_3$, 306; found, 306.

Step 2

The title compound was prepared from 1-(4-(4-bromo-1H-pyrazol-1-yl)phenyl)piperidine (306 mg, 1.0 mmol) and 3-fluoro-2-hydroxy-5-(4,4,5,5-tetramethyl-1,3,2-dioxaborolan-2-yl)benzaldehyde (532 mg, 2.0 mmol) as described in Step 2 of Example A19 to give the title compound as a yellow solid (128 mg, 35% yield). $^1$H NMR (DMSO-d6, 400 MHz) δ: 10.88 (s, 1H), 10.32 (s, 1H), 8.90 (s, 1H), 8.15 (s, 1H), 7.92 (d, J=12.0 Hz, 1H), 7.80 (s, 1H), 7.67 (d, J=8.8 Hz, 2H), 7.05 (d, J=8.8 Hz, 2H), 3.18 (m, 4H), 1.63 (m, 4H), 1.55 (m, 2H); LC-MS m/z [M+H]$^+$ calc'd for C$_{21}$H$_{20}$FN$_3$O$_2$, 366; found, 366.

Example A21: 3-fluoro-2-hydroxy-5-(1-(4-(morpholinophenyl)-1H-pyrazol-4-yl)benzaldehyde (Compound No. A21)

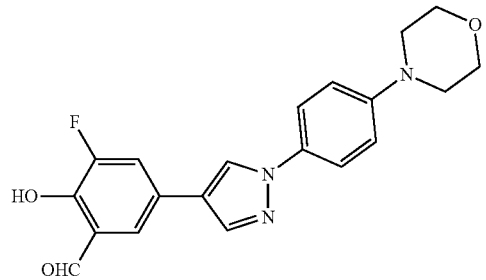 [SMILES: O=Cc1cc(-c2cnn(-c3ccc(N4CCOCC4)cc3)c2)cc(F)c1O]

Step 1: 4-(4-(4-bromo-1H-pyrazol-1-yl)phenyl)morpholine

The title compound was prepared from 4-bromo-1H-pyrazole (1.75 g, 12 mmol), 4-(4-bromophenyl)morpholine (2.42 g, 10 mmol) as described in Step 1 of Example A19 to give the title compound (1.14 g, 37% yield). LC-MS m/z [M+H]$^+$ calc'd for C$_{13}$H$_{14}$BrN$_3$O, 308; found, 308.

Step 2

The title compound was prepared from 4-(4-(4-bromo-1H-pyrazol-1-yl)phenyl)morpholine (308 mg, 1.0 mmol) and 3-fluoro-2-hydroxy-5-(4,4,5,5-tetramethyl-1,3,2-dioxaborolan-2-yl)benzaldehyde (532 mg, 2.0 mmol) as described in Step 2 of Example A19 to give the title compound as a yellow solid (63 mg, 17% yield). $^1$H NMR (DMSO-d6, 400 MHz) δ: 10.89 (s, 1H), 10.32 (s, 1H), 8.93 (s, 1H), 8.17 (s, 1H), 7.93 (d, J=12.0 Hz, 1H), 7.81 (s, 1H), 7.72 (d, J=8.8 Hz, 2H), 7.08 (d, J=9.2 Hz, 2H), 3.76 (m, 4H), 3.16 (m, 4H); LC-MS m/z [M+H]+ calc'd for C$_{20}$H$_{18}$FN$_3$O$_3$, 368; found, 368.

Example A22: 3-fluoro-2-hydroxy-5-(1-(3-(pyrrolidin-1-yl)phenyl)-1H-pyrazol-4-yl)benzaldehyde (Compound No. A22)

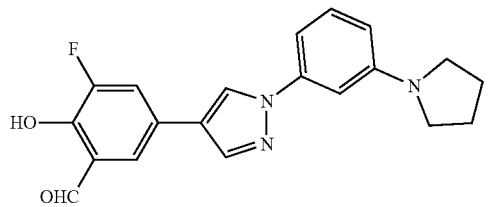 [SMILES: O=Cc1cc(-c2cnn(-c3cccc(N4CCCC4)c3)c2)cc(F)c1O]

Step 1: 4-bromo-1-(3-(pyrrolidin-1-yl)phenyl)-1H-pyrazole

The title compound was prepared from 4-bromo-1H-pyrazole (1.75 g, 12 mmol), 1-(3-bromophenyl)pyrrolidine (2.26 g, 10 mmol) as described in Step 1 of Example A19 to give the title compound (876 mg, 30% yield). LC-MS m/z [M+H]$^+$ calc'd for C$_{13}$H$_{14}$BrN$_3$, 292; found, 292.

Step 2

The title compound was prepared from 4-bromo-1-(3-(pyrrolidin-1-yl)phenyl)-1H-pyrazole (292 mg, 1.0 mmol) and 3-fluoro-2-hydroxy-5-(4,4,5,5-tetramethyl-1,3,2-dioxaborolan-2-yl)benzaldehyde (532 mg, 2.0 mmol) as described in Step 2 of Example A19 to give the title compound as light yellow solid (81 mg, 23% yield). $^1$H NMR (DMSO-d6, 400 MHz) δ: 10.91 (s, 1H), 10.33 (s, 1H), 9.02 (s, 1H), 8.20 (s, 1H), 7.96 (d, J=12.0 Hz, 1H), 7.83 (s, 1H), 7.26 (m, 1H), 7.07 (m, 1H), 7.00 (s, 1H), 6.48 (d, J=7.6 Hz, 1H), 3.31 (m, 4H), 1.99 (m, 4H); LC-MS m/z [M+H]$^+$ calc'd for $C_{20}H_{18}FN_3O_2$, 352; found, 352.

Example A23: 3-fluoro-2-hydroxy-5-(1-(3-(piperidin-1-yl)phenyl)-1H-pyrazol-4-yl)benzaldehyde (Compound No. A23)

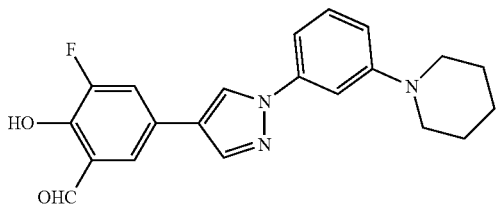 [SMILES: O=Cc1cc(-c2cnn(-c3cccc(N4CCCCC4)c3)c2)cc(F)c1O]

Step 1: 1-(3-(4-bromo-1H-pyrazol-1-yl)phenyl)piperidine

The title compound was prepared from 4-bromo-1H-pyrazole (1.75 g, 12 mmol), 1-(3-bromophenyl)piperidine (2.40 g, 10 mmol) as described in Step 1 of Example A19 to give the title compound (1.28 g, 42% yield). LC-MS m/z [M+H]$^+$ calc'd for $C_{14}H_{16}BrN_3$, 306; found, 306.

Step 2

The title compound was prepared from 1-(3-(4-bromo-1H-pyrazol-1-yl)phenyl)piperidine (306 mg, 1.0 mmol) and 3-fluoro-2-hydroxy-5-(4,4,5,5-tetramethyl-1,3,2-dioxaborolan-2-yl)benzaldehyde (532 mg, 2.0 mmol) as described in Step 2 of Example A19 to give the title compound as a yellow solid (110 mg, 30% yield). $^1$H NMR (DMSO-d6, 400 MHz) δ: 10.91 (s, 1H), 10.33 (s, 1H), 9.05 (s, 1H), 8.21 (s, 1H), 7.95 (d, J=12.0 Hz, 1H), 7.83 (s, 1H), 7.38 (s, 1H), 7.28 (m, 1H), 7.23 (m, 1H), 6.87 (d, J=8.0 Hz, 1H), 3.25 (m, 4H), 1.65 (m, 4H), 1.58 (m, 2H); LC-MS m/z [M+H]$^+$ calc'd for $C_{21}H_{20}FN_3O_2$, 366; found, 366.

Example A24: 3-fluoro-2-hydroxy-5-(1-(3-morpholinophenyl)-1H-pyrazol-4-yl)benzaldehyde (Compound No. A24)

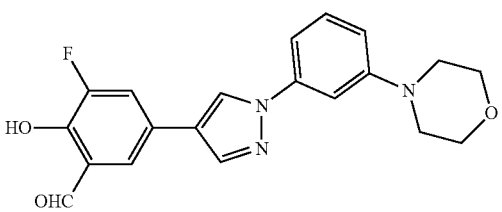

Step 1: 4-(3-(4-bromo-1H-pyrazol-1-yl)phenyl)morpholine

The title compound was prepared from 4-bromo-1H-pyrazole (1.75 g, 12 mmol), 4-(3-bromophenyl)morpholine (2.42 g, 10 mmol) as described in Step 1 of Example A19 to give the title compound (524 mg, 17% yield). LC-MS m/z [M+H]$^+$ calc'd for $C_{13}H_{14}BrN_3O$, 308; found, 308.

Step 2

The title compound was prepared from 4-(3-(4-bromo-1H-pyrazol-1-yl)phenyl)morpholine (308 mg, 1.0 mmol) and 3-fluoro-2-hydroxy-5-(4,4,5,5-tetramethyl-1,3,2-dioxaborolan-2-yl)benzaldehyde (532 mg, 2.0 mmol) as described in Step 2 of Example A19 to give the title compound as a yellow solid (144 mg, 39% yield). $^1$H NMR (DMSO-d6, 400 MHz) δ: 10.92 (s, 1H), 10.33 (s, 1H), 9.06 (s, 1H), 8.22 (s, 1H), 7.95 (d, J=12.0 Hz, 1H), 7.83 (s, 1H), 7.40 (s, 1H), 7.33 (m, 2H), 6.90 (d, J=7.6 Hz, 1H), 3.78 (m, 4H), 3.22 (m, 4H); LC-MS m/z [M+H]$^+$ calc'd for $C_{20}H_{18}FN_3O_3$, 368; found, 368.

Example A25: 2-hydroxy-3-methoxy-5-(1-phenyl-1H-pyrazol-3-yl)benzaldehyde (Compound No. A25)

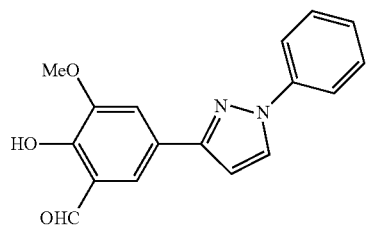 [SMILES: COc1cc(-c2ccn(-c3ccccc3)n2)cc(C=O)c1O]

The title compound was prepared from 5-bromo-2-hydroxy-3-methoxybenzaldehyde (231 mg, 1.0 mmol) and 1-phenyl-3-(4,4,5,5-tetramethyl-1,3,2-dioxaborolan-2-yl)-1H-pyrazole (324 mg, 1.2 mmol) as described in Example A1 to give the title compound as a yellow solid (163 mg, 55% yield). $^1$H NMR (500 MHz, Chloroform-d) δ 11.13 (s, 1H), 10.01 (s, 1H), 7.98 (d, J=2.5 Hz, 1H), 7.80-7.73 (m, 3H), 7.68 (d, J=1.9 Hz, 1H), 7.49 (dd, J=8.6, 7.4 Hz, 2H), 7.32 (td, J=7.4, 1.1 Hz, 1H), 6.75 (d, J=2.5 Hz, 1H), 4.03 (s, 3H); LC-MS m/z [M+H]$^+$ calc'd for $C_{17}H_{14}N_2O_3$, 295; found, 295.

Example A26: 3-fluoro-2-hydroxy-5-(1-phenyl-1H-pyrazol-3-yl)benzaldehyde (Compound No. A26)

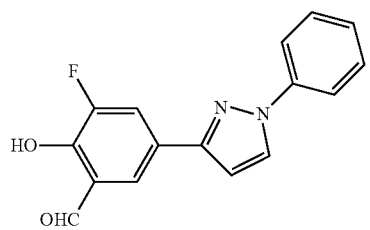 [SMILES: O=Cc1cc(-c2ccn(-c3ccccc3)n2)cc(F)c1O]

The title compound was prepared from 5-bromo-3-fluoro-2-hydroxybenzaldehyde (219 mg, 1.0 mmol) and 1-phenyl-3-(4,4,5,5-tetramethyl-1,3,2-dioxaborolan-2-yl)-1H-pyrazole (324 mg, 1.2 mmol) as described in Example A1 to give the title compound as a yellow solid (168 mg, 59% yield). $^1$H NMR (500 MHz, Chloroform-d) δ 10.98 (s, 1H), 10.02 (d, J=1.9 Hz, 1H), 7.98 (d, J=2.5 Hz, 1H), 7.92 (d, J=10.9 Hz, 2H), 7.79-7.74 (m, 2H), 7.53-7.45 (m, 2H), 7.38-7.29 (m, 1H), 6.73 (d, J=2.5 Hz, 1H); LC-MS m/z [M+H]$^+$ calc'd for $C_{16}H_{11}FN_2O_2$, 283; found, 283.

Example A27: 3-fluoro-2-hydroxy-5-(1-(4-(pyrrolidin-1-yl)phenyl)-1H-pyrazol-3-yl)benzaldehyde (Compound No. A27)

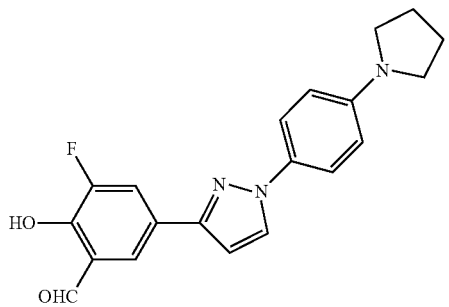 [SMILES: O=Cc1cc(-c2ccn(-c3ccc(N4CCCC4)cc3)n2)cc(F)c1O]

Step 1: 3-bromo-1-(4-(pyrrolidin-1-yl)phenyl)-1H-pyrazole

The title compound was prepared from 3-bromo-1H-pyrazole (1.75 g, 12 mmol), 1-(4-bromophenyl)pyrrolidine (2.26 g, 10 mmol) as described in Step 1 of Example A19 to give the title compound (379 mg, 13% yield). LC-MS m/z [M+H]$^+$ calc'd for $C_{13}H_{14}BrN_3$, 292; found, 292.

Step 2

The title compound was prepared from 3-bromo-1-(4-(pyrrolidin-1-yl)phenyl)-1H-pyrazole (292 mg, 1.0 mmol) and 3-fluoro-2-hydroxy-5-(4,4,5,5-tetramethyl-1,3,2-dioxaborolan-2-yl)benzaldehyde (532 mg, 2.0 mmol) as described in Step 2 of Example A19 to give the title compound as a yellow solid (77 mg, 22% yield). $^1$H NMR (DMSO-d6, 400 MHz) δ: 11.05 (br, 1H), 10.34 (s, 1H), 8.34 (s, 1H), 8.02 (m, 2H), 7.66 (m, 2H), 6.98 (s, 1H), 6.63 (m, 2H), 3.27 (m, 4H), 1.98 (m, 4H); LC-MS m/z [M+H]$^+$ calc'd for $C_{20}H_{18}FN_3O_2$, 352; found, 352.

Example A28: 3-fluoro-2-hydroxy-5-(1-(4-(piperidin-1-yl)phenyl)-1H-pyrazol-3-yl)benzaldehyde (Compound No. A28)

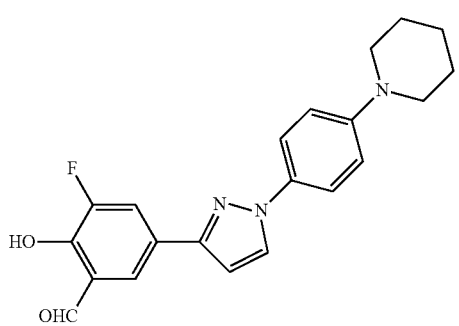 [SMILES: O=Cc1cc(-c2ccn(-c3ccc(N4CCCCC4)cc3)n2)cc(F)c1O]

Step 1: 1-(4-(3-bromo-1H-pyrazol-1-yl)phenyl)piperidine

The title compound was prepared from 3-bromo-1H-pyrazole (1.75 g, 12 mmol.), 1-(4-bromophenyl)piperidine (2.40 g, 10 mmol) as described in Step 1 of Example A19 to give the title compound (1.01 g, 33% yield). LC-MS m/z [M+H]$^+$ calc'd for $C_{14}H_{16}BrN_3$, 306; found, 306.

Step 2

The title compound was prepared from 1-(4-(3-bromo-1H-pyrazol-1-yl)phenyl)piperidine (306 mg, 1.0 mmol) and 3-fluoro-2-hydroxy-5-(4,4,5,5-tetramethyl-1,3,2-dioxaborolan-2-yl)benzaldehyde (532 mg, 2.0 mmol) as described in Step 2 of Example A19 to give the title compound as a yellow solid (92 mg, 25% yield). $^1$H NMR (DMSO-d6, 400 MHz) δ: 11.06 (br, 1H), 10.34 (s, 1H), 8.40 (s, 1H), 8.02 (m, 2H), 7.70 (d, J=8.8 Hz, 2H), 7.03 (m, 3H), 3.18 (m, 4H), 1.64 (m, 4H), 1.55 (m, 2H); LC-MS m/z [M+H]$^+$ calc'd for $C_{21}H_{20}FN_3O_2$, 366; found, 366.

Example A29: 3-fluoro-2-hydroxy-5-(1-(4-morpholinophenyl)-1H-pyrazol-3-yl)benzaldehyde (Compound No. A29)

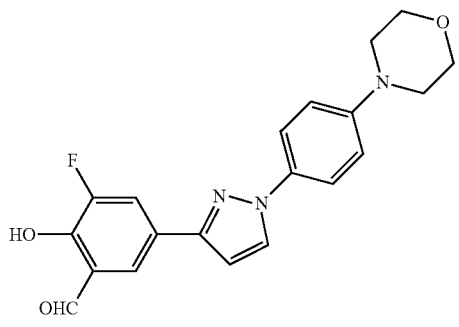 [SMILES: O=Cc1cc(-c2ccn(-c3ccc(N4CCOCC4)cc3)n2)cc(F)c1O]

Step 1: 4-(4-(3-bromo-1H-pyrazol-1-yl)phenyl)morpholine

The title compound was prepared from 3-bromo-1H-pyrazole (1.75 g, 12 mmol.), 4-(4-bromophenyl)morpholine (2.42 g, 10 mmol) as described in Step 1 of Example A19 to give the title compound (585 mg, 19% yield). LC-MS m/z [M+H]$^+$ calc'd for $C_{13}H_{14}BrN_3O$, 308; found, 308.

Step 2

The title compound was prepared from 4-(4-(3-bromo-1H-pyrazol-1-yl)phenyl)morpholine (308 mg, 1.0 mmol) and 3-fluoro-2-hydroxy-5-(4,4,5,5-tetramethyl-1,3,2-dioxaborolan-2-yl)benzaldehyde (532 mg, 2.0 mmol) as described in Step 2 of Example A19 to give the title compound as a yellow solid (118 mg, 32% yield). $^1$H NMR (DMSO-d6, 400 MHz) δ: 11.07 (br, 1H), 10.33 (s, 1H), 8.02 (m, 2H), 7.74 (d, J=8.8 Hz, 2H), 7.07 (d, J=8.8 Hz, 2H), 7.01 (s, 1H), 3.76 (m, 4H), 3.16 (m, 4H); LC-MS m/z [M+H]$^+$ calc'd for $C_{20}H_{18}FN_3O_3$, 368; found, 368.

Example A30: 3-fluoro-2-hydroxy-5-(1-(3-(pyrrolidin-1-yl)phenyl)-1H-pyrazol-3-yl)benzaldehyde (Compound No. A30)

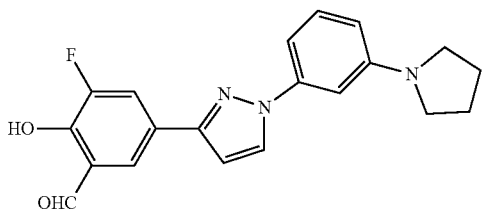 [SMILES: O=Cc1cc(-c2ccn(-c3cccc(N4CCCC4)c3)n2)cc(F)c1O]

Step 1: 3-bromo-1-(3-(pyrrolidin-1-yl)phenyl)-1H-pyrazole

The title compound was prepared from 3-bromo-1H-pyrazole (1.75 g, 12 mmol.), 1-(3-bromophenyl)pyrrolidine (2.26 g, 10 mmol) as described in Step 1 of Example A19 to give the title compound (584 mg, 20% yield). LC-MS m/z [M+H]$^+$ calc'd for $C_{13}H_{14}BrN_3$, 292; found, 292.

Step 2

The title compound was prepared from 3-bromo-1-(3-(pyrrolidin-1-yl)phenyl)-1H-pyrazole (292 mg, 1.0 mmol) and 3-fluoro-2-hydroxy-5-(4,4,5,5-tetramethyl-1,3,2-dioxaborolan-2-yl)benzaldehyde (532 mg, 2.0 mmol) as described in Step 2 of Example A19 to give the title compound as a light yellow solid (67 mg, 19% yield). $^1$H NMR (CDCl$_3$, 400 MHz) δ: 10.99 (s, 1H), 10.02 (s, 1H), 7.94 (m, 3H), 7.31 (m, 1H), 6.97 (m, 2H), 6.70 (s, 1H), 6.55 (m, 1H), 3.39 (m, 4H), 2.07 (m, 4H); LC-MS m/z [M+H]$^+$ calc'd for $C_{20}H_{18}FN_3O_2$, 352; found, 352.

Example A31: 3-fluoro-2-hydroxy-5-(1-(3-(piperidin-1-yl)phenyl)-1H-pyrazol-3-yl)benzaldehyde (Compound No. A31)

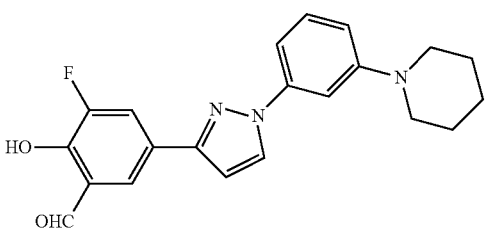 [SMILES: O=Cc1cc(-c2ccn(-c3cccc(N4CCCCC4)c3)n2)cc(F)c1O]

Step 1: 1-(3-(3-bromo-1H-pyrazol-1-yl)phenyl)piperidine

The title compound was prepared from 3-bromo-1H-pyrazole (1.75 g, 12 mmol.), 1-(3-bromophenyl)piperidine (2.40 g, 10 mmol) as described in Step 1 of Example A19 to give the title compound (370 mg, 12% yield). LC-MS m/z [M+H]$^+$ calc'd for $C_{14}H_{16}BrN_3$, 306; found, 306.

Step 2

The title compound was prepared from 1-(3-(3-bromo-1H-pyrazol-1-yl)phenyl)piperidine (306 mg, 1.0 mmol) and 3-fluoro-2-hydroxy-5-(4,4,5,5-tetramethyl-1,3,2-dioxaborolan-2-yl)benzaldehyde (532 mg, 2.0 mmol) as described in Step 2 of Example A19 to give the title compound as a light yellow solid (83 mg, 27% yield). $^1$H NMR (DMSO-d6, 400 MHz) δ: 11.10 (br, 1H), 10.34 (s, 1H), 8.57 (s, 1H), 8.04 (m, 2H), 7.39 (s, 1H), 7.28 (m, 2H), 7.05 (s, 1H), 6.89 (m, 1H), 3.24 (m, 4H), 1.65 (m, 4H), 1.57 (m, 2H); LC-MS m/z [M+H]+ calc'd for $C_{21}H_{20}FN_3O_2$, 366; found, 366.

Example A32: 3-fluoro-2-hydroxy-5-(1-(3-morpholinophenyl)-1H-pyrazol-3-yl)benzaldehyde (Compound No. A32)

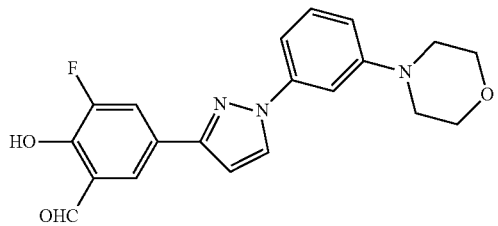 [SMILES: O=Cc1cc(-c2ccn(-c3cccc(N4CCOCC4)c3)n2)cc(F)c1O]

Step 1: 4-(3-(3-bromo-1H-pyrazol-1-yl)phenyl)morpholine

The title compound was prepared from 3-bromo-1H-pyrazole (1.75 g, 12 mmol.), 4-(3-bromophenyl)morpholine (2.42 g, 10 mmol) as described in Step 1 of Example A19 to give the title compound (524 mg, 17% yield). LC-MS m/z [M+H]$^+$ calc'd for $C_{13}H_{14}BrN_3O$, 308; found, 308.

Step 2

The title compound was prepared from 4-(3-(3-bromo-1H-pyrazol-1-yl)phenyl)morpholine (308 mg, 1.0 mmol) and 3-fluoro-2-hydroxy-5-(4,4,5,5-tetramethyl-1,3,2-dioxaborolan-2-yl)benzaldehyde (532 mg, 2.0 mmol) as described in Step 2 of Example A19 to give the title compound as a white solid (114 mg, 31% yield). $^1$H NMR (CDCl$_3$, 400 MHz) δ: 11.01 (br, 1H), 10.03 (s, 1H), 7.98 (s, 1H), 7.93 (m, 2H), 7.55 (m, 1H), 7.40 (m, 1H), 7.29 (m, 1H), 7.02 (m, 1H), 6.73 (s, 1H), 3.99 (m, 4H), 3.33 (m, 4H); LC-MS m/z [M−H]$^-$ calc'd for $C_{20}H_{18}FN_3O_3$, 366; found, 366.

Example A33: (E)-2-fluoro-6-(((4-methylpiperazin-1-yl)imino)methyl)-4-(1-phenyl-1H-pyrazol-3-yl)phenol (Compound No. A33)

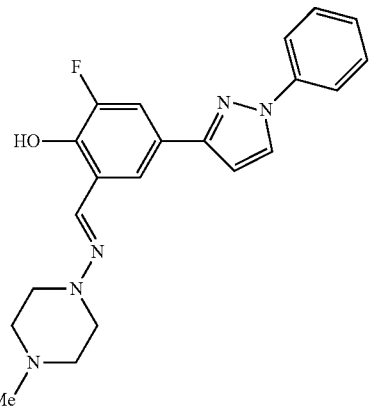

In a 20 mL sealed cap glass vial 3-fluoro-2-hydroxy-5-(1-phenyl-1H-pyrazol-3-yl)benzaldehyde (85 mg, 0.3 mmol) and 4-methylpiperazin-1-amine (65 mg, 0.3 mmol) were suspended in ethanol (5 mL) and added trifluoroacetic acid (3 drops) and warmed the mixture to get a clear solution. Then stirred at room temp for 2 hours, the resulting crashed product collected by vacuum filtration and washed the product with small amount of ethanol to give the title product as white solid (85 mg, 75% yield). $^1$H NMR (500 MHz, Chloroform-d) δ 11.86 (s, 1H), 7.94 (d, J=2.5 Hz, 1H), 7.77-7.70 (m, 3H), 7.53 (d, J=2.7 Hz, 1H), 7.50-7.42 (m, 3H), 7.29 (td, J=7.3, 1.3 Hz, 2H), 6.67 (d, J=2.5 Hz, 1H), 3.23 (t, J=5.1 Hz, 4H), 2.77-2.50 (m, 4H), 2.37 (s, 3H); LC-MS m/z [M−H]$^-$ calc'd for $C_{21}H_{22}FN_5O$, 380; found, 380.

Example A34: 2-(1,3-dioxan-2-yl)-6-fluoro-4-(1-(4-(pyrrolidin-1-yl)phenyl)-1H-pyrazol-4-yl)phenol (Compound No. A34)

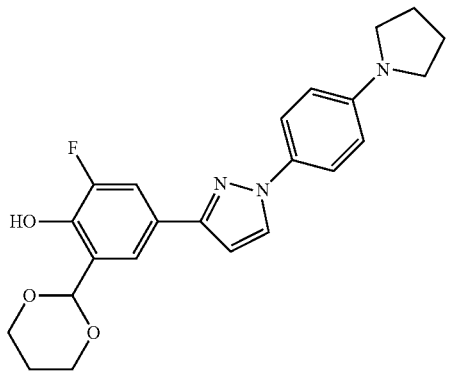 [SMILES: Oc1c(F)cc(-c2ccn(-c3ccc(N4CCCC4)cc3)n2)cc1C1OCCCO1]

A solution of 3-fluoro-2-hydroxy-5-(1-(4-(pyrrolidin-1-yl)phenyl)-1H-pyrazol-4-yl)benzaldehyde (35 mg, 0.1 mmol), propane-1,3-diol (30 mg, 0.4 mmol), and TsOH (5 mg, 0.03 mmol) in toluene was refluxed for 2 hours. The solvent was removed mostly and the residue purified by prep-TLC to give desired product as white solid (13 mg, 32% yield). $^1$H NMR (CDCl$_3$, 300 MHz) δ: 7.95 (s, 1H), 7.86 (s, 1H), 7.74 (m, 1H), 7.55 (d, J=9.0 Hz, 2H), 7.22 (m, 1H), 6.71 (m, 2H), 4.36 (m, 2H), 4.08 (m, 2H), 3.37 (m, 4H), 2.23 (m, 1H), 2.08 (m, 5H); LC-MS m/z [M+H]$^+$ calc'd for $C_{23}H_{24}FN_3O_3$, 411; found, 411.

General Procedure for Example A35 to Example A41

3-fluoro-2-hydroxy-5-(1-(4-(pyrrolidin-1-yl)phenyl)-1H-pyrazol-4-yl)benzaldehyde (1 eq.) and amine compound (2 eq.) were dissolved in ethanol or methanol. The reaction was refluxed for 2 hours. The solvent was removed mostly and the residue was filtered. The cake was washed with ethanol and dried in vacuo to give desired product.

Example A35: (E)-2-fluoro-6-(((4-methylpiperazin-1-yl)imino)methyl)-4-(1-(4-(pyrrolidin-1-yl)phenyl)-1H-pyrazol-4-yl)phenol (Compound No. A35)

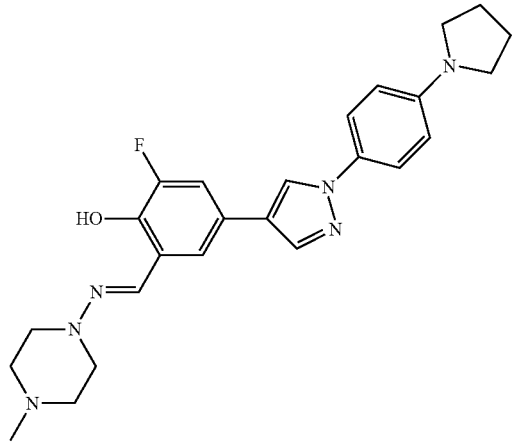 [SMILES: CN1CCN(/N=C/c2cc(-c3cnn(-c4ccc(N5CCCC5)cc4)c3)cc(F)c2O)CC1]

The title compound was prepared from 3-fluoro-2-hydroxy-5-(1-(4-(pyrrolidin-1-yl)phenyl)-1H-pyrazol-4-yl)benzaldehyde (100 mg, 0.28 mmol) and 4-methylpiperazin-1-amine (64 mg, 0.56 mmol) as described in above general procedure to give the title compound as white solid (80 mg, 63% yield). $^1$H NMR (CDCl$_3$, 400 MHz) δ: 11.60 (br, 1H), 7.93 (s, 1H), 7.85 (s, 1H), 7.72 (s, 1H), 7.52 (d, J=8.4 Hz, 2H), 7.21 (d, J=11.6 Hz, 1H), 7.12 (s, 1H), 6.61 (d, J=8.4 Hz, 2H), 3.33 (m, 8H), 2.80 (m, 4H), 2.49 (s, 3H), 2.04 (m, 4H); LC-MS m/z [M+H]$^+$ calc'd for $C_{25}H_{29}FN_6O$, 449; found, 449.

Example A36: (E)-2-(((4-cyclopropylpiperazin-1-yl)imino)methyl)-6-fluoro-4-(1-(4-(pyrrolidin-1-yl)phenyl)-1H-pyrazol-4-yl)phenol (Compound No. A36)

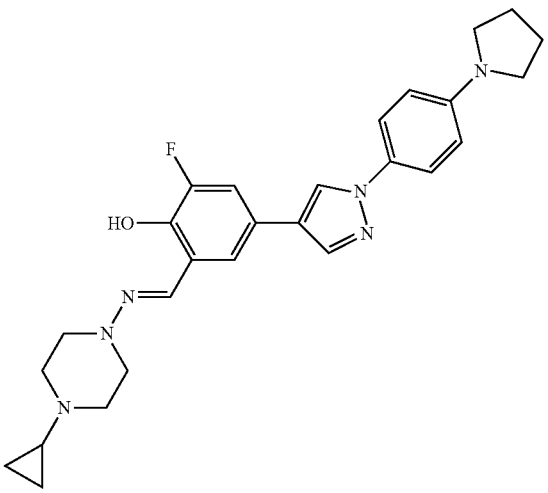 [SMILES: Oc1c(F)cc(-c2cnn(-c3ccc(N4CCCC4)cc3)c2)cc1/C=N/N1CCN(C2CC2)CC1]

The title compound was prepared from 3-fluoro-2-hydroxy-5-(1-(4-(pyrrolidin-1-yl)phenyl)-1H-pyrazol-4-yl)benzaldehyde (20 mg, 0.06 mmol) and 4-cyclopropylpiperazin-1-amine dihydrochloride (12 mg, 0.06 mmol) as described in above general procedure except that sodium acetate (5 mg, 0.06 mmol) base added to the reaction mixture and finally washed the residue with water and ethanol to give the title compound as off-white solid (11 mg, 41% yield). $^1$H NMR (DMSO-d6, 400 MHz) δ: 11.52 (br, 1H), 8.69 (s, 1H), 8.01 (s, 1H), 7.90 (m, 1H), 7.62 (d, J=8.8 Hz, 2H), 7.51 (m, 2H), 6.63 (d, J=8.8 Hz, 2H), 3.27 (m, 4H), 3.13 (m, 4H), 2.75 (m, 4H), 1.98 (m, 4H), 1.73 (m, 1H), 0.45 (m, 2H), 0.36 (m, 2H); LC-MS m/z [M+H]$^+$ calc'd for $C_{27}H_{31}FN_6O$, 475; found, 475.

Example A37: (E)-2-fluoro-6-((morpholinoimino) methyl)-4-(1-(4-(pyrrolidin-1-yl)phenyl)-1H-pyrazol-4-yl)phenol (Compound No. A37)

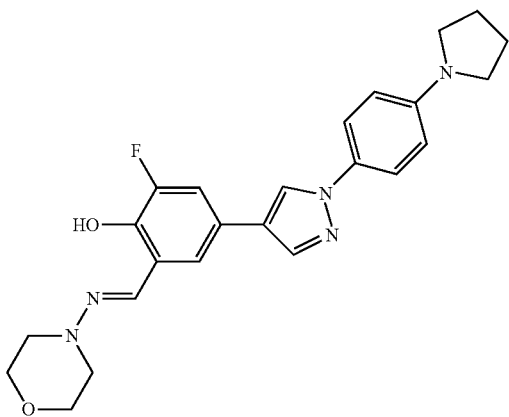 [SMILES: Oc1c(F)cc(-c2cnn(-c3ccc(N4CCCC4)cc3)c2)cc1/C=N/N1CCOCC1]

The title compound was prepared from 3-fluoro-2-hydroxy-5-(1-(4-(pyrrolidin-1-yl)phenyl)-1H-pyrazol-4-yl) benzaldehyde (100 mg, 0.28 mmol) and morpholin-4-amine (57 mg, 0.56 mmol) as described in above general procedure to give the title compound as white solid (85 mg, 69% yield). $^1$H NMR (DMSO-d6, 400 MHz) δ: 11.42 (br, 1H), 8.70 (s, 1H), 8.00 (m, 2H), 7.62 (m, 2H), 7.53 (m, 2H), 6.63 (d, J=8.8 Hz, 2H), 3.80 (m, 4H), 3.27 (m, 4H), 3.16 (m, 4H), 1.97 (m, 4H); LC-MS m/z [M+H]$^+$ calc'd for $C_{24}H_{26}FN_5O_2$, 436; found, 436.

Example A38: N'-(3-fluoro-2-hydroxy-5-(1-(4-(pyrrolidin-1-yl)phenyl)-1H-pyrazol-4-yl)benzylidene) acetohydrazide (Compound No. A38)

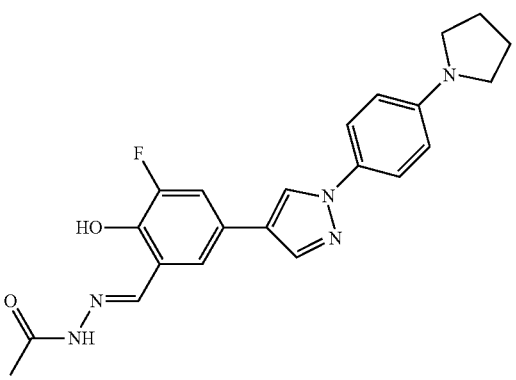 [SMILES: CC(=O)N/N=C/c1cc(-c2cnn(-c3ccc(N4CCCC4)cc3)c2)cc(F)c1O]

The title compound was prepared from 3-fluoro-2-hydroxy-5-(1-(4-(pyrrolidin-1-yl)phenyl)-1H-pyrazol-4-yl) benzaldehyde (100 mg, 0.28 mmol) and acetohydrazide (41 mg, 0.56 mmol) as described in above general procedure to give the title compound as white solid (55 mg, 47% yield). $^1$H NMR (DMSO-d6, 400 MHz) δ: 11.87 (br, 0.6H), 11.56 (br, 0.6H), 11.45 (br, 0.4H), 10.34 (br, 0.4H), 8.75 (s, 1H), 8.36 (s, 0.6H), 8.29 (s, 0.4H), 8.08 (s, 1H), 7.64 (m, 4H), 6.64 (d, J=8.4 Hz, 2H), 3.27 (m, 4H), 2.25 (s, 1H), 1.97-2.02 (m, 6H); LC-MS m/z [M+H]+ calc'd for $C_{22}H_{22}FN_5O_2$, 408; found, 408.

Example A39: (E)-2-fluoro-6-((phenylimino) methyl)-4-(1-(4-(pyrrolidin-1-yl)phenyl)-1H-pyrazol-4-yl)phenol (Compound No. A39)

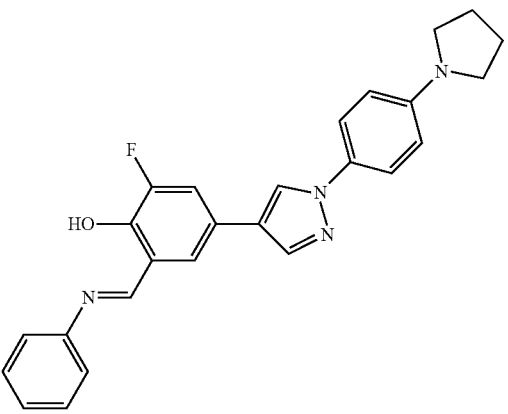 [SMILES: Oc1c(F)cc(-c2cnn(-c3ccc(N4CCCC4)cc3)c2)cc1/C=N/c1ccccc1]

The title compound was prepared from 3-fluoro-2-hydroxy-5-(1-(4-(pyrrolidin-1-yl)phenyl)-1H-pyrazol-4-yl) benzaldehyde (100 mg, 0.28 mmol) and aniline (52 mg, 0.56 mmol) as described in above general procedure to give the title compound as white solid (57 mg, 47% yield). $^1$H NMR (CDCl$_3$, 400 MHz) δ: 13.62 (br, 1H), 8.71 (s, 1H), 8.02 (s, 1H), 7.91 (s, 1H), 7.62 (d, J=7.6 Hz, 2H), 7.32-7.49 (m, 9H), 3.44 (m, 4H), 2.14 (m, 4H); LC-MS m/z [M+H]+ calc'd for $C_{26}H23FN4O$, 427; found, 427.

Example A40: (E)-3-fluoro-2-hydroxy-5-(1-(4-(pyrrolidin-1-yl)phenyl)-1H-pyrazol-4-yl)benzaldehyde O-phenyl Oxime (Compound No. A40)

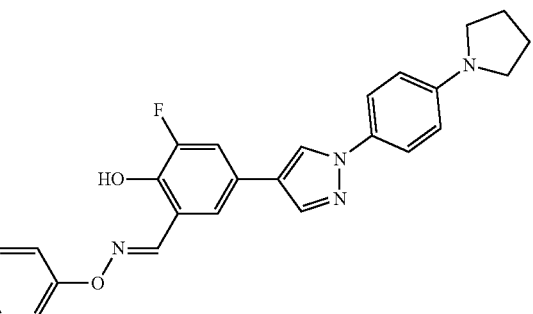

The title compound was prepared from 3-fluoro-2-hydroxy-5-(1-(4-(pyrrolidin-1-yl)phenyl)-1H-pyrazol-4-yl) benzaldehyde (50 mg, 0.14 mmol) and O-phenylhydroxylamine hydrochloride (31 mg, 0.21 mmol) as described in above general procedure except that TEA (29 mg, 0.28 mmol) base added to the reaction mixture and stirred overnight at room temperature to give the title compound as green solid (27 mg, 44% yield). $^1$H NMR (DMSO-d6, 400 MHz) δ: 10.40 (br, 1H), 8.83 (d, J=5.2 Hz, 2H), 8.13 (s, 1H), 7.87 (s, 1H), 7.73 (d, J=12.0 Hz, 1H), 7.65 (d, J=8.8 Hz, 2H), 7.39 (m, 2H), 7.32 (m, 2H), 7.08 (m, 1H), 6.64 (d, J=8.8 Hz, 2H), 3.27 (m, 4H), 1.98 (m, 4H); LC-MS m/z [M+H]$^+$ calc'd for $C_{26}H_{23}FN_4O_2$, 443; found, 443.

Example A41: 3-fluoro-2-hydroxy-5-(4-(4-(pyrrolidin-1-yl)phenyl)-1H-1,2,3-triazol-1-yl)benzaldehyde (Compound No. A42)

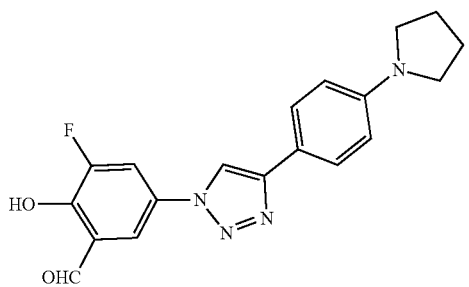 [SMILES: O=Cc1cc(-n2cc(-c3ccc(N4CCCC4)cc3)nn2)cc(F)c1O]

Step 1: 1-(3-(1,3-Dithian-2-yl)-5-fluoro-4-(4-methoxybenzyloxy)phenyl)-4-(4-(pyrrolidin-1-yl)phenyl)-1H-1,2,3-triazole

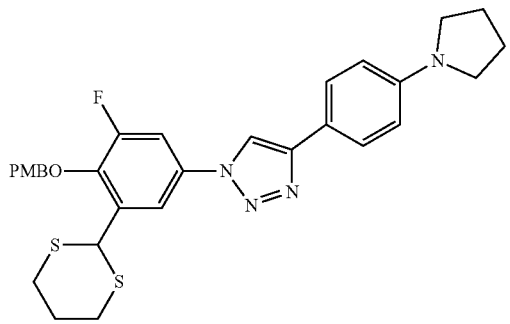

A mixture of 2-(5-azido-3-fluoro-2-(4-methoxybenzyloxy)phenyl)-1,3-dithiane (0.3 g, 0.77 mmol) (prepared as in Example A43), CuSO$_4$ (21 mg, 0.13 mmol), and L-ascorbic acid sodium salt (65 mg, 0.39 mmol) in MeOH/water (20 mL/2 mL) was purged with nitrogen for three times, then added 1-(4-Ethynylphenyl)pyrrolidine (112 mg, 0.77 mmol) to the reaction mixture. The reaction was heated at 50° C. for 1 hour. The mixture was cooled to room temperature, diluted with water (40 mL), and extracted with ethyl acetate (40 mL×3). The organic extracts were combined, washed with brine (40 mL×2), dried over anhydrous sodium sulfate, and concentrated. The residue was purified by silica gel column chromatography (petroleum ether/ethyl acetate=20:1 to 2:1) to give the desired titled product (203 mg, 47% yield). LC-MS m/z [M+H]$^+$ calc'd for $C_{30}H_{31}FN_4O_2S_2$, 563; found, 563.

Step 2

A solution of above obtained step 1 product (150 mg, 0.27 mmol), MeI (3.8 g, 26.8 mmol), and NaHCO$_3$ (448 mg, 5.3 mmol) in acetonitrile/water (15 mL/3 mL) was stirred overnight at 40° C. The solution was diluted with water and extracted with ethyl acetate for three times. The organic extracts were combined, washed with brine, dried over anhydrous sodium sulfate, and concentrated. The residue was dissolved in 4N HCl (5 mL) and the reaction was stirred for 1 hour at room temperature. The solution was poured into ice-cold sat. sodium bicarbonate and extracted with ethyl acetate for three times. The organic extracts were combined, washed with brine, dried over anhydrous sodium sulfate, and concentrated. The residue was purified by prep-TLC (DCM/MeOH=20:1) to give the desired product as yellow solid (7 mg, 7% yield). $^1$H NMR (CDCl$_3$, 400 MHz) δ: 11.07 (s, 1H), 10.03 (s, 1H), 8.01 (s, 1H), 7.84 (m, 2H), 7.75 (m, 2H), 6.68 (m, 2H), 3.36 (m, 4H), 2.05 (m, 4H); LC-MS m/z [M+H]+ calc'd for $C_{19}H_{17}FN_4O_2$, 353; found, 353.

Example A42: 3-fluoro-2-hydroxy-5-(1-(4-(pyrrolidin-1-yl)phenyl)-1H-1,2,3-triazol-4-yl)benzaldehyde (Compound No. A43)

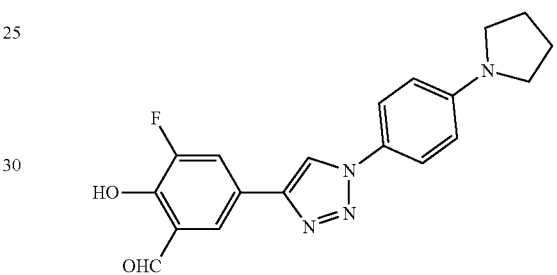

Step 1: 5-Ethynyl-3-fluoro-2-hydroxybenzaldehyde

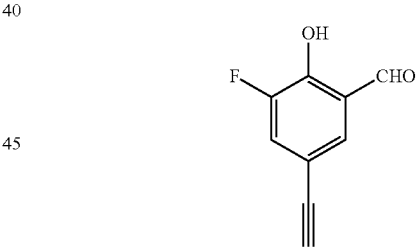

Starting materials PdCl$_2$(PPh)$_2$ (0.3 g, 0.25 mmol), CuI (0.03 g, 0.1 mmol), and ethynyltrimethylsilane (1.47 g, 15.0 mmol) were added to a solution of 5-bromo-3-fluoro-2-hydroxybenzaldehyde (2.19 g, 10.0 mmol), triethylamine (2.02 g, 20.0 mmol), and triphenylphosphine (0.045 g, 0.125 mmol) in THF (20 mL) under nitrogen protection was refluxed for 60 hours. The mixture was cooled to room temperature, diluted with water/ethyl acetate, and filtered. The cake was washed with ethyl acetate. The filtrate and wash was combined, separated, and the water phase was re-extracted with ethyl acetate for two more times. The organic extracts were combined, washed with brine, dried over anhydrous sodium sulfate, and concentrated. The residue was purified by silica gel column chromatography (petroleum ether/ethyl acetate=500:1 to 300:1) to give 3-fluoro-2-hydroxy-5-((trimethylsilyl)ethynyl)benzaldehyde (1.1 g, 47% yield). The 3-fluoro-2-hydroxy-5-((trimethylsilyl)ethynyl)benzaldehyde (1.0 g, 4.2 mmol) was dissolved in THF (15 mL) and TBAF (2.2 g, 8.4 mmol) was added. The reaction was stirred for 1 hour at room temperature. The solvent was removed in vacuo and the residue was purified by silica gel column chromatography (petroleum ether/ethyl acetate=500:1 to 300:1) to give the title product (0.31 g, 45% yield). $^1$H NMR (CDCl$_3$, 400 MHz) δ: 10.96 (br, 1H), 9.89 (d, J=8.4 Hz, 1H), 7.49 (m, 2H), 3.08 (s, 1H).

Step 2: 1-(4-Azidophenyl)pyrrolidine

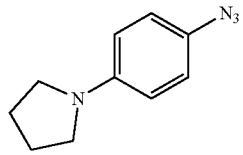 [SMILES: [N-]=[N+]=Nc1ccc(N2CCCC2)cc1]

In a 50 mL dry round bottom flask, BuLi (4 mL, 10.0 mmol, 2.5 M in THF) was added to a solution of 1-(4-bromophenyl)pyrrolidine (0.5 g, 2.2 mmol) in THF (5 mL) at −78° C. The reaction was stirred for 30 min. TsN$_3$ (1.3 g, 6.7 mmol) was added. The reaction was stirred for 5 hours at room temperature. The reaction was quenched with sat. ammonium chloride (20 mL) and extracted with EtOAc (20 mL×3). The organic layers were combined, washed with brine (20 mL), dried over anhydrous sodium sulfate, and concentrated. The residue was purified by silica gel column chromatography (petroleum ether/ethyl acetate=500:1 to 400:1) to give title product (150 mg, 36% yield). LC-MS m/z [M+H]$^+$ calc'd for C$_{10}$H$_{12}$N$_4$, 189; found, 189.

Step 3

A mixture of 1-(4-Azidophenyl)pyrrolidine (100 mg, 0.53 mmol), CuSO$_4$ (8.5 mg, 0.053 mmol), and L-ascorbic acid sodium salt (52.7 mg, 0.27 mmol) in t-BuOH/water (5 mL/5 mL) was purged with nitrogen for three times and 5-Ethynyl-3-fluoro-2-hydroxybenzaldehyde (131 mg, 0.80 mmol) was added to the reaction mixture. The reaction was heated overnight at 40° C. The mixture was cooled to room temperature, diluted with water (20 mL), and extracted with ethyl acetate (20 mL×3). The organic extracts were combined, washed with brine (20 mL×2), dried over anhydrous sodium sulfate, and concentrated. The residue was purified by silica gel column chromatography (petroleum ether/ethyl acetate=20:1 to 5:1) and prep-HPLC to give the desired final product as light yellow solid (12 mg, 6% yield). $^1$H NMR (DMSO-d6, 400 MHz) δ: 11.17 (br, 1H), 10.37 (s, 1H), 9.15 (s, 1H), 8.04 (m, 2H), 7.68 (d, J=8.8 Hz, 2H), 6.70 (d, J=9.2 Hz, 2H), 3.30 (m, 4H), 2.00 (m, 4H); LC-MS m/z [M+H]$^+$ calc'd for C$_{19}$H$_{17}$FN$_4$O$_2$, 353; found, 353.

Example A43: 3-fluoro-2-hydroxy-5-(4-(3-(pyrrolidin-1-yl)phenyl)-1H-1,2,3-triazol-1-yl)benzaldehyde (Compound No. A44)

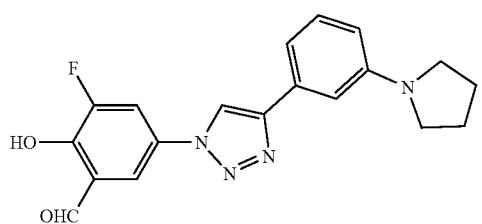 [SMILES: O=Cc1cc(-n2cc(-c3cccc(N4CCCC4)c3)nn2)cc(F)c1O]

Step 1: 2-(5-Bromo-3-fluoro-2-(4-methoxybenzyloxy)phenyl)-1,3-dithiane

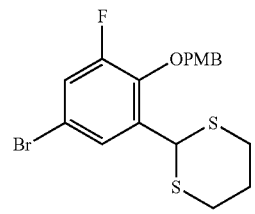

In a 100 mL dry round bottom flask, BF$_3$.OEt$_2$ (3.41 g, 24.0 mmol) was added to a solution of 5-bromo-3-fluoro-2-hydroxybenzaldehyde (4.36 g, 20.0 mmol) and propane-1,3-dithiol (2.6 g, 24.0 mmol) in DCM (20 mL) under nitrogen protection. The reaction was stirred for 3 hours at room temperature. The solution was poured into ice-water and extracted with ethyl acetate (50 mL×3). The organic extracts were combined, washed with brine (30 mL), dried over anhydrous sodium sulfate, and concentrated. The crude was dissolved in DMF (20 mL) then PMBCl (6.24 g, 40.0 mmol) and potassium carbonate (8.28 g, 60 mmol) were added. The reaction was stirred for was 2 h at 90° C. The mixture was cooled to room temperature, diluted with water (100 mL), and extracted with ethyl acetate (100 mL×3). The organic extracts were combined, washed with brine (50 mL×2), dried over anhydrous sodium sulfate, and concentrated. The residue was purified by silica gel column chromatography (petroleum ether/ethyl acetate=500:1 to 400:1) to give titled product (6.37 g, 74% yield). $^1$H NMR (CDCl$_3$, 400 MHz) δ: 7.51 (s, 1H), 7.42 (m, 2H), 7.24 (m, 1H), 6.94 (m, 2H), 5.48 (s, 1H), 5.07 (s, 2H), 3.84 (s, 3H), 2.98 (m, 2H), 2.88 (m, 2H), 2.15 (m, 1H), 1.90 (m, 1H).

Step 2: 2-(5-Azido-3-fluoro-2-(4-methoxybenzyloxy)phenyl)-1,3-dithiane

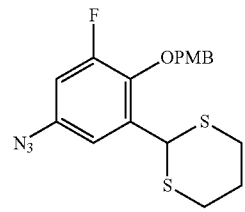

In a 100 mL dry round bottom flask, BuLi (6.6 mL, 10.5 mmol, 1.6 M in THF) was added to a solution of 2-(5-Bromo-3-fluoro-2-(4-methoxybenzyloxy)phenyl)-1,3-dithiane (1.0 g, 2.3 mmol) and TsN$_3$ (1.38 g, 7.0 mmol) in THF (10 mL) at −78° C. The reaction was stirred for 2.5 hours at room temperature. The reaction was quenched with sat. ammonium chloride (30 mL) and extracted with EtOAc (30 mL×3). The organic layers were combined, washed with brine (30 mL), dried over anhydrous sodium sulfate, and concentrated. The residue was purified by silica gel column chromatography (petroleum ether/ethyl acetate=100:1 to 50:1) to give the titled product (0.71 g, 78% yield, containing ~55% debrominated side product inside). LC-MS m/z [M+H]$^+$ calc'd for C$_{18}$H$_{18}$FN$_3$O$_2$S2, 392; found, 392.

Step 3: 5-Azido-3-fluoro-2-(4-methoxybenzyloxy)benzaldehyde

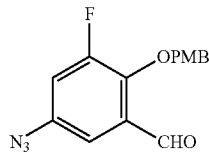

DMP (2.4 g, 5.6 mmol) was added to a solution of 2-(5-Azido-3-fluoro-2-(4-methoxybenzyloxy)phenyl)-1,3-dithiane (1.1 g, 2.8 mmol) in acetonitrile/DCM/water (16 mL/2 mL/2 mL). The reaction was stirred overnight at 45° C. . The mixture was diluted with ethyl acetate (50 mL) and filtered. The filtrate was washed with sat. sodium bicarbonate (50 mL). The organic layer was dried over anhydrous sodium sulfate and concentrated. The residue was purified by silica gel column chromatography (petroleum ether/ethyl acetate=100:1 to 50:1) to give the titled product (0.79 g, 93% yield containing ~55% debromo-byproduct inside). LC-MS m/z [M+H]$^+$ calc'd for $C_{15}H_{12}FN_3O_3$, 302; found, 302.

Step 4: 3-(Pyrrolidin-1-yl)benzaldehyde

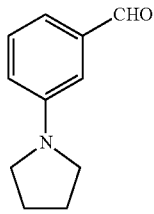 [SMILES: O=Cc1cccc(N2CCCC2)c1]

BuLi (20.6 mL, 33.2 mmol, 1.6 M in THF) was added to a solution of 1-(3-bromophenyl)pyrrolidine (5 g, 22.1 mmol) in THF (25 mL) at −78° C. The reaction was stirred for 1 hour at this temperature. A solution of DMF (2.4 g, 33.2 mmol) in THF (5 mL) was added. The reaction was stirred for 2 hours at room temperature. The reaction was quenched with sat. ammonium chloride (50 mL) and extracted with EtOAc (50 mL×3). The organic layers were combined, washed with brine (50 mL), dried over anhydrous sodium sulfate, and concentrated. The residue was purified by silica gel column chromatography (petroleum ether/ethyl acetate=500:1 to 300:1) to give the desired product (2.85 g, 74% yield). $^1$H NMR (CDCl$_3$, 400 MHz) δ: 9.97 (s, 1H), 7.79 (t, J=8.0 Hz, 1H), 7.16 (d, J=7.2 Hz, 1H), 7.04 (s, 1H), 6.83 (dd, J=8.4 Hz, 2.0 Hz, 1H), 3.36 (m, 4H), 2.06 (m, 4H).

Step 5: 1-(3-Ethynylphenyl)pyrrolidine

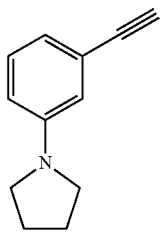

BuLi (4.3 mL, 6.9 mmol, 1.6 M in THF) was added to a solution of 3-(Pyrrolidin-1-yl)benzaldehyde (1.0 g, 5.7 mmol) in THF (10 mL) at −78° C. The reaction was stirred for 30 min. TMSN$_2$ (3.4 mL, 6.9 mmol, 2 M in THF) was added. The reaction was stirred for 1 h at −78° C. The reaction was quenched with sat. ammonium chloride (30 mL) and extracted with EtOAc (30 mL×3). The organic layers were combined, washed with brine (30 mL), dried over anhydrous sodium sulfate, and concentrated. The residue was purified by silica gel column chromatography (petroleum ether/ethyl acetate=500:1 to 400:1) to give the desired 1-(3-Ethynylphenyl)pyrrolidine (0.63 g, 64% yield).

Step 6: 3-Fluoro-2-(4-methoxybenzyloxy)-5-(4-(3-(pyrrolidin-1-yl)phenyl)-1H-1,2,3-triazol-1-yl)benzaldehyde

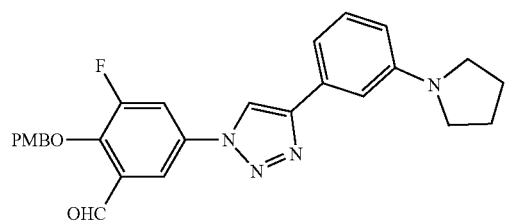

A mixture of 5-Azido-3-fluoro-2-(4-methoxybenzyloxy)benzaldehyde (0.4 g, 1.3 mmol), CuSO$_4$ (20 mg, 0.13 mmol), and L-ascorbic acid sodium salt (150 mg, 0.75 mmol) in t-BuOH/water (5 mL/5 mL) was purged with nitrogen for three times then added 1-(3-Ethynylphenyl)pyrrolidine (0.2 g, 1.2 mmol) to the reaction mixture. The reaction was heated at 40° C. overnight. The mixture was cooled to room temperature, diluted with water (20 mL), and extracted with ethyl acetate (20 mL×3). The organic extracts were combined, washed with brine (20 mL×2), dried over anhydrous sodium sulfate, and concentrated. The residue was purified by silica gel column chromatography (petroleum ether/ethyl acetate=20:1 to 2:1) to give PMB-protected desired product (120 mg, 22% yield). LC-MS m/z [M+H]$^+$ calc'd for $C_{27}H_{25}FN_4O_3$, 473; found, 473.

Step 7

A solution of 3-Fluoro-2-(4-methoxybenzyloxy)-5-(4-(3-(pyrrolidin-1-yl)phenyl)-1H-1,2,3-triazol-1-yl)benzaldehyde (120 mg, 0.25 mmol) and TFA (86 mg, 0.76 mmol) in DCM (5 mL) was stirred overnight at rt. The solution was diluted with DCM (10 mL) and washed with sat. sodium bicarbonate (10 mL). The organic layer was dried over anhydrous sodium sulfate and concentrated. The residue was purified by silica gel column chromatography (petroleum ether/ethyl acetate/DCM=20:1:1 to 5:1:1) to give the final desired product as light yellow solid (30 mg, 34% yield). $^1$H NMR (DMSO-d6, 400 MHz) δ: 11.51 (s, 1H), 10.40 (s, 1H), 9.31 (s, 1H), 8.21 (dd, J=11.2 Hz, 2.8 Hz, 1H), 8.03 (m, 1H), 7.26 (m, 1H), 7.17 (m, 1H), 7.11 (m, 1H), 6.56 (m, 1H), 3.31 (m, 4H), 2.00 (m, 4H); ; LC-MS m/z [M+H]$^+$ calc'd for $C_{19}H_{17}FN_4O_2$, 353; found, 353.

Example A44: 3-fluoro-2-hydroxy-5-(1-(3-(pyrrolidin-1-yl)phenyl)-1H-1,2,3-triazol-4-yl)benzaldehyde (Compound No. A45)

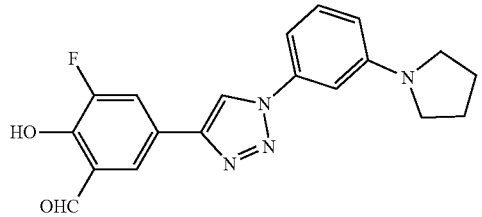 [SMILES: O=Cc1cc(-c2cn(-c3cccc(N4CCCC4)c3)nn2)cc(F)c1O]

Step 1: 1-(3-Azidophenyl)pyrrolidine

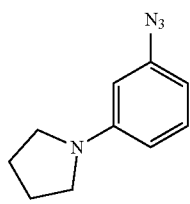 [SMILES: [N-]=[N+]=Nc1cccc(N2CCCC2)c1]

A solution of 3-(pyrrolidin-1-yl)aniline (0.5 g, 3.1 mmol) in acetonitrile (10 mL) was cooled to 0° C. Tert-Butyl nitrite (0.96 g, 9.3 mmol) and TMSN$_3$ (0.86 g, 7.4 mmol) were added. The reaction was stirred overnight at rt. The reaction was diluted with water (20 mL) and extracted with EtOAc (20 mL×3). The organic layers were combined, washed with brine (20 mL), dried over anhydrous sodium sulfate, and concentrated. The residue was purified by silica gel column chromatography (petroleum ether/ethyl acetate=300:1 to 100:1) to give the desired product (190 mg, 33% yield). LC-MS m/z [M+H]$^+$ calc'd for $C_{10}H_{12}N_4$, 189; found, 189.

Step 2

A mixture of 1-(3-Azidophenyl)pyrrolidine (100 mg, 0.53 mmol), CuSO$_4$ (8.5 mg, 0.053 mmol), and L-ascorbic acid sodium salt (52.7 mg, 0.27 mmol) in t-BuOH/water (5 mL/5 mL) was purged with nitrogen for three times then added 5-Ethynyl-3-fluoro-2-hydroxybenzaldehyde (131 mg, 0.80 mmol) (from example A43) to the reaction mixture. The reaction was heated overnight at 40° C. The mixture was cooled to room temperature, diluted with water (20 mL), and extracted with ethyl acetate (20 mL×3). The organic extracts were combined, washed with brine (20 mL×2), dried over anhydrous sodium sulfate, and concentrated. The residue was purified by silica gel column chromatography (petroleum ether/ethyl acetate=20:1 to 5:1) and prep-TLC to give the final product as white solid (15 mg, 7% yield). $^1$H NMR (CDCl$_3$, 400 MHz) δ: 11.05 (br, 1H), 10.03 (s, 1H), 8.21 (s, 1H), 8.01 (s, 1H), 7.88 (d, J=11.2 Hz, 1H), 7.44 (m, 1H), 7.34 (m, 1H), 7.19 (m, 1H), 6.92 (d, J=7.2 Hz, 1H), 3.48 (m, 4H), 2.16 (m, 4H); LC-MS m/z [M+H]$^+$ calc'd for $C_{19}H_{17}FN_4O_2$, 353; found, 353.

Example A45: 3-fluoro-2-hydroxy-5-(1-(4-(pyrrolidin-1-yl)phenyl)-1H-imidazol-4-yl)benzaldehyde (Compound A47)

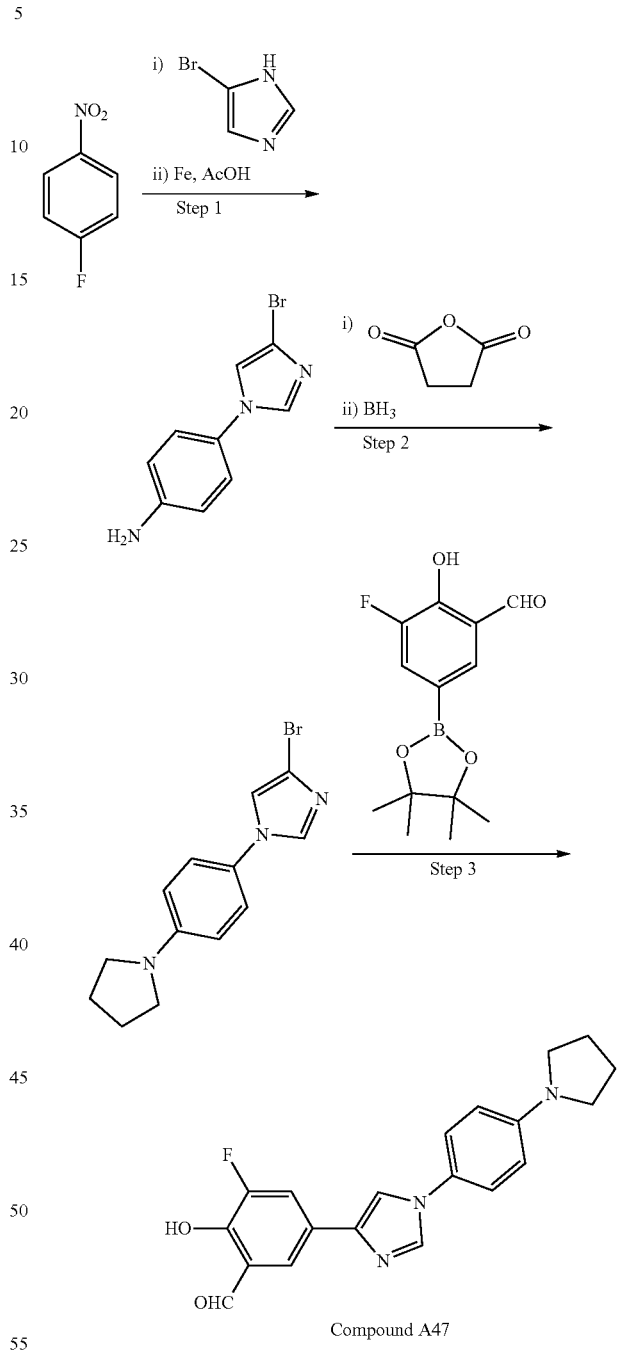

Step 1: 4-(4-bromo-1H-imidazol-1-yl)aniline

A mixture of 1-fluoro-4-nitrobenzene (1.16 g, 8.2 mmol, 1.2 eq.), 5-bromo-1H-imidazole (1 g, 6.8 mmol, 1.0 eq.), and potassium carbonate (2.84 g, 20.4 mmol, 3.0 eq.) in DMF (15 mL) was heated at 80° C. for 2 hours under N2 protection. The mixture was cooled to room temperature, poured into water, and extracted with ethyl acetate for three times. The organic extracts were combined, washed with brine, dried over anhydrous sodium sulfate, and concentrated to give crude 4-bromo-1-(4-nitrophenyl)-1H-imidazole (1.77 g, 6.63 mmol, 98% yield). LC-MS: 268.0, 270.0 (M+H)+, $C_9H_6BrN_3O_2$. In a 100 mL glass vial, iron powder (2.71 g, 48.32 mmol, 10.0 eq.) was added to a solution of 4-bromo-1-(4-nitrophenyl)-1H-imidazole (1.3 g, 4.83 mmol, 1.0 eq.) in AcOH (20 mL). The reaction was heated for 2 hours at 60° C. The reaction mixture was cooled to room temperature, poured into sat. NaHCO$_3$ and extracted with ethyl acetate for three times. The organic extracts were combined, washed with brine, dried over anhydrous sodium sulfate, and concentrated to give 4-(4-bromo-1H-imidazol-1-yl)aniline (790 mg, 3.31 mmol, 68% yield).

Step 2: 4-bromo-1-(4-(pyrrolidin-1-yl)phenyl)-1H-imidazole

A solution of 4-(4-bromo-1H-imidazol-1-yl)aniline (500 mg, 2.1 mmol, 1.0 eq.) and dihydrofuran-2,5-dione (422 mg, 4.2 mmol, 2.0 eq.) in toluene (15 mL) was stirred overnight at room temperature. The solution was poured into water and extracted with ethyl acetate for three times. The organic extracts were combined, washed with brine, dried over anhydrous sodium sulfate, and concentrated to give crude intermediate (710 mg). This intermediate was then refluxed in thionyl chloride (10 mL) for 1 hour and concentrated in vacuo to get the penultimate intermediate (690 mg). This intermediate (600 mg, 1.88 mmol, 1.0 eq.) was dissolved in THF (10 ml) and the solution was cooled to 0° C. Borane-dimethylsulfide (1.68 mL, 10 M, 9.0 eq.) was added. The reaction was stirred for 2 hours at 50° C. The system was cooled to room temperature, poured into ice water, and extracted with ethyl acetate for three times. The organic extracts were combined, washed with brine, dried over anhydrous sodium sulfate, and concentrated. The residue was purified by silica gel column chromatography (petroleum ether/EtOAc=20:1 to 10:1) to give 4-bromo-1-(4-(pyrrolidin-1-yl)phenyl)-1H-imidazole (240 mg, 0.82 mmol, 44% yield). LC-MS m/z [M+H]$^+$ calc'd for $C_{13}H_{14}BrN_3$, 292; found, 292.

Step 3

A mixture of 4-bromo-1-(4-(pyrrolidin-1-yl)phenyl)-1H-imidazole (200 mg, 0.69 mmol, 1.0 eq.), 3-fluoro-2-hydroxy-5-(4,4,5,5-tetramethyl-1,3,2-dioxaborolan-2-yl)benzaldehyde (459 mg, 1.73 mmol, 2.5 eq.), potassium carbonate (286 mg, 2.07 mmol, 3.0 eq.), PdCl$_2$(dppf) (85 mg, 0.07 mmol, 0.1 eq.) in dioxane/water (10 mL/3 mL) was heated at 100° C. for 3 hours under nitrogen atmosphere. The mixture was cooled to room temperature and poured into water. Then pH of the system was adjusted to 4-5 and extracted with ethyl acetate for three times. The organic extracts were combined, washed with brine, dried over anhydrous sodium sulfate, and concentrated. The residue was purified by silica gel column (petroleum ether/EtOAc=50:1 to 20:1) to give 3-fluoro-2-hydroxy-5-(1-(4-(pyrrolidin-1-yl)phenyl)-1H-imidazol-4-yl)benzaldehyde (42 mg, 0.12 mmol, 17% yield) as a yellow solid. $^1$H NMR (DMSO-d6, 400 MHz) δ: 10.87 (br, 1H), 10.33 (s, 1H), 8.14 (d, J=10.4 Hz, 2H), 7.97-7.92 (m, 2H), 7.45 (d, J=8.8 Hz, 2H), 6.64 (d, J=8.4 Hz, 2H), 3.27 (m, 4H), 1.98 (m, 4H); LC-MS m/z [M+H]$^+$ calc'd for $C_{20}H_{18}FN_3O_2$, 352; found, 352.

Example A46: 3-fluoro-2-hydroxy-5-(5-(4-(pyrrolidin-1-yl)phenyl)thiophen-2-yl)benzaldehyde (Compound A50)

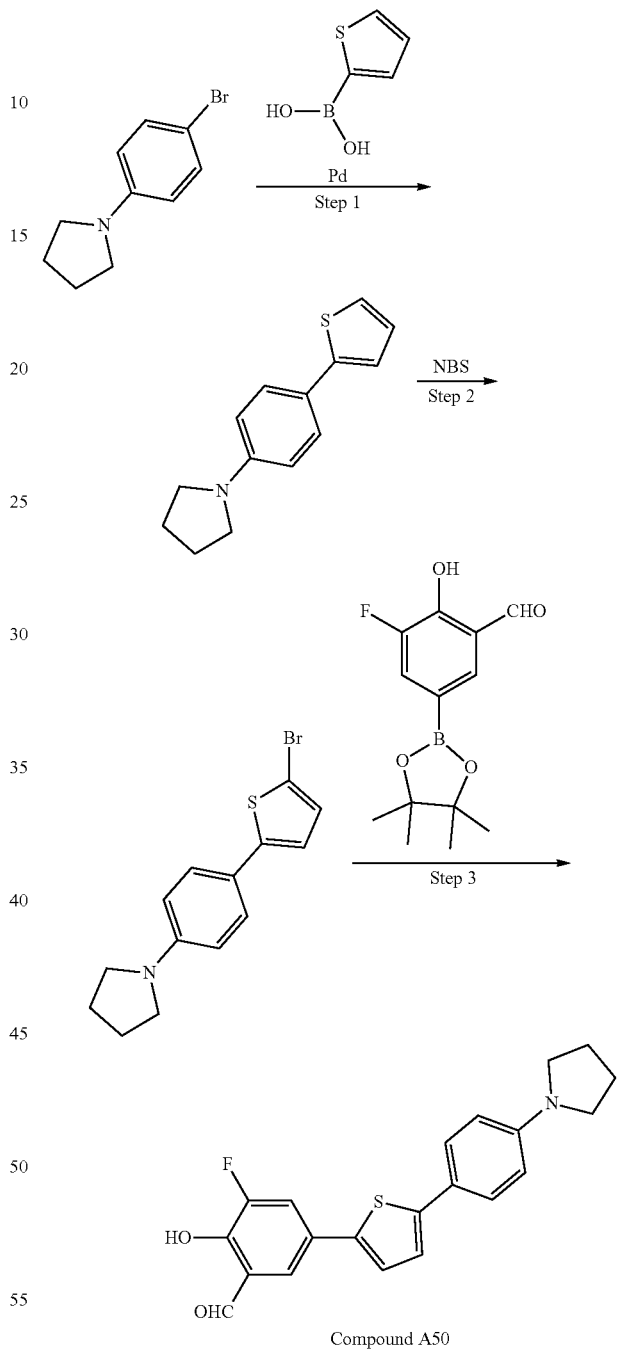

Compound A50

Step 1: 1-(4-(thiophen-2-yl)phenyl)pyrrolidine

A mixture of thiophen-2-ylboronic acid (1.7 g, 13.3 mmol, 1.5 eq.), 1-(4-bromophenyl)pyrrolidine (2 g, 8.89 mmol, 1.0 eq.), potassium carbonate (3.7 g, 26.8 mmol, 3.0 eq.), and PdCl$_2$(dppf) (0.7 g, 0.89 mmol, 0.1 eq.) in dioxane/water (9 mL/3 mL) was heated at 95° C. for 2 hours under nitrogen atmosphere. The mixture was cooled to room temperature and filtered. The cake was washed with ethyl acetate. The filtrate and wash were combined, washed with water, dried over anhydrous sodium sulfate, and concentrated. The residue was purified by silica gel column (petroleum ether/EtOAc=100 to 300:1) to give 1-(4-(thiophen-2-yl)phenyl)pyrrolidine (1.2 g, 5.24 mmol, 59% yield).

Step 2: 1-(4-(5-bromothiophen-2-yl)phenyl)pyrrolidine

A solution of 1-(4-(thiophen-2-yl)phenyl)pyrrolidine (950 mg, 4.15 mmol, 1 eq.) and NBS (1.11 g, 6.23 mmol, 1.5 eq.) in CHCl$_3$ (20 mL) was stirred for 2 h. The solution was poured into sat. sodium bicarbonate and extracted with CH$_2$Cl$_2$ for three times. The organic extracts were combined, washed with water, dried over anhydrous sodium sulfate, and concentrated. The residue was purified by silica gel column (pure petroleum ether) to give 1-(4-(5-bromothiophen-2-yl)phenyl)pyrrolidine (350 mg, 1.13 mmol, 27% yield). $^1$H NMR (DMSO-d6, 400 MHz) δ: 7.39 (dd, J=6.8 Hz, 2.0 Hz, 2H), 7.14 (d, J=4.0 Hz, 1H), 7.08 (d, J=4.0 Hz, 1H), 6.54 (d, J=8.8 Hz, 2H), 3.25 (m, 4H), 1.96 (m, 4H).

Step 3

A mixture of 1-(4-(5-bromothiophen-2-yl)phenyl)pyrrolidine (340 mg, 1.10 mmol, 1.0 eq.), 3-fluoro-2-hydroxy-5-(4,4,5,5-tetramethyl-1,3,2-dioxaborolan-2-yl)benzaldehyde (322 mg, 1.21 mmol, 1.1 eq.), potassium carbonate (456 mg, 3.30 mmol, 3.0 eq.), and PdCl$_2$(dppf) (90 mg, 0.11 mmol, 0.1 eq.) in dioxane/water (9 mL/3 mL) was heated at 95° C. for 2 hours under nitrogen atmosphere. The mixture was cooled to room temperature and poured into water. Then pH of the system was adjusted to 4-5 and extracted with ethyl acetate. The organic extracts were combined, washed with water, dried over anhydrous sodium sulfate, and concentrated. The residue was purified by silica gel column (petroleum ether/EtOAc=100:1 to 20:1) to give 3-fluoro-2-hydroxy-5-(5-(4-(pyrrolidin-1-yl)phenyl)thiophen-2-yl)benzaldehyde (110 mg, 0.30 mmol, 27% yield). $^1$H NMR (DMSO-d6, 400 MHz) δ: 11.10 (br, 1H), 10.31 (s, 1H), 7.90 (dd, J=12.0 Hz, 1.6 Hz, 1H), 7.65 (s, 1H), 7.47 (m, 3H), 7.26 (d, J=3.6 Hz, 1H), 6.57 (d, J=8.8 Hz, 2H), 3.36 (m, 4H), 1.96 (m, 4H). LC-MS m/z [M+H]$^+$ calc'd for C$_{21}$H$_{18}$FNO$_2$S, 368; found, 368.

Example A47: 3-fluoro-2-hydroxy-5-(4-(4-(pyrrolidin-1-yl)phenyl)thiophen-2-yl)benzaldehyde (Compound A51)

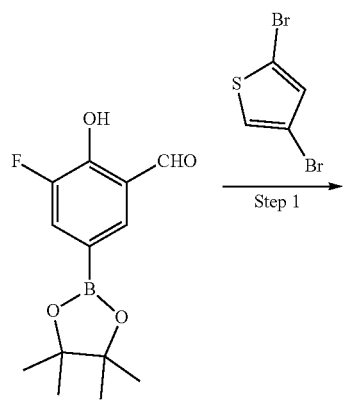

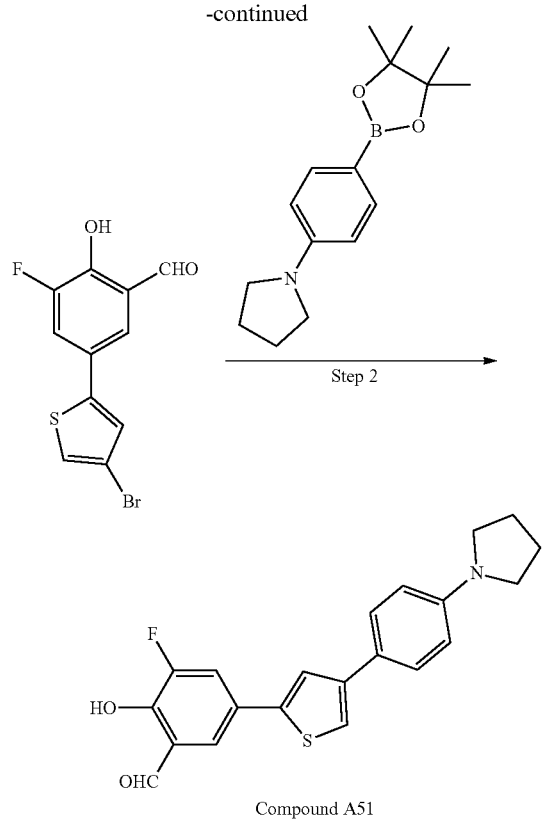

Compound A51

Step 1: 5-(4-bromothiophen-2-yl)-3-fluoro-2-hydroxybenzaldehyde

A mixture of 2,4-dibromothiophene (1 g, 4.1 mmol, 1.0 eq.), 3-fluoro-2-hydroxy-5-(4,4,5,5-tetramethyl-1,3,2-dioxaborolan-2-yl)benzaldehyde (1.2 g, 4.51 mmol, 1.08 eq.), potassium phosphate (4.4 g, 20.8 mmol, 5.0 eq.), Pd(PPh$_3$)$_4$ (0.48 g, 0.41 mmol, 0.1 eq.) in dioxane/water (20 mL/6 mL) was heated at 100° C. for 3 hours under nitrogen atmosphere. The mixture was cooled to room temperature and poured into water. Then pH of the system was adjusted to 4-5 and extracted with ethyl acetate for three times. The organic extracts were combined, washed with brine, dried over anhydrous sodium sulfate, and concentrated. The residue was purified by silica gel column (petroleum ether/EtOAc=100:1 to 20:1) to give 5-(4-bromothiophen-2-yl)-3-fluoro-2-hydroxybenzaldehyde (390 mg, 1.29 mmol, 31% yield). LC-MS m/z [M+H]$^+$ calc'd for C$_{11}$H$_6$BrFO$_2$S, 301; found, 301.

Step 2

A mixture of 5-(4-bromothiophen-2-yl)-3-fluoro-2-hydroxybenzaldehyde (302 mg, 1 mmol, 1.0 eq.), 1-(4-(4,4,5,5-tetramethyl-1,3,2-dioxaborolan-2-yl)phenyl)pyrrolidine (295 mg, 1.08 mmol, 1.08 eq.), potassium phosphate (1.06 g, 5.0 mmol, 5.0 eq.), Pd(PPh$_3$)$_4$ (116 mg, 0.1 mmol, 0.1 eq.) in dioxane/water (10 mL/3 mL) was heated at 100° C. for 3 hours under nitrogen atmosphere. The mixture was cooled to room temperature and poured into water. Then pH of the system was adjusted to 4-5 and extracted with ethyl acetate for three times. The organic extracts were combined, washed with brine, dried over anhydrous sodium sulfate, and concentrated. The residue was purified by silica gel column (petroleum ether/EtOAc=100:1 to 20:1) to give 3-fluoro-2-hydroxy-5-(4-(4-(pyrrolidin-1-yl)phenyl)thiophen-2-yl)benzaldehyde (60 mg, 0.16 mmol, 16% yield) as a yellow solid. $^1$H NMR (DMSO-d6, 400 MHz) δ: 11.13 (br, 1H), 10.32 (s, 1H), 8.00 (dd, J=12.4 Hz, 2.4 Hz, 1H), 7.93 (d, J=1.2 Hz, 1H), 7.72 (s, 1H), 7.61-7.55 (m, 3H), 6.57 (d, J=8.8 Hz, 2H), 3.26 (m, 4H), 1.97 (m, 4H). LC-MS m/z [M+H]$^+$ calc'd for $C_{21}H_{18}FNO_2S$, 368; found, 368.

Example A48: 3-fluoro-2-hydroxy-5-(5-(4-(pyrrolidin-1-yl)phenyl)thiophen-3-yl)benzaldehyde (Compound A52)

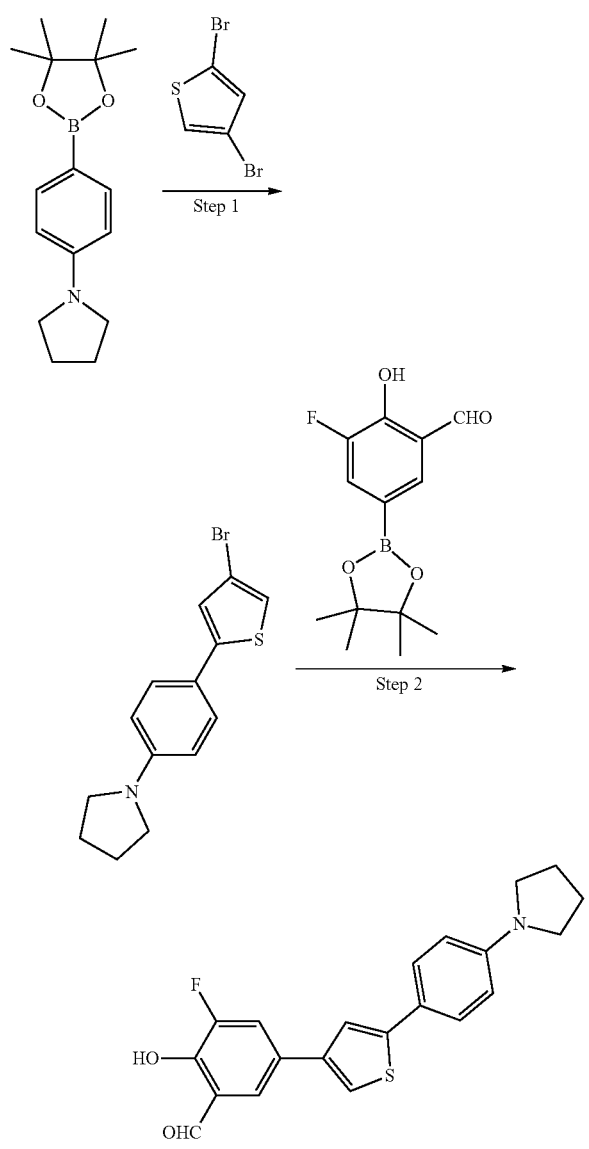

Compound A52

Step 1:
1-(4-(4-bromothiophen-2-yl)phenyl)pyrrolidine

A mixture of 2,4-dibromothiophene (1 g, 4.1 mmol, 1.0 eq.), 1-(4-(4,4,5,5-tetramethyl-1,3,2-dioxaborolan-2-yl)phenyl)pyrrolidine (1.22 g, 4.51 mmol, 1.08 eq.), potassium phosphate (4.4 g, 20.8 mmol, 5.0 eq.), Pd(PPh$_3$)$_4$ (0.48 g, 0.41 mmol, 0.1 eq.) in dioxane/water (20 mL/6 mL) was heated at 100° C. for 3 hours under nitrogen atmosphere. The mixture was cooled to room temperature and poured into water. Then pH of the system was adjusted to 4-5 and extracted with ethyl acetate for three times. The organic extracts were combined, washed with brine, dried over anhydrous sodium sulfate, and concentrated. The residue was purified by silica gel column (petroleum ether/EtOAc=100 to 500:1) to give 1-(4-(4-bromothiophen-2-yl)phenyl)pyrrolidine (260 mg, 0.84 mmol, 21% yield), used in next step.

Step 2

The title compound was prepared from 1-(4-(4-bromothiophen-2-yl)phenyl)pyrrolidine (230 mg, 0.74 mmol, 1.0 eq.) and 3-fluoro-2-hydroxy-5-(4,4,5,5-tetramethyl-1,3,2-dioxaborolan-2-yl)benzaldehyde (214 mg, 0.80 mmol, 1.08 eq.) using a method similar to that as described in Example A47 to give the final title compound (110 mg, 0.30 mmol, 41% yield) as a yellow solid. $^1$H NMR (DMSO-d6, 400 MHz) δ: 10.98 (br, 1H), 10.32 (s, 1H), 8.00 (dd, J=12.4 Hz, 2.0 Hz, 1H), 7.87 (d, J=1.2 Hz, 1H), 7.75 (d, J=1.2 Hz, 1H), 7.70 (d, J=1.2 Hz, 1H), 7.54 (d, J=8.8 Hz, 2H), 6.58 (d, J=8.8 Hz, 2H), 3.27 (m, 4H), 1.97 (m, 4H). LC-MS m/z [M+H]$^+$ calc'd for $C_{21}H_{18}FNO_2S$, 368; found, 368.

Example A49: 3-fluoro-2-hydroxy-5-(2-(4-(pyrrolidin-1-yl)phenyl)thiazol-4-yl)benzaldehyde (Compound A57)

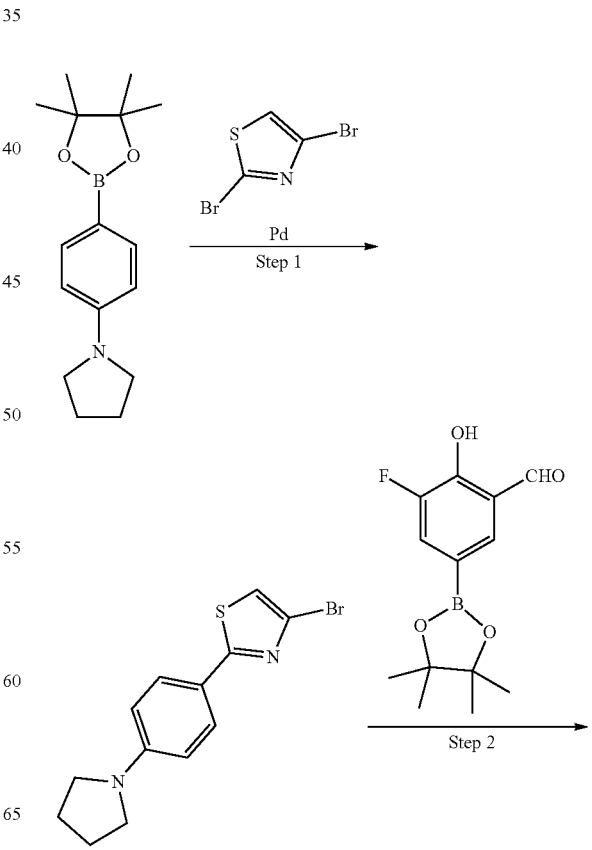

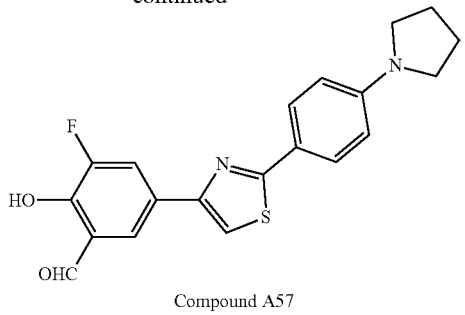

Compound A57

Step 1: 4-bromo-2-(4-(pyrrolidin-1-yl)phenyl)thiazole

A mixture of 2,4-dibromothiazole (500 mg, 2.06 mmol, 1.0 eq.), 1-(4-(4,4,5,5-tetramethyl-1,3,2-dioxaborolan-2-yl) phenyl)pyrrolidine (620 mg, 2.26 mmol, 1.1 eq.), potassium carbonate (850 mg, 6.18 mmol, 3.0 eq.), and PdCl$_2$(dppf) (170 mg, 0.21 mmol, 0.1 eq.) in dioxane/water (10 mL/5 mL) was heated at 100° C. for 1 hour under nitrogen protection. The mixture was cooled to room temperature, poured into water, and extracted with ethyl acetate for three times. The organic extracts were combined, washed with brine, dried over anhydrous sodium sulfate, and concentrated. The residue was purified by silica gel column (petroleum ether/EtOAc=100 to 500:1) to give 4-bromo-2-(4-(pyrrolidin-1-yl)phenyl)thiazole (397 mg, 1.29 mmol, 63% yield). LC-MS m/z [M+H]$^+$ calc'd for C$_{13}$H$_{13}$BrN$_2$S, 311; found, 311.

Step 2

The title compound was prepared from 3-fluoro-2-hydroxy-5-(4,4,5,5-tetramethyl-1,3,2-dioxaborolan-2-yl)benzaldehyde (415 mg, 1.56 mmol, 1.2 eq.) and 4-bromo-2-(4-(pyrrolidin-1-yl)phenyl)thiazole (400 mg, 1.30 mmol, 1.0 eq.) using a method similar to that as described in Example A47 to give the final title compound (110 mg, 0.30 mmol, 41% yield) as a yellow solid. $^1$H NMR (DMSO-d6, 400 MHz) δ: 11.12 (br, 1H), 10.35 (s, 1H), 8.14 (dd, J=10.0 Hz, 2.4 Hz, 2H), 7.97 (s, 1H), 7.82 (d, J=8.8 Hz, 2H), 6.63 (d, J=8.8 Hz, 2H), 3.31 (m, 4H), 1.98 (m, 4H). LC-MS m/z [M–H]$^-$ calc'd for C$_{20}$H$_{17}$FN$_2$O$_2$S, 367; found, 367.

Example A50: 3-fluoro-2-hydroxy-5-(5-(4-(pyrrolidin-1-yl)phenyl)-1,2,4-thiadiazol-3-yl)benzaldehyde (Compound A61)

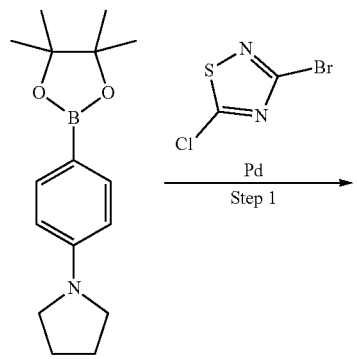

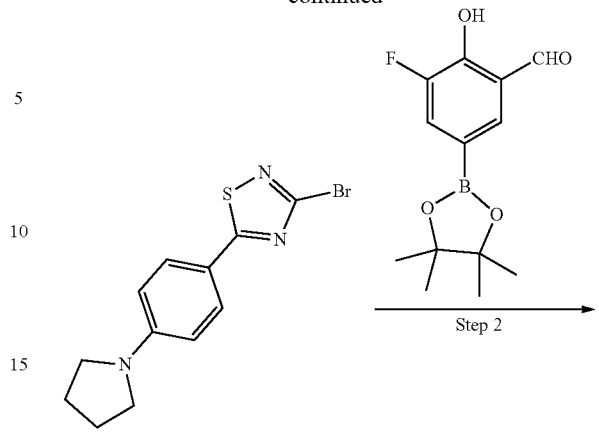

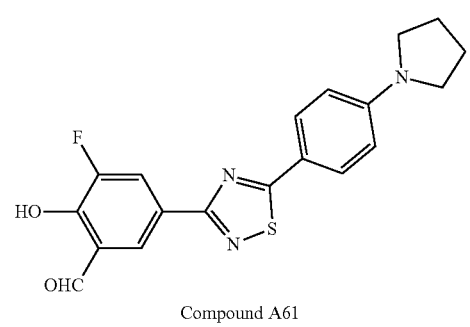

Compound A61

Step 1: 3-bromo-5-(4-(pyrrolidin-1-yl)phenyl)-1,2,4-thiadiazole

A mixture of 3-bromo-5-chloro-1,2,4-thiadiazole (0.5 g, 2.5 mmol, 1.0 eq.), 1-(4-(4,4,5,5-tetramethyl-1,3,2-dioxaborolan-2-yl)phenyl)pyrrolidine (0.75 g, 2.75 mmol, 1.1 eq.), potassium phosphate (1.59 g, 7.5 mmol, 3.0 eq.), PdCl$_2$(dppf) (204 mg, 0.25 mmol, 0.1 eq.) in DMF/water (6 mL/2 mL) was heated at 80° C. for 2.5 hours under nitrogen atmosphere. The mixture was cooled to room temperature and poured into water. Then pH of the system was adjusted to 4-5 and extracted with ethyl acetate for three times. The organic extracts were combined, washed with brine, dried over anhydrous sodium sulfate, and concentrated. The residue was purified by silica gel column (petroleum ether/EtOAc=20:1 to 50:1) to give 3-bromo-5-(4-(pyrrolidin-1-yl)phenyl)-1,2,4-thiadiazole (203 mg, 0.66 mmol, 26% yield). LC-MS m/z [M+H]$^+$ calc'd for C$_{12}$H$_{12}$BrN$_3$S, 312; found, 312.

Step 2

The title compound was prepared from 3-fluoro-2-hydroxy-5-(4,4,5,5-tetramethyl-1,3,2-dioxaborolan-2-yl)benzaldehyde (133 mg, 0.50 mmol, 1.1 eq.) and 3-bromo-5-(4-(pyrrolidin-1-yl)phenyl)-1,2,4-thiadiazole (140 mg, 0.45 mmol, 1.0 eq.) using a method similar to that as described in Example A47 to give the final title compound (30 mg, 0.08 mmol, 18% yield) as a yellow solid. $^1$H NMR (DMSO-d6, 400 MHz) δ: 11.54 (br, 1H), 10.37 (s, 1H), 8.38 (d, J=1.2 Hz, 1H), 8.24 (dd, J=11.6 Hz, 2.0 Hz, 1H), 7.89 (d, J=8.8 Hz, 2H), 6.67 (d, J=8.8 Hz, 2H), 3.35 (m, 4H), 1.99 (t, J=6.6 Hz, 4H). LC-MS m/z [M+H]$^+$ calc'd for C$_{19}$H$_{16}$FN$_3$O$_2$S, 370; found, 370.

Example A51: 3-fluoro-2-hydroxy-5-(3-(4-(pyrrolidin-1-yl)phenyl)-1,2,4-thiadiazol-5-yl)benzaldehyde (Compound A62)

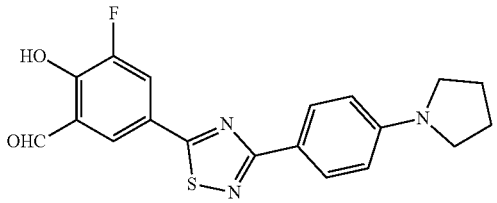 [SMILES: O=Cc1cc(-c2nc(-c3ccc(N4CCCC4)cc3)ns2)cc(F)c1O]

The title compound was prepared from 1-(4-(4,4,5,5-tetramethyl-1,3,2-dioxaborolan-2-yl)phenyl)pyrrolidine (258 mg, 0.94 mmol, 1.1 eq.) and 5-(3-bromo-1,2,4-thiadiazol-5-yl)-3-fluoro-2-hydroxybenzaldehyde (260 mg, 0.86 mmol, 1 eq.) (prepared as in Example A47) using a method similar to that as described in Example A47 to give the final title compound (87 mg, 0.24 mmol, 27% yield) as a yellow solid. $^1$H NMR (DMSO-d6, 400 MHz) δ: 11.88 (br, 1H), 10.36 (s, 1H), 8.22 (dd, J=11.2 Hz, 2.4 Hz, 1H), 8.15 (s, 1H), 8.13 (d, J=8.8 Hz, 2H), 6.65 (d, J=9.2 Hz, 2H), 3.32 (t, J=6.8 Hz, 4H), 1.98 (m, 4H). LC-MS m/z [M+H]$^+$ calc'd for $C_{19}H_{16}FN_3O_2S$, 370; found, 370.

Example A52: 3-fluoro-2-hydroxy-5-(2-phenyloxazol-5-yl)benzaldehyde (Compound A88)

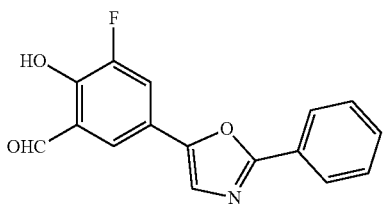 [SMILES: O=Cc1cc(-c2cnc(-c3ccccc3)o2)cc(F)c1O]

The title compound was prepared from 5-bromo-2-phenyloxazole (223 mg, 1 mmol, 1 eq.) and 3-fluoro-2-hydroxy-5-(4,4,5,5-tetramethyl-1,3,2-dioxaborolan-2-yl)benzaldehyde (244 mg, 1.08 mmol, 1.08 eq.) using a method similar to that as described in Example A47 to give the final title compound (120 mg, 0.42 mmol, 42% yield) as a yellow solid. $^1$H NMR (DMSO-d6, 400 MHz) δ: 11.35 (br, 1H), 10.35 (s, 1H), 8.12-8.06 (m, 3H), 7.92 (s, 1H), 7.86 (s, 1H), 7.57 (m, 3H). LC-MS m/z [M+H]$^+$ calc'd for $C_{16}H_{10}FNO_3$, 284; found, 284.

Example A53: 3-fluoro-2-hydroxy-5-(5-phenyloxazol-2-yl)benzaldehyde (Compound A89)

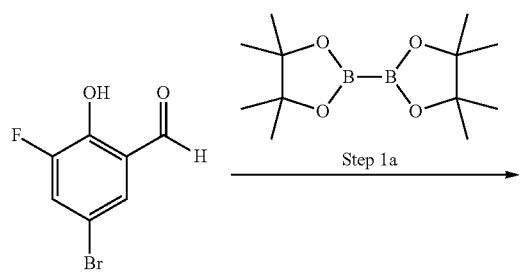

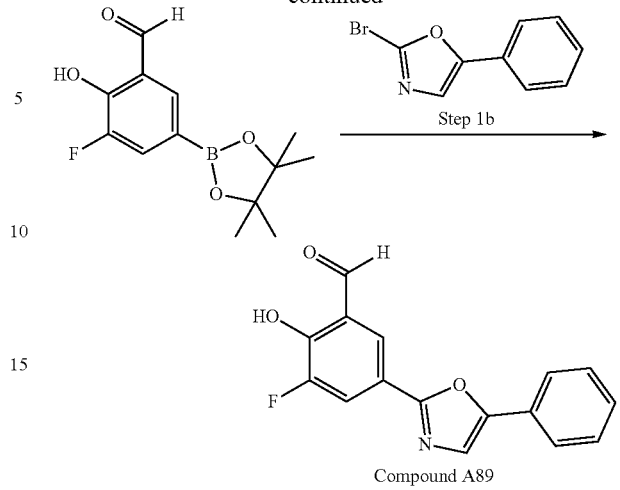

Compound A89

3-fluoro-2-hydroxy-5-(5-phenyloxazol-2-yl)benzaldehyde was synthesized in a manner similar to that described by Ji et al. (*RSC Adv.*, 2018, 8, 13643-13648.)

Step 1a 5-bromo-3-fluoro-2-hydroxybenzaldehyde (131 mg, 0.6 mmol), bis(pinacolato)diboron, (253 mg, 0.66 mmol), potassium phosphate tribasic (254.7 mg), XPhos Pd G3 (50.8 mg) and XPhos (28.6 mg) were placed in a 5 mL microwave vial with a stir bar. Dioxane (2.4 mL) was added and the vial was degassed with argon and sealed. The reaction was heated to 130° C. in a Biotage microwave for 60 minutes.

Step 1b

An aliquot (0.8 mL) of the reaction mixture from step 1a was added to a microwave vial containing 2-bromo-5-phenyloxazole (44.8 mg, 0.2 mmol), XPhos Pd G3 (8.5 mg) and XPhos (4.8 mg). The reaction was degassed with argon and heated to to 130° C. in a microwave for 30 minutes. The reaction mixture was diluted with DCM, acidified to pH=3 with citric acid and extracted 3 times with DCM. The combined organic phases were washed with brine and dried over anhydrous $Na_2SO_4$, filtered and evaporated. The crude product was purified by flash column chromatography 0-10% MeOH/DCM. Yield (6.6 mg, 12%). $^1$H NMR (500 MHz, CDCl$_3$) δ 11.22 (s, 1H), 10.04 (d, J=1.7 Hz, 1H), 8.19 (dd, J=2.0, 1.2 Hz, 1H), 8.10 (dd, J=11.0, 2.0 Hz, 1H), 7.98 (s, 1H), 7.85-7.77 (m, 2H), 7.48-7.41 (m, 2H), 7.40-7.33 (m, 1H). MS m/z [M+H]$^+$ calc'd for $C_{16}H_{10}FNO_3$, 284; found 284.

Example A54: 3-fluoro-2-hydroxy-5-(4-phenyloxazol-2-yl)benzaldehyde (Compound A90)

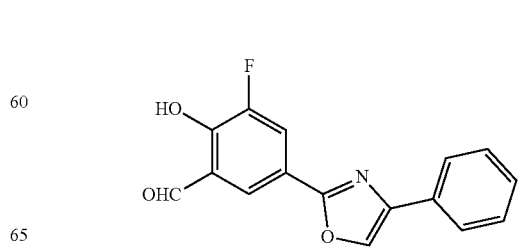

The title compound was prepared using a method similar to that as described in Example A53, using commercially available 2-bromo-4-phenyloxazole. Yield: 14%. ¹H NMR (500 MHz, CDCl₃) δ 11.22 (s, 1H), 10.04 (d, J=1.7 Hz, 1H), 8.19 (dd, J=2.0, 1.2 Hz, 1H), 8.10 (dd, J=11.0, 2.0 Hz, 1H), 7.98 (s, 1H), 7.84-7.78 (m, 2H), 7.49-7.41 (m, 2H), 7.40-7.32 (m, 1H). MS m/z [M+H]⁺ calc'd for $C_{16}H_{10}FNO_3$ 284; found 284.

Example A55: 3-fluoro-2-hydroxy-5-(2-phenylthiazol-5-yl)benzaldehyde (Compound A91)

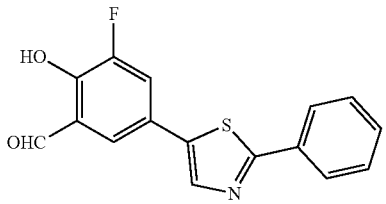

The title compound was prepared using a method similar to that as described in Example A53, using commercially available 5-bromo-2-phenylthiazole. Yield 9%. ¹H NMR (500 MHz, CDCl₃) δ 11.15 (s, 1H), 10.03 (d, J=1.8 Hz, 1H), 8.03 (dd, J=2.1, 1.2 Hz, 1H), 8.01 (s, 1H), 7.97 (dd, J=11.1, 2.1 Hz, 1H), 7.62-7.59 (m, 2H), 7.47-7.43 (m, 2H), 7.40-7.35 (m, 1H). MS m/z [M+H]⁺ calc'd for $C_{16}H_{10}FNO_2S$, 300; found 300.

Example A56: 5-(2-(4-chlorophenyl)thiazol-4-yl)-3-fluoro-2-hydroxybenzaldehyde (Compound A92)

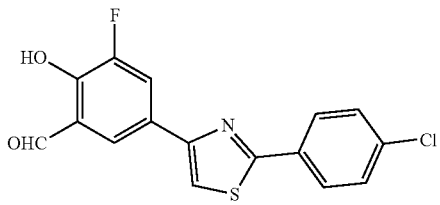 [SMILES: O=Cc1cc(-c2csc(-c3ccc(Cl)cc3)n2)cc(F)c1O]

The title compound was prepared using a method similar to that as described in Example A53, using commerically available 4-bromo-2-(4-chlorophenyl)thiazole. Yield: 14%. 1H NMR (500 MHz, Chloroform-d) δ 11.03 (s, 1H), 10.04 (d, J=1.8 Hz, 1H), 8.06 (dd, J=2.1, 1.2 Hz, 1H), 8.00-7.95 (m, 3H), 7.47-7.43 (m, 3H). MS m/z [M+H]⁺ calc'd for $C_{16}H_9ClFNO_2S$, 334; found 334.

Example A57: 3-fluoro-2-hydroxy-5-(4-phenylthiazol-2-yl)benzaldehyde (Compound A93)

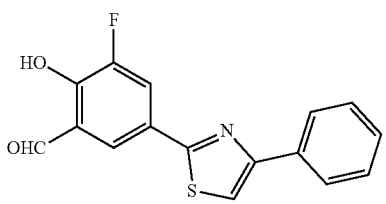 [SMILES: O=Cc1cc(-c2nc(-c3ccccc3)cs2)cc(F)c1O]

The title compound was prepared using a method similar to that as described in Example A53, using commercially available 2-bromo-4-phenylthiazole. Yield: 30%. 1H NMR (500 MHz, CDCl₃) δ 11.16 (s, 1H), 10.04 (d, J=1.8 Hz, 1H), 8.08-8.04 (m, 1H), 8.07 (s 1H), 7.99-7.97 (m, 2H), 7.50 (s, 1H), 7.49-7.44 (m, 2H), 7.40-7.36 (m, 1H). MS m/z [M+H]+ calc'd for $C_{16}H_{10}FNO_2S$ 300; found 300.

Example A58: 3-fluoro-2-hydroxy-5-(5-phenyl-1,3,4-thiadiazol-2-yl)benzaldehyde (Compound A94)

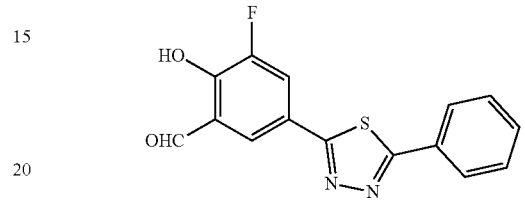

The title compound was prepared using a method similar to that as described in Example A53, using commercially available 2-bromo-5-phenyl-1,3,4-thiadiazole. Yield: 20%. ¹H NMR (500 MHz, Chloroform-d) δ 11.26 (s, 1H), 10.04 (d, J=1.7 Hz, 1H), 8.08 (dd, J=2.0, 1.2 Hz, 1H), 8.02 (tt, J=7.4, 2.1 Hz, 3H), 7.55-7.49 (m, 3H). MS m/z [M+H]⁺ calc'd for $C_{15}H_9FN_2O_2S$ 301; found 301.

Example A59: 3-fluoro-2-hydroxy-5-(3-phenyl-1,2,4-thiadiazol-5-yl)benzaldehyde (New Compound A95)

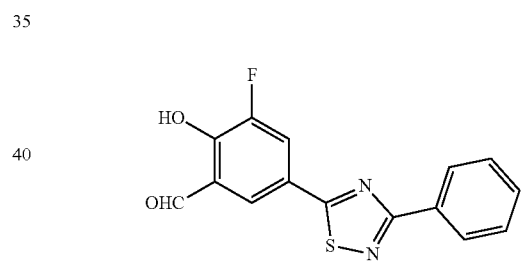

The title compound was prepared using a method similar to that as described in Example A53. However, the intermediate 3-fluoro-2-hydroxy-5-(4,4,5,5-tetramethyl-1,3,2-dioxaborolan-2-yl)benzaldehyde, was synthesized and isolated according to the procedure by DiMauro et al. (*J. Org. Chem*, 2006, 71(10), 359-3962.)

Step 1

To a 5 mL microwave vial was added 5-bromo-3fluorosalicaldehyde (329 mg, 1.5 mmol), bis(pinacolato)diboron (419 mg, 1.65 mmol), potassium acetate (295 mg, 3 mmol) and Pd(dppf)Cl₂ (109 mg, 0.15 mmol) followed by 5 mL of dioxane. The mixture was purged with argon and heated in the microwave for 45 minutes at 140° C. The mixture was cooled, transferred to a round bottom flask, concentrated to dryness and resuspended in DCM. After filtering through celite and concentrating again, the product was purified by flash column chromatography using 0-100% DCM in Hexanes as an eluent to provide 3-fluoro-2-hydroxy-5-(4,4,5,5-tetramethyl-1,3,2-dioxaborolan-2-yl)benzaldehyde as a colorless oil that solidified upon standing (237 mg, 59% yield). ¹H NMR (500 MHz, DMSO-d6) δ 11.35 (s, 1H), 10.27 (s, 1H), 7.82 (dd, J=1.6, 0.7 Hz, 1H), 7.59 (dd, J=11.1, 1.5 Hz, 1H), 1.29 (s, 12H).

Step 2

To a 2 mL microwave vial was added 3-fluoro-2-hydroxy-5-(4,4,5,5-tetramethyl-1,3,2-dioxaborolan-2-yl)benzaldehyde (40 mg, 0.15 mmol) from step 1a, 5-bromo-3-phenyl-1,2,4-thiadiazole (36 mg, 0.15 mmol), XPhos Pd G3 (6.4 mg, 0.05 eq.) and XPhos (3.6 mg, 0.05 eq.) dioxane (0.6 mL) and degassed 0.5M K₃PO₄ (0.6 mL). The microwave vessel was purged with argon and heated to 130° C. in the microwave for 30 minutes. The reaction mixture was diluted with DCM, acidified to pH=3 with citric acid and extracted 3 times with DCM. The combined organic phases were washed with brine and dried over anhydrous Na₂SO₄, filtered and evaporated. The crude product was purified by flash column chromatography 0-10% MeOH/DCM. Yield (8 mg, 17%). ¹H NMR (500 MHz, DMSO-d6) δ 12.02 (bs, 1H), 10.36 (s, 1H), 8.36-8.24 (m, 3H), 8.24-8.15 (m, 1H), 7.64-7.47 (m, 3H). MS m/z [M+H]⁺ calc'd for C₁₅H₉FN₂O₂S, 301; found 301.

Example A60: 3-fluoro-2-hydroxy-5-(3-phenyl-1H-1,2,4-triazol-5-yl)benzaldehyde (New Compound A96)

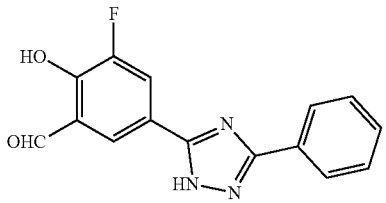 [SMILES: O=Cc1cc(-c2nc(-c3ccccc3)n[nH]2)cc(F)c1O]

The title compound was prepared using a method similar to that as described in Example A53, using commercially available 5-bromo-3-phenyl-1H-1,2,4-triazole. Yield: 8%. ¹H NMR (500 MHz, DMSO-d6) δ 14.59 (s, 1H), 11.3 (bs, 1H), 10.37 (s, 1H), 8.21 (d, J=1.9 Hz, 1H), 8.07 (d, J=8.9 Hz, 3H), 7.66-7.37 (m, 3H). MS m/z [M+H]⁺ calc'd for C₁₅H₁₀FN₃O₂, 284; found 284.

Example A61: 3-fluoro-5-(2-(4-((3aR,6aS)-hexahydrocyclopenta[c]pyrrol-2(1H)-yl)phenyl)thiazol-4-yl)-2-hydroxybenzaldehyde (Compound A97)

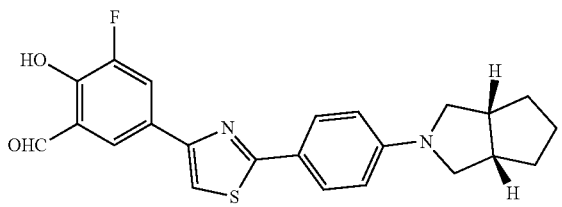 [SMILES: O=Cc1cc(-c2csc(-c3ccc(N4C[C@H]5CCC[C@H]5C4)cc3)n2)cc(F)c1O]

3-fluoro-5-(2-(4-((3aR,6aS)-hexahydrocyclopenta[c]pyrrol-2(1H)-yl)phenyl)thiazol-5-yl)-2-hydroxybenzaldehyde was synthesized from Compound A92 by a similar method described by Maiti et al. (*Chem. Sci.*, 2011, 2, 57-68.) 5-(2-(4-chlorophenyl)thiazol-4-yl)-3-fluoro-2-hydroxyben- zaldehyde (24 mg, 0.09 mmol), was added to a 2 mL microwave vial with (3aR,6aS)-octahydrocyclopenta[c]pyrrole hydrochloride (16 mg, 0.11 mmol), RuPhos Pd G3 (3.67 mg, 0.05 eq.) and RuPhos (2.05 mg, 0.05 eq.). The vial was sealed and evacuated and backfilled with argon three times. THF (0.3 mL) and and 1M LiHMDS in THF (0.3 mL) was added via syringe. The reaction mixture was heated to 65° C. with stirring overnight. The reaction mixture was then diluted with dichloromethane, washed with water, dried over Na₂SO₄, filtered and evaporated. The crude material was purified by flash column chromatography using 0-30% ethyl acetate in hexanes. Yield: 8 mg, 22%. ¹H NMR (499 MHz, Chloroform-d) δ 10.99 (s, 1H), 10.03 (d, J=1.9 Hz, 1H), 8.06 (dd, J=2.1, 1.1 Hz, 1H), 7.95 (dd, J=11.7, 2.1 Hz, 1H), 7.90-7.85 (m, 2H), 6.60 (dd, J=8.8, 6.7 Hz, 3H), 3.55 (dd, J=9.7, 7.9 Hz, 2H), 3.12 (dd, J=9.7, 3.9 Hz, 2H), 2.82 (m, 2H), 1.89 (m, 2H), 1.83-1.73 (m, 1H), 1.69-1.59 (m, 1H) 1.55 (m, 2H). MS m/z [M+H]⁺ calc'd for C₂₃H₂₁FN₂O₂S, 409; found 409.

Example A62: 3-fluoro-2-hydroxy-5-(2-(4-(pyrrolidin-1-yl)phenyl)thiazol-5-yl)benzaldehyde (Compound A55)

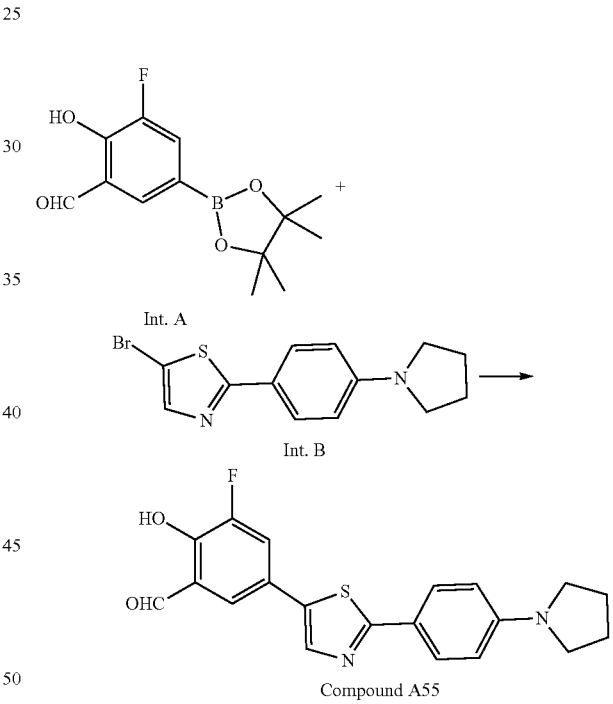

The synthesis of Intermediate B, 5-bromo-2-(4-(pyrrolidin-1-yl)phenyl)thiazole, was accomplished by adding 1-(4-(4,4,5,5-tetramethyl-1,3,2-dioxaborolan-2-yl)phenyl)pyrrolidine (476 mg, 1.7 mmol), 2,5-dibromothiazole (508 mg, 2.1 mmol), XantPhos Pd G3 (83 mg, 0.09 mmol) and Xantphos (50.4 mg, 0.09 mmol) to a 40 mL screw top pressure relief vial. Dioxane (8.7 mL) and degassed 0.5M K₃PO₄ (8.7 mL) were added and the vial was degassed with argon. The sealed reaction vessel was heated to 140° C. for 4 hours, cooled, diluted with DCM and extracted with a water and saturated aqueous NaHCO₃. The combined aqueous layers were extracted 2 times more with DCM. The combined organic layers were washed with brine, dried over Na₂SO₄, filtered and evaporated. Purified using 0-70% DCM/Hexanes to provide 5-bromo-2-(4-(pyrrolidin-1-yl)

phenyl)thiazole (274 mg, 51% yield). 1H NMR (500 MHz, DMSO-d6) δ 7.79 (s, 1H), 7.74-7.61 (m, 2H), 6.67-6.52 (m, 2H), 3.29-3.22 (m, 4H), 2.08-1.87 (m, 4H).

Compound A55, 3-Fluoro-2-hydroxy-5-(2-(4-(pyrrolidin-1-yl)phenyl)thiazol-5-yl)benzaldehyde, was synthesized by coupling Int. A, 3-fluoro-2-hydroxy-5-(4,4,5,5-tetramethyl-1,3,2-dioxaborolan-2-yl)benzaldehyde (94 mg, 0.35 mmol), with Intermediate B, 5-bromo-2-(4-(pyrrolidin-1-yl)phenyl)thiazole (109 mg, 0.35 mmol), in a method similar to that as described in Example A59. Yield: 32 mg, 25%. 1H NMR (500 MHz, DMSO-d6) δ 11.20 (bs, 1H), 10.31 (s, 1H), 8.14 (s, 1H), 7.96 (dd, J=11.9, 2.3 Hz, 1H), 7.82-7.72 (m, 2H), 7.64 (dd, J=2.3, 1.0 Hz, 1H), 6.66-6.57 (m, 2H), 3.31-3.28 (m, 4H), 2.02-1.94 (m, 4H). MS m/z [M+H]$^+$ calc'd for $C_{20}H_{17}FN_2O_2S$, 369; found 369.

Example A63: 3-fluoro-2-hydroxy-5-(4-methyl-2-(4-(pyrrolidin-1-yl)phenyl)thiazol-5-yl)benzaldehyde (Compound A98)

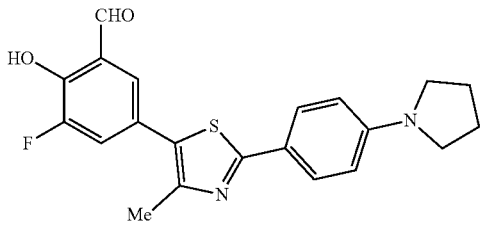 [SMILES: Cc1nc(-c2ccc(N3CCCC3)cc2)sc1-c1cc(F)c(O)c(C=O)c1]

The title compound was prepared using a method similar to that as described in Example A62 using 3-fluoro-2-hydroxy-5-(4,4,5,5-tetramethyl-1,3,2-dioxaborolan-2-yl) benzaldehyde (50 mg, 0.19 mmol) and 5-bromo-4-methyl-2-(4-(pyrrolidin-1-yl)phenyl)thiazole (58 mg, 0.19 mmol), made a method similar to that as described for Int. B in Example A62, was used to make 3-fluoro-2-hydroxy-5-(4-methyl-2-(4-(pyrrolidin-1-yl)phenyl)thiazol-5-yl)benzaldehyde (28 mg, 40% yield). $^1$H NMR (500 MHz, Chloroform-d) δ 10.98 (s, 1H), 9.97 (d, J=1.8 Hz, 1H), 7.88-7.73 (m, 2H), 7.50-7.43 (m, 2H), 6.57 (dd, J=9.1, 2.6 Hz, 2H), 3.41-3.32 (m, 4H), 2.51 (s, 3H), 2.04 (ddd, J=6.7, 4.2, 2.9 Hz, 4H). MS m/z [M+H]$^+$ calc'd for $C_{21}H_{19}FN_2O_2S$, 383; found 383.

Example A64: 5-hydroxy-2-(2-phenylthiazol-5-yl)isonicotinaldehyde (Compound A99)

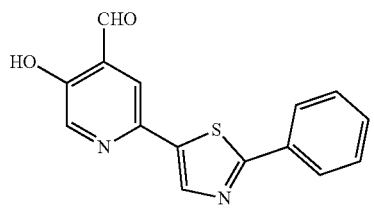 [SMILES: O=Cc1cc(-c2cnc(-c3ccccc3)s2)ncc1O]

5-Hydroxy-2-(2-phenylthiazol-5-yl)isonicotinaldehyde was synthesized by coupling 2-bromo-5-hydroxyisonicotinaldehyde (50 mg, 0.25 mmol) with commercially available 2-phenyl-5-(4,4,5,5-tetramethyl-1,3,2-dioxaborolan-2-yl) thiazole (71 mg, 0.25 mmol) using a method similar to that as described in Example A59. Yield: 8 mg, 11%. $^1$H NMR (499 MHz, Chloroform-d) δ 10.35 (s, 1H), 10.11 (d, J=0.6 Hz, 1H), 8.55 (d, J=0.7 Hz, 1H), 8.22 (s, 1H), 8.04-7.96 (m, 2H), 7.83 (d, J=0.7 Hz, 1H), 7.52-7.42 (m, 3H). MS m/z [M+H]$^+$ calc'd for $C_{15}H_{10}N_2O_2S$, 283; found 283.

Example A65: 5-(3-(4-(3,3-dimethylpyrrolidin-1-yl)phenyl)-1,2,4-thiadiazol-5-yl)-3-fluoro-2-hydroxy-benzaldehyde (Compound A100)

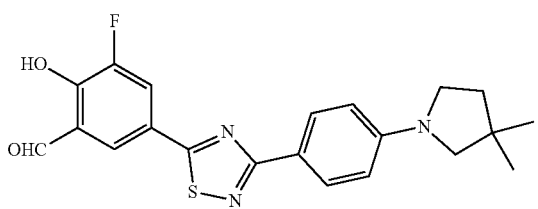 [SMILES: CC1(C)CCN(c2ccc(-c3nsc(-c4cc(F)c(O)c(C=O)c4)n3)cc2)C1]

The title compound was prepared from 3,3-dimethyl-1-(4-(4,4,5,5-tetramethyl-1,3,2-dioxaborolan-2-yl)phenyl) pyrrolidine (176 mg, 0.58 mmol, 1.1 eq) and 5-(3-bromo-1,2,4-thiadiazol-5-yl)-3-fluoro-2-hydroxybenzaldehyde (162 mg, 0.53 mmol, 1.0 eq.) (prepared as in Example A47) using a method similar to that as described in Example A46 to give the final title compound (22 mg, 0.06 mmol, 10% yield) as a yellow solid. $^1$H NMR (DMSO-d6, 400 MHz) δ: 11.87 (br, 1H), 10.36 (s, 1H), 8.23 (m, 1H), 8.16 (s, 1H), 8.10 (d, J=8.8 Hz, 2H), 6.61 (d, J=8.8 Hz, 2H), 3.41 (t, J=6.8 Hz, 2H), 3.11 (s, 2H), 1.80 (t, J=6.8 Hz, 2H), 1.13 (s, 6H). LC-MS m/z [M+H]$^+$ calc'd for $C_{21}H_{20}FN_3O_2S$, 398; found, 398.

Example A66: 3-fluoro-2-hydroxy-5-(2-(3-(pyrrolidin-1-yl)phenyl)thiazol-5-yl)benzaldehyde (Compound A101)

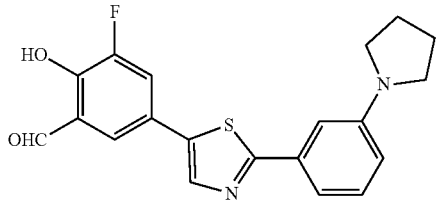 [SMILES: O=Cc1cc(-c2cnc(-c3cccc(N4CCCC4)c3)s2)cc(F)c1O]

3-Fluoro-2-hydroxy-5-(2-(3-(pyrrolidin-1-yl)phenyl)thiazol-5-yl)benzaldehyde was synthesized using a method similar to that as described in Example A62 with 3-fluoro-2-hydroxy-5-(4,4,5,5-tetramethyl-1,3,2-dioxaborolan-2-yl) benzaldehyde (11 mg, 0.04 mmol) and 5-bromo-2-(3-(pyrrolidin-1-yl)phenyl)thiazole (14 mg, 0.17 mmol), made by a method similar to that as described for Int. B in Example A62, as the starting materials. Yield: 8 mg, 51%. $^1$H NMR (500 MHz, DMSO-d6) δ 11.28 (s, 1H), 10.32 (s, 1H), 8.28 (s, 1H), 8.02 (dd, J=11.8, 2.3 Hz, 1H), 7.78-7.67 (m, 1H), 7.29 (t, J=7.9 Hz, 1H), 7.15 (dt, J=7.6, 1.1 Hz, 1H), 7.07 (t, J=2.1 Hz, 1H), 6.67 (dd, J=8.2, 2.5 Hz, 1H), 3.30-3.27 (m, 4H), 2.03-1.95 (m, 4H). MS m/z [M+H]$^+$ calc'd for $C_{20}H_{17}FN_2O_2S$, 369; found 369.

Example A67: 3-fluoro-2-hydroxy-5-(2-(6-(pyrrolidin-1-yl)pyridin-3-yl)thiazol-5-yl)benzaldehyde (New Compound A102)

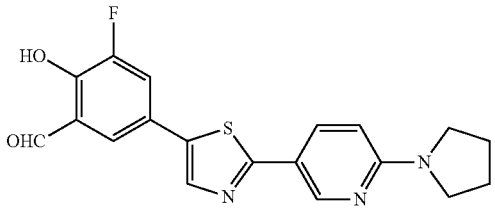

The title compound was made using a method similar to that as described in Example A62 Starting from 3-fluoro-2-hydroxy-5-(4,4,5,5-tetramethyl-1,3,2-dioxaborolan-2-yl)benzaldehyde (25 mg, 0.09 mmol) and 5-bromo-2-(6-(pyrrolidin-1-yl)pyridin-3-yl)thiazole (29 mg, 0.09 mmol), made by a method similar to that as described for Int. B in Example A62. Yield: 31 mg, 89%. $^1$H NMR (500 MHz, DMSO-d6) δ 11.24 (s, 1H), 10.31 (s, 1H), 8.65 (dd, J=2.5, 0.7 Hz, 1H), 8.19 (s, 1H), 8.01-7.94 (m, 2H), 7.65 (dd, J=2.4, 1.0 Hz, 1H), 6.56 (dd, J=9.0, 0.8 Hz, 1H), 3.45 (d, J=6.4 Hz, 4H), 2.01-1.93 (m, 4H). MS m/z [M+H]$^+$ calc'd for $C_{19}H_{16}FN_3O_2S$, 370; found 370.

Example A68: 3-fluoro-2-hydroxy-5-(4-methyl-2-(3-(pyrrolidin-1-yl)phenyl)thiazol-5-yl)benzaldehyde (Compound A103)

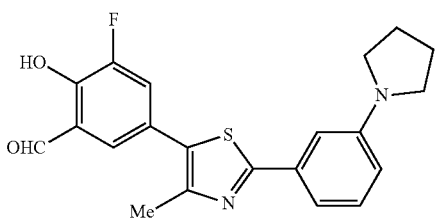 [SMILES: Cc1nc(-c2cccc(N3CCCC3)c2)sc1-c1cc(F)c(O)c(C=O)c1]

The title compound was made using a method similar to that as described in Example A62 using 3-fluoro-2-hydroxy-5-(4,4,5,5-tetramethyl-1,3,2-dioxaborolan-2-yl)benzaldehyde (46 mg, 0.17 mmol) and 5-bromo-4-methyl-2-(3-(pyrrolidin-1-yl)phenyl)thiazole (55 mg, 0.17 mmol), made in a similar manner to Int. B in Example A62. Yield: 31 mg, 47%. $^1$H NMR (500 MHz, DMSO-d6) δ 11.26 (s, 1H), 10.32 (s, 1H), 7.74 (dd, J=11.7, 2.3 Hz, 1H), 7.59 (dd, J=2.3, 1.0 Hz, 1H), 7.31-7.22 (m, 1H), 7.14-7.07 (m, 1H), 7.03 (t, J=2.1 Hz, 1H), 6.65 (ddd, J=8.3, 2.5, 0.9 Hz, 1H), 3.31-3.25 (m, 4H), 2.48 (s, 3H), 2.02-1.93 (m, 4H). MS m/z [M+H]+ calc'd for $C_{21}H19FN_2O_2S$, 383; found 383.

Example A69: 3-fluoro-2-hydroxy-5-(4-methyl-2-(6-(pyrrolidin-1-yl)pyridin-3-yl)thiazol-5-yl)benzaldehyde (Compound A104)

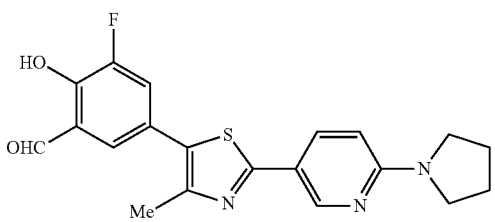 [SMILES: Cc1nc(-c2ccc(N3CCCC3)nc2)sc1-c1cc(F)c(O)c(C=O)c1]

The title compound was made using a method similar to that as described in Example A62 starting from 3-fluoro-2-hydroxy-5-(4,4,5,5-tetramethyl-1,3,2-dioxaborolan-2-yl)benzaldehyde (49 mg, 0.18 mmol) and 5-bromo-4-methyl-2-(6-(pyrrolidin-1-yl)pyridin-3-yl)thiazole (59 mg, 0.18 mmol), made in a similar manner to Int. B in Example A62. Yield: 62 mg, 89%. $^1$H NMR (499 MHz, DMSO-d6) δ 11.23 (s, 1H), 10.32 (s, 1H), 8.61 (d, J=2.4 Hz, 1H), 7.96 (dd, J=8.9, 2.5 Hz, 1H), 7.71 (dd, J=11.7, 2.3 Hz, 1H), 7.56 (dd, J=2.3, 1.0 Hz, 1H), 6.54 (dd, J=11.2, 8.9 Hz, 1H), 3.45 (d, J=6.5 Hz, 4H), 2.44 (s, 3H), 1.96 (h, J=3.3 Hz, 4H). MS m/z [M+H]$^+$ calc'd for $C_{20}H_{18}FN_3O_2S$, 384; found 384.

Example A70: 5-(4-(4-(3,3-dimethylpyrrolidin-1-yl)phenyl)thiazol-2-yl)-3-fluoro-2-hydroxybenzaldehyde (Compound A105)

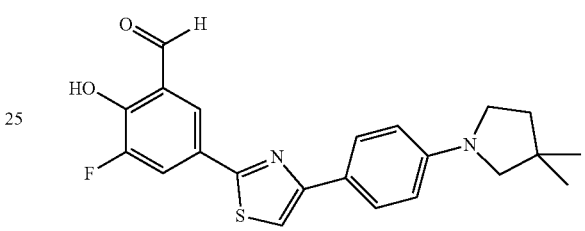

The title compound was prepared from 3,3-Dimethyl-1-(4-(4,4,5,5-tetramethyl-1,3,2-dioxaborolan-2-yl)phenyl)pyrrolidine (153 mg, 0.51 mmol, 1.1 eq.) and 5-(4-bromothiazol-2-yl)-3-fluoro-2-hydroxybenzaldehyde (140 mg, 0.46 mmol, 1.0 eq.) (prepared as in Example A47) using a method similar to that as described in Example A46 to give the final title compound (48 mg, 0.12 mmol, 26% yield) as a yellow solid. $^1$H NMR (DMSO-d6, 400 MHz) δ: 11.51 (br, 1H), 10.35 (s, 1H), 8.11 (dd, J=11.2 Hz, 2.0 Hz, 1H), 8.05 (s, 1H), 7.84 (d, J=8.8 Hz, 2H), 7.79 (s, 1H), 6.56 (d, J=8.8 Hz, 2H), 3.38 (m, 2H), 3.07 (s, 2H), 1.78 (d, J=6.8 Hz, 2H), 1.12 (s, 6H). LC-MS m/z [M-H]$^-$ calc'd for $C_{22}H_{21}FN_2O_2S$, 395; found, 395.

Example A71: 3-fluoro-2-hydroxy-5-(2-(6-(pyrrolidin-1-yl)pyridin-3-yl)thiazol-4-yl)benzaldehyde (Compound A123)

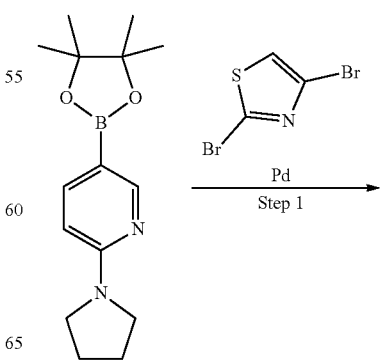

-continued

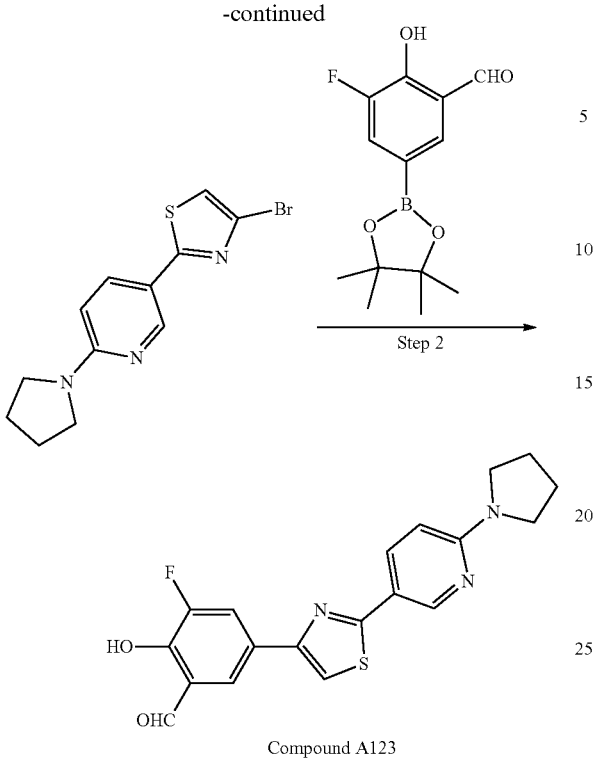

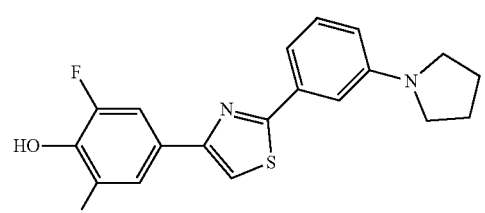

Compound A123

Step 1: 4-bromo-2-(6-(pyrrolidin-1-yl)pyridin-3-yl)thiazole

A mixture of 2,4-dibromothiazole (486 mg, 2.0 mmol, 1.0 eq.), 2-(pyrrolidin-1-yl)-5-(4,4,5,5-tetramethyl-1,3,2-dioxaborolan-2-yl)pyridine (603 mg, 2.2 mmol, 1.1 eq.), potassium carbonate (828 mg, 6.0 mmol, 3.0 eq.), and PdCl$_2$(dppf) (146 mg, 0.2 mmol, 0.1 eq.) in dioxane/water (10 mL/5 mL) was heated at 100° C. for 1 hour under nitrogen protection. The mixture was cooled to room temperature, poured into water, and extracted with ethyl acetate for three times. The organic extracts were combined, washed with brine, dried over anhydrous sodium sulfate, and concentrated. The residue was purified by silica gel column using hexane-EtOAc (0-100%)) to give 4-bromo-2-(6-(pyrrolidin-1-yl)pyridin-3-yl)thiazole (520 mg, 84% yield). LC-MS m/z [M+H]$^+$ calc'd for C$_{12}$H$_{12}$BrN$_3$S, 311; found, 311.

Step 2

In a 30 mL sealed cap glass vial, 3-fluoro-2-hydroxy-5-(4,4,5,5-tetramethyl-1,3,2-dioxaborolan-2-yl)benzaldehyde (266 mg, 1.0 mmol, 1.0 eq.), 4-bromo-2-(6-(pyrrolidin-1-yl)pyridin-3-yl)thiazole (310 mg, 1.30 mmol, 1.0 eq.), sodium carbonate (318 mg, 3.0 mmol, 3.0 eq.) combined in 1:1 dioxane-water (10 mL) then passed nitrogen for 2 min through the mixture and added Pd(PPh$_3$)$_4$ (112 mg, 0.1 mmol, 0.1 eq) and sealed the cap and continued at 105° C. for 8 hours. Then cooled room temperature and added water and extracted with EtOAc (2×25 mL) and washed with brine and dried over sodium sulfate and evaporated. The resulting crude product purified by column chromatography using hexane-EtOAc (0-100%) eluent to give the final title compound (108 mg, 29% yield) as a yellow solid. $^1$H NMR (500 MHz, Chloroform-d) δ 11.00 (s, 1H), 10.02 (d, J=1.8 Hz, 1H), 8.77 (d, J=2.4 Hz, 1H), 8.11-8.02 (m, 2H), 7.94 (dd, J=11.7, 2.0 Hz, 1H), 7.29 (s, 1H), 6.43 (d, J=8.9 Hz, 1H), 3.54 (m, 4H), 2.10-2.01 (m, 4H). LC-MS m/z [M+H]$^+$ calc'd for C$_{19}$H$_{16}$FN$_3$O$_2$S, 370; found, 370.

Example A72: 3-fluoro-2-hydroxy-5-(2-(3-(pyrrolidin-1-yl)phenyl)thiazol-4-yl)benzaldehyde (Compound A124)

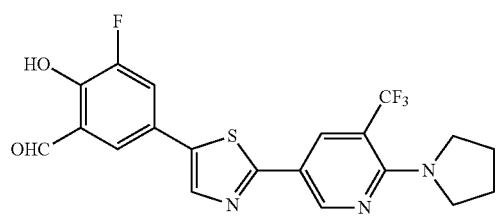 [SMILES: O=Cc1cc(-c2cnc(-c3cnc(N4CCCC4)c(C(F)(F)F)c3)s2)cc(F)c1O]

Step 1:
4-bromo-2-(3-(pyrrolidin-1-yl)phenyl)thiazole

The title compound was prepared from 1-(3-(4,4,5,5-tetramethyl-1,3,2-dioxaborolan-2-yl)phenyl)pyrrolidine (601 mg, 2.2 mmol, 1.1 eq.) and 2,4-dibromothiazole (486 mg, 2.0 mmol, 1.0 eq.) using a method similar to that as described in Example A71 to give the desired product (540 mg, 87% yield) as off-white solid. LC-MS m/z [M+H]$^+$ calc'd for C$_{13}$H$_{13}$BrN$_2$S, 310; found, 310.

Step 2

The title compound was prepared from 3-fluoro-2-hydroxy-5-(4,4,5,5-tetramethyl-1,3,2-dioxaborolan-2-yl)benzaldehyde (133 mg, 0.5 mmol, 1.0 eq.) and 4-bromo-2-(3-(pyrrolidin-1-yl)phenyl)thiazole (155 mg, 0.5 mmol, 1.0 eq.) using a method similar to that as described in Example A46 to give the final title compound (110 mg, 41% yield) as a yellow solid. $^1$H NMR (500 MHz, Chloroform-d) δ 11.01 (s, 1H), 10.04 (d, J=1.9 Hz, 1H), 8.06 (t, J=1.6 Hz, 1H), 7.97 (dd, J=11.6, 2.1 Hz, 1H), 7.40 (s, 1H), 7.33-7.27 (m, 2H), 7.20 (t, J=2.0 Hz, 1H), 6.66 (dt, J=8.2, 1.6 Hz, 1H), 3.39 m, 4H), 2.15-1.96 (m, 4H). LC-MS m/z [M+H]+ calc'd for C$_{20}$H$_{17}$FN$_2$O$_2$S, 369; found, 369.

Example A73: 3-fluoro-2-hydroxy-5-(2-(6-(pyrrolidin-1-yl)-5-(trifluoromethyl)pyridin-3-yl)thiazol-5-yl)benzaldehyde (Compound A114)

3-Fluoro-2-hydroxy-5-(2-(6-(pyrrolidin-1-yl)-5-(trifluoromethyl)pyridin-3-yl)thiazol-5-yl)benzaldehyde was synthesized using a method similar to that as described in Example A62 using 3-fluoro-2-hydroxy-5-(4,4,5,5-tetramethyl-1,3,2-dioxaborolan-2-yl)benzaldehyde (69 mg, 0.35 mmol) with 5-bromo-2-(6-(pyrrolidin-1-yl)-5-(trifluoromethyl)pyridin-3-yl)thiazole (97 mg, 0.35 mmol), synthesized using a similar method as that described for Int. B in Example A62. Yield: 50 mg, 45%. 1H NMR (499 MHz, DMSO-d6) δ 11.28 (s, 1H), 10.31 (s, 1H), 8.85 (d, J=2.3 Hz, 1H), 8.33 (d, J=2.3 Hz, 1H), 8.27 (s, 1H), 8.00 (dd, J=11.9, 2.3 Hz, 1H), 7.67 (dd, J=2.3, 1.0 Hz, 1H), 3.60 (d, J=6.3 Hz, 4H), 1.98-1.88 (m, 4H). LC-MS m/z [M–H]+ calc'd for $C_{20}H_{15}F_4N_3O_2S$, 438, found 438.

Example A74: 3-fluoro-2-hydroxy-5-(5-(3-(pyrrolidin-1-yl)phenyl)-1,2,4-thiadiazol-3-yl)benzaldehyde (Compound A125)

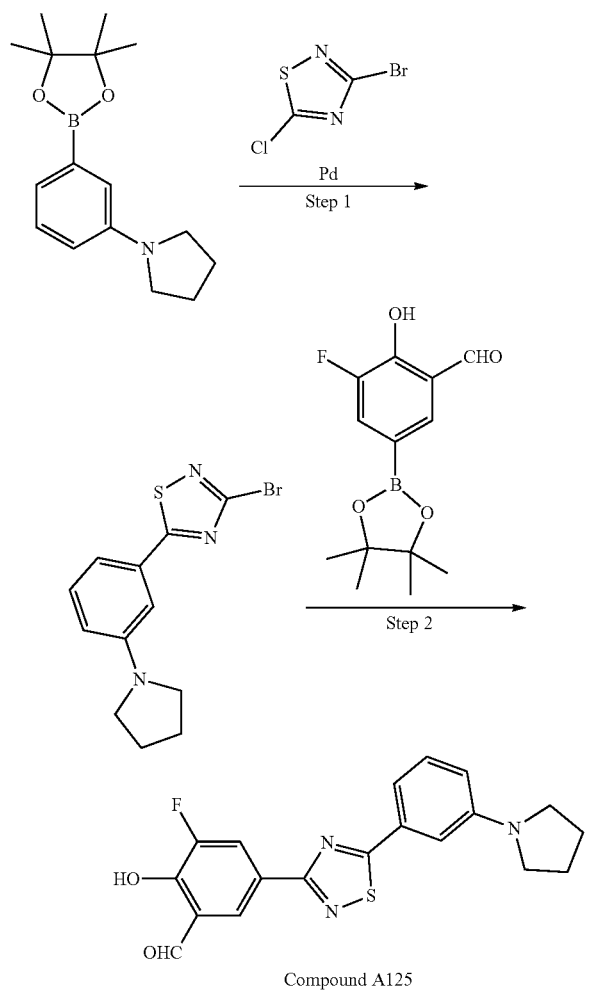

Compound A125

Step 1: 3-bromo-5-(3-(pyrrolidin-1-yl)phenyl)-1,2,4-thiadiazole

The title compound was prepared from 1-(3-(4,4,5,5-tetramethyl-1,3,2-dioxaborolan-2-yl)phenyl)pyrrolidine (601 mg, 2.2 mmol, 1.1 eq.) and 3-bromo-5-chloro-1,2,4-thiadiazole (310 mg, 2.0 mmol, 1.0 eq.) using a method similar to that as described in Example A71 to give the desired product (351 mg, 57% yield) as yellow solid. LC-MS m/z [M+H]+ calc'd for $C_{12}H_{12}BrN_3S$, 311; found, 311.

Step 2

The title compound was prepared from 3-fluoro-2-hydroxy-5-(4,4,5,5-tetramethyl-1,3,2-dioxaborolan-2-yl)benzaldehyde (200 mg, 0.75 mmol, 1.5 eq.) and 3-bromo-5-(3-(pyrrolidin-1-yl)phenyl)-1,2,4-thiadiazole (155 mg, 0.5 mmol, 1.0 eq.) using a method similar to that as described in Example A46 to give the final title compound (42 mg, 49% yield) as a yellow solid. $^1$H NMR (500 MHz, Chloroform-d) δ 11.21 (s, 1H), 10.06 (d, J=1.8 Hz, 1H), 8.46 (t, J=1.6 Hz, 1H), 8.39 (dd, J=11.4, 2.0 Hz, 1H), 7.34 (t, J=7.9 Hz, 1H), 7.28-7.23 (m, 1H), 7.17 (t, J=2.1 Hz, 1H), 6.74 (dd, J=8.3, 2.5 Hz, 1H), 3.45-3.28 (m, 4H), 2.07 (m, 4H). LC-MS m/z [M+H]+ calc'd for $C_{19}H_{16}FN_3O_2S$, 370; found, 370.

Example A75: 3-fluoro-2-hydroxy-5-(2-(6-(piperidin-1-yl)pyridin-3-yl)thiazol-4-yl)benzaldehyde (Compound A126)

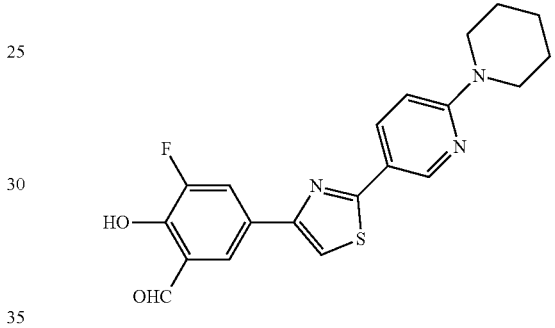

Step 1: 4-bromo-2-(6-(piperidin-1-yl)pyridin-3-yl)thiazole

The title compound was prepared from 2-(piperidin-1-yl)-5-(4,4,5,5-tetramethyl-1,3,2-dioxaborolan-2-yl)pyridine (634 mg, 2.2 mmol, 1.1 eq.) and 2,4-dibromothiazole (486 mg, 2.0 mmol, 1.0 eq.) using a method similar to that as described in Example A71 to give the desired product (352 mg, 54% yield) as yellow solid. LC-MS m/z [M+H]+ calc'd for $C_{13}H_{14}BrN_3S$, 325; found, 325.

Step 2

The title compound was prepared from 3-fluoro-2-hydroxy-5-(4,4,5,5-tetramethyl-1,3,2-dioxaborolan-2-yl)benzaldehyde (200 mg, 0.75 mmol, 1.5 eq.) and 4-bromo-2-(6-(piperidin-1-yl)pyridin-3-yl)thiazole (162 mg, 0.5 mmol, 1.0 eq.) using a method similar to that as described in Example A46 to give the final title compound (21 mg, 11% yield) as a yellow solid. $^1$H NMR (500 MHz, Chloroform-d) δ 11.00 (s, 1H), 10.03 (d, J=1.9 Hz, 1H), 8.76 (d, J=2.5 Hz, 1H), 8.07 (dd, J=9.0, 2.5 Hz, 1H), 8.04 (t, J=1.6 Hz, 1H), 7.94 (dd, J=11.7, 2.1 Hz, 1H), 7.30 (s, 1H), 6.69 (d, J=9.0 Hz, 1H), 3.74-3.40 (m, 4H), 1.74-1.63 (m, 6H). LC-MS m/z [M+H]+ calc'd for $C_{20}H_{18}FN_3O_2S$, 384; found, 384.

Example A76: 3-fluoro-2-hydroxy-5-(2-(6-(piperidin-1-yl)pyridin-3-yl)thiazol-5-yl)benzaldehyde (Compound A127)

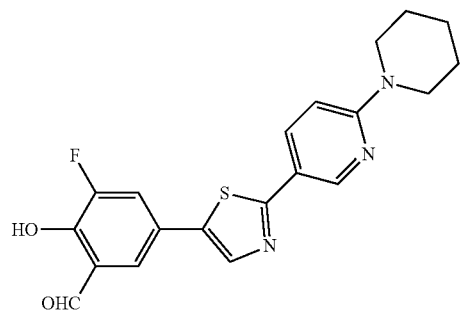 [SMILES: O=Cc1cc(-c2cnc(-c3ccc(N4CCCCC4)nc3)s2)cc(F)c1O]

Step 1: 5-bromo-2-(6-piperidin-1-yl)pyriin-3-yl)thiazole

The title compound was prepared from 2-(piperidin-1-yl)-5-(4,4,5,5-tetramethyl-1,3,2-dioxaborolan-2-yl)pyridine (634 mg, 2.2 mmol, 1.1 eq.) and 2,5-dibromothiazole (486 mg, 2.0 mmol, 1.0 eq.) using a method similar to that as described in Example A71 to give the desired product (225 mg, 35% yield) as yellow solid. LC-MS m/z [M+H]+ calc'd for $C_{13}H_{14}BrN_3S$, 325; found, 325.

Step 2

The title compound was prepared from 3-fluoro-2-hydroxy-5-(4,4,5,5-tetramethyl-1,3,2-dioxaborolan-2-yl)benzaldehyde (80 mg, 0.3 mmol, 1.2 eq.) and 5-bromo-2-(6-(piperidin-1-yl)pyridin-3-yl)thiazole (81 mg, 0.25 mmol, 1.0 eq.) using a method similar to that as described in Example A46 to give the final title compound (78 mg, 81% yield) as a yellow solid. $^1$H NMR (500 MHz, Chloroform-d) δ 10.98 (s, 1H), 9.99 (d, J=1.8 Hz, 1H), 8.70 (d, J=2.5 Hz, 1H), 8.00 (dd, J=9.0, 2.5 Hz, 1H), 7.87 (s, 1H), 7.62-7.53 (m, 2H), 6.69 (d, J=9.0 Hz, 1H), 3.77-3.48 (m, 4H), 1.75-1.63 (m, 6H). LC-MS m/z [M+H]+ calc'd for $C_{20}H_{18}FN_3O_2S$, 384; found, 384.

Example A77: 5-(2-(4-(2-azaspiro[3.3]heptan-2-yl)phenyl)thiazol-5-yl)-3-fluoro-2-hydroxybenzaldehyde (Compound A116)

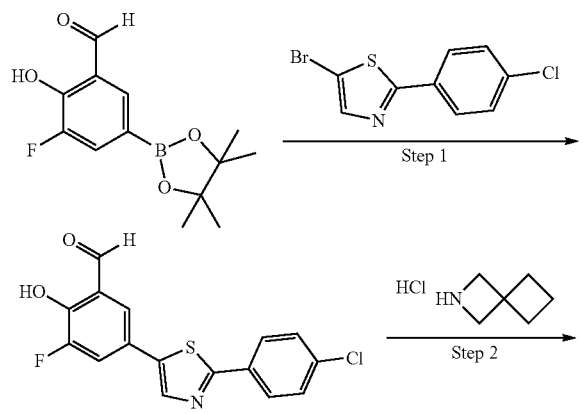

-continued

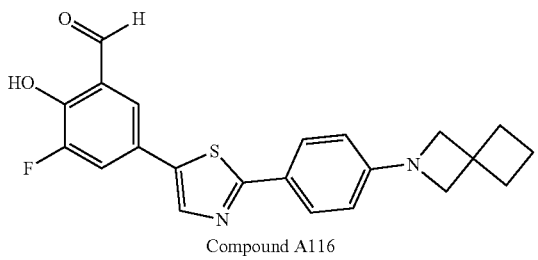

Compound A116

Step 1

Starting from 3-fluoro-2-hydroxy-5-(4,4,5,5-tetramethyl-1,3,2-dioxaborolan-2-yl)benzaldehyde (175 mg, 0.66 mmol) and commercially available 5-bromo-2-(4-chlorophenyl)thiazole (181 mg, 0.66 mmol) the procedure from Example A95 was used to make 5-(2-(4-chlorophenyl)thiazol-5-yl)-3-fluoro-2-hydroxybenzaldehyde, Compound A130 (68 mg, 31% yield). LC-MS m/z [M–H]+ calc'd for $C_{16}H_9ClFNO_2S$, 334; found, 334.

Step 2

A method similar to that as described in Example A61 was used to make 5-(2-(4-(2-azaspiro[3.3]heptan-2-yl)phenyl)thiazol-5-yl)-3-fluoro-2-hydroxybenzaldehyde in 11% yield. 1H NMR (500 MHz, DMSO-d6) δ 11.22 (s, 1H), 10.31 (d, J=3.0 Hz, 1H), 8.15 (s, 1H), 7.97-7.92 (m, 1H), 7.74 (d, J=6.7 Hz, 1H), 7.73 (s, 1H), 7.64 (dd, J=2.3, 1.0 Hz, 1H), 6.50-6.44 (m, 2H), 3.87 (s, 4H), 2.19 (t, J=7.6 Hz, 4H), 1.87-1.75 (m, 2H). LC-MS m/z [M–H]+ calc'd for $C_{22}H_{19}FN_2O_2S$, 395; found, 395.

Example A78: 5-hydroxy-2-(2-(4-(pyrrolidin-1-yl)phenyl)thiazol-5-yl)isonicotinaldehyde (Compound A112)

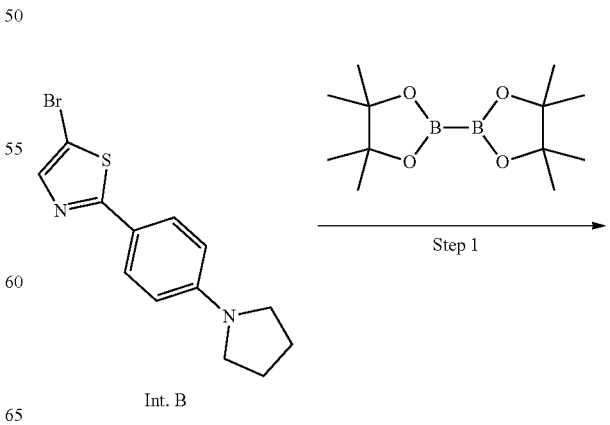

275
-continued

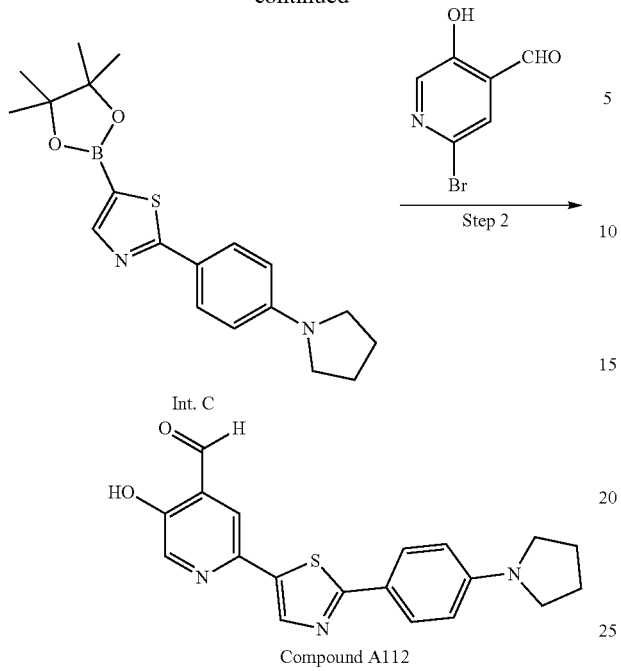

Compound A112

Step 1

The starting material, Int. B, was synthesized using a similar method as described in Example A62. Int. C, 2-(4-(pyrrolidin-1-yl)phenyl)-5-(4,4,5,5-tetramethyl-1,3,2-dioxaborolan-2-yl)thiazole, was made using a similar method used to make 3-fluoro-2-hydroxy-5-(4,4,5,5-tetramethyl-1,3,2-dioxaborolan-2-yl)benzaldehyde in Example A59. However, the Int. C was not purified before using in the next reaction. After completion of the reaction, the crude mixture was taken up in DCM filtered through celite and concentrated to dryness.

Step 2

Using a similar method as described in Example A59, crude 2-(4-(pyrrolidin-1-yl)phenyl)-5-(4,4,5,5-tetramethyl-1,3,2-dioxaborolan-2-yl)thiazole (123 mg), Int. C, and 2-bromo-5-hydroxyisonicotinaldehyde (70 mg, 0.35 mmol) were used to make 5-hydroxy-2-(2-(4-(pyrrolidin-1-yl)phenyl)thiazol-5-yl)isonicotinaldehyde (12 mg, Yield: 10%). $^1$H NMR (500 MHz, DMSO-d6) δ 11.29 (bs, 1H), 10.39 (s, 1H), 8.44 (s, 1H), 8.31 (s, 1H), 7.99 (s, 1H), 7.83-7.73 (m, 2H), 6.67-6.55 (m, 2H), 3.32-3.29 (m, 4H), 2.36-1.61 (m, 4H). LC-MS m/z [M+H]+ calc'd for $C_{19}H_{17}N_3O_2S$, 352; found 352.

Example B1: 3-fluoro-2-hydroxy-5-((4-(pyrrolidin-1-yl)phenyl)ethynyl)benzaldehyde (Compound No. B1)

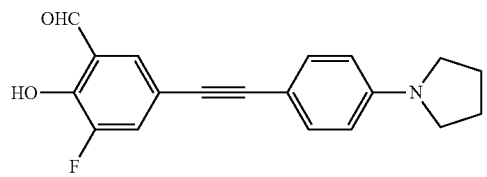 [SMILES: O=Cc1cc(C#Cc2ccc(N3CCCC3)cc2)cc(F)c1O]

276

Step 1: 1-(4-ethynylphenyl)pyrrolidine

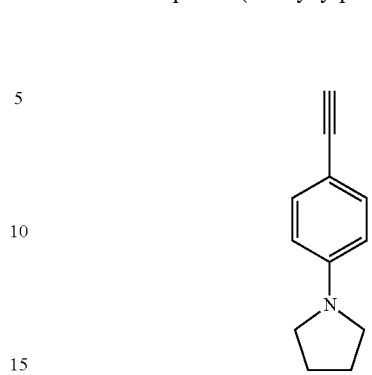

To a solution of TMS-diazomethane (17.14 mL, 34.29 mmol) in THF (50 mL) was added BuLi (13.72 mL, 34.29 mmol, 2 M in THF) at −78° C. The reaction was stirred for 30 min at −78° C. Then 4-(pyrrolidin-1-yl)benzaldehyde (5 g, 28.57 mmol) was added. The reaction was stirred for another 1 h at −78° C. The mixture was quenched with sat. NH$_4$Cl (150 mL) and then extracted with ethyl acetate (100 mL×3). The organic extracts were combined, dried over anhydrous sodium sulfate, and concentrated. The crude was purified by silica gel column chromatography (petroleum ether/ethyl acetate=200:1 to 100:1) to give the desired product as a white solid (2.1 g, 43% yield). $^1$H NMR (CDCl$_3$, 400 MHz) δ: 7.35 (d, J=8.4 Hz, 2H), 6.46 (d, J=8.4 Hz, 2H), 3.29 (t, J=6.2 Hz, 4H), 2.98 (s, 1H), 2.01 (t, J=6.2 Hz, 4H).

Step 2

A mixture of 5-bromo-3-fluoro-2-(4-methoxybenzyloxy) benzaldehyde (988 mg, 2.92 mmol), 1-(4-ethynylphenyl) pyrrolidine (600 mg, 3.51 mmol), TBAF.3H$_2$O (5.5 g, 17.54 mmol), and Pd(PPh$_3$)$_2$Cl$_2$ (62 mg, 0.09 mmol) in THF (20 mL) was heated at 80° C. for 2 h. The mixture was cooled to room temperature, diluted with water (100 mL), and then extracted with ethyl acetate (100 mL×3). The organic extracts were combined, washed with brine (80 mL), dried over anhydrous sodium sulfate, and concentrated. The residue was purified by silica gel column chromatography (petroleum ether/ethyl acetate=20:1 to 10:1) to give the PMB-protected penultimate product (417 mg, 33% yield). The PMB-protected intermediate (100 mg, 0.23 mmol) was dissolved in dichloromethane (5 mL) and TFA (3 mL) was added. The reaction was stirred for 30 min at room temp. The solvent was removed in vacuo and the residue was purified by prep-TLC (petroleum ether/ethyl acetate=5:1) to afford the title compound as yellow solid (23 mg, 32% yield). $^1$H NMR (CDCl$_3$, 400 MHz) δ: 11.00 (s, 1H), 9.90 (s, 1H), 7.52 (s, 1H), 7.46 (d, J=11.2 Hz, 1H), 7.37 (d, J=8.4 Hz, 2H), 6.51 (d, J=8.4 Hz, 2H), 3.31 (m, 4H), 2.02 (m, 4H); LC-MS m/z [M−H]− calc'd for $C_{19}H_{16}FNO_2$, 308; found, 308.

Example B2: 3-fluoro-2-hydroxy-5-((4-(piperidin-1-yl)phenyl)ethynyl)benzaldehyde (Compound No. B2)

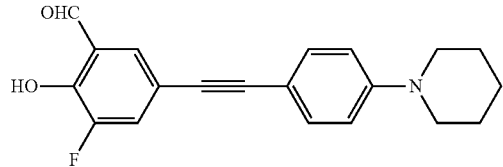 [SMILES: O=Cc1cc(C#Cc2ccc(N3CCCCC3)cc2)cc(F)c1O]

Step 1: 1-(4-ethynylphenyl)piperidine

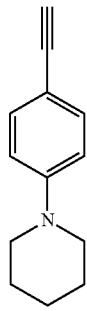

To a solution of TMS-diazomethane (6.3 mL, 12.6 mmol) in THF (20 mL) was added BuLi (6.3 mL, 12.6 mmol, 2 M in THF) at −78° C. The reaction was stirred for 30 min at −78° C. Then 4-(piperidin-1-yl)benzaldehyde (1.89 g, 10 mmol) was added in THF. The reaction was stirred for another 1 h at −78° C. The mixture was quenched with sat. NH$_4$Cl (100 mL) and then extracted with ethyl acetate (100 mL×3). The organic extracts were combined, dried over anhydrous sodium sulfate, and concentrated. The crude was purified by silica gel column chromatography to give the desired product (1.42 g, 77% yield).

Step 2

The title compound was prepared from 5-bromo-3-fluoro-2-hydroxybenzaldehyde (219 mg, 1.0 mmol) and 1-(4-ethynylphenyl)piperidine (185 mg, 1.0 mmol) using a method similar to that as described in Example B1 to give the title compound as yellow solid (91 mg, 28% yield). $^1$H NMR (DMSO-d6, 400 MHz) δ 11.33 (br, 1H), 10.26 (s, 1H), 7.67 (d, J=11.2 Hz, 1H), 7.57 (s, 1H), 7.35 (d, J=8.4 Hz, 2H), 6.93 (d, J=8.4 Hz, 2H), 3.24 (m, 4H), 1.57 (m, 6H); LC-MS m/z [M+H]$^+$ calc'd for C$_{20}$H$_{18}$FNO$_2$, 324; found, 324.

Example B3: 3-fluoro-2-hydroxy-5-((4-morpholinophenyl)ethynyl)benzaldehyde (Compound No. B3)

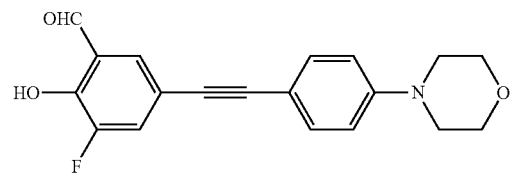 [SMILES: O=Cc1cc(C#Cc2ccc(N3CCOCC3)cc2)cc(F)c1O]

Step 1: 4-(4-ethynylphenyl)morpholine

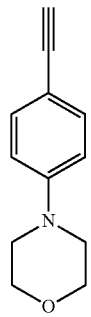

To a solution of TMS-diazomethane (6.3 mL, 12.6 mmol) in THF (20 mL) was added BuLi (6.3 mL, 12.6 mmol, 2 M in THF) at −78° C. The reaction was stirred for 30 min at −78° C. Then 4-morpholinobenzaldehyde (2 g, 10.5 mmol) was added. The reaction was stirred for another 1 h at −78° C. The mixture was quenched with sat. NH$_4$Cl (100 mL) and then extracted with ethyl acetate (100 mL×3). The organic extracts were combined, dried over anhydrous sodium sulfate, and concentrated. The crude was purified by silica gel column chromatography (petroleum ether/ethyl acetate=200:1 to 100:1) to give the desired product as a white solid (1.1 g, 56% yield).

Step 2

A mixture of 5-bromo-3-fluoro-2-(4-methoxybenzyloxy)benzaldehyde (561 mg, 3.0 mmol), 4-(4-ethynylphenyl)morpholine (1.01 g, 3.0 mmol), TBAF.3H$_2$O (5.68 g, 18.0 mmol), and Pd(PPh$_3$)$_2$Cl$_2$ (63 mg, 0.09 mmol) in THF (20 mL) was heated at 80° C. for 3 h. The mixture was cooled to rt, diluted with water (100 mL), and then extracted with ethyl acetate (100 mL×3). The organic extracts were combined, washed with brine (80 mL), dried over anhydrous sodium sulfate, and concentrated. The residue was purified by silica gel column chromatography (petroleum ether/ethyl acetate=5:1 to 1:1) to give PMB-protected penultimate product as yellow solid (410 mg, 31% yield). PMB-protected intermediate (100 mg, 0.22 mmol) was dissolved in dichloromethane (5 mL) and TFA (3 mL) was added. The reaction was stirred for 30 min at rt. The solvent was removed in vacuo and the residue was purified by prep-TLC (petroleum ether/ethyl acetate=1:1) to afford the title product as a yellow solid (27 mg, 37% yield). $^1$H NMR (DMSO-d6, 400 MHz) δ: 10.20 (s, 1H), 7.43-7.46 (m, 2H), 7.36 (d, J=8.4 Hz, 2H), 6.95 (d, J=8.4 Hz, 2H), 3.73 (m, 4H), 3.17 (m, 4H); LC-MS m/z [M+H]$^+$ calc'd for C$_{19}$H16FNO$_3$, 326; found, 326.

Example B4: 2-fluoro-6-hydroxy-4-((4-(pyrrolidin-1-yl)phenyl)ethynyl)benzaldehyde (Compound No. B4)

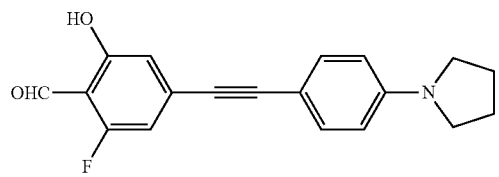

A mixture of 4-bromo-2-fluoro-6-hydroxybenzaldehyde (900 mg, 4.1 mmol), 1-(4-ethynylphenyl)pyrrolidine (847 mg, 5.0 mmol), PdCl$_2$(PPh$_3$)$_2$ (290 mg, 0.4 mmol), and TBAF.3H$_2$O (7.8 g, 24.8 mmol) in THF (30 mL) was refluxed for 3 hours under nitrogen atmosphere. The mixture was cooled to room temperature, diluted with water (100 mL), and extracted with ethyl acetate (100 mL×3). The organic extracts were combined, washed with brine (50 mL×2), dried over anhydrous sodium sulfate, and concentrated. The residue was purified by silica gel column chromatography (petroleum ether/ethyl acetate=100:1 to 20:1) to give the title product as a yellow solid (900 mg, 71% yield). $^1$H NMR (CDCl$_3$, 400 MHz) δ: 11.53 (s, 1H), 10.18 (s, 1H), 7.40 (d, J=8.8 Hz, 2H), 6.83 (s, 1H), 6.71 (m, 1H), 6.51 (d, J=8.4 Hz, 2H), 3.32 (m, 4H), 2.03 (m, 4H); LC-MS m/z [M+H]$^+$ calc'd for C$_{19}$H16FNO2, 310; found, 310.

Example B5: 2-fluoro-6-hydroxy-4-((4-(piperidin-1-yl)phenyl)ethynyl)benzaldehyde (Compound No. B5)

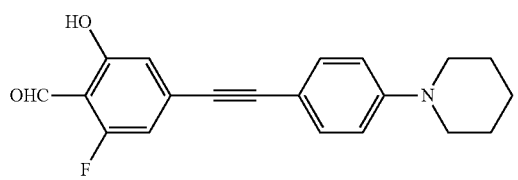 [SMILES: O=Cc1c(O)cc(C#Cc2ccc(N3CCCCC3)cc2)cc1F]

The title compound was prepared from 4-bromo-2-fluoro-6-hydroxybenzaldehyde (219 mg, 1.0 mmol) and 1-(4-ethynylphenyl)piperidine (185 mg, 1.0 mmol) using a method similar to that as described in Example B1 to give the title compound as a yellow solid (181 mg, 56% yield). $^1$H NMR (DMSO-d6, 400 MHz) δ 11.37 (br, 1H), 10.22 (s, 1H), 7.39 (d, J=8.8 Hz, 2H), 6.93 (m, 2H), 6.88 (m, 2H), 3.28 (m, 4H), 1.58 (m, 6H); LC-MS m/z [M+H]$^+$ calc'd for C$_{20}$H$_{18}$FNO$_2$, 324; found, 324.

Example B6: 2-fluoro-6-hydroxy-4-((4-morpholinophenyl)ethynyl)benzaldehyde (Compound No. B6)

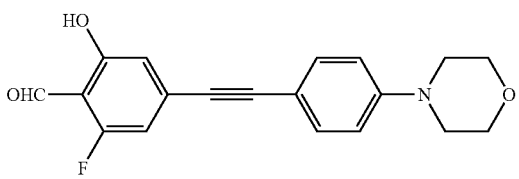

The title compound was prepared from 4-bromo-2-fluoro-6-hydroxybenzaldehyde (219 mg, 1.0 mmol) and 4-(4-ethynylphenyl)morpholine (187 mg, 1.0 mmol) using a method similar to that as described in Example B1 to give the title compound as a yellow solid (134 mg, 41% yield). $^1$H NMR (DMSO-d6, 400 MHz) δ 11.38 (br, 1H), 10.22 (s, 1H), 7.45 (d, J=8.4 Hz, 2H), 6.99 (d, J=8.4 Hz, 2H), 6.91 (m, 2H), 3.73 (m, 4H), 3.22 (m, 4H); LC-MS m/z [M+H]+ calc'd for C$_{19}$H$_{16}$FNO$_3$, 326; found, 326.

Example B7: 2-hydroxy-6-methoxy-4-((4-(pyrrolidin-1-yl)phenyl)ethynyl)benzaldehyde (Compound No. B7)

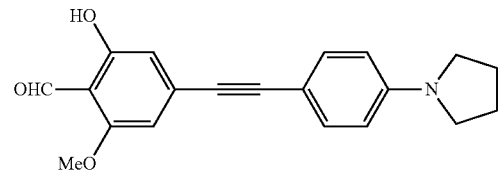

A mixture of 4-bromo-2-hydroxy-6-methoxybenzaldehyde (462 mg, 2.0 mmol), 1-(4-ethynylphenyl)pyrrolidine (340 mg, 2.0 mmol), PdCl$_2$(PPh$_3$)$_2$ (140 mg, 0.2 mmol), and TBAF.3H$_2$O (3.78 g, 12.0 mmol) in THF (30 mL) was refluxed for 2 hours under nitrogen atmosphere. The mixture was cooled to room temperature, diluted with water (100 mL), and extracted with ethyl acetate (100 mL×3). The organic extracts were combined, washed with brine (50 mL×2), dried over anhydrous sodium sulfate, and concentrated. The residue was purified by silica gel column chromatography (petroleum ether/ethyl acetate/dichlormethane=300:1:1 to 200:1:20) to give the title product as a yellow solid (320 mg, 50% yield). $^1$H NMR (CDCl$_3$, 400 MHz) δ 12.03 (s, 1H), 10.26 (s, 1H), 7.41 (d, J=8.0 Hz, 2H), 6.64 (s, 1H), 6.47-6.53 (m, 3H), 3.60 (s, 3H), 3.31 (m, 4H), 2.03 (m, 4H); LC-MS m/z [M+H]+ calc'd for C$_{20}$H$_{19}$NO$_3$, 322; found, 322.

Example B8: 2-hydroxy-3-methoxy-5-((4-morpholinophenyl)ethynyl)benzaldehyde (Compound No. B8)

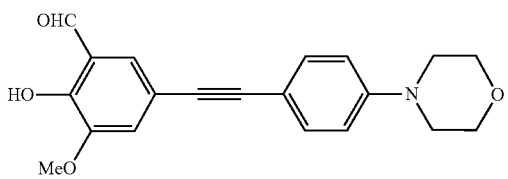

A mixture of 5-bromo-3-methoxy-2-(4-methoxybenzyloxy)benzaldehyde (1.3 g, 3.74 mmol), 4-(4-ethynylphenyl)morpholine (700 mg, 3.74 mmol), TBAF.3H$_2$O (7 g, 22.44 mmol), and Pd(PPh$_3$)$_2$Cl$_2$ (79 mg, 0.11 mmol) in THF (20 mL) was heated at 80° C. for 2 h. The mixture was cooled to rt, diluted with water (100 mL), and then extracted with ethyl acetate (100 mL×3). The organic extracts were combined, washed with brine (80 mL), dried over anhydrous sodium sulfate, and concentrated. The residue was purified by silica gel column chromatography (petroleum ether/ethyl acetate=5:1 to 1:1) to give a PMB-protected penultimate product (880 mg, 51% yield). The PMB-protected intermediate (100 mg, 0.22 mmol) was dissolved in dichloromethane (5 mL), and TFA (3 mL) was added. The reaction was stirred for 30 min at room temperature. The solvent was removed in vacuo, and the residue was purified by prep-TLC (petroleum ether/ethyl acetate=1:1) to afford the title product as a yellow solid (31 mg, 42% yield). $^1$H NMR (CDCl$_3$, 400 MHz) δ: 11.23 (s, 1H), 9.90 (s, 1H), 7.44 (m, 2H), 7.38 (s, 1H), 7.22 (s, 1H), 6.89 (m, 2H), 3.93 (s, 3H), 3.88 (m, 4H), 3.23 (m, 4H); LC-MS m/z [M+H]+ calc'd for C$_{20}$H$_{19}$NO$_4$, 338; found, 338.

Example B9: N-(3-fluoro-5-formyl-4-hydroxyphenyl)benzamide (Compound No. B9)

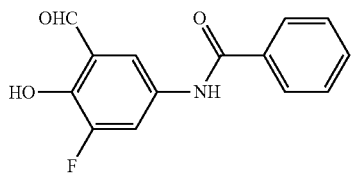 [SMILES: O=Cc1cc(NC(=O)c2ccccc2)cc(F)c1O]

Step 1: 3-fluoro-2-hydroxy-5-nitrobenzaldehyde

In a 125 mL round bottom flask, $HNO_3$ (2.23 mL, 50.0 mmol) in TFA (20 mL) was added to a solution of 3-fluoro-2-hydroxybenzaldehyde (2 g, 14.3 mmol) in acetic acid (10 mL) at 0° C. The reaction was stirred for 1 hour at 0° C. The solution was poured into ice-water, and the resulting precipitate was filtered and washed with petroleum ether to give 3-fluoro-2-hydroxy-5-nitrobenzaldehyde (1.8 g, 68% yield), which was used for next reaction without further purification. $^1$H NMR (CDCl$_3$, 400 MHz) δ: 11.67 (s, 1H), 10.05 (s, 1H), 8.45 (s, 1H), 8.27 (dd, J=10.0 Hz, 2.8 Hz, 1H).

Step 2: 2-(3-fluoro-2-(4-methoxybenzyloxy)-5-nitrophenyl)-1,3-dithiane $BF_3.Et_2O$ (4.9 mL, 18.2 mmol) was added to a mixture of 3-fluoro-2-hydroxy-5-nitrobenzaldehyde (2.8 g, 15.1 mmol) and propane-1,3-dithiol (1.82 mL, 18.2 mmol) in dichloromethane (30 mL). The reaction was stirred overnight at room temperature. The mixture was poured into ice water and the resulting precipitate was filtered and washed with petroleum ether/dichloromethane (10:1). The cake was dried to give intermediate (3.9 g, 94% yield) as a yellow solid. $^1$H NMR (DMSO-d6, 400 MHz) δ: 12.01 (br, 1H), 8.09 (m, 2H), 5.73 (s, 1H), 3.17 (m, 2H), 2.91 (m, 2H), 2.13 (m, 1H), 1.77 (m, 1H). The intermediate (2.75 g, 10.0 mmol) was dissolved in DMF (20 mL) then added PMBCl (3.12 g, 20.0 mmol) and potassium carbonate (4.1 g, 30.0 mmol, 3 eq.) to the reaction mixture. The reaction was heated at 90° C. for 3 hours. The mixture was poured into water and extracted with ethyl acetate for three times. The organic extracts were combined, washed with brine, dried over anhydrous sodium sulfate, and concentrated to give crude 2-(3-fluoro-2-(4-methoxybenzyloxy)-5-nitrophenyl)-1,3-dithiane (3.3 g, 84% yield), which was used for the next reaction without further purification.

Step 3: 3-(1,3-dithian-2-yl)-5-fluoro-4-(4-methoxybenzyloxy)aniline

A mixture of 2-(3-fluoro-2-(4-methoxybenzyloxy)-5-nitrophenyl)-1,3-dithiane (2.1 g, 5.3 mmol) and iron (3 g, 53.2 mmol) in acetic acid (20 mL) was heated at 60° C. for 3 hours. The mixture was diluted with ethyl acetate and filtered. The filtrate was neutralized with sodium bicarbonate to pH 8-9, and the organic layer was separated. The water phase was re-extracted with ethyl acetate for two more times. The organic extracts were combined, washed with brine, dried over anhydrous sodium sulfate, and concentrated to give crude 3-(1,3-dithian-2-yl)-5-fluoro-4-(4-methoxybenzyloxy)aniline (1.2 g, 62% yield), which was used for the next reaction without further purification. $^1$H NMR (DMSO-d6, 400 MHz) δ: 7.38 (d, J=8.4 Hz, 2H), 6.96 (d, J=8.0 Hz, 2H), 6.50 (s, 1H), 6.34 (d, J=13.2 Hz, 1H), 5.42 (s, 1H), 5.31 (br, 2H), 4.81 (s, 2H), 3.77 (s, 3H), 3.02 (m, 2H), 2.89 (m, 2H), 2.12 (m, 1H), 1.69 (m, 1H).

Step 4: N-(3-(1,3-dithian-2-yl)-5-fluoro-4-(4-methoxybenzyloxy)phenyl)benzamide A solution of 3-(1,3-dithian-2-yl)-5-fluoro-4-(4-methoxybenzyloxy)aniline (500 mg, 1.37 mmol), benzoyl chloride (289 mg, 2.05 mmol), and triethylamine (415 mg, 4.11 mmol) in dichloromethane (20 mL) was stirred overnight at room temperature. The solvent was removed, and the residue was purified by silica gel column chromatography (petroleum ether/ethyl acetate=20:1 to 5:1) to give N-(3-(1,3-dithian-2-yl)-5-fluoro-4-(4-methoxybenzyloxy)phenyl)benzamide (620 mg, 96% yield). LC-MS m/z [M+H]$^+$ calc'd for $C_{25}H_{24}FNO_3S_2$, 470; found, 470.

Step 5: N-(3-fluoro-5-formyl-4-hydroxyphenyl)benzamide

A mixture of N-(3-(1,3-dithian-2-yl)-5-fluoro-4-(4-methoxybenzyloxy)phenyl) benzamide (620 mg, 1.32 mmol) and DMP (1.12 g, 2.64 mmol) in acetonitrile/dichloromethane/water (16 mL/2 mL/2 mL) was stirred overnight at 45° C. The mixture was filtered and the cake was washed with dichloromethane. The filtrate and wash were washed with 5% sodium bicarbonate solution. The water phase was re-extracted with dichloromethane for two more times. The organic extracts were combined, washed with brine, dried over anhydrous sodium sulfate, and concentrated. The residue was purified by silica gel column chromatography (petroleum ether/ethyl acetate/dichloromethane=50:1:1 to 20:1:1) to give PMB-protected N-(3-fluoro-5-formyl-4-hydroxyphenyl)benzamide (250 mg, 50% yield). The PMB-protected N-(3-fluoro-5-formyl-4-hydroxyphenyl)benzamide (250 mg, 0.66 mmol) was dissolved in dichloromethane (5 mL) and added TFA (230 mg, 1.98 mmol) to the mixture. The reaction was stirred for 1 hour at room temperature. The solvent was removed in vacuo and the residue was purified by silica gel column chromatography (petroleum ether/ethyl acetate/dichloromethane=20:1:1 to 10:1:1) to give N-(3-fluoro-5-formyl-4-hydroxyphenyl)benzamide (60 mg, 0.23 mmol, 35% yield) as a white solid. $^1$H NMR (DMSO-d6, 400 MHz) δ: 10.74 (s, 1H), 10.39 (s, 1H), 10.32 (s, 1H), 7.90-8.04 (m, 4H), 7.52-7.61 (m, 3H); LC-MS m/z [M+H]$^+$ calc'd for $C_{14}H_{10}FNO_3$, 260; found, 260.

Example B10: 1-(3-fluoro-5-formyl-4-hydroxyphenyl)-3-phenylurea (Compound No. B10)

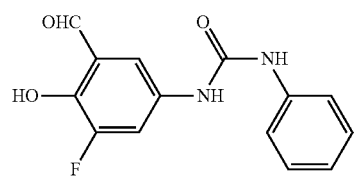

Step 1: 1-(3-(1,3-dithian-2-yl)-5-fluoro-4-(4-methoxybenzyloxy)phenyl)-3-phenylurea DPPA (1.1 g, 4 mmol) and triethylamine (0.42 g, 4 mmol) were added to a solution of benzoic acid (0.35 g, 2.9 mmol)

in dioxane (10 mL). The reaction was stirred for 30 min at room temperature. Then, 3-(1,3-dithian-2-yl)-5-fluoro-4-(4-methoxybenzyloxy)aniline (0.5 g, 1.4 mmol, 1 eq.) was added to the reaction mixture and the reaction was heated at 90° C. for 3 hours. The solvent was removed and the residue was purified by silica gel column chromatography (petroleum ether/ethyl acetate/dichloromethane=30:1:1 to 10:1:1) to give 1-(3-(1,3-dithian-2-yl)-5-fluoro-4-(4-methoxybenzyloxy)phenyl)-3-phenylurea (610 mg, 92% yield). LC-MS m/z [M+H]$^+$ calc'd for $C_{25}H_{25}FN_2O_3S_2$, 485; found, 485.

Step 2:
1-(3-fluoro-5-formyl-4-hydroxyphenyl)-3-phenylurea

A solution of 1-(3-(1,3-dithian-2-yl)-5-fluoro-4-(4-methoxybenzyloxy)phenyl)-3-phenylurea (300 mg, 0.62 mmol), MeI (1.76 g, 12.4 mmol), and NaHCO$_3$ (1 g, 12.4 mmol) in acetonitrile/water (15 mL/3 mL) was stirred overnight at 50° C. The solution was diluted with water and extracted with ethyl acetate for three times. The organic extracts were combined, washed with brine, dried over anhydrous sodium sulfate, and concentrated. The residue was purified by silica gel column chromatography (petroleum ether/ethyl acetate/dichloromethane=10:1:1 to 5:1:1) to give PMB-protected 1-(3-fluoro-5-formyl-4-hydroxyphenyl)-3-phenylurea (170 mg, 70% yield). The PMB-protected 1-(3-fluoro-5-formyl-4-hydroxyphenyl)-3-phenylurea (80 mg, 0.20 mmol) was dissolved in 6 N HCl/dioxane (5 mL) and the reaction was stirred for 30 min at room temperature. The solution was poured into ice-cold sat. sodium bicarbonate and extracted with ethyl acetate for three times. The organic extracts were combined, washed with brine, dried over anhydrous sodium sulfate, and concentrated. The residue was purified by prep-TLC (CH$_2$Cl$_2$/MeOH=20:1) to give 1-(3-fluoro-5-formyl-4-hydroxyphenyl)-3-phenylurea (30 mg, 0.23 mmol, 54% yield) as an off-white solid. $^1$H NMR (DMSO-d6, 400 MHz) δ: 10.50 (s, 1H), 10.28 (s, 1H), 8.78 (s, 1H), 8.70 (s, 1H), 7.74 (m, 1H), 7.46 (m, 3H), 7.27 (m, 2H), 6.97 (m, 1H); LC-MS m/z [M+H]$^+$ calc'd for $C_{14}H_{11}FN_2O_3$, 275; found, 275.

Example B11:
3-fluoro-5-formyl-4-hydroxy-N-phenylbenzamide (Compound No. B11)

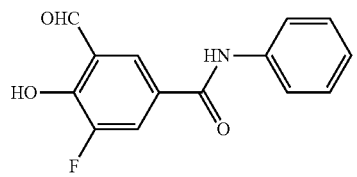

Step 1: 3-fluoro-5-formyl-4-hydroxybenzoic acid

A solution of HMPA (28 g, 0.2 mol, 2 eq.) in TFA (20 mL) was added to a solution of 3-fluoro-4-hydroxybenzoic acid (15.6 g, 0.1 mol) in TFA (30 mL). The reaction was stirred overnight at 100° C. The solution was cooled to room temperature and poured into 3 M HCl (200 mL). The mixture was stirred for 30 min and the resulting precipitate was filtered and dried to give 3-fluoro-5-formyl-4-hydroxybenzoic acid, which was used for the next reaction without further purification. LC-MS m/z [M–H]$^-$ calc'd for $C_8H_5FO_4$, 183; found, 183.

Step 2:
3-fluoro-5-formyl-4-hydroxy-N-phenylbenzamide

HATU (0.63 g, 1.7 mmol) and N-Methylmorpholine (0.67 g, 6.6 mmol) were added to a mixture of 3-fluoro-5-formyl-4-hydroxybenzoic acid (0.2 g, 1.1 mmol) and aniline hydrochloride (0.43 g, 3.3 mmol) in dichloromethane (30 mL). The mixture was stirred overnight at room temperature. The solvent was removed and the residue dissolved in a mixture of ether (6 mL) and 4 M HCl (6 mL). The mixture was stirred overnight at room temperature. The mixture was diluted with water (20 mL) and extracted with ethyl acetate (20 mL×3). The organic extracts were combined, washed with brine (20 mL), dried over anhydrous sodium sulfate, and concentrated. The residue was purified by silica gel column chromatography (petroleum ether/ethyl acetate/dichloromethane=10:1:1 to 2:1:1) to give the desired 3-fluoro-5-formyl-4-hydroxy-N-phenylbenzamide product as light yellow solid (4% yield). $^1$H NMR (DMSO-d6, 400 MHz) δ: 11.67 (br, 1H), 10.36 (s, 1H), 10.30 (s, 1H), 8.20 (s, 1H), 8.11 (dd, J=12.0 Hz, 2.4 Hz, 1H), 7.75 (d, J=7.2 Hz, 1H), 7.35 (m, 2H), 7.11 (m, 1H); LC-MS m/z [M–H]$^-$ calc'd for $C_{14}H_{10}FNO_3$, 258; found, 258.

Example B12: 3-fluoro-5-formyl-4-hydroxy-N-(4-(pyrrolidin-1-yl)phenyl)benzamide (Compound No. B12)

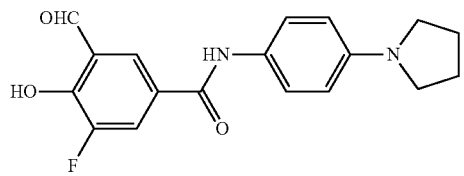

The title compound was synthesized in a similar manner as described for 3-fluoro-5-formyl-4-hydroxy-N-phenylbenzamide in Example B11 to obtain the desired product as a green solid (67% yield). $^1$H NMR (DMSO-d6, 400 MHz) δ: 11.57 (br, 1H), 10.35 (s, 1H), 10.03 (br, 1H), 8.18 (s, 1H), 8.09 (dd, J=12.0 Hz, 2.4 Hz, 1H), 7.53 (d, J=8.8 Hz, 2H), 6.55 (d, J=8.0 Hz, 2H), 3.22 (m, 4H), 1.95 (m, 4H); LC-MS m/z [M+H]$^+$ calc'd for $C_{18}H_{17}FN_2O_3$, 329; found, 329.

Example B13: 3-fluoro-5-formyl-4-hydroxy-N-(4-(trifluoromethyl)phenyl)benzamide (Compound No. B13)

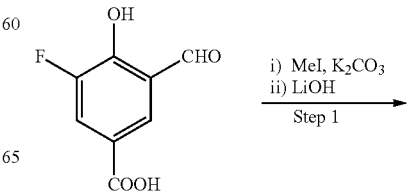

285

-continued i) (COCl)$_2$, DMF
ii)

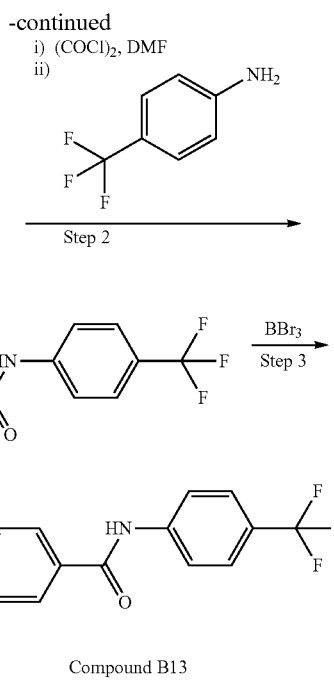

Compound B13

Step 1: 3-fluoro-5-formyl-4-methoxybenzoic Acid

A mixture of 3-fluoro-5-formyl-4-hydroxybenzoic acid (0.5 g, 2.7 mmol), MeI (1.16 g, 8.2 mmol), and potassium carbonate (1.13 g, 8.2 mmol) in DMF (5 mL) was heated at 50° C. for 3 hours. The mixture was cooled to room temperature, diluted with water (20 mL), and extracted with ethyl acetate (20 mL×3). The organic extracts were combined, washed with brine (10 mL×2), dried over anhydrous sodium sulfate, and concentrated. The residue was purified by silica gel column chromatography (petroleum ether/ethyl acetate=100:1 to 20:1) to give methyl ether intermediate (0.58 g, quantitative yield). The methyl ether intermediate (0.58 g, 2.7 mmol) was dissolved in THF/water (2 mL/2 mL), and LiOH.H$_2$O (0.57 g, 13.5 mmol) was added. The reaction was stirred for 1 hour at room temperature. The pH of the reaction system was adjusted to 4-5 and extracted three times with ethyl acetate. The organic extracts were combined, washed with brine, dried over anhydrous sodium sulfate, and concentrated to give crude 3-fluoro-5-formyl-4-methoxybenzoic acid (0.5 g, 94% yield), which was used for the next reaction without further purification.

Step 2: 3-fluoro-5-formyl-4-methoxy-N-(4-(trifluoromethyl)phenyl)benzamide

A drop of DMF was added to a solution of 3-fluoro-5-formyl-4-methoxybenzoic acid (0.2 g, 1.0 mmol) and oxalyl chloride (0.39 g, 3.0 mmol) in DCM (5 mL). The reaction was stirred for 1 hour at room temperature. The solvent was removed in vacuo and the residue was co-evaporated two times with dichloromethane. The residue was then dissolved in dichloromethane (5 mL). 4-Trifluoromethylanaline (0.5 g, 3.0 mmol), DMAP (0.02 g, 0.1 mmol), and triethylamine (0.5 g, 5.0 mmol) were added. The reaction was stirred for 1 hour. LC-MS showed formation of the desired product. The solvent was removed and the residue was purified by silica gel column chromatography (petroleum ether/ethyl acetate/dichloromethane=20:1:1 to 5:1:1) to give 3-fluoro-

286

5-formyl-4-methoxy-N-(4-(trifluoromethyl)phenyl)benzamide (130 mg, 38% yield), containing 4-trifluoromethylanaline inside at the same spot. LC-MS m/z [M+H]$^+$ calc'd for C$_{16}$H$_{11}$F$_4$NO$_3$, 342; found, 342.

Step 3: 3-fluoro-5-formyl-4-hydroxy-N-(4-(trifluoromethyl)phenyl)benzamide

BBr$_3$ (191 mg, 0.76 mmol) was added to a solution of 3-fluoro-5-formyl-4-methoxy-N-(4-(trifluoromethyl)phenyl)benzamide (130 mg, 0.38 mmol) in dichloromethane (5 mL) at −78° C. The reaction was stirred for 30 min at room temperature. The solution was diluted with dichloromethane and washed with sat. sodium bicarbonate. The organic layer was separated, dried over anhydrous sodium sulfate, and concentrated. The residue was removed in vacuo and the residue was co-evaporated two times with dichloromethane. The residue was purified by silica gel column chromatography (petroleum ether/ethyl acetate/dichloromethane=20:1:1 to 5:1:1) to give 3-fluoro-5-formyl-4-hydroxy-N-(4-(trifluoromethyl)phenyl)benzamide (50 mg, 40% yield). $^1$H NMR (DMSO-d6, 400 MHz) 3:11.77 (br, 1H), 10.62 (s, 1H), 10.36 (s, 1H), 8.22 (s, 1H), 8.13 (dd, J=12.0 Hz, 2.0 Hz, 1H), 8.00 (d, J=8.8 Hz, 2H), 7.74 (d, J=8.4 Hz, 2H); LC-MS m/z [M+H]$^+$ calc'd for C$_{15}$H$_9$F$_4$NO$_3$, 328; found, 328.

Example B14: N-(3-Chloro-4-(trifluoromethyl)phenyl)-3-fluoro-5-formyl-4-hydroxybenzamide (Compound No. B14)

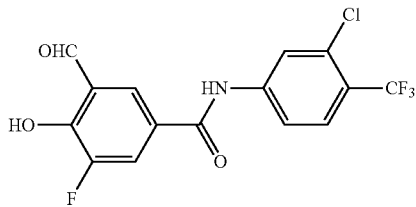 [SMILES: O=Cc1cc(C(=O)Nc2ccc(C(F)(F)F)c(Cl)c2)cc(F)c1O]

The title product was synthesized in a similar manner as described for 3-fluoro-5-formyl-4-hydroxy-N-(4-(trifluoromethyl)phenyl)benzamide in Example B13. Yield for step 3: 22%, brown solid. $^1$H NMR (DMSO-d6, 400 MHz) δ: 11.84 (br, 1H), 10.74 (s, 1H), 10.37 (s, 1H), 8.20 (m, 2H), 8.11 (dd, J=11.6 Hz, 2.0 Hz, 1H), 7.92 (m, 2H); LC-MS m/z [M+H]$^+$ calc'd for C$_{15}$H$_8$ClF$_4$NO$_3$, 362; found, 362.

Example B15: 3-fluoro-5-formyl-4-hydroxy-N-(4-(pyrrolidin-1-yl)phenyl)benzenesulfonamide (Compound B17)

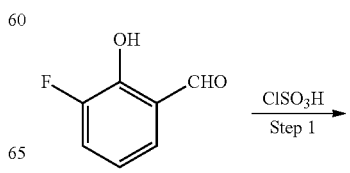

287

Example B16: 3-fluoro-5-formyl-4-hydroxy-N-(2-(pyrrolidin-1-yl)pyrimidin-5-yl)benzamide (Compound B59)

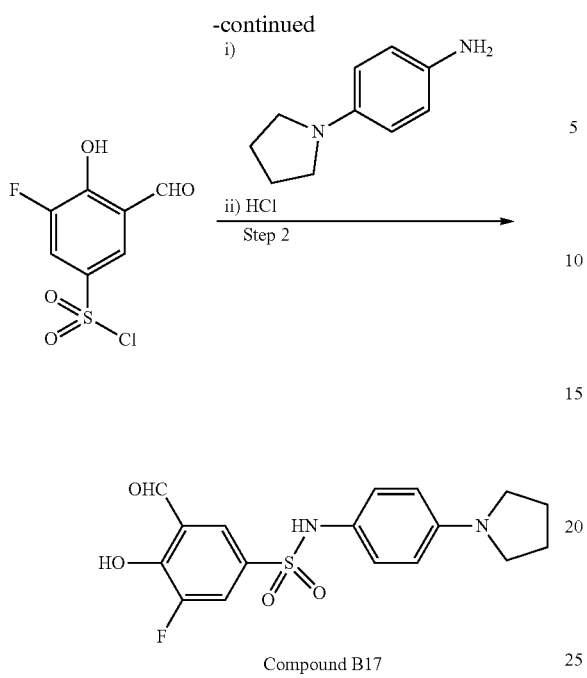

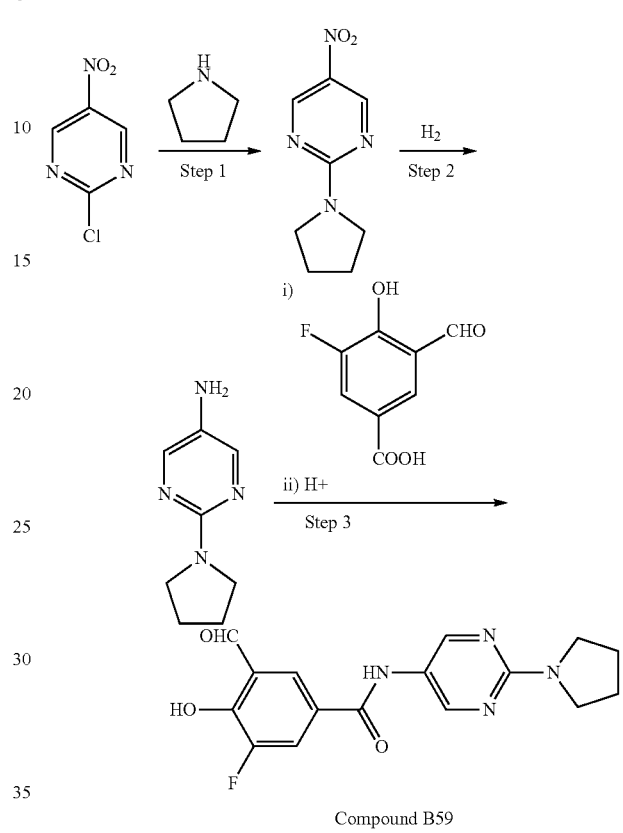

Compound B17

Step 1: 3-fluoro-5-formyl-4-hydroxybenzene-1-sulfonyl Chloride

Chlorosulfonic acid (1.66 g, 14.3 mmol, 10 eq.) was added dropwise to a solution of 3-fluoro-2-hydroxybenzaldehyde (200 mg, 1.4 mmol, 1.0 eq.) in dichloromethane (10 mL) at 0° C. The reaction was stirred overnight at room temperature. The reaction mixture was poured into ice-water (30 mL) and extracted with dichloromethane for three times. The organic extracts were combined, washed with brine, dried over anhydrous sodium sulfate and concentrated to give crude 3-fluoro-5-formyl-4-hydroxybenzene-1-sulfonyl chloride (390 mg, quantitative yield), which was used in next reaction without further purification. LC-MS m/z [M−HCl]-calc'd for $C_7H_4ClFO_4S$, 219; found, 219.

Step 2

A solution of 3-fluoro-5-formyl-4-hydroxybenzene-1-sulfonyl chloride (390 mg, 1.64 mmol, 1.0 eq.), 4-(pyrrolidin-1-yl)aniline (664 mg, 4.10 mmol, 2.5 eq.), and N-methyl morpholine (497 mg, 4.92 mmol, 3.0 eq.) in dichloromethane (10 mL) was stirred for 5 hours. The reaction mixture was poured into 4 N HCl. The reaction was stirred for 3 hours and then extracted with ethyl acetate for three times. The organic extracts were combined, washed with brine, dried over anhydrous sodium sulfate, and concentrated. The residue was purified by silica gel column chromatography and prep-TLC to give 3-fluoro-5-formyl-4-hydroxy-N-(4-(pyrrolidin-1-yl)phenyl)benzenesulfonamide (23 mg, 0.06 mmol, 4% yield) as a yellow solid. $^1$H NMR (DMSO-d6, 400 MHz) δ: 12.03 (br, 1H), 10.26 (br, 1H), 9.57 (s, 1H), 7.75 (s, 1H), 7.62 (dd, J=10.4 Hz, 2.4 Hz, 1H), 6.82 (d, J=8.8 Hz, 2H), 6.38 (d, J=8.0 Hz, 2H), 3.13 (m, 4H), 1.90 (m, 4H). LC-MS m/z [M+H]$^+$ calc'd for $C_{17}H_{17}FN_2O_4S$, 365; found, 365.

288

Compound B59

Step 1: 5-nitro-2-(pyrrolidin-1-yl)pyrimidine

A mixture of 2-chloro-5-nitropyrimidine (2 g, 12.6 mmol, 1.0 eq.), pyrrolidine (1.3 g, 18.9 mmol, 1.5 eq.), and potassium carbonate (3.5 g, 25.2 mmol, 2.0 eq.) in DMF (10 mL) was stirred for 5 hours at room temperature. The mixture was poured into water (100 mL) and extracted with ethyl acetate for three times. The organic extracts were combined, washed with brine, dried over anhydrous sodium sulfate, and concentrated to give 5-nitro-2-(pyrrolidin-1-yl)pyrimidine (2.3 g, 94% yield), which was used for next reaction without further purification. LC-MS m/z [M+H]$^+$ calc'd for $C_8H_{10}N_4O_2$, 195; found, 195.

Step 2: 2-(pyrrolidin-1-yl)pyrimidin-5-amine

A mixture of 5-nitro-2-(pyrrolidin-1-yl)pyrimidine (2.3 g, 11.9 mmol, 1.0 eq.) and Pd/C (0.2 g) in methanol (10 mL) was hydrogenated for 2 hours. Pd/C was filtered off and washed with methanol. The filtrate and wash were combined and concentrated to give 2-(pyrrolidin-1-yl)pyrimidin-5-amine (1.63 g, 84% yield), which was used for next reaction without further purification. LC-MS m/z [M+H]$^+$ calc'd for $C_8H_{12}N_4$, 165; found, 165.

Step 3

HATU (0.71 g, 1.87 mmol, 1.5 eq.) and N-methyl morpholine (0.4 g, 3.74 mmol, 3.0 eq.) were added to a mixture of 3-fluoro-5-formyl-4-hydroxybenzoic acid (0.23 g, 1.25 mmol, 1.0 eq.) and 2-(pyrrolidin-1-yl)pyrimidin-5-amine (0.5 g, 3.05 mmol, 2.5 eq.) in dichloromethane (30 mL). The mixture was stirred overnight at 30° C. The solvent was removed and the residue dissolved in a mixture of dioxane (6 mL) and 4 N HCl (6 mL). The mixture was stirred for 2 hours at 55° C. The mixture was diluted with water (20 mL) and washed with ethyl acetate (30 mL). The wash was discarded. The water phase was neutralized with sodium bicarbonate and extracted with ethyl acetate for three times. The organic extracts were combined, washed with brine (20 mL), dried over anhydrous sodium sulfate, and concentrated. The residue was purified by silica gel column chromatography (petroleum ether/acetone=20:1 to 5:1) to give 3-fluoro-5-formyl-4-hydroxy-N-(2-(pyrrolidin-1-yl)pyrimidin-5-yl)benzamide (15 mg, 0.05 mmol, 4% yield) as a pale yellow solid. $^1$H NMR (DMSO-d6, 400 MHz) 3:11.70 (br, 1H), 10.35 (s, 1H), 10.22 (br, 1H), 8.59 (s, 2H), 8.20 (s, 1H), 8.07 (dd, J=11.6 Hz, 2.0 Hz, 1H), 3.48 (m, 4H), 1.94 (m, 4H). LC-MS m/z [M+H]$^+$ calc'd for $C_{16}H_{15}FN_4O_3$, 331; found, 331.

Example B17: 3-fluoro-5-formyl-4-hydroxy-N-(6-(pyrrolidin-1-yl)pyridin-3-yl)benzamide (Compound B61)

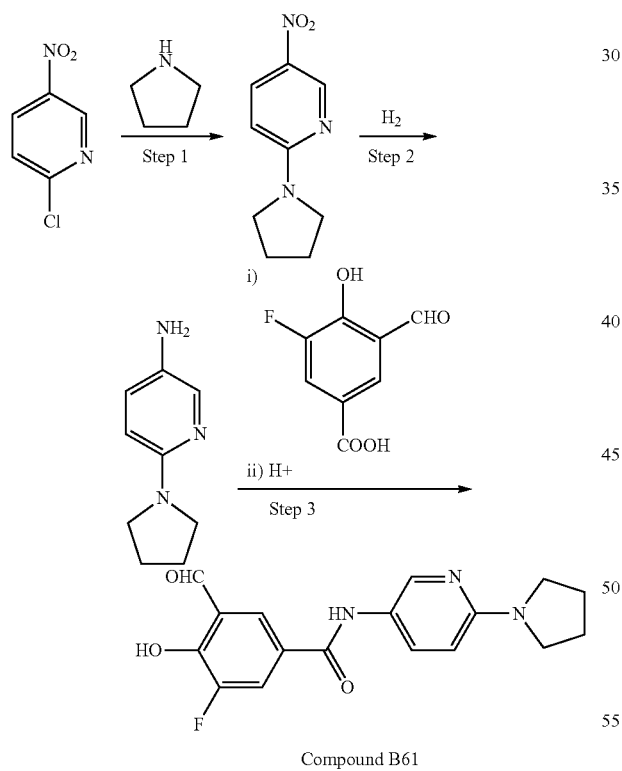

Compound B61

Step 1: 5-nitro-2-(pyrrolidin-1-yl)pyridine

A mixture of 2-chloro-5-nitropyridine (2 g, 12.6 mmol, 1.0 eq.), pyrrolidine (1.3 g, 18.9 mmol, 1.5 eq.), and potassium carbonate (3.5 g, 25.2 mmol, 2.0 eq.) in DMF (10 mL) was stirred for 5 hours at room temperature. The mixture was poured into water (100 mL) and extracted with ethyl acetate for three times. The organic extracts were combined, washed with brine, dried over anhydrous sodium sulfate, and concentrated to give 5-nitro-2-(pyrrolidin-1-yl)pyridine (2.4 g, 99% yield), which was used for next reaction without further purification. LC-MS m/z [M+H]$^+$ calc'd for $C_9H_{11}N_3O_2$, 194; found, 194.

Step 2: 6-(pyrrolidin-1-yl)pyridin-3-amine

A mixture of 5-nitro-2-(pyrrolidin-1-yl)pyridine (2 g, 10.4 mmol, 1.0 eq.) and Pd/C (0.2 g) in methanol (10 mL) was hydrogenated for 2 h. Pd/C was filtered off and washed with methanol. The filtrate and wash were combined and concentrated to give 6-(pyrrolidin-1-yl)pyridin-3-amine (1.38 g, 82% yield), which was used for next reaction without further purification. LC-MS m/z [M+H]$^+$ calc'd for $C_9H_{13}N_3$, 164; found, 164.

Step 3

HATU (1.24 g, 3.26 mmol, 1.5 eq.) and N-methyl morpholine (0.66 g, 6.51 mmol, 3.0 eq.) were added to a mixture of 3-fluoro-5-formyl-4-hydroxybenzoic acid (0.4 g, 2.17 mmol, 1.0 eq.) and 6-(pyrrolidin-1-yl)pyridin-3-amine (0.89 g, 5.43 mmol, 2.5 eq.) in DCM (30 mL). The mixture was stirred overnight at 30° C. The solvent was removed and the residue dissolved in a mixture of dioxane (6 mL) and 4 N HCl (6 mL). The mixture was stirred for 3 h at 55° C. The mixture was neutralized with lithium hydroxide to pH 9-10 and washed with dichloromethane and ethyl acetate each for two times. The water phase was then treated with HCl to pH-3 then to pH-7-8 with sodium bicarbonate. The mixture was then extracted with ethyl acetate for three times. The organic extracts were combined, washed with brine (20 mL), dried over anhydrous sodium sulfate, and concentrated. The residue was purified by silica gel column chromatography (petroleum ether/acetone=20:1 to 5:1) to give 3-fluoro-5-formyl-4-hydroxy-N-(6-(pyrrolidin-1-yl)pyridin-3-yl)benzamide (75 mg, 0.23 mmol, 11% yield) as a pale yellow solid. $^1$H NMR (DMSO-d6, 400 MHz) δ: 11.69 (br, 1H), 10.35 (br, 1H), 10.11 (br, 1H), 8.34 (s, 1H), 8.18 (s, 1H), 8.07 (d, J=10.8 Hz, 1H), 7.82 (m, 1H), 6.47 (d, J=9.2 Hz, 1H), 3.45 (m, 4H), 1.94 (m, 4H). LC-MS m/z [M+H]$^+$ calc'd for $C_{17}H_{16}FN_3O_3$, 330; found, 330.

Example B18: 3-fluoro-5-formyl-4-hydroxy-N-(4-(1-methyl-1H-pyrazol-4-yl)phenyl)benzamide (Compound B63)

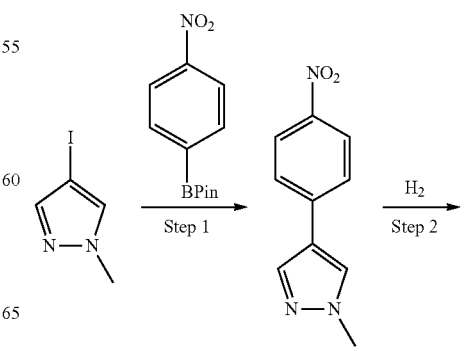

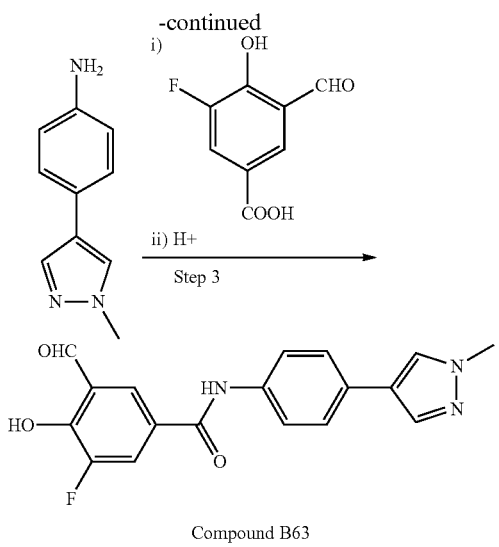

Compound B63

Step 1: 1-methyl-4-(4-nitrophenyl)-1H-pyrazole

A mixture of 4-iodo-1-methyl-1H-pyrazole (0.7 g, 3.4 mmol, 1.0 eq.), 4,4,5,5-tetramethyl-2-(4-nitrophenyl)-1,3,2-dioxaborolane (1.1 g, 5.0 mmol, 1.5 eq.), potassium carbonate (1.4 g, 10.1 mmol, 3.0 eq.) and Pd(dppf)Cl$_2$ (0.2 g, 0.34 mmol, 0.1 eq.) in dioxane/water (30 mL/10 mL) was heated for 3 hours at 90° C. The mixture was concentrated, diluted with water (30 mL), and then extracted with ethyl acetate for three times. The organic extracts were combined, washed with brine, dried over anhydrous sodium sulfate, and concentrated. The residue was purified by silica gel column chromatography (petroleum ether/EtOAc/DCM=50:1:1 to 5:1:1) to give 1-methyl-4-(4-nitrophenyl)-1H-pyrazole (0.6 g, 88% yield). LC-MS m/z [M+H]$^+$ calc'd for $C_{10}H_9N_3O_2$, 204; found, 204.

Step 2: 4-(1-methyl-1H-pyrazol-4-yl)aniline

A mixture of 1-methyl-4-(4-nitrophenyl)-1H-pyrazole (0.6 g, 3.0 mmol, 1.0 eq.) and Pd/C (0.1 g) in methanol (10 mL) was hydrogenated for 2 hours. Pd/C was filtered off and washed with methanol. The filtrate and wash were combined and concentrated to give 4-(1-methyl-1H-pyrazol-4-yl)aniline (0.48 g, 94% yield) as a grey solid, which was used for next reaction without further purification. LC-MS m/z [M+H]$^+$ calc'd for $C_{10}H_{11}N_3$, 174; found, 174.

Step 3

HATU (0.66 g, 1.74 mmol, 1.5 eq.) and N-methyl morpholine (0.35 g, 3.48 mmol, 3.0 eq.) were added to a mixture of 3-fluoro-5-formyl-4-hydroxybenzoic acid (0.21 g, 1.16 mmol, 1.0 eq.) and 4-(1-methyl-1H-pyrazol-4-yl)aniline (0.4 g, 2.31 mmol, 2.0 eq.) in dichloromethane (30 mL). The reaction was stirred overnight at rt. The resulting precipitate was filtered and dissolved in a mixture of dioxane (6 mL) and 3 N HCl (6 mL). The mixture was stirred for 2 hours at room temperature and extracted with ethyl acetate for three times. The organic extracts were combined, washed with brine, dried over anhydrous sodium sulfate, and concentrated. The solid was stirred in dichloromethane (10 mL) for 10 min and filtered. The filtrate was concentrated, dissolved in dichloromethane (5 mL), and petroleum ether was added slowly. The resulting precipitate was collected and dried to give 3-fluoro-5-formyl-4-hydroxy-N-(4-(1-methyl-1H-pyrazol-4-yl)phenyl)benzamide (45 mg, 0.13 mmol, 11% yield) as a yellow solid. $^1$H NMR (DMSO-d6, 400 MHz) δ: 11.65 (br, 1H), 10.35 (s, 1H), 10.27 (s, 1H), 8.19 (s, 1H), 8.09 (m, 2H), 7.83 (s, 1H), 7.74 (d, J=8.8 Hz, 2H), 7.54 (d, J=8.4 Hz, 2H), 3.86 (s, 3H). LC-MS m/z [M+H]$^+$ calc'd for $C_{18}H_{14}FN_3O_3$, 340; found, 340.

Example B19: 1-(3-fluoro-5-formyl-4-hydroxyphenyl)-3-(4-fluorophenyl)urea (Compound B64)

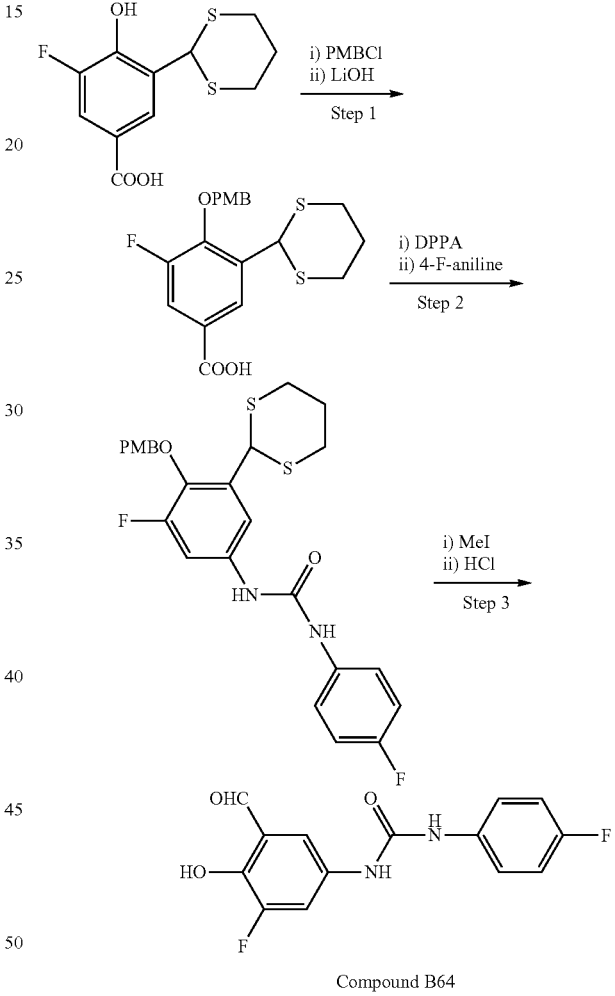

Compound B64

Step 1: 3-(1,3-dithian-2-yl)-5-fluoro-4-(4-methoxybenzyloxy)benzoic Acid

A mixture of 3-(1,3-dithian-2-yl)-5-fluoro-4-hydroxybenzoic acid (1 g, 3.6 mmol, 1.0 eq.), PMBCl (1.2 g, 7.6 mmol, 2.1 eq.), and potassium carbonate (1 g, 7.2 mmol, 2.0 eq.) in DMF (5 mL) was heated for 3 hours at 90° C. The mixture was poured into water (30 mL) and extracted with ethyl acetate for three times. The organic extracts were combined, washed with brine, dried over anhydrous sodium sulfate, and concentrated to give crude intermediate (1.9 g, quantitative yield), which was used for next reaction without further purification. The crude intermediate (1.9 g, 3.6 mmol, 1.0 eq.) was dissolved in water/THF (5 mL/5 mL) and LiOH.H₂O (0.76 g, 18.0 mmol, 5.0 eq.) was added. The reaction was stirred for 5 hours at 80° C. pH of the system was adjusted to 3-4 with 5% KHSO₄. The resulting mixture was extracted with ethyl acetate for three times. The organic extracts were combined, washed with brine, dried over anhydrous sodium sulfate, and concentrated to give crude 3-(1,3-dithian-2-yl)-5-fluoro-4-(4-methoxybenzyloxy)benzoic acid (1.4 g, quantitative yield), which was used for next reaction without further purification. LC-MS m/z [M–H]⁻ calc'd for $C_{19}H_{19}FO_4S_2$, 393; found, 393.

Step 2: 1-(3-(1,3-dithian-2-yl)-5-fluoro-4-(4-methoxybenzyloxy)phenyl)-3-(4-fluorophenyl)urea A solution of 3-(1,3-dithian-2-yl)-5-fluoro-4-(4-methoxybenzyloxy)benzoic acid (0.3 g, 0.76 mmol, 1.0 eq.), DPPA (251 mg, 0.91 mmol, 1.2 eq.), and TEA (231 mg, 2.28 mmol, 3.0 eq.) in dioxane (10 mL) was stirred for 30 min at room temperature and 4-fluoroaniline (169 mg, 1.52 mmol, 2.0 eq.) was added. The reaction was then heated overnight at 90° C. The reaction mixture was cooled to room temperature, poured into water, and extracted with ethyl acetate for three times. The organic extracts were combined, washed with brine, dried over anhydrous sodium sulfate, and concentrated. The residue was purified by silica gel column chromatography (petroleum ether/EtOAc=20:1 to 3:1) to give 1-(3-(1,3-dithian-2-yl)-5-fluoro-4-(4-methoxybenzyloxy)phenyl)-3-(4-fluorophenyl)urea (240 mg, 63% yield). LC-MS m/z [M+H]+ calc'd for $C_{25}H_{24}F_2N_2O_3S_2$, 503; found, 503.

Step 3

MeI (6.5 g, 45.8 mmol, 100 eq.) was added to a mixture of 1-(3-(1,3-dithian-2-yl)-5-fluoro-4-(4-methoxybenzyloxy) phenyl)-3-(4-fluorophenyl)urea (230 mg, 0.46 mmol, 1.0 eq.) and NaHCO₃ (770 mg, 9.17 mmol, 20.0 eq.) in acetonitrile/water (30 mL/6 mL). The reaction was heated for 6 hours at 40° C. The reaction mixture was cooled to room temperature, poured into water, and extracted with ethyl acetate for three times. The organic extracts were combined, washed with brine, dried over anhydrous sodium sulfate, and concentrated. The residue was stirred in dichloromethane (3 mL) and the solid was collected to give the intermediate (~100 mg). The intermediate (~100 mg) was dissolved in dioxane (2 mL) and 6 N HCl/dioxane (3 mL) was added. The reaction was stirred for 1 hour at room temperature. The solution was poured into ice-cold sat. NaHCO₃ and extracted with ethyl acetate for three times. The organic extracts were combined, washed with brine, dried over anhydrous sodium sulfate, and concentrated. The solid was stirred in dichloromethane (3 mL) for 10 min and filtered. The cake was collected and dried to give 1-(3-fluoro-5-formyl-4-hydroxyphenyl)-3-(4-fluorophenyl)urea (45 mg, 0.15 mmol, 34% yield) as an off-white solid. ¹H NMR (DMSO-d6, 400 MHz) δ: 10.51 (br, 1H), 10.27 (s, 1H), 8.77 (d, J=14.4 Hz, 2H), 8.69 (dd, J=12.8 Hz, 2.4 Hz, 1H), 7.45 (m, 3H), 7.12 (m, 2H). LC-MS m/z [M+H]⁺ calc'd for $C_{14}H_{10}F_2N_2O_3$, 293; found, 293.

Example B20: 1-(3-fluoro-5-formyl-4-hydroxyphenyl)-3-(4-(pyrrolidin-1-yl)phenyl)urea (Compound B65)

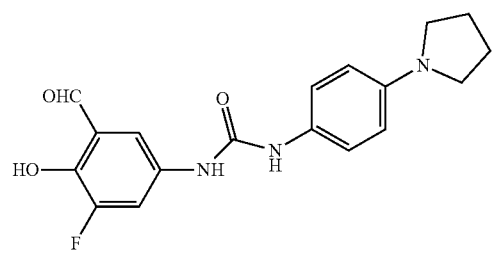 [SMILES: O=Cc1cc(NC(=O)Nc2ccc(N3CCCC3)cc2)cc(F)c1O]

4-(Pyrrolidin-1-yl)aniline (176 mg, 1.09 mmol, 1.0 eq.) was added to a solution of 3-fluoro-5-formyl-4-hydroxybenzoic acid (200 mg, 1.09 mmol, 1.0 eq.) in dioxane (5 mL). The reaction was stirred for 10 min at room temperature. The resulting mixture was concentrated and the residue was stirred in dichloromethane (20 mL) for 10 min, and then filtered. The cake was dried and re-suspended in dioxane (30 mL). DPPA (448 mg, 1.63 mmol, 1.5 eq.) and TEA (329 mg, 3.26 mmol, 3.0 eq.) were added. The reaction was stirred for 30 min at room temperature. Then 4-(pyrrolidin-1-yl)aniline (176 mg, 1.09 mmol, 1.0 eq.) was added and the reaction was heated for 3 hours at 90° C. The mixture was cooled to room temperature and poured into 4 N HCl/water (50 mL). After stirring for 1 hour at room temperature, the mixture was extracted with ethyl acetate for three times and dichloromethane for 4 times. The organic extracts were combined, dried over anhydrous sodium sulfate, and concentrated. The residue was purified by silica gel column chromatography (petroleum ether/EtOAc=20:1 to 3:1) and prep-TLC to give 1-(3-fluoro-5-formyl-4-hydroxyphenyl)-3-(4-(pyrrolidin-1-yl)phenyl)urea (25 mg, 0.07 mmol, 7% yield) as a green solid. ¹H NMR (DMSO-d6, 400 MHz) δ: 10.45 (br, 1H), 10.27 (s, 1H), 8.63 (br, 1H), 8.57 (br, 1H), 7.71 (dd, J=13.2 Hz, 2.4 Hz, 1H), 7.46 (s, 1H), 7.31 (m, 2H), 6.74 (m, 2H), 3.93 (m, 4H), 1.99 (m, 4H). LC-MS m/z [M+H]⁺ calc'd for $C_{18}H_{18}FN_3O_3$, 344; found, 344.

Example B21: 3-fluoro-5-formyl-4-hydroxy-N-(4-(piperidin-1-yl)phenyl)benzamide (New Compound B66)

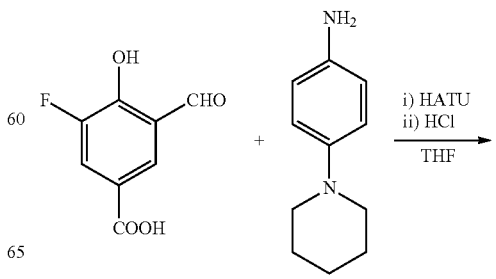

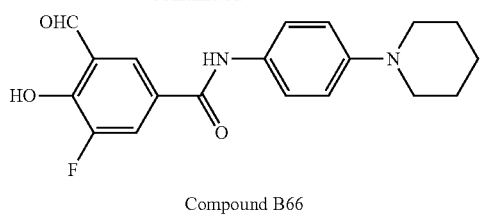

Compound B66

In a 50 mL glass vial, a solution of 3-fluoro-5-formyl-4-hydroxybenzoic acid (200 mg, 1.09 mmol, 1.0 eq.), 4-(piperidin-1-yl)aniline (478 mg, 2.73 mmol, 2.5 eq.), HATU (619 mg, 1.63 mmol, 1.5 eq.), and N-methyl morpholine (329 mg, 3.26 mmol, 3.0 eq.) in THF (10 mL) was stirred overnight at room temperature. The reaction mixture was poured into 4 N HCl. The reaction was stirred for 30 min and then extracted with ethyl acetate for three times. The organic extracts were combined, washed with brine, dried over anhydrous sodium sulfate, and concentrated. The residue was purified by silica gel column chromatography and prep-TLC to give 3-fluoro-5-formyl-4-hydroxy-N-(4-(piperidin-1-yl)phenyl)benzamide (23 mg, 0.04 mmol, 4% yield) as a yellow solid. $^1$H NMR (CDCl$_3$, 400 MHz) δ: 11.30 (br, 1H), 10.02 (s, 1H), 8.03 (s, 1H), 7.89 (d, J=10.0 Hz, 1H), 7.74 (br, 1H), 7.51 (m, 2H), 7.02 (m, 2H), 3.16 (m, 4H), 1.76 (m, 6H). ). LC-MS m/z [M+H]$^+$ calc'd for C$_{19}$H$_{19}$FN$_2$O$_3$, 343; found, 343.

Example B22: N-(4-(3,3-difluoropyrrolidin-1-yl)phenyl)-3-fluoro-5-formyl-4-hydroxybenzamide (Compound B67)

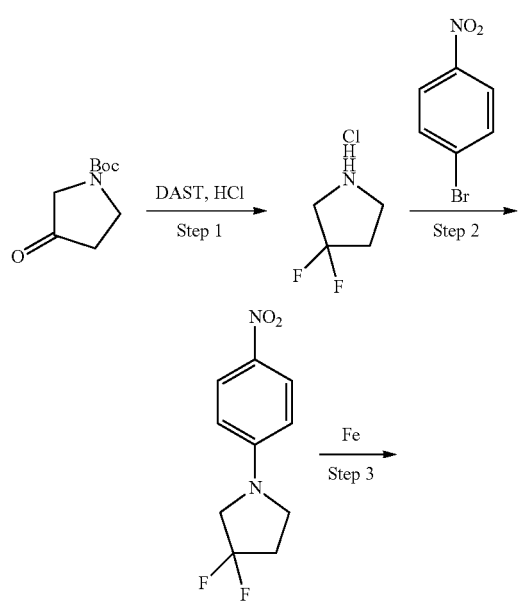

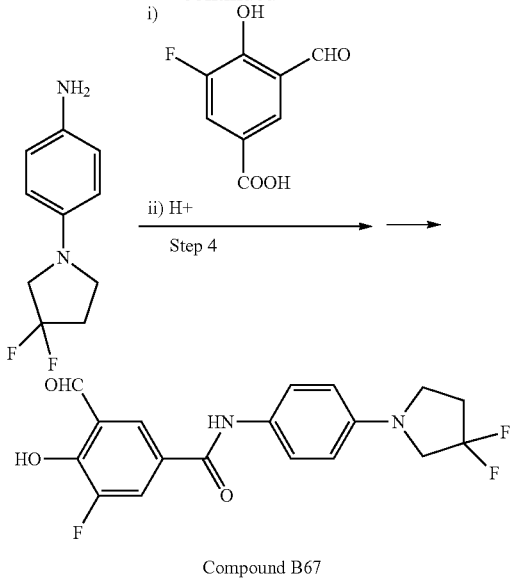

Compound B67

Step 1: 3,3-difluoropyrrolidine Hydrochloride

DAST (4.03 g, 67.6 mmol, 2.5 eq.) was added to a solution of tert-butyl 3-oxopyrrolidine-1-carboxylate (5 g, 27.0 mmol, 1.0 eq.) in dichloromethane (30 mL). The reaction was stirred for 5 hours at room temperature. The reaction mixture was poured into ice cold sat. NaHCO$_3$ solution (100 mL) and extracted with dichloromethane for three times. The organic extracts were combined, washed with brine, dried over anhydrous sodium sulfate, and concentrated to give crude Boc-3,3-difluoropyrrolidine (5.9 g, quantitative yield), which was then treated with 6 N HCl in dioxane to give 3,3-difluoropyrrolidine hydrochloride (4.1 g, quantitative yield). LC-MS m/z [M+H]$^+$ calc'd for C$_4$H$_8$ClF$_2$N, 110; found, 110.

Step 2: 3,3-difluoro-1-(4-nitrophenyl)pyrrolidine

A mixture of 3,3-difluoropyrrolidine hydrochloride (1.43 g, 1.0 mmol, 1.0 eq.) 1-bromo-4-nitrobenzene (2.01 g, 1.0 mmol, 1 eq.), BINAP (0.94 g, 0.15 mmol, 0.15 eq.), Cs$_2$CO$_3$ (8.15 g, 2.5 mmol, 2.5 eq.), and Pd(OAc)$_2$ (0.23 g, 0.1 mmol, 0.1 eq.) in toluene (20 mL) was heated overnight at 95° C. The reaction mixture was cooled to room temperature, poured into water (100 mL) and extracted with ethyl acetate for three times. The organic extracts were combined, washed with brine, dried over anhydrous sodium sulfate, and concentrated. The residue was purified by silica gel column chromatography to give 3,3-difluoro-1-(4-nitrophenyl)pyrrolidine (1.5 g, 66% yield). LC-MS m/z [M+H]$^+$ calc'd for C$_{10}$H$_{10}$F$_2$N$_2$O$_2$, 229; found, 229.

Step 3: 4-(3,3-difluoropyrrolidin-1-yl)aniline

Iron powder (3.7 g, 66.1 mmol, 10.0 eq.) was added to a solution of 3,3-difluoro-1-(4-nitrophenyl)pyrrolidine (1.5 g, 6.6 mmol, 1.0 eq.) in AcOH (30 mL). The reaction was heated for 2 hours at 60° C. The reaction mixture was cooled to room temperature, poured into sat. NaHCO$_3$ and extracted with ethyl acetate for three times. The organic extracts were combined, washed with brine, dried over anhydrous sodium sulfate, and concentrated to give crude 4-(3,3-difluoropyrrolidin-1-yl)aniline (1.1 g, 84% yield), which was used for next reaction without further purification. LC-MS m/z [M+H]+ calc'd for $C_{10}H_{12}F_2N_2$, 199; found, 199.

Step 4

A solution of 3-fluoro-5-formyl-4-hydroxybenzoic acid (200 mg, 1.09 mmol, 1.0 eq.), 4-(3,3-difluoropyrrolidin-1-yl)aniline (430 mg, 2.17 mmol, 2.0 eq.), HATU (619 mg, 1.63 mmol, 1.5 eq.), and N-methyl morpholine (329 mg, 3.26 mmol, 3.0 eq.) in THF (10 mL) was stirred overnight at room temperature. The reaction mixture was poured into 4 N HCl. The reaction was stirred for 30 min and then extracted with ethyl acetate for three times. The organic extracts were combined, washed with brine, dried over anhydrous sodium sulfate, and concentrated. The residue was purified by silica gel column chromatography and prep-TLC to give N-(4-(3,3-difluoropyrrolidin-1-yl)phenyl)-3-fluoro-5-formyl-4-hydroxybenzamide (50 mg, 0.13 mmol, 12% yield) as a yellow solid. $^1$H NMR (DMSO-d6, 400 MHz) δ: 11.61 (br, 1H), 10.35 (s, 1H), 10.10 (br, 1H), 8.18 (s, 1H), 8.09 (dd, J=12.0 Hz, 2.0 Hz, 1H), 7.59 (d, J=8.8 Hz, 2H), 6.63 (d, J=9.2 Hz, 2H), 3.68 (t, J=9.6 Hz, 2H), 3.43 (m, 4H). LC-MS m/z [M+H]+ calc'd for $C_{18}H_{15}F_3N_2O_3$, 365; found, 365.

Example B23: N-(4-(44A-difluoropiperidin-1-yl)phenyl)-3-fluoro-5-formyl-4-hydroxybenzamide (New Compound B68)

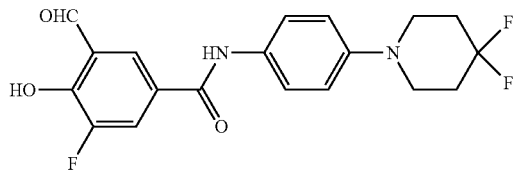 [SMILES: O=Cc1cc(C(=O)Nc2ccc(N3CCC(F)(F)CC3)cc2)cc(F)c1O]

A solution of 3-fluoro-5-formyl-4-hydroxybenzoic acid (200 mg, 1.09 mmol, 1.0 eq.), 4-(4,4-difluoropiperidin-1-yl)aniline (460 mg, 2.17 mmol, 2.0 eq.) (prepared as in Example B22), HATU (619 mg, 1.63 mmol, 1.5 eq.), and N-methyl morpholine (329 mg, 3.26 mmol, 3.0 eq.) in THF (10 mL) was stirred overnight at room temperature. The reaction mixture was poured into 4 N HCl. The reaction was stirred for 30 min and then extracted with ethyl acetate for three times. The organic extracts were combined, washed with brine, dried over anhydrous sodium sulfate, and concentrated. The residue was purified by silica gel column chromatography and prep-TLC to give N-(4-(4,4-difluoropiperidin-1-yl)phenyl)-3-fluoro-5-formyl-4-hydroxybenzamide (13 mg, 0.03 mmol, 3% yield) as a yellow solid. $^1$H NMR (DMSO-d6, 400 MHz) δ: 11.63 (br, 1H), 10.35 (s, 1H), 10.15 (br, 1H), 8.18 (s, 1H), 8.09 (d, J=11.6 Hz, 1H), 7.61 (d, J=8.8 Hz, 2H), 7.01 (d, J=8.8 Hz, 2H), 3.29 (m, 4H), 2.05 (m, 4H). LC-MS m/z [M+H]+ calc'd for $C_{19}H_{17}F_3N_2O_3$, 379; found, 379.

Example B24: N-(4-(4-cyclopropylpiperazin-1-yl)phenyl)-3-fluoro-5-formyl-4-hydroxybenzamide (Compound B69)

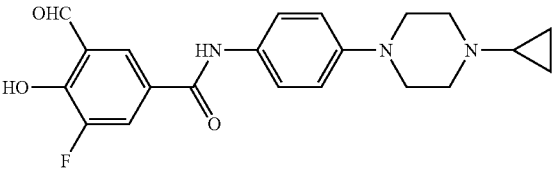 [SMILES: O=Cc1cc(C(=O)Nc2ccc(N3CCN(C4CC4)CC3)cc2)cc(F)c1O]

A solution of 3-fluoro-5-formyl-4-hydroxybenzoic acid (200 mg, 1.09 mmol, 1.0 eq.), 4-(4-cyclopropylpiperazin-1-yl)aniline (590 mg, 2.73 mmol, 2.5 eq.) (prepared as in Example B22), HATU (619 mg, 1.63 mmol, 1.5 eq.), and N-methyl morpholine (329 mg, 3.26 mmol, 3.0 eq.) in THF (10 mL) was stirred overnight at room temperature. The reaction mixture was poured into 4 N HCl. The reaction was stirred for 30 min and then extracted with ethyl acetate for three times. The organic extracts were combined, washed with brine, dried over anhydrous sodium sulfate, and concentrated. The residue was purified by silica gel column chromatography and prep-TLC to give N-(4-(4-cyclopropylpiperazin-1-yl)phenyl)-3-fluoro-5-formyl-4-hydroxybenzamide (25 mg, 0.03 mmol, 6% yield) as a pale yellow solid. $^1$H NMR (DMSO-d6, 400 MHz) δ: 11.65 (br, 1H), 10.36 (s, 1H), 10.21 (s, 1H), 8.19 (s, 1H), 8.10 (dd, J=11.6 Hz, 2.0 Hz, 1H), 7.65 (d, J=9.2 Hz, 2H), 7.01 (d, J=8.8 Hz, 2H), 3.77 (m, 2H), 3.54 (m, 2H), 3.36 (m, 2H), 3.06 (m, 2H), 2.93 (m, 1H), 1.10 (m, 2H), 0.82 (m, 2H). LC-MS m/z [M+H]+ calc'd for $C_{21}H_{22}FN_3O_3$, 384; found, 384.

Example B25: N-(4-(4-cyclopropyl-1,4-diazepan-1-yl)phenyl)-3-fluoro-5-formyl-4-hydroxybenzamide (New Compound B70)

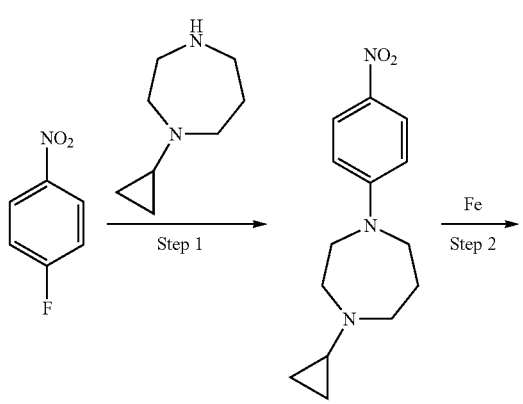

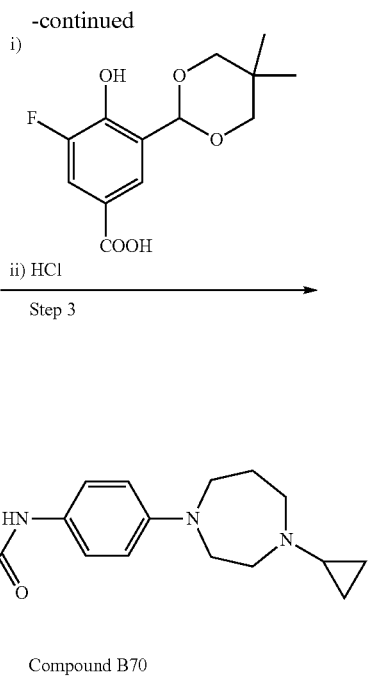

Compound B70

Step 1:
1-cyclopropyl-4-(4-nitrophenyl)-1,4-diazepane

In a 100 mL glass vial, a mixture of 1-fluoro-4-nitrobenzene (1.1 g, 7.80 mmol, 1.1 eq.), 1-cyclopropyl-1,4-diazepane (1 g, 7.14 mmol, 1.0 eq.), and $K_2CO_3$ (4.9 g, 35.5 mmol, 5.0 eq.) in DMF (20 mL) was heated for 7 hours at 50° C. The mixture was poured into water and extracted with ethyl acetate for three times. The organic extracts were combined, washed with brine, dried over anhydrous sodium sulfate, and concentrated. The residue was purified by silica gel column chromatography (pure DCM) to give 1-cyclopropyl-4-(4-nitrophenyl)-1,4-diazepane (1.57 g, 6.01 mmol, 84% yield) as a yellow oil. LC-MS m/z [M+H]$^+$ calc'd for $C_{14}H_{19}N_3O_2$, 262; found, 262.

Step 2: 4-(4-cyclopropyl-1,4-diazepan-1-yl)aniline

In a 100 mL glass vial, iron powder (794 mg, 14.18 mmol, 10 eq.) was added to a solution of 1-cyclopropyl-4-(4-nitrophenyl)-1,4-diazepane (370 mg, 1.42 mmol, 1.0 eq.) in AcOH (10 mL). The reaction was heated for 2 hours at 60° C. The reaction mixture was cooled to room temperature, poured into sat. $NaHCO_3$ and extracted with ethyl acetate for three times. The organic extracts were combined, washed with brine, dried over anhydrous sodium sulfate, and concentrated to give 4-(4-cyclopropyl-1,4-diazepan-1-yl)aniline (290 mg, 1.26 mmol, 88% yield). LC-MS m/z [M+H]$^+$ calc'd for $C_{14}H_{21}N_3$, 232; found, 232.

Step 3a: 3-(5,5-dimethyl-1,3-dioxan-2-yl)-5-fluoro-4-hydroxybenzoic Acid

In a 100 mL glass vial, a solution of 3-fluoro-5-formyl-4-hydroxybenzoic acid (2 g, 10.9 mmol, 1.0 eq.), 2,2-dimethylpropane-1,3-diol (2.26 g, 21.8 mmol, 2.0 eq.), and p-TsOH·H$_2$O (414 mg, 2.18 mmol, 0.2 eq.) in toluene (30 mL) was heated for 3 hours at 90° C. The solvent was removed in vacuo and the residue was dissolved in water/EtOAc. The mixture was then extracted with ethyl acetate for three times. The organic extracts were combined, washed with brine, dried over anhydrous sodium sulfate, and concentrated to give crude 3-(5,5-dimethyl-1,3-dioxan-2-yl)-5-fluoro-4-hydroxybenzoic acid (2.97 g, quantitative yield). LC-MS m/z [M+H]$^+$ calc'd for $C_{13}H_{15}FO_5$, 271; found, 271.

Step 3

In a 100 mL glass vial, a solution of 3-(5,5-dimethyl-1,3-dioxan-2-yl)-5-fluoro-4-hydroxybenzoic acid (193 mg, 0.71 mmol, 1.0 eq.), 4-(4-cyclopropyl-1,4-diazepan-1-yl)aniline (180 mg, 0.79 mmol, 1.1 eq.), HATU (324 mg, 0.85 mmol, 1.2 eq.), and NMM (215 mg, 2.13 mmol, 3.0 eq.) in THF (10 mL) was stirred for 4 hours at room temperature. The solution was poured into sat. $NaHCO_3$ and extracted with ethyl acetate for three times. The organic extracts were combined, washed with brine, dried over anhydrous sodium sulfate, and concentrated. The residue was purified by silica gel column chromatography ($CH_2Cl_2$/MeOH=300:1 to 150:1) and prep-TLC to give the intermediate (40 mg, 0.08 mmol, 12% yield). The intermediate (30 mg, 0.06 mmol, 1.0 eq.) was dissolved in THF/4 N HCl (2 mL/4 mL) and the reaction was stirred for 30 min at room temperature. pH of the system was adjusted to 7-7.5 and extracted with ethyl acetate for three times. The organic extracts were combined, washed with brine, dried over anhydrous sodium sulfate, and concentrated. The residue was purified by prep-TLC to give N-(4-(4-cyclopropyl-1,4-diazepan-1-yl)phenyl)-3-fluoro-5-formyl-4-hydroxybenzamide (7 mg, 0.02 mmol, 29% yield) as a yellow solid. $^1$H NMR (DMSO-d6, 400 MHz) δ: 10.32 (s, 1H), 9.96 (s, 1H), 8.14 (s, 1H), 8.00 (d, J=12.0 Hz, 1H), 7.50 (d, J=8.8 Hz, 2H), 6.68 (d, J=9.2 Hz, 2H), 3.49 (m, 4H), 2.92 (m, 2H), 2.75 (m, 2H), 2.01 (m, 1H), 1.89 (m, 2H), 0.47 (m, 2H), 0.38 (m, 2H). LC-MS m/z [M+H]$^+$ calc'd for $C_{22}H_{24}FN_3O_3$, 398; found, 398.

Example B26: 3-fluoro-5-formyl-4-hydroxy-N-(3-(pyrrolidin-1-yl)phenyl)benzamide (Compound B71)

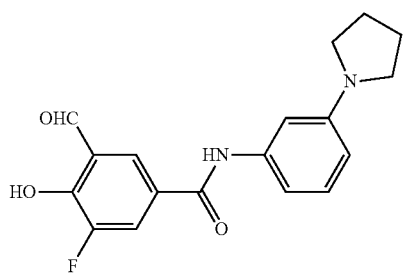 [SMILES: O=Cc1cc(C(=O)Nc2cccc(N3CCCC3)c2)cc(F)c1O]

In a 100 mL glass vial, a solution of 3-(5,5-dimethyl-1,3-dioxan-2-yl)-5-fluoro-4-hydroxybenzoic acid (300 mg, 1.11 mmol, 1.0 eq.), 3-(pyrrolidin-1-yl)aniline (180 mg, 1.11 mmol, 1.0 eq.), HATU (633 mg, 1.67 mmol, 1.5 eq.), and NMM (336 mg, 3.33 mmol, 3.0 eq.) in THF (10 mL) was stirred overnight at rt. The solution was poured into sat. $NaHCO_3$ and extracted with ethyl acetate for three times. The organic extracts were combined, washed with brine, dried over anhydrous sodium sulfate, and concentrated. The residue was purified by silica gel column chromatography (Petroleum ether/EtOAc=20:1 to 5:1) to give an intermediate (110 mg, 0.27 mmol, 24% yield). The intermediate (100 mg, 0.24 mmol, 1.0 eq.) was dissolved in THF/4 N HCl (2 mL/4 mL) and the reaction was stirred for 30 min at room temperature. The mixture was extracted with ethyl acetate for three times. The organic extracts were combined, washed with brine, dried over anhydrous sodium sulfate, and concentrated. The residue was purified by silica gel column chromatography (Petroleum ether/EtOAc=10:1 to 5:1) to give 3-fluoro-5-formyl-4-hydroxy-N-(3-(pyrrolidin-1-yl)phenyl)benzamide (65 mg, 0.20 mmol, 83% yield) as a yellow solid. $^1$H NMR (DMSO-d6, 400 MHz) δ: 11.62 (br, 1H), 10.35 (s, 1H), 10.07 (s, 1H), 8.19 (s, 1H), 8.10 (dd, J=11.6 Hz, 1.6 Hz, 1H), 7.08 (m, 2H), 7.00 (d, J=2.0 Hz, 1H), 6.29 (m, 1H), 3.22 (m, 4H), 1.97 (m, 4H). LC-MS m/z [M+H]$^+$ calc'd for $C_{18}H_{17}FN_2O_3$, 329; found, 329.

Example B27: 3-fluoro-5-formyl-4-hydroxy-N-(3-(piperidin-1-yl)phenyl)benzamide (Compound B72)

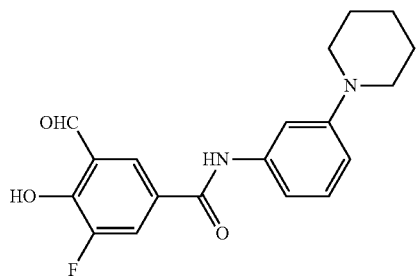 [SMILES: O=Cc1cc(C(=O)Nc2cccc(N3CCCCC3)c2)cc(F)c1O]

The title compound was prepared from 3-(5,5-dimethyl-1,3-dioxan-2-yl)-5-fluoro-4-hydroxybenzoic acid (250 mg, 0.93 mmol, 1 eq.) and 3-(piperidin-1-yl)aniline (163 mg, 0.93 mmol, 1 eq.) using a method similar to that as described in Example B25 to give the title compound 3-fluoro-5-formyl-4-hydroxy-N-(3-(piperidin-1-yl)phenyl)benzamide (7 mg, 0.02 mmol, 11% yield) as a light yellow solid. $^1$H NMR (DMSO-d6, 400 MHz) δ: 11.66 (br, 1H), 10.35 (s, 1H), 10.11 (s, 1H), 8.19 (s, 1H), 8.10 (dd, J=11.6 Hz, 2.0 Hz, 1H), 7.36 (m, 1H), 7.22 (m, 1H), 7.15 (m, 1H), 6.69 (m, 1H), 3.14 (m, 4H), 1.62 (m, 4H), 1.55 (m, 2H). LC-MS m/z [M+H]$^+$ calc'd for $C_{19}H_{19}FN_2O_3$, 343; found, 343.

Example B28: N-(4-(3,3-dimethylpyrrolidin-1-yl)phenyl)-3-fluoro-5-formyl-4-hydroxybenzamide (Compound B73)

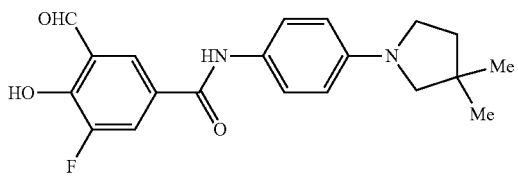 [SMILES: CC1(C)CCN(c2ccc(NC(=O)c3cc(F)c(O)c(C=O)c3)cc2)C1]

The title compound was prepared from 3-(5,5-dimethyl-1,3-dioxan-2-yl)-5-fluoro-4-hydroxybenzoic acid (270 mg, 1.0 mmol, 1.0 eq.) and 4-(3,3-dimethylpyrrolidin-1-yl)aniline (190 mg, 1 mmol, 1.0 eq.) (prepared as in Example B25) using a method similar to that as described in Example B25 to give the title compound (130 mg, 0.37 mmol, 74% yield) as a yellow solid. $^1$H NMR (DMSO-d6, 400 MHz) δ: 11.60 (br, 1H), 10.34 (s, 1H), 9.99 (s, 1H), 8.16 (d, J=1.2 Hz, 1H), 8.06 (dd, J=11.6 Hz, 2.0 Hz, 1H), 7.50 (d, J=8.8 Hz, 2H), 6.47 (d, J=9.2 Hz, 2H), 3.35-3.28 (m, 2H), 3.00 (s, 2H), 1.75 (t, J=10.8 Hz, 2H), 1.11 (s, 6H). LC-MS m/z [M+H]+ calc'd for $C_{20}H_{21}FN_2O_3$, 357; found, 357.

Example B29: N-(4-(3-azabicyclo[3.1.0]hexan-3-yl)phenyl)-3-fluoro-5-formyl-4-hydroxybenzamide (Compound B74)

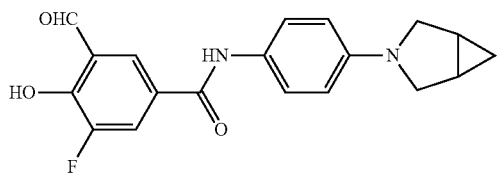 [SMILES: O=Cc1cc(C(=O)Nc2ccc(N3CC4CC4C3)cc2)cc(F)c1O]

The title compound was prepared from 3-(5,5-dimethyl-1,3-dioxan-2-yl)-5-fluoro-4-hydroxybenzoic acid (310 mg, 1.15 mmol, 1.0 eq.) and 4-(3-azabicyclo[3.1.0]hexan-3-yl)aniline (200 mg, 1.15 mmol, 1.0 eq.) (prepared as in Example B25) using a method similar to that as described in Example B25 to give the title compound (60 mg, 0.18 mmol, 39% yield). $^1$H NMR (DMSO-d6, 400 MHz) δ: 11.62 (br, 1H), 10.34 (s, 1H), 10.01 (s, 1H), 8.16 (d, J=1.6 Hz, 1H), 8.06 (dd, J=12.0 Hz, 2.0 Hz, 1H), 7.50 (d, J=8.8 Hz, 2H), 6.53 (d, J=9.2 Hz, 2H), 3.48 (d, J=9.2 Hz, 2H), 3.12 (m, 2H), 1.67 (m, 2H), 0.70 (m, 1H), 0.27 (m, 1H). LC-MS m/z [M+H]$^+$ calc'd for $C_{19}H_{17}FN_2O_3$, 341; found, 341.

Example B30: 3-fluoro-5-formyl-4-hydroxy-N-(4-((3aR,6aS)-tetrahydro-1H-furo[3,4-c]pyrrol-5(3H)-yl)phenyl)benzamide (Compound B75)

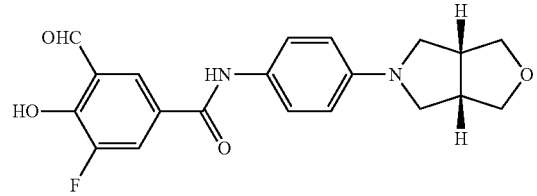 [SMILES: O=Cc1cc(C(=O)Nc2ccc(N3C[C@H]4COC[C@H]4C3)cc2)cc(F)c1O]

The title compound was prepared from 3-(5,5-dimethyl-1,3-dioxan-2-yl)-5-fluoro-4-hydroxybenzoic acid (270 mg, 1.0 mmol, 1.0 eq.) and 4-((3aR,6aS)-dihydro-1H-furo[3,4-c]pyrrol-5(3H,6H,6aH)-yl)aniline (204 mg, 1.0 mmol, 1.0 eq.) (prepared as in Example B25) using a method similar to that as described in Example B25 to give the title compound (60 mg, 0.16 mmol, 36% yield). $^1$H NMR (DMSO-d6, 400 MHz) δ: 11.59 (br, 1H), 10.34 (s, 1H), 10.06 (s, 1H), 8.17 (s, 1H), 8.08 (dd, J=12.0 Hz, 2.0 Hz, 1H), 7.54 (d, J=8.8 Hz, 2H), 6.63 (d, J=8.8 Hz, 2H), 3.85 (m, 2H), 3.54 (m, 2H), 3.31 (m, 2H), 3.15 (m, 2H), 2.98 (m, 2H). LC-MS m/z [M+H]$^+$ calc'd for $C_{20}H_{19}FN_2O_4$, 371; found, 371.

Example B31: 3-fluoro-5-formyl-N-(4-((3aR,6aS)-hexahydrocyclopenta[c]pyrrol-2(1H)-yl)phenyl)-4-hydroxybenzamide (Compound B76)

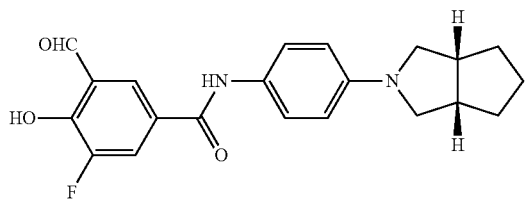 [SMILES: O=Cc1cc(C(=O)Nc2ccc(N3C[C@H]4CCC[C@H]4C3)cc2)cc(F)c1O]

The title compound was prepared from 3-(5,5-dimethyl-1,3-dioxan-2-yl)-5-fluoro-4-hydroxybenzoic acid (270 mg, 1.0 mmol, 1.0 eq.) and 4-((3aR,6aS)-hexahydrocyclopenta[c]pyrrol-2(1H)-yl)aniline (202 mg, 1.0 mmol, 1.0 eq.) (prepared as in Example B25) using a method similar to that as described in Example B25 to give the title compound (220 mg, 0.60 mmol, 62% yield). $^1$H NMR (DMSO-d6, 400 MHz) δ: 11.60 (br, 1H), 10.34 (s, 1H), 10.04 (s, 1H), 8.17 (d, J=1.6 Hz, 1H), 8.08 (dd, J=12.0 Hz, 2.0 Hz, 1H), 7.52 (d, J=9.2 Hz, 2H), 6.60 (d, J=9.2 Hz, 2H), 3.36 (m, 2H), 2.94 (m, 2H), 2.74 (m, 2H), 1.79 (m, 2H), 1.54 (m, 1H), 1.49 (m, 1H), 1.45 (m, 2H). LC-MS m/z [M+H]$^+$ calc'd for $C_{21}H_{21}FN_2O_3$, 369; found, 369.

Example B32: N-(4-(2-azaspiro[3.3]heptan-2-yl)phenyl)-3-fluoro-5-formyl-4-hydroxybenzamide (Compound B77)

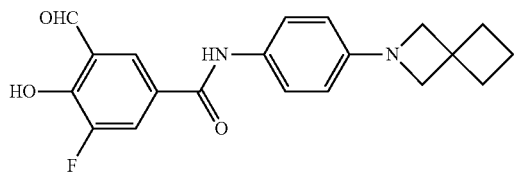

The title compound was prepared from 3-(5,5-dimethyl-1,3-dioxan-2-yl)-5-fluoro-4-hydroxybenzoic acid (270 mg, 1.0 mmol, 1.0 eq.) and 4-(2-azaspiro[3.3]heptan-2-yl)aniline (188 mg, 1 mmol, 1.0 eq.) (Ref: 2-Azaspiro[3.3]heptane, hydrochloride prepared as in Zhang, Hui et al., PCT Int. Appl., 2013013504, 31 Jan. 2013) (prepared as in Example B25) using a method similar to that as described in Example B25 to give the title compound (140 mg, 0.40 mmol, 53% yield) as a yellow solid. $^1$H NMR (DMSO-d6, 400 MHz) δ: 11.60 (br, 1H), 10.34 (s, 1H), 10.05 (s, 1H), 8.16 (d, J=1.6 Hz, 1H), 8.07 (dd, J=11.6 Hz, 2.0 Hz, 1H), 7.51 (d, J=8.8 Hz, 2H), 6.39 (d, J=8.8 Hz, 2H), 3.74 (s, 4H), 2.16 (t, J=5.0 Hz, 4H), 1.84-1.80 (m, 2H). LC-MS m/z [M+H]$^+$ calc'd for $C_{20}H_{19}FN_2O_3$, 355; found, 355.

Example B33: 3-fluoro-5-formyl-4-hydroxy-N-(4-(6-oxo-5-azaspiro[2.4]heptan-5-yl)phenyl)benzamide (Compound B78)

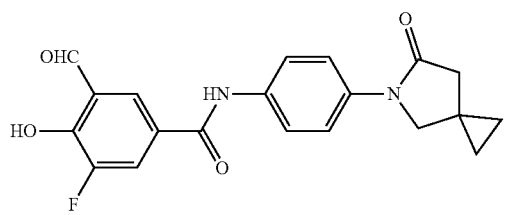 [SMILES: O=Cc1cc(C(=O)Nc2ccc(N3CC4(CC4)CC3=O)cc2)cc(F)c1O]

The title compound was prepared from 3-(5,5-dimethyl-1,3-dioxan-2-yl)-5-fluoro-4-hydroxybenzoic acid (281 mg, 1.04 mmol, 1.0 eq.) and 5-(4-aminophenyl)-5-azaspiro[2.4]heptan-6-one (210 mg, 1.04 mmol, 1.0 eq.) (prepared as in Example B22) using a method similar to that as described in Example B25 to give the title compound (100 mg, 0.27 mmol, 49% yield) as a white solid. $^1$H NMR (DMSO-d6, 400 MHz) δ: 11.68 (br, 1H), 10.36 (s, 1H), 10.33 (s, 1H), 8.20 (s, 1H), 8.11 (dd, J=11.6 Hz, 2.0 Hz, 1H), 7.75 (d, J=8.8 Hz, 2H), 7.62 (d, J=9.2 Hz, 2H), 3.75 (s, 2H), 2.56 (s, 2H), 0.70 (s, 4H). LC-MS m/z [M+H]$^+$ calc'd for $C_{20}H_{17}FN_2O_4$, 369; found, 369.

Example B34: N-(4-(5-azaspiro[2.4]heptan-5-yl)phenyl)-3-fluoro-5-formyl-4-hydroxybenzamide (Compound B79)

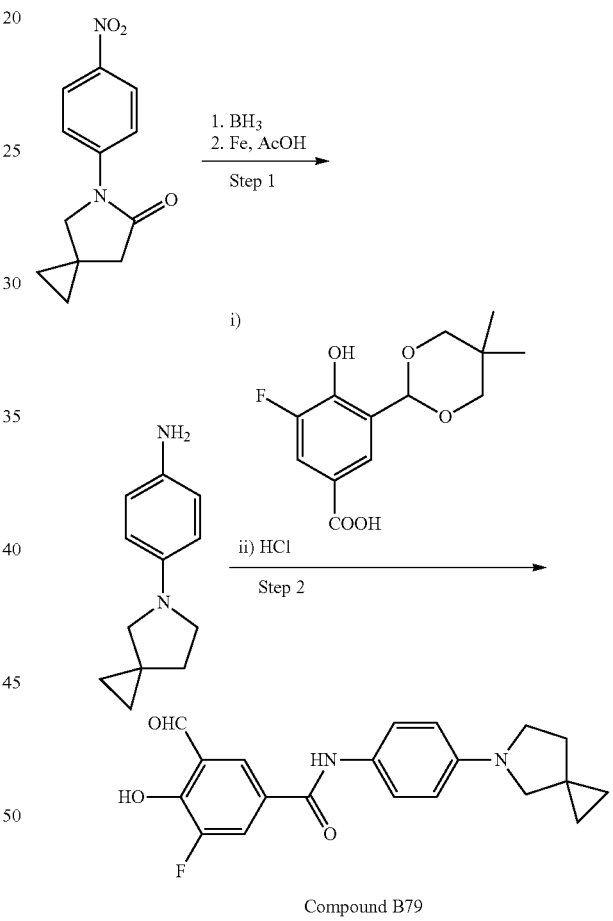

Compound B79

Step 1: 4-(5-azaspiro[2.4]heptan-5-yl)aniline 5-(4-Nitrophenyl)-5-azaspiro[2.4]heptan-6-one (300 mg, 1.29 mmol, 1.0 eq.) was dissolved in THF (10 ml) and the solution was cooled to 0° C. Borane-dimethylsulfide (0.26 mL, 10 M in DMS, 2.58 mmol, 2.0 eq.) was added. The reaction was stirred for 1 hour at 50° C. The system was cooled to room temperature, poured into ice water, and extracted with ethyl acetate for three times. The organic extracts were combined, washed with brine, dried over anhydrous sodium sulfate, and concentrated to give crude 5-(4-nitrophenyl)-5-azaspiro[2.4]heptane (305 mg, quantitative yield). In a 100 mL glass vial, iron powder (770 mg, 13.75 mmol, 10 eq.) was added to a solution of 5-(4-nitrophenyl)-5-azaspiro[2.4]heptane (305 mg, 1.29 mmol, 1.0 eq.) in AcOH (20 mL). The reaction was heated for 2 hours at 60° C. The reaction mixture was cooled to room temperature, poured into sat. NaHCO₃ and extracted with ethyl acetate for three times. The organic extracts were combined, washed with brine, dried over anhydrous sodium sulfate, and concentrated to give crude 4-(5-azaspiro[2.4]heptan-5-yl)aniline (180 mg, 0.96 mmol, 74% yield), which was used for next reaction without further purification.

Step 2

The title compound was prepared from 3-(5,5-dimethyl-1,3-dioxan-2-yl)-5-fluoro-4-hydroxybenzoic acid (284 mg, 1.05 mmol, 1.0 eq.) and 4-(5-azaspiro[2.4]heptan-5-yl)aniline (180 mg, 0.96 mmol, 1 eq.) using a method similar to that as described in Example B25 to give the title compound (70 mg, 0.20 mmol, 44% yield) as a yellow solid. ¹H NMR (DMSO-d6, 400 MHz) δ: 10.34 (br, 1H), 10.00 (br, 1H), 8.16 (s, 1H), 8.06 (d, J=11.6 Hz, 1H), 7.53 (d, J=8.8 Hz, 2H), 6.49 (d, J=8.8 Hz, 2H), 3.36 (m, 2H), 3.15 (s, 2H), 1.91 (t, J=6.4 Hz, 2H), 0.62 (d, J=8.0 Hz, 4H). LC-MS m/z [M+H]⁺ calc'd for $C_{20}H_{19}FN_2O_3$, 355; found, 355.

Example B35: N-cyclopropyl-4-((3-fluoro-5-formyl-4-hydroxyphenyl)ethynyl)benzamide (Compound B80)

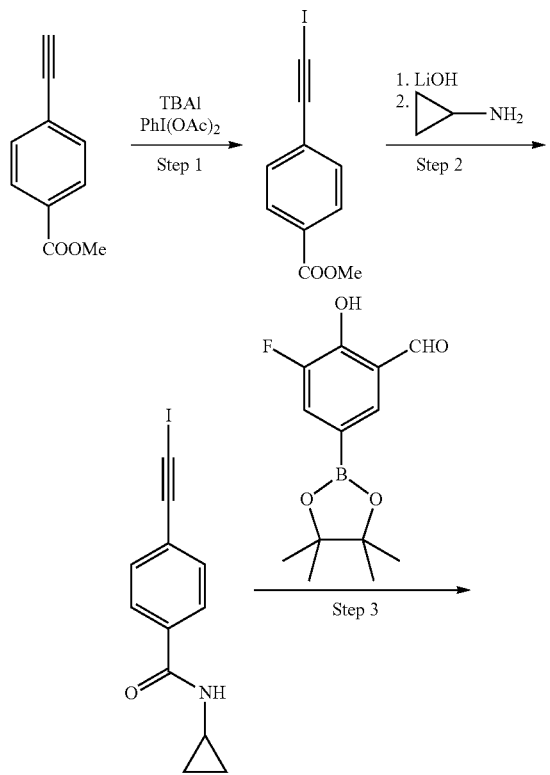

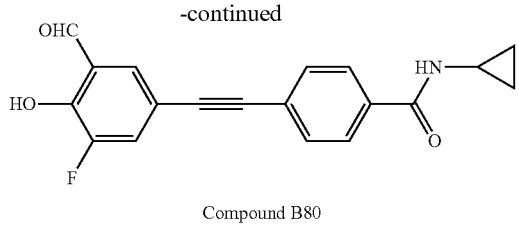

Compound B80

Step 1: methyl 4-(iodoethynyl)benzoate

In a 100 mL glass vial, PhI(OAc)₂ (3.66 g, 11.4 mmol, 1.0 eq.) was added to a solution of methyl 4-ethynylbenzoate (1.82 g, 11.4 mmol, 1.0 eq.) and TBAI (5.04 g, 13.7 mmol, 1.2 eq.) in acetonitrile (20 mL). The reaction was stirred for 5 hours at room temperature. The mixture was poured into water (50 mL) and extracted with ethyl acetate for three times. The organic extracts were combined, washed with brine, dried over anhydrous sodium sulfate, and concentrated to give crude methyl 4-(iodoethynyl)benzoate (3.64 g, quantitative yield) as a yellow solid, which was used for next reaction without further purification.

Step 2: N-cyclopropyl-4-(iodoethynyl)benzamide

In a 50 mL glass vial, LiOH·H₂O (1.34 g, 28.4 mmol, 2.5 eq.) was added to a solution of methyl 4-(iodoethynyl)benzoate (crdue, 3.64 g, 11.4 mmol, 1.0 eq.) in water/THF (10 mL/10 mL). The reaction was stirred for 2 hours at room temperature. The solution was diluted with water and extracted with petroleum ether for two times. The petroleum ether layers were discarded. Then pH of the water phase was adjusted to 3-4 with 5% KHSO₄ and then the mixture was extracted with ethyl acetate for three times. The organic extracts were combined, washed with brine, dried over anhydrous sodium sulfate, and concentrated to give acid (2.36 g, 76% yield) as a white solid. The resulting acid (2.36 g, 8.7 mmol, 1.0 eq.) was dissolved in CH₂Cl₂ (10 mL) in a 50 mL glass vial. HATU (3.96 g, 10.4 mmol, 1.2 eq.), cyclopropanamine (1.24 g, 21.7 mmol, 2.5 eq.), and N-methyl morpholine (2.63 g, 26.0 mmol, 3.0 eq.) were added. The mixture was stirred for 2 hours at room temperature. The mixture was poured into water and extracted with CH₂Cl₂ for two times. The organic extracts were combined, washed with brine (20 mL), dried over anhydrous sodium sulfate, and concentrated. The residue was purified by silica gel column chromatography (petroleum ether/EtOAc=20:1 to 5:1) to give N-cyclopropyl-4-(iodoethynyl)benzamide (1.86 g, 6.0 mmol, 69% yield) as a yellow solid. LC-MS m/z [M+H]⁺ calc'd for $C_{12}H_{10}NO$, 312; found, 312.

Step 3

In a 100 mL glass vial, a mixture of N-cyclopropyl-4-(iodoethynyl)benzamide (520 mg, 1.67 mmol, 1.0 eq.), 3-fluoro-2-hydroxy-5-(4,4,5,5-tetramethyl-1,3,2-dioxaborolan-2-yl)benzaldehyde (488 mg, 1.83 mmol, 1.1 eq.), K₂CO₃ (690 mg, 5.0 mmol, 3.0 eq.), and Pd(dppf)Cl₂ (136 mg, 0.17 mmol, 0.1 eq.) in dioxane/water (9 mL/3 mL) was stirred for 1 hour at room temperature. The mixture was poured into water, acidified to pH 4-5 with 5% KHSO₄, and extracted with ethyl acetate for three times. The organic extracts were combined, washed with brine, dried over anhydrous sodium sulfate, and concentrated. The residue was purified by silica gel column chromatography (CH₂Cl₂/MeOH=100 to 300:1)

to give N-cyclopropyl-4-((3-fluoro-5-formyl-4-hydroxyphenyl)ethynyl)benzamide (13 mg, 0.04 mmol, 2% yield) as a yellow solid. $^1$H NMR (DMSO-d6, 400 MHz) δ: 11.52 (br, 1H), 10.28 (s, 1H), 8.55 (d, J=4.0 Hz, 1H), 7.86 (d, J=8.0 Hz, 2H), 7.78 (dd, J=11.2 Hz, 2.0 Hz, 1H), 7.67-7.61 (m, 3H), 2.84 (m, 1H), 0.85 (m, 2H), 0.72 (m, 2H). LC-MS m/z [M+H]$^+$ calc'd for $C_{19}H_{14}FNO_3$, 324; found, 324.

Example B36: 3-fluoro-5-formyl-4-hydroxy-N-(4-(isoindolin-2-yl)phenyl)benzamide (New Compound B81)

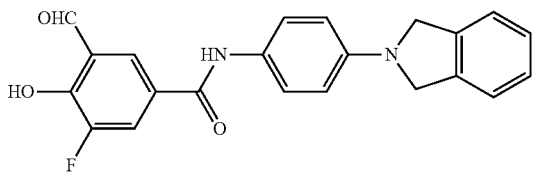

The title compound was prepared from 3-(5,5-dimethyl-1,3-dioxan-2-yl)-5-fluoro-4-hydroxybenzoic acid (296 mg, 1.1 mmol, 1.0 eq.) and 4-(isoindolin-2-yl)aniline (230 mg, 1.10 mmol, 1.0 eq.) (prepared as in Example B25) using a method similar to that as described in Example B25 to give the title compound (190 mg, 0.51 mmol, 60% yield). $^1$H NMR (DMSO-d6, 400 MHz) δ: 11.57 (br, 1H), 10.36 (s, 1H), 10.08 (s, 1H), 8.20 (s, 1H), 8.10 (d, J=11.6 Hz, 1H), 7.62 (d, J=8.8 Hz, 2H), 7.41 (m, 2H), 7.31 (m, 2H), 6.68 (d, J=8.8 Hz, 2H), 4.61 (s, 4H). LC-MS m/z [M+H]$^+$ calc'd for $C_{22}H_{17}FN_2O_3$, 377; found, 377.

Example B37: N-(4-(3,4-dihydroisoquinolin-2(1H)-yl)phenyl)-3-fluoro-5-formyl-4-hydroxybenzamide (Compound B82)

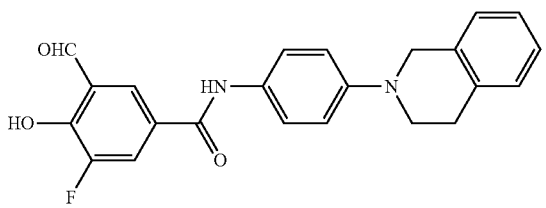 [SMILES: O=Cc1cc(C(=O)Nc2ccc(N3CCc4ccccc4C3)cc2)cc(F)c1O]

The title compound was prepared from 3-(5,5-dimethyl-1,3-dioxan-2-yl)-5-fluoro-4-hydroxybenzoic acid (416 mg, 1.56 mmol, 1.0 eq.) and 4-(3,4-dihydroisoquinolin-2(1H)-yl)aniline (350 mg, 1.56 mmol, 1.0 eq.) (prepared as in Example B25) using a method similar to that as described in Example B25 to give the title compound (130 mg, 0.33 mmol, 51% yield). $^1$H NMR (DMSO-d6, 400 MHz) δ: 11.66 (br, 1H), 10.35 (s, 1H), 10.10 (s, 1H), 8.17 (s, 1H), 8.07 (dd, J=11.6 Hz, 1.6 Hz, 1H), 7.61 (d, J=8.8 Hz, 2H), 7.23-7.16 (m, 4H), 7.01 (d, J=8.8 Hz, 2H), 4.36 (s, 2H), 3.51 (t, J=5.6 Hz, 2H), 2.91 (d, J=5.6 Hz, 2H). LC-MS m/z [M+H]$^+$ calc'd for $C_{23}H_{19}FN_2O_3$, 391; found, 391.

Example B38: 3-fluoro-5-formyl-4-hydroxy-N-(4-(4-phenylpiperazin-1-yl)phenyl)benzamide (Compound B83)

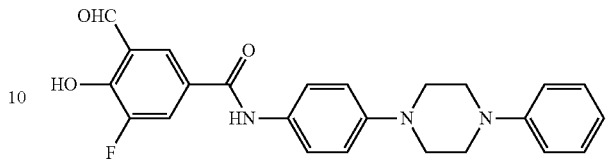

The title compound was prepared from 3-(5,5-dimethyl-1,3-dioxan-2-yl)-5-fluoro-4-hydroxybenzoic acid (373 mg, 1.38 mmol, 1.0 eq.) and 4-(4-phenylpiperazin-1-yl)aniline (350 mg, 1.38 mmol, 1.0 eq.) (prepared as in Example B25) using a method similar to that as described in Example B25 to give the title compound (4 mg, 0.01 mmol, 2% yield). $^1$H NMR (DMSO-d6, 400 MHz) δ: 11.60 (br, 1H), 10.35 (br, 1H), 10.14 (br, 1H), 8.19 (s, 1H), 8.10 (d, J=10.0 Hz, 1H), 7.63 (m, 2H), 7.24 (m, 2H), 7.02 (m, 2H), 6.81 (m, 1H), 3.27 (m, 8H). LC-MS m/z [M+H]$^+$ calc'd for $C_{24}H_{22}FN_3O_3$, 420; found, 420.

Example B39: 3-fluoro-5-formyl-4-hydroxy-N-(4-(4-(pyrrolidin-1-yl)piperidin-1-yl)phenyl)benzamide (Compound B84)

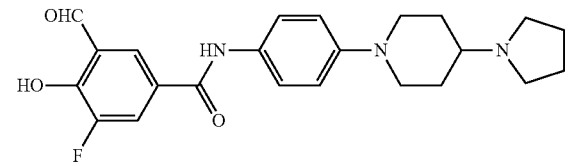

The title compound was prepared from 3-(5,5-dimethyl-1,3-dioxan-2-yl)-5-fluoro-4-hydroxybenzoic acid (170 mg, 0.63 mmol, 1.0 eq.) and 4-(4-(pyrrolidin-1-yl)piperidin-1-yl)aniline (140 mg, 0.57 mmol, 1.0 eq.) (prepared as in Example B25) using a method similar to that as described in Example B25 to give the title compound (47 mg, 0.11 mmol, 48% yield). $^1$H NMR (DMSO-d6, 400 MHz) δ: 10.14 (s, 1H), 9.51 (s, 1H), 7.86 (d, J=2.8 Hz, 1H), 7.55 (d, J=9.2 Hz, 2H), 7.45 (d, J=13.6 Hz, 2.4 Hz, 1H), 6.88 (d, J=9.2 Hz, 2H), 3.60 (d, J=12.4 Hz, 2H), 2.75 (m, 4H), 2.641 (t, J=11.6 Hz, 2H), 2.54 (m, 1H), 1.97 (d, J=12.0 Hz, 2H), 1.75 (m, 4H), 1.55 (m, 2H). LC-MS m/z [M+H]$^+$ calc'd for $C_{23}H_{26}FN_3O_3$, 412; found, 412.

Example B40: 3-fluoro-5-formyl-4-hydroxy-N-(4-(4-(pyrrolidin-1-yl)piperidin-1-yl)phenyl)benzamide (Compound B85)

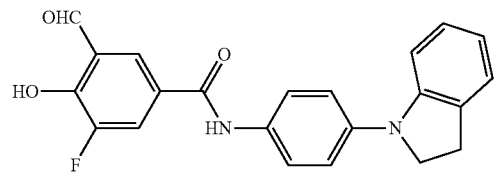 [SMILES: O=Cc1cc(C(=O)Nc2ccc(N3CCc4ccccc43)cc2)cc(F)c1O]

The title compound was prepared from 3-(5,5-dimethyl-1,3-dioxan-2-yl)-5-fluoro-4-hydroxybenzoic acid (283 mg, 1.05 mmol, 1.1 eq.) and 4-(indolin-1-yl)aniline (200 mg, 0.95 mmol, 1 eq.) (prepared as in Example B25) using a method similar to that as described in Example B25 to give the title compound (7 mg, 0.02 mmol, 7% yield). $^1$H NMR (DMSO-d6, 400 MHz) δ: 11.63 (br, 1H), 10.36 (s, 1H), 10.25 (s, 1H), 8.20 (d, J=1.6 Hz, 1H), 8.11 (dd, J=12.0 Hz, 2.0 Hz, 1H), 7.73 (d, J=8.8 Hz, 2H), 7.23 (dd, J=8.8 Hz, 2.8 Hz, 2H), 7.16 (d, J=7.2 Hz, 1H), 7.04 (m, 2H), 6.71 (m, 1H), 3.92 (d, J=8.4 Hz, 2H), 3.09 (d, J=8.4 Hz, 2H). LC-MS m/z [M+H]$^+$ calc'd for $C_{22}H_{17}FN_2O_3$, 377; found, 377.

Example B41: 3-fluoro-5-formyl-4-hydroxy-N-(6-(isoindolin-2-yl)pyridin-3-yl)benzamide (Compound B86)

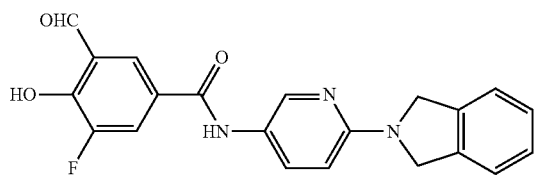

The title compound was prepared from 3-(5,5-dimethyl-1,3-dioxan-2-yl)-5-fluoro-4-hydroxybenzoic acid (637 mg, 2.37 mmol, 1.0 eq.) and 6-(isoindolin-2-yl)pyridin-3-amine (500 mg, 2.37 mmol, 1.0 eq.) (prepared as in Example B16) using a method similar to that as described in Example B25 to give the title compound (47 mg, 0.12 mmol, 15% yield). $^1$H NMR (DMSO-d6, 400 MHz) δ: 11.81 (br, 1H), 10.76 (br, 1H), 10.36 (s, 1H), 8.65 (s, 1H), 8.37 (d, J=7.2 Hz, 1H), 8.24-8.21 (m, 2H), 7.45 (m, 2H), 7.39 (m, 2H), 7.20 (d, J=7.2 Hz, 1H), 4.95 (s, 4H). LC-MS m/z [M+H]$^+$ calc'd for $C_{21}H_{16}FN_3O_3$, 378; found, 378.

Example B42: N-(6-(3,3-dimethylindolin-1-yl)pyridin-3-yl)-3-fluoro-5-formyl-4-hydroxybenzamide (Compound B87)

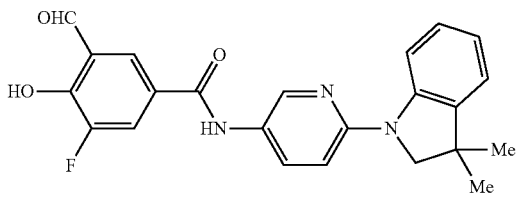 [SMILES: CC1(C)CN(c2ccc(NC(=O)c3cc(F)c(O)c(C=O)c3)cn2)c2ccccc21]

The title compound was prepared from 3-(5,5-dimethyl-1,3-dioxan-2-yl)-5-fluoro-4-hydroxybenzoic acid (475 mg, 1.76 mmol, 1.0 eq.) and 6-(3,3-dimethylindolin-1-yl)pyridin-3-amine (420 mg, 1.76 mmol, 1.0 eq.) (prepared as in Example B16) using a method similar to that as described in Example B25 to give the title compound (87 mg, 0.21 mmol, 25% yield). $^1$H NMR (DMSO-d6, 400 MHz) δ: 11.67 (br, 1H), 10.36 (s, 1H), 10.34 (s, 1H), 8.63 (d, J=2.8 Hz, 1H), 8.22 (d, J=1.6 Hz, 1H), 8.18-8.04 (m, 3H), 7.20 (dd, J=7.6 Hz, 1.2 Hz, 1H), 7.14 (m, 1H), 6.89 (m, 1H), 6.85 (m, 1H), 3.78 (s, 2H), 1.35 (s, 6H). LC-MS m/z [M+H]$^+$ calc'd for $C_{23}H_{20}FN_3O_3$, 406; found, 406.

Example B43: 3-fluoro-N-(6-(5-fluoro-3,3-dimethylindolin-1-yl)pyridin-3-yl)-5-formyl-4-hydroxybenzamide (Compound B99)

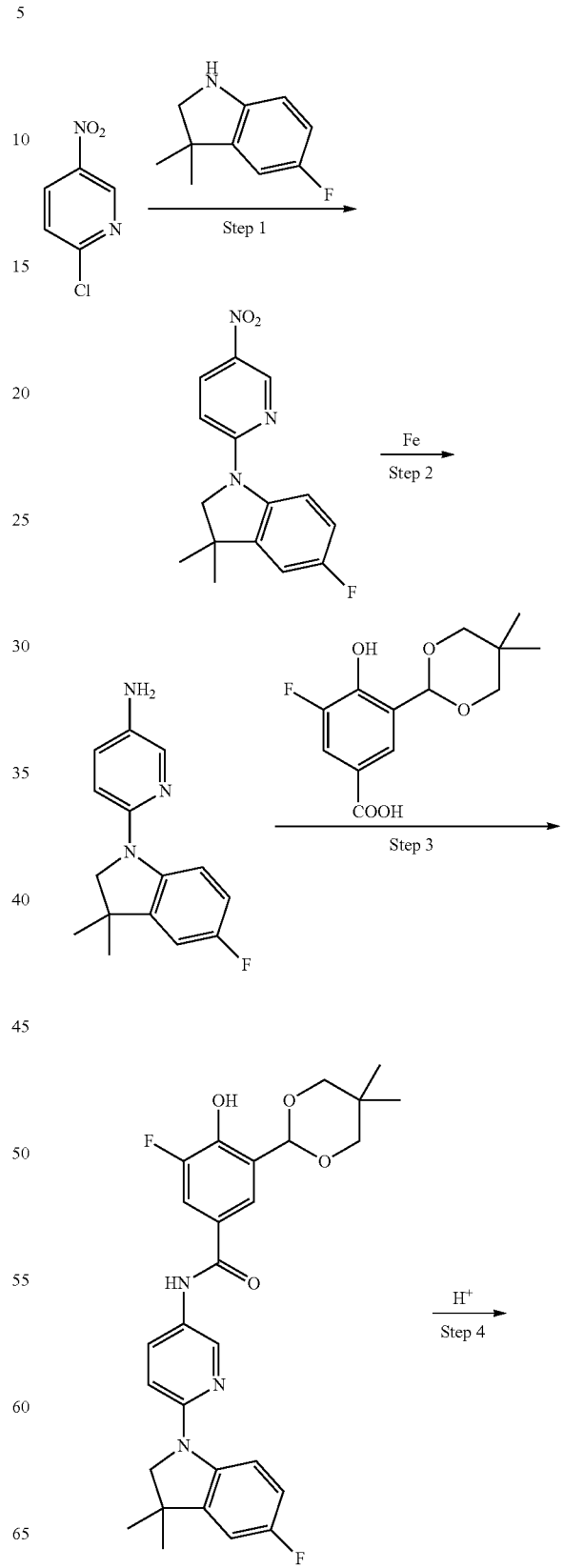

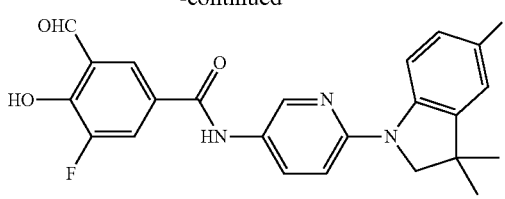

Compound B99

Step 1: 5-fluoro-3,3-dimethyl-1-(5-nitropyridin-2-yl)indoline

A mixture of 5-fluoro-3,3-dimethylindoline (1 g, 6.1 mmol, 1.0 eq.), 2-chloro-5-nitropyridine (1.44 g, 9.1 mmol, 1.5 eq.), cesium carbonate (4.94 g, 15.2 mmol, 2.5 eq.), BINAP (566 mg, 0.91 mmol, 0.15 eq.), and Pd(OAc)$_2$ (136 mg, 0.61 mmol, 0.1 eq.) in toluene (30 mL) was heated at 95° C. for 30 min. The mixture was cooled to room temperature, poured into water, and extracted with ethyl acetate for three times. The organic extracts were combined, washed with brined, dried over anhydrous sodium sulfate, and concentrated. The residue was purified by silica gel column chromatography (petroleum ether/EtOAc=300:1 to 100:1) to give 5-fluoro-3,3-dimethyl-1-(5-nitropyridin-2-yl)indoline (910 mg, 52% yield), used in next step.

Step 2

6-(5-fluoro-3,3-dimethylindolin-1-yl)pyridin-3-amine
6-(5-Fluoro-3,3-dimethylindolin-1-yl)pyridin-3-amine (690 mg, 2.7 mmol, 87% yield) was prepared from 5-fluoro-3,3-dimethyl-1-(5-nitropyridin-2-yl)indoline (900 mg, 3.1 mmol, 1.0 eq.) and Fe (1.76 g, 31.4 mmol, 10 eq.) following the similar procedure for 4-(3,3-dimethylpyrrolidin-1-yl)aniline in Example B25. LC-MS m/z [M+H]$^+$ calc'd for $C_{15}H_{16}FN_3$, 258; found, 258.

Step 3: 3-(5,5-dimethyl-1,3-dioxan-2-yl)-5-fluoro-N-(6-(5-fluoro-3,3-dimethylindolin-1-yl)pyridin-3-yl)-4-hydroxybenzamide 3-(5,5-Dimethyl-1,3-dioxan-2-yl)-5-fluoro-N-(6-(5-fluoro-3,3-dimethylindolin-1-yl)pyridin-3-yl)-4-hydroxybenzamide (550 mg, 47% yield) was prepared from 6-(5-fluoro-3,3-dimethylindolin-1-yl)pyridin-3-amine (600 mg, 2.3 mmol, 1.0 eq.) and 3-(5,5-dimethyl-1,3-dioxan-2-yl)-5-fluoro-4-hydroxybenzoic acid (630 mg, 2.3 mmol, 1.0 eq.) following the similar procedure for 3-(5,5-dimethyl-1,3-dioxan-2-yl)-N-(4-(3,3-dimethylpyrrolidin-1-yl)phenyl)-5-fluoro-4-hydroxybenzamide in Example B25. LC-MS m/z [M+H]$^+$ calc'd for $C_{28}H_{29}F_2N_3O_4$, 510; found, 510.

Step 4

3-Fluoro-N-(6-(5-fluoro-3,3-dimethylindolin-1-yl)pyridin-3-yl)-5-formyl-4-hydroxybenzamide (80 mg, 18% yield) was prepared as a yellow solid from 3-(5,5-dimethyl-1,3-dioxan-2-yl)-5-fluoro-N-(6-(5-fluoro-3,3-dimethylindolin-1-yl)pyridin-3-yl)-4-hydroxybenzamide (550 mg, 1.08 mmol, 1.0 eq.) following the similar procedure as in Example B25. Pos. LC-MS: 423.9 (M+H)+, $C_{23}H_{19}F_2N_3O_3$. $^1$H NMR (DMSO-d6, 400 MHz) δ: 11.67 (br, 1H), 10.36 (br, 1H), 10.33 (br, 1H), 8.62 (br, 1H), 8.22 (m, 2H), 8.13-8.06 (m, 2H), 7.11 (m, 1H), 6.95-6.89 (m, 2H), 3.80 (s, 2H), 1.35 (s, 6H). LC-MS m/z [M+H]$^+$ calc'd for $C_{23}H_{19}F_2N_3O_3$, 424; found, 424.

Example B44: N-(4-(2,3-dihydro-4H-benzo[b][1,4]oxazin-4-yl)phenyl)-3-fluoro-5-formyl-4-hydroxybenzamide (Compound B90)

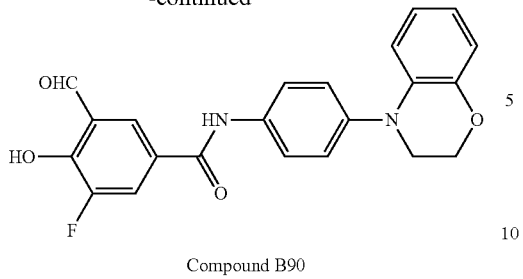

Compound B90

Example B45: 3-fluoro-5-formyl-4-hydroxy-N-(4-(methyl(neopentyl)amino)phenyl)benzamide (Compound B94)

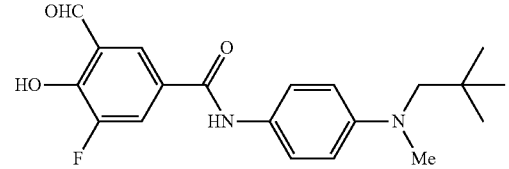

Step 1: 4-(4-nitrophenyl)-3,4-dihydro-2H-benzo[b][1,4]oxazine 4-(4-Nitrophenyl)-3,4-dihydro-2H-benzo[b][1,4]oxazine (1.43 g, 5.6 mmol, 56% yield) was prepared from 3,4-dihydro-2H-benzo[b][1,4]oxazine (1.35 g, 10.0 mmol, 1.0 eq.) and 1-fluoro-4-nitrobenzene (1.7 g, 12.0 mmol, 1.1 eq.) following the similar procedure for 3,3-dimethyl-1-(4-nitrophenyl)pyrrolidine in Example B25. No LCMS was taken for this compound.

Step 2: 4-(2H-benzo[b][1,4]oxazin-4(3H)-yl)aniline 4-(2H-Benzo[b][1,4]oxazin-4(3H)-yl)aniline (847 mg, 3.75 mmol, 67% yield) was prepared from 4-(4-nitrophenyl)-3,4-dihydro-2H-benzo[b][1,4]oxazine (1.43 g, 5.59 mmol, 1.0 eq.) and Fe (3.13 g, 55.9 mmol, 10 eq.) following the similar procedure for 4-(3,3-dimethylpyrrolidin-1-yl)aniline in Example B25. LC-MS m/z [M+H]$^+$ calc'd for $C_{14}H_{14}N_2O$, 227; found, 227.

Step 3: N-(4-(2H-benzo[b][1,4]oxazin-4(3H)-yl)phenyl)-3-(5,5-dimethyl-1,3-dioxan-2-yl)-5-fluoro-4-hydroxybenzamide N-(4-(2H-Benzo[b][1,4]oxazin-4(3H)-yl)phenyl)-3-(5,5-dimethyl-1,3-dioxan-2-yl)-5-fluoro-4-hydroxybenzamide (403 mg, 0.84 mmol, 45% yield) was prepared from 4-(2H-benzo[b][1,4]oxazin-4(3H)-yl)aniline (420 mg, 1.86 mmol, 1 eq.) and 3-(5,5-dimethyl-1,3-dioxan-2-yl)-5-fluoro-4-hydroxybenzoic acid (502 mg, 1.86 mmol, 1.0 eq.) following the similar procedure for 3-(5,5-dimethyl-1,3-dioxan-2-yl)-N-(4-(3,3-dimethylpyrrolidin-1-yl)phenyl)-5-fluoro-4-hydroxybenzamide in Example B25. LC-MS m/z [M+H]$^+$ calc'd for $C_{27}H_{27}FN_2O_5$, 479; found, 479.

Step 4

N-(4-(2H-Benzo[b][1,4]oxazin-4(3H)-yl)phenyl)-3-fluoro-5-formyl-4-hydroxybenzamide (110 mg, 0.28 mmol, 33% yield) was prepared as a yellow solid from N-(4-(2H-benzo[b][1,4]oxazin-4(3H)-yl)phenyl)-3-(5,5-dimethyl-1,3-dioxan-2-yl)-5-fluoro-4-hydroxybenzamide (400 mg, 0.84 mmol, 1.0 eq.) following the similar procedure for Example B25. $^1$H NMR (DMSO-d6, 400 MHz) δ: 11.67 (br, 1H), 10.36 (s, 1H), 10.31 (s, 1H), 8.20 (d, J=1.6 Hz, 1H), 8.10 (dd, J=11.6 Hz, 2.8 Hz, 1H), 7.76 (d, J=8.8 Hz, 2H), 7.24 (d, J=8.8 Hz, 2H), 6.81-6.69 (m, 4H), 4.25 (t, J=4.0 Hz, 2H), 3.67 (d, J=4.0 Hz, 2H). LC-MS m/z [M+H]+ calc'd for $C_{22}H_{17}FN_2O_4$, 393; found, 393.

Step 1: N-methyl-N-neopentyl-4-nitroaniline

N-Methyl-N-neopentyl-4-nitroaniline (670 mg, 3.02 mmol, 91% yield) was prepared from N,2,2-trimethylpropan-1-amine hydrochloride (500 mg, 3.64 mmol, 1.1 eq.) and 1-fluoro-4-nitrobenzene (466 mg, 3.30 mmol, 1.0 eq.) following the similar procedure for 3,3-dimethyl-1-(4-nitrophenyl)pyrrolidine in Example B25. No LCMS was taken for this compound.

Step 2: N1-methyl-N1-neopentylbenzene-1,4-diamine

N1-Methyl-N1-neopentylbenzene-1,4-diamine (320 mg, 1.66 mmol, 55% yield) was prepared from N-methyl-N-neopentyl-4-nitroaniline (670 mg, 3.02 mmol, 1.0 eq.) and Fe (1.69 g, 30.2 mmol, 10 eq.) following the similar procedure for 4-(3,3-dimethylpyrrolidin-1-yl)aniline in Example B25. LC-MS m/z [M+H]$^+$ calc'd for $C_{12}H_{20}N_2$, 193; found, 193.

Step 3: 3-(5,5-dimethyl-1,3-dioxan-2-yl)-5-fluoro-4-hydroxy-N-(4-(methyl(neopentyl) amino)phenyl)benzamide 3-(5,5-Dimethyl-1,3-dioxan-2-yl)-5-fluoro-4-hydroxy-N-(4-(methyl(neopentyl)amino)phenyl) benzamide (170 mg, 0.38 mmol, 74% yield) was prepared from N1-methyl-N1-neopentylbenzene-1,4-diamine (100 mg, 0.52 mmol, 1 eq.) and 3-(5,5-dimethyl-1,3-dioxan-2-yl)-5-fluoro-4-hydroxybenzoic acid (155 mg, 0.57 mmol, 1.1 eq.) following the similar procedure for 3-(5,5-dimethyl-1,3-dioxan-2-yl)-N-(4-(3,3-dimethylpyrrolidin-1-yl)phenyl)-5-fluoro-4-hydroxybenzamide in Example B25. LC-MS m/z [M+H]$^+$ calc'd for $C_{25}H_{33}FN_2O_4$, 445; found, 445.

Step 4

3-Fluoro-5-formyl-4-hydroxy-N-(4-(methyl(neopentyl)amino)phenyl)benzamide (60 mg, 0.17 mmol, 44% yield) was prepared as a yellow solid from 3-(5,5-dimethyl-1,3-dioxan-2-yl)-5-fluoro-4-hydroxy-N-(4-(methyl(neopentyl)amino)phenyl)benzamide (170 mg, 0.38 mmol, 1 eq.) following the similar procedure for Example B25. $^1$H NMR (CDCl$_3$, 400 MHz) 3:11.26 (br, 1H), 10.00 (br, 1H), 7.97 (s, 1H), 7.85 (d, J=10.8 Hz, 1H), 7.56 (br, 1H), 7.39 (d, J=8.4 Hz, 2H), 6.74 (br, 2H), 3.14 (s, 2H), 3.00 (s, 3H), 1.00 (s, 9H). LC-MS m/z [M+H]$^+$ calc'd for $C_{20}H_{23}FN_2O_3$, 359; found, 359.

Example B46: N-(4-(7-azabicyclo[2.2.1]heptan-7-yl)phenyl)-3-fluoro-5-formyl-4-hydroxybenzamide (Compound B95)

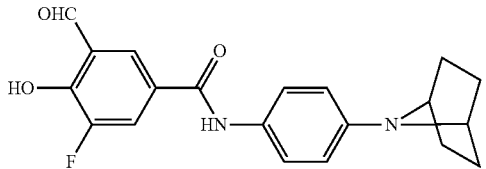 [SMILES: O=Cc1cc(C(=O)Nc2ccc(N3C4CCC3CC4)cc2)cc(F)c1O]

Step 1: (1s,4s)-7-(4-nitrophenyl)-7-azabicyclo[2.2.1]heptane (1s,4s)-7-(4-Nitrophenyl)-7-azabicyclo[2.2.1]heptane (710 mg, 3.26 mmol, 96% yield) was prepared from (1s,4s)-7-azabicyclo[2.2.1]heptane hydrochloride (500 mg, 3.73 mmol, 1.1 eq.) and 1-fluoro-4-nitrobenzene (480 mg, 3.40 mmol, 1.1 eq.) following the similar procedure for 3,3-dimethyl-1-(4-nitrophenyl)pyrrolidine in Example B25. No LCMS was taken for this compound.

Step 2: 4-((1s,4s)-7-azabicyclo[2.2.1]heptan-7-yl)aniline 4-((1s,4s)-7-Azabicyclo[2.2.1]heptan-7-yl)aniline (490 mg, 2.61 mmol, 80% yield) was prepared from (1s,4s)-7-(4-nitrophenyl)-7-azabicyclo[2.2.1]heptane (710 mg, 3.26 mmol, 1 eq.) and Fe (1.8 g, 32.6 mmol, 10 eq.) following the similar procedure for 4-(3,3-dimethylpyrrolidin-1-yl)aniline in Example B25. LC-MS m/z [M+H]$^+$ calc'd for $C_{12}H_{16}N_2$, 189; found, 189.

Step 3: N-(4-((1s,4s)-7-azabicyclo[2.2.1]heptan-7-yl)phenyl)-3-(5,5-dimethyl-1,3-dioxan-2-yl)-5-fluoro-4-hydroxybenzamide N-(4-((1s,4s)-7-Azabicyclo[2.2.1]heptan-7-yl)phenyl)-3-(5,5-dimethyl-1,3-dioxan-2-yl)-5-fluoro-4-hydroxybenzamide (360 mg, 0.82 mmol, 37% yield) was prepared from 4-((1s,4s)-7-azabicyclo[2.2.1]heptan-7-yl)aniline (420 mg, 2.23 mmol, 1 eq.) and 3-(5,5-dimethyl-1,3-dioxan-2-yl)-5-fluoro-4-hydroxybenzoic acid (660 mg, 2.44 mmol, 1.1 eq.) following the similar procedure for 3-(5,5-dimethyl-1,3-dioxan-2-yl)-N-(4-(3,3-dimethylpyrrolidin-1-yl)phenyl)-5-fluoro-4-hydroxybenzamide in Example B25. LC-MS m/z [M+H]$^+$ calc'd for $C_{25}H_{29}FN_2O_4$, 441; found, 441.

Step 4

N-(4-((1s,4s)-7-Azabicyclo[2.2.1]heptan-7-yl)phenyl)-3-fluoro-5-formyl-4-hydroxybenzamide (75 mg, 0.21 mmol, 59% yield) was prepared as a light yellow solid from N-(4-((1s,4s)-7-azabicyclo[2.2.1]heptan-7-yl)phenyl)-3-(5,5-dimethyl-1,3-dioxan-2-yl)-5-fluoro-4-hydroxybenzamide (160 mg, 0.36 mmol, 1 eq.) following the similar procedure for Example B25. $^1$H NMR (CDCl$_3$, 400 MHz) δ: 11.28 (br, 1H), 9.98 (d, J=1.2 Hz, 1H), 7.96 (s, 1H), 7.84 (d, J=10.8 Hz, 1H), 7.65 (s, 1H), 7.41 (d, J=8.4 Hz, 2H), 6.89 (d, J=8.8 Hz, 2H), 4.16 (t, J=2.0 Hz, 2H), 1.80 (t, J=3.2 Hz, 4H), 1.44 (d, J=6.8 Hz, 4H). LC-MS m/z [M+H]$^+$ calc'd for $C_{20}H_{19}FN_2O_3$, 355; found, 355.

Example B47: N-(4-(8-azabicyclo[3.2.1]octan-8-yl)phenyl)-3-fluoro-5-formyl-4-hydroxybenzamide (Compound B96)

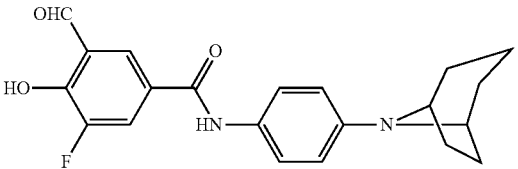 [SMILES: O=Cc1cc(C(=O)Nc2ccc(N3C4CCCC3CC4)cc2)cc(F)c1O]

Step 1: (1R,5S)-8-(4-nitrophenyl)-8-azabicyclo[3.2.1]octane (1R,5S)-8-(4-Nitrophenyl)-8-azabicyclo[3.2.1]octane (740 mg, 3.19 mmol, 98% yield) was prepared from (1R,5S)-8-azabicyclo[3.2.1]octane hydrochloride (500 mg, 3.39 mmol, 1.05 eq.) and 1-fluoro-4-nitrobenzene (455 mg, 3.23 mmol, 1.0 eq.) following the similar procedure for 3,3-dimethyl-1-(4-nitrophenyl)pyrrolidine in Example B25. No LCMS was taken for this compound.

Step 2: 4-((1R,5S)-8-azabicyclo[3.2.1]octan-8-yl)aniline 4-((1R,5S)-8-Azabicyclo[3.2.1]octan-8-yl)aniline (610 mg, 3.02 mmol, 95% yield) was prepared from (1R,5S)-8-(4-nitrophenyl)-8-azabicyclo[3.2.1]octane (740 mg, 3.19 mmol, 1.0 eq.) and Fe (1.8 g, 31.9 mmol, 10 eq.) following the similar procedure for 4-(3,3-dimethylpyrrolidin-1-yl)aniline in Example B25. No LCMS was taken for this compound.

Step 3: N-(4-((1R,5S)-8-azabicyclo[3.2.1]octan-8-yl)phenyl)-3-(5,5-dimethyl-1,3-dioxan-2-yl)-5-fluoro-4-hydroxybenzamide N-(4-((1R,5S)-8-Azabicyclo[3.2.1]octan-8-yl)phenyl)-3-(5,5-dimethyl-1,3-dioxan-2-yl)-5-fluoro-4-hydroxybenzamide (420 mg, 0.93 mmol, 47% yield) was prepared from 4-((1R,5S)-8-azabicyclo[3.2.1]octan-8-yl)aniline (400 mg, 1.98 mmol, 1 eq.) and 3-(5,5-dimethyl-1,3-dioxan-2-yl)-5-fluoro-4-hydroxybenzoic acid (588 mg, 2.18 mmol, 1.1 eq.) following the similar procedure for 3-(5,5-dimethyl-1,3-dioxan-2-yl)-N-(4-(3,3-dimethylpyrrolidin-1-yl)phenyl)-5-fluoro-4-hydroxybenzamide in Example B25. LC-MS m/z [M+H]$^+$ calc'd for $C_{26}H_{31}FN_3O_4$, 455; found, 455.

Step 4

N-(4-((1R,5S)-8-Azabicyclo[3.2.1]octan-8-yl)phenyl)-3-fluoro-5-formyl-4-hydroxybenzamide (190 mg, 0.52 mmol, 56% yield) was prepared as a yellow solid from N-(4-((1R,5S)-8-azabicyclo[3.2.1]octan-8-yl)phenyl)-3-(5,5-dimethyl-1,3-dioxan-2-yl)-5-fluoro-4-hydroxybenzamide (420 mg, 0.93 mmol, 1 eq.) following the similar procedure for Example B25. Pos. LC-MS: 369.0 (M+H)+, $C_{21}H_{21}FN_2O_3$. $^1$H NMR (CDCl$_3$, 400 MHz) δ: 11.26 (br, 1H), 10.00 (s, 1H), 7.96 (s, 1H), 7.98 (s, 1H), 7.86 (d, J=10.8 Hz, 1H), 7.63 (br, 1H), 7.43 (d, J=8.0 Hz, 2H), 7.77 (br, 2H), 4.18 (br, 2H), 2.09 (m, 2H), 1.98-1.81 (m, 4H), 1.56 (m, 2H), 1.23 (m, 2H). LC-MS m/z [M+H]$^+$ calc'd for $C_{21}H21FN_2O_3$, 369; found, 369.

Example B48: 3-fluoro-5-formyl-4-hydroxy-N-(4-(pyrrolidin-1-yl)-3-(trifluoromethyl)phenyl) benzamide (Compound B91)

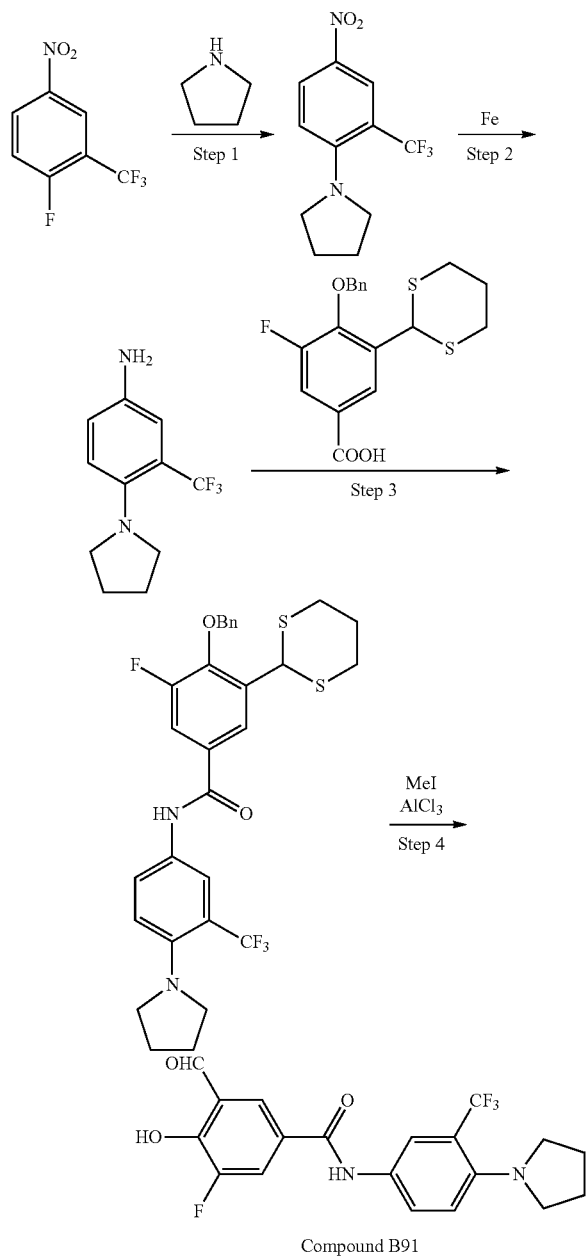

Step 1: 1-(4-nitro-2-(trifluoromethyl)phenyl)pyrrolidine 1-(4-Nitro-2-(trifluoromethyl)phenyl)pyrrolidine (930 mg, 3.6 mmol, 75% yield) was prepared from pyrrolidine (357 mg, 5.0 mmol, 1.05 eq.) and 1-fluoro-4-nitro-2-(trifluoromethyl)benzene (1 g, 4.8 mmol, 1.0 eq.) following the similar procedure for 3,3-dimethyl-1-(4-nitrophenyl)pyrrolidine in Example B25. No LCMS was taken for this compound.

Step 2: 4-(pyrrolidin-1-yl)-3-(trifluoromethyl)aniline 4-(Pyrrolidin-1-yl)-3-(trifluoromethyl)aniline (790 mg, 3.4 mmol, 98% yield) was prepared from 1-(4-nitro-2-(trifluoromethyl)phenyl)pyrrolidine (900 mg, 3.5 mmol, 1.0 eq.) and Fe (1.94 g, 34.6 mmol, 10 eq.) following the similar procedure for 4-(3,3-dimethylpyrrolidin-1-yl)aniline in Example B25. LC-MS m/z [M+H]$^+$ calc'd for $C_{11}H_{13}N_3O_2$, 231; found, 231.

Step 3: 4-(benzyloxy)-3-(1,3-dithian-2-yl)-5-fluoro-N-(4-(pyrrolidin-1-yl)-3-(trifluoromethyl)phenyl) benzamide Benzyl bromide (BnBr) (3.62 g, 21.2 mmol, 2.0 eq.) was added to a solution of 3-(1,3-dithian-2-yl)-5-fluoro-4-hydroxybenzoic acid (2.9 g, 10.6 mmol, 1.0 eq.) and potassium carbonate (2.9 g, 21.0 mmol, 2.0 eq.) in DMF (25 mL). The mixture was stirred for 3 hours at room temperature and poured into water. The mixture was then extracted with ethyl acetate for three times. The organic extracts were combined, washed with brine, dried over anhydrous sodium sulfate, and concentrated to give crude bis-Bn protected ester (3.1 g, 6.8 mmol, 64% yield) as light yellow solid. The ester (3.1 g, 6.8 mmol, 1.0 eq.) was mixed with LiOH.H$_2$O (833 mg, 20.5 mmol, 3 eq.) in THF/water (5 mL/5 mL). The reaction was stirred for 2 hours at room temperature. Then pH of the reaction system was acidified to 3-4 and the mixture was extracted with ethyl acetate for three times. The organic extracts were combined, washed with brine, dried over anhydrous sodium sulfate, and concentrated. The residue was crystallized in ethyl acetate/petroleum ether to give 4-(benzyloxy)-3-(1,3-dithian-2-yl)-5-fluorobenzoic acid (1.5 g, 4.1 mmol, 60% yield) as white solid. The resulting 4-(benzyloxy)-3-(1,3-dithian-2-yl)-5-fluorobenzoic acid (445 mg, 1.2 mmol, 1.0 eq.) was dissolved in dichloromethane (10 mL) and oxalyl chloride (311 mg, 2.4 mmol, 2.0 eq.) and DMF (1 drop) was added. The reaction was stirred for 2 hours at room temperature. The solvent was removed in vacuo and the residue was co-evaporated with dichloromethane for two times. The residue was then dissolved in dichloromethane and the solution was cooled to 0° C. Then, 4-(pyrrolidin-1-yl)-3-(trifluoromethyl)aniline (309 mg, 1.3 mmol, 1.1 eq.) and TEA (369 mg, 3.6 mmol, 3.0 eq.) were added successively. The reaction was stirred for 3 hours at room temperature. The solution was poured into water and extracted with dichloromethane for two times. The organic extracts were washed with 1% KHSO4, dried over anhydrous sodium sulfate, and concentrated. The residue was purified by silica gel column chromatography (petroleum ether/ethyl acetate=20:1 to 5:1) to give 4-(benzyloxy)-3-(1,3-dithian-2-yl)-5-fluoro-N-(4-(pyrrolidin-1-yl)-3-(trifluoromethyl)phenyl)benzamide (370 mg, 0.64 mmol, 53% yield) as a yellow powder. LC-MS m/z [M+H]$^+$ calc'd for $C_{29}H_{28}F_4N_2O_2S_2$, 577; found, 577.

Step 4

A mixture of 4-(benzyloxy)-3-(1,3-dithian-2-yl)-5-fluoro-N-(4-(pyrrolidin-1-yl)-3-(trifluoromethyl)phenyl)benzamide (350 mg, 0.61 mmol, 1.0 eq.), MeI (12.3 g, 60.8 mmol, 100 eq.), and sodium bicarbonate (1.46 g, 12.2 mmol, 20 eq.) in acetonitrile/water (25 mL/5 mL) was heated at 40° C. for 2 hours. The mixture was cooled to room temperature, poured into water, and extracted with ethyl acetate for three times. The organic extracts were combined, washed with brine, dried over anhydrous sodium sulfate, and concentrated. The residue was purified by silica gel column chromatography (petroleum ether/EtOAc=100:1 to 20:1) to give the intermediate (290 mg, 0.60 mmol, 98% yield) as a yellow solid. The intermediate (190 mg, 0.39 mmol, 1.0 eq.) was dissolved in dichloromethane (10 mL) and anhydrous AlCl₃ (208 mg, 1.56 mmol, 4.0 eq.) was added. The reaction was stirred overnight at room temperature. The mixture was poured into ice-water and dichloromethane. The insoluble stuff was filtered off and the filtrate was extracted with DCM for three times. The organic extracts were combined, dried over anhydrous sodium sulfate, and concentrated. The residue was purified by prep-TLC to give 4-(benzyloxy)-3-fluoro-5-formyl-N-(4-(pyrrolidin-1-yl)-3-(trifluoromethyl)phenyl)benzamide (80 mg, 0.20 mmol, 52% yield) as a yellow solid. ¹H NMR (DMSO-d6, 400 MHz) δ: 10.34 (s, 1H), 10.30 (s, 1H), 8.19 (s, 1H), 8.07 (m, 2H), 7.88 (dd, J=9.2 Hz, 2.0 Hz, 1H), 7.20 (d, J=9.2 Hz, 1H), 3.20 (m, 4H), 1.89 (m, 4H). LC-MS m/z [M+H]⁺ calc'd for $C_{19}H_{16}F_4N_2O_3$, 397; found, 397.

Example B49: 3-fluoro-5-formyl-4-hydroxy-N-(6-(4-phenylpiperazin-1-yl)pyridin-3-yl)benzamide (Compound B102)

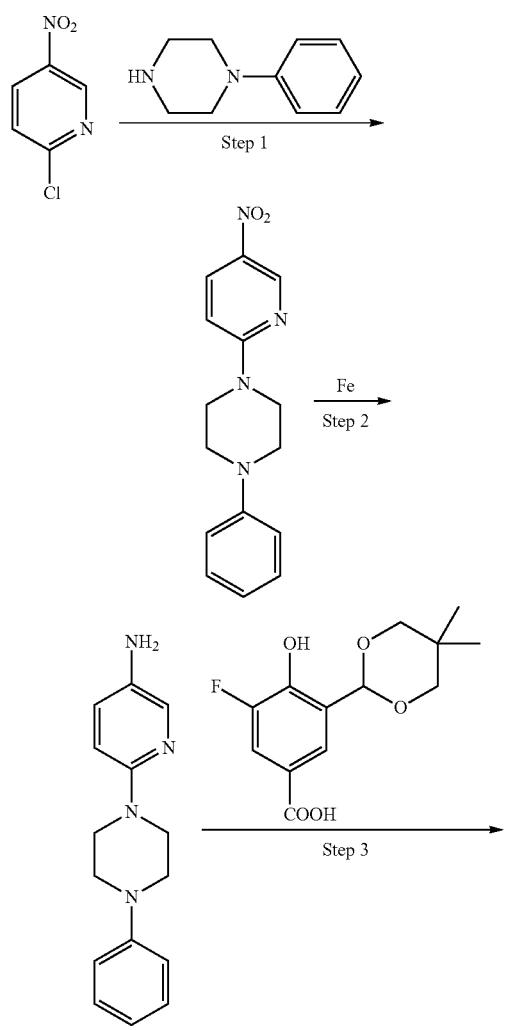

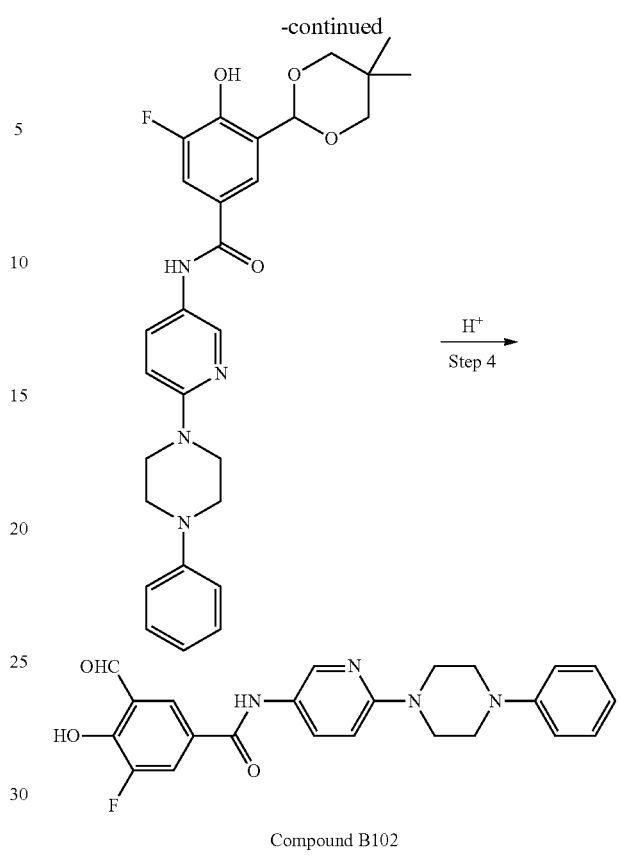

Compound B102

Step 1: 1-(5-nitropyridin-2-yl)-4-phenylpiperazine 1-(5-Nitropyridin-2-yl)-4-phenylpiperazine (2.1 g, 7.4 mmol, 74% yield) was prepared from 1-phenylpiperazine hydrochloride (1.78 g, 11.0 mmol, 1.1 eq.), potassium carbonate (4.4 g, 31.89 mmol, 3.0 eq.), and 2-chloro-5-nitropyridine (1.58 g, 10.0 mmol, 1.0 eq.) following the similar procedure for 3,3-dimethyl-1-(4-nitrophenyl)pyrrolidine in Example B25. No LCMS was taken for this compound.

Step 2: 6-(4-phenylpiperazin-1-yl)pyridin-3-amine 6-(4-Phenylpiperazin-1-yl)pyridin-3-amine (750 mg, 2.95 mmol, 84% yield) was prepared from 1-(5-nitropyridin-2-yl)-4-phenylpiperazine (1 g, 3.52 mmol, 1.0 eq.) and Fe (1.97 g, 35.2 mmol, 10 eq.) following the similar procedure for 4-(3,3-dimethylpyrrolidin-1-yl)aniline in Example B25. No LCMS was taken for this compound.

Step 3: 3-(5,5-dimethyl-1,3-dioxan-2-yl)-5-fluoro-4-hydroxy-N-(6-(4-phenylpiperazin-1-yl)pyridin-3-yl)benzamide 3-(5,5-Dimethyl-1,3-dioxan-2-yl)-5-fluoro-4-hydroxy-N-(6-(4-phenylpiperazin-1-yl)pyridin-3-yl)benzamide (270 mg, 0.53 mmol, 53% yield) was prepared from 6-(4-phenylpiperazin-1-yl)pyridin-3-amine (254 mg, 1.0 mmol, 1.0 eq.) and 3-(5,5-dimethyl-1,3-dioxan-2-yl)-5-fluoro-4-hydroxybenzoic acid (270 mg, 1.0 mmol, 1.0 eq.) following the similar procedure for 3-(5,5-dimethyl-1,3-dioxan-2-yl)-N-(4-(3,3-dimethylpyrrolidin-1-yl)phenyl)-5-fluoro-4-hydroxybenzamide in Example B25. LC-MS m/z [M+H]+ calc'd for $C_{28}H_{31}FN_4O_4$, 507; found, 507.

Step 4

3-Fluoro-5-formyl-4-hydroxy-N-(6-(4-phenylpiperazin-1-yl)pyridin-3-yl)benzamide (120 mg, 0.29 mmol, 54% yield) was prepared as a yellow solid from 3-(5,5-dimethyl-1,3-dioxan-2-yl)-5-fluoro-4-hydroxy-N-(6-(4-phenylpiperazin-1-yl)pyridin-3-yl)benzamide (270 mg, 0.53 mmol, 1 eq.) following the similar procedure for Example B25. $^1$H NMR (DMSO-d6, 400 MHz) δ: 11.69 (br, 1H), 10.35 (br, 1H), 10.21 (s, 1H), 8.47 (d, J=2.0 Hz, 1H), 8.19 (s, 1H), 8.08 (dd, J=11.6 Hz, 1H), 7.93 (dd, J=8.8 Hz, 2.0 Hz, 1H), 7.24 (m, 2H), 6.99 (m, 2H), 6.96 (d, J=8.8 Hz, 1H), 6.81 (m, 1H), 3.61 (m, 4H), 3.25 (m, 4H). LC-MS m/z [M+H]+ calc'd for $C_{23}H_{21}FN_4O_3$, 421; found, 421.

Example B50: 3-fluoro-5-formyl-N-(6-((3aR,6aS)-hexahydrocyclopenta[c]pyrrol-2(1H)-yl)pyridin-3-yl)-4-hydroxybenzamide (Compound B103)

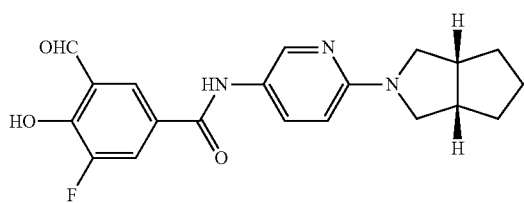

Step 1: (3aR,6aS)-2-(5-nitropyridin-2-yl)octahydrocyclopenta[c]pyrrole (3aR,6aS)-2-(5-Nitropyridin-2-yl)octahydrocyclopenta[c]pyrrole (680 mg, 2.9 mmol, 86% yield) was prepared from (3aR,6aS)-octahydrocyclopenta[c]pyrrole hydrochloride (0.5 g, 3.4 mmol, 1.0 eq.), potassium carbonate (1.4 g, 10.2 mmol, 3.0 eq.), and 2-chloro-5-nitropyridine (0.53 g, 3.7 mmol, 1.1 eq.) following the similar procedure for 3,3-dimethyl-1-(4-nitrophenyl)pyrrolidine in Example B25. No LCMS was taken for this compound.

Step 2: 6-((3aR,6aS)-hexahydrocyclopenta[c]pyrrol-2(1H)-yl)pyridin-3-amine 6-((3aR,6aS)-Hexahydrocyclopenta[c]pyrrol-2(1H)-yl)pyridin-3-amine (410 mg, 2.0 mmol, 94% yield) was prepared from (3aR,6aS)-2-(5-nitropyridin-2-yl)octahydrocyclopenta[c]pyrrole (0.5 g, 2.1 mmol, 1.0 eq.) and Fe (1.2 g, 21.5 mmol, 10 eq.) following the similar procedure for 4-(3,3-dimethylpyrrolidin-1-yl)aniline in Example B25. No LCMS was taken for this compound.

Step 3: 3-(5,5-dimethyl-1,3-dioxan-2-yl)-5-fluoro-N-(6-((3aR,6aS)-hexahydrocyclopenta[c]pyrrol-2(1H)-yl)pyridin-3-yl)-4-hydroxybenzamide 3-(5,5-Dimethyl-1,3-dioxan-2-yl)-5-fluoro-N-(6-((3aR,6aS)-hexahydrocyclopenta[c]pyrrol-2(1H)-yl)pyridin-3-yl)-4-hydroxybenzamide (160 mg, 0.35 mmol, 33% yield) was prepared from 6-((3aR,6aS)-hexahydrocyclopenta[c]pyrrol-2(1H)-yl)pyridin-3-amine (240 mg, 1.18 mmol, 1.1 eq.) and 3-(5,5-dimethyl-1,3-dioxan-2-yl)-5-fluoro-4-hydroxybenzoic acid (290 mg, 1.07 mmol, 1.0 eq.) following the similar procedure for 3-(5,5-dimethyl-1,3-dioxan-2-yl)-N-(4-(3,3-dimethylpyrrolidin-1-yl)phenyl)-5-fluoro-4-hydroxybenzamide in Example B25. LC-MS m/z [M+H]+ calc'd for $C_{25}H_{30}FN_3O_4$, 456; found, 456.

Step 4

3-Fluoro-5-formyl-N-(6-((3aR,6aS)-hexahydrocyclopenta[c]pyrrol-2(1H)-yl)pyridin-3-yl)-4-hydroxybenzamide (70 mg, 0.19 mmol, 54% yield) was prepared as a yellow solid from 3-(5,5-dimethyl-1,3-dioxan-2-yl)-5-fluoro-N-(6-((3aR,6aS)-hexahydrocyclopenta[c]pyrrol-2(1H)-yl)pyridin-3-yl)-4-hydroxybenzamide (160 mg, 0.35 mmol, 1 eq.) following the similar procedure for Example B25. $^1$H NMR (CDCl$_3$, 400 MHz) δ: 10.01 (br, 1H), 8.78 (br, 1H), 8.39 (s, 1H), 8.26 (s, 1H), 8.17 (m, 1H), 8.03 (d, J=10.8 Hz, 1H), 6.50 (d, J=9.2 Hz, 1H), 3.72 (m, 2H), 3.32 (m, 2H), 2.84 (m, 2H), 1.92 (m, 2H), 1.78 (m, 1H), 1.65 (m, 1H), 1.53 (m, 2H). LC-MS m/z [M+H]+ calc'd for $C_{20}H_{20}FN_3O_3$, 370; found, 370.

Biological Example 1: In Vitro Assay i. TLR2 Assays

Synthetic diacylated lipoprotein (Pam2CSK4, TLR2/6 agonist) and synthetic triacylated lipoprotein (Pam3CSK4, TLR1/2 agonist) were obtained from InvivoGen and were dissolved in endotoxin-free water to a concentration 1 mg/mL, vortexed until complete solubilization, and stored in aliquots at −20° C. Prior to addition to cells, an aliquot of the dissolved ligand was vortexed shortly and then was diluted in medium to 25 ng/mL Pam2CSK4 or 1000 ng/mL Pam3CSK4. The $EC_{50}$ of the agonists for each assay run was determined by using 3-fold dilutions of each agonist from the following starting concentrations: 5 ng/mL for Pam2CSK4, and 200 ng/mL for Pam3CSK4.

Test compounds were solubilized fresh to 10-20 mM stocks in DMSO and sonicated for 5-10 minutes in a water bath sonicator. Serial dilutions were prepared in DMSO, and then diluted in medium. The final concentration of DMSO used in the assay was 1%.

HEK-Blue hTLR2 reporter cells (InvivoGen) are HEK-293 cells stably expressing both the human TLR2 gene and a secreted embryonic alkaline phosphatase (SEAP) reporter construct downstream of NFκB promotor sites. HEK-Blue hTLR2 reporters were cultured according to manufacturer's protocol using Dulbecco's Modified Eagle Medium (DMEM; Gibco) containing 1× GlutaMax (Gibco), 10% heat-inactivated Fetal Bovine Serum (Gibco), Pen-Strep (50 U/mL penicillin, 50 μg/mL streptomycin, Gibco), 100 μg/mL Normocin (InvivoGen), and the selective antibiotic, 1×HEK-Blue Selection (InvivoGen). Quanti-Blue reagent (InvivoGen) for detection and quantification of secreted alkaline phosphatase was dissolved in 100 mL of endotoxin-free water, warmed to 37° C. for 30 minutes and then filtered using a 0.2 μm membrane.

ii. TLR9 Assay

Synthetic ODNs (ODN 2006 (ODN7909), class B CpG oligonucleotide, TLR9 agonist) was obtained from Invivo-Gen and was dissolved in endotoxin-free water to a concentration 500 μM, vortexed until complete solubilization, and stored in aliquots at −20° C. Prior to addition to cells, an aliquot of the dissolved ligand was vortexed shortly and then was diluted in medium to 50 μM. The $EC_{50}$ of the agonist for each assay run was determined by using 3-fold dilutions from the starting concentration 10 μM.

Test compounds were solubilized fresh to 10-20 mM stocks in DMSO and sonicated for 5-10 minutes in a water bath sonicator. Serial dilutions were prepared in DMSO, and then diluted in medium. The final concentration of DMSO used in the assay was 1%.

HEK-Blue hTLR9 reporter cells (InvivoGen) are HEK-293 cells stably expressing both the human TLR9 gene and a secreted embryonic alkaline phosphatase (SEAP) reporter construct downstream of NFκB promotor sites. HEK-Blue hTLR9 cells were cultured according to manufacturer's protocol using Dulbecco's Modified Eagle Medium (DMEM; Gibco) containing 1× GlutaMax (Gibco), 10% heat-inactivated Fetal Bovine Serum (Gibco), Pen-Strep (50 U/mL penicillin, 50 µg/mL streptomycin, Gibco), 100 µg/mL Normocin (InvivoGen), and the selective antibiotics, 10 µg/mL Blasticidin (InvivoGen), and 100 µg/mL Zeocin (InvivoGen). Quanti-Blue reagent (InvivoGen) for detection and quantification of secreted alkaline phosphatase was dissolved in 100 mL of endotoxin-free water, warmed to 37° C. for 30 minutes and then filtered using a 0.2 µm membrane.

Biological Example 2: HEK-Blue hTLR2 Antagonism Assay i. TLR2 Assays

On day 1, 50 µL of each test compound dilution in duplicates or a vehicle control was added to each well of a 96-well plate followed by addition of 150 µL of HEK-Blue hTLR2 cell suspension (1×10$^5$ cells/well) and incubated at 37° C./5% $CO_2$ for 2 h. Next, 50 µL of an approximate 3×$EC_{50}$ concentration of each agonist (Pam2CSK4 or Pam3CSK4) was added to the wells containing test compounds or the vehicle control. The plates were then incubated at 37° C./5% $CO_2$ for 18 h. For each assay run, non-treated HEK-Blue hTLR2 cells were treated with serial dilutions of agonists to determine $EC_{50}$ values for the respective run.

On day 2, secreted alkaline phosphatase (SEAP) activity was detected in cell culture supernatants. In brief, 20 µL was collected from each well and transferred to a 96-well plate. Next, 200 µL of Quanti-Blue detection reagent was added to each well. Plates were incubated at room temperature for 15 min. and SEAP activity was assessed by spectrophotometer OD reading at 655 nm. Table A and Table B show the activities of the compounds tested in HEK cells using Pam2CSK4 and Pam3CSK4 as agonists. The activities of the compounds against Pam2CSK4 and Pam3CSK4 are presented as $IC_{50}$ values which were defined as concentrations of the compounds where percent inhibition of the signal induced by agonist is equal to 50. $IC_{50}$ values were calculated based on 8-point dilutions for each compound.

ii. TLR9 Assay

On day 1, 50 µL of each test compound dilution in duplicates or a vehicle control was added to each well of a 96-well plate followed by addition of 150 µL of HEK-Blue hTLR9 cell suspension (1×10$^5$ cells/well) and incubated at 37° C./5% $CO_2$ for 2 h. Next, 50 µL of an approximate 3×$EC_{50}$ concentration of TLR9 agonist, ODN 2006, was added to the wells containing test compounds or the vehicle control. The plates were then incubated at 37° C./5% $CO_2$ for 18 h. For each assay run, vehicle-treated HEK-Blue hTLR9 cells were treated with serial dilutions of agonist to determine $EC_{50}$ values for the respective run.

On day 2, secreted alkaline phosphatase (SEAP) activity was detected in cell culture supernatants. In brief, 30 µL was collected from each well and transferred to a 96-well plate. Next, 200 µL of Quanti-Blue detection reagent was added to each well. Plates were incubated at 37° C. for 60 min. and SEAP activity was assessed by spectrophotometer OD reading at 655 nm. Table A and Table B show the activities of the compounds tested in HEK-Blue hTLR9 cells against ODN 2006. The activities of the compounds against ODN 2006 are presented as $IC_{50}$ values which were defined as concentrations of the compounds where percent inhibition of the signal induced by agonist is equal to 50. Exact $IC_{50}$ values were calculated based on 8-point dilutions for each compound. Approximate $IC_{50}$ values (~ or <) were calculated based on 4-point dilutions for each compound.

TABLE A

| Example No. | Compound No. | $IC_{50}$ (µM) with Pam2CSK4 | $IC_{50}$ (µM) with Pam3CSK4 | ~IC50 (µM) with ODN2006 |
|---|---|---|---|---|
| A1 | A1 | 2.2 | 0.9 | ~2 |
| A2 | A2 | >100 | >100 | >33 |
| A3 | A3 | 9.9 | 8.3 | ND |
| A4 | A4 | 8.5 | 10.5 | ND |
| A5 | A5 | >100 | >100 | ND |
| A6 | A6 | 14.1 | 12.0 | ND |
| A7 | A7 | 36.8 | 42.3 | >33 |
| A8 | A8 | 85.5 | >100 | >33 |
| A9 | A9 | 3.8 | 5.1 | ND |
| A10 | A10 | 5.2 | 5.2 | ND |
| A11 | A11 | 2.3 | 2.0 | ND |
| A12 | A12 | >100 | >100 | >33 |
| A13 | A13 | 45.7 | 39.7 | >33 |
| A14 | A14 | 42.2 | 42.6 | >33 |
| A15 | A15 | >100 | >100 | >33 |
| A16 | A16 | >100 | >100 | >33 |
| A17 | A17 | 52.6 | 43.4 | ND |
| A18 | A18 | >100 | >100 | ND |
| A19 | A19 | 0.5 | 0.5 | <1.2 |
| A20 | A20 | 0.5 | 0.2 | ND |
| A21 | A21 | 2.6 | 1.1 | ND |
| A22 | A22 | 0.9 | 0.9 | >10 |
| A23 | A23 | 0.8 | 0.9 | ND |
| A24 | A24 | 4.3 | 5.4 | ND |
| A25 | A25 | 1.9 | 1.2 | ~3 |
| A26 | A26 | 2.9 | 2.7 | ~3 |
| A27 | A27 | 0.9 | 0.8 | <1.2 |
| A28 | A28 | 0.9 | 0.8 | ND |
| A29 | A29 | 6.4 | 7.6 | ND |
| A30 | A30 | 2.1 | 2.2 | ND |
| A31 | A31 | 3.4 | 6.2 | ND |
| A32 | A32 | 12.7 | 17.4 | ND |
| A33 | A33 | 4.0 | 3.6 | ~4 |
| A34 | A34 | 6.9 | 3.9 | ND |
| A35 | A35 | 1.6 | 0.7 | ND |
| A36 | A36 | >100 | >100 | ND |
| A37 | A37 | >100 | >100 | ND |
| A38 | A38 | 0.4 | 0.4 | ND |
| A39 | A39 | 0.5 | 0.5 | ND |
| A40 | A40 | 7.2 | 2.7 | ND |
| A41 | A42 | 0.4 | 0.3 | 0.1 |
| A42 | A43 | 1.1 | 1.1 | <1.2 |
| A43 | A44 | 1.0 | 0.7 | ~1.2 |
| A44 | A45 | 1.3 | 1.3 | ND |
| A45 | A47 | 2.3 | 1.3 | <1.2 |
| A46 | A50 | 4.1 | 0.9 | ND |
| A47 | A51 | 1.7 | 0.7 | <1.2 |
| A48 | A52 | 0.7 | 0.2 | <1.2 |
| A49 | A57 | 1.0 | 0.3 | 0.3 |
| A50 | A61 | 3.2 | 1.0 | <1.2 |
| A51 | A62 | 0.7 | 0.4 | 0.2 |
| A52 | A88 | 2.1 | 1.3 | ~3 |
| A53 | A89 | >100 | >100 | ND |
| A54 | A90 | 6.5 | 4.5 | ND |
| A55 | A91 | 3.8 | 2.1 | <1.2 |
| A56 | A92 | 3.5 | 0.9 | ND |
| A57 | A93 | 4.8 | 2.1 | <1.2 |
| A58 | A94 | 14.8 | 9.2 | <1.2 |
| A59 | A95 | 3.0 | 2.3 | ~1.4 |
| A60 | A96 | 12.1 | 8.8 | ~6.3 |

TABLE A-continued

| Example No. | Compound No. | IC$_{50}$ (μM) with Pam2CSK4 | IC$_{50}$ (μM) with Pam3CSK4 | ~IC50 (μM) with ODN2006 |
|---|---|---|---|---|
| A61 | A97 | 0.9 | 0.3 | ND |
| A62 | A55 | 0.6 | 0.4 | 0.2 |
| A63 | A98 | 1.4 | 1.0 | ND |
| A64 | A99 | 3.3 | 2.2 | ND |
| A65 | A100 | 1.4 | 0.6 | ND |
| A66 | A101 | 3.2 | 1.0 | ND |
| A67 | A102 | 1.9 | 1 | ND |
| A68 | A103 | 3.9 | 1.3 | ND |
| A69 | A104 | 6.8 | 3.9 | ND |
| A70 | A105 | 1.9 | 0.5 | ND |
| A71 | A123 | 1.7 | 1.5 | ND |
| A72 | A124 | 1.7 | 1.0 | ND |
| A73 | A114 | 0.7 | 0.4 | ND |
| A74 | A125 | 3.3 | 2.0 | ND |
| A75 | A126 | 1.1 | 0.6 | ND |
| A76 | A127 | 1.2 | 0.7 | ND |
| A77 | A116 | 1.3 | 0.6 | ND |
| A78 | A112 | 0.3 | 0.2 | ND |

ND = Not Determined

TABLE B

| Example No. | Compound No. | IC$_{50}$ (μM) with Pam2CSK4 | IC$_{50}$ (μM) with Pam3CSK4 | ~IC50 (μM) with ODN2006 |
|---|---|---|---|---|
| B1 | B1 | 1.1 | 0.7 | <1.2 |
| B2 | B2 | 0.5 | 0.3 | ND |
| B3 | B3 | 3.7 | 2.2 | <1.2 |
| B4 | B4 | 6.3 | 2.7 | ~1.5 |
| B5 | B5 | 1.9 | 1.1 | ND |
| B6 | B6 | 3.8 | 1.8 | ND |
| B7 | B7 | 35.7 | 20.8 | >33 |
| B8 | B8 | 2.9 | 1.6 | ND |
| B9 | B9 | 8.1 | 6.8 | ND |
| B10 | B10 | 11.6 | 7.2 | ND |
| B11 | B11 | 12.0 | 10.6 | <1.2 |
| B12 | B12 | 2.7 | 2.0 | 0.7 |
| B13 | B13 | 1.9 | 1.9 | ND |
| B14 | B14 | 1.3 | 1.5 | >33 |
| B15 | B17 | 12.7 | 6.6 | ~2.9 |
| B16 | B59 | 32.7 | 19.8 | ND |
| B17 | B61 | 16.4 | 9.3 | ND |
| B18 | B63 | 30.1 | 11.3 | ND |
| B19 | B64 | 10.9 | 8.0 | ND |
| B20 | B65 | 8.7 | 3.7 | <1.2 |
| B21 | B66 | 1.8 | 1.0 | ND |
| B22 | B67 | 3.3 | 1.2 | <1.2 |
| B23 | B68 | 3.5 | 1.0 | <1.2 |
| B24 | B69 | 7.6 | 2.3 | ND |
| B25 | B70 | 11.5 | 6.5 | ND |
| B26 | B71 | 2.6 | 1.7 | ~2.5 |
| B27 | B72 | 4.6 | 2.4 | ND |
| B28 | B73 | 0.6 | 0.3 | 0.3 |
| B29 | B74 | 1.6 | 0.8 | <1.2 |
| B30 | B75 | 13.0 | 6.0 | ~4.7 |
| B31 | B76 | 1.2 | 0.6 | <1.2 |
| B32 | B77 | 0.6 | 0.3 | <1.2 |
| B33 | B78 | 34.4 | 18.5 | ND |
| B34 | B79 | 4.1 | 1.4 | ND |
| B35 | B80 | 15.5 | 35.9 | ND |
| B36 | B81 | 1.0 | 0.5 | ND |
| B37 | B82 | 1.2 | 0.7 | ND |
| B38 | B83 | 1.0 | 0.3 | ND |
| B39 | B84 | 33.9 | 14.3 | ND |
| B40 | B85 | 1.3 | 0.7 | ND |
| B41 | B86 | 4.3 | 1.8 | ND |
| B42 | B87 | 0.5 | 0.4 | 0.1 |
| B43 | B99 | 0.6 | 0.5 | ND |
| B44 | B90 | 2.9 | 1.9 | ND |
| B45 | B94 | 1.0 | 0.9 | ND |
| B46 | B95 | 3.7 | 2.8 | ND |
| B47 | B96 | 1.4 | 1.1 | ND |

TABLE B-continued

| Example No. | Compound No. | IC$_{50}$ (μM) with Pam2CSK4 | IC$_{50}$ (μM) with Pam3CSK4 | ~IC50 (μM) with ODN2006 |
|---|---|---|---|---|
| B48 | B91 | 2.2 | 1.6 | ND |
| B49 | B102 | 2.0 | 1.0 | ND |
| B50 | B103 | 1.7 | 1.0 | ND |

ND = Not Determined

The invention claimed is:

1. A compound of Formula (A):

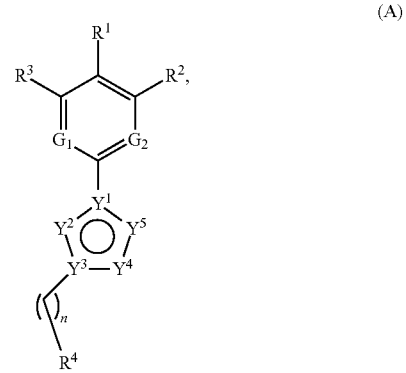

(A)

or a tautomer, or a pharmaceutically acceptable salt of any of the foregoing, wherein $R^1$ is —OH;

$R^2$ is —C(O)H;

$R^3$ is $C_1$-$C_6$alkoxy or halogen;

$G_1$ and $G_2$ are each CH;

◯ indicates that the ring is aromatic;

$Y^1$ is C or N;

$Y^2$ is CH, N, NH, S, or O;

$Y^3$ is C or N;

$Y^4$ is CH, N, NH, S, or O;

$Y^5$ is $CR^7$, N, NH, S, or O;

wherein no more than one of $Y^1$, $Y^2$, $Y^3$, $Y^4$, and $Y^5$ is S or O and no more than four of $Y^1$, $Y^2$, $Y^3$, $Y^4$, and $Y^5$ are N or NH;

$R^7$ is H or $C_1$-$C_6$alkyl;

n is 0, 1, 2, or 3;

$R^4$ is

indicates that the ring is saturated, partially unsaturated, or fully unsaturated;

G$_3$ is CH(X$_1$—R$^{6a}$), C(X$_1$—R$^{6a}$), N, N(X$_1$—R$^{6a}$), S, or O;

G$_4$ is CH(X$_2$—R$^{6b}$), C(X$_2$—R$^{6b}$), N, N(X$_2$—R$^{6b}$), S, or O;

G$_5$ is CH(X$_3$—R$^{6c}$), C(X$_3$—R$^{6c}$), N, N(X$_3$—R$^{6c}$), S, or O;

G$_6$ is CH(X$_4$—R$^{6d}$), C(X$_4$—R$^{6d}$), N, N(X$_4$—R$^{6d}$), S, or O; and G$_7$ is N, C, or CH;

X$_1$, X$_2$, X$_3$, and X$_4$ are each independently absent,

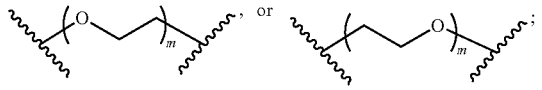

m is 1-6;

R$^{6a}$, R$^{6b}$, R$^{6c}$, and R$^{6d}$ are each independently hydrogen, C$_1$-C$_6$alkyl, C$_1$-C$_6$alkoxy, halo, —OH, —NR$^p$R$^q$, aryl, heterocyclyl, heteroaryl, —C$_1$-C$_6$alkyl-heterocyclyl, —OC(O)-heterocyclyl, —C(O)R$^h$, —S(O)$_2$NR$^{w1}$R$^{w2}$, —S(O)$_2$R$^y$, or —NR$^{z1}$S(O)$_2$R$^{z2}$, wherein the C$_1$-C$_6$alkyl and C$_1$-C$_6$alkoxy of R$^{6a}$, R$^{6b}$, R$^{6c}$, and R$^{6d}$ are each independently unsubstituted or substituted with one or more groups selected from the group consisting of cycloalkyl and halogen; the aryl and heteroaryl of R$^{6a}$, R$^{6b}$, R$^{6c}$, and R$^{6d}$ are each independently unsubstituted or substituted with one or more groups selected from the group consisting of C$_1$-C$_6$alkyl, C$_1$-C$_6$alkoxy, C$_3$-C$_8$cycloalkyl, —OH, and C$_1$-C$_6$alkyl-OH; and the heterocyclyl, —C$_1$-C$_6$alkyl-heterocyclyl, and —OC(O)-heterocyclyl of R$^{6a}$, R$^{6b}$, R$^{6c}$, and R$^{6d}$ are each independently unsubstituted or substituted with one or more groups selected from the group consisting of C$_1$-C$_6$alkyl, C$_1$-C$_6$alkoxy, halo, —OH, C$_1$-C$_6$alkyl-OH, =O, and =S;

each R$^h$ is independently selected from the group consisting of H, C$_1$-C$_6$alkyl, C$_1$-C$_6$alkoxy, and C$_3$-C$_8$cycloalkyl, and —NR$^r$R$^s$;

each R$^p$ is independently H or C$_1$-C$_6$alkyl;

each R$^q$ is independently C$_2$-C$_3$alkyl, —C(O)R$^t$, —C(O)OR$^u$, or —C(O)NR$^v$;

each R$^r$, R$^s$, R$^{w1}$, and R$^{z1}$ is independently selected from H and C$_1$-C$_6$alkyl; and each R$^t$, R$^u$, R$^v$, R$^{w2}$, R$^y$, and R$^{z2}$ is independently selected from H, C$_1$-C$_6$alkyl, unsubstituted or substituted C$_3$-C$_8$cycloalkyl, and unsubstituted or substituted heterocyclyl;

or

G$_5$ is CH(X$_3$—R$^{6c}$) or C(X$_3$—R$^{6c}$), G$_6$ is CH(X$_4$—R$^{6d}$) or C(X$_4$—R$^{6d}$), and R$^{6c}$ and R$^{6d}$ are taken together with the carbon atoms to which they are attached to form a 6-membered aryl, a 6-membered heterocyclyl, or a 6-membered heteroaryl ring; wherein the 6-membered aryl, 6-membered heterocyclyl, and 6-membered heteroaryl rings are each independently unsubstituted or substituted.

2. The compound of claim 1, or a tautomer thereof, or a pharmaceutically acceptable salt of any of the foregoing, wherein R$^3$ is selected from the group consisting of —OCH$_3$, Cl, and F.

3. The compound of claim 1, or a tautomer thereof, or a pharmaceutically acceptable salt of any of the foregoing, wherein

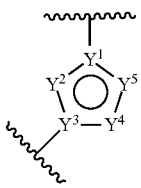

is selected from the group consisting of

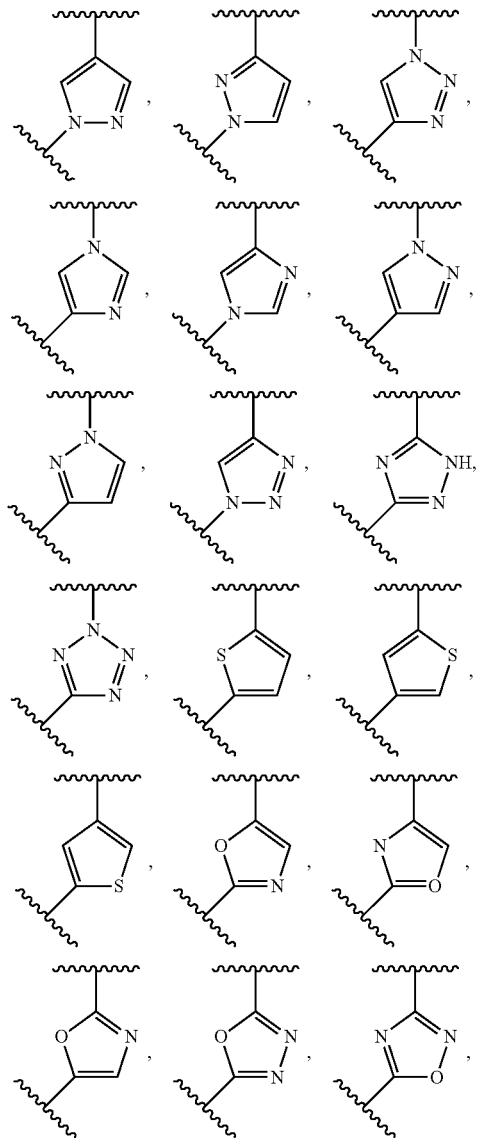

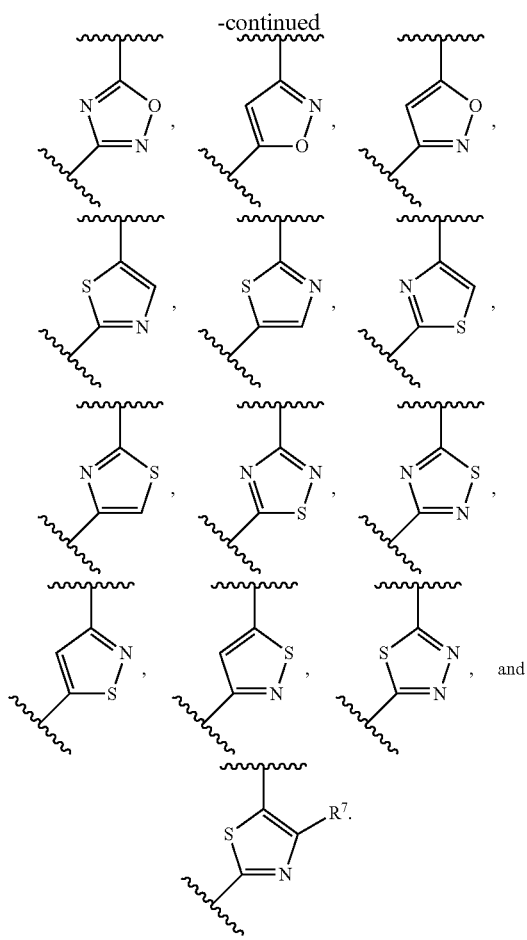

4. The compound of claim 1, or a tautomer thereof, or a pharmaceutically acceptable salt of any of the foregoing, wherein n is 0.

5. The compound of claim 1, or a tautomer thereof, or a pharmaceutically acceptable salt of any of the foregoing, wherein $G_3$ is $C(X_1—R^{6a})$; $X_1$ is absent,

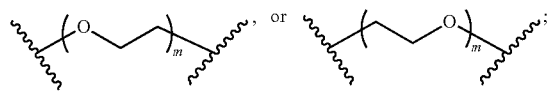

m is 1-6; $R^{6a}$ is hydrogen, $C_1$-$C_6$alkyl, $C_1$-$C_6$haloalkyl, halo, $C_6$-$C_{12}$ aryl, 3- to 10-membered heterocyclyl, or 5- to 10-membered heteroaryl;

$G_4$ is $C(X_2—R^{6b})$ or N; $X_2$ is absent,

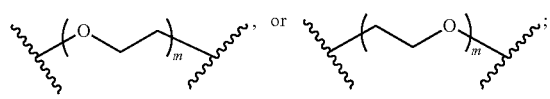

m is 1-6; and $R^{6b}$ is hydrogen, $C_1$-$C_6$alkyl, $C_1$-$C_6$haloalkyl, halo, $C_6$-$C_{12}$ aryl, 3- to 10-membered heterocyclyl, or 5- to 10-membered heteroaryl;

$G_5$ is $C(X_3—R^{6c})$; $X_3$ is absent,

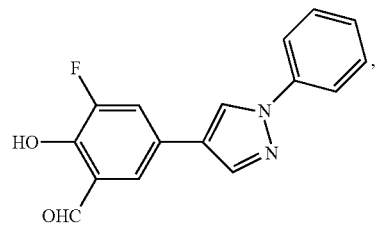

m is 1-6; and $R^{6c}$ is hydrogen, $C_1$-$C_6$alkyl, $C_1$-$C_6$haloalkyl, halo, $C_6$-$C_{12}$ aryl, 3- to 10-membered heterocyclyl, or 5- to 10-membered heteroaryl;

$G_6$ is $C(X_4—R d)$; $X_4$ is absent,

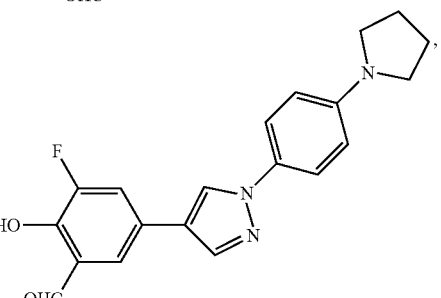

m is 1-6; and $R^{6d}$ is hydrogen, $C_1$-$C_6$alkyl, $C_1$-$C_6$haloalkyl, halo, $C_6$-$C_{12}$ aryl, 3- to 10-membered heterocyclyl, or 5- to 10-membered heteroaryl; and $G_7$ is C.

6. The compound of claim 1, or a tautomer thereof, or a pharmaceutically acceptable salt of any of the foregoing, wherein one or more of $R^6$, $R^{6b}$, $R^{6c}$, and $R^{6d}$ are independently selected from the group consisting of $C_1$-$C_6$alkyl, $C_1$-$C_6$alkoxy, halo, —OH, —NR$^p$R$^q$, aryl, heterocyclyl, heteroaryl, —C$_1$-C$_6$alkyl-heterocyclyl, —OC(O)-heterocyclyl, —C(O)R$^h$, —S(O)$_2$NR$^{w1}$R$^{w2}$, —S(O)$_2$R$^y$, and —NR$^{z1}$S(O)$_2$R$^{z2}$.

7. The compound of claim 1, or a tautomer thereof, or a pharmaceutically acceptable salt of any of the foregoing, wherein the compound is

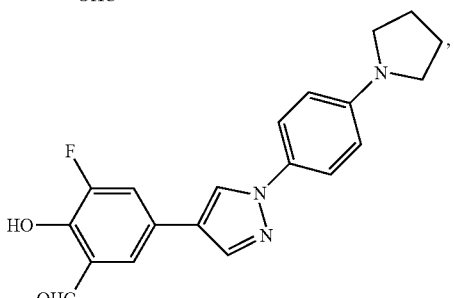

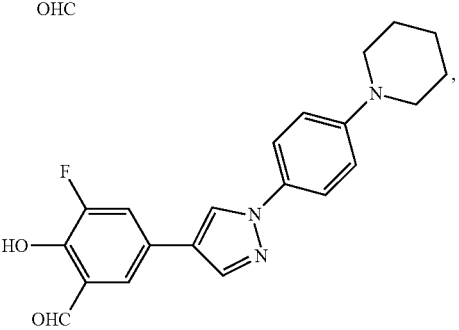

331
-continued
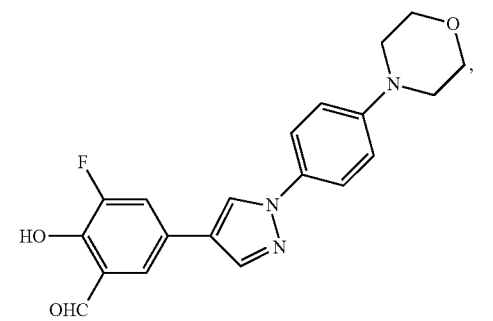
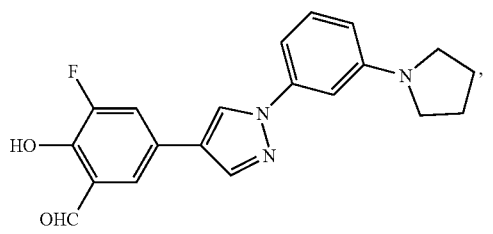
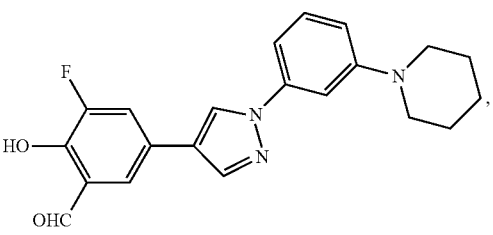
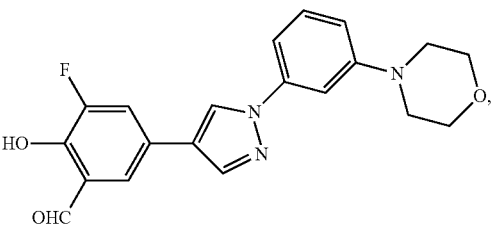
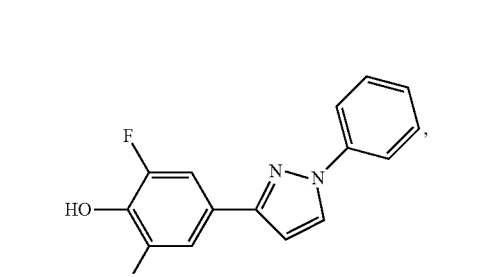
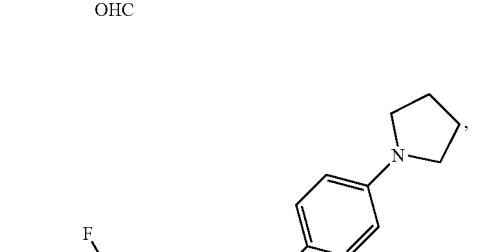
332
-continued
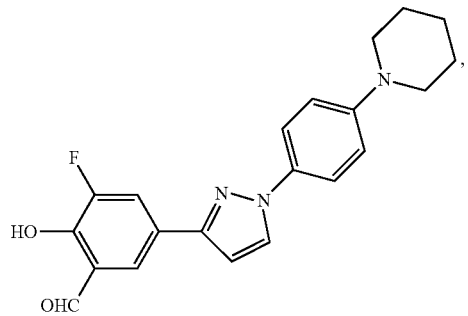

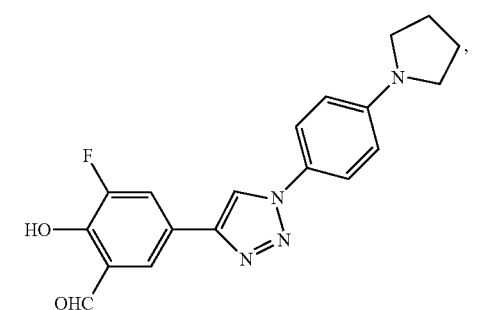
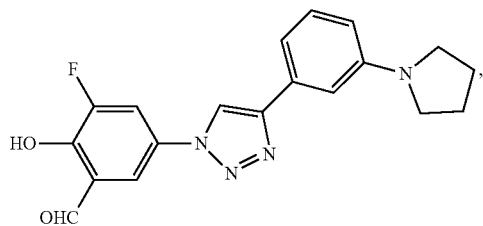
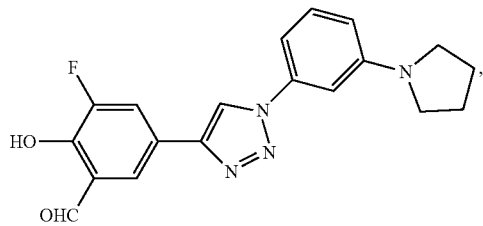
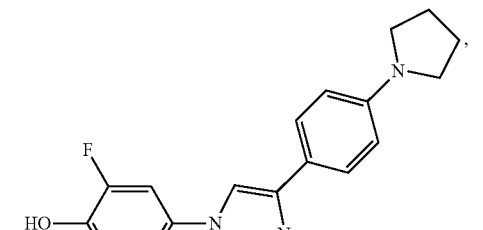
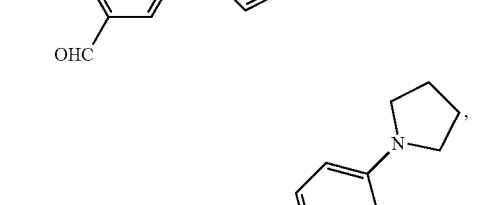
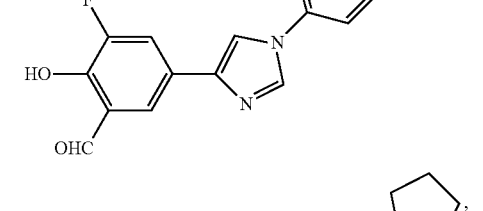
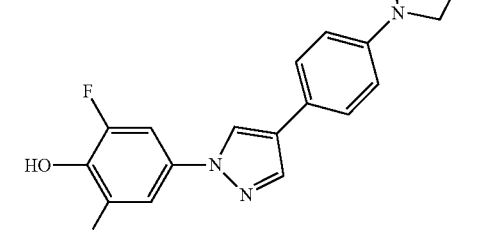
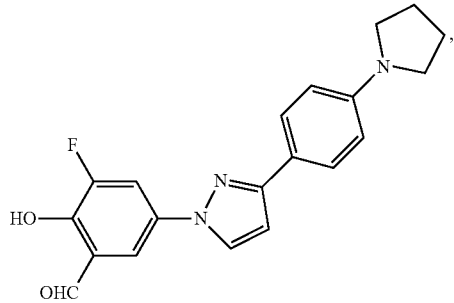
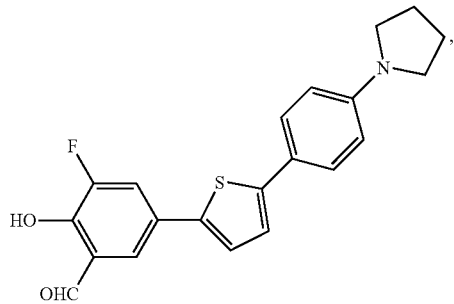
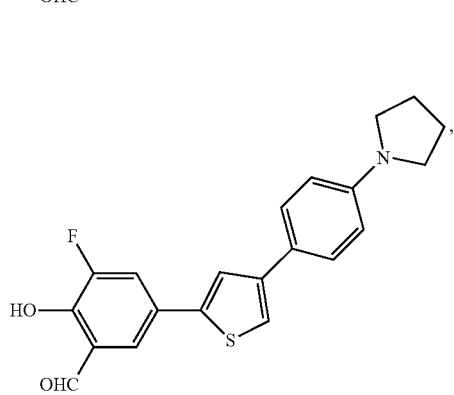
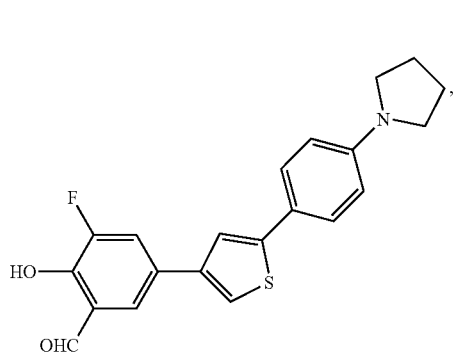
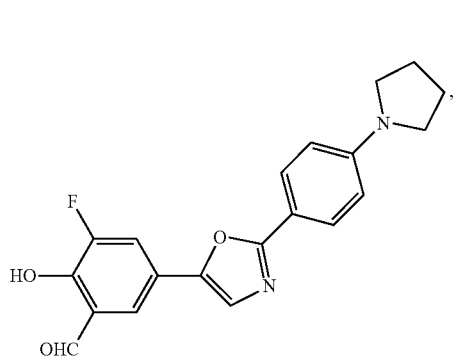

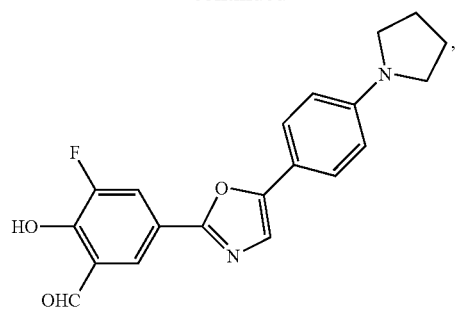
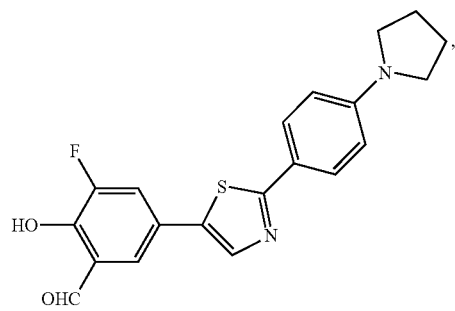
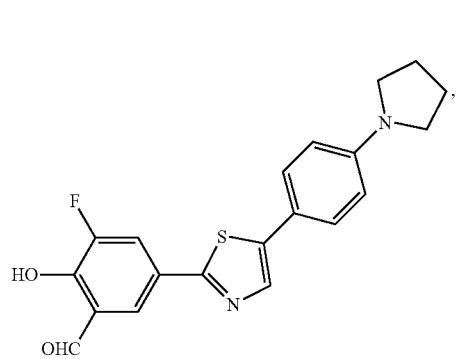
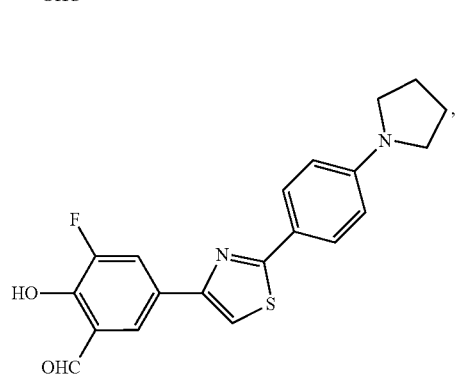
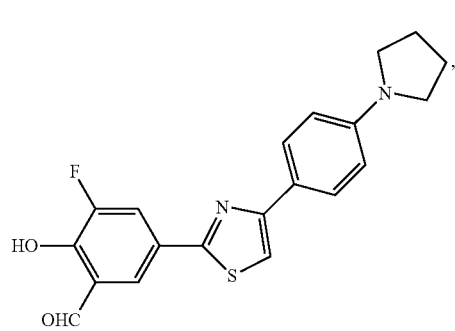
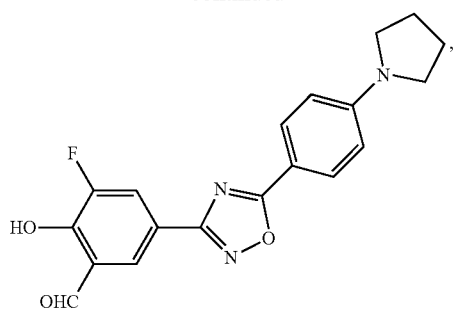
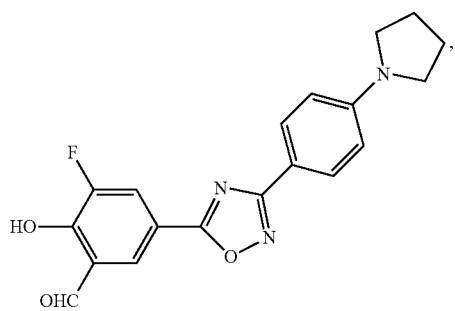
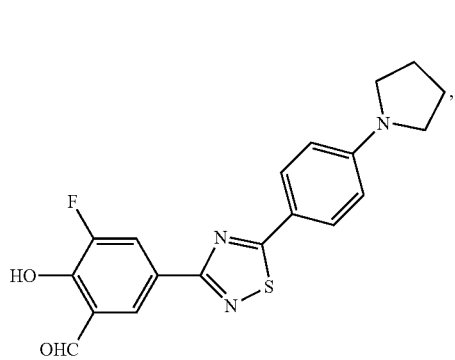
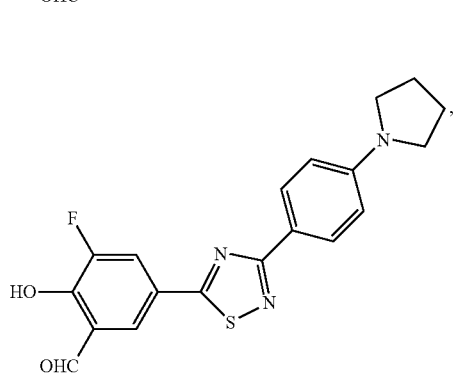
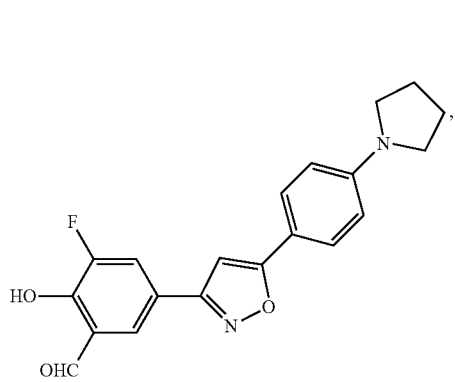

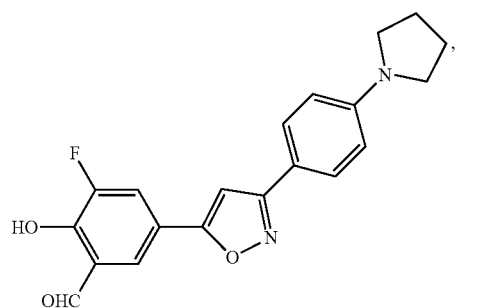
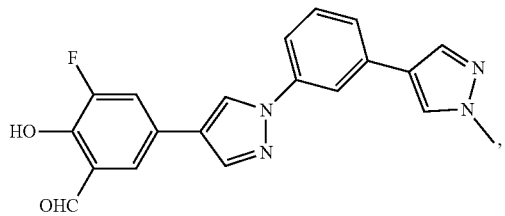
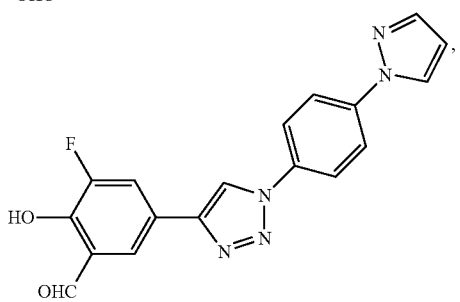
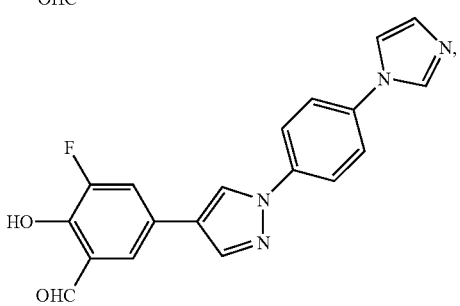
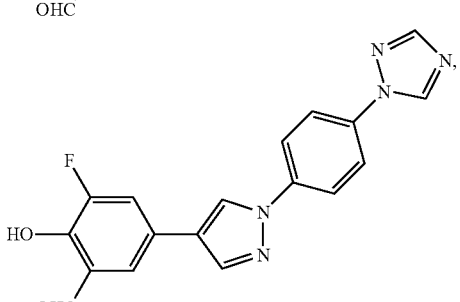
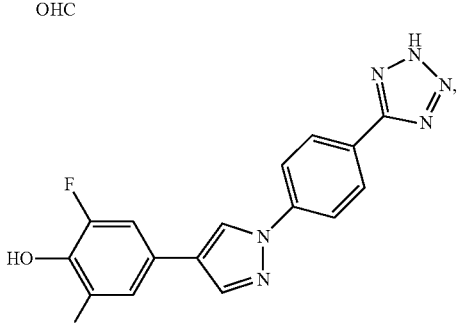
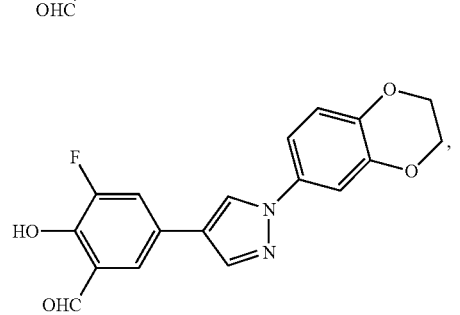

-continued
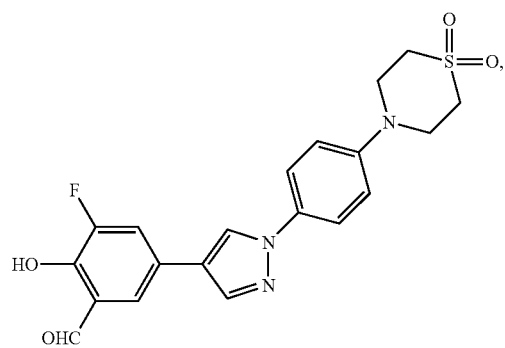
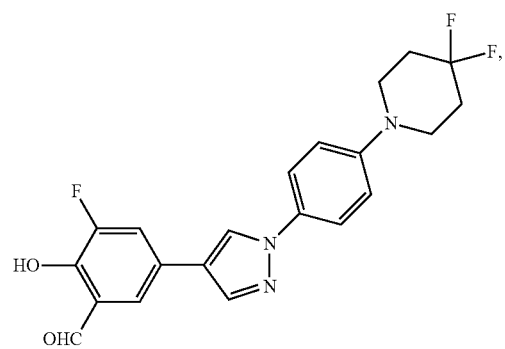
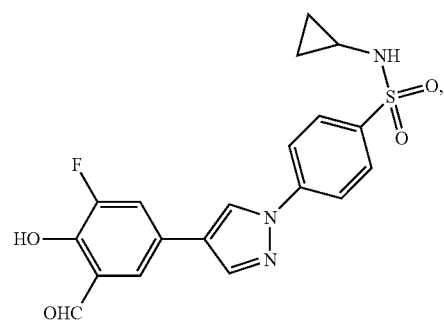
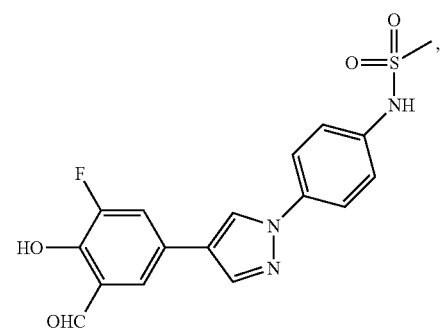
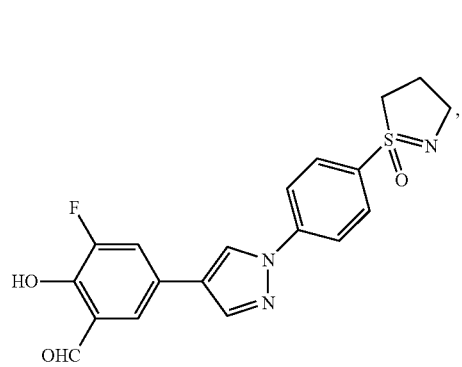
-continued
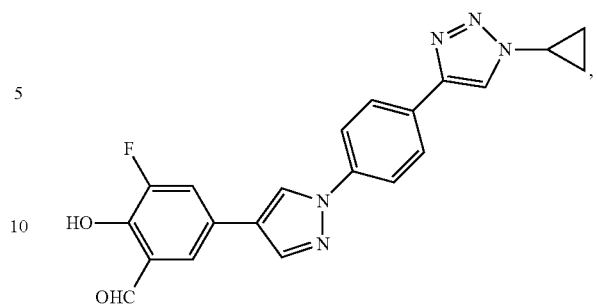
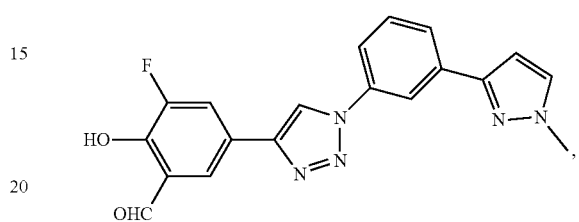
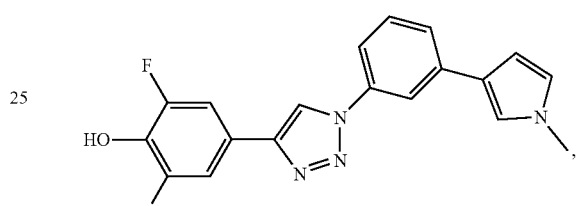
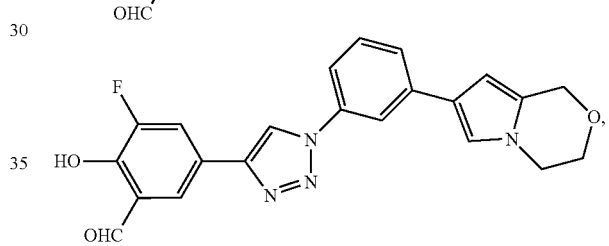
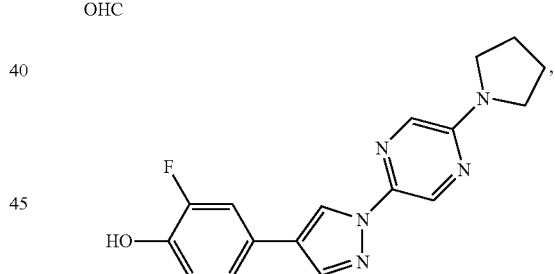
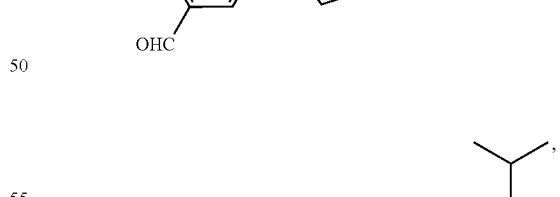

-continued
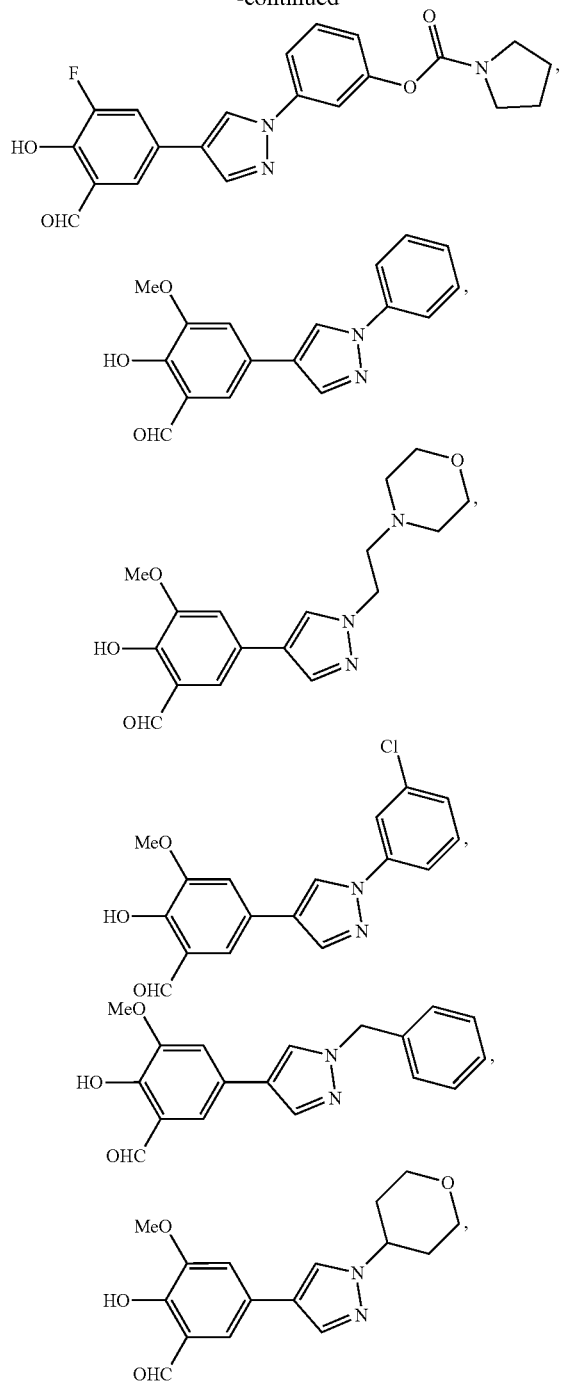
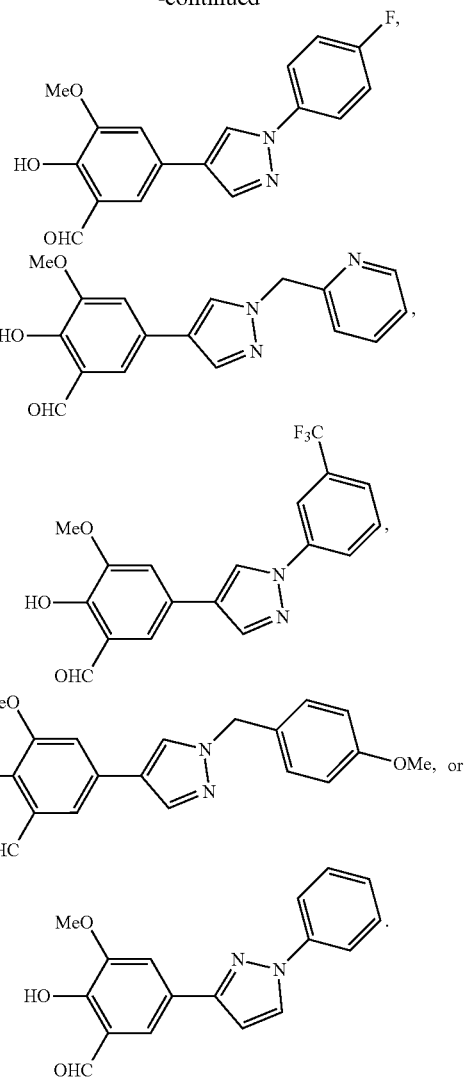
8. A pharmaceutical composition comprising at least one compound according to claim 1, or a tautomer thereof, or a pharmaceutically acceptable salt of any of the foregoing, optionally further comprising a pharmaceutically acceptable excipient.
* * * * *